US012268737B2

(12) United States Patent
Mascola et al.

(10) Patent No.: US 12,268,737 B2
(45) Date of Patent: Apr. 8, 2025

(54) STABILIZED INFLUENZA HEMAGGLUTININ STEM REGION TRIMERS AND USES THEREOF

(71) Applicant: The United States of America, as represented by the Secretary, Department of Health and Human Services, Bethesda, MD (US)

(72) Inventors: John R. Mascola, Rockville, MD (US); Jeffrey C. Boyington, Clarksburg, MD (US); Hadi M. Yassine, Doha (QA); Peter D. Kwong, Washington, DC (US); Barney S. Graham, Smyrna, GA (US); Masaru Kanekiyo, North Bethesda, MD (US)

(73) Assignees: The United States of America, as represented by the Secretary, Department of Health and Human Services, Bethesda, MD (US); Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/648,190

(22) Filed: Apr. 26, 2024

(65) Prior Publication Data
US 2024/0285749 A1    Aug. 29, 2024

Related U.S. Application Data

(62) Division of application No. 18/314,052, filed on May 8, 2023, now Pat. No. 11,969,466, which is a division of application No. 17/504,002, filed on Oct. 18, 2021, now Pat. No. 11,679,151, which is a division of application No. 16/455,242, filed on Jun. 27, 2019, now Pat. No. 11,147,867, which is a division of application No. 15/313,265, filed as application No. PCT/US2015/032695 on May 27, 2015, now Pat. No. 10,363,301.

(60) Provisional application No. 62/003,471, filed on May 27, 2014.

(51) Int. Cl.
| | |
|---|---|
| *A61K 39/145* | (2006.01) |
| *A61K 39/12* | (2006.01) |
| *C07K 14/005* | (2006.01) |
| *C07K 14/47* | (2006.01) |
| *C12N 7/00* | (2006.01) |
| *A61K 39/00* | (2006.01) |

(52) U.S. Cl.
CPC .......... *A61K 39/145* (2013.01); *A61K 39/12* (2013.01); *C07K 14/005* (2013.01); *C07K 14/47* (2013.01); *C12N 7/00* (2013.01); *A61K 2039/55555* (2013.01); *A61K 2039/55566* (2013.01); *A61K 2039/6031* (2013.01); *C07K 2319/00* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| 9,441,019 B2 | 9/2016 | Nabel et al. |
| 10,363,301 B2 | 7/2019 | Mascola et al. |
| 2011/0177122 A1 | 7/2011 | Nabel et al. |

FOREIGN PATENT DOCUMENTS

| WO | WO 2013/044203 | 3/2013 |

OTHER PUBLICATIONS

Cotter et al., "A Single Amino Acid in the Stalk Region of the H1N1pdm Influenza Virus HA Protein Affects Viral Fusion, Stability and Infectivity," PLOS Pathogens 10.1: e1003831, Jan. 2014 (9 pages).
Kenekiyo et al., "Self-assembling influenza nanoparticle vaccines elicit broadly neutralizing HINI antibodies", Nature 499.456: 102-106, Jul. 2013.
Khanna et al., "Protective Immunity Based on the Conserved Hemagglutinin Stalk Domain and its Prospects for Universal Influenza Vaccine Development", Biomed Res Internatl. 284.13: 1655-1657, Jan. 1, 2014.
Krammer et al., "Influenza virus hemagglutinin stalk-based antibodies and vaccines", Curr Opin Virol. 3.51: 521-530, Oct. 1, 2013.
Robertson, "Sequence Analysis of the Haemagglutinin of A/Taiwan/ 1/86, a New Variant of Human Influenza A(HINI) Virus", J Gen Virol. 68.4: 1205-1208, Apr. 1, 1987.
Sagawa et al., "The immunological activity of a deletion mutant of influenza virus haemagglutinin lacking the globular region 11", J Gen Virol. 77.7: 1483-1487, Jan. 1, 1996.
Steel et al., "Influenza virus vaccine based on the conserved hemagglutinin stalk Domain", MBIO 1.1: e00018-10, May 18, 2010.
Sunil et al., "Vaccines based on structure-based design provide protection against infectious diseases", Expert Reviews of Vaccines 12.11: 1301-1311, Nov. 1, 2013.

(Continued)

Primary Examiner — Agnieszka Boesen
(74) Attorney, Agent, or Firm — Klarquist Sparkman, LLP

(57) ABSTRACT

Vaccines that elicit broadly protective anti-influenza antibodies. Some vaccines comprise nanoparticles that display HA trimers from influenza virus on their surface. The nanoparticles are fusion proteins comprising a monomeric subunit (e.g., ferritin) joined to the stem region of an influenza HA protein. The fusion proteins self-assemble to form the HA-displaying nanoparticles. The vaccines comprise only the stem region of an influenza HA protein joined to a trimerization domain. Also provided are fusion proteins, and nucleic acid molecules encoding such proteins, and assays using nanoparticles of the invention to detect anti-influenza antibodies.

21 Claims, 42 Drawing Sheets

Specification includes a Sequence Listing.

(56) References Cited

OTHER PUBLICATIONS

Yang et al., "Structures of Receptor Complexes of a North American H7N2 Influenza Hemagglutinin with a Loop Deletion in the Receptor Binding Site", PLoS Pathog 6.9: e1001081, 2010 (11 pages).
International Search Report and Written Opinion prepared by the European Patent Office on Aug. 25, 2015, for International Application No. PCT/US2015/032695.
International Preliminary Report on Patentability for International (PCT) Patent Application No. PCT/US2015/032695, dated Dec. 8, 2016, 9 pages.
Official Action for Canada Patent Application No. 2,950,085, dated Oct. 30, 2017, 6 pages.
Official Action for European Patent Application No. 15727824.3, dated Dec. 11, 2017, 5 pages.
Official Action for European Patent Application No. 15727824.3, dated Jun. 22, 2018, 8 pages.
Official Action for U.S. Appl. No. 15/313,265, dated Feb. 8, 2018, 9 pages, Restriction Requirement.
Official Action for U.S. Appl. No. 15/313,265, dated May 29, 2018, 12 pages.
Official Action for U.S. Appl. No. 15/313,265, dated Dec. 11, 2018, 7 pages.
Notice of Allowance for U.S. Appl. No. 15/313,265, dated Mar. 11, 2019, 5 pages.
Official Action for Canada Patent Application No. 2,950,085, dated Dec. 17, 2018, 6 pages.
English Translation of Official Action for China Patent Application No. 201580041202.3, dated Oct. 22, 2019, 15 pages.
Official Action for European Patent Application No. 15727824.3, dated May 16, 2019, 6 pages.
Official Action for European Patent Application No. 15727824.3, dated Nov. 6, 2019, 4 pages.

| HA stem percentage of immunogen surface | | |
|---|---|---|
| | Gen 4 | Gen6 |
| HA | HS-SS | HS-SS |
| 37% | 71% | 94% | variable ▭ conserved

Figure 1b

H1-SS-np cryo-EM 2D radial density profile

Figure 5

Gen6_H1NC99_K394M/E446L/E448Q/R449W/D452L/Y437D/N438L_N19Q

Plasmid map: Gen6 H1NC99 rpk3, 5579 bp

Features:
- Kan.
- CMV/R Gen6 H1NC99 rpk3
- CMV IE Enhancer/Promoter
- HTLV-1 R Region/Splicing Donor
- CMV IE Splicing Acceptor
- Gen6 H1NC99 rpk3
- Tbgh

| | |
|---|---|
| Nucleotide of sequence insert | SEQ ID NO: 263 |
| Nucleotide sequence of entire plasmid | SEQ ID NO: 266 |

Gen6_H1CA09_K394M/E446L/E448Q/R449W/D452L/Y437D/N438L_N19Q

Nucleotide of sequence insert          SEQ ID NO: 270

Nucleotide sequence of entire plasmid          SEQ ID NO:273

Figure 8

Gen6_H5Ind05_K394M/M445L/E446L/E448Q/R449W/D452L/Y437D/N438L/S49bW_N19Q

Plasmid map: Gen6 H5Ind05 rpk3, 5588 bp

Features:
- Kan.
- CMVR Gen6 H5Ind05 rpk3
- CMV IE Enhancer/Promoter
- HTLV-1 R Region/Splicing Donor
- CMV IE Splicing Acceptor
- Gen6 H5Ind05 rpk3
- Tbgh

| | |
|---|---|
| Nucleotide of sequence insert | SEQ ID NO: 284 |
| Nucleotide sequence of entire plasmid | SEQ ID NO: 287 |

Figure 9

Gen6_H1NC99_K394M/E446L_N19Q

[Plasmid map: Gen6 H1NC99 rpk22 DL-YN, 5579 bp, with labeled features: Kan., CMV/R Gen6 H1NC99 rpk22 DL-YN, CMV IE Enhancer/Promoter, HTLV-1 R Region/Splicing Donor, CMV IE Splicing Acceptor, Gen6 H1NC99 rpk22 DL-YN, Tbgh]

| | |
|---|---|
| Nucleotide of sequence insert | SEQ ID NO: 291 |
| Nucleotide sequence of entire plasmid | SEQ ID NO: 294 |

Figure 10

Gen6_H1NC99_K394M/E446L/Y437D/N438L_N19Q

CMV/R Gen6 H1NC99 rpk22

Kan.

CMV IE Enhancer/Promoter

HTLV-1 R Region/Splicing Donor

CMV IE Splicing Acceptor

Gen6 H1NC99 rpk22
5579 bp

Gen6 H1NC99 rpk22

Tbgh

Nucleotide of sequence insert       SEQ ID NO: 298

Nucleotide sequence of entire plasmid       SEQ ID NO: 301

Figure 11

Gen6_H1NC99_K394I/E446I/Y437D/N438L_N19Q

Plasmid map: Gen6 H1NC99 rpk22 II, 5579 bp

Features:
- Kan.
- CMV/R Gen6 H1NC99 rpk22 II
- CMV IE Enhancer/Promoter
- HTLV-1 R Region/Splicing Donor
- CMV IE Splicing Acceptor
- Gen6 H1NC99 rpk22 II
- Tbgh Nucleotide of sequence insert        SEQ ID NO: 305

Nucleotide sequence of entire plasmid        SEQ ID NO: 308

Nucleotide of sequence insert          SEQ ID NO: 312

Nucleotide sequence of entire plasmid      SEQ ID NO: 315

Figure 13

Gen6_H1NC99_K394L/E446L/Y437D/N438L_N19Q

Plasmid map: Gen6 H1NC99 rpk22 LL, 5579 bp

Features:
- Kan.
- CMV/R Gen6 H1NC99 rpk22 LL
- CMV IE Enhancer/Promoter
- HTLV-1 R Region/Splicing Donor
- CMV IE Splicing Acceptor
- Gen6 H1NC99 rpk22 LL
- Tbgh

| | |
|---|---|
| Nucleotide of sequence insert | SEQ ID NO: 319 |
| Nucleotide sequence of entire plasmid | SEQ ID NO: 322 |

Figure 14

Gen6_H1NC99_K394M/E446M/Y437D/N438L_N19Q

CMV/R Gen6 H1NC99 rpk22 MM
CMV IE Enhancer/Promoter
Kan.
HTLV-1 R Region/Splicing Donor
CMV IE Splicing Acceptor
Gen6 H1NC99 rpk22 MM
5579 bp
Gen6 H1NC99 rpk22 MM
Tbgh

| | |
|---|---|
| Nucleotide of sequence insert | SEQ ID NO: 326 |
| Nucleotide sequence of entire plasmid | SEQ ID NO: 329 |

Figure 15

Gen6_H1NC99_K394Q/E446Q/Y437D/N438L_N19Q

CMV/R Gen6 H1NC99 rpk22 QQ

CMV IE Enhancer/Promoter

Kan.

HTLV-1 R Region/Splicing Donor

CMV IE Splicing Acceptor

Gen6 H1NC99 rpk22 QQ
5579 bp

Gen6 H1NC99 rpk22 QQ

Tbgh

Nucleotide of sequence insert       SEQ ID NO: 333

Nucleotide sequence of entire plasmid       SEQ ID NO: 336

Figure 16

Gen6_H1NC99_K394M/E446L/Y437D/N438L/H45N/V47T_N19Q

CMV/R Gen6 H1NC99 rpk22 gly4

CMV IE Enhancer/Promoter

Kan.

HTLV-1 R Region/Splicing Donor

CMV IE Splicing Acceptor

Gen6 H1NC99 rpk22 gly4
5579 bp

Gen6 H1NC99 rpk22 gly4

Tbgh

| | |
|---|---|
| Nucleotide of sequence insert | SEQ ID NO: 340 |
| Nucleotide sequence of entire plasmid | SEQ ID NO: 343 |

Figure 17

Gen6_H1NC99_V36I/K394M/L445M/E446L/E448Q/R449F/D452L/Y437D/N438L_N19Q

```
            CMV/R Gen6 H1NC99 rpk8
  Kan.                           CMV IE Enhancer/Promoter HTLV-1 R Region/Splicing Donor
       Gen6 H1NC99 rpk8          CMV IE Splicing Acceptor
           5579 bp Gen6 H1NC99 rpk8

Tbgh
```

Nucleotide of sequence insert          SEQ ID NO: 347

Nucleotide sequence of entire plasmid     SEQ ID NO: 350

Figure 18

Gen6_H1NC99_K394M/E446L/E448Q/R449W/D452L/S402aN/G402cT/S402dG/T402fA/Y437D/N438L_N19Q

Plasmid map: Gen6 H1NC99 rpk3 gly1, 5579 bp. Features labeled: Kan., CMV/R Gen6 H1NC99 rpk3 gly1, CMV IE Enhancer/Promoter, HTLV-1 R Region/Splicing Donor, CMV IE Splicing Acceptor, Gen6 H1NC99 rpk3 gly1, Tbgh.

| | |
|---|---|
| Nucleotide of sequence insert | SEQ ID NO: 354 |
| Nucleotide sequence of entire plasmid | SEQ ID NO: 357 |

Figure 19

Gen6_H1NC99_K394M/E446L/E448Q/R449W/D452L/S402bG/G402cN/S402eT/T402fA/Y437D/N438L_N19Q

Plasmid map: Gen6 H1NC99 rpk3 gly2, 5579 bp

Features labeled:
- Kan.
- CMV/R Gen6 H1NC99 rpk3 gly2
- CMV IE Enhancer/Promoter
- HTLV-1 R Region/Splicing Donor
- CMV IE Splicing Acceptor
- Gen6 H1NC99 rpk3 gly2
- Tbgh

| | |
|---|---|
| Nucleotide of sequence insert | SEQ ID NO: 361 |
| Nucleotide sequence of entire plasmid | SEQ ID NO: 364 |

Figure 20

Gen6_H1NC99_K394M/E446L/E448Q/R449W/D452L/S402eN/Y437D/N438L_N19Q

Plasmid map: Gen6 H1NC99 rpk3 gly3, 5579 bp. Features labeled: Kan., CMV/R Gen6 H1NC99 rpk3 gly3, CMV IE Enhancer/Promoter, HTLV-1 R Region/Splicing Donor, CMV IE Splicing Acceptor, Gen6 H1NC99 rpk3 gly3, Tbgh.

Nucleotide of sequence insert          SEQ ID NO: 368
Nucleotide sequence of entire plasmid          SEQ ID NO: 371

Figure 21

Gen6_H1NC99_K394M/E446L/E448Q/R449W/D452L/G402cN/G402eT/T402fA/Q370N/E372T/Y437D/N438L_S21T

Plasmid map: Gen6 H1NC99 rpk3 gly2-6-7, 5579 bp

Features:
- Kan.
- CMV/R Gen6 H1NC99 rpk3 gly2-6-7
- CMV IE Enhancer/Promoter
- HTLV-1 R Region/Splicing Donor
- CMV IE Splicing Acceptor
- Gen6 H1NC99 rpk3 gly2-6-7
- Tbgh

| | |
|---|---|
| Nucleotide of sequence insert | SEQ ID NO: 375 |
| Nucleotide sequence of entire plasmid | SEQ ID NO: 378 |

Figure 22

Gen6_H1NC99_K394M/E446L/E448Q/R449W/D452L/G402cN/G402eT/T402fA/Q370N/E372T/Y437D/N438L_S21T/Q69N

Plasmid map: Gen6 H1NC99 rpk3 gly2-5-6-7, 5579 bp

Features:
- Kan.
- CMV/R Gen6 H1NC99 rpk3 gly2-5-6-7
- CMV IE Enhancer/Promoter
- HTLV-1 R Region/Splicing Donor
- CMV IE Splicing Acceptor
- Gen6 H1NC99 rpk3 gly2-5-6-7
- Tbgh

| | |
|---|---|
| Nucleotide of sequence insert | SEQ ID NO: 382 |
| Nucleotide sequence of entire plasmid | SEQ ID NO: 385 |

Figure 23

Gen6_H1NC99_K394M/E446L/Y437D/N438L/Δ172-174

Plasmid map: Gen6 H1NC99 rpk22 LS1, 5528 bp

Features:
- Kan.
- CMV/R Gen6 H1NC99 rpk22 LS1
- CMV IE Enhancer/Promoter
- HTLV-1 R Region/Splicing Donor
- CMV IE Splicing Acceptor
- Gen6 H1NC99 rpk22 LS1
- Tbgh

| | |
|---|---|
| Nucleotide of sequence insert | SEQ ID NO: 389 |
| Nucleotide sequence of entire plasmid | SEQ ID NO: 392 |

Figure 24

Gen6_H1NC99_rpk3_Dloop2

Gen6 H1NC99 rpk3 Dloop2
Kan.
CMV IE Enhancer/Promoter
HTLV-1 R Region/Splicing Donor
CMV IE Splicing Acceptor
Gen6 H1NC99 rpk3 Dloop2
5528 bp
Gen6 H1NC99 rpk3 Dloop2
Tbgh

| | |
|---|---|
| Nucleotide sequence of insert | SEQ ID NO: 396 |
| Nucleotide sequence of entire plasmid | SEQ ID NO: 399 |

STABILIZED INFLUENZA HEMAGGLUTININ STEM REGION TRIMERS AND USES THEREOF

CROSS REFERENCE TO RELATED APPLICATIONS

This application is a divisional of U.S. patent application Ser. No. 18/314,052, filed May 8, 2023, which is a divisional of U.S. patent application Ser. No. 17/504,002, filed Oct. 18, 2021, issued as U.S. Pat. No. 11,679,151, which is a divisional of U.S. patent application Ser. No. 16/455,242, filed Jun. 27, 2019, issued as U.S. Pat. No. 11,147,867, which is a divisional of U.S. application Ser. No. 15/313,265, filed Nov. 22, 2016, issued as U.S. Pat. No. 10,363,301, which is the U.S. National Stage of International Application No. PCT/US2015/032695, filed May 27, 2015, which designates the United States and was published in English under PCT Article 21(2), which in turn claims the benefit of U.S. Provisional Application Ser. No. 62/003,471 filed May 27, 2014. Each of these disclosures are incorporated herein by reference in their entirety.

SEQUENCE LISTING

This application contains a Sequence Listing submitted as an XML file named "4239-104867-30_Sequence.xml", having a file size of 776,500 bytes, and created on Apr. 17, 2024. The information contained in this electronic file is hereby incorporated by reference in its entirety pursuant to 37 CFR § 1.52(e)(5).

SUMMARY OF THE INVENTION

The present invention provides novel hemagglutinin (HA) protein-based influenza vaccines that are easily manufactured, potent, and which elicit broadly neutralizing influenza antibodies against the stem region of the influenza HA protein. In particular, the present invention provides modified influenza HA stem-region proteins in the pre-fusion conformation, and portions thereof, that are useful for inducing the production of neutralizing antibodies. The present invention also provides novel nanoparticle (np)-based vaccines that express the influenza HA protein on their surface. Such nanoparticles comprise fusion proteins, each of which comprises a monomeric subunit of ferritin joined to an antigenic or immunogenic portion of the stem region from an influenza HA protein. Because such nanoparticles display influenza HA protein stem regions on their surface, they can be used to vaccinate an individual against influenza virus.

BACKGROUND

Protective immune responses induced by vaccination against influenza viruses are primarily directed to the viral HA protein, which is a glycoprotein on the surface of the virus responsible for interaction of the virus with host cell receptors. HA proteins on the virus surface are trimers of HA protein monomers that are enzymatically cleaved to yield amino-terminal HA1 and carboxy-terminal HA2 polypeptides. The globular head consists exclusively of the major portion of the HA1 polypeptide, whereas the stem that anchors the HA protein into the viral lipid envelope is comprised of HA2 and part of HA1. The globular head of a HA protein includes two domains: the receptor binding domain (RBD), an ~148-amino acid residue domain that includes the sialic acid-binding site, and the vestigial esterase domain, a smaller ~75-amino acid residue region just below the RBD. The globular head includes several antigenic sites that include immunodominant epitopes. Examples include the Sa, Sb, $Ca_1$, $Ca_2$ and Cb antigenic sites (see, for example, Caton A J et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, the HA stem is highly conserved and experiences little antigenic drift. Unfortunately, unlike the immunodominant head, the conserved HA stem is not very immunogenic. Furthermore, gene segments of the viral genome can undergo reassortment (antigenic shift) in host species, creating new viruses with altered antigenicity that are capable of becoming pandemics [Salomon, R. et al. *Cell* 136, 402-410 (2009)]. Until now, each year, influenza vaccine is updated to reflect the predicted HA and neuraminidase (NA) for upcoming circulating viruses.

Recently, an entirely new class of broadly neutralizing antibodies against influenza viruses was isolated that recognize the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)]. Unlike strain-specific antibodies, those antibodies are capable of neutralizing multiple antigenically distinct viruses, and hence inducing such antibodies has been a focus of next generation universal vaccine development [Nabel, G. J. et al. *Nat Med* 16, 1389-1391 (2010)]. However, robustly eliciting these antibodies with such heterologous neutralizing profile by vaccination has been difficult [Steel, J. et al. *MBio* 1, e0018 (2010); Wang, T. T. et al. *PLoS Pathog* 6, e1000796 (2010); Wei, C. J. et al. *Science* 329, 1060-1064 (2010)]. Removal of the immunodominant head region of HA (which contains competing epitopes) and stabilization of the resulting stem domain through genetic manipulation is one potential way to improve the elicitation of these broadly neutralizing stem antibodies.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs that often comprise HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded, trimeric HA spikes that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLoS One* 5, e9784 (2010)]. Moreover, the immunity induced by the VLPs is essentially the same as current vaccines, and thus, will not likely significantly improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. *Science* 257, 522-523 (1992); Naitou, M. et al. U.S. Patent 2011/0038025 (2011); Yamashita, I. *Biochim Biophys Acta* 1800, 846-857 (2010)], including a potential vaccine platform for displaying exogenous epitope peptides [Carter, D. C. et al. U.S. Patent 2006/0251679 (2006); Li, C. Q. et al. *Industrial Biotechnol* 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

There remains a need for an efficacious influenza vaccine that provides robust protection against influenza virus. There particularly remains a need for an influenza vaccine that protects individuals from heterologous strains of influenza virus, including evolving seasonal and pandemic influenza virus strains of the future. The present invention meets this need by providing a novel nanoparticle-based vaccine consisting of a novel HA stabilized stem (SS) without the variable immunodominant head region genetically fused to the surface of nanoparticles (gen6 HA-SS np) resulting in an influenza vaccine that is easily manufactured, potent, and elicits antibodies that are broadly heterosubtypic protective.

BRIEF DESCRIPTION OF THE FIGURES

FIG. 1b shows the surface representations of the HA portions of H1N1 HA ectodomain (PDB ID 1GBN), Gen4 HA-SS and Gen6 HA-SS respectively without the foldon domains, shaded by sequence conservation with H5N1 2004 VN (dark gray, variable; white, conserved). The HA stem percentage of the immunogens without foldon domains increase for Gen4 and Gen6 HA-SS respectively. *This immunogen was evaluated further and is referred to as H1-SS-np in the Examples section of this disclosure.

FIGS. 5-24 provide the plasmid map and sequences used in producing the peptide constructs of the present invention. As described in detail in Table 2 of this disclosure, FIG. 5 shows the map of Gen6_H1NC99_K394M/E446L/E448Q/R449W/D452L/Y437D/N438L_N19Q comprising SEQ ID NO: 266. FIG. 6 shows the map of Gen6_H1CA09_K394M/E446L/E448Q/R449W/D452L/Y437D/N438L_N19Q comprising SEQ ID NO: 273. FIG. 7 shows the map of Gen6_H2Sing57_K394M/M445L/E446L/E448Q/R449W/D452L/Y437D/N438L_N19Q comprising SEQ ID NO: 280. FIG. 8 shows the map of Gen6_H5Ind05 K394M/M445L/E446L/E448Q/R449W/D452L/Y437D/N438L/S49bW_N19Q comprising SEQ ID NO: 287. FIG. 9 shows the map of Gen6_H1NC99_K394M/E446L_N19Q comprising SEQ ID NO: 294. FIG. 10 shows the map of Gen6_H1NC99_K394M/E446L/Y437D/N438L_N19Q comprising SEQ ID NO: 301. FIG. 11 shows the map of Gen6_H1NC99_K394I/E446I/Y437D/N438L_N19Q comprising SEQ ID NO: 308. FIG. 12 shows the map of Gen6 H1NC99 K394L/E446I/Y437D/N438L_N19Q comprising SEQ ID NO: 315. FIG. 13 shows the map of Gen6_H1NC99_K394L/E446L/Y437D/N438L_N19Q comprising SEQ ID NO: 322. FIG. 14 shows the map of Gen6_H1NC99_K394M/E446M/Y437D/N438L_N19Q comprising SEQ ID NO: 329. FIG. 15 shows the map of Gen6 H1NC99 K394Q/E446Q/Y437D/N438L_N19Q comprising SEQ ID NO: 336. FIG. 16 shows the map of Gen6 H1NC99 K394M/E446L/Y437D/N438L/H45N/V47T_N19Q comprising SEQ ID NO: 343. FIG. 17 shows the map of Gen6 H1NC99 V36I/K394M/L445M/E446L/E448Q/R449F/D452L/Y437D/N438L N19Q comprising SEQ ID NO: 350. FIG. 18 shows the map of Gen6_H1NC99_K394M/E446L/E448Q/R449W/D452L/S402aN/G402cT/S402dG/T402fA/Y437D/N438L_N19Q comprising SEQ ID NO: 357. FIG. 19 shows the map of Gen6_H1NC99_K394M/E446L/E448Q/R449W/D452L/S402bG/G402cN/S402eT/T402fA/Y437D/N438L_N19Q comprising SEQ ID NO: 364. FIG. 20 shows the map of Gen6_H1NC99_K394M/E446L/E448Q/R449W/D452L/S402eN/Y437D/N438L_N19Q comprising SEQ ID NO: 371. FIG. 21 shows the map of Gen6 H1NC99 K394M/E446L/E448Q/R449W/D452L/G402cN/G402eT/T402fA/Q370N/E372T/Y437D/N438L_S21T comprising SEQ ID NO: 378. FIG. 22 shows the map of Gen6_H1NC99_K394M/E446L/E448Q/R449W/D452L/G402cN/G402eT/T402fA/Q370N/E372T/Y437D/N438L_S21T/Q69N comprising SEQ ID NO: 386. FIG. 23 shows the map of Gen6_H1NC99_K394M/E446L/Y437D/N438L/Δ172-174 comprising SEQ ID NO: 392. FIG. 24 shows the map of Gen6_H1NC99_rpk3_Dloop2 comprising SEQ ID NO: 399.

DETAILED DESCRIPTION OF THE INVENTION

Figure 1A:
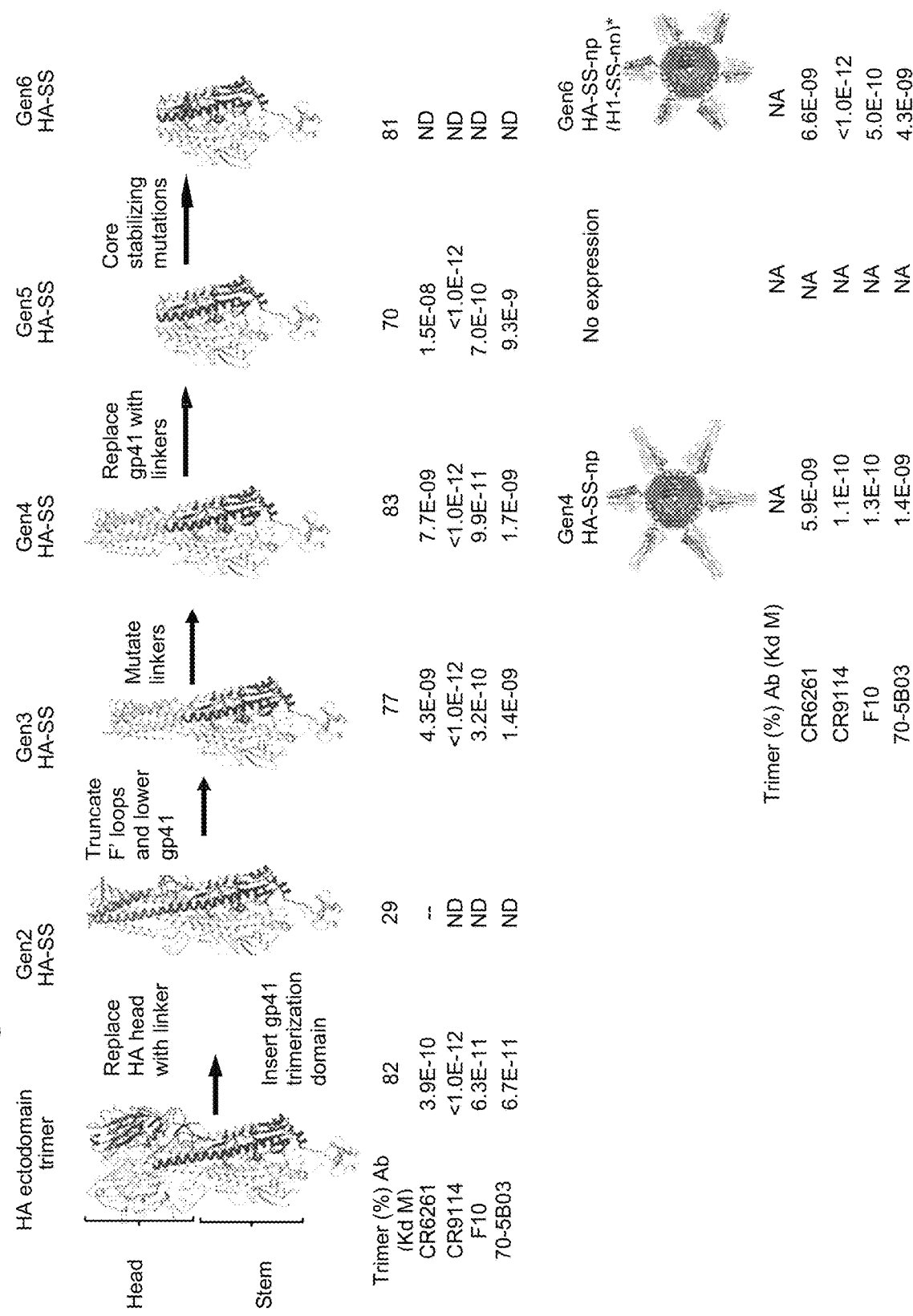
FIG. 1a shows the structure-based removal of the HA head allows for preservation of stem immunogen antigenicity. The ribbon models depict the HA-SS design pathway starting with the model of an HA ectodomain fused to a T4 foldon trimerization domain (in green below HA ectodomain). The last three HA-SS designs (Gen4-6) were genetically fused to ferritin nanoparticles (lower panel). One monomer of each HA trimer is shaded. The core stabilizing mutations for creating Gen6 are shown as spheres. The percent trimerization (including foldon) and antigenic affinity constants ($K_D$, M) to specified mAbs are shown below each HA-SS immunogen design. ND, not determined; NA, not applicable.

The present invention relates to a novel vaccine for influenza virus. More specifically, the present invention relates to novel, influenza HA protein-based vaccines that elicit an immune response against the stem region of the HA protein from a broad range of influenza viruses. It also relates to self-assembling nanoparticles that display immunogenic portions of the pre-fusion conformation of the stem region from the influenza HA protein on their surface. Such nanoparticles are useful for vaccinating individuals against influenza virus. Accordingly, the present invention also relates to protein constructs for producing such nanoparticles and nucleic acid molecules encoding such proteins. Additionally, the present invention relates to methods of producing nanoparticles of the present invention, and methods of using such nanoparticles to vaccinate individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In addition to the above, unless specifically defined otherwise, the following terms and phrases, which are common to the various embodiments disclosed herein, are defined as follows:

As used herein, a protein construct is a protein made by the hand of man, in which two or more amino acid sequences have been covalently joined in a way not found in nature. The amino acid sequences being joined can be related or unrelated. As used herein, polypeptide sequences are unrelated, if their amino acid sequences are not normally found joined together via a covalent bond in their natural environment(s) (e.g., inside a cell). For example, the amino acid sequences of monomeric subunits that make up ferritin, and the amino acid sequences of influenza HA proteins are not normally found joined together via a covalent bond. Thus, such sequences are considered unrelated.

Protein constructs can also comprise related amino acid sequences. For example, the structure of the influenza HA protein is such that the head region amino acid sequence is flanked on both ends by stem region amino acid sequences. Through genetic means, it is possible to create a deletion version of an HA protein by removing amino acid residues from the middle of the head region, while maintaining a portion of the head region flanked by stem regions sequences. While the order of the sequences in the final molecule would remain the same, the spatial relationship between the amino acids would differ from the natural protein. Thus, such a molecule would be considered a protein construct. According to the present invention, protein constructs may also be referred to as fusion proteins.

Amino acid sequences in a protein construct can be joined directly to each other or they can be joined using a linker sequence. A linker sequence, peptide, or polypeptide, is a short (e.g., 2-20) amino acid sequence used to connect two proteins having a desired characteristic (e.g., structure, epitope, immunogenicity, activity, etc.). A linker sequence typically does not have its own activity and is usually used to allow other parts of the protein construct to assume a desired conformation. Linker sequences are typically made from small amino acid residues and/or runs thereof, such as, for examples, serine, alanine and glycine, although the use of other amino acid residues is not excluded.

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 93% identical, at least 94% identical, at least 95% identical, at least 96% identical, at least 97% identical, at least 98% identical or at least 99% identical. Methods of determining the percent identity between two amino acid or nucleic acid sequence are known in the art.

As used herein, an immune response to a vaccine, or nanoparticle, of the present invention is the development in a subject of a humoral and/or a cellular immune response to a HA protein present in the vaccine. For purposes of the present invention, a "humoral immune response" refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to an HA protein present in the vaccine. These responses may serve to neutralize infectivity (e.g., antibody-dependent protection), and/or mediate antibody-complement, or antibody dependent cell cytotoxicity (ADCC) to provide protection to an immunized individual. Such responses can be determined using standard immunoassays and neutralization assays, well known in the art.

As used herein, the term antigenic, antigenicity, and the like, refers to a protein that is bound by an antibody or a group of antibodies. Similarly, an antigenic portion of a protein is any portion that is recognized by an antibody or a group of antibodies. According to the present invention, recognition of a protein by an antibody means the antibody selectively binds to the protein. As used herein, the phrase selectively binds, selective binding, and the like, refer to the ability of an antibody to preferentially bind an HA protein as opposed to binding proteins unrelated to HA, or non-protein components in the sample or assay. An antibody that preferentially binds HA is one that binds HA but does not significantly bind other molecules or components that may be present in the sample or assay. Significant binding is considered, for example, binding of an anti-HA antibody to a non-HA molecule with an affinity or avidity great enough to interfere with the ability of the assay to detect and/or determine the level of anti-influenza antibodies, or HA protein, in the sample. Examples of other molecules and compounds that may be present in the sample, or the assay, include, but are not limited to, non-HA proteins, such as albumin, lipids and carbohydrates. According to the present invention, a non-HA protein is a protein having an amino acid sequence sharing less than 60% identity with the sequence of an influenza HA protein disclosed herein. In some embodiments, the antibody or antibodies provide broad heterosubtypic protection. In some embodiments, the antibody or antibodies are neutralizing.

As used herein, neutralizing antibodies are antibodies that prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane. According to the present invention, a neutralizing antibody is one that inhibits one or more such steps.

As used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group I influenza virus may neutralize a Group 2 virus. As an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15, H16, H17 or H18.

According to the present invention all nomenclature used to classify influenza virus is that commonly used by those skilled in the art. Thus, a Type, or Group, of influenza virus refers to influenza Type A, influenza Type B or influenza type C. It is understood by those skilled in the art that the designation of a virus as a specific Type relates to sequence difference in the respective M1 (matrix) protein or NP (nucleoprotein). Type A influenza viruses are further divided into Groupi and Group 2. These Groups are further divided into subtypes, which refers to classification of a virus based on the sequence of its HA protein. Examples of current commonly recognized subtypes are H1, H2, H3, H4, H5, H6, H7, H8, H8, H10, H11, H12, H13, H14, H15, H16, H17 or H18. Group 1 influenza subtypes are H1, H2, H5, H6, H8, H9, H11, H12, H13, H16, H17 and H18. Group 2 influenza subtypes are H3, H4, H7, H10, H14, and H15. Finally, the term strain refers to viruses within a subtype that differ from one another in that they have small, genetic variations in their genome.

As used herein, an influenza hemagglutinin protein, or HA protein, refers to a full-length influenza hemagglutinin protein or any portion thereof, that is useful for producing protein constructs and nanoparticles of the invention or that are capable of eliciting an immune response. Preferred HA proteins are those that are capable of forming a trimer. An epitope of a full-length influenza HA protein refers to a portion of such protein that can elicit an antibody response against the homologous influenza strain, i.e., a strain from which the HA is derived. In some embodiments, such an epitope can also elicit an antibody response against a heterologous influenza strain, i.e., a strain having an HA that is not identical to that of the HA of the immunogen. In some embodiments, the epitope elicits a broadly heterosubtypic protective response. In some embodiments, the epitope elicits neutralizing antibodies.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing or non-neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein. In variants into which insertions have been made, the inserted amino acids may be referred to by referencing the amino acid residue after which the insertion was made. For example, an insertion of four amino acid residues after amino acid residue 402 could be referred to as 402a-402d. Moreover, if one of those inserted amino acids are later substituted with another amino acid, such a change can be referred to by reference to the letter position. For example, substitution of an inserted glycine (in the further position of the insert) with a threonine can be referred to as S402dT.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties: 1) hydrophobic: Met, Ala, Val, Leu, Ile; 2) neutral hydrophilic: Cys, Ser, Thr; 3) acidic: Asp, Glu; 4) basic: Asn, Gln, His, Lys, Arg; 5) residues that influence chain orientation: Gly, Pro; and 6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 1.

TABLE 1

| Amino Acid Substitutions | |
| --- | --- |
| Original Amino Acid | Exemplary Substitutions |
| Ala | Val, Leu, Ile |
| Arg | Lys, Gln, Asn |
| Asn | Gln |
| Asp | Glu |
| Cys | Ser, Ala |
| Gln | Asn |

TABLE 1-continued

| Amino Acid Substitutions | |
| --- | --- |
| Original Amino Acid | Exemplary Substitutions |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such an activity may be measured, for example, as the ability of a protein to elicit protective antibodies against an influenza virus. Such activity may be measured by measuring the titer of such antibodies against influenza virus, the ability of such antibodies to protect against influenza infection or by measuring the number of types, subtypes or strains neutralized by the elicited antibodies. Methods of determining antibody titers, performing protection assays and performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

As used herein, a vaccinated subject is a subject that has been administered a vaccine that is intended to provide a protective effect against an influenza virus.

As used herein, the terms exposed, exposure, and the like, indicate the subject has come in contact with a person of animal that is known to be infected with an influenza virus.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

One embodiment of the present invention is a protein construct comprising an influenza HA protein wherein the head region of the influenza HA protein has been replaced with an amino acid sequence comprising less than 5 contiguous amino acid residues from the head region of the HA protein. As used herein, an HA protein, refers to a full-length influenza HA protein or any portion/portions and/or variants thereof, that is/are useful for producing protein constructs and nanoparticles of the invention. Accordingly, the present invention is drawn to molecules that are capable of eliciting an immune response to the stem region of influenza HA protein. In some embodiments, the sequence of the HA protein construct has been further altered (i.e., mutated) to stabilize the stem region of the protein in a form that can be presented to the immune system. Some representative examples of such HA proteins, and protein constructs made there from, are shown in Table 2 below.

TABLE 2

| PCT SEQ ID NO | Comments |
|---|---|
| | FERRITIN |
| 1 | Coding sequence for ferritin monomeric subunit protein from *H. pylori* |
| 2 | Amino acid sequence encoded by SEQ ID NO: 1 |
| 3 | Complement of SEQ ID NO1 |
| 4 | Nucleic acid sequence encoding amino acids 5-167 from SEQ ID NO: 2; Asn19 has been replaced with Gln |
| 5 | Amino acid sequence encoded by SEQ ID NO: 3 |
| 6 | Complement of SEQ ID NO3 |
| | FULL LENGTH HA |
| 7 | Nucleic acid sequence encoding full length hemagglutinin protein from A/New Caledonia/20/1999 (1999 NC, H1)(GenBank: AY289929) |
| 8 | Amino acid sequence encoded by SEQ ID NO: 7 (full length hemagglutinin protein from A/New Caledonia/20/1999 (1999 NC, H1)(GenBank: AY289929)) |
| 9 | Complement of SEQ ID NO: 7 |
| 10 | Nucleic acid sequence encoding full length hemagglutinin protein from A/California/4/2009 (H1) |
| 11 | Amino acid sequence encoded by SEQ ID NO: 10 |
| 12 | Complement of SEQ ID NO: 10 |
| 13 | Nucleic acid sequence encoding full length hemagglutinin protein from A/Singapore/1957 (H2) |
| 14 | Amino acid sequence encoded by SEQ ID NO: 13 |
| 15 | Complement of SEQ ID NO: 13 |
| 16 | Nucleic acid sequence encoding full length hemagglutinin protein from A/Indonesia/05/2005 (H5) |
| 17 | Amino acid sequence encoded by SEQ ID NO: 16 |
| 18 | Complement of SEQ ID NO: 16 |
| | STEM REGION FLANKS |
| 19 | Nucleic acid sequence encoding SEQ ID NO: 20 |
| 20 | Amino acid sequence flanking amino end of head region from H1 NC 1999 |
| 21 | Complement of SEQ ID NO: 19 |
| 22 | Nucleic acid sequence encoding SEQ ID NO: 24 |
| 23 | Amino acid sequence flanking carboxyl end of head region from H1 NC 1999. Contains internal loop region. Long version |
| 24 | Complement of SEQ ID NO: 22 |
| 25 | Nucleic acid sequence encoding SEQ ID NO: 27 |
| 26 | Amino acid sequence flanking carboxyl end of head region from H1 NC 1999. Internal loop region replaced with Ser-Gly loop. Long version |
| 27 | Complement of SEQ ID NO: 25 |
| 28 | Nucleic acid sequence encoding SEQ ID NO: 30 |
| 29 | Amino acid sequence flanking carboxyl end of head region from H1 NC 1999. Contains internal loop region. short version |

TABLE 2-continued

| PCT SEQ ID NO | Comments |
|---|---|
| 30 | Complement of SEQ ID NO: 28 |
| 31 | Nucleic acid sequence SEQ ID NO: 33 |
| 32 | Amino acid sequence flanking carboxyl end of head region from H1 NC 1999. Internal loop region replaced with Ser-Gly loop. short version |
| 33 | Complement of SEQ ID NO: 31 |
| 34 | Nucleic acid sequence encoding SEQ ID NO: 35 |
| 35 | Amino acid sequence flanking amino end of head region from H1 CA 2009 |
| 36 | Complement of SEQ ID NO: 34 |
| 37 | Nucleic acid sequence encoding SEQ ID NO: 38 |
| 38 | Amino acid sequence flanking carboxyl end of head region from H1 CA (2009). Contains internal loop region. Long version |
| 39 | Complement of SEQ ID NO: 37 |
| 40 | Nucleic acid sequence encoding SEQ ID NO: 31 |
| 41 | Amino acid sequence flanking carboxyl end of head region from H1 CA (2009). Internal loop region replaced with Ser-Gly loop. Long version |
| 42 | Complement of SEQ ID NO: 40 |
| 43 | Nucleic acid sequence encoding SEQ ID NO: 44 |
| 44 | Amino acid sequence flanking carboxyl end of head region from H1 CA (2009). Contains internal loop region. short version |
| 45 | Complement of SEQ ID NO: 43 |
| 46 | Nucleic acid sequence encoding SEQ ID NO: 47 |
| 47 | Amino acid sequence flanking carboxyl end of head region from H1 CA (2009). Internal loop region replaced with Ser-Gly loop. Short version |
| 48 | Complement of SEQ ID NO: 46 |
| 49 | Nucleic acid sequence encoding SEQ ID NO: 50 |
| 50 | Amino acid sequence flanking amino end of head region from H2 Sing 1957 |
| 51 | Complement of SEQ ID NO: 49 |
| 52 | Nucleic acid sequence encoding SEQ ID NO: 53 |
| 53 | Amino acid sequence flanking carboxyl end of head region from H2 Sing (1957) Contains internal loop region. Long version |
| 54 | Complement of SEQ ID NO: 52 |
| 55 | Nucleic acid sequence encoding SEQ ID NO: 56 |
| 56 | Amino acid sequence flanking carboxyl end of head region from H2 Sing (1957). Internal loop region replaced with Ser-Gly loop. Long version |
| 57 | Complement of SEQ ID NO: 55 |
| 58 | Nucleic acid sequence encoding SEQ ID NO: 59 |
| 59 | Amino acid sequence flanking carboxyl end of head region from H2 Sing (1957) Contains internal loop region. short version |
| 60 | Complement of SEQ ID NO: 58 |
| 61 | Nucleic acid sequence encoding SEQ ID NO: 62 |
| 62 | Amino acid sequence flanking carboxyl end of head region from H2 Sing (1957). Internal loop region replaced with Ser-Gly loop. short version |
| 63 | Complement of SEQ ID NO: 61 |
| 64 | Nucleic acid sequence encoding SEQ ID NO: 65 |
| 65 | Amino acid sequence flanking amino end of head region from H5 Indo (2005) |
| 66 | Complement of SEQ ID NO: 64 |
| 67 | Nucleic acid sequence encoding SEQ ID NO: 68 |
| 68 | Amino acid sequence flanking carboxyl end of head region from H5 Indo (2005) Contains internal loop region. Long version |
| 69 | Complement of SEQ ID NO: 67 |
| 70 | Nucleic acid sequence encoding SEQ ID NO: 71 |
| 71 | Amino acid sequence flanking carboxyl end of head region from H5 Indo (2005). Internal loop region replaced with Ser-Gly loop. Long version |
| 72 | Complement of SEQ ID NO: 70 |
| 73 | Nucleic acid sequence encoding SEQ ID NO: 74 |
| 74 | Amino acid sequence flanking carboxyl end of head region from H5 Indo (2005) Contains internal loop region. short version |
| 75 | Complement of SEQ ID NO: 73 |
| 76 | Nucleic acid sequence encoding SEQ ID NO: 77 |
| 77 | Amino acid sequence flanking carboxyl end of head region from H5 Indo (2005). Internal loop region replaced with Ser-Gly loop. short version |
| 78 | Complement of SEQ ID NO: 76 |

HA CONSTRUCTS 1

| | |
|---|---|
| 79 | Nucleic acid sequence encoding SEQ ID NO: 80 |
| 80 | Gen_H1NC99_01 (rpk-03) K394M/E446L/E448Q/R449W/D452L H1N1 A/New Caledonia/20/1999 |
| 81 | Complement of SEQ ID NO: 79 |
| 82 | Nucleic acid sequence encoding SEQ ID NO: 83 |
| 83 | Gen6_H1CA09_01 (rpk-3) K394M/E446L/E448Q/R449W/D452L H1N1 A/California/4/2009 |
| 84 | Complement of SEQ ID NO: 82 |
| 85 | Nucleic acid sequence encoding SEQ ID NO: 86 |
| 86 | Gen_H2Sing57_01 (rpk-3) K394M/M445L/E446L/E448Q/R449W/D452L H2N2 A/Singapore/1957 |

TABLE 2-continued

| PCT SEQ ID NO | Comments |
|---|---|
| 87 | Complement of SEQ ID NO: 85 |
| 88 | Nucleic acid sequence encoding SEQ ID NO: 89 |
| 89 | Gen6_H5Ind05_01 (rpk-3) K394M/M445L/E446L/E448Q/R449W/D452L H5N1 A/Indonesia/05/2005 |
| 90 | Complement of SEQ ID NO: 88 |
| 91 | Nucleic acid sequence encoding SEQ ID NO: 92 |
| 92 | Gen6_H1NC99_02 (rpk-22) K394M/E446L H1N1 A/New Caledonia/20/1999 |
| 93 | Complement of SEQ ID NO: 91 |
| 94 | Nucleic acid sequence encoding SEQ ID NO: 95 |
| 95 | Gen6_H1NC99_03 (rpk-08) V36I/K394M/L445M/E446L/E448Q/W449F/D452L H1N1 A/New Caledonia/20/1999 |
| 96 | Complement of SEQ ID NO: 94 |
| 97 | Nucleic acid sequence encoding SEQ ID NO: 98 |
| 98 | Gen6_H1NC99_04 (rpk-3, gly1) S402bN/G402dT/S402eG/T450A H1N1 A/New Caledonia/20/1999 |
| 99 | Complement of SEQ ID NO: 97 |
| 100 | Nucleic acid sequence encoding SEQ ID NO: 101 |
| 101 | Gen6_H1NC99_05 (rpk-3, gly2) S402bG/G402cN/S402eT/T450A H1N1 A/New Caledonia/20/1999 |
| 102 | Complement of SEQ ID NO: 100 |
| 103 | Nucleic acid sequence encoding SEQ ID NO: 104 |
| 104 | Gen6_H1NC99_06 (rpk-3, gly3) S402eN H1N1 A/New Caledonia/20/1999 |
| 105 | Complement of SEQ ID NO: 103 |
| | HA-FERRITIN FUSIONS |
| 106 | Nucleic acid sequence encoding SEQ ID NO: 107 |
| 107 | Gen_H1NC99_01 (rpk-03) K394M/E446L/E448Q/R449W/D452L H1N1 A/New Caledonia/20/1999 |
| 108 | Complement of SEQ ID NO: 106 |
| 109 | Nucleic acid sequence encoding SEQ ID NO: 110 |
| 110 | Gen6_H1CA09_01 (rpk-3) K394M/E446L/E448Q/R449W/D452L H1N1 A/California/4/2009 |
| 111 | Complement of SEQ ID NO: 109 |
| 112 | Nucleic acid sequence encoding SEQ ID NO: 113 |
| 113 | Gen6_H2Sing57_01 (rpk-3) K394M/M445L/E446L/E448Q/R449W/D452L H2N2 A/Singapore/1957 |
| 114 | Complement of SEQ ID NO: 112 |
| 115 | Nucleic acid sequence encoding SEQ ID NO: 116 |
| 116 | Gen6_H5Ind05_01 (rpk-3) K394M/M445L/E446L/E448Q/R449W/D452L H5N1 A/Indonesia/05/2005 |
| 117 | Complement of SEQ ID NO: 115 |
| 118 | Nucleic acid sequence encoding SEQ ID NO: 119 |
| 119 | Gen6_H1NC99_02 (rpk-22) K394M/E446L H1N1 A/New Caledonia/20/1999 |
| 120 | Complement of SEQ ID NO: 118 |
| 121 | Nucleic acid sequence encoding SEQ ID NO: 122 |
| 122 | Gen6_H1NC99_03 (rpk-08) V36I/K394M/L445M/E446L/E448Q/W449F/D452L H1N1 A/New Caledonia/20/1999 |
| 123 | Complement of SEQ ID NO: 121 |
| 124 | Nucleic acid sequence encoding SEQ ID NO: 125 |
| 125 | Gen6_H1NC99_04 (rpk-3, gly1) S402bN/G402dT/S402eG/T450A H1N1 A/New Caledonia/20/1999 |
| 126 | Complement of SEQ ID NO: 124 |
| 127 | Nucleic acid sequence encoding SEQ ID NO: 128 |
| 128 | Gen6_H1NC99_05 (rpk-3, gly2) S402bG/G402cN/S402eT/T450A H1N1 A/New Caledonia/20/1999 |
| 129 | Complement of SEQ ID NO: 127 |
| 130 | Nucleic acid sequence encoding SEQ ID NO: 131 |
| 131 | Gen6_H1NC99_06 (rpk-3, gly3) S402eN H1N1 A/New Caledonia/20/1999 |
| 132 | Complement of SEQ ID NO: 130 |
| | INTERNAL LOOP SEQUENCES |
| 133 | Internal loop sequence From H1 NC NTQFTAVGKEFNKLERRMENLNKKVDDGFLDIW |
| 134 | NTQFTAVGKEFN; Fragment of SEQ ID NO: 133 |
| 135 | NKLERRMENLNK Fragment of SEQ ID NO: 133 |
| 136 | KKVDDGFLDIW Fragment of SEQ ID NO: 133 |
| 137 | Internal loop sequence from H1 CA 2009 NTQFTAVGKEFNHLEKRIENLNKKVDDGFLDIW |
| 138 | NTQFTAVGKEF; Fragment of SEQ ID NO: 137 |
| 139 | FNHLEKRIENL; Fragment of SEQ ID NO: 137 |
| 140 | LNKKVDDGFLDIW; Fragment of SEQ ID NO: 137 |
| 141 | Internal loop sequence from H5Sing 1957 NTQFEAVGKEFSNLERRLENLNKKMEDGFLDVW |
| 142 | NTQFEAVGKEF; Fragment of SEQ ID NO: 141 |

TABLE 2-continued

| PCT SEQ ID NO | Comments |
|---|---|
| 143 | FSNLERRLENLN; Fragment of SEQ ID NO: 141 |
| 144 | NKKMEDGFLDVW; Fragment of SEQ ID NO: 141 |
| 145 | Internal loop sequence from H5 Indo 2005 NTQFEAVGREFNNLERRIENLNKKMEDGFLDVW |
| 146 | NTQFEAVGREF; Fragment of SEQ ID NO: 145 |
| 147 | FNNLERRIENLN; Fragment of SEQ ID NO: 145 |
| 148 | NKKMEDGFLDVW; Fragment of SEQ ID NO: 145 |

MUTATION REGIONS

| | |
|---|---|
| 149 | Mutation region for H1 NC 99 KVNSVIEKMNTQFTAVGKEFNKLERRMENLNKKVDDGFLDIWTYNAELLVLLE |
| 150 | KVNSVIEKMTYNAELLVLLE; SEQ ID NO149 minus internal loop |
| 151 | Mutation region for H1 CA 2009 KVNSVIEKMNTQFTAVGKEFNHLEKRIENLNKKVDDGFLDIWTYNAELLVLLE |
| 152 | KVNSVIEKMTYNAELLVLLE SEQ ID NO: 151 minus internal loop |
| 153 | Mutation region for H2 Sing 1957 KVNSVIEKMNTQFEAVGKEFSNLERRLENLNKKMEDGFLDVWTYNAELLVLME |
| 154 | KVNSVIEKMTYNAELLVLME; SEQ ID NO: 153 minus internal loop |
| 155 | Mutation region for H2 Indo 2005 KVNSIIDKMNTQFEAVGREFNNLERRIENLNKKMEDGFLDVWTYNAELLVLME |
| 156 | KVNSIIDKMTYNAELLVLME; SEQ ID NO: 155 minus internal loop |

ADDITIONAL CONSTRUCTS

| | |
|---|---|
| 157 | Nucleic acid sequence encoding SEQ ID NO: 158 |
| 158 | Gen6_H1NC99_xx (rpk-22[MM]) K394M/E446M H1N1 A/New Caledonia/20/1999 HA Construct |
| 159 | Complement of SEQ ID NO: 157 |
| 160 | Nucleic acid sequence encoding SEQ ID NO: 161 |
| 161 | Gen6_H1NC99_xx (rpk-22[MM]) K394M/E446M H1N1 A/New Caledonia/20/1999 HA-Ferritin Construct |
| 162 | Complement of SEQ ID NO: 160 |
| 163 | Nucleic acid sequence encoding SEQ ID NO: 164 |
| 164 | Gen6_H1NC99_xx (rpk-22[II]) K394I/E446I H1N1 A/New Caledonia/20/1999 HA Construct |
| 165 | Complement of SEQ ID NO: 163 |
| 166 | Nucleic acid sequence encoding SEQ ID NO: 167 |
| 167 | Gen6_H1NC99_xx (rpk-22[II]) K394I/E446I H1N1 A/New Caledonia/20/1999 HA-Ferritin Construct |
| 168 | Complement of SEQ ID NO: 166 |
| 169 | Nucleic acid sequence encoding SEQ ID NO: 170 |
| 170 | Gen6_H1NC99_xx (rpk-22[LI]) K394I/E446I H1N1 A/New Caledonia/20/1999 HA Construct |
| 171 | Complement of SEQ ID NO: 169 |
| 172 | Nucleic acid sequence encoding SEQ ID NO: 173 |
| 173 | Gen6_H1NC99_xx (rpk-22[LI]) K394I/E446I H1N1 A/New Caledonia/20/1999 HA Ferritin Construct |
| 174 | Complement of SEQ ID NO: 172 |
| 175 | Nucleic acid sequence encoding SEQ ID NO: 176 |
| 176 | Gen6_H1NC99_xx (rpk-22[LL]) K394L/E446L H1N1 A/New Caledonia/20/1999 HA Construct |
| 177 | Complement of SEQ ID NO: 175 |
| 178 | Nucleic acid sequence encoding SEQ ID NO: 179 |
| 179 | Gen6_H1NC99_xx (rpk-22[LL]) K394L/E446L H1N1 A/New Caledonia/20/1999 HA-Ferritin Consruct |
| 180 | Complement of SEQ ID NO: 178 |
| 181 | Nucleic acid sequence encoding SEQ ID NO: 182 |
| 182 | GEN6_H1NC99_06 (RPK-3, GLY2-6-7(+3 GLY) H1N1 A/NEW CALEDONIA/20/1999 HA Construct |
| 183 | Complement of SEQ ID NO: 181 |
| 184 | Nucleic acid sequence encoding SEQ ID NO: 185 |
| 185 | GEN6_H1NC99_06 (RPK-3, GLY2-6-7 (+3 GLY) H1N1 A/NEW CALEDONIA/20/1999 HA-Ferritin Construct |
| 186 | Complement of SEQ ID NO: 184 |
| 187 | Nucleic acid sequence encoding SEQ ID NO: 188 |
| 188 | GEN6_H1NC99_06 (RPK-3, GLY2-5-6-7 (+4 GLY) H1N1 A/NEW CALEDONIA/20/1999 HA Construct |
| 189 | Complement of SEQ ID NO: 187 |
| 190 | Nucleic acid sequence encoding SEQ ID NO: 191 |
| 191 | GEN6_H1NC99_06 (RPK-3, GLY2-5-6-7 (+4 GLY) H1N1 A/NEW CALEDONIA/20/1999 HA-Ferritin Construct |
| 192 | Complement of SEQ ID NO: 190 |
| 193 | Nucleic acid sequence encoding SEQ ID NO: 194 |
| 194 | SP|O66529|RISB_AQUAE 6,7-DIMETHYL-8-RIBITYLLUMAZINE SYNTHASE OS = *AQUIFEX AEOLICUS* (STRAIN VF5) LUMAZINE SYNTHASE |

TABLE 2-continued

| PCT SEQ ID NO | Comments |
|---|---|
| 195 | Complement of SEQ ID NO: 193 |
| 196 | Nucleic acid sequence encoding SEQ ID NO: 197 |
| 197 | H1-NC99_GEN6_LS-01 HA Construct |
| 198 | Complement of SEQ ID NO: 196 |
| 199 | Nucleic acid sequence encoding SEQ ID NO: 200 |
| 200 | H1-NC99_GEN6_LS-01 HA-Lumazine Construct |
| 201 | Complement of SEQ ID NO: 199 |
| 202 | Nucleic acid sequence encoding SEQ ID NO: 203 |
| 203 | H1-NC99_GEN6_LS-02 HA Construct |
| 204 | Complement of SEQ ID NO: 202 |
| 205 | Nucleic acid sequence encoding SEQ ID NO: 206 |
| 206 | H1-NC99_GEN6_LS-02 HA-Lumazine Construct |
| 207 | Complement of SEQ ID NO: 205 |
| 208 | Nucleic acid sequence encoding SEQ ID NO: 209 |
| 209 | GEN6_H1NC99_K394M/E446L/E448Q/R449W/D452L/Y437D/N438L_N19Q (RPK-3 WT CLEAVAGE) H1N1 A/NEW CALEDONIA/20/1999 HA Construct |
| 210 | Complement of SEQ ID NO: 208 |
| 211 | Nucleic acid sequence encoding SEQ ID NO: 212 |
| 212 | GEN6_H1NC99_K394M/E446L/E448Q/R449W/D452L/Y437D/N438L_N19Q (RPK-3 WT CLEAVAGE) H1N1 A/NEW CALEDONIA/20/1999 HA-Ferritin Construct |
| 213 | Complement of SEQ ID NO: 211 |
| 214 | GEN6_H1CA09_K394M/E446L/E448Q/R449W/D452L/Y437D/N438L_N19Q (RPK-3 WT CLEAVAGE) H1N1 A/CALIFORNIA/4/2009 HA Construct |
| 215 | GEN6_H1CA09_K394M/E446L/E448Q/R449W/D452L/Y437D/N438L_N19Q (RPK-3 WT CLEAVAGE) H1N1 A/CALIFORNIA/4/2009 HA-Feritin Construct |
| 216 | Nucleic acid sequence encoding SEQ ID NO: 217 |
| 217 | GEN6_H1NC99_K394M/E446L/S339Q/I340R/Q341E/S342T_N19Q (RPK-22, DL→YN WT CLEAVAGE) H1N1 A/NEW CALEDONIA/20/1999 HA Construct |
| 218 | Complement of SEQ ID NO: 216 |
| 219 | Nucleic acid sequence encoding SEQ ID NO: 220 |
| 220 | GEN6_H1NC99_K394M/E446L/S339Q/I340R/Q341E/S342T_N19Q (RPK-22, DL→YN WT CLEAVAGE) H1N1 A/NEW CALEDONIA/20/1999 HA-Ferritin Construct |
| 221 | Complement of SEQ ID NO: 219 |
| 222 | GEN6_H1NC99_K394M/E446L/Y437D/N438L_N19Q (RPK-22, WT CLEAVAGE) H1N1 A/NEW CALEDONIA/20/1999 HA Construct |
| 223 | GEN6_H1NC99_K394M/E446L/Y437D/N438L_N19Q (RPK-22, WT CLEAVAGE) H1N1 A/NEW CALEDONIA/20/1999 HA-Ferritin Construct |
| 224 | GEN6_H1NC99_K394I/E446I/Y437D/N438L_N19Q (RPK-22 [II], WT CLEAVAGE) H1N1 A/NEW CALEDONIA/20/1999 HA Construct |
| 225 | GEN6_H1NC99_K394I/E446I/Y437D/N438L_N19Q (RPK-22 [II], WT CLEAVAGE) H1N1 A/NEW CALEDONIA/20/1999 HA-Ferritin Construct |
| 226 | GEN6_H1NC99_K394L/E446I/Y437D/N438L_N19Q (RPK-22 [LI], WT CLEAVAGE) H1N1 A/NEW CALEDONIA/20/1999 HA Construct |
| 227 | GEN6_H1NC99_K394L/E446I/Y437D/N438L_N19Q (RPK-22 [LI], WT CLEAVAGE) H1N1 A/NEW CALEDONIA/20/1999 HA-Ferritin Construct |
| 228 | GEN6_H1NC99_K394L/E446L/Y437D/N438L_N19Q (RPK-22 [LL], WT CLEAVAGE) H1N1 A/NEW CALEDONIA/20/1999 HA Construct |
| 229 | GEN6_H1NC99_K394L/E446L/Y437D/N438L_N19Q (RPK-22 [LL], WT CLEAVAGE) H1N1 A/NEW CALEDONIA/20/1999 HA-Ferritin Construct |
| 230 | GEN6_H1NC99_K394M/E446M/Y437D/N438L_N19Q (RPK-22 [MM], WT CLEAVAGE) H1N1 A/NEW CALEDONIA/20/1999 HA Construct |
| 231 | GEN6_H1NC99_K394M/E446M/Y437D/N438L_N19Q (RPK-22 [MM],WT CLEAVAGE) H1N1 A/NEW CALEDONIA/20/1999 HA-Ferritin Construct |
| 232 | GEN6_H1NC99_K394Q/E446Q/Y437D/N438L_N19Q (RPK-22 [QQ], WT CLEAVAGE) H1N1 A/NEW CALEDONIA/20/1999 HA Construct |
| 233 | GEN6_H1NC99_K394Q/E446Q/Y437D/N438L_N19Q (RPK-22 [QQ], WT CLEAVAGE) H1N1 A/NEW CALEDONIA/20/1999 HA-Ferritin Construct |
| 234 | Nucleic aicd sequence encoding SEQ ID NO: 235 |
| 235 | GEN6_H1NC99_K394M/E446L/Y437D/N438L/H45N/V47T_N19Q (RPK-22, H3-LIKE GLY, WT CLEAVAGE) H1N1 A/NEW CALEDONIA/20/1999 HA Construct |
| 236 | Complement of SEQ ID NO: 234 |
| 237 | Nucleic aicd sequence encoding SEQ ID NO: 238 |
| 238 | GEN6_H1NC99_K394M/E446L/Y437D/N438L/H45N/V47T_N19Q (RPK-22, H3-LIKE GLY, WT CLEAVAGE) H1N1 A/NEW CALEDONIA/20/1999 HA-Ferritin Construct |
| 239 | Complement of SEQ ID NO: 237 |
| 240 | GEN6_H1NC99_V36I/K394M/L445M/E446L/E448Q/R449F/D452L/Y437D/N438L_N19Q (RPK-08, WT CLEAVAGE) H1N1 A/NEW CALEDONIA/20/1999 HA Construct |
| 241 | GEN6_H1NC99_V36I/K394M/L445M/E446L/E448Q/R449F/D452L/Y437D/N438L_N19Q (RPK-08, WT CLEAVAGE) H1N1 A/NEW CALEDONIA/20/1999 HA-Ferritin Construct |
| 242 | Gen6_H1NC99_K394M/E446L/E448Q/R449W/D452L/S402bN/G402dT/S402eG/T402gA/Y437D/N438L_N19Q (rpk-3, gly1, wt cleavage) H1N1 A/New Caledonia/20/1999 HA Construct |
| 243 | Gen6_H1NC99_K394M/E446L/E448Q/R449W/D452L/S402bN/G402dT/S402eG/T402gA/Y437D/N438L_N19Q (rpk-3, gly1, wt cleavage) H1N1 A/New Caledonia/20/1999 HA-Ferritin construct |

TABLE 2-continued

| PCT SEQ ID NO | Comments |
|---|---|
| 244 | Gen6_H1NC99_K394M/E446L/E448Q/R449W/D452L/S402bG/G402cN/S402eT/T402gA/Y437D/N438L_N19Q (rpk-3, gly2, wt cleavage) H1N1 A/New Caledonia/20/1999 HA Construct |
| 245 | Gen6_H1NC99_K394M/E446L/E448Q/R449W/D452L/S402bG/G402cN/S402eT/T402gA/Y437D/N438L_N19Q (rpk-3, gly2, wt cleavage) H1N1 A/New Caledonia/20/1999 HA-Ferritin Construct |
| 246 | GEN6_H1NC99_K394M/E446L/E448Q/R449W/D452L/S402EN/Y437D/N438L_N19Q (RPK-3, GLY3, WT CLEAVAGE) H1N1 A/NEW CALEDONIA/20/1999 HA Construct |
| 247 | GEN6_H1NC99_K394M/E446L/E448Q/R449W/D452L/S402EN/Y437D/N438L_N19Q (RPK-3, GLY3, WT CLEAVAGE) H1N1 A/NEW CALEDONIA/20/1999 HA-Ferritin Construct |
| 248 | Gen6_H1NC99_K394M/E446L/E448Q/R449W/D452L/G402cN/G402eT/T402gA/Q370N/E372T/Y437D/N438L_S21T (rpk-3, gly2-6-7, wt cleavage) H1N1 A/New Caledonia/20/1999 HA Construct |
| 249 | Gen6_H1NC99_K394M/E446L/E448Q/R449W/D452L/G402cN/G402eT/T402gA/Q370N/E372T/Y437D/N438L_S21T (rpk-3, gly2-6-7, wt cleavage) H1N1 A/New Caledonia/20/1999 HA-Ferritin Construct |
| 250 | Gen6_H1NC99_K394M/E446L/E448Q/R449W/D452L/G402cN/G402eT/T402gA/Q370N/E372T/Y437D/N438L_S21T/Q69N (rpk-3, gly2-5-6-7, wt cleavage) H1N1 A/New Caledonia/20/1999 HA Construct |
| 251 | Gen6_H1NC99_K394M/E446L/E448Q/R449W/D452L/G402cN/G402eT/T402gA/Q370N/E372T/Y437D/N438L_S21T/Q69N (rpk-3, gly2-5-6-7, wt cleavage) H1N1 A/New Caledonia/20/1999 HA-Ferritin Construct |
| 252 | GEN6_H1NC99_LS1_K394M/E446L/Y437D/N438L/A515-517 (RPK-22_LS1, WT CLEAVAGE) HA-Construct |
| 253 | GEN6_H1NC99_LS1_K394M/E446L/Y437D/N438L/A515-517 (RPK-22_LS1,WT CLEAVAGE)HA-Lumazine Construct |
| 254 | H1-NC99_GEN6_LS2_K394M/E446L/Y437D/N438L/A515-517 (RPK-22_LS2, WT CLEAVAGE) HA Construct |
| 255 | H1-NC99_GEN6_LS2_K394M/E446L/Y437D/N438L/A515-517 (RPK-22_LS2, WT CLEAVAGE) HA-Lumazine Construct |
| 256 | H1-NC99_GEN6_LS3_K394M/E446L/Y437D/N438L/A512-517 (RPK-22_LS3, WT CLEAVAGE) HA Construct |
| 257 | H1-NC99_GEN6_LS3_K394M/E446L/Y437D/N438L/A512-517 (RPK-22_LS3, WT CLEAVAGE) HA-Lumazine |
| 258 | H1-NC99_GEN6_LS4_K394M/E446L/Y437D/N438L/A512-517 (RPK-22_LS4, WT CLEAVAGE)HA Construct |
| 259 | H1-NC99_GEN6_LS4_K394M/E446L/Y437D/N438L/A512-517 (RPK-22_LS4, WT CLEAVAGE) HA-Lumazine Construct |
| 260 | Nucleic acid sequence encoding SEQ ID NO: 261 |
| 261 | Gen6_H1NC99_K394M/E446L/E448Q/R449W/D452L/Y437D/N438L_N19Q HA portion of insert |
| 262 | Complement of SEQ ID NO: 260 |
| 263 | Nucleic acid sequence encoding SEQ ID NO: 264 |
| 264 | Gen6_H1NC99_K394M/E446L/E448Q/R449W/D452L/Y437D/N438L_N19Q HA-Ferritin insert |
| 265 | Complement of SEQ ID NO: 263 |
| 266 | Sequence of entire plasmid from FIG. 5 |
| 267 | Nucleic acid sequence encoding SEQ ID NO: 268 |
| 268 | Gen6_H1CA09_K394M/E446L/E448Q/R449W/D452L/Y437D/N438L_N19Q HA portion of insert |
| 269 | Complement of SEQ ID NO: 267 |
| 270 | Nucleic acid sequence encoding SEQ ID NO: 271 |
| 271 | Gen6_H1CA09_K394M/E446L/E448Q/R449W/D452L/Y437D/N438L_N19Q HA-Ferritin insert |
| 272 | Complement of SEQ ID NO: 270 |
| 273 | Sequence of entire plasmid from FIG. 6 |
| 274 | Nucleic acid sequence encoding SEQ ID NO: 275 |
| 275 | Gen6_H2Sing57_K394M/M445L/E446L/E448Q/R449W/D452L/Y437D/N438L_N19Q HA portion of insert |
| 276 | Complement of SEQ ID NO: 274 |
| 277 | Nucleic acid sequence encoding SEQ ID NO: 278 |
| 278 | Gen6_H2Sing57_K394M/M445L/E446L/E448Q/R449W/D452L/Y437D/N438L_N19Q HA-Ferritin insert |
| 279 | Complement of SEQ ID NO: 277 |
| 280 | Sequence of entire plasmid from FIG. 7 |
| 281 | Nucleic acid sequence encoding SEQ ID NO: 282 |
| 282 | Gen6_H5Ind05_K394M/M445L/E446L/E448Q/R449W/D452L/Y437D/N438L/S49bW_N19Q HA portion of insert |
| 283 | Complement of SEQ ID NO: 281 |
| 284 | Nucleic acid sequence encoding SEQ ID NO: 285 |
| 285 | Gen6_H5Ind05_K394M/M445L/E446L/E448Q/R449W/D452L/Y437D/N438L/S49bW_N19Q HA-Ferritin insert |
| 286 | Complement of SEQ ID NO: 284 |
| 287 | Sequence of entire plasmid from FIG. 8 |
| 288 | Nucleic acid sequence encoding SEQ ID NO: 289 |

TABLE 2-continued

| PCT SEQ ID NO | Comments |
|---|---|
| 289 | Gen6_H1NC99_K394M/E446L_N19Q HA portion of insert |
| 290 | Complement of SEQ ID NO: 288 |
| 291 | Nucleic acid sequence encoding SEQ ID NO: 292 |
| 292 | Gen6_H1NC99_K394M/E446L_N19Q HA-Ferritin insert |
| 293 | Complement of SEQ ID NO: 291 |
| 294 | Sequence of entire plasmid from FIG. 9 |
| 295 | Nucleic acid sequence encoding SEQ ID NO: 296 |
| 296 | Gen6_H1NC99_K394M/E446L/Y437D/N438L_N19Q HA portion of insert |
| 297 | Compement of SEQ ID NO: 295 |
| 298 | Nucleic acid sequence encoding SEQ ID NO: 299 |
| 299 | Gen6_H1NC99_K394M/E446L/Y437D/N438L_N19Q HA-Ferritin insert |
| 300 | Complement of SEQ ID NO: 298 |
| 301 | Sequence of entire plasmid from FIG. 10 |
| 302 | Nucleic acid sequence encoding SEQ ID NO: 303 |
| 303 | Gen6_H1NC99_K394I/E446I/Y437D/N438L_N19Q HA portion of insert |
| 304 | Complement of SEQ ID NO: 302 |
| 305 | Nucleic acid sequence encoding SEQ ID NO: 306 |
| 306 | Gen6_H1NC99_K394I/E446I/Y437D/N438L_N19Q HA-Ferritin insert |
| 307 | Complement of SEQ ID NO: 305 |
| 308 | Sequence of entire plasmid from FIG. 11 |
| 309 | Nucleic acid sequence encoding SEQ ID NO: 310 |
| 310 | Gen6_H1NC99_K394L/E446I/Y437D/N438L_N19Q HA portion of insert |
| 311 | Complement of SEQ ID NO: 309 |
| 312 | Nucleic acid sequence encoding SEQ ID NO: 313 |
| 313 | Gen6_H1NC99_K394L/E446I/Y437D/N438L_N19Q HA-Ferritin Insert |
| 314 | Complement of SEQ ID NO: 312 |
| 315 | Sequence of entire plasmid from FIG. 12 |
| 316 | Nucleic acid sequence encoding SEQ ID NO: 317 |
| 317 | Gen6_H1NC99_K394L/E446L/Y437D/N438L_N19Q HA portion of Insert |
| 318 | Complement of SEQ ID NO: 316 |
| 319 | Nucleic acid sequence encoding SEQ ID NO: 320 |
| 320 | Gen6_H1NC99_K394L/E446L/Y437D/N438L_N19Q HA-Ferritin Insert |
| 321 | Complement of SEQ ID NO: 319 |
| 322 | Sequence of entire plasmid from FIG. 13 |
| 323 | Nucleic acid sequence encoding SEQ ID NO: 324 |
| 324 | Gen6_H1NC99_K394M/E446M/Y437D/N438L_N19Q HA portion of Insert |
| 325 | Complement of SEQ ID NO: 323 |
| 326 | Nucleic acid sequence encoding SEQ ID NO: 327 |
| 327 | Gen6_H1NC99_K394M/E446M/Y437D/N438L_N19Q HA-Ferritin Insert |
| 328 | Complement of SEQ ID NO: 326 |
| 329 | Sequence of entire plasmid from FIG. 14 |
| 330 | Nucleic acid sequence encoding SEQ ID NO: 331 |
| 331 | Gen6_H1NC99_K394Q/E446Q/Y437D/N438L_N19Q HA portion of Insert |
| 332 | Complement of SEQ ID NO: 330 |
| 333 | Nucleic acid sequence encoding SEQ ID NO: 334 |
| 334 | Gen6_H1NC99_K394Q/E446Q/Y437D/N438L_N19Q HA-Ferritin Insert |
| 335 | Complement of SEQ ID NO: 333 |
| 336 | Sequence of entire plasmid from FIG. 15 |
| 337 | Nucleic acid sequence encoding SEQ ID NO: 338 |
| 338 | Gen6_H1NC99_K394M/E446L/Y437D/N438L/H45N/V47T_N19Q HA portion of Insert |
| 339 | Complement of SEQ ID NO: 337 |
| 340 | Nucleic acid sequence encoding SEQ ID NO: 341 |
| 341 | Gen6_H1NC99_K394M/E446L/Y437D/N438L/H45N/V47T_N19Q HA-Ferritin Insert |
| 342 | Complement of SEQ ID NO: 340 |
| 343 | Sequence of entire plasmid from FIG. 16 |
| 344 | Nucleic acid sequence encoding SEQ ID NO: 345 |
| 345 | Gen6_H1NC99_V36I/K394M/L445M/E446L/E448Q/R449F/D452L/Y437D/N438L_N19Q HA portion of Insert |
| 346 | Complement of SEQ ID NO: 344 |
| 347 | Nucleic acid sequence encoding SEQ ID NO: 348 |
| 348 | Gen6_H1NC99_V36I/K394M/L445M/E446L/E448Q/R449F/D452L/Y437D/N438L_N19Q HA-Ferritin Insert |
| 349 | Complement of SEQ ID NO: 347 |
| 350 | Sequence of entire plasmid from FIG. 17 |
| 351 | Nucleic acid sequence encoding SEQ ID NO: 352 |
| 352 | Gen6_H1NC99_K394M/E446L/E448Q/R449W/D452L/S402bN/G402dT/S402eG/T402gA/Y437D/N438L_N19Q HA portion of Insert |
| 353 | Complement of SEQ ID NO: 351 |
| 354 | Nucleic acid sequence encoding SEQ ID NO: 355 |
| 355 | Gen6_H1NC99_K394M/E446L/E448Q/R449W/D452L/S402bN/G402dT/S402eG/T402gA/Y437D/N438L_N19Q HA-Ferritin Insert |
| 356 | Complement of SEQ ID NO: 354 |
| 357 | Sequence of entire plasmid from FIG. 18 |
| 358 | Nucleic acid sequence encoding SEQ ID NO: 359 |
| 359 | Gen6_H1NC99_K394M/E446L/E448Q/R449W/D452L/S402bG/G402cN/S402eT/T402gA/Y437D/N438L_N19Q HA portion of Insert |

TABLE 2-continued

| PCT SEQ ID NO | Comments |
|---|---|
| 360 | Complement of SEQ ID NO: 358 |
| 361 | Nucleic acid sequence encoding SEQ ID NO: 362 |
| 362 | Gen6_H1NC99_K394M/E446L/E448Q/R449W/D452L/S402bG/G402cN/S402eT/T402gA/ Y437D/N438L_N19Q HA-Ferritin Insert |
| 363 | Complement of SEQ ID NO: 361 |
| 364 | Sequence of entire plasmid from FIG. 19 |
| 365 | Nucleic acid sequence encoding SEQ ID NO: 366 |
| 366 | Gen6_H1NC99_K394M/E446L/E448Q/R449W/D452L/S402eN/Y437D/N438L_N19Q HA portion of Insert |
| 367 | Complement of SEQ ID NO: 365 |
| 368 | Nucleic acid sequence encoding SEQ ID NO: 369 |
| 369 | Gen6_H1NC99_K394M/E446L/E448Q/R449W/D452L/S402eN/Y437D/N438L_N19Q HA-Ferritin Insert |
| 370 | Complement of SEQ ID NO: 368 |
| 371 | Sequence of entire plasmid from FIG. 20 |
| 372 | Nucleic acid sequence encoding SEQ ID NO: 373 |
| 373 | Gen6_H1NC99_K394M/E446L/E448Q/R449W/D452L/G402dN/G402fT/T402gA/Q370N/ E372T/Y437D/N438L_S21T HA portion of Insert |
| 374 | Complement of SEQ ID NO: 372 |
| 375 | Nucleic acid sequence encoding SEQ ID NO: 376 |
| 376 | Gen6_H1NC99_K394M/E446L/E448Q/R449W/D452L/G402dN/G402fT/T402gA/Q370N/ E372T/Y437D/N438L_S21T HA-Ferritin Insert |
| 377 | Complement of SEQ ID NO: 375 |
| 378 | Sequence of entire plasmid from FIG. 21 |
| 379 | Nucleic acid sequence encoding SEQ ID NO: 380 |
| 380 | Gen6_H1NC99_K394M/E446L/E448Q/R449W/D452L/G402dN/G402fT/T402gA/Q370N/ E372T/Y437D/N438L_S21T/Q69N HA portion of Insert |
| 381 | Complement of SEQ ID NO: 379 |
| 382 | Nucleic acid sequence encoding SEQ ID NO: 383 |
| 383 | Gen6_H1NC99_K394M/E446L/E448Q/R449W/D452L/G402dN/G402fT/T402gA/Q370N/ E372T/Y437D/N438L_S21T/Q69N HA-Ferritin Insert |
| 384 | Complement of SEQ ID NO: 382 |
| 385 | Sequence of entire plasmid from FIG. 22 |
| 386 | Nucleic acid sequence encoding SEQ ID NO: 387 |
| 387 | Gen6_H1NC99_K394M/E446L/Y437D/N438L/Δ515-517 HA portion of insert |
| 388 | Complement of SEQ ID NO: 386 |
| 389 | Nucleic acid sequence encoding SEQ ID NO: 390 |
| 390 | Gen6_H1NC99_K394M/E446L/Y437D/N438L/Δ515-517 HA-Ferritin Insert |
| 391 | Complement of SEQ ID NO: 389 |
| 392 | Sequence of entire plasmid from FIG. 23 |
| 393 | Nucleic acid sequence encoding SEQ ID NO: 394 |
| 394 | Gen6_H1NC99_rpk3Dloop2 |
| 395 | Complement of SEQ ID NO: 393 |
| 396 | Nucleic acid sequence encoding SEQ ID NO: 397 |
| 397 | Gen6_H1NC99_rpk3Dloop2 |
| 398 | Complement of SEQ ID NO: 396 |
| 399 | Sequence of entire plasmid from FIG. 24 |
| 400 | Gen6_H1NC99_K394M/E446L/E448Q/R449W/D452L/Y437D/N438L/I337G/G355S/Δ338- 354_N19Q (rpk-3, Dloop2) H1N1 A/New Caledonia/20/1999 HA Construct |
| 401 | Gen6_H1NC99_K394M/E446L/E448Q/R449W/D452L/Y437D/N438L/I337G/G355S/Δ338- 354_N19Q (rpk-3, Dloop2) H1N1 A/New Caledonia/20/1999 HA-Ferritin Construct |

The trimeric HA protein on the surface of the virus comprises a globular head region and a stem, or stalk, region, which anchors the HA protein into the viral lipid envelope. The head region of influenza HA is formed exclusively from a major portion of the HA1 polypeptide, whereas the stalk region is made from segments of HA1 and HA2. According to the present invention, the head region consists of, approximately, the amino acids of an HA protein corresponding to amino acids 59-291 of the full-length HA protein of influenza H1N1 NC (SEQ ID NO:8). Similarly, as used herein, the stem region consists of, approximately, amino acids 1-58 and the amino acids of an HA protein corresponding to amino acids 328-564 of the full-length HA protein of influenza H1N1 NC (SEQ ID NO:8). As used herein, the term approximately, with regard to the head and stem regions means that the sequences cited above may vary in length by several amino acids without affecting the nature of the invention. Thus, for example, the head region may consist of amino acids 50-291, amino acids 59-296 or amino acids 59-285. Generally the head and stem region will not vary from the locations recited above by more than ten amino acids; however, in one embodiment the carboxy end of the head region can extend as far as an amino acid corresponding to amino acid 327 of SEQ ID NO:8. In one embodiment, the head region consists of the amino acid sequence between, and including, the amino acid residues corresponding to Cys59 and Cys291 of influenza A/New Caledonia/20/1999 (SEQ ID NO:8). With regard to HA proteins, it is understood by those skilled in the art that HA proteins from different influenza viruses may have different lengths due to mutations (insertions, deletions) in the protein. Thus, reference to a corresponding region refers to a region of another proteins that is identical, or nearly so (e.g., at least 90% identical, at least 95%, identical, at least 98% identical or at least 99% identical), in sequence, structure and/or function to the region being compared. For example, with regard to the stem region of an HA protein, the corresponding region in another HA protein may not have the same residue numbers, but will have a nearly identical sequence and will perform the same function. As an example, in the embodiment stated above, the head region of the HA protein from A/New Caledonia/20/1999 (SEQ ID NO:8) ends at amino acid C291. The corresponding amino acid at the end of the head region in A/California/4/2009 (H1) (SEQ ID NO:11) is cysteine 292. To better clarify sequences comparisons between viruses, numbering systems are used by those in the field, which relate amino acid positions to a reference sequence. Thus, corresponding amino acid residues in HA proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the 100$^{th}$ residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. While the H3 numbering system can be used to identify the location of amino acids, unless otherwise noted, the location of amino acid residues in HA proteins will be identified by general reference to the position of a corresponding amino acid from a sequence disclosed herein.

The inventors have also discovered that by combining specific sequences of the influenza virus HA protein with unrelated molecules that are capable of presenting the HA protein to the immune system, immune responses to targeted regions of the HA protein can be elicited. One embodiment of the present invention is a protein construct comprising an influenza HA protein joined to at least a portion of a monomeric subunit protein, wherein the head region of the influenza HA protein has been replaced with an amino acid sequence comprising less than 5 contiguous amino acid residues from the head region of the HA protein, and wherein the protein construct is capable of forming a nanoparticle.

By joining at least a portion of the influenza HA protein to a monomeric subunit, protein constructs of the present invention are capable of assembling into nanoparticles expressing trimers of HA on their surface. It should be appreciated that the HA proteins making up such trimers are in a pre-fusion form and that connection to the monomeric subunit and expression on a nanoparticle stabilize the pre-fusion proteins in their trimeric form. This is significant since the HA protein is presented in a more native form meaning certain surfaces of the stem polypeptides are not exposed, thereby reducing the risk that the stem polypeptides may induce an unfavorable antibody response.

In one embodiment, the HA protein comprises at least one immunogenic portion from the stem region of influenza HA protein, wherein the protein elicits protective antibodies against an influenza virus. In one embodiment, the HA protein comprises at least one immunogenic portion from the stem region of an HA protein from a virus selected from the group consisting of influenza type A viruses, influenza type B viruses and influenza type C viruses, wherein the protein elicits protective antibodies against an influenza virus. In one embodiment, the HA protein comprises at least one immunogenic portion from the stem region of an HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein.

In one embodiment, the HA protein comprises at least one immunogenic portion from a protein comprising an amino acid sequence at least 80% identical to a sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence at least 80% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the HA protein comprises at least one immunogenic portion from a protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, such proteins comprising immunogenic portions of the HA protein elicit the production of broadly protective antibodies against influenza virus.

Immunogenic portions of proteins comprise epitopes, which are clusters of amino acid residues that are recognized by the immune system, thereby eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that epitopes require a minimum of six amino acid residues in order to be recognized by the immune system. Thus, in one embodiment the immunogenic portion from the influenza HA protein comprises at least one epitope. In one embodiment the HA protein comprises at least 6 amino acids, at least 10 amino acids, at least 25 amino acids, at least 50 amino acids, at least 75 amino acids or at least 100 amino acids from the stem region of influenza HA protein. In one embodiment the HA protein comprises at least 6 amino acids, at least 10 amino acids, at least 25 amino acids, at least 50 amino acids, at least 75 amino acids or at least 100 amino acids from the stem region of an HA protein from a virus selected from the group consisting of influenza type A viruses, influenza type B viruses and influenza type C viruses. In one embodiment the HA protein comprises at least 6 amino acids, at least 10 amino acids, at least 25 amino acids, at least 50 amino acids, at least 75 amino acids or at least 100 amino acids from the stem region of an HA protein selected from the group consisting an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. In one embodiment the HA protein comprises at least 6 amino acids, at least 10 amino acids, at least 25 amino acids, at least 50 amino acids, at least 75 amino acids or at least 100 amino acids from the stem region of an HA protein from a strain of virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B), and variants thereof. In one embodiment, the amino acids are contiguous amino acids from the stem region of the HA protein. In one embodiment, such proteins comprising at least 6 amino acids, at least 10 amino acids, at least 25 amino acids, at least 50 amino acids, at least 75 amino acids or at least 100 amino acids from the stem region of an HA protein elicit the production of broadly protective antibodies against influenza virus. One embodiment of the present invention is a protein construct comprising at least 6 amino acids, at least 10 amino acids, at least 25 amino acids, at least 50 amino acids, at least 75 amino acids or at least 100 amino acids from the stem region of an HA protein comprising an amino acid sequence selected from the group consisting of SEQ ID NO:8, SEQ ID NO:11, SEQ ID NO:14 and SEQ ID NO:17. One embodiment of the present invention is a protein construct comprising at least 6 amino acids, at least 10 amino acids, at least 25 amino acids, at least 50 amino acids, at least 75 amino acids or at least 100 amino acids from the stem region of an HA protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the amino acids are contiguous amino acids from the stem region of the HA protein. In one embodiment, the amino acids are non-contiguous, but are in close spatial proximity in the final protein.

While the present application exemplifies the use of stem region sequences from several exemplary HA proteins, the invention may also be practiced using stem regions from proteins comprising variations of the disclosed HA sequences. Thus, in one embodiment, the HA protein is from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B), and variants thereof. In one embodiment of the HA protein comprises an amino acid sequence at least 80%, at least 85%, at least 90%, at least 92%, at least 94%, at least 96%, at least 98% or at least 99% identical the stem region of an HA protein comprising an amino acid sequence selected from the group consisting of SEQ ID NO:8, SEQ ID NO:, SEQ ID NO:11, SEQ ID NO:14, SEQ ID NO:17. In one embodiment the HA protein comprises an amino acid sequence selected from the group consisting of SEQ ID NO:8, SEQ ID NO:, SEQ ID NO:11, SEQ ID NO:14, SEQ ID NO:17.

In one embodiment, the head region sequence of the HA protein is replaced with a linker sequence. Any linker sequence may be used so long as the stem region sequences are able to form the desired structure. While any amino acids may be used to make the linker sequence, it is preferred to use amino acids lacking large or charged side chains. Preferred amino acids include, but are not limited to, serine, glycine and alanine. In one embodiment, the linker is made from serine and glycine residues. The length of the linker sequence may vary, but preferred embodiments use the shortest possible sequence in order to allow the stem sequences to form the desired structure. In one embodiment, the linker sequence is less than 10 amino acids in length. In one embodiment, the linker sequence is less than 5 amino acids in length. In preferred embodiments, the linker sequence lacks contiguous amino acid sequences from the head region of an HA protein. In one embodiment, the linker sequence comprises less than 5 contiguous amino acids from the head region of an HA protein.

As noted above, the HA sequence is linked to a portion of a monomeric subunit protein. As used herein, a monomeric subunit protein refers to a protein monomer that is capable of binding to other monomeric subunit proteins such that the monomeric subunit proteins self-assemble into a nanoparticle. Any monomeric subunit protein can be used to produce the protein construct of the present invention, so long as the protein construct is capable of forming a multimeric structure displaying HA protein on its surface. In one embodiment the monomeric subunit is ferritin.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO:2. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the nanoparticle three-fold axis and extends to the surface, while the E helices pack together at the four-fold axis with the C-terminus extending into the particle core. The consequence of this packing creates two pores on the nanoparticle surface. It is expected that one or both of these pores represent the point by which the hydrated iron diffuses into and out of the nanoparticle. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Examples of such proteins include, but are not limited to SEQ ID NO:2 and SEQ ID NO:5. Amino acid sequences from monomeric ferritin subunits of any known ferritin protein can be used to produce protein constructs of the present invention, so long as the monomeric ferritin subunit is capable of self-assembling into a nanoparticle displaying HA on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori*.

Protein constructs of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

In one embodiment the HA protein is joined to at least 50, at least 100 or least 150 amino acids from ferritin, wherein the protein construct is capable of forming a nanoparticle. In one embodiment the HA protein is joined to at least 50, at least 100 or least 150 amino acids from SEQ ID NO:2 or SEQ ID NO:5, wherein the protein construct is capable of forming a nanoparticle. In one embodiment the HA protein is joined to a protein comprising an amino acid sequence at least 85%, at least 90% or at least 95% identical to the sequence of ferritin, wherein the protein construct is capable of forming a nanoparticle. In one embodiment the HA protein is joined to a protein comprising an amino acid sequence at least 85%, at least 90%, at least 95% identical to SEQ ID NO:2 or SEQ ID NO:5, wherein the protein construct is capable of forming a nanoparticle.

In one embodiment the monomeric subunit is lumazine synthase. In one embodiment the HA protein is joined to at least 50, at least 100 or least 150 amino acids from lumazine synthase, wherein the protein construct is capable of forming a nanoparticle. Thus, in one embodiment the HA protein is joined to a protein at least 85%, at least 90%, at least 95% identical to lumazine synthase, wherein the protein construct is capable of forming a nanoparticle.

As used herein, a nanoparticle of the present invention refers to a three-dimensional particle formed by self-assembly of protein constructs (fusion proteins) of the present invention. Nanoparticles of the present invention are generally spheroid in shape, although other shapes are not excluded, and are generally from about 20 nm to about 100 nm in diameter. Nanoparticles of the present invention may, but need not, comprise other molecules, such as proteins, lipids, carbohydrates, etc., than the protein constructs from which they are formed.

Protein constructs of the present invention can be made using recombinant technology to link together portions of HA proteins, linkers and monomeric subunits. In this way, protein constructs can be produced that comprise only those sequences necessary to produce nanoparticle vaccines. Thus, one embodiment of the present invention is a protein construct (also referred to as a fusion protein) comprising a first amino acid sequence from the stem region of an influenza virus HA protein and a second amino acid sequence from the stem region of an influenza virus HA protein, the first and second amino acid sequences being covalently linked by a linker sequence,
  wherein the first amino acid sequence comprises at least 20 contiguous amino acid residues from the amino acid sequence upstream of the amino-terminal end of the head region sequence;
  wherein the second amino acid sequence comprises at least 20 contiguous amino acid residues from the amino acid sequence downstream of the carboxyl-terminal end of the head region sequence; and,
  wherein the first or second amino acid sequence is joined to at least a portion of a monomeric subunit domain such that the protein construct is capable of forming a nanoparticle.

In one embodiment, the first amino acid sequence is from the stem region of an HA protein from a virus selected from the group consisting of influenza A viruses, influenza B viruses and influenza C viruses. In one embodiment, the first amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the first amino acid sequence is from the stem region of an HA protein from a virus selected from the group consisting of influenza A/New Caledonia/20/1999 (1999 NC, H1), A/California/04/2009 (2009 CA, H1), A/Singapore/i/1957 (1957 Sing, H2), A/Hong Kong/i/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the first amino acid sequence is from the stem region of an HA protein having an amino acid sequences at least 85%, at least 90%, at least 95% or at least 97% identical to a sequence selected from the group consisting of SEQ ID NO:8, SEQ ID NO:, SEQ ID NO:11, SEQ ID NO:14 and SEQ ID NO:17. In one embodiment, the first amino acid sequence is from the stem region of an HA protein comprising a sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence at least 85%, at least 90%, at least 95% or at least 97% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the HA protein comprises at least one immunogenic portion from a protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17. In one embodiment, the HA protein comprises at least one immunogenic portion from a protein comprising an amino acid sequence at least 85%, at least 90%, at least 95% or at least 97% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the HA protein comprises at least one immunogenic portion from a protein comprising an amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:150, SEQ ID NO:152, SEQ ID NO:154, SEQ ID NO:156, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

As noted above, the first amino acid sequence comprises at least 20 contiguous amino acid residues from the amino acid sequence upstream of the amino-terminal end of the head region sequence. According to the present invention, the term upstream refers to the entirety of the amino acid sequence linked to the amino-terminal end of the first amino acid residue of the head region. In one embodiment, the amino-terminal end of the head region is located at the amino acid residue corresponding to Cys59 of the HA protein of influenza A New Caledonia/20/1999 (H1) (SEQ ID NO:8) Thus, in one embodiment, the first amino acid sequence comprises at least 20 contiguous amino acid residues from the region of an HA protein corresponding to amino acid residues 1-58 of influenza A New Caledonia/20/1999 (H1) (SEQ ID NO:8). In one embodiment, the first amino acid sequence comprises at least 20 contiguous amino acid residues from a sequence at least 85%, at least 90%, at least 95% or at least 97% identical to a sequence selected from the group consisting of SEQ ID NO:20, SEQ ID NO:35, SEQ ID NO:50 and SEQ ID NO:65. In one embodiment, the first amino acid sequence comprises at least 20 contiguous amino acid residues from a sequence selected from the group consisting of SEQ ID NO:20, SEQ ID NO: 35, SEQ ID NO:50 and SEQ ID NO:65.

In one embodiment, the first amino acid sequence comprises at least 40 contiguous amino acid residues from the amino acid region of an HA protein corresponding to amino acid residues 1-58 of influenza A New Caledonia/20/1999 (H1) (SEQ ID NO:8). In one embodiment, the first amino acid sequence comprises at least 40 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 40 contiguous amino acid residues from a sequence selected from the group consisting of SEQ ID NO:20, SEQ ID NO: 35, SEQ ID NO:50 and SEQ ID NO:65.

In one embodiment, the first amino acid sequence comprises a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises a sequence selected from the group consisting of SEQ ID NO:20, SEQ ID NO: 35, SEQ ID NO:50 and SEQ ID NO:65.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17.

As noted above, the second amino acid sequence comprises at least 20 contiguous amino acid residues from the amino acid sequence downstream of the carboxyl-terminal end of the head region sequence. According to the present invention, the term downstream refers to the entire amino acid sequence linked to the carboxyl-terminal amino acid residue of the head region. In one embodiment, the carboxyl-terminal end of the head region is located at the amino acid position corresponding to Cys291 of the HA protein of influenza A New Caledonia/20/1999 (H1) (SEQ ID NO:8) Thus, in one embodiment, the second amino acid sequence comprises at least 20 contiguous amino acids from the amino acid region of an HA protein corresponding to amino acid residues 292-517 of influenza A New Caledonia/20/1999 (H1) (SEQ ID NO:8). In one embodiment, the second amino acid sequence comprises at least 20 contiguous amino acids from the amino acid region of an HA protein corresponding to amino acid residues 328-517 of influenza A New Caledonia/20/1999 (H1) (SEQ ID NO:8). In one embodiment, the second amino acid sequence comprises at least 20 contiguous amino acid residues from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises at least 20 contiguous amino acid residues from a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77.

In one embodiment, the second amino acid sequence comprises at least 40, at least 60, at least 75, at least 100, or at least 150 contiguous amino acids from the amino acid sequence downstream of the carboxyl-terminal end of the head region sequence. In one embodiment, the second amino acid sequence comprises at least 40, at least 60, at least 75, at least 100, or at least 150 contiguous amino acids from the amino acid region of an HA protein corresponding to amino acid residues 292-517 of influenza A New Caledonia/20/1999 (H1) (SEQ ID NO:8). In one embodiment, the second amino acid sequence comprises at least 40, at least 60, at least 75, at least 100, or at least 150 contiguous amino acids from the amino acid region of an HA protein corresponding to amino acid residues 328-517 of influenza A New Caledonia/20/1999 (H1) (SEQ ID NO:8). In one embodiment, the second amino acid sequence comprises at least 40, at least 60, at least 75, at least 100, or at least 150 contiguous amino acids from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises at least 40, at least 60, at least 75, at least 100, or at least 150 contiguous amino acids from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises an amino acid sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the second amino acid sequence comprises a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77.

As noted above, the first and second amino acid sequences of the protein construct can be joined by a linker sequence. Any linker sequence can be used as long as the linker sequence has less than five contiguous amino acid residues from the head region of an HA protein and so long as the first and second amino acids are able to form the desired conformation. In one embodiment, the linker sequence is less than 10 amino acids, less than 7 amino acids or less than 5 amino acids in length. In one embodiment, the linker sequence comprises glycine and serine. In one embodiment, the linker sequence joins the carboxyl-terminal end of the first amino acid sequence to the amino-terminal end of the second amino acid sequence. In one embodiment, the linker sequence joins the carboxyl-terminal end of the second amino acid sequence to the amino-terminal end of the first amino acid sequence.

As noted above, either the first or second amino acid sequence of the protein construct is joined to at least a portion of a monomeric subunit protein such that the protein construct is capable of forming a nanoparticle. In one embodiment, the at least a portion of the monomeric subunit protein is joined to the second amino acid sequence. In a preferred embodiment, the at least a portion of the monomeric subunit protein is joined to the carboxyl end of the second amino acid sequence. In one embodiment, the portion comprises at least 50, at least 100 or at least 150 amino acids from a monomeric subunit. In one embodiment, the monomeric subunit is ferritin. In one embodiment, the monomeric subunit is lumazine synthase. In one embodiment, the portion comprises at least 50, at least 100 or at least 150 amino acids from SEQ ID NO:2, SEQ ID NO:5 or SEQ ID NO:194. In one embodiment, the monomeric subunit comprises a sequence at least 85% identical, at least 90% identical or at least 95% identical to SEQ ID NO:2, SEQ ID NO:5 or SEQ ID NO:194. In one embodiment, the monomeric subunit comprises a sequence selected from the group consisting of SEQ ID NO:2, SEQ ID NO:5 and SEQ ID NO:194.

The inventors have discovered that modification of the influenza HA sequences of the heretofore described protein constructs leads to improved stability of the protein construct. For example, the inventors have found that deletion from an HA protein of the amino acid region corresponding to amino acids N403-W435 of the HA protein of influenza A New Caledonia/20/1999 (H1) (SEQ ID NO:8) results in a more stable protein construct. Upon deletion of this region, the amino acid sequences flanking this region can be joined together directly, or they can be joined with a linker sequence such as, for example, glycine-serine-glycine Thus, in one embodiment, the second amino acid sequence comprises a polypeptide sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:133, SEQ ID NO:134, SEQ ID NO:135 or SEQ ID NO:136 from the HA protein of influenza A/New Caledonia 1999 (SEQ ID NO:8). In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:133, SEQ ID NO:134, SEQ ID NO:135 or SEQ ID NO:136 of the HA protein of influenza A/New Caledonia 1999 (SEQ ID NO:8).

In one embodiment, the second amino acid sequence comprises a polypeptide sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:137, SEQ ID NO:138, SEQ ID NO:139 or SEQ ID NO:140 of the HA protein of influenza A/California/4/2009 (SEQ ID NO:10). In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:137, SEQ ID NO:138, SEQ ID NO:139 or SEQ ID NO:140 of the HA protein of influenza A/California/4/2009 (SEQ ID NO:10).

In one embodiment, the second amino acid sequence comprises an amino acid sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:141, SEQ ID NO:142, SEQ ID NO:143 or SEQ ID NO:144 of the HA protein of influenza A/Singapore/1957 (SEQ ID NO:12). In one embodiment, the second amino acid sequence comprises an amino acid sequence at least 85%, at least 90% or at least 95% identical to at least 100 contiguous amino acid residues from the amino acid sequence downstream of the carboxyl-terminal end of the head region sequence, wherein the polypeptide sequence lacks a region corresponding to SEQ ID NO:141, SEQ ID NO:142, SEQ ID NO:143 or SEQ ID NO:144 of the HA protein of influenza A/Singapore/1957 (SEQ ID NO:12).

In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:145, SEQ ID NO:146, SEQ ID NO:147 or SEQ ID NO:148 of the HA protein of influenza A/Indonesia/05/2005 (H5) (SEQ ID NO:16). In one embodiment, the second amino acid sequence comprises at least 100 contiguous amino acid residues from the amino acid sequence downstream of the carboxyl-terminal end of the head region sequence, wherein the polypeptide sequence lacks a region corresponding to SEQ ID NO:145, SEQ ID NO:146, SEQ ID NO:147 or SEQ ID NO:148 of the HA protein of influenza A/Indonesia/05/2005 (H5) (SEQ ID NO:16).

In one embodiment, the second amino acid sequence comprises a sequence at least 85%, at least 90% or at least 95% identical to 100 contiguous amino acids from SEQ ID NO:23, SEQ ID NO:26 or SEQ ID NO:29, wherein the 100 contiguous amino acids do not comprise a sequence selected from the group consisting of SEQ ID NO:133, SEQ ID NO:134, SEQ ID NO:135 and SEQ ID NO:136. In one embodiment, the second amino acid sequence comprises 100 contiguous amino acids from SEQ ID NO:23, SEQ ID NO:26 or SEQ ID NO:29, wherein the 100 contiguous amino acids do not comprise a sequence selected from the group consisting of SEQ ID NO:133, SEQ ID NO:134, SEQ ID NO:135 and SEQ ID NO:136.

In one embodiment, the second amino acid sequence comprises a sequence at least 85%, at least 90% or at least 95% identical to 100 contiguous amino acids from SEQ ID NO:38, SEQ ID NO:41 or SEQ ID NO:44, wherein the 100 contiguous amino acids do not comprise a sequence selected from the group consisting of SEQ ID NO:137, SEQ ID NO:138, SEQ ID NO:139 and SEQ ID NO:140. In one embodiment, the second amino acid sequence comprises 100 contiguous amino acids from SEQ ID NO:38, SEQ ID NO:41 or SEQ ID NO:44, wherein the 100 contiguous amino acids do not comprise a sequence selected from the group consisting of SEQ ID NO:137, SEQ ID NO:138, SEQ ID NO:139 and SEQ ID NO:140.

In one embodiment, the second amino acid sequence comprises a sequence at least 85%, at least 90% or at least 95% identical to 100 contiguous amino acids from SEQ ID NO:53, SEQ ID NO:56 or SEQ ID NO:59, wherein the 100 contiguous amino acids do not comprise a sequence selected from the group consisting of SEQ ID NO:141, SEQ ID NO:142, SEQ ID NO:143 and SEQ ID NO:144. In one embodiment, the second amino acid sequence comprises 100 contiguous amino acids from SEQ ID NO:53, SEQ ID NO:56 or SEQ ID NO:59, wherein the 100 contiguous amino acids do not comprise a sequence selected from the group consisting of SEQ ID NO:141, SEQ ID NO:142, SEQ ID NO:143 and SEQ ID NO:144.

In one embodiment, the second amino acid sequence comprises a sequence at least 85%, at least 90% or at least 95% identical to 100 contiguous amino acids from SEQ ID NO:68, SEQ ID NO:71 or SEQ ID NO:74, wherein the 100 contiguous amino acids do not comprise a sequence selected from the group consisting of SEQ ID NO:145, SEQ ID NO:146, SEQ ID NO:147 and SEQ ID NO:148. In one embodiment, the second amino acid sequence comprises 100 contiguous amino acids from SEQ ID NO:68, SEQ ID NO:71 or SEQ ID NO:74, wherein the 100 contiguous amino acids do not comprise a sequence selected from the group consisting of SEQ ID NO:145, SEQ ID NO:146, SEQ ID NO:147 and SEQ ID NO:148.

In one embodiment, the second amino acid sequence comprises a sequence at least 85%, at least 90% or at least 95% identical to 100 contiguous amino acids from a sequence selected from the group consisting of SEQ ID NO:26, SEQ ID NO:28, SEQ ID NO:32, SEQ ID NO:41, SEQ ID NO:44, SEQ ID NO:47, SEQ ID NO:56, SEQ ID NO:59, SEQ ID NO:62, SEQ ID NO:71 and SEQ ID NO:77. In one embodiment, the second amino acid sequence comprises at least 100 contiguous amino acids from a sequence selected from the group consisting of SEQ ID NO:26, SEQ ID NO:32, SEQ ID NO:41, SEQ ID NO:47, SEQ ID NO:56, SEQ ID NO:62, SEQ ID NO:71 and SEQ ID NO:77. In one embodiment, the second amino acid sequence comprises a sequence selected from the group consisting of SEQ ID NO:26, SEQ ID NO:32, SEQ ID NO:41, SEQ ID NO:47, SEQ ID NO:56, SEQ ID NO:62, SEQ ID NO:71, SEQ ID NO:74 and SEQ ID NO:77

The inventors have also discovered that alteration of the sequence of the HA stem region sequence results in a more stable protein construct. For example, in the folded HA protein, the amino acid residues corresponding to K394 and E446 of influenza A New Caledonia/20/1999 (H1) (corresponding to K1 and E53 of SEQ ID NO:149) form a salt bridge, helping to stabilize the folded protein. The inventors have discovered that by substituting the lysine and glutamic acid residues with the appropriate amino acids, the interaction between the two amino acid residues can be strengthened, which improves the stability of the molecule and allows more extensive manipulation thereto. Thus, one embodiment of the present invention is a protein construct comprising a first amino acid sequence from the stem region of an influenza virus HA protein and a second amino acid sequence from the stem region of an influenza virus HA protein, the first and second amino acid sequences being covalently linked by a linker sequence,
  wherein the first amino acid sequence comprises at least 20 contiguous amino acid residues from the amino acid sequence upstream of the amino-terminal end of the head region sequence,
  wherein the second amino acid sequence comprises at least 60 contiguous amino acids from the amino acid sequence downstream of the carboxyl-terminal end of the head region sequence,
  wherein the 60 contiguous amino acids comprise a polypeptide sequence corresponding to the sequence of SEQ ID NO:149 or SEQ ID NO:150 from A/New Caledonia/20/1999, and
  wherein the amino acid residue in the polypeptide sequence that corresponds to K1 of SEQ ID NO:149 or K1 of SEQ ID NO:150 is substituted with an amino acid other than lysine,
  and the amino acid residue corresponding to E53 of SEQ ID NO:149 or E20 of SEQ ID NO:150 is substituted with an amino acid residue other than glutamic acid, such that the strength of the interaction between the substituted amino acid residues is greater than the strength of the interaction in the wild-type protein.

As noted above, the amino acid residues corresponding to K394 and E446 of influenza A New Caledonia/20/1999 (H1) form a salt bridge, which is a type of bond. It is known in the art that other types of bonds between amino acids exist, the strength of which vary depending on the type of bond. Examples of such bonds include, but are not limited to, a hydrophobic bond and a hydrogen bond, both of which are generally stronger than a salt bridge. Thus, in one embodiment, the amino acid residue in the polypeptide corresponding to K1 of SEQ ID NO:149 or K1 of SEQ ID NO:150 and the amino acid residue in the polypeptide corresponding to E53 of SEQ ID NO:149 or E20 of SEQ ID NO:150 are altered so that they form a hydrogen bond in the final folded protein. In one embodiment, the amino acid residue in the polypeptide corresponding to K1 of SEQ ID NO:149 or K1 of SEQ ID NO:150 and the amino acid residue in the polypeptide corresponding to E53 of SEQ ID NO:149 or E20 of SEQ ID NO:150 are altered so that they form a hydrophobic bond in the final folded protein.

The amino acids corresponding to K1 of SEQ ID NO:149, K1 of SEQ ID NO:150, E53 of SEQ ID NO:149 or E20 of SEQ ID NO:150 can be substituted with any amino acid residue, as long as the resulting interaction between the two amino acids is stronger than the salt-bridge in the unaltered protein. Examples of substitutions that increase the strength of the interaction between the amino acids corresponding to K394 and E446 of influenza A New Caledonia/20/1999 (H1) (K1 and E53 of SEQ ID NO:149) include, but are not limited to:

wherein the amino acid residue in the polypeptide sequence that corresponds to K1 of SEQ ID NO:149 is substituted with methionine, and the amino acid residue corresponding to E53 of SEQ ID NO:149 is substituted with a leucine;

wherein the amino acid residue in the polypeptide sequence that corresponds to K1 of SEQ ID NO:149 is substituted with methionine, and the amino acid residue corresponding to E53 of SEQ ID NO:149 is substituted with a methionine;

wherein the amino acid residue in the polypeptide sequence that corresponds to K1 of SEQ ID NO:149 is substituted with leucine, and the amino acid residue corresponding to E53 of SEQ ID NO:149 is substituted with a leucine;

wherein the amino acid residue in the polypeptide sequence that corresponds to K1 of SEQ ID NO:149 is substituted with isoleucine, and the amino acid residue corresponding to E53 of SEQ ID NO:149 is substituted with a isoleucine;

wherein the amino acid residue in the polypeptide sequence that corresponds to K1 of SEQ ID NO:149 is substituted with leucine, and the amino acid residue corresponding to E53 of SEQ ID NO:149 is substituted with an isoleucine;

wherein the amino acid residue in the polypeptide sequence that corresponds to K1 of SEQ ID NO:149 is substituted with glutamine, and the amino acid residue corresponding to E53 of SEQ ID NO:149 is substituted with a glutamine.

In one embodiment, the first amino acid sequence is from the stem region of an HA protein from a virus selected from the group consisting of influenza A viruses, influenza B viruses and influenza C viruses. In one embodiment, the first amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the first amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the first amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the first amino acid sequence is from the stem region of an HA protein comprising a sequence selected from the group consisting of SEQ ID NO:8, SEQ ID NO:11, SEQ ID NO:14 and SEQ ID NO:17.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17.

In one embodiment, the first amino acid sequence comprises at least 20 contiguous amino acid residues from the region of an HA protein corresponding to amino acid residues 1-58 of influenza A New Caledonia/20/1999 (H1) (SEQ ID NO:8). In one embodiment, the first amino acid sequence comprises at least 20 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 20 contiguous amino acid residues from a sequence selected from the group consisting of SEQ ID NO:20, SEQ ID NO: 35, SEQ ID NO:50 and SEQ ID NO:65.

In one embodiment, the first amino acid sequence comprises at least 40 contiguous amino acid residues from the amino acid region of an HA protein corresponding to amino acid residues 1-58 of influenza A New Caledonia/20/1999 (H1) (SEQ ID NO:8). In one embodiment, the first amino acid sequence comprises at least 40 contiguous amino acid residues from a sequence at least 85%, at least 90%, at least 95% or at least 97% identical to a sequence selected from the group consisting of SEQ ID NO:20, SEQ ID NO: 35, SEQ ID NO:50 and SEQ ID NO:65. In one embodiment, the first amino acid sequence comprises at least 40 contiguous amino acid residues from a sequence selected from the group consisting of SEQ ID NO:20, SEQ ID NO: 35, SEQ ID NO:50 and SEQ ID NO:65. In one embodiment, the first amino acid sequence comprises a sequence at least 85%, at least 90% or at least 95% identical to a sequence selected from the group consisting of SEQ ID NO:20, SEQ ID NO: 35, SEQ ID NO:50 and SEQ ID NO:65. In one embodiment, the first amino acid sequence comprises a sequence selected from the group consisting of SEQ ID NO:20, SEQ ID NO: 35, SEQ ID NO:50 and SEQ ID NO:65.

In one embodiment, the second amino acid sequence is from the stem region of an HA protein from a virus selected from the group consisting of influenza A viruses, influenza B viruses and influenza C viruses. In one embodiment, the second amino acid sequence is from the stem region of an HA protein from a virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. In one embodiment, the second amino acid sequence is from the stem region of an HA protein from a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B). In one embodiment, the second amino acid sequence is from the stem region of an HA protein having an amino acid sequences at least 85%, at least 90%, at least 95% or at least 97% identical to a sequence selected from the group consisting of SEQ ID NO:8, SEQ ID NO:11, SEQ ID NO:14 and SEQ ID NO:17. In one embodiment, the second amino acid sequence is from the stem region of an HA protein comprising a sequence selected from the group consisting of SEQ ID NO:8, SEQ ID NO:11, SEQ ID NO:14 and SEQ ID NO:17.

In one embodiment, the at least 60 contiguous amino acids of the second amino acid sequence are from the amino acid region of an HA protein corresponding to amino acid residues 292-517 of influenza A New Caledonia/20/1999 (H1) (SEQ ID NO:8). In one embodiment, the at least 60 contiguous amino acids of the second amino acid sequence are from the amino acid region of an HA protein corresponding to amino acid residues 328-517 of influenza A New Caledonia/20/1999 (H1) (SEQ ID NO:8). In one embodiment, the at least 60 contiguous amino acids of the second amino acid sequence are from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. In one embodiment, the at least 60 contiguous amino acids of the second amino acid sequence are from a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77.

In one embodiment, the second amino acid sequence comprises at least 75, at least 100, at least 150 or at least 200 contiguous amino acids from the amino acid sequence downstream of the carboxyl-terminal end of the head region sequence, wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150 or at least 200 contiguous amino acids from the amino acid region of an HA protein corresponding to amino acid residues 292-517 of influenza A New Caledonia/20/1999 (H1) (SEQ ID NO:8), wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150 or at least 200 contiguous amino acids from the amino acid region of an HA protein corresponding to amino acid residues 328-517 of influenza A New Caledonia/20/1999 (H1) (SEQ ID NO:8), wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150 or at least 200 contiguous amino acids from a sequence at least 85%, at least 90%, at least 95% or at least 97% identical to a sequence selected from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77, wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein. In one embodiment, the second amino acid sequence comprises at least 75, at least 100, at least 150, or at least 200 contiguous amino acids from the group consisting of SEQ ID NO:23, SEQ ID NO:26, SEQ ID NO:29, SEQ ID NO:32, SEQ ID NO:38, SEQ ID NO:41, SEQ ID NO:44, SEQ ID NO:47, SEQ ID NO:53, SEQ ID NO:56, SEQ ID NO:59, SEQ ID NO:62, SEQ ID NO:68, SEQ ID NO:71, SEQ ID NO:74 and SEQ ID NO:77. wherein the at least 75, at least 100, at least 150 or at least 200 contiguous amino acids comprise a polypeptide sequence corresponding to the sequence of SEQ ID NO:149 or SEQ ID NO:150 of H1N1 NC, and wherein the amino acid residue in the polypeptide sequence corresponding to K1 of SEQ ID NO:149 or K1 of SEQ ID NO:150, and the amino acid residue in the polypeptide sequence that corresponds to E53 of SEQ ID NO:149 or E20 of SEQ ID NO:150 have been substituted with amino acids other than lysine and glutamic acid, respectively, such that the strength of the interaction between the substituted amino acid residues is greater than the strength of the interaction in the wild-type protein.

Protein constructs containing the specified site-specific mutations can be used to make nanoparticles of the present invention by joining them to monomeric subunits. Thus, in one embodiment, the protein construct containing the disclosed site-specific mutations (e.g., K1 of SEQ ID NO:149 or SEQ ID NO:150 and E53 of SEQ ID N0149 or E20 of SEQ ID NO:150) is joined to at least a portion of a monomeric subunit protein, wherein the portion of the monomeric subunit protein is capable of directing self-assembly of protein constructs. In one embodiment, the at least a portion of the monomeric subunit protein is joined to the second amino acid sequence. In a preferred embodiment, the at least a portion of the monomeric subunit protein is joined to the carboxyl end of the second amino acid sequence. In one embodiment, the portion comprises at least 50, at least 100 or at least 150 amino acids from a monomeric subunit. In one embodiment, the monomeric subunit is ferritin. In one embodiment, the monomeric subunit is lumazine synthase. In one embodiment, the monomeric subunit comprises a sequence at least 85% identical, at least 90% identical or at least 95% identical to SEQ ID NO:2, SEQ ID NO:5 or SEQ ID NO:194. In one embodiment, the monomeric subunit comprises a sequence selected from the group consisting of SEQ ID NO:2, SEQ ID NO:5 and SEQ ID NO:194.

While the modifications made to the HA proteins disclosed herein have been described as separate embodiments, it should be appreciated that all such modification may be contained in a single protein construct. For example, a protein construct could be made in which a first amino acid sequence is joined by a linker to a second amino acid sequence, wherein the second amino acid sequence comprises amino acid sequence from the region downstream of the carboxyl-terminal end of the head region but lacks the internal loop sequence represented by SEQ ID NOs:133-148, and wherein amino acids in the second amino acid sequence corresponding to K1 of SEQ ID NO:149 or K1 of SEQ ID NO:50 and E53 of SEQ ID NO:149 or E20 of SEQ ID NO:150 have been substituted with amino acids other than lysine and glutamic acid, respectively, in order to increase the strength of the interaction between these amino acid residues in the folded protein. Thus, one embodiment of the present invention is a protein construct comprising a first amino acid sequence from the stem region of an influenza virus HA protein and a second amino acid sequence from the stem region of an influenza virus HA protein, the first and second amino acid sequences being covalently linked by a linker sequence,
  wherein the first amino acid sequence comprises at least 20 contiguous amino acid residues from the amino acid sequence upstream of the amino-terminal end of the head region sequence;
  wherein the second amino acid sequence comprises a polypeptide sequence at least 85%, at least 90% or at least 95% identical to at least 100 contiguous amino acid residues from the amino acid sequence downstream of the carboxyl-terminal end of the head region sequence,
  wherein the polypeptide sequence comprises a sequence corresponding to the sequence in influenza A New Caledonia/20/1999 (H1) represented by SEQ ID NO:150, the sequence in influenza A California/2009 (H1) represented by SEQ ID NO:152, the sequence in influenza A Singapore/1957 (H2) represented by SEQ ID NO:154, and the sequence in influenza A Indonesia/2005 H5) represented by SEQ ID NO:156; and,
  wherein the amino acid residue in the polypeptide sequence that corresponds to K1 of SEQ ID NO:150 has been substituted with an amino acid other than lysine and the amino acid residue corresponding to E20 of SEQ ID NO:150 has been substituted with an amino acid other than glutamic acid.

In one embodiment, the polypeptide comprises at least 100 contiguous amino acids from the amino acid sequence downstream of the carboxyl-terminal end of the head region sequence. In one embodiment, the at least 100 contiguous amino acids comprise SEQ ID NO:150. In one embodiment, the at least 100 contiguous amino acids comprise SEQ ID NO:152. In one embodiment, the at least 100 contiguous amino acids sequence comprise SEQ ID NO:154. In one embodiment, the at least 100 contiguous amino acids comprise SEQ ID NO:156. It should be appreciated that in the above-described constructs, when the internal loop region is removed, the respective ends of the remaining HA protein can be directly joined together. However, in some cases, such direct linkage may reduce the flexibility of the peptide backbone. Thus, in some cases, it may be beneficial to replace the internal loop region with a linker sequence. As an example, if a six amino acid linker sequence were inserted into SEQ ID NO:150, the final sequence may appear as follows: VNSVIEKMGSGGSGTYNAELLVLL.

Accordingly, in one embodiment, the polypeptide sequence of the protein construct comprises SEQ ID NO:150, into which is inserted a short linker sequence. In one embodiment, the polypeptide sequence of the protein construct comprises SEQ ID NO:152, into which is inserted a short linker sequence. In one embodiment, the polypeptide sequence of the protein construct comprises SEQ ID NO:154, into which is inserted a short linker sequence. In one embodiment, the polypeptide sequence of the protein construct comprises SEQ ID NO:156, into which is inserted a short linker sequence. In one embodiment, the linker is made from serine and glycine residues. In one embodiment, the linker is less than ten amino acids in length. In one embodiment, the linker is less than 5 amino acids in length. In one embodiment, the linker is less than three amino acids in length.

While the protein constructs described heretofore can be used to produce nanoparticles capable of generating an immune response against one or more influenza viruses, in some embodiments, it may be useful to engineer further mutations into the amino acid sequences of proteins of the present invention. For example, it may be useful to alter sites such as enzyme recognition sites or glycosylation sites in the monomeric subunit protein, the trimerization domain, or linker sequences, in order to give the protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site. One such sequence of a mutated monomeric ferritin subunit is represented by SEQ ID NO:5.

Protein construct sequences can also be altered to include further useful mutations. For example, in some instances, it may be desirable to block the production of an immune response against certain amino acid sequences in the protein construct. This may be done by adding a glycosylation site near the site to be blocked such that the glycans sterically hinder the ability of the immune system to reach the blocked site. Thus, in one embodiment, the sequence of the protein construct has been altered to include one or more glycosylation sites. Examples of such sites include, but are not limited to, Asn-X-Ser, Asn-X-Thr and Asn-X-Cys. In some instances, the glycosylation site can be introduced into a linker sequence. Further examples of useful sites at which to introduce glycosylation sites include, but are not limited to, the amino acid corresponding to amino acids 45-47, or amino acids 370-372 from the HA protein of influenza A New Caledonia/20/1999 (H1). Methods of introducing glycosylation sites are known to those skilled in the art.

The disclosure herein demonstrates that mutations at specific locations in the HA or monomeric subunit protein produce useful protein constructs and consequently nanoparticles of the present invention. Examples of useful locations in a ferritin protein at which to introduce mutations include an amino acid corresponding to an amino acid position selected from the group consisting of amino acid position 18, amino acid position 20 and amino acid position 68 of SEQ ID NO:2. Examples of useful locations at which to introduce mutations include an amino acid in the HA protein corresponding to an amino acid position selected from the group consisting of amino acid position 36, amino acid position 45, amino acid position 47, amino acid position 49, amino acid position 339, amino acid position 340, amino acid position 341, amino acid position 342, amino acid position 361, amino acid position 372, amino acid position 394, amino acid position 402, amino acid position 437, amino acid position 438, amino acid position 445, amino acid position 446, amino acid position 448, amino acid 449, amino acid position 450 and amino acid position 452 of HA protein of influenza A New Caledonia/20/1999 (H1) (SEQ ID NO:8). Some examples of such mutations are listed in Table 2. In one embodiment, the HA portion of the protein construct comprises an isoleucine, or an amino acid residue having similar properties thereto, at the position corresponding to amino acid position 36 of HA protein of influenza A New Caledonia/20/1999 (H1). In one embodiment, the HA portion of the protein construct comprises an asparagine, or an amino acid residue having similar properties thereto, at the position corresponding to amino acid position 45 of HA protein of influenza A New Caledonia/20/1999 (H1). In one embodiment, the HA portion of the protein construct comprises a threonine, or an amino acid residue having similar properties thereto, at the position corresponding to amino acid position 47 of HA protein of influenza A New Caledonia/20/1999 (H1). In one embodiment, the HA portion of the protein construct comprises a tryptophan, or an amino acid residue having similar properties thereto, at the position corresponding to amino acid position 49 of HA protein of influenza A New Caledonia/20/1999 (H1). In one embodiment, the HA portion of the protein construct comprises an glutamine, or an amino acid residue having similar properties thereto, at the position corresponding to amino acid position 339 of HA protein of influenza A New Caledonia/20/1999 (H1). In one embodiment, the HA portion of the protein construct comprises an arginine, or an amino acid residue having similar properties thereto, at the position corresponding to amino acid position 340 of HA protein of influenza A New Caledonia/20/1999 (H1). In one embodiment, the HA portion of the protein construct comprises a glutamic acid, or an amino acid residue having similar properties thereto, at the position corresponding to amino acid position 341 of HA protein of influenza A New Caledonia/20/1999 (H1). In one embodiment, the HA portion of the protein construct comprises a threonine, or an amino acid residue having similar properties thereto, at the position corresponding to amino acid position 342 of HA protein of influenza A New Caledonia/20/1999 (H1). In one embodiment, the HA portion of the protein construct comprises a threonine, or an amino acid residue having similar properties thereto, at the position corresponding to amino acid position 372 of HA protein of influenza A New Caledonia/20/1999 (H1). In one embodiment, the HA portion of the protein construct comprises a methionine, an isoleucine, a leucine, a glutamine, or an amino acid residue having similar properties thereto, at the position corresponding to amino acid position 394 of HA protein of influenza A New Caledonia/20/1999 (H1). In one embodiment, the HA portion of the protein construct comprises an asparagine, a threonine, a glycine, an asparagine, or an amino acid residue having similar properties thereto, at the position corresponding to amino acid position 402 of HA protein of influenza A New Caledonia/20/1999 (H1). In one embodiment, the HA portion of the protein construct comprises an aspartic acid, or an amino acid residue having similar properties thereto, at the position corresponding to amino acid position 437 of HA protein of influenza A New Caledonia/20/1999 (H1). In one embodiment, the HA portion of the protein construct comprises a leucine, or an amino acid residue having similar properties thereto, at the position corresponding to amino acid position 438 of HA protein of influenza A New Caledonia/20/1999 (H1). In one embodiment, the HA portion of the protein construct comprises a leucine, a methionine, or an amino acid residue having similar properties thereto, at the position corresponding to amino acid position 445 of HA protein of influenza A New Caledonia/20/1999 (H1). In one embodiment, the HA portion of the protein construct comprises an isoleucine, a leucine, a methionine, a glutamine, or an amino acid residue having similar properties thereto, at the position corresponding to amino acid position 446 of HA protein of influenza A New Caledonia/20/1999 (H1). In one embodiment, the HA portion of the protein construct comprises a glutamine, or an amino acid residue having similar properties thereto, at the position corresponding to amino acid position 448 of HA protein of influenza A New Caledonia/20/1999 (H1). In one embodiment, the HA portion of the protein construct comprises a tryptophan, a phenylalanine, or an amino acid residue having similar properties thereto, at the position corresponding to amino acid position 449 of HA protein of influenza A New Caledonia/20/1999 (H1). In one embodiment, the HA portion of the protein construct comprises an alanine, or an amino acid residue having similar properties thereto, at the position corresponding to amino acid position 450 of HA protein of influenza A New Caledonia/20/1999 (H1). In one embodiment, the HA portion of the protein construct comprises a leucine, or an amino acid residue having similar properties thereto, at the position corresponding to amino acid position 452 of HA protein of influenza A New Caledonia/20/1999 (H1). In one embodiment, the HA portion of the protein construct lacks one or more amino acids corresponding to amino acids 515-517 of the HA protein of influenza A New Caledonia/20/1999 (Hi).

One embodiment of the present invention is a protein construct comprising an amino acid sequence at least 85%, at least 90%, at least 95% or at least 97% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

In one embodiment, the amino acid residue corresponding to K1 of SEQ ID NO:149 or K1 of SEQ ID NO:150 is substituted with an amino acid other than lysine, and the amino acid residue corresponding to E53 of SEQ ID NO:149 or E20 of SEQ ID NO:20 is substituted with an amino acid other than glutamic acid, such that the strength of the interaction between the substituted amino acids is increased in the folded protein.

One embodiment of the present invention is a protein construct comprising a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment, the protein construct is capable of forming a nanoparticle when linked to a monomeric subunit protein, wherein the nanoparticle is capable of eliciting an immune response against an influenza virus.

As has been discussed previously, protein constructs made from influenza HA protein can be used to make nanoparticles of the present invention by joining them to monomeric subunits. Thus, in one embodiment, the protein construct is joined to at least a portion of a monomeric subunit protein, wherein the portion of the monomeric subunit protein is capable of directing self-assembly of protein constructs. In one embodiment, the at least a portion of the monomeric subunit protein is joined to the second amino acid sequence. In a preferred embodiment, the at least a portion of the monomeric subunit protein is joined to the carboxyl end of the second amino acid sequence. In one embodiment, the portion comprises at least 50, at least 100 or at least 150 amino acids from a monomeric subunit. In one embodiment, the monomeric subunit is ferritin. In one embodiment, the monomeric subunit is lumazine synthase. In one embodiment, the monomeric subunit comprises a sequence at least 85% identical, at least 90% identical or at least 95% identical to SEQ ID NO:2, SEQ ID NO:5 or SEQ ID NO:194. In one embodiment, the monomeric subunit comprises a sequence selected from the group consisting of SEQ ID NO:2, SEQ ID NO:5 and SEQ ID NO:194.

One embodiment of the present invention is a protein construct comprising an amino acid sequence at least 85%, at least 90%, at least 95% or at least 97% identical to a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397. In one embodiment, the amino acid residue corresponding to K1 of SEQ ID NO:149 or K1 of SEQ ID NO:150 is substituted with an amino acid other than lysine, and the amino acid residue corresponding to E53 of SEQ ID NO:149 or E20 of SEQ ID NO:20 is substituted with an amino acid other than glutamic acid, such that the strength of the interaction between the substituted amino acids is increased in the folded protein. In one embodiment, the HA portion of the protein construct comprises an isoleucine, or an amino acid residue having similar properties thereto, at the position corresponding to amino acid position 36 of HA protein of influenza A New Caledonia/20/1999 (H1). In one embodiment, the HA portion of the protein construct comprises an asparagine, or an amino acid residue having similar properties thereto, at the position corresponding to amino acid position 45 of HA protein of influenza A New Caledonia/20/1999 (H1). In one embodiment, the HA portion of the protein construct comprises a threonine, or an amino acid residue having similar properties thereto, at the position corresponding to amino acid position 47 of HA protein of influenza A New Caledonia/20/1999 (H1). In one embodiment, the HA portion of the protein construct comprises a tryptophan, or an amino acid residue having similar properties thereto, at the position corresponding to amino acid position 49 of HA protein of influenza A New Caledonia/20/1999 (H1). In one embodiment, the HA portion of the protein construct comprises an glutamine, or an amino acid residue having similar properties thereto, at the position corresponding to amino acid position 339 of HA protein of influenza A New Caledonia/20/1999 (H1). In one embodiment, the HA portion of the protein construct comprises an arginine, or an amino acid residue having similar properties thereto, at the position corresponding to amino acid position 340 of HA protein of influenza A New Caledonia/20/1999 (H1). In one embodiment, the HA portion of the protein construct comprises a glutamic acid, or an amino acid residue having similar properties thereto, at the position corresponding to amino acid position 341 of HA protein of influenza A New Caledonia/20/1999 (H1). In one embodiment, the HA portion of the protein construct comprises a threonine, or an amino acid residue having similar properties thereto, at the position corresponding to amino acid position 342 of HA protein of influenza A New Caledonia/20/1999 (H1). In one embodiment, the HA portion of the protein construct comprises a threonine, or an amino acid residue having similar properties thereto, at the position corresponding to amino acid position 372 of HA protein of influenza A New Caledonia/20/1999 (H1). In one embodiment, the HA portion of the protein construct comprises a methionine, an isoleucine, a leucine, a glutamine, or an amino acid residue having similar properties thereto, at the position corresponding to amino acid position 394 of HA protein of influenza A New Caledonia/20/1999 (H1). In one embodiment, the HA portion of the protein construct comprises an asparagine, a threonine, a glycine, an asparagine, or an amino acid residue having similar properties thereto, at the position corresponding to amino acid position 402 of HA protein of influenza A New Caledonia/20/1999 (H1). In one embodiment, the HA portion of the protein construct comprises an aspartic acid, or an amino acid residue having similar properties thereto, at the position corresponding to amino acid position 437 of HA protein of influenza A New Caledonia/20/1999 (H1). In one embodiment, the HA portion of the protein construct comprises a leucine, or an amino acid residue having similar properties thereto, at the position corresponding to amino acid position 438 of HA protein of influenza A New Caledonia/20/1999 (H1). In one embodiment, the HA portion of the protein construct comprises a leucine, a methionine, or an amino acid residue having similar properties thereto, at the position corresponding to amino acid position 445 of HA protein of influenza A New Caledonia/20/1999 (H1). In one embodiment, the HA portion of the protein construct comprises an isoleucine, a leucine, a methionine, a glutamine, or an amino acid residue having similar properties thereto, at the position corresponding to amino acid position 446 of HA protein of influenza A New Caledonia/20/1999 (H1). In one embodiment, the HA portion of the protein construct comprises a glutamine, or an amino acid residue having similar properties thereto, at the position corresponding to amino acid position 448 of HA protein of influenza A New Caledonia/20/1999 (H1). In one embodiment, the HA portion of the protein construct comprises a tryptophan, a phenylalanine, or an amino acid residue having similar properties thereto, at the position corresponding to amino acid position 449 of HA protein of influenza A New Caledonia/20/1999 (H1). In one embodiment, the HA portion of the protein construct comprises an alanine, or an amino acid residue having similar properties thereto, at the position corresponding to amino acid position 450 of HA protein of influenza A New Caledonia/20/1999 (H1). In one embodiment, the HA portion of the protein construct comprises a leucine, or an amino acid residue having similar properties thereto, at the position corresponding to amino acid position 452 of HA protein of influenza A New Caledonia/20/1999 (H1). In one embodiment, the HA portion of the protein construct lacks one or more amino acids corresponding to amino acids 515-517 of the HA protein of influenza A New Caledonia/20/1999 (H1).

One embodiment of the present invention is a protein construct comprising a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397.

One embodiment of the present invention is a protein construct encoded by a nucleic acid molecule comprising a nucleic acid sequence at least 85%, at least 90%, at least 95% or at least 97% identical to a sequence selected from the group consisting of SEQ ID NO:266, SEQ ID NO:273, SEQ ID NO:SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399. One embodiment of the present invention is a protein construct encoded by a nucleic acid molecule comprising a nucleic acid sequence selected from the group consisting of SEQ ID NO:266, SEQ ID NO:273, SEQ ID NO:SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399.

Proteins and protein constructs of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual*, 3$^{rd}$ edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a protein construct of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

One embodiment is a nucleic acid molecule encoding an influenza HA protein comprising an amino acid sequence at least 80%, at least 85%, at least 90%, at least 92%, at least 94%, at least 96%, at least 98% or at least 99% identical to a sequence selected from the group consisting of SEQ ID NO:150, SEQ ID NO152, SEQ ID NO:154 and SEQ ID NO:156. One embodiment is a nucleic acid molecule encoding an influenza HA protein comprising an amino acid sequence selected from the group consisting of SEQ ID NO:150, SEQ ID NO152, SEQ ID NO:154 and SEQ ID NO:156.

In one embodiment the nucleic acid molecule encodes an influenza HA protein comprising an amino acid sequence at least 80%, at least 85%, at least 90%, at least 92%, at least 94%, at least 96%, at least 98% or at least 99% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400. In one embodiment the nucleic acid molecule encodes an influenza HA protein comprising an amino acid selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

One embodiment of the present invention is a nucleic acid molecule comprising a nucleic acid sequence comprising an amino acid sequence at least 80%, at least 85%, at least 90%, at least 92%, at least 94%, at least 96%, at least 98% or at least 99% identical to a sequence selected from the group consisting of SEQ ID NO:79, SEQ ID NO:82, SEQ ID NO:85, SEQ ID NO:88, SEQ ID NO:91, SEQ ID NO:94, SEQ ID NO:97, SEQ ID NO:100, SEQ ID NO:103, SEQ ID NO:157, SEQ ID NO:163, SEQ ID NO:169, SEQ ID NO:175, SEQ ID NO:181, SEQ ID NO:187, SEQ ID NO:196, SEQ ID NO:202, SEQ ID NO:208, SEQ ID NO:216, SEQ ID NO:234, SEQ ID NO:260, SEQ ID NO:267, SEQ ID NO:274, SEQ ID NO:281, SEQ ID NO:288, SEQ ID NO:295, SEQ ID NO:302, SEQ ID NO:309, SEQ ID NO:316, SEQ ID NO:323, SEQ ID NO:330, SEQ ID NO:337, SEQ ID NO:344, SEQ ID NO:351, SEQ ID NO:358, SEQ ID NO:365, SEQ ID NO:372, SEQ ID NO:379, SEQ ID NO:386 and SEQ ID NO:393. One embodiment of the present invention is a nucleic acid molecule comprising a nucleic acid sequence selected from the group consisting of SEQ ID NO:79, SEQ ID NO:82, SEQ ID NO:85, SEQ ID NO:88, SEQ ID NO:91, SEQ ID NO:94, SEQ ID NO:97, SEQ ID NO:100, SEQ ID NO:103, SEQ ID NO:157, SEQ ID NO:163, SEQ ID NO:169, SEQ ID NO:175, SEQ ID NO:181, SEQ ID NO:187, SEQ ID NO:196, SEQ ID NO:202, SEQ ID NO:208, SEQ ID NO:216, SEQ ID NO:234, SEQ ID NO:260, SEQ ID NO:267, SEQ ID NO:274, SEQ ID NO:281, SEQ ID NO:288, SEQ ID NO:295, SEQ ID NO:302, SEQ ID NO:309, SEQ ID NO:316, SEQ ID NO:323, SEQ ID NO:330, SEQ ID NO:337, SEQ ID NO:344, SEQ ID NO:351, SEQ ID NO:358, SEQ ID NO:365, SEQ ID NO:372, SEQ ID NO:379, SEQ ID NO:386 and SEQ ID NO:393.

Preferred nucleic acid molecules are those that encode a monomeric subunit, a HA protein, and/or a protein construct comprising a monomeric subunit protein joined to an influenza HA protein. Thus, one embodiment of the present invention is a nucleic acid molecule comprising a nucleic acid sequence encoding a protein that comprises a monomeric subunit of a ferritin protein joined to an influenza HA protein. In one embodiment, the monomeric subunit comprises an amino acid sequence at least 80%, at least 85%, at least 90%, at least 92%, at least 94%, at least 96%, at least 98% or at least 99% identical to a sequence selected from the group consisting of SEQ ID NO:2 and SEQ ID NO:5. In one embodiment, the monomeric subunit comprises an amino acid sequence selected from the group consisting of SEQ ID NO:2 and SEQ ID NO:5.

One embodiment of the present invention is a nucleic acid molecule comprising a nucleic acid sequence encoding a protein that comprises a monomeric subunit of lumazine synthase joined to an influenza HA protein. In one embodiment, the monomeric subunit comprises an amino acid sequence at least 80%, at least 85%, at least 90%, at least 92%, at least 94%, at least 96%, at least 98% or at least 99% identical to SEQ ID NO:194. In one embodiment, the monomeric subunit comprises SEQ ID NO:194.

One embodiment of the present invention is a nucleic acid molecule encoding a protein construct comprising an amino acid sequence at least 80%, at least 85%, at least 90%, at least 92%, at least 94%, at least 96%, at least 98% or at least 99% identical to a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397. One embodiment of the resent invention is a nucleic acid molecule encoding a protein construct comprising a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397.

One embodiment of the present invention is a nucleic acid molecule comprising a nucleic acid sequence at least 80%, at least 85%, at least 90%, at least 92%, at least 94%, at least 96%, at least 98% or at least 99% identical to a sequence selected from the group consisting of SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:160, SEQ ID NO:166, SEQ ID NO:172, SEQ ID NO:178, SEQ ID NO:184, SEQ ID NO:190, SEQ ID NO:199, SEQ ID NO:205, SEQ ID NO:211, SEQ ID NO:219, SEQ ID NO:237, SEQ ID NO:263, SEQ ID NO:270, SEQ ID NO:277, SEQ ID NO:284, SEQ ID NO:291, SEQ ID NO:298, SEQ ID NO:305, SEQ ID NO:312, SEQ ID NO:319, SEQ ID NO:326, SEQ ID NO:333, SEQ ID NO:340, SEQ ID NO:347, SEQ ID NO:354, SEQ ID NO:361, SEQ ID NO:368, SEQ ID NO:375, SEQ ID NO:382, SEQ ID NO:389 and SEQ ID NO:396. One embodiment of the present invention is a nucleic acid molecule comprising a nucleic acid sequence selected from the group consisting of SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:160, SEQ ID NO:166, SEQ ID NO:172, SEQ ID NO:178, SEQ ID NO:184, SEQ ID NO:190, SEQ ID NO:199, SEQ ID NO:205, SEQ ID NO:211, SEQ ID NO:219, SEQ ID NO:237, SEQ ID NO:263, SEQ ID NO:270, SEQ ID NO:277, SEQ ID NO:284, SEQ ID NO:291, SEQ ID NO:298, SEQ ID NO:305, SEQ ID NO:312, SEQ ID NO:319, SEQ ID NO:326, SEQ ID NO:333, SEQ ID NO:340, SEQ ID NO:347, SEQ ID NO:354, SEQ ID NO:361, SEQ ID NO:368, SEQ ID NO:375, SEQ ID NO:382, SEQ ID NO:389 and SEQ ID NO:396.

Also encompassed by the present invention are expression systems for producing protein constructs of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a nucleic acid molecule comprising a nucleic acid sequence at least 85%, at least 90%, at least 95% or at least 97% identical to a sequence selected from the group consisting of SEQ ID NO:266, SEQ ID NO:273, SEQ ID NO:SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399. One embodiment of the present invention is a nucleic acid molecule comprising a nucleic acid sequence selected from the group consisting of SEQ ID NO:266, SEQ ID NO:273, SEQ ID NO:SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399.

One embodiment of the present invention is a recombinant cell comprising a nucleic acid molecule of the present invention. One embodiment of the present invention is a recombinant virus comprising a nucleic acid molecule of the present invention.

As indicated above, the recombinant production of the protein constructs of the present invention can be accomplished using any suitable conventional recombinant technology currently known in the field. For example, production of a nucleic acid molecule encoding a fusion protein can be carried out in *E. coli* using a nucleic acid molecule encoding a suitable monomeric subunit protein, such as the *Helicobacter pylori* ferritin monomeric subunit, ad fusing it to a nucleic acid molecule encoding a suitable influenza protein disclosed herein. The construct may then be transformed into protein expression cells, grown to suitable size, and induced to produce the fusion protein.

As has been described, because protein constructs of the present invention comprise a monomeric subunit protein, they can self-assemble. According to the present invention, the supramolecule resulting from such self-assembly is referred to as an HA expressing, monomeric subunit-based nanoparticle. For ease of discussion, the HA expressing, monomeric subunit-based nanoparticle will simply be referred to as a, or the, nanoparticle (np). Nanoparticles of the present invention have similar structural characteristics as the nanoparticles of the monomeric protein from which they are made. For example, with regard to ferritin, a ferritin-based nanoparticle contains 24 subunits and has 432 symmetry. In the case of nanoparticles of the present invention, the subunits are the protein constructs comprising a monomeric subunit (e.g., ferritin, lumazine synthase, etc.) joined to an influenza HA protein. Such nanoparticles display at least a portion of the HA protein on their surface as HA trimers. In such a construction, the HA trimer is accessible to the immune system and thus can elicit an immune response. Thus, one embodiment of the present invention is a nanoparticle comprising a protein construct of the present invention, wherein the protein construct comprises amino acids from the stem region of an HA protein joined to a monomeric subunit protein. In one embodiment, the nanoparticle displays the HA protein on its surface as a HA trimer. In one embodiment, the influenza HA protein is capable of eliciting protective antibodies to an influenza virus.

In one embodiment of the present invention, the nanoparticle comprises a protein construct comprising a first amino acid sequence from the stem region of an influenza virus HA protein and a second amino acid sequence from the stem region of an influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence;

wherein the second amino acid sequence comprises at least 20 contiguous amino acid residues from the amino acid sequence downstream of the carboxyl-terminal end of the head region sequence; and, wherein the first or second amino acid sequence is joined to at least a portion of a monomeric subunit domain.

In one embodiment of the present invention, the nanoparticle comprises a protein construct comprising a first amino acid sequence from the stem region of an influenza virus HA protein and a second amino acid sequence from the stem region of an influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence;

wherein the second amino acid sequence comprises a polypeptide sequence at least 85%, at least 90% or at least 95% identical to at least 100 contiguous amino acid residues from the amino acid sequence downstream of the carboxyl-terminal end of the head region sequence, wherein the polypeptide sequence comprises a sequence corresponding to the sequence in influenza A New Caledonia/20/1999 (H1) represented by SEQ ID NO:150, the sequence in influenza A California/2009 (H1) represented by SEQ ID NO:152, the sequence in influenza A Singapore/1957 (H2) represented by SEQ ID NO:154, and the sequence in influenza A Indonesia/2005 H5) represented by SEQ ID NO:156; and, wherein the first or second amino acid sequence is joined to a monomeric subunit protein.

In a further embodiment, the amino acid residue in the polypeptide sequence that corresponds to K1 of SEQ ID NO:150 has been substituted with an amino acid other than lysine and the amino acid residue corresponding to E20 of SEQ ID NO:150 has been substituted with an amino acid other than glutamic acid.

In one embodiment, additional mutations have been made in the monomeric subunit portion and/or the first and/or second amino acid sequences of the protein construct that makes up the nanoparticle. Examples of useful locations in a ferritin protein at which to introduce mutations include an amino acid corresponding to an amino acid position selected from the group consisting of amino acid position 18, amino acid position 20 and amino acid position 68 of SEQ ID NO:2. In one embodiment, the protein construct comprises a mutation at an amino acid position corresponding to an amino acid position selected from the group consisting of amino acid position 36, amino acid position 45, amino acid position 47, amino acid position 49, amino acid position 339, amino acid position 340, amino acid position 341, amino acid position 342, amino acid position 361, amino acid position 372, amino acid position 394, amino acid position 402, amino acid position 437, amino acid position 438, amino acid position 445, amino acid position 446, amino acid position 448, amino acid position 449, amino acid position 450 and amino acid position 452 of HA protein of influenza A New Caledonia/20/1999 (H1) (SEQ ID NO:8). In one embodiment, the HA portion of the protein construct comprises an isoleucine, or an amino acid residue having similar properties thereto, at the position corresponding to amino acid position 36 of HA protein of influenza A New Caledonia/20/1999 (H1). In one embodiment, the HA portion of the protein construct comprises an asparagine, or an amino acid residue having similar properties thereto, at the position corresponding to amino acid position 45 of HA protein of influenza A New Caledonia/20/1999 (H1). In one embodiment, the HA portion of the protein construct comprises a threonine, or an amino acid residue having similar properties thereto, at the position corresponding to amino acid position 47 of HA protein of influenza A New Caledonia/20/1999 (H1). In one embodiment, the HA portion of the protein construct comprises a tryptophan, or an amino acid residue having similar properties thereto, at the position corresponding to amino acid position 49 of HA protein of influenza A New Caledonia/20/1999 (H1). In one embodiment, the HA portion of the protein construct comprises an glutamine, or an amino acid residue having similar properties thereto, at the position corresponding to amino acid position 339 of HA protein of influenza A New Caledonia/20/1999 (H1). In one embodiment, the HA portion of the protein construct comprises an arginine, or an amino acid residue having similar properties thereto, at the position corresponding to amino acid position 340 of HA protein of influenza A New Caledonia/20/1999 (H1). In one embodiment, the HA portion of the protein construct comprises a glutamic acid, or an amino acid residue having similar properties thereto, at the position corresponding to amino acid position 341 of HA protein of influenza A New Caledonia/20/1999 (H1). In one embodiment, the HA portion of the protein construct comprises a threonine, or an amino acid residue having similar properties thereto, at the position corresponding to amino acid position 342 of HA protein of influenza A New Caledonia/20/1999 (H1). In one embodiment, the HA portion of the protein construct comprises a threonine, or an amino acid residue having similar properties thereto, at the position corresponding to amino acid position 372 of HA protein of influenza A New Caledonia/20/1999 (H1). In one embodiment, the HA portion of the protein construct comprises a methionine, an isoleucine, a leucine, a glutamine, or an amino acid residue having similar properties thereto, at the position corresponding to amino acid position 394 of HA protein of influenza A New Caledonia/20/1999 (H1). In one embodiment, the HA portion of the protein construct comprises an asparagine, a threonine, a glycine, an asparagine, or an amino acid residue having similar properties thereto, at the position corresponding to amino acid position 402 of HA protein of influenza A New Caledonia/20/1999 (H1). In one embodiment, the HA portion of the protein construct comprises an aspartic acid, or an amino acid residue having similar properties thereto, at the position corresponding to amino acid position 437 of HA protein of influenza A New Caledonia/20/1999 (H1). In one embodiment, the HA portion of the protein construct comprises a leucine, or an amino acid residue having similar properties thereto, at the position corresponding to amino acid position 438 of HA protein of influenza A New Caledonia/20/1999 (H1). In one embodiment, the HA portion of the protein construct comprises a leucine, a methionine, or an amino acid residue having similar properties thereto, at the position corresponding to amino acid position 445 of HA protein of influenza A New Caledonia/20/1999 (H1). In one embodiment, the HA portion of the protein construct comprises an isoleucine, a leucine, a methionine, a glutamine, or an amino acid residue having similar properties thereto, at the position corresponding to amino acid position 446 of HA protein of influenza A New Caledonia/20/1999 (H1). In one embodiment, the HA portion of the protein construct comprises a glutamine, or an amino acid residue having similar properties thereto, at the position corresponding to amino acid position 448 of HA protein of influenza A New Caledonia/20/1999 (H1). In one embodiment, the HA portion of the protein construct comprises a tryptophan, a phenylalanine, or an amino acid residue having similar properties thereto, at the position corresponding to amino acid position 449 of HA protein of influenza A New Caledonia/20/1999 (H1). In one embodiment, the HA portion of the protein construct comprises an alanine, or an amino acid residue having similar properties thereto, at the position corresponding to amino acid position 450 of HA protein of influenza A New Caledonia/20/1999 (H1). In one embodiment, the HA portion of the protein construct comprises a leucine, or an amino acid residue having similar properties thereto, at the position corresponding to amino acid position 452 of HA protein of influenza A New Caledonia/20/1999 (H1). In one embodiment, the HA portion of the protein construct lacks one or more amino acids corresponding to amino acids 515-517 of the HA protein of influenza A New Caledonia/20/1999 (H1).

In one embodiment, a nanoparticle of the present invention comprises a monomeric subunit protein comprising at least 50 amino acids, at least 100 amino acids, or at least 150 amino acids from lumazine synthase. In one embodiment, the monomeric subunit protein comprises at least 50 amino acids, at least 100 amino acids, or at least 150 amino acids from an amino acid sequence selected from SEQ ID NO:194, and/or comprises an amino acid sequence at least 85%, at least 90%, at least 95%, at least 97% at least 99% identical to SEQ ID NO:194. In one embodiment, the monomeric subunit comprises SEQ ID NO:194.

In one embodiment, the monomeric subunit protein comprises at least 50 amino acids, at least 100 amino acids, or at least 150 amino acids from a ferritin protein. In one embodiment, the monomeric subunit protein comprises at least 50 amino acids, at least 100 amino acids, or at least 150 amino acids from an amino acid sequence selected from the group consisting of SEQ ID NO:2 and SEQ ID NO:5, and/or comprises an amino acid sequence at least 85%, at least 90%, at least 95%, at least 97% at least 99% identical to an amino acid sequence selected from the group consisting of SEQ ID NO:2 and SEQ ID NO:5. In one embodiment, the monomeric ferritin subunit comprises SEQ ID NO:2 or SEQ ID NO:5.

In one embodiment, the nanoparticle comprises a protein construct comprising a monomeric protein of the present invention joined to at least one immunogenic portion of an HA protein from a virus selected from the group consisting of influenza type A viruses, influenza type B viruses and influenza type C viruses. In one embodiment the protein construct comprises a monomeric protein of the present invention joined to at least one immunogenic portion of an HA protein selected from the group consisting of an H1 influenza virus HA protein, an H2 influenza virus HA protein, H3 influenza virus HA protein, an H4 influenza virus HA protein, an H5 influenza virus HA protein, an H6 influenza virus HA protein, an H7 virus influenza HA protein, an H8 influenza virus HA protein, an H9 influenza virus HA protein, an H10 influenza virus HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. In, one embodiment the immunogenic portion comprises at least one epitope.

In one embodiment, the nanoparticle comprises a protein construct comprising a monomeric protein of the present invention joined to amino acid sequence at least about 80%, at least about 85%, at least about 90%, at least about 95%, at least about 97% or at least about 99% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400, wherein the protein construct is capable of selectively binding anti-influenza antibodies. In one embodiment, the nanoparticle comprises a protein construct comprising a monomeric protein of the present invention joined to amino acid sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400, wherein the protein construct is capable of selectively binding anti-influenza antibodies.

In one embodiment of the present invention, the nanoparticle comprises a protein construct comprising an amino acid sequence at least 80%, at least about 85%, at least about 90%, at least about 95%, at least about 97% or at least about 99% identical to a sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397, wherein the protein construct is capable of selectively binding anti-influenza antibodies. In one embodiment of the present invention, the nanoparticle comprises a protein construct comprising an amino acid sequence selected from the group consisting of SEQ ID NO:107, SEQ ID NO:110, SEQ ID NO:113, SEQ ID NO:116, SEQ ID NO:119, SEQ ID NO:122, SEQ ID NO:125, SEQ ID NO:128, SEQ ID NO:131, SEQ ID NO:161, SEQ ID NO:167, SEQ ID NO:173, SEQ ID NO:179, SEQ ID NO:185, SEQ ID NO:191, SEQ ID NO:200, SEQ ID NO:206, SEQ ID NO:212, SEQ ID NO:215, SEQ ID NO:220, SEQ ID NO:223, SEQ ID NO:225, SEQ ID NO:227, SEQ ID NO:229, SEQ ID NO:231, SEQ ID NO:233, SEQ ID NO:238, SEQ ID NO:241, SEQ ID NO:243, SEQ ID NO:245, SEQ ID NO:247, SEQ ID NO:249, SEQ ID NO:251, SEQ ID NO:253, SEQ ID NO:255, SEQ ID NO:257, SEQ ID NO:259, SEQ ID NO:264, SEQ ID NO:271, SEQ ID NO:278, SEQ ID NO:285, SEQ ID NO:292, SEQ ID NO:299, SEQ ID NO:306, SEQ ID NO:313, SEQ ID NO:320, SEQ ID NO:327, SEQ ID NO:334, SEQ ID NO:341, SEQ ID NO:348, SEQ ID NO:355, SEQ ID NO:362, SEQ ID NO:369, SEQ ID NO:376, SEQ ID NO:383, SEQ ID NO:390 and SEQ ID NO:397.

In one embodiment, a nanoparticle of the invention comprises a protein construct encoded by a nucleic acid molecule comprising a nucleic acid sequence at least 85%, at least 90%, at least 95% or at least 97% identical to a sequence selected from the group consisting of SEQ ID NO:266, SEQ ID NO:273, SEQ ID NO:SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399. In one embodiment, a nanoparticle of the invention comprises a protein construct encoded by a nucleic acid molecule comprising a nucleic acid sequence selected from the group consisting of SEQ ID NO:266, SEQ ID NO:273, SEQ ID NO:SEQ ID NO:280, SEQ ID NO:287, SEQ ID NO:294, SEQ ID NO:301, SEQ ID NO:308, SEQ ID NO:315, SEQ ID NO:322, SEQ ID NO:329, SEQ ID NO:336, SEQ ID NO:343, SEQ ID NO:350, SEQ ID NO:357, SEQ ID NO:364, SEQ ID NO:371, SEQ ID NO:378, SEQ ID NO:385 SEQ ID NO:392 and SEQ ID NO:399.

Nanoparticles of the present invention can be used to elicit an immune response to influenza virus. One type of immune response is a B-cell response, which results in the production of antibodies against the antigen that elicited the immune response. Thus, in one embodiment that the nanoparticle elicits antibodies that bind to the stem region of influenza HA protein from a virus selected from the group consisting of influenza A viruses, influenza B viruses and influenza C viruses. One embodiment of the present invention is a nanoparticle that elicits antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies that bind to the stem region of influenza HA protein from a strain of virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B), and variants thereof.

While all antibodies are capable of binding to the antigen which elicited the immune response that resulted in antibody production, preferred antibodies are those that provide broad heterosubtypic protection against influenza virus. Thus, one embodiment of the present invention is a nanoparticle that elicits protective antibodies that bind to the stem region of influenza HA protein from a virus selected from the group consisting of influenza A viruses, influenza B viruses and influenza C viruses. One embodiment of the present invention is a protein that elicits protective antibodies that bind to the stem region of influenza HA protein selected from the group consisting of an H1 influenza virus HA protein, an H2 influenza virus HA protein, an H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies against a virus selected from the group consisting of influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1) and B/Brisbane/60/2008 (2008 Bris, B). One embodiment of the present invention is a nanoparticle that elicits antibodies that bind to a protein comprising an amino acid sequence at least 80% identical to a sequence selected from the group consisting of SEQ ID NO:8, SEQ ID NO:11, SEQ ID NO:14 and SEQ ID NO:17. One embodiment of the present invention is a nanoparticle that elicits antibodies that bind to a protein comprising an amino acid sequence selected from the group consisting of SEQ ID NO:8, SEQ ID NO:11, SEQ ID NO:14 and SEQ ID NO:17.

Protective antibodies elicited by proteins of the present invention can protect against viral infections by affecting any step in the life cycle of the virus. For example, protective antibodies may prevent an influenza virus from attaching to a cell, entering a cell, releasing viral ribonucleoproteins into the cytoplasm, forming new viral particles in the infected cell and budding new viral particles from the infected host cell membrane. In one embodiment, protective antibodies elicited by proteins of the present invention prevent influenza virus from entering the host cell. In one embodiment, protective antibodies elicited by proteins of the present invention prevent fusion of viral membranes with endosomal membranes. In one embodiment, protective antibodies elicited by proteins of the present invention prevent release of ribonucleoproteins into the cytoplasm of the host cell. In one embodiment, protective antibodies elicited by proteins of the present invention prevent assembly of new virus in the infected host cell. In one embodiment, protective antibodies elicited by proteins of the present invention prevent release of newly formed virus from the infected host cell.

Because the amino acid sequence of the stem region of influenza virus is highly conserved, protective antibodies elicited by nanoparticles of the present invention may be broadly protective. That is, protective antibodies elicited by nanoparticles of the present invention may protect against influenza viruses of more than one type, subtype and/or strain, Thus, one embodiment of the present invention is a protein that elicits broadly protective antibodies that bind the stem region of influenza HA protein. One embodiment is a nanoparticle that elicits antibodies that bind the stem region of an HA protein from more than one type of influenza virus selected from the group consisting of influenza type A viruses, influenza type B viruses and influenza type C viruses. One embodiment is a nanoparticle that elicits antibodies that bind the stem region of an HA protein from more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. One embodiment is a nanoparticle that elicits antibodies that bind the stem region of an HA protein from more than strain of influenza virus. One embodiment of the present invention is a nanoparticle that elicits antibodies that bind more than one protein comprising an amino acid sequence at least 80% identical to a sequence selected from the group consisting of SEQ ID NO:8, SEQ ID NO:11, SEQ ID NO:14 and SEQ ID NO:17. One embodiment of the present invention is a nanoparticle that elicits antibodies that bind to more than one protein comprising an amino acid sequence selected from the group consisting of SEQ ID NO:8, SEQ ID NO:11, SEQ ID NO:14 and SEQ ID NO:17.

Because nanoparticles of the present invention can elicit an immune response to an influenza virus, they are useful as vaccines to protect individuals against infection by influenza virus. Thus, one embodiment of the present invention is a vaccine comprising a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the present invention is a nanoparticle vaccine that includes more than one influenza HA protein. Such a vaccine can include a combination of different influenza HA proteins, either on a single nanoparticle or as a mixture of nanoparticles, at least two of which have unique influenza HA proteins. A multivalent vaccine can comprise as many influenza HA proteins as necessary in order to result in production of the immune response necessary to protect against a desired breadth of virus strains. In one embodiment, the vaccine comprises an HA protein from at least two different influenza strains (bi-valent). In one embodiment, the vaccine comprises a HA protein from at least three different influenza strains (tri-valent). In one embodiment, the vaccine comprises an HA protein from at least four different influenza strains (tetra-valent). In one embodiment, the vaccine comprises an HA protein from at least five different influenza strains (penta-valent). In one embodiment, the vaccine comprises an HA protein from at least six different influenza strains (hexa-valent). In various embodiments, a vaccine comprises an HA protein from each of 7, 8, 9, or 10 different strains of influenza virus. An example of such a combination is a nanoparticle vaccine that comprises influenza A group 1 HA protein, an influenza A group 2 HA protein, and an influenza B HA protein. In one embodiment, the influenza HA proteins are H1 HA, H3 HA, and B HA. In one embodiment, the influenza HA proteins are those included in the 2011-2012 influenza vaccine. Another example of a multivalent vaccine is a nanoparticle vaccine that comprises HA proteins from four different influenza viruses. In one embodiment, the multivalent vaccine comprises HA proteins from influenza A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1) and B/Brisbane/60/2008 (2008 Bris, B).

One embodiment of the present invention is a method to vaccinate an individual against influenza virus, the method comprising administering a nanoparticle to an individual such that an immune response against influenza virus is produced in the individual, wherein the nanoparticle comprises a monomeric subunit protein joined to an influenza HA protein, and wherein the nanoparticle displays the influenza HA on its surface. In one embodiment, the nanoparticle is a monovalent nanoparticle. In one embodiment, the nanoparticle is multivalent nanoparticle. Another embodiment of the present invention is a method to vaccinate an individual against infection with influenza virus, the method comprising:

a) obtaining a nanoparticle comprising monomeric subunits, wherein the monomeric subunits are joined to an influenza hemagglutinin protein, and wherein the nanoparticle displays the influenza HA on its surface; and, b) administering the nanoparticle to an individual such that an immune response against an influenza virus is produced.

One embodiment of the present invention is a method to vaccinate an individual against influenza virus, the method comprising administering a vaccine of the embodiments to an individual such that an immune response against influenza virus is produced in the individual, wherein the vaccine comprises at least one nanoparticle comprising a monomeric subunit joined to an influenza HA protein, and wherein the nanoparticle displays the influenza HA on its surface. In one embodiment, the vaccine is a monovalent vaccine. In one embodiment, the vaccine is multivalent vaccine. Another embodiment of the present invention is a method to vaccinate an individual against infection with influenza virus, the method comprising:

a) obtaining a vaccine comprising at least one nanoparticle comprising a protein construct of the present invention, wherein the protein construct comprises a monomeric subunit protein joined to an influenza HA protein, and wherein the nanoparticle displays the influenza HA on its surface; and, b) administering the vaccine to an individual such that an immune response against an influenza virus is produced.

In one embodiment, the nanoparticle is a monovalent nanoparticle. In one embodiment, the nanoparticle is multivalent nanoparticle.

In one embodiment, the nanoparticle has octahedral symmetry. In one embodiment, the influenza HA protein is capable of eliciting antibodies to an influenza virus. In one embodiment, the influenza HA protein is capable of eliciting broadly antibodies to an influenza virus. In preferred embodiments the elicited antibodies are protective antibodies. In a preferred embodiment, the elicited antibodies are broadly heterosubtypic protective.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle of the present invention. In one embodiment, the first vaccine composition comprises a nanoparticle comprising amino acid sequences from the HA protein of an influenza virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005

(2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B).

In one embodiment, the individual being vaccinated has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", $18^{th}$ ed., 1990, Mack Publishing Co., Easton, PA. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous influenza virus. That is, a vaccine made using HA protein from one strain of influenza virus is capable of protecting an individual against infection by different strains of influenza. For example, a vaccine made using HA protein from influenza A/New Caledonia/20/1999 (1999 NC, H1), can be used to protect an individual against infection by an influenza virus including, but not limited to A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 indo, H5), A/Perth/16/2009 (2009 Per, H3), and/or A/Brisbane/59/2007 (2007 Bris, H1).

In one embodiment, vaccines, or nanoparticles, of the present invention can be used to protect an individual against infection by an antigenically divergent influenza virus. Antigenically divergent refers to the tendency of a strain of influenza virus to mutate over time, thereby changing the amino acids that are displayed to the immune system. Such mutation over time is also referred to as antigenic drift. Thus, for example, a vaccine made using HA protein from a A/New Caledonia/20/1999 (1999 NC, H1) strain of influenza virus is capable of protecting an individual against infection by earlier, antigenically divergent New Caledonia strains of influenza, and by evolving (or diverging) influenza strains of the future.

Because nanoparticles of the present invention display HA proteins that are antigenically similar to an intact HA, they can be used in assays for detecting antibodies against influenza virus (anti-influenza antibodies).

Thus, one embodiment of the present invention is a method for detecting anti-influenza virus antibodies using nanoparticles of the present invention. A detection method of the present invention can generally be accomplished by:
a. contacting at least a portion of a sample being tested for the presence of anti-influenza antibodies with a nanoparticle of the present invention; and,
b. detecting the presence of a nanoparticle/antibody complex;
wherein the presence of a nanoparticle/antibody complex indicates that the sample contains anti-influenza antibodies.

In one embodiment of the present invention, a sample is obtained, or collected, from an individual to be tested for the presence of anti-influenza virus antibodies. The individual may or may not be suspected of having anti-influenza antibodies or of having been exposed to influenza virus. A sample is any specimen obtained from the individual that can be used to test for the presence of anti-influenza virus antibodies. A preferred sample is a body fluid that can be used to detect the presence of anti-influenza virus antibodies. Examples of body fluids that may be used to practice the present method include, but are not limited to, blood, plasma, serum, lacrimal fluid and saliva. Those skilled in the art can readily identify samples appropriate for practicing the disclosed methods.

Blood, or blood-derived fluids such as plasma, serum, and the like, are particularly suitable as the sample. Such samples can be collected and prepared from individuals using methods known in the art. The sample may be refrigerated or frozen before assay.

Any nanoparticle of the present invention can be used to practice the disclosed method as long as the nanoparticle binds to anti-influenza virus antibodies. Useful nanoparticles, and methods of their production, have been described in detail herein. In a preferred embodiment, the nanoparticle comprises a protein construct, wherein the protein construct comprises at least 25, at least 50, at least 75, at least 100, or at least 150 contiguous amino acids from a monomeric subunit protein joined to (fused to) at least one epitope from an influenza HA protein such that the nanoparticle comprises trimers of the influenza virus HA protein epitope on its surface, and wherein the protein construct is capable of self-assembling into nanoparticles.

As used herein, the term contacting refers to the introduction of a sample being tested for the presence of anti-influenza antibodies to a nanoparticle of the present invention, for example, by combining or mixing the sample and the nanoparticle of the present invention, such that the nanoparticle is able to come into physical contact with antibodies in the sample, if present. When anti-influenza virus antibodies are present in the sample, an antibody/nanoparticle complex is then formed. Such complex formation refers to the ability of an anti-influenza virus antibodies to selectively bind to the HA portion of the protein construct in the nanoparticle in order to form a stable complex that can be detected. Binding of anti-influenza virus antibodies in the sample to the nanoparticle is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, agglutination assays, precipitation assays, enzyme immunoassays (e.g., ELISA), immunoprecipitation assays, immunoblot assays and other immunoassays as described, for example, in Sambrook et al., Molecular Cloning: A Laboratory Manual, (Cold Spring Harbor Labs Press, 1989), and Harlow et al., Antibodies, a Laboratory Manual (Cold Spring Harbor Labs Press, 1988), both of which are incorporated by reference herein in their entirety. These references also provide examples of complex formation conditions.

As used herein, the phrases selectively binds HA, selective binding to HA, and the like, refer to the ability of an antibody to preferentially bind a HA protein as opposed to binding proteins unrelated to HA, or non-protein components in the sample or assay. An antibody that selectively binds HA is one that binds HA but does not significantly bind other molecules or components that may be present in the sample or assay. Significant binding, is considered, for example, binding of an anti-HA antibody to a non-HA molecule with an affinity or avidity great enough to interfere with the ability of the assay to detect and/or determine the level of, anti-influenza antibodies in the sample. Examples of other molecules and compounds that may be present in the sample, or the assay, include, but are not limited to, non-HA proteins, such as albumin, lipids and carbohydrates.

In one embodiment, an anti-influenza virus antibody/nanoparticle complex, also referred to herein as an antibody/nanoparticle complex, can be formed in solution. In one embodiment an antibody/nanoparticle complex can be formed in which the nanoparticle is immobilized on (e.g., coated onto) a substrate. Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (polyvinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a cotton thread, a plastic chip, an immunoblot membrane, an immunoblot paper and a flow-through membrane. In one embodiment, a substrate, such as a particulate, can include a detectable marker. For descriptions of examples of substrate materials, see, for example, Kemeny, D. M. (1991) A Practical Guide to ELISA, Pergamon Press, Elmsford, NY pp 33-44, and Price, C. and Newman, D. eds. Principles and Practice of Immunoassay, 2nd edition (1997) Stockton Press, NY, NY, both of which are incorporated herein by reference in their entirety.

In accordance with the present invention, once formed, an anti-influenza virus antibody/nanoparticle complex is detected. Detection can be qualitative, quantitative, or semi-quantitative. As used herein, the phrases detecting complex formation, detecting the complex, and the like, refer to identifying the presence of anti-influenza virus antibody complexed with the nanoparticle. If complexes are formed, the amount of complexes formed can, but need not be, quantified. Complex formation, or selective binding, between a putative anti-influenza virus antibody and a nanoparticle can be measured (i.e., detected, determined) using a variety of methods standard in the art (see, for example, Sambrook et al. supra.), examples of which are disclosed herein. A complex can be detected in a variety of ways including, but not limited to use of one or more of the following assays: a hemagglutination inhibition assay, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG=s Immunodot System, Fribourg, Switzerland), and an immunoblot assay (e.g., a western blot), an phosphorescence assay, a flow-through assay, a chromatography assay, a PAGe-based assay, a surface plasmon resonance assay, a spectrophotometric assay, and an electronic sensory assay. Such assays are well known to those skilled in the art.

Assays can be used to give qualitative or quantitative results depending on how they are used. Some assays, such as agglutination, particulate separation, and precipitation assays, can be observed visually (e.g., either by eye or by a machines, such as a densitometer or spectrophotometer) without the need for a detectable marker.

In other assays, conjugation (i.e., attachment) of a detectable marker to the nanoparticle, or to a reagent that selectively binds to the nanoparticle, aids in detecting complex formation. A detectable marker can be conjugated to the nanoparticle, or nanoparticle-binding reagent, at a site that does not interfere with ability of the nanoparticle to bind to an anti-influenza virus antibody. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

In one embodiment, an antibody/nanoparticle complex can be detected by contacting a sample with a specific compound, such as an antibody, that binds to an anti-influenza antibody, ferritin, or to the antibody/nanoparticle complex, conjugated to a detectable marker. A detectable marker can be conjugated to the specific compound in such a manner as not to block the ability of the compound to bind to the complex being detected. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

In another embodiment, a complex is detected by contacting the complex with an indicator molecule. Suitable indicator molecules include molecules that can bind to the anti-influenza virus antibody/nanoparticle complex, the anti-influenza virus antibody, or the nanoparticle. As such, an indicator molecule can comprise, for example, a reagent that binds the anti-influenza virus antibody, such as an antibody that recognizes immunoglobulins. Preferred indicator molecules that are antibodies include, for example, antibodies reactive with the antibodies from species of individual in which the anti-influenza virus antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

Because assays of the present invention can detect anti-influenza virus antibodies in a sample, including a blood sample, such assays can be used to identify individuals having anti-influenza antibodies. Thus, one embodiment of the present invention is a method to identify an individual having anti-influenza virus antibodies, the method comprising:
 a. contacting a sample from an individual being tested for anti-influenza antibodies with a nanoparticle of the present invention; and,
 b. analyzing the contacted sample for the presence of a nanoparticle/antibody complex
 wherein the presence of a nanoparticle/antibody complex indicates the individual has anti-influenza antibodies.

Any of the disclosed assay formats can be used to conduct the disclosed method. Examples of useful assay formats include, but are not limited to, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG=s Immunodot System, Fribourg, Switzerland), and an immunoblot assay (e.g., a western blot), an phosphorescence assay, a flow-through assay, a chromatography assay, a PAGe-based assay, a surface plasmon resonance assay, bio-layer interferometry assay, a spectrophotometric assay, and an electronic sensory assay.

If no anti-influenza antibodies are detected in the sample, such a result indicates the individual does not have anti-influenza virus antibodies. The individual being tested may or may not be suspected of having antibodies to influenza virus. The disclosed methods may also be used to determine if an individual has been exposed to one or more specific type, group, sub-group or strain of influenza virus. To make such a determination, a sample is obtained from an individual that has tested negative for antibodies (i.e., lacked antibodies) to one or more specific type, group, sub-group or strain of influenza virus sometime in their past (e.g., greater than about 1 year, greater than about 2 years, greater than about 3 years, greater than about 4 years, greater than about 5 years, etc.). The sample is then tested for the presence of anti-influenza virus antibodies to one or more type, group, sub-group or strain, of influenza virus using a nanoparticle-based assay of the present invention. If the assay indicates the presence of such antibodies, the individual is then identified as having been exposed to one or more type, group sub-group or strain, of influenza virus sometime after the test identifying them as negative for anti-influenza antibodies. Thus, one embodiment of the present invention is method to identify an individual that has been exposed to influenza virus, the method comprising:
 contacting at least a portion of a sample from an individual being tested for anti-influenza antibodies with a nanoparticle of the present invention; and,
 analyzing the contacted sample for the presence or level of a antibody/nanoparticle complex, wherein the presence or level of antibody/nanoparticle complex indicates the presence or level of recent anti-influenza antibodies;
 comparing the recent anti-influenza antibody level with a past anti-influenza antibody level;
 wherein an increase in the recent anti-influenza antibody level over the past anti-influenza antibody level indicates the individual has been exposed to influenza virus subsequent to determination of the past anti-influenza antibody level.

Methods of the present invention are also useful for determining the response of an individual to a vaccine. Thus, one embodiment is a method for measuring the response of an individual to an influenza vaccine, the method comprising:
 a. administering to the individual a vaccine for influenza virus;
 b. contacting at least a portion of a sample from the individual with a nanoparticle of the present invention;
 c. analyzing the contacted sample for the presence or level of a antibody/nanoparticle complex, wherein the presence or level of antibody/nanoparticle complex indicates the presence or level of recent anti-influenza antibodies
  wherein an increase in the level of antibody in the sample over the pre-vaccination level of antibody in the individual indicates the vaccine induced an immune response in the individual.

The influenza vaccine administered to the individual may, but need not, comprise a vaccine of the present invention, as long as the nanoparticle comprises an HA protein that can bind an anti-influenza antibody induced by the administered vaccine. Methods of administering influenza vaccines are known to those of skill in the art.

Analysis of the sample obtained from the individual may be performed using any of the disclosed assay formats. In one embodiment, analysis of the sample is performed using an assay format selected from the group consisting of, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG=s Immunodot System, Fribourg, Switzerland), and an immunoblot assay (e.g., a western blot), an phosphorescence assay, a flow-through assay, a chromatography assay, a PAGE-based assay, a surface plasmon resonance assay, bio-layer interferometry assay, a spectrophotometric assay, and an electronic sensory assay.

In one embodiment, the method includes a step of determining the level of anti-influenza antibody present in the individual prior to administering the vaccine. However, it is also possible to determine the level of anti-influenza antibody present in the individual from prior medical records, if such information is available.

While not necessary to perform the disclosed method, it may be preferable to wait some period of time between the step of administering the vaccine and the step of determining the level of anti-influenza antibody in the individual. In one embodiment, determination of the level of anti-influenza antibodies present in the individual is performed at least 1 day, at least 2 days, at least 3 days, at least 4 days, at least 5 days, at least 6 days, at least one week, at least two weeks, at least three weeks, at least four weeks, at least two months, at least three months or at least six months, following administration of the vaccine.

The present invention also includes kits suitable for detecting anti-influenza antibodies. Suitable means of detection include the techniques disclosed herein, utilizing nanoparticles of the present invention. Kits may also comprise a detectable marker, such as an antibody that selectively binds to the nanoparticle, or other indicator molecules. The kit can also contain associated components, such as, but not limited to, buffers, labels, containers, inserts, tubings, vials, syringes and the like.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1: Iterative Structure-Based Design of HA Stabilized-Stem (HA-SS) Constructs This example shows the six iterative cycles of structure-based design (Gen1-Gen6) used to produce the HA stabilized-stem (HA-SS) immunogens that lack the immunodominant head domain.

Influenza A viruses comprise 18 HA subtypes of which two, H1 and H3, currently cause the majority of human infections. Seasonal influenza vaccines provide some protection against circulating H1 and H3 strains, but little protection against the divergent H5, H7, and H9 subtypes that cause occasional outbreaks of human infection as zoonoses from avian and/or swine reservoirs. The inventors hypothesized that an immune response focused on the conserved hemagglutinin (HA) stem could potentially elicit broad heterosubtypic influenza protection against diverse strains. The inventors therefore used iterative structure-based design to develop HA stabilized-stem (HA-SS) glycoproteins, which lack the immunodominant HA head region (FIG. 1).

The ectodomain sequence of A/New Caledonia/20/1999 (1999 NC) HA and the crystal structure (PDB ID 1GBN) of A/South Carolina/1/1918 (1918 SC) were used as design templates, and each generation of HA-SS variant was evaluated for expression as soluble trimers, and for antigenicity based on stem-specific monoclonal antibody (mAb) reactivity similar to wild-type (wt) HA trimer.

Plasmids encoding full-length HA and neuraminidase (NA) from 1999 NC, 1986 SG, 2009 CA, H2 2005 CAN, H5 2005 IND and H5 2004 VN were synthesized using human-preferred codons. Various versions of HA-SS were generated by overlapping PCR and site-directed mutagenesis. All HA, HA-SS proteins and mAbs were expressed in freestyle 293 (293F; Life Technologies) cells or 293 GnTI$^{-/-}$ cells (for Gen4 HA-SS crystallization) and purified as previously described (Wei, C. J., et al. Elicitation of broadly neutralizing influenza antibodies in animals with previous influenza exposure. Sci. Transl. Med. 4, 147ra114 (2012)). Construction, purification, and characterization of HA-np and Gen1-Gen6 HA-SS and Gen4-6 HA-SS-np were performed as described (Kanekiyo, M., et al. Nature 499, 102-106 (2013)).

The first generation design (Gen1 HA-SS) replaced the receptor-binding domain (residues HA1 51-277, H3 numbering) with a GSG linker (FIG. 1). The HA ectodomain trimer and all trimeric HA-SS designs were each generated with the C-terminal transmembrane and cytoplasmic residues HA2 175-220 (H3 numbering) replaced with a short linker, T4 foldon, thrombin cleavage site and His tag. The HA1/HA2 cleavage site was mutated to prevent cleavage. To model the structures of the HA-SS designs, 1918 SC HA (PDB ID 1GBN) and the bacteriophage T4 foldon trimer (PDB ID 1RFO) were used as templates, loops and connections were designed using LOOPY (Xiang, et. al. *Proc. Natl. Acad. Sci. U.S.A.* 99, 7432-7437 (2002)), side chains were mutated using SCAP (Xiang, et al., *J. Mol. Biol.* 311, 421-430 (2001)) and structural superpositions were performed using LSQMAN (Kleywegt, et al., in International Tables for Crystallography, Vol. F, 353-367 (Kluwer Academic Publishers, Dordrecht, The Netherlands, 2001)). The energetics of particular mutations were assessed computationally using the Rosetta program DDG_MONOMER (Kellogg, et al., *Proteins* 79, 830-838 (2011)). Chimera (Pettersen, E. F., et al. *Journal of Computational Chemistry* 25, 1605-1612 (2004)) was used to perform surface area calculations. Approximately 700 trimeric structures in the Protein Data Bank (PDB) were examined to find a suitable trimerization domain to further stabilize HA-SS immunogen. This search revealed HIV-1 gp41 (PDB ID 1SZT) to be optimal for (i) its size (less than 70 amino acids per monomer), (ii) its thermostability ($T_m$=70° C.), (iii) ease of transplantation, with N- and C-termini located at the same end of the trimer, and (iv) structural complementarity between the C-terminal ends of the inner heptad repeat 1 (HR1) helices of gp41 and the inner C helices of the HA-SS trimer. Gen1 HA-SS failed to express as a trimer, despite the presence of a C-terminal foldon trimerization domain.

To increase trimer stability in the second generation, the inventors replaced HA2 residues 66-85 at the membrane-distal region of the HA-SS with a thermostable HIV-1 gp41 trimerization domain (see Tan, et al., *Proc. Natl. Acad. Sci. U.S.A.* 94, 12303-12308 (1997)) in which the inner heptad repeat 1 (HR1) helices are structurally complementary with the inner C helices of the HA stem. Connecting gp41 and HA-SS necessitated circular permutation of gp41 helices HR1 and HR2, which were reversed in order and reconnected with a glycine-rich linker (FIG. 1). To insert the six-helix bundle of the post-fusion form of HIV-1 gp41 into Gen2 HA-SS, residues 28-32 (residues 573-577, HXBc2 numbering) from the three inner helices of gp41 were superimposed onto HA inner helix residues HA2 81-85 (from PDB ID 1RU7) with a root mean square deviation (RMSD) of 1.41 Å for 15 Cα atoms. HA2 residues 66-85 were replaced with the gp41 heptad repeat (HR) 2 helix (residues 628-654, HXBc2 numbering) followed by a six-residue glycine rich linker (NGTGGG) containing the sequon for an N-linked glycosylation site and the gp41 HR1 helix (residues 548-577). HR1 was designed to be in frame with helix C of HA2 to generate a long central chimeric helix. Efforts to stabilize the membrane distal portion of the F' region through the addition of salt bridges, shortening loops and reducing its hydrophobicity did not improve the trimerization or antigenicity of the Gen2 HA-SS design. Expression of Gen2 HA-SS resulted in 29% trimerization.

To improve trimerization in the third generation, a 44-residue portion of the HA1 F' region with irregular secondary structure was removed, and the inner helix C of HA-SS was truncated by six residues for better complementarity between gp41 and HA2. This resulted in a soluble Gen3 HA-SS with 77% trimerization, which was recognized by HA stem broadly neutralizing mAbs (bNAbs) with affinities similar overall to those of the soluble HA trimer (FIG. 1). In Gen3 HA-SS HA2 residues 43-50, and 278-313 of the F' region were replaced with a GWG linker, and HA2 residues 60-65 and 86-92 were removed. To realign gp41 with a lower region of the HA stem, residues 30-34 (575-579 Hxbc2 numbering) from the three inner helices of gp41 were superimposed onto HA inner helix residues HA2 90-94 with an RMSD of 0.59 Å for 15 Cα atoms. Faster off-rates were observed for CR6261 and 70-5B03 which may be due in part to the loss of the HA F' region that can make limited contact with the CR6261 heavy chain.

To characterize the Gen3 HA-SS at the atomic-level, the inventors determined the crystal structure of Gen3 HA-SS in complex with the antigen-binding fragment (Fab) of the murine bNAb C179 (see Okuno, Y., et al. J. Virol. 67, 2552-2558 (1993)) at 3.19 Å resolution (FIG. 2*a*, left panel); the C179 antibody was the first broadly neutralizing HA stem-directed antibody to be discovered with heterosubtypic neutralization.

C179 harvested from hybridoma cells was cleaved into Fabs as previously described (Ofek, G., et al. *J. Virol.* 78, 10724-10737 (2004)) with the following modifications: LysC (Roche) was used at a ratio of 1:20,000 (w/w) to C179 and the crystallizable fragment (Fe) was removed from the digestion solution by passing through a mercapto-ethyl-pyridine column (Pall Life Sciences) in 50 mM Tris pH 8.0 and the C179 Fab was eluted with 50 mM NaAc pH 5.0.

The complex of Gen3 HA-SS (expressed in 293 $GnTI^{-/-}$ cells) with C179 Fab was obtained by passing a 1:1.25 (Gen3 HA-SS/C179 molar ratio) mixture through a Superdex 200 26/60 (GE Healthcare) gel filtration column and collecting the peak eluting at 152.0 mLs. The complex was concentrated to 10 mg/ml in 150 mM NaCl, 10 mM Tris HCl pH 7.5 and crystallized at 20° C. by hanging drop vapor diffusion in 15% (W/V) polyethylene glycol 1500, 5% (V/V) 2-methyl-2,4-pentanediol, 200 mM $NH_4Cl$ and 100 mM Tris HCl pH 8.5, derived from the precipitant synergy crystallization screen (Majeed, S., et al. *Structure* 11, 1061-1070 (2003)). Crystals were cryocooled without any additional cryoprotectant and stored in liquid nitrogen prior to data collection.

X-ray data was collected to 3.19 Å resolution at a temperature of 100K using a wavelength of 1.000 Å at the Southeast Regional Collaborative Access Team (SER-CAT) 22-BM beamline at the Advanced Photon Source (APS), Argonne National Laboratory. X-ray data was processed with HKL2000 in the trigonal space group H3 and the structure of the complex was determined by molecular replacement using five separate search models. PHASER (Mccoy, A. J., et al. *J. Appl. Crystallogr.* 40, 658-674 (2007)) was used to search with the HA stem monomer from the structure of 1934 PR8 (PDB ID 1RU7, residues 5-36, 315-323 HA1 chain A and residues 514-559, 590-660 HA2 chain B), the HIV-1 gp41 monomer (PDB ID 1SZT, residues 3-29, 42-67), the heavy chain variable domain of the murine antibody S25-2 (PDB ID 1Q9K, residues 1-111), and the light chain variable domain of the murine antibody MN16C13F4 (PDB ID 1UWX, residues 3-108). MOLREP (Collaborative Computational Project. *Acta Crystallogr. D Biol. Crystallogr.* 50, 760-763 (1994)) was used to locate the T4 foldon monomer (PDB ID 1RFO, chain A) which confirmed an independent fitting by hand. The C179 Fab constant domains were fit into Fo-Fc density by eye prior to refinement using the constant domains of the above Abs (PDB IDs 1Q9K and 1UWX) as templates. Model building and refinement were performed using COOT (Emsley, P. & Cowtan, K. Coot: *D Biol. Crystallogr.* 60, 2126-2132 (2004)) and PHENIX (Adams, P. D., et al. *Acta Crystallogr. D Biol. Crystallogr.* 58, 1948-1954 (2002)) with riding hydrogens, respectively. All of the residues of the Gen3 HA-SS were modeled into electron density except for the HA cleavage loop (residues 48-52), the glycine rich loop connecting the gp41 helices (residues 139-144), the linker connecting HA-SS to the foldon (residues 256-259) and the thrombin cleavage site and His tag C-terminal to the foldon domain (residues 286-302). Carbohydrates were observed and built on Asn residues 23, 119 and 236. The C179 structure included heavy chain residues 1-213 and light chain residues 1-214. The Ramachandran statistics as determined by PHENIX revealed 91.64% of residues in favored regions, 7.49% in allowed and 0.86% as outliers.

The co-crystal structure revealed C179 recognition of Gen3 HA-SS to be similar to the recognition of an H2N2 trimeric HA in the recently published co-crystal structure of C179 with an A/Japan/305/1957 (1957 JP) HA (see Dreyfus, et al., *J. Virol.* 87, 7149-7154 (2013).) (FIG. 2*a*, right panel). While these findings confirmed the preservation of the stem epitope on the Gen3 HA-SS; the overall structure revealed several unexpected differences (FIG. 2*a*, left and middle panel). First, the stem trimer subunits were splayed apart at their C-termini by approximately 15 Å relative to HA (FIG. 2*a*, middle panel). Second, the C-terminal foldon trimerization domain was inverted and tucked inside the stem trimer into the splayed region (FIG. 2*a*, left panel). Finally, the outer helix A of the HA stem forms a continuous helix with the outer HR2 helix of the gp41 six-helix bundle, rather than forming two separate helices separated by a glycine linker.

To address these issues, a fourth generation HA-SS was created containing three mutations (outlined in FIG. 1) in an effort to remove potential side chain clashes and disrupt the continuous helix between helix B of HA2 and the gp41 HR2 (FIG. 2*b*).

To crystalize the Gen4 HA-SS/CR6261 complex, the Gen4 HA-SS (expressed in 293 GnTI-cells) was deglycosylated by incubating with endoglycosidase H (77 U/μg Gen4 HA-SS) for 4 hrs. at 37° C. followed by passage through a concanavalin A column (Sigma) to remove protein with uncleaved N-linked glycans. The complex with CR6261 Fab was obtained by passing a 1:1.25 (Gen4 HA-SS/CR6261 molar ratio) mixture through a Superdex 200 10/300 (GE Healthcare) gel filtration column and collecting the peak eluting at 12.5 mLs. The complex was concentrated to 11 mg/ml in 150 mM NaCl, 10 mM Tris HCl pH 7.5 and crystallized at 20° C. by hanging drop vapor diffusion in 7% (w/v) polyethylene glycol 4000, 4.5% (v/v) isopropanol, 100 mM imidazole pH 6.5. The crystal was soaked in a reservoir solution containing an additional 5% (v/v) 2R,3R butanediol (Sigma) for six hours at room temperature followed by a brief 30 second transfer to a reservoir solution containing 15% 2R,3R butanediol before flash cooling.

X-ray data was collected to 4.30 Å resolution at a temperature of 100K using a wavelength of 1.000 Å at the SER-CAT BM-22 beamline of APS. Data was processed with HKL2000 (ref 37) in the space group H3 and the structure of the complex was determined by molecular replacement using three separate search models. PHASER was used to search with the HA stem monomer from the structure of 1934 PR8, the HIV-1 gp41 monomer (same models as above), and the variable and constant domains of CR6261 (PDB ID 3GBM). Model building and refinement were performed using COOT and PHENIX, respectively. All of the residues of the Gen4 HA-SS were modeled into electron density except for the HA cleavage loop (residues 48-52), the glycine rich loop connecting the gp41 helices (residues 137-145), and the C-terminal foldon (residues 256-259), the thrombin cleavage site and His tag C-terminal to the foldon domain (residues 286-302). While density was visible inside of the HA stem in the same region observed in the Gen3 HA-SS structure, it was not sufficient to uniquely place or stably refine a foldon domain. The CR6261 Fab structure included heavy chain residues 1-213 and light chain residues 3-107 and 113-215. The Ramachandran statistics as determined by PHENIX revealed 93.19% of residues in favored regions, 6.09% in allowed and 1.06% as outliers.

For cryo-electron microscopy analysis, particles were vitrified over holey carbon films (Quantfoil, Großlöbichau, Germany) using a Vitrobot Mark IV (FEI Company, Hillsboro, OR). Cryo-images of particles were collected on a Titan Krios electron microscope (FEI Company, Hillsboro, OR), operated at liquid nitrogen temperatures and operated at 300 kV. Images were collected on a 4,096×4,096 charge-coupled-device (CCD) camera (Gatan Inc., Warrendale, PA) at a pixel size of 1.2 Å with defocus values ranging from approx. 2.8 to approx. 6 m, and at doses ranging from approx. 10 to 20 e–/Å$^2$. Observed defocus values were fit using ctffind3 (Mindell, J. A. & Grigorieff, N. *J Struct Biol* 142, 334-347 (2003)), and images that exhibited drift or astigmatism were excluded from further analysis. Particles (13,464) were manually picked from images. Reference-free 2D classification indicated octahedral symmetry, which was imposed during 3D refinement. A smooth, spike less, low-pass filtered ferritin (PDB ID 2JD6) was used as a staring model. After removal of overlapping particles during the refinement process, the reconstruction (3D map) was calculated from 6,540 particles. All image analyses (2D and 3D) were carried out with the Relion package (Scheres, S. H. W. *J. Mol. Biol.* 415, 406-418 (2012).). Visualization and molecular docking of model coordinates were performed with Chimera.

Atomic coordinates and structure factors for Gen3 HA-SS in complex with C179 and Gen4 HA-SS complex with CR6261 have been deposited under PDB codes 4MKD and 4MKE respectively. The cryo-electron microscopy map for H1-SS-np has been deposited under the EMDB code EMD-6332.

The co-crystal structure at 4.30 Å resolution of Gen4 HA-SS complexed with a Fab of the bNAb CR6261 (see Ekiert, D. C., et al. *Science* 324, 246-251 (2009)) revealed that the splaying relative to gp41 persists, with an additional rotation of ~190 (FIG. 2b, middle panel). However, the level of trimerization (83%), preservation of stem-epitope conformation, and HA stem bNAb binding (nM to four bNAbs) were near optimal in the Gen4 HA-SS (FIGS. 1a and 2b).

The inventors were concerned about the implications of an immunogenic HIV-1 gp41 region, and therefore sought to replace gp41 with a short glycine-rich linker (FIG. 1a), as this would also increase the percentage of the HA stem on the immunogen surface (FIG. 1b). The gp41 replacement was carried out in two contexts, a Gen5 HA-SS, which retained the Gen4 stabilized-stem region, and a Gen 6 HA-SS, in which an internal salt bridge comprising Lys51-Glu103 (HA2, H3 numbering) was replaced by a nearly isosteric Met-Leu hydrophobic pair (Gen6 HA-SS, FIG. 1c).

The Gen5 HA-SS was created by completely removing the gp41 trimerization domain, connecting HA2 residues 58-93 with a GSGGSG loop and introducing the HA2 mutations Y94D and N95L.

Figure 1C:
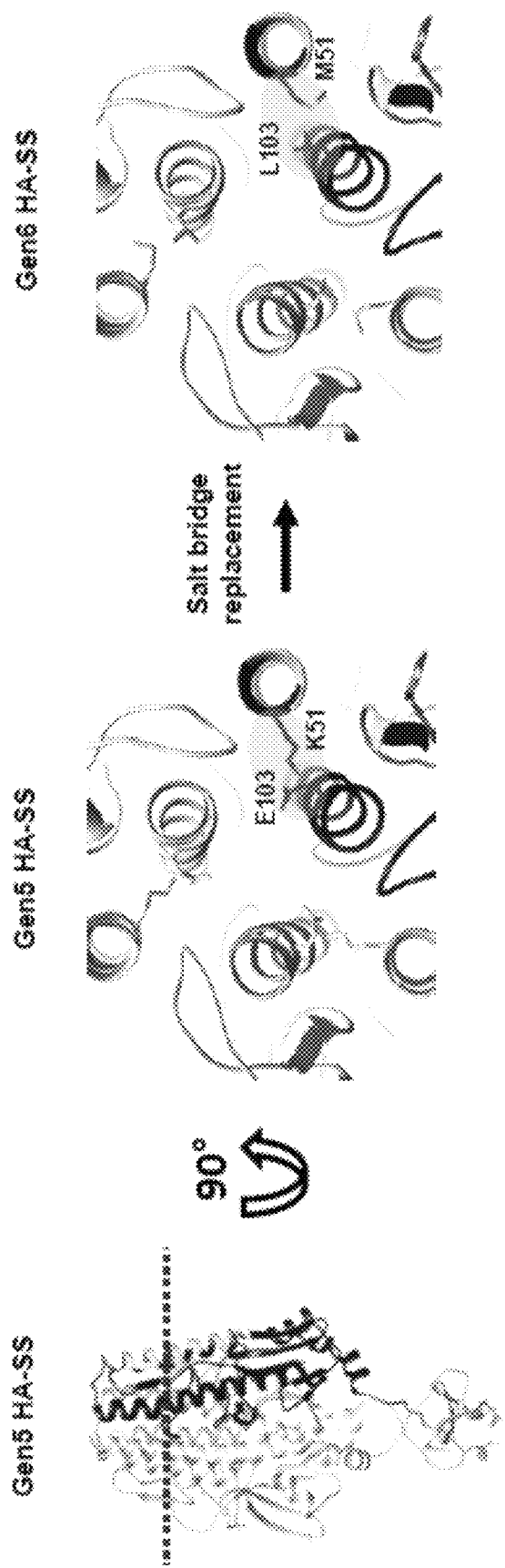
FIG. 1c show a ribbon representation depicting a cross-sectional view of the replacement of the Glu103-Lys51 salt bridge with the Leu103-Met51 hydrophobic pair in Gen6 HA-SS. The dotted line (left) indicates the location of the cross-section.
Figure 1D:
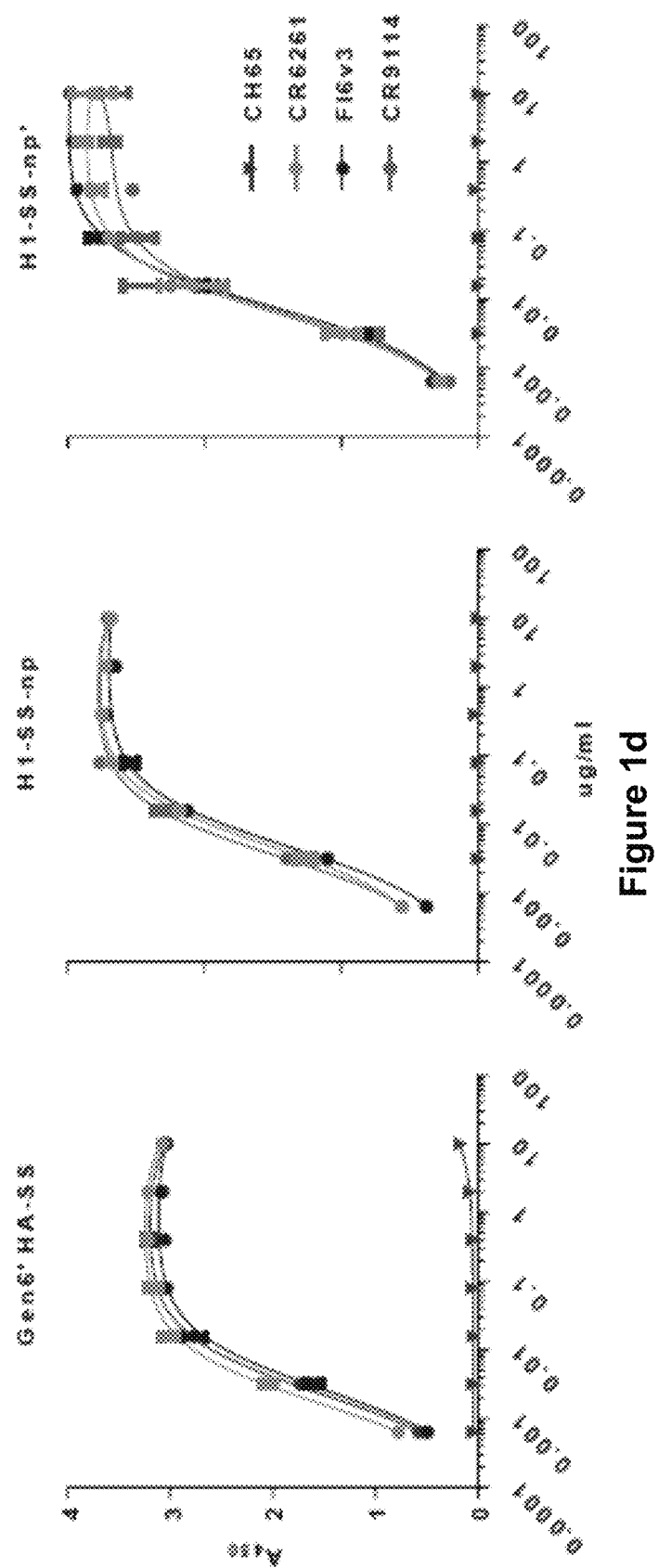
FIG. 1d shows the antigenicity of Gen6 HA-SS presented in its soluble and nanoparticle formats. The three panels show ELISA binding of one head (CH65) and three stem-specific antibodies (CR6261, CR9114, FI6v3) to Gen6' HA-SS (left panel), H1-SS-np (middle panel), and H1-SS-np' (right panel). ELISA binding of antibodies ranging in concentration from $10\text{-}6.40 \times 10^{-4}$ μg/mL.
Figure 2A:
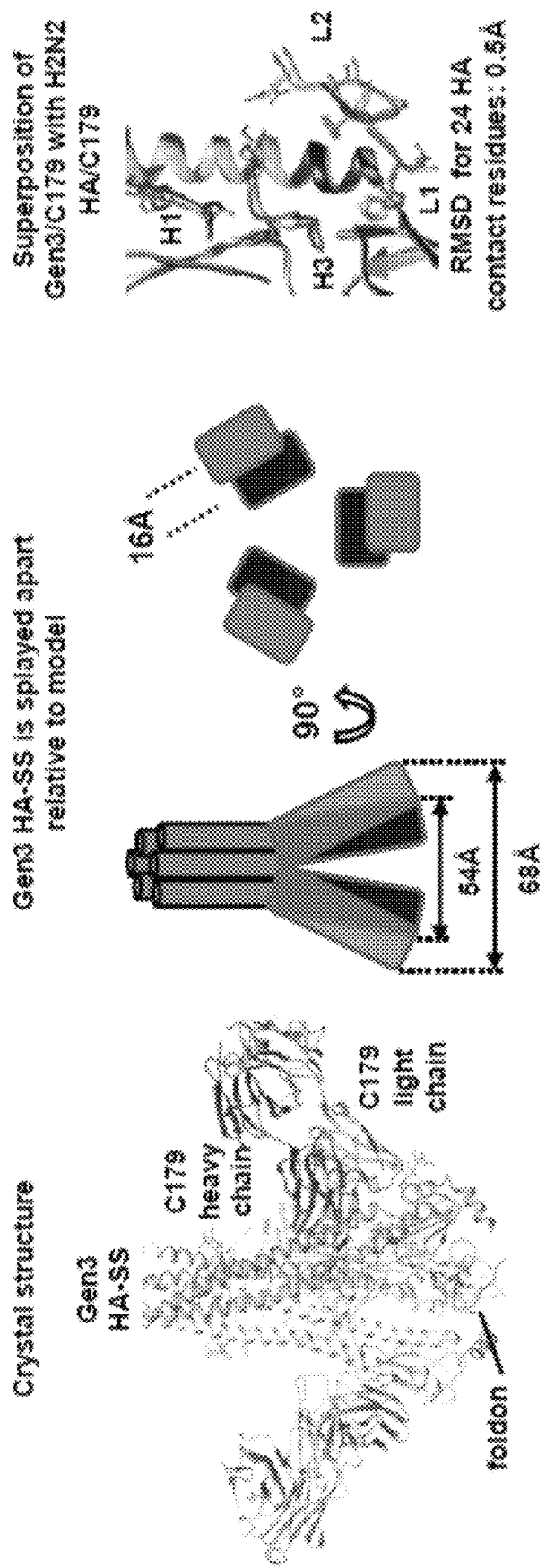
FIG. 2a shows that the trimeric, but not nanoparticle stem immunogens, display HA stem splaying. The left panel depicts a ribbon diagram of the crystal structure of the complex between Gen3 HA-SS (dark and gray) and mAb C179 (labeled). The middle panel of FIG. 2a shows a cartoon comparing the splaying of the crystal structure (light) with the model (dark) in two different views (side and bottom). The right panel of FIG. 2a shows a superposition of the Gen3 HA-SS/C179 binding interface with a 1957 H2N2 HA/C179 binding interface (PDB ID 4HLZ). Antibody CDR loops are labeled by "H" for heavy chain and "L" for light chain. The heavy chain framework 3 loop is labeled FR3. RMSD, root mean square deviation.
Figure 2B:
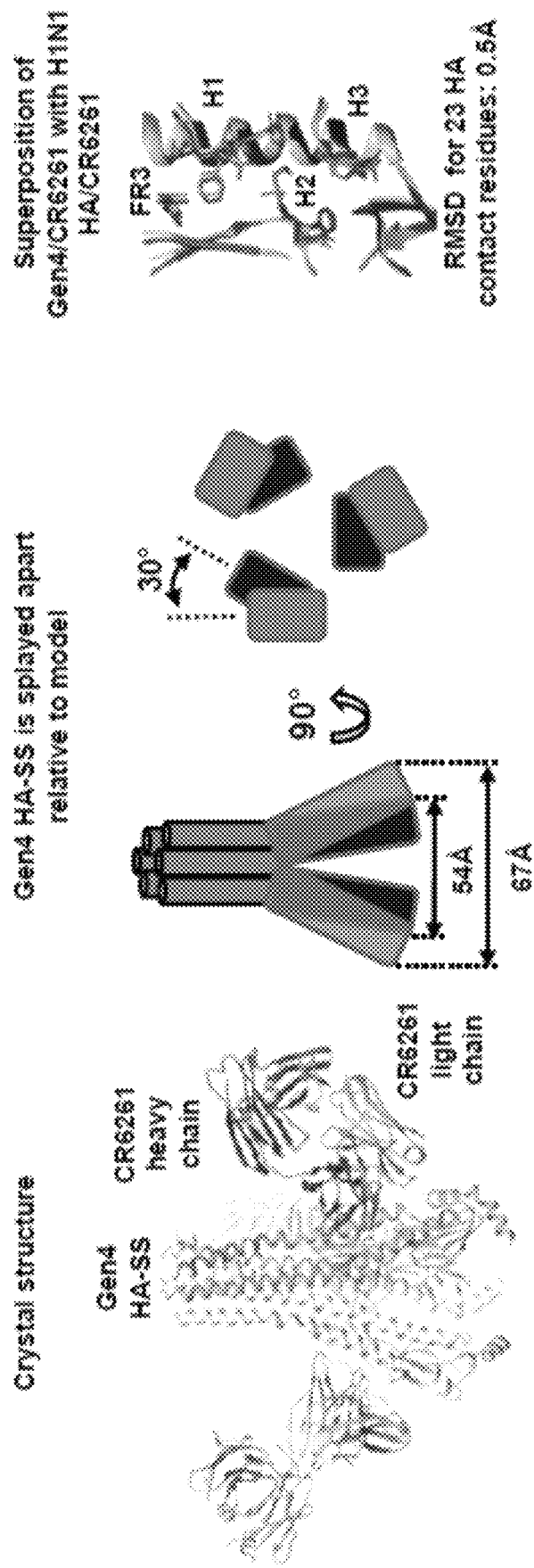
FIG. 2b depicts the same panel format as in FIG. 2a, showing Gen4 HA-SS and in the right panel a superposition of the Gen4 HA-SS/CR6261 heavy chain binding interface with the 1918 H1N1 HA/CR6261 binding interface (PDB ID 3GBN).
Figure 2C:
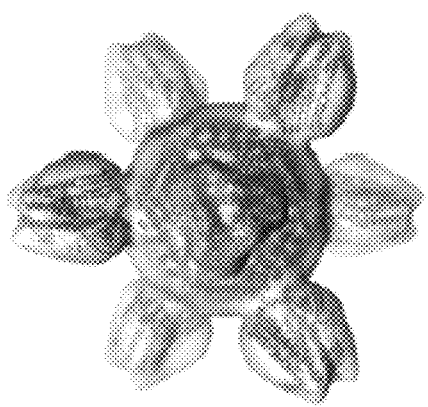
FIG. 2c shows the H1-SS-np cryo-electron microscopy analysis. The first two panels show the Gen4 HA-SS crystal structure (cropped) and the H1-SS-np model, respectively, fit into the cryo-electron microscopy map for one H1-SS-np spike. The next two panels of FIG. 2c show two different views of the entire H1-SS-np model fit into the H1-SS-np cryo-electron microscopy map.
Figure 2C:
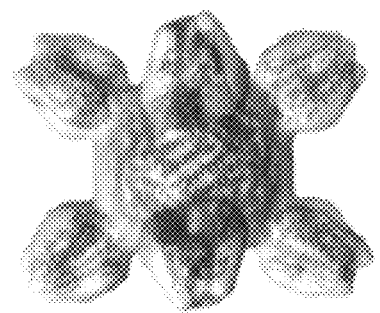
Figure 2C:
Figure 2D:
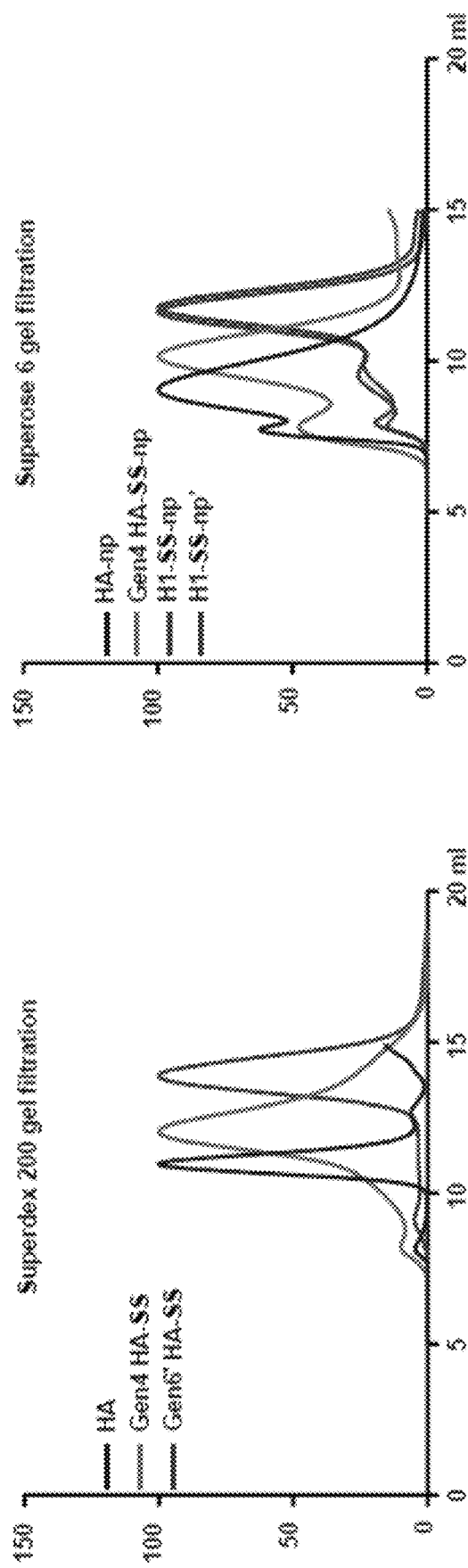
FIG. 2d shows the characterization of influenza virus HA and HA-SS insoluble and nanoparticle formats in the size exclusion chromatogram of HA, Gen4 HA-SS and H1-SS-np' (left panel), and HA np, Gen4 HA-SS-np and H1-SS-np' and H1-SS-np (right panel) with a Superdex 20010/300 and Superose 610/300 column, respectively.
Figure 2E:
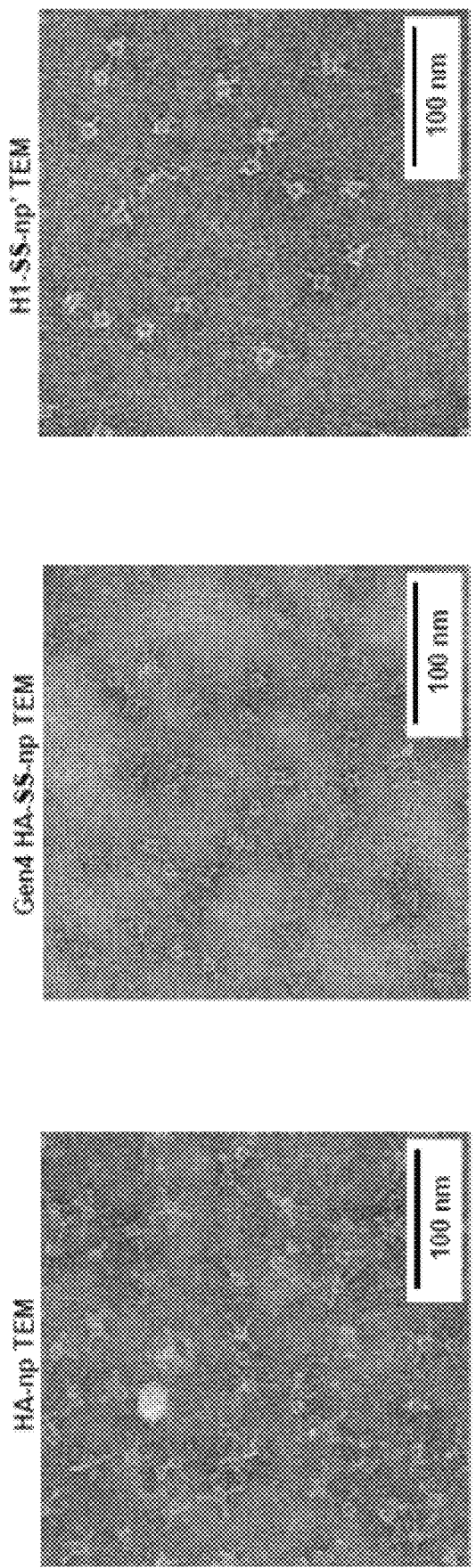
FIG. 2e negatively stained transmission electron microscopy images of HA-np (left panel) and Gen4 HA-SS-np (middle panel) and H1-SS-np (right panel). Images were originally recorded at 67,000× magnification.
Figure 2F:
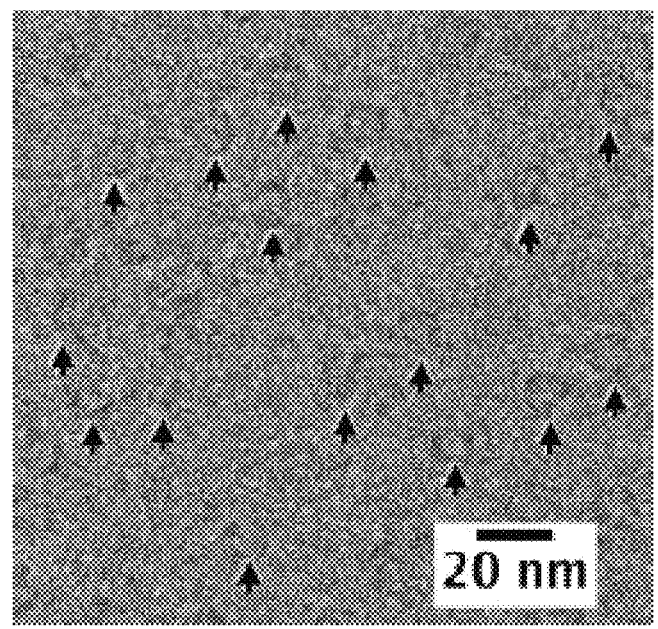
FIG. 2f shows a cryo-EM image of a field of H1-SS-np. Arrows depict some ring-like nanoparticles; scalebar is 20 nm.
Figure 2G:
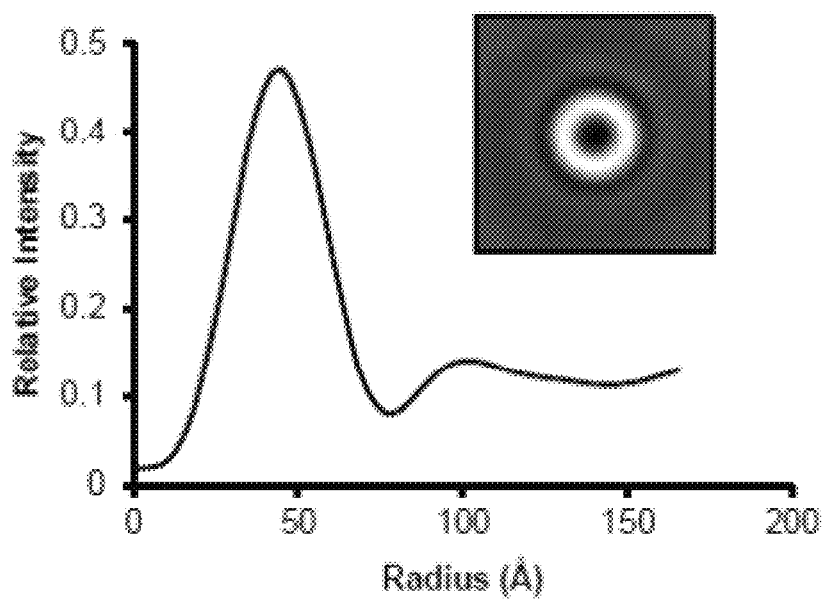
FIG. 2g shows a size analysis of H1-SS-np by 2D radial density profile (curve) of the global circular average of nanoparticles (inset). The profile illustrates a two-layered structure with a base peak centered at about 40 Å from the particle center and a second peak spanning the range of about 80 Å to 140 Å. The difference in peak heights is consistent for a more continuous protein layer topped by a layer containing a few discrete spikes.
Figure 2H:
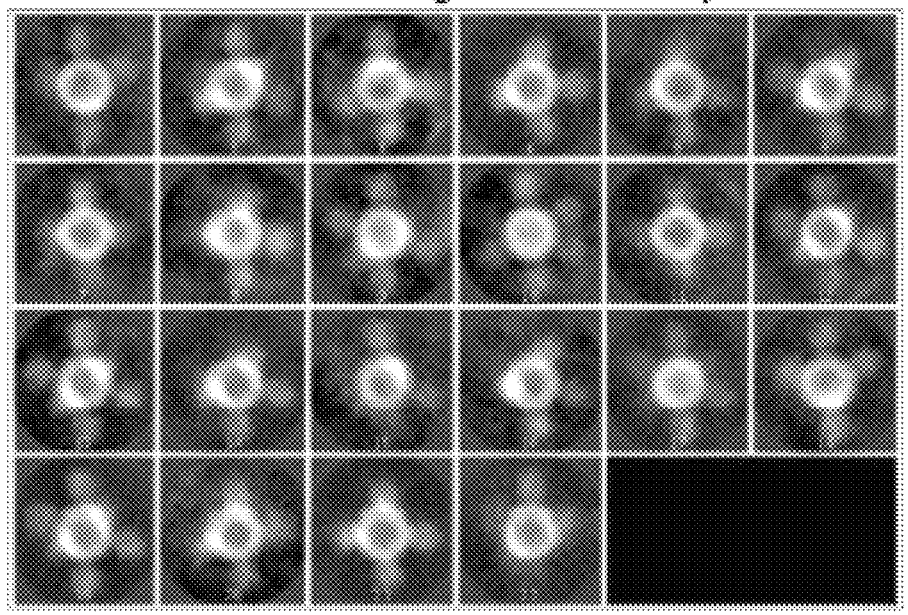
FIG. 2h shows the reference-free 2D class averages of H1-SS-np with no symmetry imposed. Classes indicate distinct views of a particle with a protein shell and protruding spike densities and views are consistent with expected octahedral symmetry.
Figure 2I:
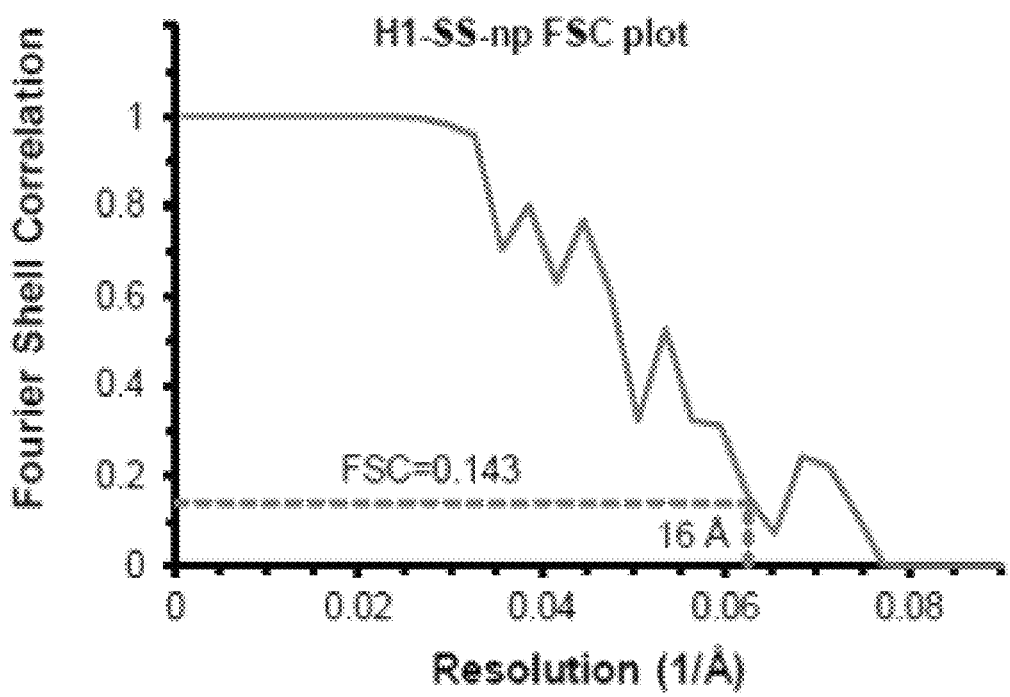
FIG. 2i resolution assessment of the H1-SS-np 3D reconstruction by Fourier shell correlation (FSC) plot. FSC (0.143) was used as the cut-off following the gold-standard procedure as implemented in the RELION software package.

To design Gen6 HA-SS, five mutations were initially created to stabilize the inner core of the HA stem HA2: K51M, E103L, E105Q, R106W, and D109L (referred to as Gen6' HA-SS). Trimerization and recognition by HA stem antibodies were preserved for all three immunogens (FIG. 1a). The intermediate version of Gen6 HA-SS (referred to as Gen6' HA-SS) containing three additional internal stabilizing mutations displayed similar antigenicity (FIG. 1d), but mutations E105Q, R106W, and D109L were ultimately observed not to be required for stabilization of Gen6 HA-SS and fusion with ferritin and were not used in the final H1-SS-np construct (FIG. 1c).

Example 2: Creation of Self-Assembling Ferritin Nanoparticles

This example describes the fusion of Gen4, Gen5, Gen6', and Gen6 HA-SS to the self-assembling ferritin nanoparticle through their respective HA C-termini.

Immunogenicity of HA is substantially increased in the context of a self-assembling nanoparticle (HA-np) (see Kanekiyo, M., et al., *Nature* 499, 102-106 (2013)). Moreover, the inventors speculated that a C-terminal fusion to the nanoparticle might reduce the splaying of the membrane-proximal regions of the stem. The inventors therefore genetically fused Gen4, Gen5, Gen6', and Gen6 HA-SS through their respective HA C-termini (replacing the foldon) to the self-assembling ferritin nanoparticle of *H. pylori* to create HA-SS-nanoparticles (HA-SS-np).

Gen4-6 HA-SS were fused to *H. pylori* ferritin N-terminus (residues 5-167) with a SGG linker to produce HA-SS ferritin nanoparticles (Gen4 HA-SS-np, H1-SS-np and H1-SS-np') as described (Kanekiyo, M., et al. *Nature* 499, 102-106 (2013)).

A fortéBio Octet Red384 instrument was used to measure binding kinetics of HA and HA-SS molecules to mAbs CR6261, CR9114, F10 scFv and 70-5B03. All the assays were performed at 30° C. with agitation set to 1,000 rpm in PBS supplemented with 1% BSA in order to minimize nonspecific interactions. The final volume for all the solutions was 100 μl/well. Assays were performed at 30° C. in solid black 96-well plates (Geiger Bio-One). HA or HA-SS with a C-terminal biotinylated Avi-Tag (25 g/ml) and HA-np or HA-SS-np in 10 mM acetate pH 5.0 buffer were used to load streptavidin and amine-reactive biosensor probes respectively for 300 s. Typical capture levels were between 0.8 and 1 nm, and variability within a row of eight tips did not exceed 0.1 nm. Biosensor tips were equilibrated for 300 s in PBS/1% BSA buffer prior to binding measurements of the Fabs or F10 scFv in solution (0.01 to 0.5 µM). Upon antibody addition, association was allowed to proceed for 300 s; binding was then allowed to dissociate for 300 s. Dissociation wells were used only once to prevent contamination. Parallel correction to subtract systematic baseline drift was carried out by subtracting the measurements recorded for a sensor loaded with HA or HA-SS molecules incubated in PBS/1% BSA. To remove nonspecific binding responses, a biotinylated gp120 resurfaced core molecule was loaded onto the streptavidin probe and incubated with anti-stem antibodies, and the nonspecific responses were subtracted from HA and HA-SS response data. Data analysis and curve fitting were carried out using Octet software, version 7.0. Experimental data were fitted with the binding equations describing a 1:1 interaction. Global analyses of the complete data sets assuming binding was reversible (full dissociation) were carried out using nonlinear least-squares fitting allowing a single set of binding parameters to be obtained simultaneously for all concentrations used in each experiment.

ELISA, hemagglutination inhibition (HAI) assay and pseudotype neutralization assays were performed as previously described (Wei, C. J., et al. Science 329:1060-1064 (2010)). The recombinant HA/NA lentiviral vectors expressing a luciferase reporter gene were produced as described (Wei, C. J., et al. Sci. Transl. Med. 2, 24ra21 (2010)). All influenza viruses were obtained from Centers for Disease Control and Prevention (CDC; Atlanta, GA).

Figure 1E:
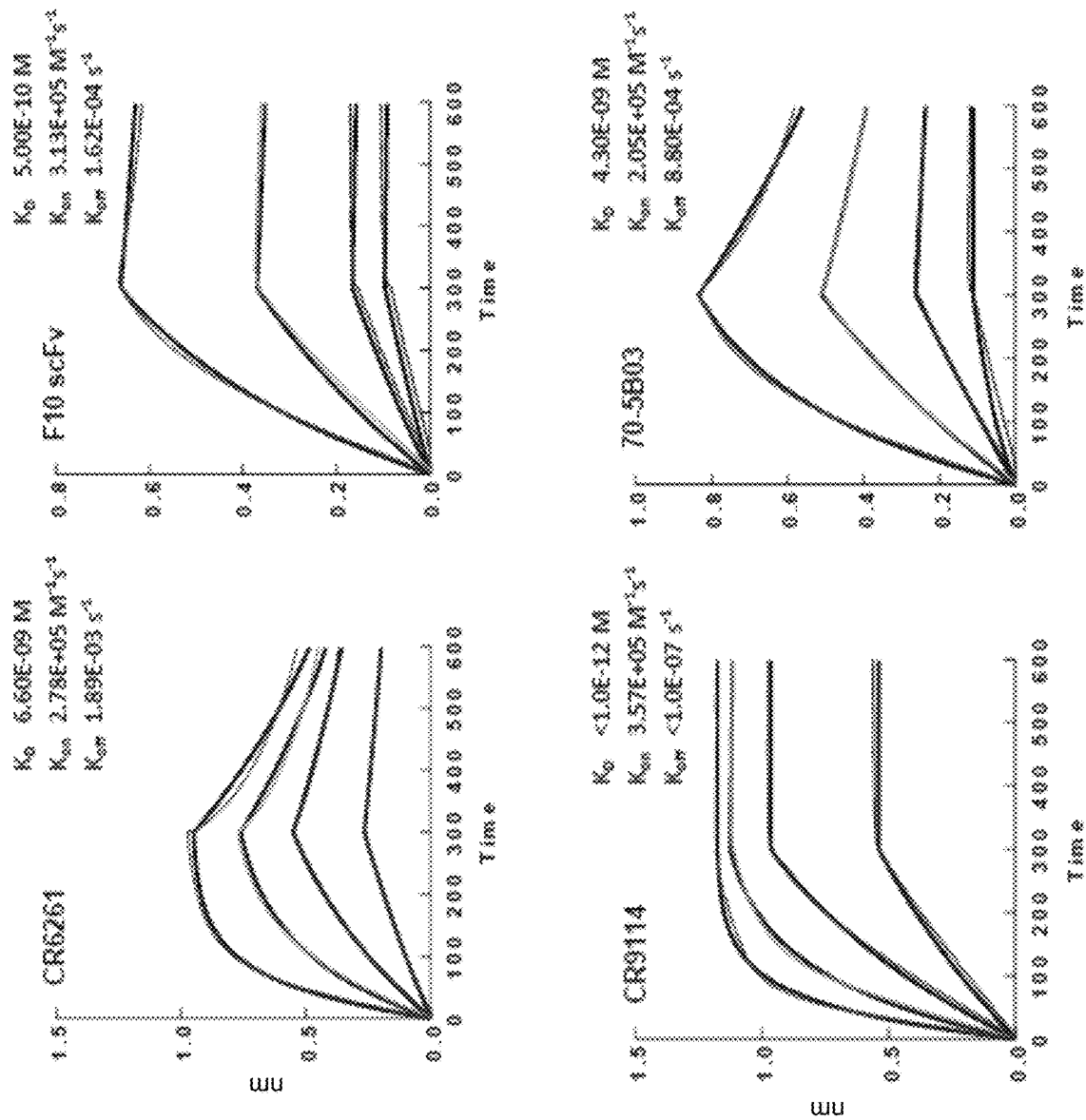
FIG. 1e and FIG. 1f show the Octet sensorgrams of H1-SS-np (FIG. 1e) and H1-SS-np' (FIG. 1f) binding to HA stem-directed bNAbs. H1-SS-np was immobilized onto an Octet probe and incubated with varying concentrations of antibody binding fragments Fab or scFv stem-directed antibodies, which are indicated on top of each sensorgram.
Figure 1F:
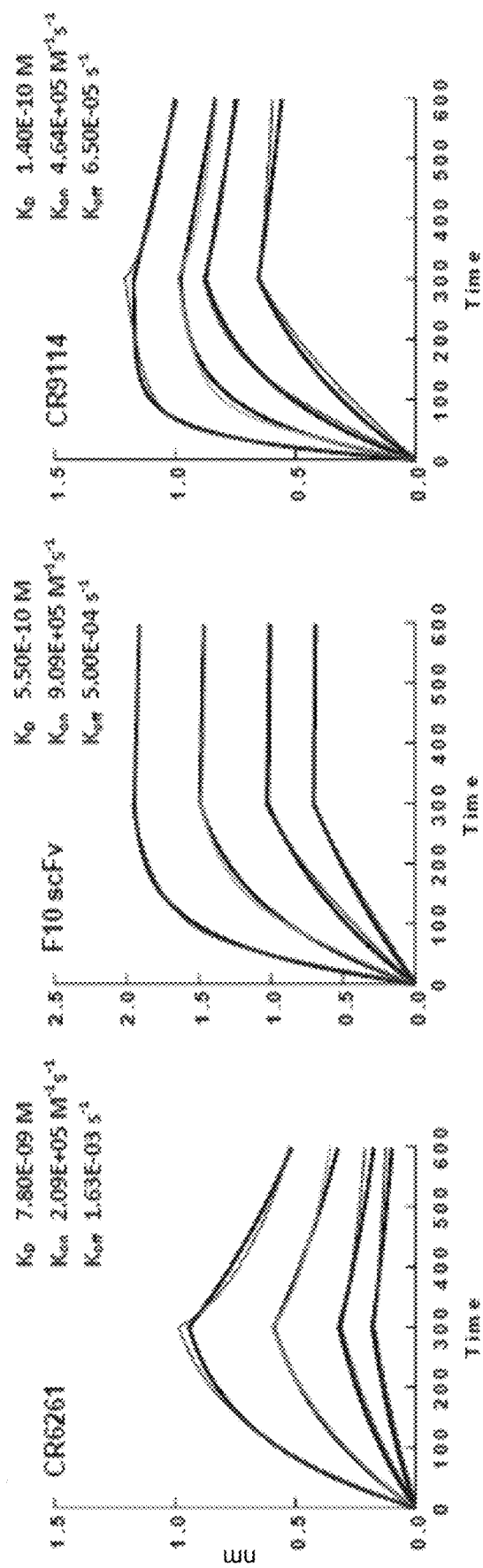

Gen4, Gen6 and Gen6' HA-SS-np each expressed as nanoparticles as confirmed by transmission electron microscopic analysis and gel filtration (FIG. 2). However, Gen5 HA-SS-np failed to express. Gen6 and Gen6' HA-SS-np were selected for further evaluation and hereafter are referred to in these Examples as H1-SS-np and H1-SS-np' respectively. Cryo-electron microscopy (EM) analysis of H1-SS-np performed to a resolution of 16 Å revealed symmetrical, spherical particles, each with eight spikes protruding from the surface (FIG. 2c). Notably, the membrane-proximal region of the Gen6 HA-SS stem fits better into electron density than Gen4 HA-SS, suggesting that the splaying is either mitigated or no longer present (FIG. 2c, left panel). Moreover, both H1-SS-np and H1-SS-np' had the desired antigenic properties, being recognized by CR6261, CR9114, F10, and 70-5B03 (see, Ekiert, D. C., et al. Science 324, 246-251 (2009); Sui, J., et al. Nat. Struct. Mol. Biol. 16, 265-273 (2009); Dreyfus, C., et al. Science 337, 1343-1348 (2012); Wrammert, J., et al. J. Exp. Med. 208, 181-193 (2011)) in ELISA and biolayer interferometry measurements, indicating the authentic HA-SS structure was preserved upon fusion to ferritin (FIGS. 1a, 1e and 1f).

Example 3: Assessing Vaccine Efficacy

This example demonstrates the characterization of various measures of vaccine efficacy for the ferritin nanoparticles fused to the HA constructs.

The inventors assessed the capacity of H1-SS-np to trigger signaling by membrane-anchored germline-reverted CR6261 B cell receptor (BCR) compared to full length HA-np using a calcium flux assay (Novak, et. al. Cytometry 17, 135-141 (1994)).

For the BCR activation assay, germline CR6261 BCRs (wild type and double I53A/F54A mutant) were stably expressed by lentiviral transfection (FEEKW vector; Luo, X. M., et al. Blood 113, 1422-1431 (2009)) of light chain and membrane-anchored IgM heavy chain into a surface IgM negative clone of Ramos B cell line. Germline CR6261 BCR positive cells were then sorted by flow cytometry (BD FACSAria; BD Biosciences) and amplified. Cells expressing >95% positivity for germline CR6261 BCR (wild type or I53A/F54A mutant) were assessed for surface expression and correct HA antigenicity. For signaling, 2500 nM of either H1-SS-np, HA np (with HA containing Y98F mutation to abolish nonspecific binding to sialic acid) or empty np was presented to $1\times10^6$ Ramos B cells expressing germline CR6261 BCRs. The kinetics of calcium flux in response to BCR stimulation was measured by flow cytometry as the ratio of the $Ca^{2+}$ bound/unbound states of the dye Fura Red. This ratio for $Ca^{2+}$ flux is presented 10 seconds after exposure to ligand. A 30 second baseline was acquired prior to stimulation. Ratiometric measures for individual cells were averaged and smoothened by Kinetic analysis, FlowJo software. Functionality between germline CR6261 BCR versus germline CR6261 BCR with I53A/F54A mutation was compared by $Ca^{2+}$ flux following exposure to 0.5 µg/1 anti-human IgM F(ab')$_2$ (Southern Biotech).

Figure 1G:
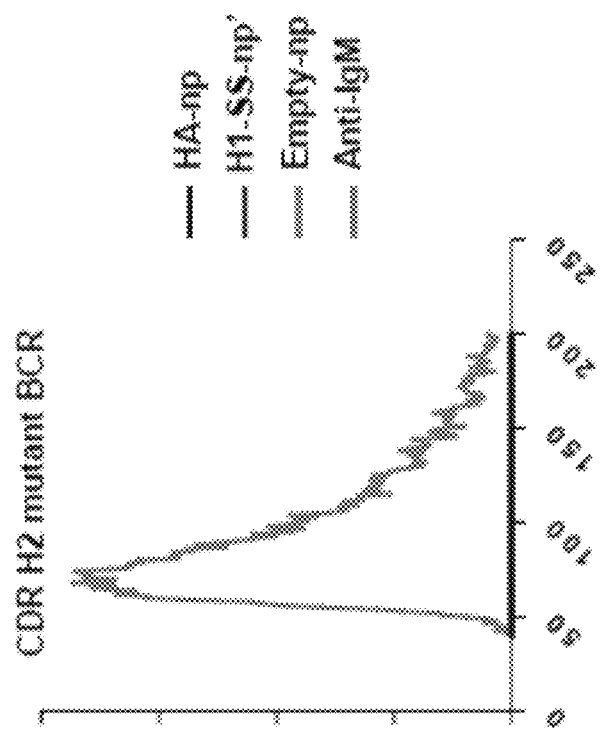
FIG. 1g shows the stimulation of wild-type IGHV1-69 v-gene reverted CR6261 BCR (left panel) vs. double Ile53Ala/Phe54Ala CDRH2 mutant BCR (right panel) by anti-IgM (=total receptor activity), empty np, HA-np (with HA containing a Y98F mutation to abolish nonspecific binding to sialic acid), and H1-SS-np' was measured by flow cytometry as the ratio of the Ca2+ bound/unbound states of the Ca2+ sensitive dye FuraRed.
Figure 1G:
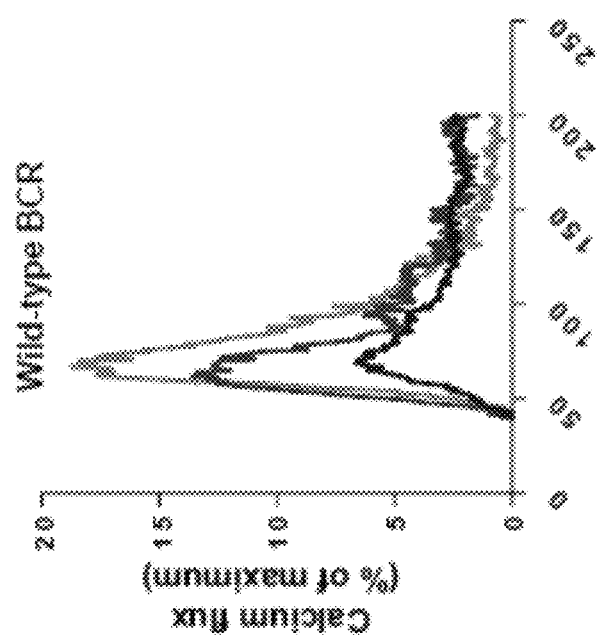

In contrast to empty ferritin particles, H1-SS-np induced effective signaling through wild-type BCR as did full-length HA-np to a lesser extent, and no signaling was observed through a BCR mutated in two critical contact residues in the second heavy chain complementarity determining region (CDR H2) (FIG. 1g). This finding confirms the ability of H1-SS-np to engage the IGHV1-69 germline precursor of CR6261 and stimulate naïve B cells through CDR H2-dependent recognition, characteristic of broadly neutralizing stem-directed antibodies found in humans.

To evaluate H1-SS-np vaccine efficacy the inventors immunized mice and ferrets using the Sigma Adjuvant System (SAS) as SAS has been reported to induce HA responses similar to MF59, another squalene-based adjuvant approved for use in humans.

For the immunization studies, a total of three animal experiments, two in mice and one in ferrets, were performed for this study. In the first mouse experiment, female BALB/c mice (6-8 weeks old, Jackson Laboratories) were immunized intramuscularly with 2 µg H1-SS-np, 2 µg of empty ferritin np, 0.2 µg of H5 2005 IND HA-np or TIV (HA molar equivalent) at week 0 and 4. Blood was collected 14 days after each immunization and serum was isolated. For the second mouse immunization experiment, female BALB/c mice were immunized three times with 3 µg of H1-SS-np or empty ferritin np at weeks 0, 8, and 12. For ferret immunization, 6 month old male Fitch ferrets (Triple F Farms, Sayre, PA), seronegative for exposure to currently circulating pandemic H1N1, seasonal H1N1, H3N2, and B influenza strains, were housed and cared for at BIOQUAL, Inc. (Rockville, MD). These facilities are accredited by the American Association for the Accreditation of Laboratory Animal Care International and meet NIH standards as set forth in the Guidefor the Care and Use of Laboratory Animals. Ferrets were immunized intramuscularly with 20 µg of H1-SS-np', or empty ferritin np or TIV (equivalent to 2.5 µg of H1 HA) in 500 µl of PBS at weeks 0 and 4. Ferrets in the positive control group were immunized with 250 µg plasmid DNA expressing H5 2005 IND followed by 2.5 µg HA of H5N1 2005 IND MIV at weeks 0 and 4. The vaccine was administered via intramuscular injections into the upper thigh muscle. Sigma Adjuvant System (SAS, Sigma) was used for all protein or np-based immunization. Blood was collected 14 days after each immunization and serum was isolated. Animal experiments were conducted in full compliance with all relevant federal regulations and NIH guidelines.

For the passive transfer studies, 150 mice were first vaccinated with H1-SS-np protein (2 µg/dose with SAS) at weeks 0 and 4, to generate HA-SS immune Ig, and sera were collected at weeks 1, 2, and 3 (terminal) post boost. Ig from immune sera was purified with protein G (Life Technologies) using the manufacturer protocol. 24 hour before challenge, two groups of BALB/c mice (n=10/group, Taconic inc.) received either naïve (Molecular innovations) or immune Ig via an intraperitoneal route. Sera were collected from infused animals 24 hours post passive transfer for serological analysis.

For virus challenge studies, the H5N1 strain, A/Vietnam/1203/04, was obtained from the Centers for Disease Control and Prevention (Atlanta, GA) (CDC #2004706280, E1/E3 (1/19/07) and amplified in 10-day old embryonated hen's eggs (Charles River, North Franklin, CT) at BIOQUAL Inc. The challenge stock has an infectious titer of $10^{10}$ TCID$_{50}$/ml. For blood collection, bleeds, and challenge procedure, the animals were anesthetized with a solution of ketamine/dexmedetomidine formulated to provide doses of 25 mg/kg ketamine and 0.001 mg/kg dexmedetomidine to each animal. Mice were inoculated intranasally with 50 µl of virus, approximately 25 µl to each nostril and ferrets were inoculated intranasally with 500 µl of virus, approximately 250 µl to each nostril. The challenge dose was 25 LD$_{50}$ in mice and 1000 TCID$_{50}$ in ferrets. Based on previous studies these challenge doses were expected to result in 100% lethality in naïve control mice and ferrets respectively. Clinical signs of infection, weight, and temperatures were recorded twice daily for ferrets. Activity scores were assigned as follows: 0, alert and playful; 1, alert but playful only when stimulated; 2, alert, but not playful when stimulated; and 3, neither alert nor playful when stimulated. Ferrets that showed signs of severe disease (prolonged fever; diarrhea; nasal discharge interfering with eating, drinking, or breathing; severe lethargy; or neurological signs) or had >20% weight loss were euthanized immediately.

Figure 3A:
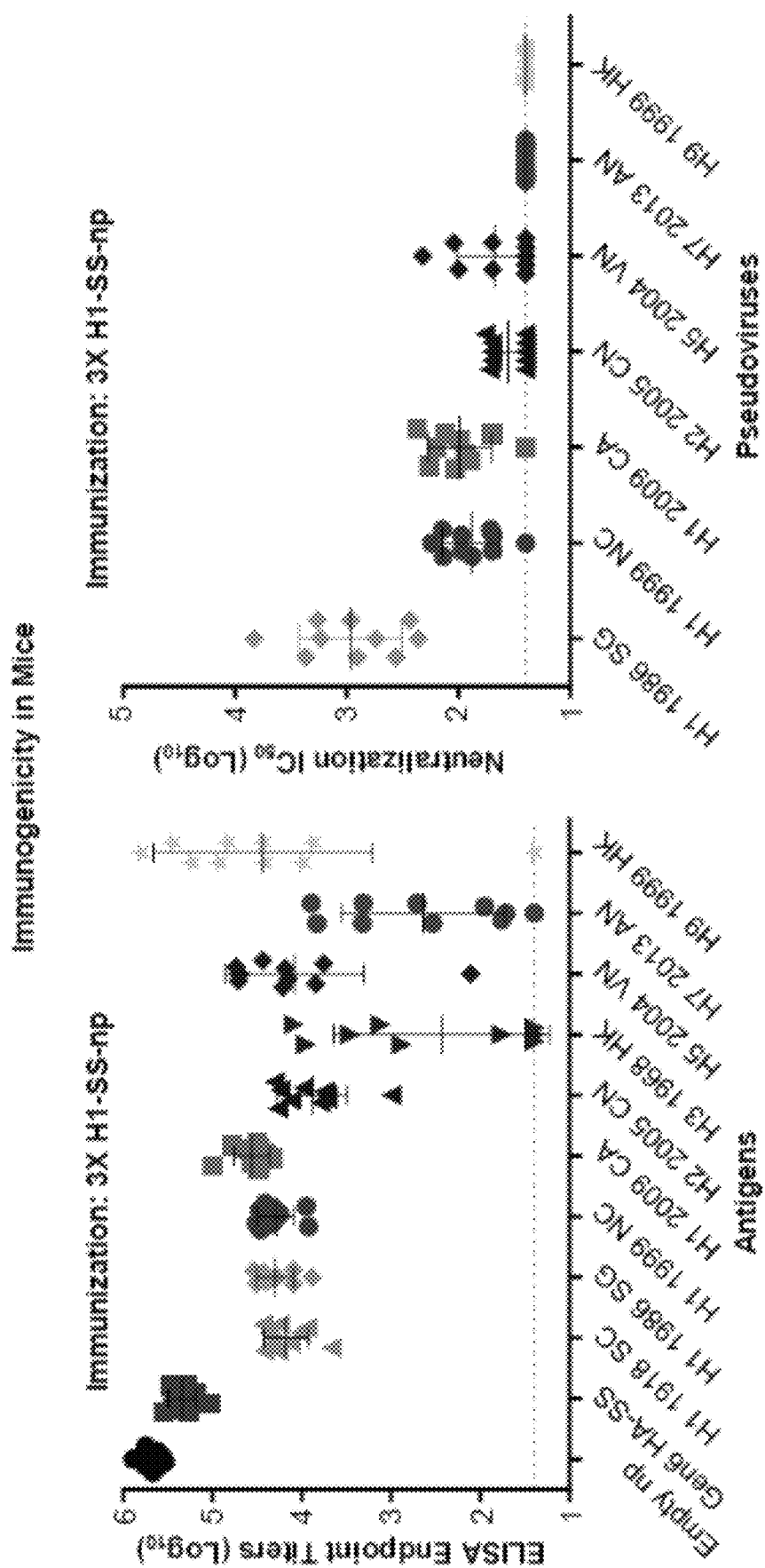
FIG. 3a shows the immune responses of immunized mice and ferrets. The left panel shows the antibody endpoint titers to diverse HA proteins and the right panel shows the neutralization titers of sera from mice (n=10 per group) immunized with SAS-adjuvanted H1-SS-np.
Figure 3B:
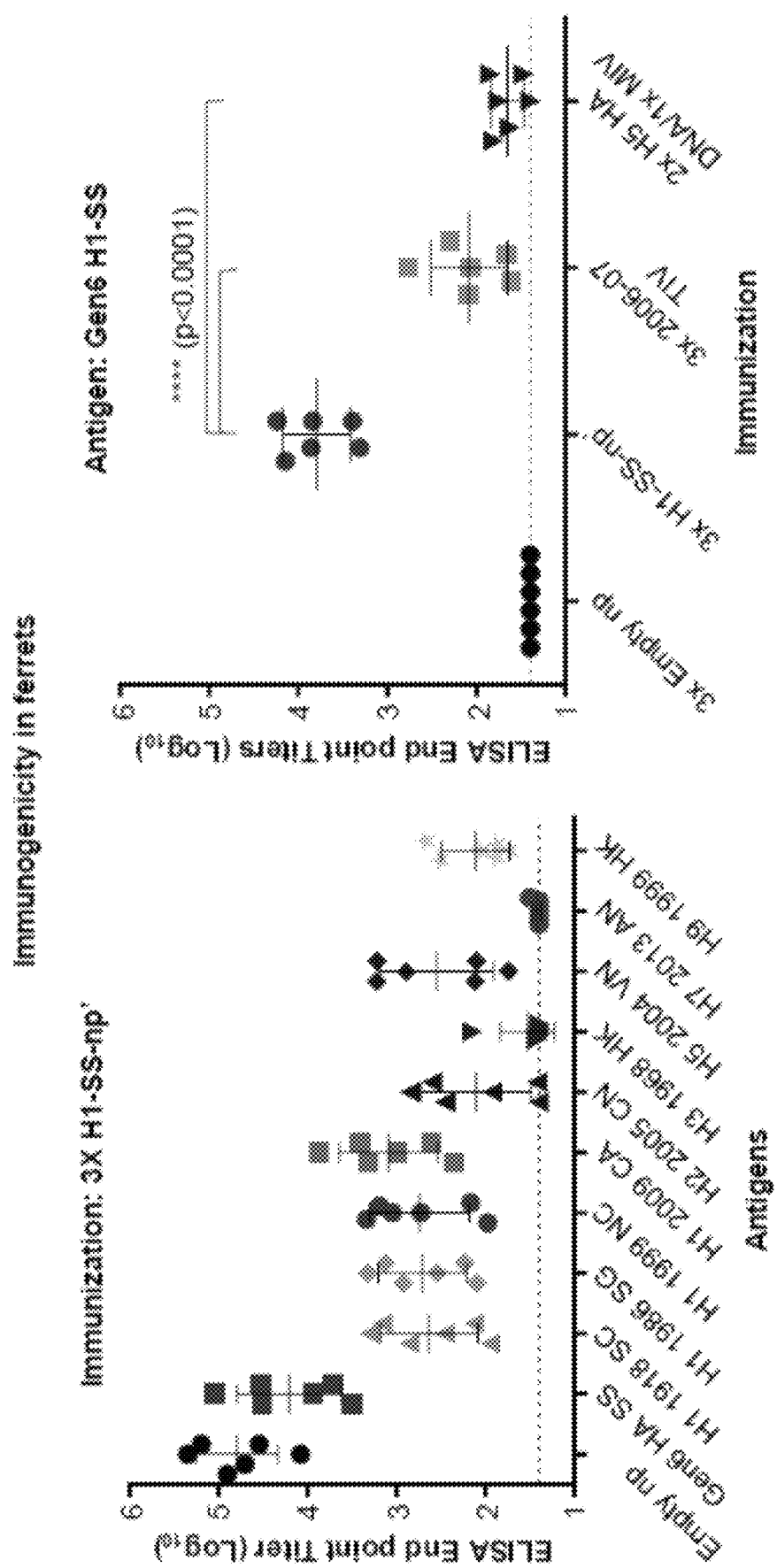
FIG. 3b shows the immune responses of ferrets immunized with SAS-adjuvanted empty np (n=5), H1-SS-np' (n=6), 2006-07 TIV (n=6) or with H5 HA (2×DNA/1x MIV; n=6). The left panel of FIG. 3b shows the antibody endpoint titers of H1-SS-np' immune sera to diverse HA proteins and the right panel shows the HA stem reactivity of sera from the four immunization regimens.
Figure 3C:
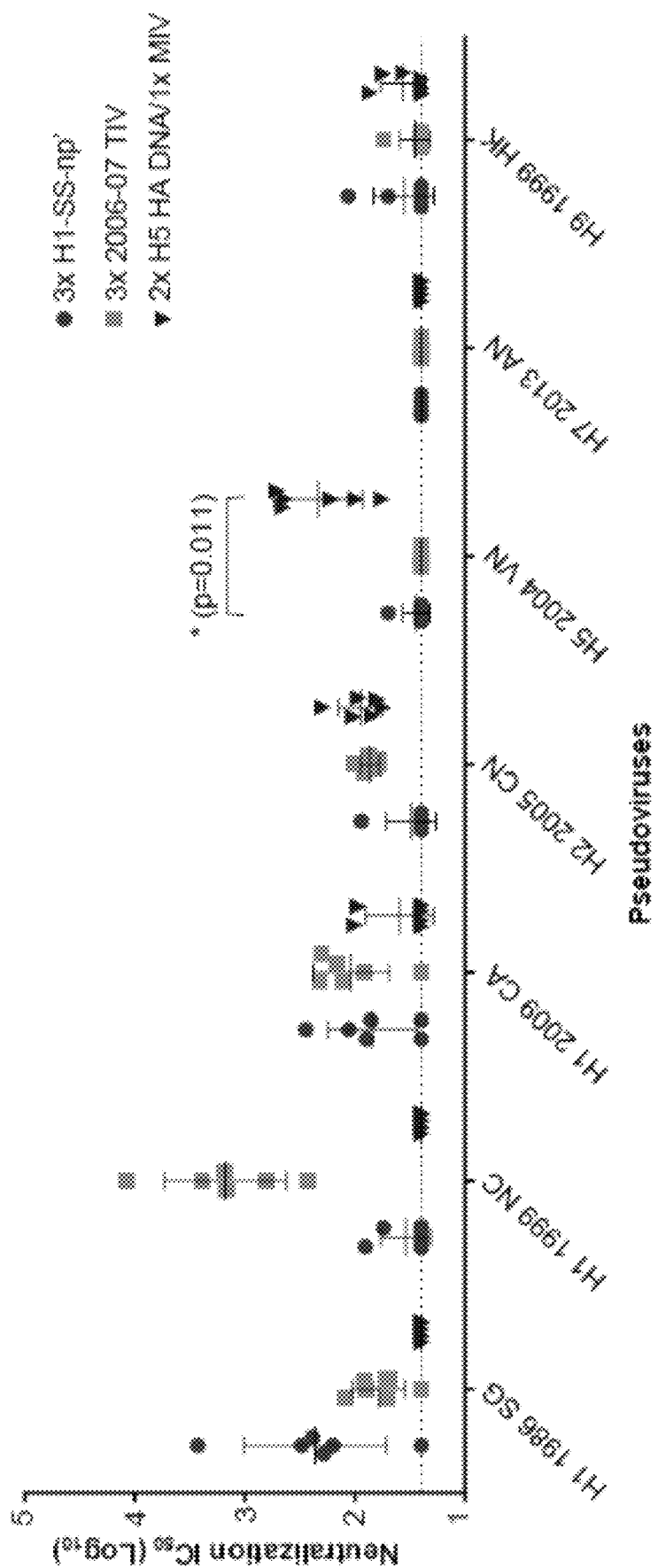
FIG. 3c shows the neutralization titers of sera from ferrets immunized with three administration regimens. Antibody endpoint and $IC_{50}$ titers are shown for each individual animal two weeks post boost. The dotted line indicates the baseline (1:25 dilution) for both ELISA and pseudotyped lentiviral reporter assays. Error bars represent mean±s.d.; statistical analysis was performed using a two-tailed student's t-test.

H1-SS-np and H1-SS-np' elicited broad antibody responses against group 1 HA subtypes (seasonal and pandemic Hi, H2, H5 and H9) in both mice and ferrets respectively (FIGS. 3a, 3b and 3C). Furthermore, H1-SS-np induced substantial group 2 (H3 and H7) responses equivalent to those of H2 and H5 in half of the mice (FIG. 3a, left panel). The antibody response to HA stem elicited by Hi-SS-np was significantly higher than that of trivalent inactivated influenza vaccine (TIV) in both mice and ferrets (FIG. 3b, right panel). Although a considerable response to ferritin was also observed (FIGS. 3a and 3b, left panel), previous studies have shown that immunization with bacterial ferritin does not induce immunity to autologous ferritin in mice, nor does it mitigate HA-specific antibody responses to subsequent immunizations. Measurement of serum neutralization activity (NT) using a highly sensitive HA-NA lentiviral reporter assay (Wei, C. J., et al. Sci. Transl. Med. 2, 24ra21 (2010)) revealed appreciable activity against the divergent H1N1 strains A/California/04/2009 (2009 CA) and A/Singapore/6/1986 (1986 SG) and the homologous 1999 NC strain in both mice and ferrets. However, NT against heterosubtypic H5N1 A/Vietnam/1203/2004 (H5N1 2004 VN), human origin H2N2 A/Canada/720/2005 (H2N2 2005 CA), H7N9 A/Anhui/1/2013 (H7N9 2013 AN) and H9N2 A/Hong Kong/1074/1999 (H9N2 1999 HK) was low or undetectable in both mice and ferrets (FIGS. 3a and 3c). The minimal heterosubtypic neutralization observed despite strong heterosubtypic antibody reactivity is likely due to the precise targeting of a single epitope region required for stem neutralization, making it more sensitive to minor structural differences than other parts of the HA stem which is 20-fold greater in surface area. TIV-immunized animals had the highest NT against homologous 1999 NC, detectable NT against the heterologous H1N1 strains, and no NT against heterosubtypic H5N1 in both mice and ferrets (FIG. 3b). As expected, TIV-immunized animals had significant hemagglutination inhibition (HAI) titers and NT activity elicited by H1-SS-np and H1-SS-np' was not associated with HAI.

Figure 4A:
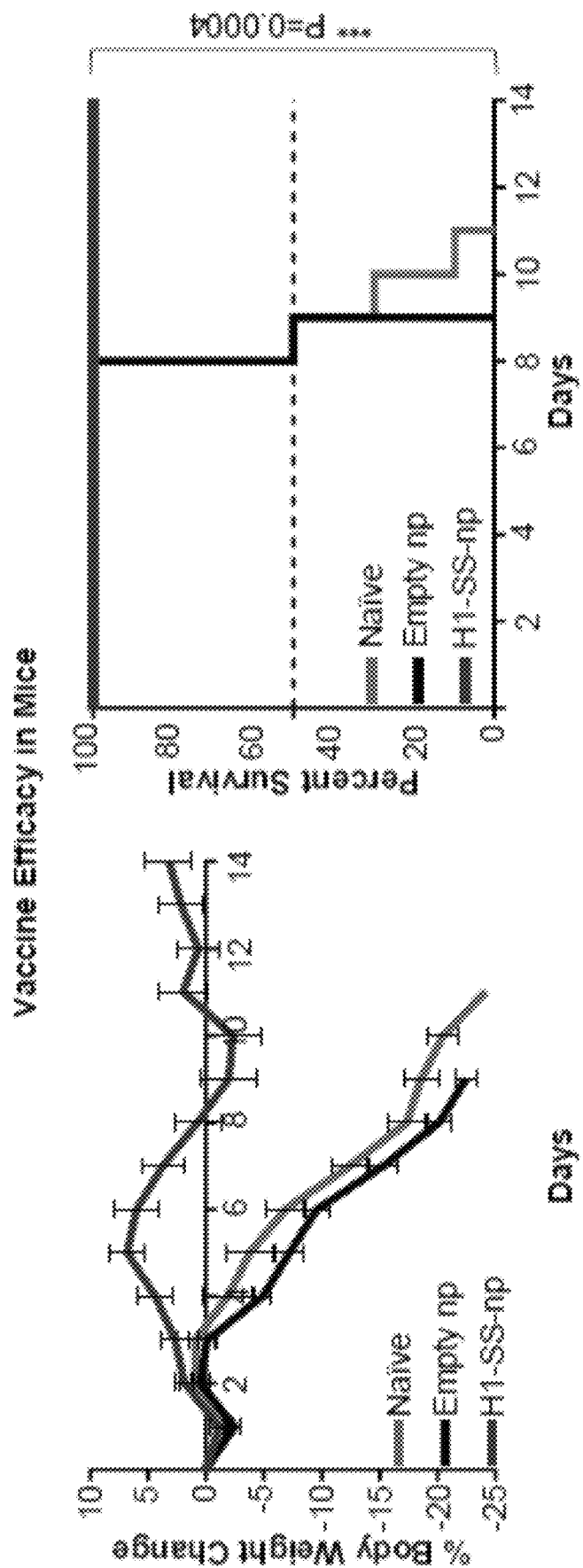
FIG. 4a shows the immune protection conferred against lethal H5N1 2004 VN influenza virus challenge in mice and ferrets. BALB/c mice (n=10 per group) were vaccinated three times with SAS-adjuvanted empty np or H1-SS-np at weeks 0, 8, and 11 or left unvaccinated (naïve). Four weeks post final vaccination, mice were challenged with high dose (25 LD50) of H5N1 2004 VN virus and monitored for body weight loss (left panel) and survival (right panel) for 14 days.
Figure 4B:
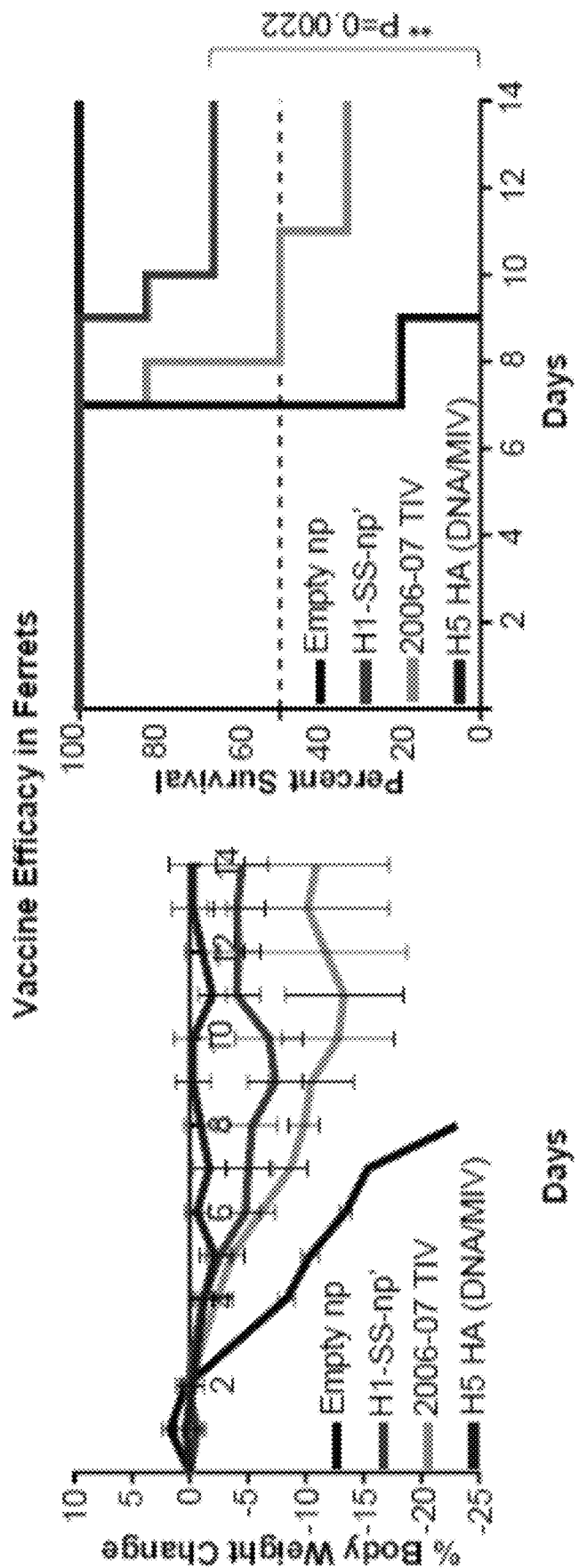
FIG. 4b shows ferrets vaccinated three times with SAS-adjuvanted empty np (n=5), H1-SS-np' (n=6), 2006-07 TIV (n=6), or H5 HA (DNA/MIV; n=6) and challenged six weeks after the final immunization with 1000 $TCID_{50}$ of H5N1 2004 V N. Body weight loss (left panel) and survival (right panel) were monitored for 14 days.

To assess protection, immunized mice and ferrets were challenged with a high lethal dose of highly pathogenic H5N1 2004 VN virus. All naïve mice and those immunized with empty np died and notably, all those immunized with H1-SS-np survived (FIG. 4a). All ferrets immunized with empty ferritin nanoparticles succumbed to infection, and all ferrets immunized with an H5N1 HA DNA/monovalent inactivated vaccine (MIV) prime-boost survived (FIG. 4b). Consistent with the mouse study, four out of six H1N1-based H1-SS-np'-immunized ferrets survived H5N1 challenge. Although two out of six TIV-immunized ferrets survived, one of the two survivors experienced severe weight loss (FIG. 4a), and there was no evidence of H5 serological response in the other survivor which had minimal weight loss, suggesting infection did not occur. Apart from one seronegative animal, the TIV-immunized group was not different in weight loss or fever compared to empty ferritin-np controls and showed greater illness as evidenced by post challenge activity scores than the H1-SS-np'-immunized ferrets. There was a considerable reduction in day 6 weight loss, fever and illness based on activity scores in the H1-SS-np'-immunized ferrets compared to empty ferritin-immunized controls (FIG. 4). The HAI titers to H5N1 2004 VN present at day 14 post-challenge in the surviving ferrets indicates that while H1-SS-np' was able to protect against illness, it did not prevent infection. Tables 3 and 4 provide the summary of these immunization studies in the mice and ferrets.

TABLE 3

Post challenge sera HAI antibody titers to H1N1 1999 NC and H5N1 2004 VN in mice immunized with H1-SS-np.

| | H1-SS-np | |
|---|---|---|
| Mouse # | H1N1 1999 NC (Post challenge) | H5N1 2004 VN (Post challenge) |
| 1 | <10 | 40 |
| 2 | <10 | 80 |
| 3 | <10 | 10 |
| 4 | <10 | 160 |
| 5* | N/A | N/A |
| 6 | <10 | 160 |
| 7 | <10 | <10 |
| 8 | <10 | <10 |
| 9 | <10 | 160 |
| 10 | <10 | <10 |

*This mouse died one day before challenge.

TABLE 4

Pre challenge HAI antibody titer to homologous H1N1 1999 NC
and post challenge HAI antibody titer to challenge strain
H5N1 2004 VN in ferrets immunized with indicated regimens.

| | H1N1 1999 NC (Pre Challenge) | | | | H5N1 2004 VN (post challenge) | | | |
|---|---|---|---|---|---|---|---|---|
| Ferret # | Empty np | H1-SS-np' | H5 HA (DNA/MIV) | 2006-07 TIV | Empty np | H1-SS-np' | H5 HA (DNA/MIV) | 2006-07 TIV |
| 1 | 10 | 10 | 10 | 640 | N/A | ≥1280 | <10 | 640 |
| 2 | 10 | 10 | 10 | 1280 | N/A | N/A | <10 | N/A |
| 3 | 10 | 10 | 10 | 2560 | N/A | ≥1280 | <10 | <10 |
| 4 | 10 | 10 | 10 | 1280 | N/A | ≥1280 | ≥1280 | N/A |
| 5 | 10 | 10 | 10 | 2560 | N/A | 640 | ≥1280 | N/A |
| 6 | N/A | 10 | 10 | 2560 | NA | N/A | ≥1280 | N/A |

Figure 4C:
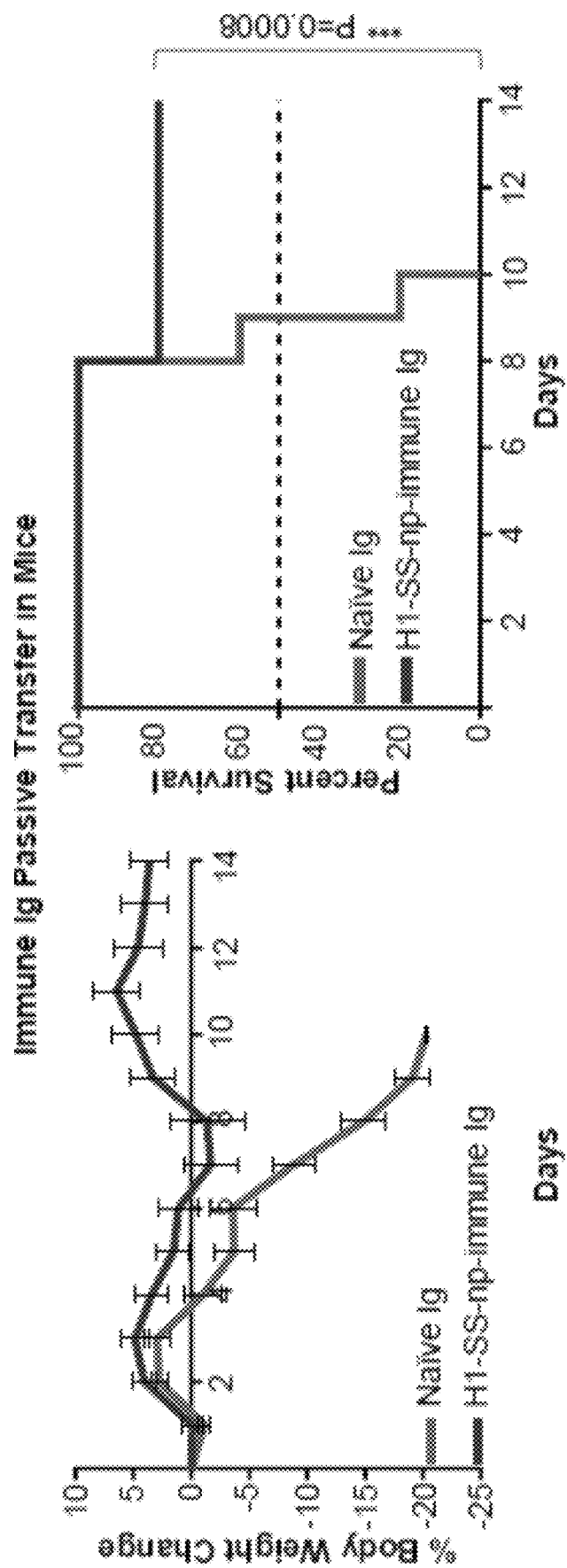
FIG. 4c shows BALB/c mice (n=10 per group) passively immunized (intraperitoneal) with 10 mg Ig from either naïve or H1-SS-np-immune animals 24 hours before challenge with a high dose (25 $LD_{50}$) of H5N1 2004 VN influenza virus. Body weight loss (left panel) and survival (right panel) were monitored for 14 days. In each of FIGS. 4a, 4b and 4c, the black dotted line (right panels) indicate 50% survival. Statistical analysis was performed with a Log-Rank (Mantel-Cox) test.
Figure 4D:
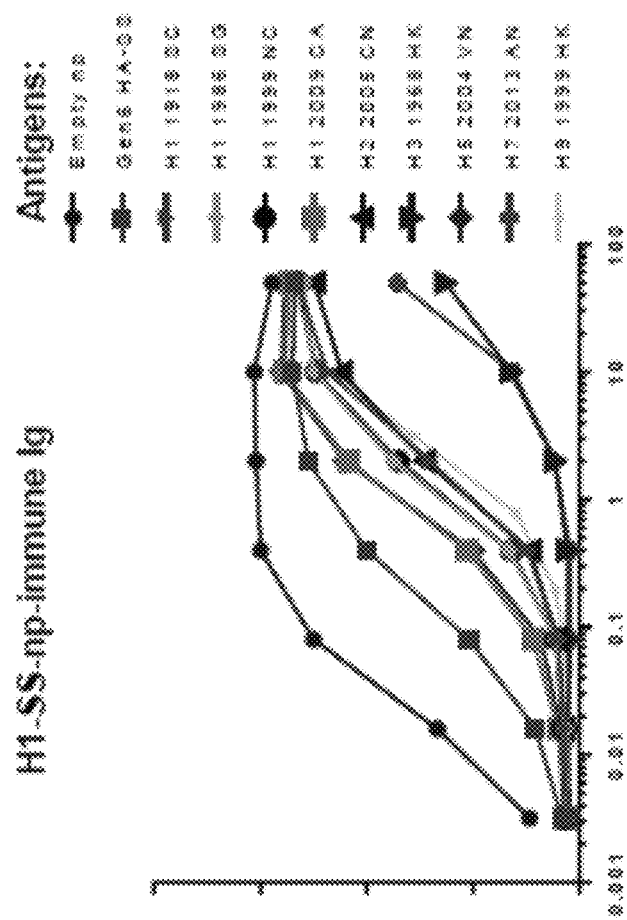
FIG. 4d shows the characterization of naïve and H1-SS-np-immune Ig. By ELISA binding of naïve Ig (left) and H1-SS-np-immune Ig (right) to empty ferritin np and various HA proteins.
Figure 4D:
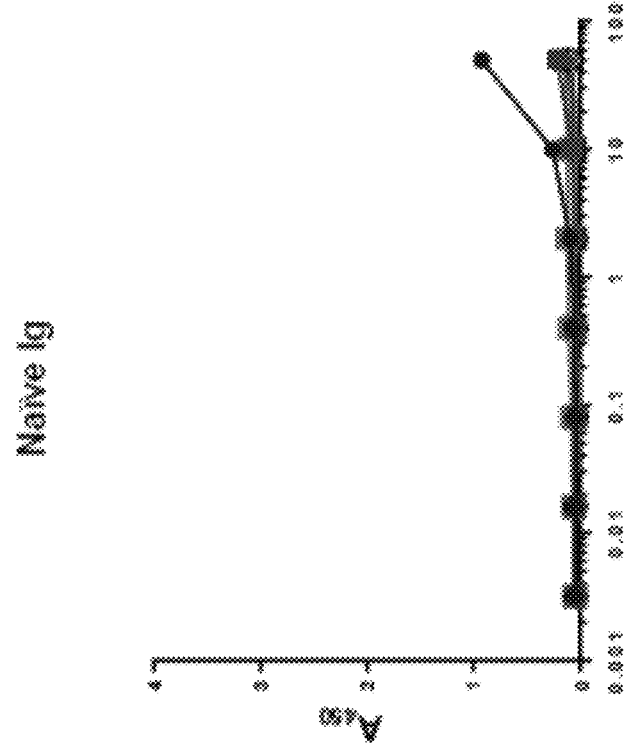
Figure 4E:
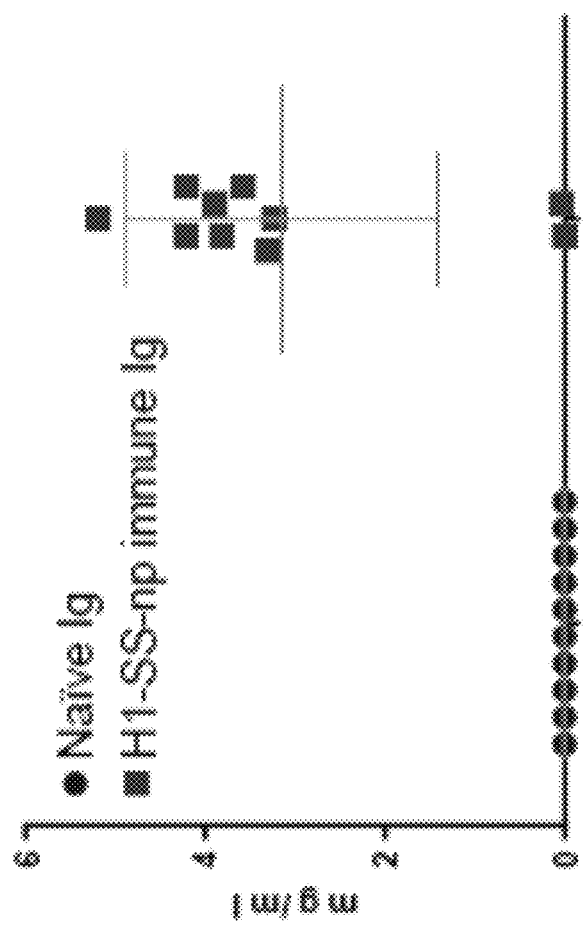
FIG. 4e shows the estimated concentration of Gen6 HA-SS specific Ig in mice sera 24 hours post infusion with polyclonal Ig.
Figure 6:
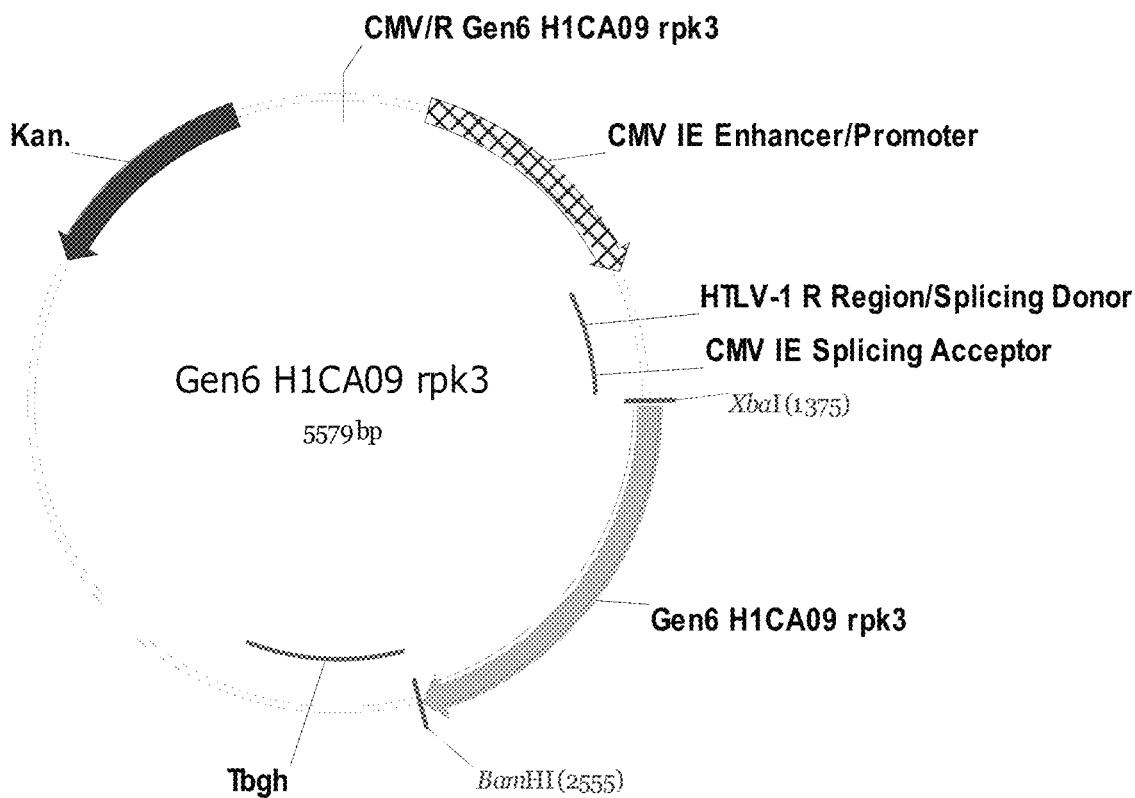
Figure 7:
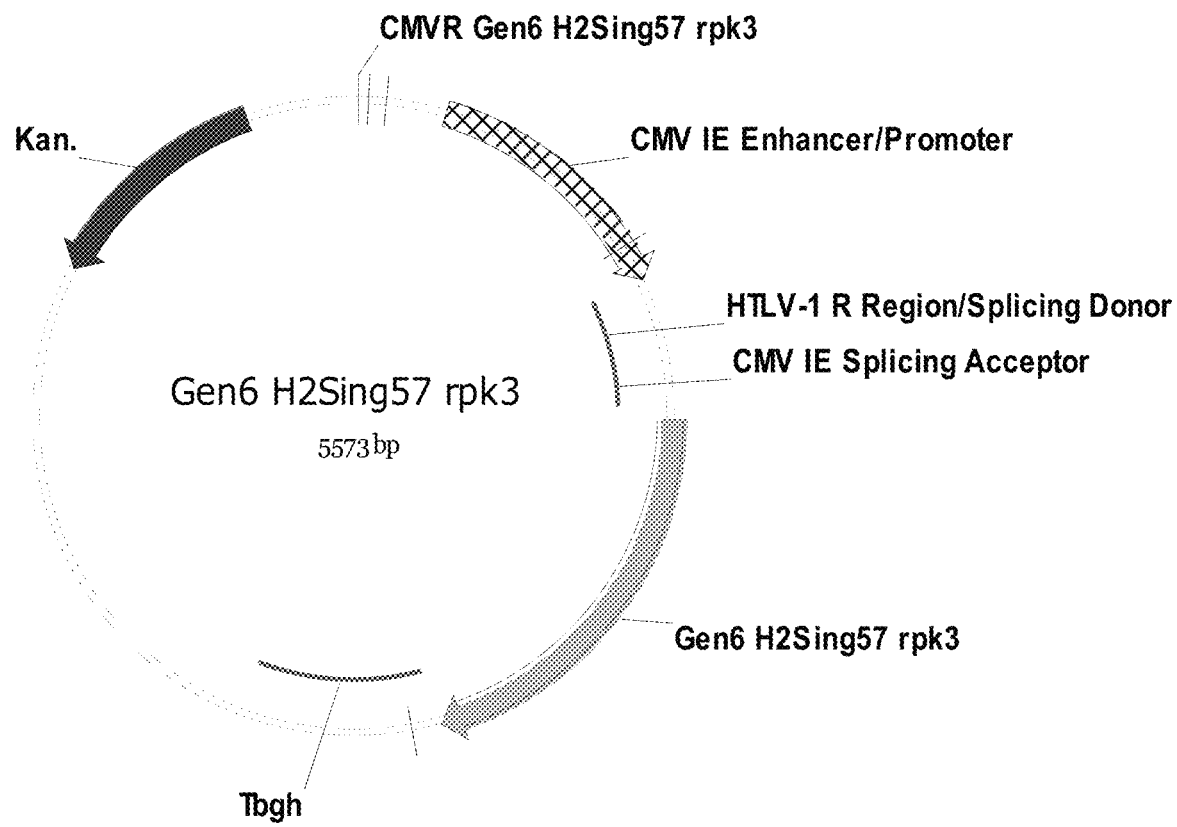
Figure 12:
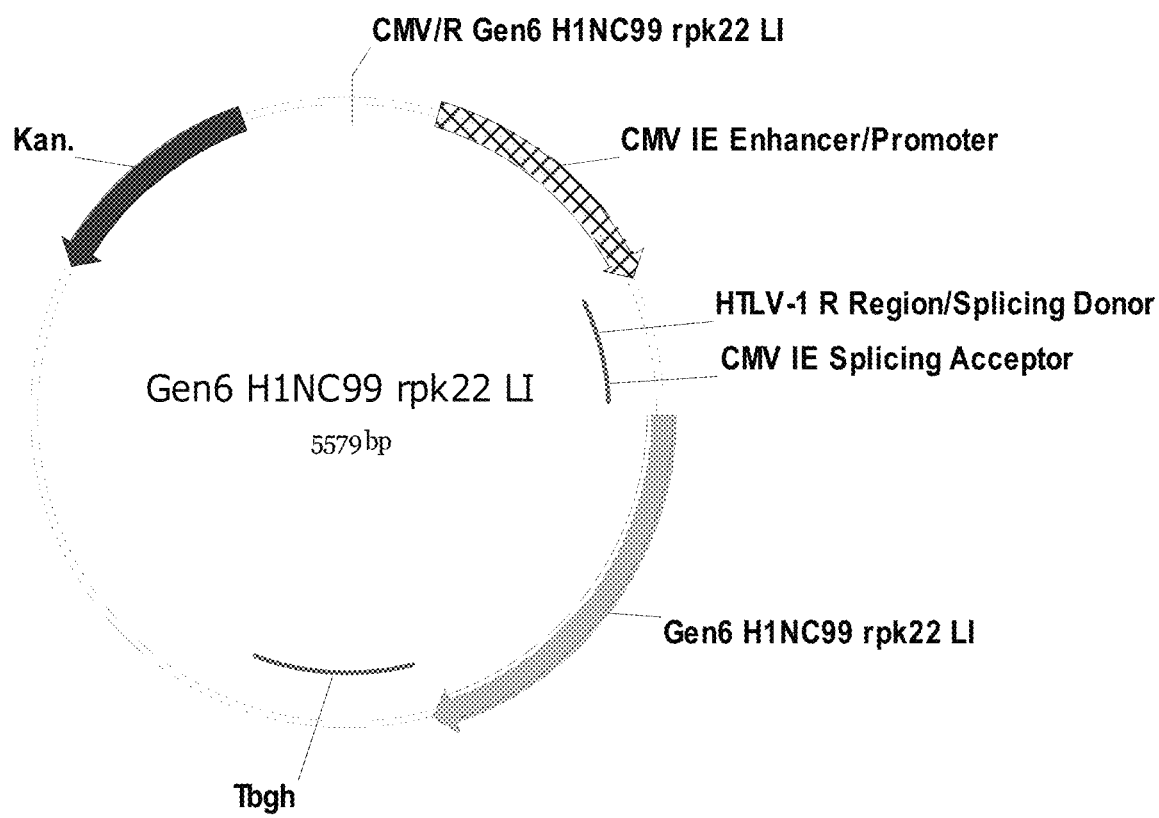

The negligible H5N1 NT activity elicited by H1-SS-np' (FIG. 3c) does not explain the heterosubtypic protection observed. However, there was a correlation between HA stem antibody titer and survival as well as between antibody titers and body weight in the H1-SS-np'-immunized ferrets. To further investigate this correlation, the inventors passively transferred H1-SS-np-immune Ig to naïve mice (10 mg/animal) 24 hour before challenge with a high lethal dose of H5N1 2004 VN virus. The transferred Ig had strong reactivity with the group 1 HA subtypes (H1, H2, H5, and H9), weaker binding to group 2 subtypes (H3 and H7), and minimal NT activity (FIGS. 4d and 4e). The IC50 neutralization titer of H1-SS-np immune Ig to diverse influenza pseudoviruses is shown in Table 5.

TABLE 5

$IC_{50}$ pseudovirus neutralization titer of H1-SS-np-immune Ig.

| Virus | H1N1 1986 SG | H1N1 1999 NC | H1N1 2009 CA | H2N2 2004 CN | H5N1 2004 VN | H7N9 2013 AN | H9N2 1999 HK |
|---|---|---|---|---|---|---|---|
| IC50 | 11 mg/ml | >50 mg/ml | >50 mg/ml | >50 mg/ml | >50 mg/ml | >50 mg/ml | >50 mg/ml |

While all the mice that received naïve Ig died from infection, eight out of ten mice that received immune Ig were completely protected from lethal H5N1 heterosubtypic challenge. Low sera reactivity to homologous H1 1999 NC HA in the two mice that died in the immune Ig group indicate they may not have received the appropriate Ig administration (FIG. 4c).

Together, these data show that antibody-mediated protection based on functional mechanisms other than neutralization such as antibody-dependent cell-mediated cytotoxicity (ADCC) or antibody-dependent complement-mediated lysis are responsible for protection elicited by H1-SS-np and H1-SS-np' immunizations. Influenza protection in mice by broadly neutralizing HA stem antibodies have been reported to be dependent on Fc interactions (DiLillo, et. al. Nat Med 20, 143-151 (2014)) and cross-reactive ADCC against influenza HA in the absence of neutralization has been reported in both human and macaque plasma (Jegaskanda, S., et al. J Immunol 190, 1837-1848 (2013); Jegaskanda, et al. J. Virol. 87, 5512-5522 (2013); Jegaskanda, et al. J Immunol 193, 469-475 (2014)). Consistent with these reports, the results presented herein suggest that HA stem-based influenza vaccines need not necessarily be focused on neutralizing epitopes to induce broad protection.

Using structure-based design and avoiding immunodominant responses to the HA head domain, combined with a nanoparticle antigen display platform, the inventors have successfully generated an HA stem-only nanoparticle vaccine immunogen that elicits antibody-mediated heterosubtypic protective immunity against H5N1 disease in ferrets. These results demonstrate that elicitation of non-neutralizing antibodies by an HA-stem-only nanoparticle vaccine can provide broad protection against severe disease and should be used to develop universal influenza vaccines.

SEQUENCE LISTING

Sequence total quantity: 401
SEQ ID NO: 1         moltype = DNA   length = 504
FEATURE              Location/Qualifiers
source               1..504
                     mol_type = unassigned DNA
                     organism = Helicobacter pylori

```
SEQUENCE: 1
atgctgtccg acatcatcaa gctgctgaac gaacaggtga acaaggagat gcagagctcc  60
aacctgtaca tgagtatgtc tagttggtgt tatacacact cactggacgg cgctgggctg  120
ttcctgtttg atcacgcagc cgaggaatac gaacatgcaa agaaactgat cattttcctg  180
aatgagaaca atgtgcccgt ccagctgact tcaatcagcg cccctgaaca taagttcgag  240
ggcctgaccc agatctttca gaaagcttac gaacacgagc agcatatttc cgaatctatc  300
aacaatattg tggaccacgc cattaagagc aaagatcatg ctaccttcaa ctttctgcag  360
tggtacgtgg ccgagcagca cgaggaggag gtcctgttta aggacatcct ggataaaatc  420
gaactgattg gaaacgagaa tcatggcctg tacctggcag atcagtatgt gaagggcatt  480
gccaagtcca gaaaaagtgg gtca                                        504

SEQ ID NO: 2            moltype = AA  length = 168
FEATURE                 Location/Qualifiers
source                  1..168
                        mol_type = protein
                        organism = Helicobacter pylori
SEQUENCE: 2
MLSDIIKLLN EQVNKEMQSS NLYMSMSSWC YTHSLDGAGL FLFDHAAEEY EHAKKLIIFL  60
NENNVPVQLT SISAPEHKFE GLTQIFQKAY EHEQHISESI NNIVDHAIKS KDHATFNFLQ  120
WYVAEQHEEE VLFKDILDKI ELIGNENHGL YLADQYVKGI AKSRKSGS              168

SEQ ID NO: 3            moltype = DNA  length = 504
FEATURE                 Location/Qualifiers
source                  1..504
                        mol_type = unassigned DNA
                        organism = Helicobacter pylori
SEQUENCE: 3
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg atgtcggaca gcat                                        504

SEQ ID NO: 4            moltype = DNA  length = 492
FEATURE                 Location/Qualifiers
source                  1..492
                        mol_type = unassigned DNA
                        organism = Influenza A virus
SEQUENCE: 4
atcatcaagc tgctgaacga acaggtgaac aaggagatgc agagctccaa cctgtacatg  60
agtatgtcta gttggtgtta tacacactca ctggacggcg ctgggctgtt cctgtttgat  120
cacgcagccg aggaatacga acatgcaaag aaactgatca ttttcctgaa tgagaacaat  180
gtgcccgtcc agctgacttc aatcagcgcc cctgaacata agttcgaggg cctgacccag  240
atctttcaga aagcttacga acacgagcag catatttccg aatctatcaa caatattgtg  300
gaccacgcca ttaagagcaa agatcatgct accttcaact ttctgcagtg gtacgtggcc  360
gagcagcacg aggaggaggt cctgtttaag gacatcctgg ataaaatcga actgattgga  420
aacgagaatc atggcctgta cctggcagat cagtatgtga agggcattgc caagtccaga  480
aaaagtgggt ca                                                     492

SEQ ID NO: 5            moltype = AA  length = 165
FEATURE                 Location/Qualifiers
source                  1..165
                        mol_type = protein
                        organism = Influenza A virus
SEQUENCE: 5
DIIKLLNEQV NKEMQSSNLY MSMSSWCYTH SLDGAGLFLF DHAAEEYEHA KKLIIFLNEN  60
NVPVQLTSIS APEHKFEGLT QIFQKAYEHE QHISESINNI VDHAIKSKDH ATFNFLQWYV  120
AEQHEEEVLF KDILDKIELI GNENHGLYLA DQYVKGIAKS RKSGS                 165

SEQ ID NO: 6            moltype = DNA  length = 492
FEATURE                 Location/Qualifiers
source                  1..492
                        mol_type = unassigned DNA
                        organism = Influenza A virus
SEQUENCE: 6
tgacccactt tttctggact tggcaatgcc cttcacatac tgatctgcca ggtacaggcc  60
atgattctcg tttccaatca gttcgatttt atccaggatg tccttaaaca ggacctcctc  120
ctcgtgctgc tcggccacgt accactgcag aaagttgaag gtagcatgat ctttgctctt  180
aatggcgtgg tccacaatat tgttgataga ttcggaaata tgctgctcgt gttcgtaagc  240
tttctgaaag atctgggtca ggccctcgaa cttatgttca ggggcgctga ttgaagtcag  300
ctggacgggc acattgttct cattcaggaa aatgatcagt ttctttgcat gttcgtattc  360
ctcggctgcg tgatcaaaca ggaacagccc agcgccgtcc agtgagtgtg tataacacca  420
actagacata ctcatgtaca ggttggagct ctgcatctcc ttgttcacct gttcgttcag  480
cagcttgatg at                                                     492
```

| SEQ ID NO: 7 | moltype = DNA length = 1695 |
| --- | --- |
| FEATURE | Location/Qualifiers |
| source | 1..1695 |
| | mol_type = unassigned DNA |
| | organism = Influenza A virus |

SEQUENCE: 7

```
atgaaggcca aactgctggt gctgctgtgt acctttaccg ccacctacgc cgacacaatc   60
tgtatcggct accacgccaa caatagcacc gacaccgtgg atacagtgct ggagaagaac  120
gtgaccgtga cccactctgt gaacctgctg gaggacagcc acaatggcaa gctgtgtctg  180
ctgaaaggca ttgcccctct gcagctgggc aattgttctg tggccggatg gattctgggc  240
aaccccgagt gtgagctgct gatttctaag gagagctgga gctacatcgt ggagaccccc  300
aatcctgaga atggcacctg ctaccctggc tacttcgccg attacgagga gctgcgcgag  360
cagctgtcta gcgtgtccag cttcgagaga ttcgagatct ccccaagga gtccagctgg   420
cctaatcaca cagtgacagg cgtgtctgcc agctgtagcc acaatggcaa aagcagcttc  480
taccggaacc tgctgtggct gacaggcaag aatggcctgt accccaacct gagcaagagc  540
tacgtgaaca acaaggaaaa ggaagtgctg gtgctgtggg gagtgcacca ccctcccaac  600
atcggaaatc agcgggccct gtaccacaca gagaacgcct atgtgagcgt ggtgtccagc  660
cactacagca gaagattcac ccccgacatc gccaagagac ccaaagtgag agaccaggag  720
ggccggatca attactactg gaccctgctg gagcctggcg ataccatcat cttcgaggcc  780
aacggcaatc tgatcgcccc ttggtatgcc tttgccctga gcagaggctt ggcagcgggc  840
atcatcacaa gcaacgcccc catggatgag tgtgatgcca agtgccagac acctcagggc  900
gccatcaata gcagcctgcc cttccagaat gtgcaccctg tgaccatcgg cgagtgccc  960
aagtatgtga aagcgccaa gctgagaatg gtgaccggcc tgagaaacat ccctagcatc 1020
cagagcagag actgtgtttgg agccatcgcc ggattcatcg agggaggatg gacaggcatg 1080
gtggatggct ggtacggcta ccaccaccag aatgagcagg gctctggata tgccgccgat 1140
cagaagtcta cccagaacgc catcaacggc atcaccaaca aggtgaacag cgtgatcgag 1200
aagatgaaca cccagtttac cgctgtgggc aaggagttca acaagctgga gcggaggatg 1260
gagaacctga caagaaggt ggacgacggc tttctggaca tctggaccta caatgccgaa 1320
ctcctggtcc tcctcgagaa tgagaggacc ctggacttcc acgacagcaa cgtgaagaac 1380
ctgtatgaga aggtgaagag ccagctgaag aacaacgcca aaggaatcgg caacggctgc 1440
ttcgagttct accacaagtg taacaacgag tgtatggaga gcgtgaagaa cggcacctac 1500
gactacccta gtacagcga ggagagcaag ctgaaccggg agaagatcga tggcgtgaag 1560
ctggagagca tgggcgtgta tcagatcctg gccatctaca gcacagtggc ctcttctctg 1620
gtgctgctgg tgtctctggg cgccatctcc ttttggatgt gctccaacgg cagcctgcag 1680
tgcaggatct gtatc                                                  1695
```

| SEQ ID NO: 8 | moltype = AA length = 565 |
| --- | --- |
| FEATURE | Location/Qualifiers |
| source | 1..565 |
| | mol_type = protein |
| | organism = Influenza A virus |

SEQUENCE: 8

```
MKAKLLVLLC TFTATYADTI CIGYHANNST DTVDTVLEKN VTVTHSVNLL EDSHNGKLCL   60
LKGIAPLQLG NCSVAGWILG NPECELLISK ESWSYIVETP NPENGTCYPG YFADYEELRE  120
QLSSVSSFER FEIFPKESSW PNHTVTGVSA SCSHNGKSSF YRNLLWLTGK NGLYPNLSKS  180
YVNNKEKEVL VLWGVHHPPN IGNQRALYHT ENAYVSVVSS HYSRRFTPEI AKRPKVRDQE  240
GRINYYWTLL EPGDTIIFEA NGNLIAPWYA FALSRGFGSG IITSNAPMDE CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FLDIWTYNAE LLVLLENERT LDFHDSNVKN LYEKVKSQLK NNAKEIGNGC  480
FEFYHKCNNE CMESVKNGTY DYPKYSEESK LNREKIDGVK LESMGVYQIL AIYSTVASSL  540
VLLVSLGAIS FWMCSNGSLQ CRICI                                        565
```

| SEQ ID NO: 9 | moltype = DNA length = 1695 |
| --- | --- |
| FEATURE | Location/Qualifiers |
| source | 1..1695 |
| | mol_type = unassigned DNA |
| | organism = Influenza A virus |

SEQUENCE: 9

```
gatacagatc ctgcactgca ggctgccgtt ggagcacatc caaaggaga tggcgcccag    60
agacaccagc agcaccagag aagaggccac tgtgctgtag atggccagga tctgatacac  120
gcccatgctc tccagcttca cgccatcgat cttctcccgg ttcagcttgc tctcctcgct  180
gtacttaggg tagtcgtagg tgccgttctt cacgctctcc atacactcgt tgttacactt  240
gtggtagaac tcgaagcagc cgttgccgat ctccttgcg tgttcttca gctggctctt  300
caccttctca tacaggttct tcacgttgct gtcgtggaag tccagggtcc tctcattctc  360
gaggaggacc aggagttcgg cattgtaggt ccagatgtcc agaaagccgt cgtccacctt  420
cttgttcagg ttctccatcc tccgctccag cttgttgaac tccttgccca cagcggtaaa  480
ctgggtgttc atcttctcga tcacgctgtt caccttgttg gtgatgccgt tgatggcgtt  540
ctgggtagac ttctgatgc cggcatatcc agagccctgc tcattctggt ggtggtagcc  600
gtaccagcca tccaccatgc ctgtccatcc tccctcgatg aatccggcga tggctccaaa  660
cagtcctctg ctctggatgc tagggatgtt tctcaggccg gtcaccatgc tcagcttggc  720
gcttctcaca tacttgggc actgccgat ggtcacaggg tgcacattct ggaagggcag  780
gctgctattg atggcgccct gaggtgtctg cacttggca tcacactcat ccatggggc  840
gttgctgtg atgatgccg tgccaaagcc tctgctcagg caaaaggcat accaagggc  900
gatcagattg ccgttggcct cgaagatgat ggtatcgcca ggctccagca gggtccagta  960
gtaattgatc cggcccctcc ggtctctcac tttgggtctc ttggcgatct cgggggtgaa 1020
tcttctgctg tagtggctgg acaccacgct cacataggcg ttctctgtgt ggtacagggc 1080
ccgctgattt ccgatgttgg gagggtggtg cactccccac agcaccagca ttccttttc  1140
cttgttgttc acgtagctct tgctcaggtt ggggtacagg ccattcttgc ctgtcagcca 1200
```

```
cagcaggttc cggtagaagc tgcttttgcc gttgtggcta cagctggcag acacgcctgt  1260
cactgtgtga ttaggccagc tggactcctt ggggaagatc tcgaatctct cgaagctgga  1320
cacgctagac agctgctcgc gcagctcctc gtaatcggcg aagtagccag ggtagcaggt  1380
gccattctca ggattggggg tctccacgat gtagctccag ctctccttag aaatcagcag  1440
ctcacactcg ggttgcccca gaatccatcc ggccacagaa caattgccca gctgcagagg  1500
ggcaatgcct ttcagcagac acagcttgcc attgtggctg tcctccagca ggttcacaga  1560
gtgggtcacg gtcacgttct tctccagcac tgtatccacg gtgtcggtgc tattgttggc  1620
gtggtagccg atacagattg tgtcggcgta ggtggcggta aaggtacaca gcagcaccag  1680
cagtttggcc ttcat                                                   1695
```

```
SEQ ID NO: 10          moltype = DNA  length = 1698
FEATURE                Location/Qualifiers
source                 1..1698
                       mol_type = unassigned DNA
                       organism = Influenza A virus
SEQUENCE: 10
atgaaggcta ttttggtcgt gctcctgtac acctttgcca cagccaatgc cgataccctt  60
tgtattggct accatgcaaa caactctacc gatacggtcg acacggtgct cgaaaagaat  120
gttactgtca cccactctgt gaacttgctg gaggataaac acaatggcaa gctctgcaaa  180
ctgcgagggg tggctcccct gcatctggga aaatgtaata ttgccggctg gatactgggt  240
aatccagaat gcgaatcctt gagtacggca tccagttggt cctatatcgt cgagaccccg  300
tcaagtgaca atgggacctg ctacccaggc gacttcattg attatgaaga gctgagggag  360
cagttgtcat ccgtaagcag cttcgaaagg tttgagattt tcccgaaaac tagctcctgg  420
cccaatcatg actctaacaa aggagttact gcagcctgtc ctcatgcggg cgcgaaaagc  480
ttctacaaga acctgatatg gctcgtgaag aaaggcaatt catacccaaa actgtctaag  540
agctacataa acgataaagg gaaagaggtt ctggtgcttt ggggcataca ccacccatct  600
acctcagccg accagcagtc tctgtatcag aacgccgaca catacgtgtt tgtgggcagc  660
tcccgctatt ctaagaagtt caaacccgag atcgccatca gaccaaaggt gagagaccag  720
gaaggaagga tgaattatta ctggaccttg gtcgaacctg gcgataagat aacgtttgag  780
gctacgggca acctggtcgt gccgagatat gcttttgcca tggagaggaa tgcggggagc  840
ggaattatca tcagcgacac tccagttcat gactgtaata ccacatgtca gacaccgaag  900
ggcgccatca acacgagctt gccctttcag aatatacatc caatcacaat cggaaaatgc  960
cccaagtacg tgaaaagcac taaactgaga ctcgccaccg gactcaggaa tatcccaagc  1020
atccagtcac ggggtctgtt cggcgctatc gccggattta ttgaaggcgg ctggacgggg  1080
atggtggacg gttggtacgg ctaccatcat caaaatgagc agggctccgg atacgccgct  1140
gacctgaaat ctacgcagaa tgccatagat gagatcacaa acaaggtcaa tagtgtgata  1200
gaaaaaatga atactcagtt cacagctgtt ggaaaggagt ttaaccacct cgagaagcga  1260
attgagaacc tgaacaagaa ggtggacgat ggcttttgg atatctggac gtataacgct  1320
gagctgcttg ttctgctgga gaacgaaaga accettgact accacgattc caacgtgaag  1380
aatctgtatg agaaagtgcg aagccagttg aaaaacaacg caaaagaaat aggcaacggc  1440
tgtttcgagt tctaccacaa atgcgataac acctgcatgg agagtgtgaa gaacggaacg  1500
tacgattatc caaaatactc cgaggaggcc aaactcaata gggaggagat agacggtgtt  1560
aagctggagt ccacacgcat ctatcagatt ctggcgatct actctactgt ggcttccagc  1620
ctggtgctgg tcgtttccct tggggcgatc agcttctgga tgtgcagcaa tggctccctg  1680
caatgccgca tctgcatc                                                1698
```

```
SEQ ID NO: 11          moltype = AA  length = 566
FEATURE                Location/Qualifiers
source                 1..566
                       mol_type = protein
                       organism = Influenza A virus
SEQUENCE: 11
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGNSYPKLSK  180
SYINDKGKEV LVLWGIHHPS TSADQQSLYQ NADTYVFVGS SRYSKKFKPE IAIRPKVRDQ  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEIDGV KLESTRIYQI LAIYSTVASS  540
LVLVVSLGAI SFWMCSNGSL QCRICI                                       566
```

```
SEQ ID NO: 12          moltype = DNA  length = 1698
FEATURE                Location/Qualifiers
source                 1..1698
                       mol_type = unassigned DNA
                       organism = Influenza A virus
SEQUENCE: 12
gatgcagatg cggcattgca gggagccatt gctgcacatc cagaagctga tcgccccaag  60
ggaaacgacc agcaccaggc tggaagccac agtagagtag atcgccagaa tctgatagat  120
gcgtgtggac tccagcttaa caccgtctat ctcctcccta ttgagtttgg cctcctcgga  180
gtattttgga taatcgtacg ttccgttctt cacactctcc atgcaggtgt tatcgcattt  240
gtggtagaac tcgaaacagc cgttgcctat ttcttttgcg ttgtttttca actggcttcg  300
cactttctca tacagattct tcacgttgga atcgtggtag tcaagggttc tttcgttctc  360
cagcagaaca agcagctcag cgttatacgt ccagatatcc aaaaagccat cgtccacctt  420
cttgttcagg ttctcaattc gcttctcgag gtggttaaac tcctttccaa cagctgtgaa  480
ctgagtattc atttttteta tcacactatt gaccttgttt gtgatctcat ctatggcatt  540
ctgcgtagat ttcaggtcag cggcgtatcc ggagccctgc tcattttgat gatggtagcc  600
```

```
gtaccaaccg tccaccatcc ccgtccagcc gccttcaata aatccggcga tagcgccgaa  660
cagaccccgt gactggatgc ttgggatatt cctgagtccg gtggcgagtc tcagtttagt  720
gcttttcacg tacttggggc attttccgat tgtgattgga tgtatattct gaaagggcaa  780
gctcgtgttg atggcgccct tcggtgtctg acatgtggta ttacagtcat gaactggagt  840
gtcgctgatg ataattccgc tccccgcatt cctctccatg gcaaaagcat atctcggcac  900
gaccaggttg cccgtagcct caaacgttat cttatcgcca ggttcgacca aggtccagta  960
ataattcatc cttccttcct ggtctctcac ctttggtctg atggcgatct cgggtttgaa  1020
cttcttagaa tagcgggagc tgcccacaaa cacgtatgtg tcggcgttct gatacagaga  1080
ctgctggtcg gctgaggtag atgggtggtg tatgccccaa agcaccagaa cctctttccc  1140
tttatcgttt atgtagctct tagacagttt tgggtatgaa ttgcctttct tcacgagcca  1200
tatcaggttc ttgtagaagc ttttcgcgcc cgcatgagga caggctgcag taactccttt  1260
gttagagtca tgattgggcc aggagctagt tttcgggaaa atctcaaacc tttcgaagct  1320
gcttacggat gacaactgct ccctcagctc ttcataatca atgaagtcgc ctgggtagca  1380
ggtcccattg tcacttgacg gggtctcgac gatataggac caactggatg ccgtactcaa  1440
ggattcgcat tctggattac ccagtatcca gccggcaata ttacattttc ccagatgcag  1500
gggagccacc cctcgcagtt tgcagagctt gccattgtgt ttatcctcca gcaagttcac  1560
agagtgggtg acagtaacat tcttttcgag caccgtgtcg accgtatcgg tagagttgtt  1620
tgcatggtag ccaatacaaa gggtatcggc attggctgtg gcaaaggtgt acaggagcac  1680
gaccaaaata gccttcat                                                1698

SEQ ID NO: 13           moltype = DNA  length = 1683
FEATURE                 Location/Qualifiers
source                  1..1683
                        mol_type = unassigned DNA
                        organism = Influenza A virus
SEQUENCE: 13
atggccatca tctacctgat cctgctgttt acagctgtga gaggcgacca gatctgtatc  60
ggctaccacg ccaacaatag caccgagaag gtggacacca tcctggagag aaacgtgaca  120
gtgacccacg ccaaggacat cctggaaaag acccacaacg gcaagctgtg taagctgaac  180
ggcatccctc ctctggaact gggcgattgt tctatcgccg gatggctgct gggaaacccc  240
gagtgtgata ggctgctgtc tgtgcctgag tggagctaca tcatggagaa ggagaaccct  300
agggacggcc tgtgttaccc tggcagcttc aacgattacg aggagctgaa gcacctgctg  360
tctagcgtga agcacttcga gaaggtgaag atcctgccca aggacagatg gacccagcac  420
acaacaacag gaggaagcag agcctgcgcc gtgtctggca accccagctt cttccggaat  480
atggtgtggc tgaccaagaa gggcagcaat taccctgtgg cccagggcag ctacaataat  540
accagcggcg agcagatgct gatcatctgg ggagtgcacc accctaatga cgagaccgag  600
cagagaaccc tgtaccagaa tgtgggcacc tacgtgtctg tgggcaccag caccctgaat  660
aagagaagca cccccgagat tgccacaaga cccaaggtga acggccaggg aggaagaatg  720
gagttcagct ggaccctgct ggatatgtgg gacaccatca actttgagag caccggcaat  780
ctgatcgccc ctgagtacgg cttcaagatc agcaagagag gcagcagcgg catcatgaaa  840
accgagggca ccctggagaa ttgtgagacc aagtgccaga cacctctggg cgccatcaat  900
accaccctgc ccttccacaa tgtgcaccct ctgaccatcg gcgagtgccc taagtatgtg  960
aagagcgaga agctggtgct ggccacagga ctgagaaacg tgccccagat cgagagcaga  1020
ggcctgtttg gagccatcgc cggattcatc gagggaggat ggcagggaat ggtcgatggc  1080
tggtacggct accaccacag caatgatcag ggctctggct atgccgccga taaggagtct  1140
acccagaagg cctttgacgg catcaccaac aaggtgaaca gcgtgatcga gaagatgaac  1200
acccagtttg aggctgtggg caaggagttt agcaacctgg agcggagact ggagaacctg  1260
aacaagaaga tggaggacgg cttcctggat gtgtggacct acaatgccga actgctggtg  1320
ctgatggaga atgagcggac cctggacttc cacgacagca acgtgaagaa cctgtacgac  1380
aaagtgagga tgcagctgag ggacaacgtg aaggaactgg gcaatggctg cttcgagttc  1440
taccacaagt gtgacgacga gtgtatgaac tccgtgaaga acggcaccta cgactaccct  1500
aagtacgagg aggagagcaa gctgaaccgg aacgagatca agggcgtgaa gctgtctagc  1560
atgggcgtgt atcagatcct ggccatctat gccacagtgg ccggatctct gagcctggca  1620
attatgatgg ctggaatcag cttctggatg tgctccaatg gcagcctgca gtgccggatc  1680
tgt                                                                1683

SEQ ID NO: 14           moltype = AA  length = 564
FEATURE                 Location/Qualifiers
source                  1..564
                        mol_type = protein
                        organism = Influenza A virus
SEQUENCE: 14
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTKKGSN YPVAKGSYNN  180
TSGEQMLIIW GVHHPNDETE QRTLYQNVGT YVSVGTSTLN KRSTPDYHIA TRPKVNGQGG  240
RMEFSWTLLD MWDTINFEST GNLIAPEYGF KISKRGSSGI MKTEGTLENC ETKCQTPLGA  300
INTTLPFHNV HPLTIGECPK YVKSEKLVLA TGLRNVPQIE SRGLFGAIAG FIEGGWQGMV  360
DGWYGYHHSN DQGSGYAADK ESTQKAFDGI TNKVNSVIEK MNTQFEAVGK EFSNLERRLE  420
NLNKKMEDGF LDVWTYNAEL LVLMENERTL DFHDSNVKNL YDKVRMQLRD NVKELGNGCF  480
EFYHKCDDEC MNSVKNGTYD YPKYEEESKL NRNEIKGVKL SSMGVYQILA IYATVAGSLS  540
LAIMMAGISF WMCSNGSLQC RICI                                         564

SEQ ID NO: 15           moltype = DNA  length = 1683
FEATURE                 Location/Qualifiers
source                  1..1683
                        mol_type = unassigned DNA
                        organism = Influenza A virus
```

-continued

```
SEQUENCE: 15
acagatccgg cactgcaggc tgccattgga gcacatccag aagctgattc cagccatcat  60
aattgccagg ctcagagatc cggccactgt ggcatagatg gccaggatct gatacacgcc  120
catgctagac agcttcacgc ccttgatctc gttccggttc agcttgctct cctcctcgta  180
cttagggtag tcgtaggtgc cgttcttcac ggagttcata cactcgtcgt cacacttgtg  240
gtagaactcg aagcagccat tgcccagttc cttcacgttg tccctcagct gcatcctcac  300
tttgtcgtac aggttcttca cgttgctgtc gtggaagtcc agggtccgct cattctccat  360
cagcaccagc agttcggcat tgtaggtcca cacatccagg aagccgtcct ccatcttctt  420
gttcaggttc tccagtctcc gctccaggtt gctaaactcc ttgcccacag cctcaaactg  480
ggtgttcatc ttctcgatca cgctgttcac cttgttggtg atgccgtcaa aggccttctg  540
ggtagactcc ttatcggcgg catagccaga gccctgatca ttgctgtggt ggtagccgta  600
ccagccatcg accattccct gccatcctcc ctcgatgaat ccggcgatgg ctccaaacag  660
gcctctgctc tcgatctggg gcacgtttct cagtcctgtg gccagcacca gcttctcgct  720
cttcacatac ttagggcact cgccgatggt cagagggtgc acattgtgga agggcagggt  780
ggtattgatg gcgcccagag gtgtctggca cttggtctca caattctcca gggtgccctc  840
ggttttcatg atgccgctgc tgcctctctt gctgatcttg aagccgtact caggggcgat  900
cagattgccg gtgctctcaa agttgatggt gtcccacata tccagcaggg tccagctgaa  960
ctccattctt cctccctggc cgttcacctt gggtcttgtg gcaatctcgg gggtgcttct  1020
cttattcagg gtgctggtgc ccacagacac gtaggtgccc acattctggt acagggttct  1080
ctgctcggtc tcgtcattag ggtggtgcac tccccagatg atcagcatct gctcgccgct  1140
ggtattattg tagctgccct gggccacagg gtaattgctg cccttcttgg tcagccacac  1200
catattccgg aagaagctgg ggttgccaga cacggcgcag gctctgcttc ctcctgttgt  1260
tgtgtgctgg gtccatctgt ccttgggcag gatcttcacc ttctcgaagt gcttcacgct  1320
agacagcagg tgcttcagct cctcgtaatc gttgaagctg ccagggtaac acaggccgtc  1380
cctagggttc tccttctcca tgatgtagct ccactcaggc acagacagca gcctatcaca  1440
ctcggggttt cccagcagcc atccggcgat agaacaatcg cccagttcca gaggagggat  1500
gccgttcagc ttacacagct tgccgttgtg ggtcttttcc aggatgtcct tggcgtgggt  1560
cactgtcacg tttctctcca ggatggtgtc caccttctcg gtgctattgt tggcgtggta  1620
gccgatacag atctggtcgc ctctcacagc tgtaaacagc aggatcaggt agatgatggc  1680
cat                                                               1683

SEQ ID NO: 16           moltype = DNA  length = 1704
FEATURE                 Location/Qualifiers
source                  1..1704
                        mol_type = unassigned DNA
                        organism = Influenza A virus
SEQUENCE: 16
atggaaaaga tcgtgctgct gctggccatt gtgagcctgg tgaagagcga ccagatctgc  60
attggctacc acgccaacaa tagcacagag caggtggaca ccatcatgga aaaaaacgtg  120
accgtgaccc acgctcagga catcctggaa aagacccaca acggcaagct gtgtgatctg  180
gacggcgtga agcctctgat cctgagagat tgtagcgtgg ctggatggct gctgggcaac  240
cctatgtgcg acgagttcat caacgtgccc gagtggagct atatcgtgga gaaggccaac  300
cccaccaacg atctgtgtta ccccggcagc ttcaacgatt acgaggaact gaagcacctg  360
ctgtcccgga tcaaccactt cgagaagatc cagatcatcc ccaagtcctc ttggagcgat  420
cacgaagcct ctagcggagt gtctagcgcc tgtccttacc tgggcagccc cagcttcttc  480
agaaacgtgg tgtggctgat caagaagaac agcacctacc ccaccatcaa gaagagctac  540
aacaacacca accaggaaga tctgctggtc ctgtggggaa tccaccaccc taatgatgcc  600
gccgagcaga ccagactgta ccagaacccc accacctata tcagcatcgg caccagcacc  660
ctgaatcaga gactggtgcc caagatcgcc accagatcca aggtgaacgg ccagagcggc  720
aggatggaat tcttctggac catcctgaag cccaacgacg ccatcaactt cgagagcaac  780
ggcaacttta tcgcccctga gtacgcctac aagatcgtga agaagggcga cagcgccatc  840
atgaagagcg agctggaata cggcaactgc aacaccaagt gccagacacc tatgggcgcc  900
atcaacagca gcatgccctt ccacaacatc caccctctga ccatcggcga gtgccctaag  960
tacgtgaaga gcaacagact ggtgctggcc acaggcctga gaaatagccc ccagcgggag  1020
agcagaagaa agaagagggg cctgtttgga gccatcgccg gctttattga aggcggctgg  1080
cagggaatgg tggatggctg gtacggctac caccacagca atgagcaggg ctctggatat  1140
gccgccgaca aagagtctac ccagaaggcc atcgacggcg tcaccaacaa ggtgaacagc  1200
atcatcgaca agatgaacac ccagttcgag gctgtgggca gagagttcaa caacctggaa  1260
cggcggatcg agaacctgaa caagaaaatg gaagatggct tcctggatgt gtggacctac  1320
aatgccgaac tgctggtgct gatggaaaac gagcggaccc tggacttcca cgacagcaac  1380
gtgaagaacc tgtacgacaa agtgcggctg cagctgagag acaacgccaa agagctgggc  1440
aacggctgct tcgagttcta ccacaagtgc gacaacgagt gcatggaaag catccggaac  1500
ggcacctaca actaccctca gtacagcgag gaagccaggc tgaagaggga agagatcagc  1560
ggcgtgaaac tggaatccat cggcacctac cagatcctga gcatctacag cacagtggcc  1620
tcttctctgg ccctggccat tatgatggcc ggactgagcc tgtggatgtg cagcaatggc  1680
agcctgcagt gcaggatctg catc                                        1704

SEQ ID NO: 17           moltype = AA  length = 568
FEATURE                 Location/Qualifiers
source                  1..568
                        mol_type = protein
                        organism = Influenza A virus
SEQUENCE: 17
MEKIVLLLAI VSLVKSDQIC IGYHANNSTE QVDTIMEKNV TVTHAQDILE KTHNGKLCDL  60
DGVKPLILRD CSVAGWLLGN PMCDEFINVP EWSYIVEKAN PTNDLCYPGS FNDYEELKHL  120
LSRINHFEKI QIIPKSSWSD HEASSGVSSA CPYLGSPSFF RNVVWLIKKN STYPTIKKSY  180
NNTNQEDLLV LWGIHHPNDA AEQTRLYQNP TTYISIGTST LNQRLVPKIA TRSKVNGQSG  240
RMEFFWTILK PNDAINFESN GNFIAPEYAY KIVKKGDSAI MKSELEYGNC NTKCQTPMGA  300
INSSMPFHNI HPLTIGECPK YVKSNRLVLA TGLRNSPQRE SRRKKRGLFG AIAGFIEGGW  360
```

```
QGMVDGWYGY HHSNEQGSGY AADKESTQKA IDGVTNKVNS IIDKMNTQFE AVGREFNNLE    420
RRIENLNKKM EDGFLDVWTY NAELLVLMEN ERTLDFHDSN VKNLYDKVRL QLRDNAKELG    480
NGCFEFYHKC DNECMESIRN GTYNYPQYSE EARLKREEIS GVKLESIGTY QILSIYSTVA    540
SSLALAIMMA GLSLWMCSNG SLQCRICI                                      568

SEQ ID NO: 18              moltype = DNA  length = 1704
FEATURE                    Location/Qualifiers
source                     1..1704
                           mol_type = unassigned DNA
                           organism = Influenza A virus
SEQUENCE: 18
gatgcagatc ctgcactgca ggctgccatt gctgcacatc cacaggctca gtccggccat      60
cataatggcc agggccagag aagaggccac tgtgctgtag atgctcagga tctggtaggt     120
gccgatggat tccagtttca cgccgctgat ctcttccctc ttcagcctgg cttcctcgct     180
gtactgaggg tagttgtagg tgccgttccg gatgctttcc atgcactcgt tgtcgcactt     240
gtggtagaac tcgaagcagc cgttgcccag ctctttggcg ttgtctctca gctgcagccg     300
cactttgtcg tacaggttct tcacgttgct gtcgtggaag tccagggtcc gctcgttttc     360
catcagcacc agcagttcgg cattgtaggt ccacacatga aggaagccat cttccatttt     420
cttgttcagg ttctcgatcc gccgttccag gttgttgaac tctctgccca cagcctcgaa     480
ctgggtgttc atcttgtcga tgatgctgtt caccttgttg gtgacgccgt cgatggcctt     540
ctgggtagac tctttgtcgg cggcatatcc agagccctgc tcattgctgt ggtggtagcc     600
gtaccagcca tccaccattc cctgccagcc gccttcaata aagccgggca tggctccaaa     660
caggcccctc ttctttcttc tgctctcccg ctgggggcta tttctcaggc ctgtggccag     720
caccagtctg ttgctcttca cgtacttagg gcactcgccg atggtcagag ggtggatgtt     780
gtggaagggc atgctgctgt tgatggcgcc cataggtgtc tggcacttgg tgttgcagtt     840
gccgtattcc agctcgctct tcatgatggc gctgtcgctc ttcttcacga tcttgtaggc     900
gtactcaggg gcgataaagt tgccgttgct ctcgaagttg atggcgtcgt tgggcttcag     960
gatggtccag aagaattcca tcctgccgct ctggccgttc accttggatc tggtggcgat    1020
cttgggcacc agtctctgat tcagggtgct ggtgccgatg ctgatatagg tggtggggtt    1080
ctggtacagt ctggtctgct cggcggcatc attagggtgg tggattcccc acaggaccag    1140
cagatcttcc tggttggtgt tgttgtagct cttcttgatg gtggggtagg tgctgttctt    1200
cttgatcagc cacaccacgt ttctgaagaa gctggggctg cccaggtaag gacaggcgct    1260
agacactccg ctagaggctt cgtgatcgct ccaagaggac ttggggatga tctggatctt    1320
ctcgaagtgg ttgatccggg acagcaggtg cttcagttcc tcgtaatcgt tgaagctgcc    1380
ggggtaacac agatcgttgg tggggttggc cttctccacg atatagctcc actcgggcac    1440
gttgatgaac tcgtcgcaca tagggttgcc cagcagccat ccagccacgc tacaatctct    1500
caggatcaga ggcttcacgc cgtccagatc acacagcttg ccgttgtggg tcttttccag    1560
gatgtcctga gcgtgggtca cggtcacgtt ttttccatg atggtgtcca cctgctctgt    1620
gctattgttg gcgtggtagc caatgcagat ctggtcgctc ttcaccaggc tcacaatggc    1680
cagcagcagc acgatctttt ccat                                          1704

SEQ ID NO: 19              moltype = DNA  length = 147
FEATURE                    Location/Qualifiers
source                     1..147
                           mol_type = unassigned DNA
                           organism = Influenza A virus
SEQUENCE: 19
atgaaggcca aactgctggt gctgctgtgt acctttaccg ccacctacgc cgacacaatc      60
tgtatcggct accacgccaa caatagcacc gacaccgtgg atacagtgct ggagaagaac     120
gtgaccgtga cccactctgt gaacctg                                        147

SEQ ID NO: 20              moltype = AA  length = 49
FEATURE                    Location/Qualifiers
source                     1..49
                           mol_type = protein
                           organism = Influenza A virus
SEQUENCE: 20
MKAKLLVLLC TFTATYADTI CIGYHANNST DTVDTVLEKN VTVTHSVNL                 49

SEQ ID NO: 21              moltype = DNA  length = 147
FEATURE                    Location/Qualifiers
source                     1..147
                           mol_type = unassigned DNA
                           organism = Influenza A virus
SEQUENCE: 21
caggttcaca gagtgggtca cggtcacgtt cttctccagc actgtatcca cggtgtcggt      60
gctattgttg gcgtggtagc cgatacagat tgtgtcggcg taggtggcgg taaaggtaca     120
cagcagcacc agcagtttgg ccttcat                                        147

SEQ ID NO: 22              moltype = DNA  length = 678
FEATURE                    Location/Qualifiers
source                     1..678
                           mol_type = unassigned DNA
                           organism = Influenza A virus
SEQUENCE: 22
gatgccaagt gccagacacc tcagggcgcc atcaatagca gcctgccctt ccagaatgtg      60
caccctgtga ccatcggcga gtgccccaag tatgtgaaga cgccaagct gagaatggtg     120
accgcctga gaaacatccc tagcatccag agcagaggac tgtttggagc catcgccgga     180
ttcatcgagg aggatggac aggcatgtg atggctggt acggctacca ccaccagaat      240
```

```
gagcagggct ctggatatgc cgccgatcag aagtctaccc agaacgccat caacggcatc    300
accaacaagg tgaacagcgt gatcgagaag atgaacaccc agtttaccgc tgtgggcaag    360
gagttcaaca agctggagcg gaggatggag aacctgaaca agaaggtgga cgacggcttt    420
ctggacatct ggacctacaa tgccgaactc ctggtcctcc tcgagaatga gaggaccctg    480
gacttccacg acagcaacgt gaagaacctg tatgagaagg tgaagagcca gctgaagaac    540
aacgccaagg agatcggcaa cggctgcttc gagttctacc acaagtgtaa caacgagtgt    600
atggagagcg tgaagaacgg cacctacgac taccctaagt acagcgagga gagcaagctg    660
aaccgggaga agatcgat                                                  678

SEQ ID NO: 23              moltype = AA  length = 226
FEATURE                    Location/Qualifiers
source                     1..226
                           mol_type = protein
                           organism = Influenza A virus
SEQUENCE: 23
DAKCQTPQGA INSSLPFQNV HPVTIGECPK YVRSAKLRMV TGLRNIPSIQ SRGLFGAIAG     60
FIEGGWTGMV DGWYGYHHQN EQGSGYAADQ KSTQNAINGI TNKVNSVIEK MNTQFTAVGK    120
EFNKLERRME NLNKKVDDGF LDIWTYNAEL LVLLENERTL DFHDSNVKNL YEKVKSQLKN    180
NAKEIGNGCF EFYHKCNNEC MESVKNGTYD YPKYSEESKL NREKID                   226

SEQ ID NO: 24              moltype = DNA  length = 678
FEATURE                    Location/Qualifiers
source                     1..678
                           mol_type = unassigned DNA
                           organism = Influenza A virus
SEQUENCE: 24
atcgatcttc tcccggttca gcttgctctc ctcgctgtac ttaggggtagt cgtaggtgcc    60
gttcttcacg ctctccatac actcgttgtt acacttgtgg tagaactcga agcagccgtt   120
gccgatctcc ttggcgttgt tcttcagctg gctcttcacc ttctcataca ggttcttcac   180
gttgctgtcg tggaagtcca gggtcctctc attctcgagg aggaccagga gttcggcatt   240
gtaggtccag atgtccagaa agccgtcgtc caccttcttg ttcaggttct ccatcctccg   300
ctccagcttg ttgaactcct tgccacagc ggtaaactgg tgttcatct ctcgatcac     360
gctgttcacc ttgttggtga tgccgttgat ggcgttctgg gtagttct gatcggcggc    420
atatccagag ccctgctcat tctggtggtg gtagccgatc cagccatcca ccatgcctgt    480
ccatcctccc tcgatgaatc cggcgatggc tccaaacagt cctctgtct ggatgctagg    540
gatgttctc aggccggtca ccattctcag cttggcgctt ctcacatact ggggcactc     600
gccgatggtc acagggtgca cattctggaa gggcaggctg ctattgatgg cgccctgagg    660
tgtctggcac ttggcatc                                                 678

SEQ ID NO: 25              moltype = DNA  length = 576
FEATURE                    Location/Qualifiers
source                     1..576
                           mol_type = unassigned DNA
                           organism = Influenza A virus
SEQUENCE: 25
gatgccaagt gccagacacc tcagggcgcc atcaatagca gcctgccctt ccagaatgtg     60
caccctgtga ccatcggcga gtgccccaag tatgtgagca gcgccaagct gagaatggtg    120
accggcctga aaacatccc tagcatccag agcagaggac tgtttggagc catcgccgga    180
ttcatcgagg gaggatggac aggcatggtg gatggctggt acggctacca ccaccagaat    240
gagcagggct ctggatatgc cgccgatcag aagtctaccc agaacgccat caacggcatc    300
accaacaagg tgaacagcgt gatcgagaag atgtacaatg ccgaactcct ggtcctcctc    360
gagaatgaga ggaccctgga cttccacgac agcaacgtga gaacctgta tgagaaggtg    420
aagagcagc tgaagaacaa cgccaaggag atcggcaacg gctgcttcga gttctaccac    480
aagtgtaaca acgagtgtat ggagagcgtg aagaacggca cctacgacta ccctaagtac    540
agcgaggaga gcaagctgaa ccgggagaag atcgat                             576

SEQ ID NO: 26              moltype = AA  length = 193
FEATURE                    Location/Qualifiers
source                     1..193
                           mol_type = protein
                           organism = Influenza A virus
SEQUENCE: 26
DAKCQTPQGA INSSLPFQNV HPVTIGECPK YVRSAKLRMV TGLRNIPSIQ SRGLFGAIAG     60
FIEGGWTGMV DGWYGYHHQN EQGSGYAADQ KSTQNAINGI TNKVNSVIEK MTYNAELLVL    120
LENERTLDFH DSNVKNLYEK VKSQLKNNAK EIGNGCFEFY HKCNNECMES VKNGTYDYPK    180
YSEESKLNRE KID                                                      193

SEQ ID NO: 27              moltype = DNA  length = 576
FEATURE                    Location/Qualifiers
source                     1..576
                           mol_type = unassigned DNA
                           organism = Influenza A virus
SEQUENCE: 27
atcgatcttc tcccggttca gcttgctctc ctcgctgtac ttaggggtagt cgtaggtgcc    60
gttcttcacg ctctccatac actcgttgtt acacttgtgg tagaactcga agcagccgtt   120
gccgatctcc ttggcgttgt tcttcagctg gctcttcacc ttctcataca ggttcttcac   180
gttgctgtcg tggaagtcca gggtcctctc attctcgagg aggaccagga gttcggcatt   240
gtacatcttc tcgatcacgc tgttcacctt gttggtgatg ccgttgatgg cgttctgggt    300
agacttctga tcggcggcat atccagagcc ctgctcattc tggtggtggt agccgtacca    360
```

-continued

```
gccatccacc atgcctgtcc atcctccctc gatgaatccg gcgatggctc caaacagtcc  420
tctgctctgg atgctaggga tgtttctcag gccggtcacc attctcagct tggcgcttct  480
cacatacttg gggcactcgc cgatggtcac agggtgcaca ttctggaagg gcaggctgct  540
attgatggcg ccctgaggtg tctggcactt ggcatc                            576

SEQ ID NO: 28          moltype = DNA  length = 570
FEATURE                Location/Qualifiers
source                 1..570
                       mol_type = unassigned DNA
                       organism = Influenza A virus
SEQUENCE: 28
ctgagaatgg tgaccggcct gagaaacatc cctagcatcc agagcagagg actgtttgga  60
gccatcgccg gattcatcga gggaggatgg acaggcatgg tggatggctg gtacggctac  120
caccaccaga atgagcaggg ctctggatat gccgccgatc agaagtctac ccagaacgcc  180
atcaacggca tcaccaacaa ggtgaacagc gtgatcgaga agatgaacac ccagtttacc  240
gctgtgggca aggagttcaa caagctggag cggaggatgg agaacctgaa caagaaggtg  300
gacgacggct ttctggacat ctggacctac aatgccgaac tcctggtcct cctcgagaat  360
gagaggaccc tggacttcca cgacagcaac gtgaagaacc tgtatgagaa ggtgaagagc  420
cagctgaaga acaacgccaa ggagatcggc aacggctgct tcgagttcta ccacaagtgt  480
aacaacgagt gtatggagag cgtgaagaac ggcacctacg actaccctaa gtacagcgag  540
gagagcaagc tgaaccggga gaagatcgat                                   570

SEQ ID NO: 29          moltype = AA  length = 194
FEATURE                Location/Qualifiers
source                 1..194
                       mol_type = protein
                       organism = Influenza A virus
SEQUENCE: 29
LRMVTGLRNI PQRETSIQSR GLFGAIAGFI EGGWTGMVDG WYGYHHQNEQ GSGYAADQKS  60
TQNAINGITN KVNSVIEKMN TQFTAVGKEF NKLERRMENL NKKVDDGFLD IWTYNAELLV  120
LLENERTLDF HDSNVKNLYE KVKSQLKNNA KEIGNGCFEF YHKCNNECME SVKNGTYDYP  180
KYSEESKLNR EKID                                                     194

SEQ ID NO: 30          moltype = DNA  length = 570
FEATURE                Location/Qualifiers
source                 1..570
                       mol_type = unassigned DNA
                       organism = Influenza A virus
SEQUENCE: 30
atcgatcttc tcccggttca gcttgctctc ctcgctgtac ttagggtagt cgtaggtgcc  60
gttcttcacg ctctccatac actcgttgtt acacttgtgg tagaactcga agcagccgtt  120
gccgatctcc ttggcgttgt tcttcagctg gctcttcacc ttctcataca ggttcttcac  180
gttgctgtcg tggaagtcca gggtcctctc attctcgagg aggaccagga gttcggcatt  240
gtaggtccag atgtccagaa agccgtcgtc caccttcttg ttcaggttct ccatcctccg  300
ctccagcttg ttgaactcct tgcccacagc ggtaaactgg gtgttcatct tctcgatcac  360
gctgttcacc ttgttggtga tgccgttgat ggcgttctgg gtagacttct gatcggcggc  420
atatccagag ccctgctcat tctggtggtg gtagccgtac cagccatcca ccatgcctgt  480
ccatcctccc tcgatgaatc cggcgatggc tccaaacagt cctctgctct ggatgctagg  540
gatgtttctc aggccggtca ccattctcag                                   570

SEQ ID NO: 31          moltype = DNA  length = 468
FEATURE                Location/Qualifiers
source                 1..468
                       mol_type = unassigned DNA
                       organism = Influenza A virus
SEQUENCE: 31
ctgagaatgg tgaccggcct gagaaacatc cctagcatcc agagcagagg actgtttgga  60
gccatcgccg gattcatcga gggaggatgg acaggcatgg tggatggctg gtacggctac  120
caccaccaga atgagcaggg ctctggatat gccgccgatc agaagtctac ccagaacgcc  180
atcaacggca tcaccaacaa ggtgaacagc gtgatcgaga agatgtacaa tgccgaactc  240
ctggtcctcc tcgagaatga gaggaccctg gacttccacg acagcaacgt gaagaacctg  300
tatgagaagg tgaagagcca gctgaagaac aacgccaagg agatcggcaa cggctgcttc  360
gagttctacc acaagtgtaa caacgagtgt atggagagcg tgaagaacgg cacctacgac  420
taccctaagt acagcgagga gagcaagctg aaccgggaga agatcgat               468

SEQ ID NO: 32          moltype = AA  length = 157
FEATURE                Location/Qualifiers
source                 1..157
                       mol_type = protein
                       organism = Influenza A virus
SEQUENCE: 32
LRMVTGLRNI PQRETRGLFG AIAGFIEGGW TGMVDGWYGY HHQNEQGSGY AADQKSTQNA  60
INGITNKVNS VIEKMTYNAE LLVLLENERT LDFHDSNVKN LYEKVKSQLK NNAKEIGNGC  120
FEFYHKCNNE CMESVKNGTY DYPKYSEESK LNREKID                            157

SEQ ID NO: 33          moltype = DNA  length = 468
FEATURE                Location/Qualifiers
```

```
source                  1..468
                        mol_type = unassigned DNA
                        organism = Influenza A virus
SEQUENCE: 33
atcgatcttc tcccggttca gcttgctctc ctcgctgtac ttagggtagt cgtaggtgcc  60
gttcttcacg ctctccatac actcgttgtt acacttgtgg tagaactcga agcagccgtt  120
gccgatctcc ttggcgttgt tcttcagctg gctcttcacc ttctcataca ggttcttcac  180
gttgctgtcg tggaagtcca gggtcctctc attctcgagg aggaccagga gttcggcatt  240
gtacatcttc tcgatcacgc tgttcacctt gttggtgatg ccgttgatgg cgttctgggt  300
agacttctga tcggcggcat atccagagcc ctgctcattc tggtggtggt agccgtacca  360
gccatccacc atgcctgtcc atcctccctc gatgaatccg gcgatggctc caaacagtcc  420
tctgctctgg atgctaggga tgtttctcag gccggtcacc attctcag             468

SEQ ID NO: 34           moltype = DNA  length = 147
FEATURE                 Location/Qualifiers
source                  1..147
                        mol_type = unassigned DNA
                        organism = Influenza A virus
SEQUENCE: 34
atgaaggcta ttttggtcgt gctcctgtac acctttgcca cagccaatgc cgataccctt  60
tgtattggct accatgcaaa caactctacc gatacggtcg acacggtgct cgaaaagaat  120
gttactgtca cccactctgt gaacttg                                     147

SEQ ID NO: 35           moltype = AA  length = 49
FEATURE                 Location/Qualifiers
source                  1..49
                        mol_type = protein
                        organism = Influenza A virus
SEQUENCE: 35
MKAILVVLLY TFATANADTL CIGYHANNST DTVDTVLEKN VTVTHSVNL              49

SEQ ID NO: 36           moltype = DNA  length = 147
FEATURE                 Location/Qualifiers
source                  1..147
                        mol_type = unassigned DNA
                        organism = Influenza A virus
SEQUENCE: 36
caagttcaca gagtgggtga cagtaacatt cttttcgagc accgtgtcga ccgtatcggt  60
agagttgttt gcatggtagc caatacaaag ggtatcggca ttggctgtgg caaaggtgta  120
caggagcacg accaaaatag ccttcat                                     147

SEQ ID NO: 37           moltype = DNA  length = 672
FEATURE                 Location/Qualifiers
source                  1..672
                        mol_type = unassigned DNA
                        organism = Influenza A virus
SEQUENCE: 37
acatgtcaga caccgaaggg cgccatcaac acgagcttgc cctttcagaa tatacatcca  60
atcacaatcg gaaaatgccc caagtacgtg aaaagcacta aactgagact cgccaccgga  120
ctcaggaata tcccaagcat ccagtcacgg ggtctgttcg gcgctatcgc cggatttatt  180
gaaggcggct ggacggggat ggtggacggt tggtacggct accatcatca aaatgagcag  240
ggctccggat acgccgctga cctgaaatct acgcagaatg ccatagatga gatcacaaac  300
aaggtcaata gtgtgataga aaaaatgaat actcagttca cagctgttgg aaaggagttt  360
aaccacctcg agaagcgaat tgagaacctg aacaagaagg tggacgatgg cttttggat  420
atctggacgt ataacgctga gctgcttgtt ctgctggaga acgaaagaac ccttgactac  480
cacgattcca acgtgaagaa tctgtatgag aaagtgcgaa gccagttgaa aaacaacgca  540
aaagaaatag gcaacggctg tttcgagttc taccacaaat gcgataacac ctgcatggag  600
agtgtgaaga acggaacgta cgattatcca aaatactccg aggaggccaa actcaatagg  660
gaggagatag ac                                                     672

SEQ ID NO: 38           moltype = AA  length = 224
FEATURE                 Location/Qualifiers
source                  1..224
                        mol_type = protein
                        organism = Influenza A virus
SEQUENCE: 38
TCQTPKGAIN TSLPFQNIHP ITIGKCPKYV KSTKLRLATG LRNIPSIQSR GLFGAIAGFI  60
EGGWTGMVDG WYGYHHQNEQ GSGYAADLKS TQNAIDEITN KVNSVIEKMN TQFTAVGKEF  120
NHLEKRIENL NKKVDDGFLD IWTYNAELLV LLENERTLDY HDSNVKNLYE KVRSQLKNNA  180
KEIGNGCFEF YHKCDNTCME SVKNGTYDYP KYSEEAKLNR EEID                  224

SEQ ID NO: 39           moltype = DNA  length = 672
FEATURE                 Location/Qualifiers
source                  1..672
                        mol_type = unassigned DNA
                        organism = Influenza A virus
SEQUENCE: 39
gtctatctcc tccctattga gtttggcctc ctcggagtat tttggataat cgtacgttcc  60
gttcttcaca ctctccatgc aggtgttatc gcatttgtgg tagaactcga aacagccgtt  120
```

```
gcctatttct tttgcgttgt ttttcaactg gcttcgcact ttctcataca gattcttcac  180
gttggaatcg tggtagtcaa gggttctttc gttctccagc agaacaagca gctcagcgtt  240
atacgtccag atatccaaaa agccatcgtc caccttcttg ttcaggttct caattcgctt  300
ctcgaggtgg ttaaactcct ttccaacagc tgtgaactga gtattcattt tttctatcac  360
actattgacc ttgtttgtga tctcatctat ggcattctgc gtagatttca ggtcagcggc  420
gtatccggag ccctgctcat tttgatgatg gtagccgtac caaccgtcca ccatccccgt  480
ccagccgcct tcaataaatc cggcgatagc gccgaacaga ccccgtgact ggatgcttgg  540
gatattcctg agtccggtgg cgagtctcag tttagtgctt ttcacgtact tggggcattt  600
tccgattgtg attggatgta tattctgaaa gggcaagctc gtgttgatgg cgcccttcgg  660
tgtctgacat gt                                                    672

SEQ ID NO: 40           moltype = DNA  length = 573
FEATURE                 Location/Qualifiers
source                  1..573
                        mol_type = unassigned DNA
                        organism = Influenza A virus
SEQUENCE: 40
acatgtcaga caccgaaggg cgccatcaac acgagcttgc cctttcagaa tatacatcca  60
atcacaatcg gaaaatgccc caagtacgtg aaaagcacta aactgagact cgccaccgga  120
ctcaggaata tcccaagcat ccagtcacgg ggtctgttcg gcgctatcgc cggatttatt  180
gaaggcggct ggacggggat ggtggacggt tggtacggct accatcatca aaatgagcag  240
ggctccggat acgccgctga cctgaaatct acgcagaatg ccatagatga gatcacaaac  300
aaggtcaata gtgtgataga aaaaatgacg tataacgctg agctgcttgt tctgctggag  360
aacgaaagaa cccttgacta ccacgattcc aacgtgaaga atctgtatga gaaagtgcga  420
agccagttga aaaacaacgc aaaagaaata ggcaacggct gtttcgagtt ctaccacaaa  480
tgcgataaca cctgcatgga gagtgtgaag aacggaacgt acgattatcc aaaatactcc  540
gaggaggcca aactcaatag ggaggagata gac                             573

SEQ ID NO: 41           moltype = AA  length = 191
FEATURE                 Location/Qualifiers
source                  1..191
                        mol_type = protein
                        organism = Influenza A virus
SEQUENCE: 41
TCQTPKGAIN TSLPFQNIHP ITIGKCPKYV KSTKLRLATG LRNIPSIQSR GLFGAIAGFI  60
EGGWTGMVDG WYGYHHQNEQ GSGYAADLKS TQNAIDEITN KVNSVIEKMT YNAELLVLLE  120
NERTLDYHDS NVKNLYEKVR SQLKNNAKEI GNGCFEFYHK CDNTCMESVK NGTYDYPKYS  180
EEAKLNREEI D                                                     191

SEQ ID NO: 42           moltype = DNA  length = 573
FEATURE                 Location/Qualifiers
source                  1..573
                        mol_type = unassigned DNA
                        organism = Influenza A virus
SEQUENCE: 42
gtctatctcc tccctattga gtttggcctc ctcggagtat tttggataat cgtacgttcc  60
gttcttcaca ctctccatgc aggtgttatc gcatttgtgg tagaactcga aacagccgtt  120
gcctatttct tttgcgttgt ttttcaactg gcttcgcact ttctcataca gattcttcac  180
gttggaatcg tggtagtcaa gggttctttc gttctccagc agaacaagca gctcagcgtt  240
atacgtcatt ttttctatca cactattgac cttgtttgtg atctcatcta tggcattctg  300
cgtagatttc aggtcagcgg cgtatccgga gccctgctca ttttgatgat ggtagccgta  360
ccaaccgtcc accatccccg tccagccgcc ttcaataaat ccggcgatag cgccgaacag  420
accccgtgac tggatgcttg ggatattcct gagtccggtg gcgagtctca gtttagtgct  480
tttcacgtac ttggggcatt ttccgattgt gattggatgt atattctgaa agggcaagct  540
cgtgttgatg gcgcccttcg gtgtctgaca tgt                             573

SEQ ID NO: 43           moltype = DNA  length = 507
FEATURE                 Location/Qualifiers
source                  1..507
                        mol_type = unassigned DNA
                        organism = Influenza A virus
SEQUENCE: 43
ctgagactcg ccaccggact caggaatatc ccaagcatcc agtcacgggg tctgttcggc  60
gctatcgccg gatttattga aggcggctgg acggggatgg tggacggttg gtacggctac  120
catcatcaaa atgagcaggg ctccggatac gccgctgacc tgaaatctac gcagaatgcc  180
atagatgaga tcacaaacaa ggtcaatagt gtgatagaaa aaatgaatac tcagttcaca  240
gctgttggaa aggagtttaa ccacctcgag aagcgaattg agaacctgaa caagaaggtg  300
gacgatggct tttggatat ctggacgtat aacgctgagc tgcttgttct gctggagaac  360
gaaagaaccc ttgactacca cgattccaac gtgaagaatc tgtatgagaa agtgcgaagc  420
cagttgaaaa acaacgcaaa agaaataggc aacggctgtt tcgagttcta ccacaaatgc  480
gataacacct gcatggagag tgtgaag                                    507

SEQ ID NO: 44           moltype = AA  length = 190
FEATURE                 Location/Qualifiers
source                  1..190
                        mol_type = protein
                        organism = Influenza A virus
```

```
SEQUENCE: 44
LRLATGLRNI PSIQSRGLFG AIAGFIEGGW TGMVDGWYGY HHQNEQGSGY AADLKSTQNA    60
IDEITNKVNS VIEKMNTQFT AVGKEFNHLE KRIENLNKKV DDGFLDIWTY NAELLVLLEN   120
ERTLDYHDSN VKNLYEKVRS QLKNNAKEIG NGCFEFYHKC DNTCMESVKN GTYDYPKYSE   180
EAKLNREEID                                                          190

SEQ ID NO: 45           moltype = DNA   length = 507
FEATURE                 Location/Qualifiers
source                  1..507
                        mol_type = unassigned DNA
                        organism = Influenza A virus
SEQUENCE: 45
cttcacactc tccatgcagg tgttatcgca tttgtggtag aactcgaaac agccgttgcc    60
tatttctttt gcgttgtttt tcaactggct tcgcactttc tcatacagat tcttcacgtt   120
ggaatcgtgg tagtcaaggg ttctttcgtt ctccagcaga acaagcagct cagcgttata   180
cgtccagata tccaaaaagc catcgtccac cttcttgttc aggttctcaa ttcgcttctc   240
gaggtggtta aactcctttc caacagctgt gaactgagta ttcattttt ctatcacact    300
attgaccttg tttgtgatct catctatggc attctgcgta gatttcaggt cagcggcgta   360
tccggagccc tgctcatttt gatgatggta gccgtaccaa ccgtccacca tccccgtcca   420
gccgccttca ataaatccgg cgatagcgcc gaacagaccc cgtgactgga tgcttgggat   480
attcctgagt ccggtggcga gtctcag                                       507

SEQ ID NO: 46           moltype = DNA   length = 471
FEATURE                 Location/Qualifiers
source                  1..471
                        mol_type = unassigned DNA
                        organism = Influenza A virus
SEQUENCE: 46
ctgagactcg ccaccggact caggaatatc ccaagcatcc agtcacgggg tctgttcggc    60
gctatcgccg gatttattga aggcgctgg acggggatgg tggacggttg gtacggctac    120
catcatcaaa atgagcaggg ctccggatac gccgctgacc tgaaatctac gcagaatgcc   180
atagatgaga tcacaaacaa ggtcaatagt gtgatagaaa aaatgacgta taacgctgag   240
ctgcttgttc tgctggagaa cgaaagaacc cttgactacc acgattccaa cgtgaagaat   300
ctgtatgaga aagtgcgaag ccagttgaaa aacaacgcaa agaaaatagg caacggctgt   360
ttcgagttct accacaaatg cgataacacc tgcatggaga gtgtgaagaa cggaacgtac   420
gattatccaa aatactccga ggaggccaaa ctcaataggg aggagataga c            471

SEQ ID NO: 47           moltype = AA   length = 157
FEATURE                 Location/Qualifiers
source                  1..157
                        mol_type = protein
                        organism = Influenza A virus
SEQUENCE: 47
LRLATGLRNI PSIQSRGLFG AIAGFIEGGW TGMVDGWYGY HHQNEQGSGY AADLKSTQNA    60
IDEITNKVNS VIEKMTYNAE LLVLLENERT LDYHDSNVKN LYEKVRSQLK NNAKEIGNGC   120
FEFYHKCDNT CMESVKNGTY DYPKYSEEAK LNREEID                             157

SEQ ID NO: 48           moltype = DNA   length = 471
FEATURE                 Location/Qualifiers
source                  1..471
                        mol_type = unassigned DNA
                        organism = Influenza A virus
SEQUENCE: 48
gtctatctcc tccctattga gtttggcctc ctcggagtat tttggataat cgtacgttcc    60
gttcttcaca ctctccatgc aggtgttatc gcatttgtgg tagaactcga aacagccgtt   120
gcctatttct tttgcgttgt tttcaactgg cttcgcactt tctcataca gattcttcac    180
gttggaatcg tggtagtcaa gggttctttc gttctccagc agaacaagca gctcagcgtt   240
atacgtcatt ttttctatca cactattgac cttgtttgtg atctcatcta tggcattctg   300
cgtagatttc aggtcagcgg cgtatccgga gccctgctca ttttgatgat ggtagccgta   360
ccaaccgtcc accatcccg tccagccgcc ttcaataaat ccggcgatag cgccaacag    420
accccgtgac tggatgcttg ggatattcct gagtccggtg gcgagtctca g             471

SEQ ID NO: 49           moltype = DNA   length = 141
FEATURE                 Location/Qualifiers
source                  1..141
                        mol_type = unassigned DNA
                        organism = Influenza A virus
SEQUENCE: 49
atggccatca tctacctgat cctgctgttt acagctgtga gaggcgacca gatctgtatc    60
ggctaccacg ccaacaatag caccgagaag gtggacacca tcctggagag aaacgtgaca   120
gtgacccacg ccaaggacat c                                              141

SEQ ID NO: 50           moltype = AA   length = 47
FEATURE                 Location/Qualifiers
source                  1..47
                        mol_type = protein
                        organism = Influenza A virus
SEQUENCE: 50
MAIIYLILLF TAVRGDQICI GYHANNSTEK VDTILERNVT VTHAKDI                  47
```

```
SEQ ID NO: 51            moltype = DNA  length = 141
FEATURE                  Location/Qualifiers
source                   1..141
                         mol_type = unassigned DNA
                         organism = Influenza A virus
SEQUENCE: 51
gatgtccttg gcgtgggtca ctgtcacgtt tctctccagg atggtgtcca ccttctcggt     60
gctattgttg gcgtggtagc cgatacagat ctggtcgcct ctcacagctg taaacagcag    120
gatcaggtag atgatggcca t                                              141

SEQ ID NO: 52            moltype = DNA  length = 672
FEATURE                  Location/Qualifiers
source                   1..672
                         mol_type = unassigned DNA
                         organism = Influenza A virus
SEQUENCE: 52
aagtgccaga cacctctggg cgccatcaat accaccctgc ccttccacaa tgtgcaccct     60
ctgaccatcg gcgagtgccc taagtatgtg aagagcgaga agctggtgct ggccacagga    120
ctgagaaacg tgccccagat cgagagcaga ggcctgtttg gagccatcgc cggattcatc    180
gagggaggat ggcagggaat ggtcgatggc tggtacggct accaccacag caatgatcag    240
ggctctggct atgccgccga taaggagtct acccagaagg cctttgacgg catcaccaac    300
aaggtgaaca gcgtgatcga aagatgaac acccagtttg aggctgtggg caaggagttt    360
agcaacctgg agcggagact ggagaacctg aacaagaaga tggaggacgg cttcctggat    420
gtgtggacct acaatgccga actgctggtg ctgatggaga atgagcggac cctggacttc    480
cacgacagca acgtgaagaa cctgtacgac aaagtgagaa tgcagctgag agacaacgtg    540
aaggaactgg gcaatggctg cttcgagttt taccaagt gtgacgacga gtgtatgaac    600
tccgtgaaga acggcaccta cgactaccct aagtacgagg aggagagcaa gctgaaccgg    660
aacgagatca ag                                                        672

SEQ ID NO: 53            moltype = AA  length = 224
FEATURE                  Location/Qualifiers
source                   1..224
                         mol_type = protein
                         organism = Influenza A virus
SEQUENCE: 53
KCQTPLGAIN TTLPFHNVHP LTIGECPKYV KSEKLVLATG LRNVPQIESR GLFGAIAGFI     60
EGGWQGMVDG WYGYHHSNDQ GSGYAADKES TQKAFDGITN KVNSVIEKMN TQFEAVGKEF    120
SNLERRLENL NKKMEDGFLD VWTYNAELLV LMENERTLDF HDSNVKNLYD KVRMQLRDNV    180
KELGNGCFEF YHKCDDECMN SVKNGTYDYP KYEEESKLNR NEIK                     224

SEQ ID NO: 54            moltype = DNA  length = 672
FEATURE                  Location/Qualifiers
source                   1..672
                         mol_type = unassigned DNA
                         organism = Influenza A virus
SEQUENCE: 54
cttgatctcg ttccggttca gcttgctctc ctcctcgtac ttagggtagt cgtaggtgcc     60
gttcttcacg gagttcatac actcgtcgtc acacttgtgg tagaactcga agcagccatt    120
gcccagttcc ttcacgttgt ccctcagctg catcctcact ttgtcgtaca ggttcttcac    180
gttgctgtcg tggaagtcca gggtccgctc atttctccatc agcaccagca gttcggcatt    240
gtaggtccac acatccagga agccgtcctc catcttcttg ttcaggttct ccagtctccg    300
ctccaggttg ctaaactcct tgcccacagc ctcaaactgg gtgttcatct tctcgatcac    360
gctgttcacc ttgttggtga tgccgtcaaa ggccttctgg gtagactcct tatcggcggc    420
atagccagag ccctgatcat tgctgtggtg gtagccgtac cagccatcga ccattccctg    480
ccatcctccc tcgatgaatc cggcgatggc tccaaacagg cctctgctct cgatctgggg    540
cacgttctc agtcctgtgg ccagcaccag cttctcgctc ttcacatact agggcactc    600
gccgatggtc agagggtgca cattgtggaa gggcagggtg gtattgatgg cgcccagagg    660
tgtctggcac tt                                                        672

SEQ ID NO: 55            moltype = DNA  length = 573
FEATURE                  Location/Qualifiers
source                   1..573
                         mol_type = unassigned DNA
                         organism = Influenza A virus
SEQUENCE: 55
aagtgccaga cacctctggg cgccatcaat accaccctgc ccttccacaa tgtgcaccct     60
ctgaccatcg gcgagtgccc taagtatgtg aagagcgaga agctggtgct ggccacagga    120
ctgagaaacg tgccccagat cgagagcaga ggcctgtttg gagccatcgc cggattcatc    180
gagggaggat ggcagggaat ggtcgatggc tggtacggct accaccacag caatgatcag    240
ggctctggct atgccgccga taaggagtct acccagaagg cctttgacgg catcaccaac    300
aaggtgaaca gcgtgatcga aagatgacc tacaatgccg aactgctggt gctgatggag    360
aatgagcgga ccctggactt ccacgacagc aacgtgaaga acctgtacga caaagtgagg    420
atgcagctga gggacaacgt gaaggaactg gcaatggct gcttcgagtt ctaccacaag    480
tgtgacgacg agtgtatgaa ctccgtgaag aacggcacct acgactaccc taagtacgag    540
gaggagagca agctgaaccg gaacgagatc aag                                 573

SEQ ID NO: 56            moltype = AA  length = 191
FEATURE                  Location/Qualifiers
```

```
source                      1..191
                            mol_type = protein
                            organism = Influenza A virus
SEQUENCE: 56
KCQTPLGAIN TTLPFHNVHP LTIGECPKYV KSEKLVLATG LRNVPQIESR GLFGAIAGFI      60
EGGWQGMVDG WYGYHHSNDQ GSGYAADKES TQKAFDGITN KVNSVIEKMT YNAELLVLME     120
NERTLDFHDS NVKNLYDKVR MQLRDNVKEL GNGCFEFYHK CDDECMNSVK NGTYDYPKYE     180
EESKLNRNEI K                                                          191

SEQ ID NO: 57               moltype = DNA   length = 573
FEATURE                     Location/Qualifiers
source                      1..573
                            mol_type = unassigned DNA
                            organism = Influenza A virus
SEQUENCE: 57
cttgatctcg ttccggttca gcttgctctc ctcctcgtac ttagggtagt cgtaggtgcc      60
gttcttcacg gagttcatac actcgtcgtc acacttgtgg tagaactcga agcagccatt     120
gcccagttcc ttcacgttgt ccctcagctg catcctcact ttgtcgtaca ggttcttcac     180
gttgctgtcg tggaagtcca gggtccgctc attctccatc agcaccagca gttcggcatt     240
gtaggtcatc ttctcgatca cgctgttcac cttgttggtg atgccgtcaa aggccttctg     300
ggtagactcc ttatcggcgg catagccaga gccctgatca ttgctgtggt ggtagccgta     360
ccagccatcg accattccct gccatcctcc ctcgatgaat ccggcgatgg ctccaaacag     420
gcctctgctc tcgatctggg gcacgtttct cagtcctgtg gccagcacca gcttctcgct     480
cttcacatac ttagggcact cgccgatggt cagagggtgc acattgtgga agggcagggt     540
ggtattgatg gcgcccagag gtgtctggca ctt                                  573

SEQ ID NO: 58               moltype = DNA   length = 570
FEATURE                     Location/Qualifiers
source                      1..570
                            mol_type = unassigned DNA
                            organism = Influenza A virus
SEQUENCE: 58
ctggtgctgg ccacaggact gagaaacgtg ccccagatcg agagcagagg cctgtttgga      60
gccatcgccg gattcatcga gggaggatgg cagggaatgg tcgatggctg gtacggctac     120
caccacagca atgatcaggg ctctggctat gccgccagca aggagtcctac ccagaaggcc    180
tttgacggca tcaccaacaa ggtgaacagc gtgatcgaga gatgaacac ccagtttgag      240
gctgtgggca aggagtttag caacctggag cggagactgg agaacctgaa caagaagatg     300
gaggacggct tcctggatgt gtggacctac aatgccgaac tgctggtgct gatggagaat     360
gagcggaccc tggacttcca cgacagcaac gtgaagaacc tgtacgacaa agtgaggatg     420
cagctgaggg acaacgtgaa ggaactgggc aatggctgct cgagttcta ccacaagtgt      480
gacgacgagt gtatgaactc cgtgaagaac ggcacctacg actaccctaa gtacgaggag     540
gagagcaagc tgaaccggaa cgagatcaag                                      570

SEQ ID NO: 59               moltype = AA   length = 190
FEATURE                     Location/Qualifiers
source                      1..190
                            mol_type = protein
                            organism = Influenza A virus
SEQUENCE: 59
LVLATGLRNV PQIESRGLFG AIAGFIEGGW QGMVDGWYGY HHSNDQGSGY AADKESTQKA      60
FDGITNKVNS VIEKMNTQFE AVGKEFSNLE RRLENLNKKM EDGFLDVWTY NAELLVLMEN     120
ERTLDFHDSN VKNLYDKVRM QLRDNVKELG NGCFEFYHKC DDECMNSVKN GTYDYPKYEE     180
ESKLNRNEIK                                                            190

SEQ ID NO: 60               moltype = DNA   length = 570
FEATURE                     Location/Qualifiers
source                      1..570
                            mol_type = unassigned DNA
                            organism = Influenza A virus
SEQUENCE: 60
cttgatctcg ttccggttca gcttgctctc ctcctcgtac ttagggtagt cgtaggtgcc      60
gttcttcacg gagttcatac actcgtcgtc acacttgtgg tagaactcga agcagccatt     120
gcccagttcc ttcacgttgt ccctcagctg catcctcact ttgtcgtaca ggttcttcac     180
gttgctgtcg tggaagtcca gggtccgctc attctccatc agcaccagca gttcggcatt     240
gtaggtccac acatccagga agccgtcctc catcttcttg ttcaggttct ccagtctccg     300
ctccaggttg ctaaactcct tgcccacagc ctcaaactgg gtgttcatct tctcgatcac     360
gctgttcacc ttgttggtga tgccgtcaaa ggccttctgg gtagactcct tatcggcggc     420
atagccagac cctgatcat tgctgtggtg gtagccgtac agccatcgac cattccctg      480
ccatcctccc tcgatgaatc cggcgatggc tccaaacagg cctctgctct cgatctgggg    540
cacgtttctc agtcctgtgg ccagcaccag                                     570

SEQ ID NO: 61               moltype = DNA   length = 471
FEATURE                     Location/Qualifiers
source                      1..471
                            mol_type = unassigned DNA
                            organism = Influenza A virus
SEQUENCE: 61
ctggtgctgg ccacaggact gagaaacgtg ccccagatcg agagcagagg cctgtttgga      60
gccatcgccg gattcatcga gggaggatgg cagggaatgg tcgatggctg gtacggctac     120
```

-continued

```
caccacagca atgatcaggg ctctggctat gccgccgata aggagtctac ccagaaggcc    180
tttgacggca tcaccaacaa ggtgaacagc gtgatcgaga agatgaccta caatgccgaa    240
ctgctggtgc tgatggagaa tgagcggacc ctggacttcc acgacagcaa cgtgaagaac    300
ctgtacgaca agtgaggat gcagctgagg acaacgtga aggaactggg caatggctgc     360
ttcgagttct accacaagtg tgacgacgag tgtatgaact ccgtgaagaa cggcacctac    420
gactacccta agtacgagga ggagagcaag ctgaaccgga acgagatcaa g             471

SEQ ID NO: 62          moltype = AA   length = 157
FEATURE                Location/Qualifiers
source                 1..157
                       mol_type = protein
                       organism = Influenza A virus
SEQUENCE: 62
LVLATGLRNV PQIESRGLFG AIAGFIEGGW QGMVDGWYGY HHSNDQGSGY AADKESTQKA     60
FDGITNKVNS VIEKMTYNAE LLVLMENERT LDFHDSNVKN LYDKVRMQLR DNVKELGNGC    120
FEFYHKCDDE CMNSVKNGTY DYPKYEEESK LNRNEIK                             157

SEQ ID NO: 63          moltype = DNA   length = 471
FEATURE                Location/Qualifiers
source                 1..471
                       mol_type = unassigned DNA
                       organism = Influenza A virus
SEQUENCE: 63
cttgatctcg ttccggttca gcttgctctc ctcctcgtac ttagggtagt cgtaggtgcc     60
gttcttcacg gagttcatac actcgtcgtc acacttgtgg tagaactcga agcagccatt    120
gcccagttcc ttcacgttgt ccctcagctg catcctcact ttgtcgtaca ggttcttcac    180
gttgctgtcg tggaagtcca gggtccgctc attctccatc agcaccagca gttcggcatt    240
gtaggtcatc ttctcgatca cgctgttcac cttgttggtg atgccgtcaa aggcctttctg    300
ggtagactcc ttatcggcgg catagccaga gccctgatca ttgctgtggt ggtagccgta    360
ccagccatcg accattccct gccatcctcc ctcgatgaat ccggcgatgg ctccaaacag    420
gcctctgctc tcgatctggg gcacgtttct cagtcctgtg gccagcacca g             471

SEQ ID NO: 64          moltype = DNA   length = 150
FEATURE                Location/Qualifiers
source                 1..150
                       mol_type = unassigned DNA
                       organism = Influenza A virus
SEQUENCE: 64
gccaccatgg aaaagatcgt gctgctgctg gccattgtga gcctggtgaa gagcgaccag     60
atctgcattg gctaccacgc caacaatagc acagagcagg tggacaccat catggaaaaa    120
aacgtgaccg tgacccacgc tcaggacatc                                     150

SEQ ID NO: 65          moltype = AA   length = 48
FEATURE                Location/Qualifiers
source                 1..48
                       mol_type = protein
                       organism = Influenza A virus
SEQUENCE: 65
MEKIVLLLAI VSLVKSDQIC IGYHANNSTE QVDTIMEKNV TVTHAQDI                   48

SEQ ID NO: 66          moltype = DNA   length = 150
FEATURE                Location/Qualifiers
source                 1..150
                       mol_type = unassigned DNA
                       organism = Influenza A virus
SEQUENCE: 66
gatgtcctga gcgtgggtca cggtcacgtt tttttccatg atggtgtcca cctgctctgt     60
gctattgttg gcgtggtagc caatgcagat ctggtcgctc ttcaccaggc tcacaatggc    120
cagcagcagc acgatctttt ccatggtggc                                     150

SEQ ID NO: 67          moltype = DNA   length = 681
FEATURE                Location/Qualifiers
source                 1..681
                       mol_type = unassigned DNA
                       organism = Influenza A virus
SEQUENCE: 67
aagtgccaga cacctatggg cgccatcaac agcagcatgc ccttccacaa catccaccct     60
ctgaccatcg gcgagtgccc taagtacgtg aagagcaaca gactggtgct ggccacaggc    120
ctgagaaata gccccagcg ggagagcaga agaaagagaa gggggctgtt tggagccatc    180
gccggcttta ttgaaggcgg ctggcaggga atggtggatg gctggtacgg ctaccaccac    240
agcaatgagc agggctctgg atatgccgcc gacaaagagt ctacccagaa ggccatcgac    300
ggcgtcacca caaggtgaa cagcatcatc gacaagatga cacccagtt cgaggctgtg    360
ggcagagagt tcaacaacct ggaacggcgg atcgagaacc tgaacaagaa aatggaagat    420
ggcttcctgg atgtgtggac ctacaatgcc gaactgctgg tgctgatgga aaacgagcgg    480
accctggact ccacgacag caacgtgaag aacctgtacg acaaagtgcg gctgcagctg    540
agagacaacg tcaaagagct gggcaacggc tgcttcgagt tctaccacaa gtgcgacaac    600
gagtgcatgg aaagcatccg gaacggcacc tacaactacc ctcagtacag cgaggaagcc    660
aggctgaaga gggaagagat c                                              681
```

-continued

```
SEQ ID NO: 68             moltype = AA   length = 227
FEATURE                   Location/Qualifiers
source                    1..227
                          mol_type = protein
                          organism = Influenza A virus
SEQUENCE: 68
KCQTPMGAIN SSMPFHNIHP LTIGECPKYV KSNRLVLATG LRNSPQRESR RKKRGLFGAI    60
AGFIEGGWQG MVDGWYGYHH SNEQGSGYAA DKESTQKAID GVTNKVNSII DKMNTQFEAV   120
GREFNNLERR IENLNKKMED GFLDVWTYNA ELLVLMENER TLDFHDSNVK NLYDKVRLQL   180
RDNAKELGNG CFEFYHKCDN ECMESIRNGT YNYPQYSEEA RLKREEI                 227

SEQ ID NO: 69             moltype = DNA   length = 681
FEATURE                   Location/Qualifiers
source                    1..681
                          mol_type = unassigned DNA
                          organism = Influenza A virus
SEQUENCE: 69
gatctcttcc ctcttcagcc tggcttcctc gctgtactga gggtagttgt aggtgccgtt    60
ccggatgctt tccatgcact cgttgtcgca cttgtggtag aactcgaagc agccgttgcc   120
cagctctttg gcgttgtctc tcagctgcag ccgcactttg tcgtacaggt tcttcacgtt   180
gctgtcgtgg aagtccaggg tccgctcgtt ttccatcagc accagcagtt cggcattgta   240
ggtccacaca tccaggaagc catcttccat ttttcttgtt aggttctgaa tccgccgttc   300
caggttgttg aactctctgc ccacagcctc gaactgggtg ttcatcttgt cgatgatgct   360
gttcaccttg ttggtgacgc cgtcgatggc cttctgggta gactctttgt cggcggcata   420
tccagagccc tgctcattgc tgtggtggta gccgtaccag ccatccacca ttccctgcca   480
gccgccttca ataaagccgg cgatggctcc aaacaggccc tcttctttc ttctgctctc   540
ccgctggggg ctatttctca ggcctgtggc cagcaccagt ctgttgctct tcacgtactt   600
agggcactcg ccgatggtca gagggtggat gttgtggaag gcatgctgc tgttgatggc   660
gcccataggt gtctggcact t                                             681

SEQ ID NO: 70             moltype = DNA   length = 582
FEATURE                   Location/Qualifiers
source                    1..582
                          mol_type = unassigned DNA
                          organism = Influenza A virus
SEQUENCE: 70
aagtgccaga cacctatggg cgccatcaac agcagcatgc ccttccacaa catccaccct    60
ctgaccatcg gcgagtgccc taagtacgtg aagagcaaca actggtgct ggccacaggc   120
ctgagaaata gccccagcg ggagagcaga agaaagaaga ggggcctgtt tggagccatc   180
gccggcttta ttgaaggcgg ctggcaggga atggtggatg gctggtacgg ctaccaccac   240
agcaatgagc agggctctgg atatgccgcc gacaaagagt caccccagaa gccatccgaa   300
ggcgtcacca acaaggtgaa cagcatcatc gacaagatga cctacaatgc cgaactgctg   360
gtgctgatgg aaaacgagcg gaccctggac ttccacgaca gcaacgtgaa gaacctgtac   420
gacaaagtgc ggctgcagct gagagacaac gccaaagagc tgggcaacgg ctgcttcgag   480
ttctaccaca gtgcgacaa cgagtgcatg gaaagcatcc ggaacggcac ctacaactac   540
cctcagtaca gcgaggaagc caggctgaag agggaagaga tc                     582

SEQ ID NO: 71             moltype = AA   length = 194
FEATURE                   Location/Qualifiers
source                    1..194
                          mol_type = protein
                          organism = Influenza A virus
SEQUENCE: 71
KCQTPMGAIN SSMPFHNIHP LTIGECPKYV KSNRLVLATG LRNSPQRESR RKKRGLFGAI    60
AGFIEGGWQG MVDGWYGYHH SNEQGSGYAA DKESTQKAID GVTNKVNSII DKMTYNAELL   120
VLMENERTLD FHDSNVKNLY DKVRLQLRDN AKELGNGCFE FYHKCDNECM ESIRNGTYNY   180
PQYSEEARLK REEI                                                     194

SEQ ID NO: 72             moltype = DNA   length = 582
FEATURE                   Location/Qualifiers
source                    1..582
                          mol_type = unassigned DNA
                          organism = Influenza A virus
SEQUENCE: 72
gatctcttcc ctcttcagcc tggcttcctc gctgtactga gggtagttgt aggtgccgtt    60
ccggatgctt tccatgcact cgttgtcgca cttgtggtag aactcgaagc agccgttgcc   120
cagctctttg gcgttgtctc tcagctgcag ccgcactttg tcgtacaggt tcttcacgtt   180
gctgtcgtgg aagtccaggg tccgctcgtt ttccatcagc accagcagtt cggcattgta   240
ggtcatcttg tcgatgatgc tgttcacctt gttggtgacg ccgtcgatgg ccttctgggt   300
agactctttg tcggcggcat atccagagcc ctgctcattg ctgtggtggt agccgtacca   360
gccatccacc attccctgcc agccgccttc aataaagccg gcgatggctc caaacaggcc   420
ctcttctttc ttctgctctc ccgctggggg ctatttctca ggcctgtggc cagcaccag   480
tctgttgctc ttcacgtact agggcactcg ccgatggtc agagggtgga tgttgtggaa   540
gggcatgctg ctgttgatgg cgcccatagg tgtctggcac tt                     582

SEQ ID NO: 73             moltype = DNA   length = 579
FEATURE                   Location/Qualifiers
```

```
source                  1..579
                        mol_type = unassigned DNA
                        organism = Influenza A virus
SEQUENCE: 73
ctggtgctgg ccacaggcct gagaaatagc ccccagcggg agagcagaag aaagaagagg    60
ggcctgtttg gagccatcgc cggctttatt gaaggcggct ggcagggaat ggtggatggc   120
tggtacggct accaccacag caatgagcag ggctctggat atgccgccga caaagagtct   180
acccagaagg ccatcgacgg cgtcaccaac aaggtgaaca gcatcatcga caagatgaac   240
acccagttcg aggctgtggg cagagagttc aacaacctgg aacggcggat cgagaacctg   300
aacaagaaaa tggaagatgg cttcctggat gtgtggacct acaatgccga actgctggtg   360
ctgatggaaa acgagcggac cctggacttc cacgacagca acgtgaagaa cctgtacgac   420
aaagtgcggc tgcagctgag agacaacgcc aaagagctgg gcaacggctg cttcgagttc   480
taccacaagt gcgacaacga gtgcatggaa agcatccgga acggcaccta caactaccct   540
cagtacagcg aggaagccag gctgaagagg aagagatc                           579

SEQ ID NO: 74           moltype = AA   length = 193
FEATURE                 Location/Qualifiers
source                  1..193
                        mol_type = protein
                        organism = Influenza A virus
SEQUENCE: 74
LVLATGLRNS PQRESRRKKR GLFGAIAGFI EGGWQGMVDG WYGYHHSNEQ GSGYAADKES    60
TQKAIDGVTN KVNSIIDKMN TQFEAVGREF NNLERRIENL NKKMEDGFLD VWTYNAELLV   120
LMENERTLDF HDSNVKNLYD KVRLQLRDNA KELGNGCFEF YHKCDNECME SIRNGTYNYP   180
QYSEEARLKR EEI                                                      193

SEQ ID NO: 75           moltype = DNA   length = 579
FEATURE                 Location/Qualifiers
source                  1..579
                        mol_type = unassigned DNA
                        organism = Influenza A virus
SEQUENCE: 75
gatctcttcc ctcttcagcc tggcttcctc gctgtactga gggtagttgt aggtgccgtt    60
ccggatgctt tccatgcact cgttgtcgca cttgtggtag aactcgaagc agccgttgcc   120
cagctctttg gcgttgtctc tcagctgcag ccgcactttg tcgtacaggt tcttcacgtt   180
gctgtcgtgg aagtccaggg tccgctcgtt ttccatcagc accagcagtt cggcattgta   240
ggtccacaca tccaggaagc catcttccat tttcttgttc aggttctcga tccgccgttc   300
caggttgttg aactctctgc ccacagcctc gaactgggtg ttcatcttgt cgatgatgct   360
gttcaccttg ttggtgacgc cgtcgatggc cttctgggta gactctttgt cggcggcata   420
tccagagccc tgctcattgc tgtggtggta gccgtaccag ccatccacca ttccctgcca   480
gccgccttca ataaagccgg cgatggctcc aaacagggcc ctcttctttc ttctgctctc   540
ccgctggggg ctatttctca ggcctgtggc cagcaccag                          579

SEQ ID NO: 76           moltype = DNA   length = 480
FEATURE                 Location/Qualifiers
source                  1..480
                        mol_type = unassigned DNA
                        organism = Influenza A virus
SEQUENCE: 76
ctggtgctgg ccacaggcct gagaaatagc ccccagcggg agagcagaag aaagaagagg    60
ggcctgtttg gagccatcgc cggctttatt gaaggcggct ggcagggaat ggtggatggc   120
tggtacggct accaccacag caatgagcag ggctctggat atgccgccga caaagagtct   180
acccagaagg ccatcgacgg cgtcaccaac aaggtgaaca gcatcatcga caagatgacc   240
tacaatgccg aactgctggt gctgatggaa acgagcggac cctggacttc cacgacagc    300
aacgtgaaga acctgtacga caaagtgcgg ctgcagctga gagacaacgc caaagagctg   360
ggcaacggct gcttcgagtt ctaccacaag tgcgacaacg agtgcatcgg aagcatccgg   420
aacggcacct acaactaccc tcagtacagc gaggaagcca ggctgaagag gaagagatc   480

SEQ ID NO: 77           moltype = AA   length = 160
FEATURE                 Location/Qualifiers
source                  1..160
                        mol_type = protein
                        organism = Influenza A virus
SEQUENCE: 77
LVLATGLRNS PQRESRRKKR GLFGAIAGFI EGGWQGMVDG WYGYHHSNEQ GSGYAADKES    60
TQKAIDGVTN KVNSIIDKMT YNAELLVLME NERTLDFHDS NVKNLYDKVR LQLRDNAKEL   120
GNGCFEFYHK CDNECMESIR NGTYNYPQYS EEARLKREEI                         160

SEQ ID NO: 78           moltype = DNA   length = 480
FEATURE                 Location/Qualifiers
source                  1..480
                        mol_type = unassigned DNA
                        organism = Influenza A virus
SEQUENCE: 78
gatctcttcc ctcttcagcc tggcttcctc gctgtactga gggtagttgt aggtgccgtt    60
ccggatgctt tccatgcact cgttgtcgca cttgtggtag aactcgaagc agccgttgcc   120
cagctctttg gcgttgtctc tcagctgcag ccgcactttg tcgtacaggt tcttcacgtt   180
gctgtcgtgg aagtccaggg tccgctcgtt ttccatcagc accagcagtt cggcattgta   240
ggtcatcttg tcgatgatgc tgttcacctt gttggtgacg ccgtcgatgg ccttctgggt   300
```

```
                                                        agactctttg tcggcggcat atccagagcc ctgctcattg ctgtggtggt agccgtacca   360
                                                        gccatccacc attccctgcc agccgccttc aataaagccg gcgatggctc caaacaggcc   420
                                                        cctcttcttt cttctgctct cccgctgggg gctatttctc aggcctgtgg ccagcaccag   480

SEQ ID NO: 79            moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 79
atgaaggcca aactgctggt cctgctgtgt acttttaccg caacctacgc tgacactatc   60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaaccagtg gactctgctg ttccacgata gcaacgtgaa gaatctgtat   480
gagaaggtca atcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645

SEQ ID NO: 80            moltype = AA    length = 215
FEATURE                  Location/Qualifiers
REGION                   1..215
                         note = Synthetic
source                   1..215
                         mol_type = protein
                         organism = synthetic construct
SEQUENCE: 80
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV   120
NSVIEKMGSG GSGTDLAELL VLLLNQWTLL FHDSNVKNLY EKVKSQLKNN AKEIGNGCFE   180
FYHKCNNECM ESVKNGTYDY PKYSEESKLN REKID                              215

SEQ ID NO: 81            moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 81
gtcaattttc tctcgattca gcttactctc ttcagaatat tgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagccag   240
gtctgttccg gagcctccgc tgcccatttt ttcgatgaca gaattcacca tgttagtaat   300
gccattgatt gcgttctgtg tagacttctg atcagcgagc tagccgctgc cctgctcatt   360
ctgatggtgg tagccgtacc acccgtccac cattcctgtc cacccgccct caataaaccc   420
tgcgatagcg ccgaacagtc ctctgttttc ccgctgtggg atgttgcgca gtccggtgac   480
catcctcagt ccgctgccca gattcactga gtgggtgaca gtcacgttct tctccaggac   540
ggtatccact gtgtcggtgg agttgtttgc gtgatagccg atgcagatag tgtcagcgta   600
ggttgcggta aaagtacaca gcaggaccag cagtttggcc ttcat                   645

SEQ ID NO: 82            moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 82
atgaaggcaa tcctggtcgt cctgctgtat actttcgcta ccgctaacgc tgacaccctg   60
tgcatcggct atcacgctaa caactcaacc gacacagtgg atactgtcct ggagaagaac   120
gtgactgtca cccactctgt gaatctgggc agtggactga ggctggcaac tggactgcga   180
aacatcccac agcgggaaac cagaggactg ttcggcgcta tcgcagggtt tattgagggc   240
gggtggacag gaatggtgga cgggtggtac ggctaccacc atcagaacga gcagggatca   300
ggctacgccg ctgacctgaa gagcacacag aatgcaatcg atgaaattac taacatggtg   360
aattccgtca tcgagaaaat gggcagcgga ggctccggaa ccgacctggc agaactgctg   420
gtgctgctgc tgaaccagtg gacactgctg taccacgata gtaacgtgaa gaatctgtat   480
gagaaagtca gatcacagct gaagaacaat gctaaagaaa tcgggaatgg atgcttcgag   540
ttttaccata agtgcgacaa cacctgtatg gagagcgtga aaaatggcac atacgattat   600
cccaagtatt ccgaggaagc caaactgaac agagaggaaa ttgac                   645

SEQ ID NO: 83            moltype = AA    length = 215
FEATURE                  Location/Qualifiers
```

```
REGION                       1..215
                             note = Synthetic
source                       1..215
                             mol_type = protein
                             organism = synthetic construct
SEQUENCE: 83
MKAKLLVLLC TFTATYADTL CIGYHANNST DTVDTVLEKN VTVTHSVNLG SGLRLATGLR    60
NIPQRETRGL FGAIAGFIEG GWTGMVDGWY GYHHQNEQGS GYAADLKSTQ NAIDEITNMV   120
NSVIEKMGSG GSGTDLAELL VLLLNQWTLL YHDSNVKNLY EKVRSQLKNN AKEIGNGCFE   180
FYHKCDNTCM ESVKNGTYDY PKYSEEAKLN REEID                              215

SEQ ID NO: 84                moltype = DNA   length = 645
FEATURE                      Location/Qualifiers
misc_feature                 1..645
                             note = Synthetic
source                       1..645
                             mol_type = other DNA
                             organism = synthetic construct
SEQUENCE: 84
gtcaatttcc tctctgttca gtttggcttc ctcggaatac ttgggataat cgtatgtgcc    60
atttttcacg ctctccatac aggtgttgtc gcacttatgg taaaactcga agcatccatt   120
cccgatttct ttagcattgt tcttcagctg tgatcgact ttctcataca gattcttcac    180
gttactatcg tggtacagca gtgtccactg gttcagcagc agcaccagca gttctgccag   240
gtcggttccg gagcctccgc tgcccatttt ctcgatgacg gaattcacca tgttagtaat   300
ttcatcgatt gcattctgtg tgctcttcag gtcagcggcg tagcctgatc cctgctcgtt   360
ctgatggtgg tagccgtacc acccgtccac cattcctgtc cacccgccct caataaaccc   420
tgcgatagcg ccgaacagtc ctctggtttc ccgctgtggg atgtttcgca gtccagttgc   480
cagcctcagt ccactgccca gattcacaga gtgggtgaca gtcacgttct tctccaggac   540
agtatccact gtgtcggttg agttgttagc gtgatagccg atgcacaggg tgtcagcgtt   600
agcggtagcg aaagtataca gcaggacgac caggattgcc ttcat                   645

SEQ ID NO: 85                moltype = DNA   length = 639
FEATURE                      Location/Qualifiers
misc_feature                 1..639
                             note = Synthetic
source                       1..639
                             mol_type = other DNA
                             organism = synthetic construct
SEQUENCE: 85
atggctatca tctacctgat cctgctgttc actgctgtgc gggggggacca gatttgcatc    60
ggctaccacg ctaataattc aactgagaag gtggatacta tcctggagcg gaacgtgacc   120
gtcacacacg ctaaagacat tggcagcgga ctggtgctgg caaccggact gaggaatgtc   180
ccacagatcg agtcccgcgg actgttcggc gctatcgcag ggtttattga aggcgggtgg   240
cagggaatga ttgatgggtg gtacggctac caccattcta acgacaggg aagtggctac   300
gccgctgata aggagagtac tcagaaagcc ttcgatggca tcaccaacat ggtgaattca   360
gtcattgaga agatgggcag cggaggctcc ggaaccgacc tggcagaact gctggtgctg   420
ctgctgaatc agtggacact gctgtttcac gactctaacg tgaagaatct gtatgataaa   480
gtccggatgc agctgagaga caacgtgaag gagctgggga atggatgctt cgaatttac   540
cataagtgcg acgatgagtg tatgaacagt gtcaaaaatg gcacatacga ttatcccaag   600
tatgaggaag agtcaaaact gaaccgaaat gaaatcaag                          639

SEQ ID NO: 86                moltype = AA    length = 213
FEATURE                      Location/Qualifiers
REGION                       1..213
                             note = Synthetic
source                       1..213
                             mol_type = protein
                             organism = synthetic construct
SEQUENCE: 86
MAIIYLILLF TAVRGDQICI GYHANNSTEK VDTILERNVT VTHAKDIGSG LVLATGLRNV    60
PQIESRGLFG AIAGFIEGGW QGMIDGWYGY HHSNDQGSGY AADKESTQKA FDGITNMVNS   120
VIEKMGSGGS GTDLAELLVL LLNQWTLLFH DSNVKNLYDK VRMQLRDNVK ELGNGCFEFY   180
HKCDDECMNS VKNGTYDYPK YEEESKLNRN EIK                                213

SEQ ID NO: 87                moltype = DNA   length = 639
FEATURE                      Location/Qualifiers
misc_feature                 1..639
                             note = Synthetic
source                       1..639
                             mol_type = other DNA
                             organism = synthetic construct
SEQUENCE: 87
cttgatttca ttttcggttca gttttgactc ttcctcatac ttgggataat cgtatgtgcc    60
atttttgaca ctgttcatac actcatcgtc gcacttatgg taaaattcga agcatccatt   120
ccccagctcc ttcacgttgt ctctcagctg catccggact ttatcataca gattcttcac   180
gttagagtcg tgaaacagca gtgtccactg attcagcagc agcaccagca gttctgccag   240
gtcggttccg gagcctccgc tgcccatctt ctcaatgact gaattcacca tgttggtgat   300
gccatcgaag gctttctgag tactctcctt atcagcggcg tagccacttc cttggtcgtt   360
agaatggtgg tagccgtacc acccatcaat cattccctgc cacccgcctt caataaaccc   420
```

-continued

```
tgcgatagcg ccgaacagtc cgcgggactc gatctgtggg acattcctca gtccggttgc  480
cagcaccagt ccgctgccaa tgtctttagc gtgtgtgacg gtcacgttcc gctccaggat  540
agtatccacc ttctcagttg aattattagc gtgtgtagccg atgcaaatct ggtcccccg   600
cacagcagtg aacagcagga tcaggtagat gatagccat                          639

SEQ ID NO: 88          moltype = DNA   length = 651
FEATURE                Location/Qualifiers
misc_feature           1..651
                       note = Synthetic
source                 1..651
                       mol_type = other DNA
                       organism = synthetic construct
SEQUENCE: 88
atggaaaaaa tcgtgctgct gctggctatc gtgtccctgg tgaagtccga ccagatctgt   60
attgggtatc atgctaacaa ctccacagaa caggtggata ctatcatgga agaaacgtg   120
accgtcacac acgctcagga cattggatgg ggactggtcc tggcaaccgg actgagaaat  180
tcaccacaga gggaaagccg gagaaagaaa cgcggactgt tcggcgctat cgcagggttt  240
attgagggcg ggtggcaggg aatggtggat gggtggtacg gctaccacca ttccaacgaa  300
cagggatctg gctacgccgc tgataaggag tctactcaga aagctatcga cggcgtgacc  360
aacatggtca atagtatcat tgataagatg ggctctggag cagtggaaac cgacctggca  420
gagctgctgg tgctgctgct gaaccagtgg acactgctgt tccacgactc taacgtgaag  480
aatctgtatg ataaagtccg actgcagctg cgggacaacg ctaaggaact ggggaatgga  540
tgcttcgagt tctaccataa gtgcgataac gaatgtatgg agagcatccg aaacggcaca  600
tacaattatc cccagtattc cgaggaagct aggctgaaac gcgaggaaat t            651

SEQ ID NO: 89          moltype = AA    length = 217
FEATURE                Location/Qualifiers
REGION                 1..217
                       note = Synthetic
source                 1..217
                       mol_type = protein
                       organism = synthetic construct
SEQUENCE: 89
MEKIVLLLAI VSLVKSDQIC IGYHANNSTE QVDTIMEKNV TVTHAQDIGW GLVLATGLRN   60
SPQRESRRKK RGLFGAIAGF IEGGWQGMVD GWYGYHHSNE QGSGYAADKE STQKAIDGVT   120
NMVNSIIDKM GSGGSGTDLA ELLVLLLNQW TLLFHDSNVK NLYDKVRLQL RDNAKELGNG   180
CFEFYHKCDN ECMESIRNGT YNYPQYSEEA RLKREEI                            217

SEQ ID NO: 90          moltype = DNA   length = 651
FEATURE                Location/Qualifiers
misc_feature           1..651
                       note = Synthetic
source                 1..651
                       mol_type = other DNA
                       organism = synthetic construct
SEQUENCE: 90
aatttcctcg cgtttcagcc tagcttcctc ggaatactgg ggataattgt atgtgccgtt   60
tcggatgctc tccatacatt cgttatcgca cttatggtag aactcgaagc atccattccc   120
cagttccttg gcgttgtccc gcagctgcag tcggacttta tcatacagat tcttcacgtt   180
agagtcgtgg aacagcagtg tccactggtt cagcagcagc accagcagct ctgccaggtc   240
ggttccactg cctccagagc ccatcttatc aatgatacta ttgaccatgt tggtcacgcc   300
gtcgatagct ttctgagtag actccttatc agcggcgtag ccagatccct gttcgttgga   360
atggtgtag ccgtaccacc catccaccat tccctgccac cgccctcaa taaaccctgc    420
gatagcgccg aacagtccgc gtttctttct ccggctttcc ctctgtggtg aatttctcag   480
tccggttgcc aggaccagtc ccatccaat gtcctgagcg tgtgtgacgg tcacgttctt    540
ctccatgata gtatccacct gttctgtgga gttgttagca tgataccaa tacagatctg    600
gtcggacttc accagggaca cgatagccag cagcagcacg attttttcca t             651

SEQ ID NO: 91          moltype = DNA   length = 645
FEATURE                Location/Qualifiers
misc_feature           1..645
                       note = Synthetic
source                 1..645
                       mol_type = other DNA
                       organism = synthetic construct
SEQUENCE: 91
atgaaggcca aactgctggt cctgctgtgt acttttaccg caacctacgc tgacactatc   60
tgcatcggct atcacgcaaa caactccacc gacacagtga taccgtcct ggagaagaac    120
gtgactgtca cccactcagt gaatctgggc agcggactga ggatggtcac cggactgcgg  180
aacatcccac agcgggaaac aagaggactg ttcggcgcta tcgcagggtt tattgagggc   240
gggtggacag gaatggtgga cggtggtac ggctaccacc atcagaatga gcagggcagc   300
ggctacgccg ctgatcagaa gtctacacag aacgcaatca atggcattac taacatggtg   360
aatttctgtca tcgaaaaat gggcagcgga ggctccggaa cagacctggc tgagctgctg   420
gtgctgctga tgaacgatcg gactctggat ttcacgata caacgtgaa gaatctgtat    480
gagaaggtca aatcccagct gaagaacaat gccaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645

SEQ ID NO: 92          moltype = AA    length = 215
```

| FEATURE | Location/Qualifiers |
|---|---|
| REGION | 1..215 |
| | note = Synthetic |
| source | 1..215 |
| | mol_type = protein |
| | organism = synthetic construct |

SEQUENCE: 92

```
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                             215
```

| SEQ ID NO: 93 | moltype = DNA  length = 645 |
|---|---|
| FEATURE | Location/Qualifiers |
| misc_feature | 1..645 |
| | note = Synthetic |
| source | 1..645 |
| | mol_type = other DNA |
| | organism = synthetic construct |

SEQUENCE: 93

```
gtcaattttc tctcgattca gcttactctc ttcagaatat tgggatagt cgtaagtgcc   60
gttcttcaca gactccatac attcattgtt gcacttatgg taaaactcga agcatccatt  120
cccgatttct ttggcattgt tcttcagctg gatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645
```

| SEQ ID NO: 94 | moltype = DNA  length = 645 |
|---|---|
| FEATURE | Location/Qualifiers |
| misc_feature | 1..645 |
| | note = Synthetic |
| source | 1..645 |
| | mol_type = other DNA |
| | organism = synthetic construct |

SEQUENCE: 94

```
atgaaggcca aactgctggt cctgctgtgt acttttaccg caacctacgc tgacactatc   60
tgcatcggct atcacgcaaa caactccacc gacacagtgg ataccattct ggagaagaac  120
gtgactgtca cccactcagt gaatctgggc agcggactga ggatggtcac cggactgcgc  180
aacatcccac agcggaaac aagaggactg ttcggcgcta tcgcaggggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcagcgga ggctccggaa cagacctgg tgagctgctg  420
gtgctgatgc tgaaccagtt cactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga gaacggcac ttacgactat  600
cccaaatatt ctgaagagag taagctgaat cgagagaaaa ttgac                  645
```

| SEQ ID NO: 95 | moltype = AA  length = 215 |
|---|---|
| FEATURE | Location/Qualifiers |
| REGION | 1..215 |
| | note = Synthetic |
| source | 1..215 |
| | mol_type = protein |
| | organism = synthetic construct |

SEQUENCE: 95

```
MKAKLLVLLC TFTATYADTI CIGYHANNST DTVDTILEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGSG GSGTDLAELL VLMLNQFTLL FHDSNVKNLY EKVKSQLKNN AKEIGNGCFE  180
FYHKCNNECM ESVKNGTYDY PKYSEESKLN REKID                             215
```

| SEQ ID NO: 96 | moltype = DNA  length = 645 |
|---|---|
| FEATURE | Location/Qualifiers |
| misc_feature | 1..645 |
| | note = Synthetic |
| source | 1..645 |
| | mol_type = other DNA |
| | organism = synthetic construct |

SEQUENCE: 96

```
gtcaattttc tctcgattca gcttactctc ttcagaatat tgggatagt cgtaagtgcc   60
gttcttcaca gactccatac attcattgtt gcacttatgg taaaactcga agcatccatt  120
cccgatttct ttggcattgt tcttcagctg gatttgacc ttctcataca gattcttcac  180
gttgctatcg tggaacagca gagtgaactg gttcagcatc agcaccagca gctcagccag  240
gtctgttccg gagcctccgc tgcccatttt ttcgatgaca gaattcacca tgttagtaat  300
gccattgatt gcgttctgtg tagacttctg atcagcggcg tagccgctgc cctgctcatt  360
```

```
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccagaat  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 97          moltype = DNA   length = 645
FEATURE                Location/Qualifiers
misc_feature           1..645
                       note = Synthetic
source                 1..645
                       mol_type = other DNA
                       organism = synthetic construct
SEQUENCE: 97
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcaatgga acaggcggag ctgacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645

SEQ ID NO: 98          moltype = AA   length = 215
FEATURE                Location/Qualifiers
REGION                 1..215
                       note = Synthetic
source                 1..215
                       mol_type = protein
                       organism = synthetic construct
SEQUENCE: 98
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGNG TGGADLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 99          moltype = DNA   length = 645
FEATURE                Location/Qualifiers
misc_feature           1..645
                       note = Synthetic
source                 1..645
                       mol_type = other DNA
                       organism = synthetic construct
SEQUENCE: 99
gtcaattttc tctcgattca gcttactctc ttcagaatat ttgggatagt cgtaagtgcc  60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctccg cctgttccat tgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 100         moltype = DNA   length = 645
FEATURE                Location/Qualifiers
misc_feature           1..645
                       note = Synthetic
source                 1..645
                       mol_type = other DNA
                       organism = synthetic construct
SEQUENCE: 100
atgaaggcca aactgctggt cctgctgtgt acttttaccg caacctacgc tgacactatc  60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacatggtg  360
aattctgtca tcgaaaaaat gggcggaaat ggcactggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac                  645
```

```
SEQ ID NO: 101          moltype = AA   length = 215
FEATURE                 Location/Qualifiers
REGION                  1..215
                        note = Synthetic
source                  1..215
                        mol_type = protein
                        organism = synthetic construct
SEQUENCE: 101
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 102          moltype = DNA   length = 645
FEATURE                 Location/Qualifiers
misc_feature            1..645
                        note = Synthetic
source                  1..645
                        mol_type = other DNA
                        organism = synthetic construct
SEQUENCE: 102
gtcaattttc tctcgattca gcttactctc ttcagaatat tgggatagt cgtaagtgcc    60
gttcttcaca gactccatac attcattgtt gcacttatgg taaaaactcga agcatccatt 120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtacga gtcacgttct tctccaggac  540
ggtatccact gtgtcggtgg agttgtttgc gtgatagccg atgcagatag tgtcagcgta  600
ggttgcggta aaagtacaca gcaggaccag cagtttggcc ttcat                  645

SEQ ID NO: 103          moltype = DNA   length = 645
FEATURE                 Location/Qualifiers
misc_feature            1..645
                        note = Synthetic
source                  1..645
                        mol_type = other DNA
                        organism = synthetic construct
SEQUENCE: 103
atgaaggcca aactgctggt cctgctgtgt acttttaccg caacctacgc tgacactatc    60
tgcatcggct atcacgcaaa caactccacc gacacagtcc tggagaagaa c            120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag aatggtgga cggctggtac ggctaccacc atcagaatga gcagggcagc    300
ggctacgccg ctgatcagaa gtctacacag aacgcaatca atggcattac taacatggtg   360
aattctgtca tcgaaaaaat gggcagcgga ggcaacggaa cagacctggc tgagctgctg   420
gtgctgctgc tgaaccagtg gactctgctg ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645

SEQ ID NO: 104          moltype = AA   length = 215
FEATURE                 Location/Qualifiers
REGION                  1..215
                        note = Synthetic
source                  1..215
                        mol_type = protein
                        organism = synthetic construct
SEQUENCE: 104
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGSG GNGTDLAELL VLLLNQWTLL FHDSNVKNLY EKVKSQLKNN AKEIGNGCFE  180
FYHKCNNECM ESVKNGTYDY PKYSEESKLN REKID                             215

SEQ ID NO: 105          moltype = DNA   length = 645
FEATURE                 Location/Qualifiers
misc_feature            1..645
                        note = Synthetic
source                  1..645
                        mol_type = other DNA
                        organism = synthetic construct
SEQUENCE: 105
gtcaattttc tctcgattca gcttactctc ttcagaatat tgggatagt cgtaagtgcc    60
gttcttcaca gactccatac attcattgtt gcacttatgg taaaaactcga agcatccatt 120
cccgatttct ttggcattgt tcttcagctg ggatttgacc ttctcataca gattcttcac  180
gttgctatcg tggaacagca gagtccactg gttcagcagc agcaccagca gctcagccag  240
gtctgttccg ttgcctccgc tgcccatttt ttcgatgaca gaattcacca tgttagtaat  300
```

```
gccattgatt gcgttctgtg tagacttctg atcagcggcg tagccgctgc cctgctcatt    360
ctgatggtgg tagccgtacc acccgtccac cattcctgtc cacccgccct caataaaccc    420
tgcgatagcg ccgaacagtc ctcttgtttc ccgctgtggg atgttgcgca gtccggtgac    480
catcctcagt ccgctgccca gattcactga gtgggtgaca gtcacgttct tctccaggac    540
ggtatccact gtgtcggtgg agttgtttgc gtgatagccg atgcagatag tgtcagcgta    600
ggttgcggta aaagtacaca gcaggaccag cagtttggcc ttcat                    645
```

```
SEQ ID NO: 106          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 106
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcggaaaac aagaggactg ttcggcgcta tcgcagggtt tattgagggc    240
gggtggacag gaatggtgga cggtggtac ggctaccacc atcagaatga gcagggcagc    300
ggctacgccg ctgatcagaa gtctacacag aacgcaatca atggcattac taacatggtg    360
aattctgtca tcgaaaaaat gggcagcgga ggctccggaa cagacctggc tgagctgctg    420
gtgctgctgc tgaaccagtg gactctgctg ttccacgata gcaacgtgaa gaatctgtat    480
gagaaggtca atccccagct gaagaacaat gccaaagaaa tcgggaatgg atgcttcgag    540
ttttaccata gtgcaacaa tgaatgtatg gagtctgtga gaacggcac ttacgactat    600
cccaaatatt ctgaagagag taagctgaat cgagagaaaa ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg gctgttcct gtttgatcac    780
gcagccgagg aatacgaaca tgcaaagaaa ctgatcattt tcctgaatga gaacaatgtg    840
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtca                                                           1149
```

```
SEQ ID NO: 107          moltype = AA  length = 383
FEATURE                 Location/Qualifiers
REGION                  1..383
                        note = Synthetic
source                  1..383
                        mol_type = protein
                        organism = synthetic construct
SEQUENCE: 107
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNMV    120
NSVIEKMGSG GSGTDLAELL VLLLNQWTLL FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383
```

```
SEQ ID NO: 108          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 108
tgacccactt tttctggact tggcaatgcc cttcacatac tgatctgcca ggtacaggcc     60
atgattctcg tttccaatca gttcgatttt atccaggatg tccttaaaca ggacctcctc    120
ctcgtgctgc tcggcacgt accactgcag aaagttgaag gtagcatgat ctttgctctt    180
aatggcgtgg tccacaatat tgttgataga ttcggaaata tgctgctcgt gttcgtaagc    240
tttctgaaaa atctgggtca ggccctcgaa cttatgttca gggcgctga ttgaagtcag    300
ctggacgggc acattgttct cattcaggaa aatgatcagt ttctttgcat gttcgtattc    360
ctcggctgcg tgatcaaaca ggaacagccc agcgccgtcc agtgagtgt tataaccaca    420
actagacata ctcatgtaca ggttggagct ctgcatctcc ttgttcacct gttcgttcag    480
cagcttgatg atgtcgcccc cactgtcaat ttttctctcga ttcagcttac tctcttcaga    540
atattggga tagtcgtaag tgccgttctt cacagactcc atacattcat tgttcactt    600
atggtaaaac tcgaagcatc cattcccgat ttctttggca ttgttcttca gctgggattt    660
gaccttctca tacagattct tcacgttgct actgtgaag acagaagtcc actggttcag    720
cagcagcacc agcagctcag ccaggtctgt tccggagcc cgctgccca tttttttgat    780
gacagaattc accatgttag taatgccatt gattgcgttc tgtgtagact ctgatcagc    840
ggcgtagccg ctgccctgct cattctgatg gtggtagccg taccaccgt ccaccattcc    900
tgtccacccg ccctcaataa accctgcgat agcgccgaac agtcctcttg tttcccgctg    960
tgggatgttg cgcagtccgg tgaccatcct cagtccgctg cccagattca ctgagtgggt   1020
```

```
gacagtcacg ttcttctcca ggacggtatc cactgtgtcg gtggagttgt ttgcgtgata 1080
gccgatgcag atagtgtcag cgtaggttgc ggtaaaagta cacagcagga ccagcagttt 1140
ggccttcat                                                         1149
```

| SEQ ID NO: 109 | moltype = DNA length = 1149 |
|---|---|
| FEATURE | Location/Qualifiers |
| misc_feature | 1..1149 |
|  | note = Synthetic |
| source | 1..1149 |
|  | mol_type = other DNA |
|  | organism = synthetic construct |

```
SEQUENCE: 109
atgaaggcaa tcctggtcgt cctgctgtat actttcgcta ccgctaacgc tgacaccctg 60
tgcatcggct atcacgctaa caactcaacc gacacagtgg atactgtcct ggagaagaac 120
gtgactgtca cccactctgt gaatctgggc agtggactga ggctggcaac tggactgcga 180
aacatcccac agcgggaaac cagaggactg ttcggcgcta tcgcagggtt tattgagggc 240
gggtggacag aatggtgga cgggtggtac ggctaccacc atcagaacga gcagggatca 300
ggctacgccg ctgacctgaa gagcacacag aatgcaatcg atgaaattac taacatgtg 360
aattccgtca tcgagaaaat gggcagcgga ggctccggaa ccgacctggc agaactgctg 420
gtgctgctgc tgaaccagtg gacactgctg taccacgata gtaacgtgaa gaatctgtat 480
gagaaagtcc gatcacagct gaagaacaat gctaaagaaa tcgggaatgg atgcttcgag 540
ttttaccata agtgcgacaa cacctgtatg gagagcgtga aaaatggcac atacgattat 600
cccaagtatt ccgaggaagc caaactgaac agagaggaaa ttgactctgg gggcgacatc 660
atcaagctgc tgaacgaaca ggtcaacaag gagatgcaga gctccaatct gtacatgtcc 720
atgtctagtt ggtgttatac ccactctctg gacgcgctg gctgttcct gtttgatcac 780
gcagccgagg aatacgaaca tgcaaagaaa ctgatcattt tcctgaacaa gaacaatgtg 840
cccgtccagc tgacatcaat cagcgcccct gaacataagt tcgagggcct gactcagatc 900
tttcagaaag cttacgaaca cgagcagcat atttccgaat ctatcaacaa tattgtggac 960
cacgccatta gagtaaaga tcatgctacc ttcaattttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg cattgccaa gagccggaaa 1140
agtgggtca                                                         1149
```

| SEQ ID NO: 110 | moltype = AA length = 383 |
|---|---|
| FEATURE | Location/Qualifiers |
| REGION | 1..383 |
|  | note = Synthetic |
| source | 1..383 |
|  | mol_type = protein |
|  | organism = synthetic construct |

```
SEQUENCE: 110
MKAKLLVLLC TFTATYADTL CIGYHANNST DTVDTVLEKN VTVTHSVNLG SGLRLATGLR   60
NIPQRETRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                          383
```

| SEQ ID NO: 111 | moltype = DNA length = 1149 |
|---|---|
| FEATURE | Location/Qualifiers |
| misc_feature | 1..1149 |
|  | note = Synthetic |
| source | 1..1149 |
|  | mol_type = other DNA |
|  | organism = synthetic construct |

```
SEQUENCE: 111
tgacccactt ttccggctct tggcaatgcc cttcacatac tgatctgcca ggtacaggcc 60
atgattctcg tttccaatca gttcgatttt atccaggatg tccttaaaca ggacctcctc 120
ctcgtgctgc tcggccacgt accactgcag aaaattgaag gtagcatgat ctttactctt 180
aatggcgtgg tccacaatat tgttgataga ttcggaaata tgctgctcgt gttcgtaagc 240
tttctgaaaa atctgagtca ggccctcgaa cttatgttca ggggcgctga ttgatgtcag 300
ctggacgggc acattgttct cgttcaggaa aatgatcagt ttctttgcat gttcgtattc 360
ctcggctgcg tgatcaaaca ggaacagccc agcgccgtcc agagagtggg tataacaca 420
actagacatg gacatgtaca gattggagct ctgcatctcc ttgttgacct gttcgttcag 480
cagcttgatg atgtcgcccc cagagtcaat ttcctctctg ttcagtttgg cttcctcgga 540
atacttggga taatcgtatg tgccattttt cacgctctcc atacaggtgt tgtcgcactt 600
atggtaaaac tcgaagcatc cattcccgat ttctttagca ttgttcttca gctgtgatcg 660
gactttctca tacagattct tcacgttact atcgtggtac agcagtgtcc actggttcag 720
cagcagcacc agcagttctg ccaggtcggt tccggagcct ccgctgccca tttttctcgat 780
gacggaattc accatgttag taatttcatc gattgcattc tgtgtgctct tcaggtcagc 840
ggcgtagcct gatccctgct cgttctgatg gtggtagccg taccacgt ccaccattcc 900
tgtccacccg ccctcaataa accctgcgat agcgccgaac agtcctctgg tttccgctg 960
tgggtgtttt cgcagtccag ttgccagcct cagtccactg cccagattca cagagtgggt 1020
gacagtcacg ttcttctcca ggacagtatc cactgtgtcg gttgagttgt tagcgtgata 1080
gccgatgcac agggtgtcag cgttagcggt agcgaaagta tacagcagga cgaccaggat 1140
tgccttcat                                                         1149
```

| SEQ ID NO: 112 | moltype = DNA length = 1143 |

```
FEATURE                 Location/Qualifiers
misc_feature            1..1143
                        note = Synthetic
source                  1..1143
                        mol_type = other DNA
                        organism = synthetic construct
SEQUENCE: 112
atggctatca tctacctgat cctgctgttc actgctgtgc gggggggacca gatttgcatc    60
ggctaccacg ctaataattc aactgagaag gtggatacta tcctggagcg gaacgtgacc   120
gtcacacacg ctaaagacat tggcagcgga ctggtgctgg caaccggact gaggaatgtc   180
ccacagatcg agtcccgcgg actgttcggc gctatcgcag ggtttattga aggcgggtgg   240
cagggaatga ttgatgggtg gtacggctac caccattcta acgaccaagg aagtggctac   300
gccgctgata aggagagtac tcagaaagcc ttcgatggca tcaccaacat ggtgaattca   360
gtcattggaa agatgggcag cggaggctcc ggaaccgacc tggcagaact gctggtgctg   420
ctgctgaatc agtggacact gctgtttcac gactctaacg tgaagaatct gtatgataaa   480
gtccggatgc agctgagaga caacgtgaag gagctgggga atggatgctt cgaattttac   540
cataagtgcg acgatgagtg tatgaacagt gtcaaaaatg gcatacgat tatcccaag    600
tatgaggaag agtcaaaact gaaccgaaat gaaatcaaga gcggggcga catcatcaag   660
ctgctgaacg agcaagtgaa taggaaatg cagagctcca acctgtacat gtccatgtct   720
agttggtgtt atactcactc tctggatggc gccgggctgt tcctgtttga ccacgcagcc   780
gaagagtacg agcatgctaa gaaactgatc attttcctga cgaaaacaa cgtgcccgtc   840
cagctgacat caatcagcgc acctgagcat aagttcgaag gatctttcag            900
aaagcttacg agcacgaaca gcatattcc gagtctatca acaatattgt ggaccacgcc   960
atcaagagca agatcatgc taccttcaac tttctgcagt ggtacgtggc cgagcagcac  1020
gaagaggaag tcctgtttaa ggacatcctg gataaaatcg agctgattgg aaacgaaaat  1080
catggcctgt acctggcaga ccagtatgtg aagggcattg ccaagtccag aaaaagtggg  1140
tca                                                                1143

SEQ ID NO: 113          moltype = AA  length = 381
FEATURE                 Location/Qualifiers
REGION                  1..381
                        note = Synthetic
source                  1..381
                        mol_type = protein
                        organism = synthetic construct
SEQUENCE: 113
MAIIYLILLF TAVRGDQICI GYHANNSTEK VDTILERNVT VTHAKDIGSG LVLATGLRNV    60
PQIESRGLFG AIAGFIEGGW QGMIDGWYGY HHSNDQGSGY AADKESTQKA FDGITNMVNS   120
VIEKMGSGGS GTDLAELLVL LLNQWTLLFH DSNVKNLYDK VRMQLRDNVK ELGNGCFEFY   180
HKCDDECMNS VKNGTYDYPK YEEESKLNRN EIKSGGDIIK LLNEQVNKEM QSSNLYMSMS   240
SWCYTHSLDG AGLFLFDHAA EEYEHAKKLI IFLNENNVPV QLTSISAPEH KFEGLTQIFQ   300
KAYEHEQHIS ESINNIVDHA IKSKDHATFN FLQWYVAEQH EEEVLFKDIL DKIELIGNEN   360
HGLYLADQYV KGIAKSRKSG S                                            381

SEQ ID NO: 114          moltype = DNA  length = 1143
FEATURE                 Location/Qualifiers
misc_feature            1..1143
                        note = Synthetic
source                  1..1143
                        mol_type = other DNA
                        organism = synthetic construct
SEQUENCE: 114
tgacccactt tttctggact tggcaatgcc cttcacatac tggtctgcca ggtacaggcc    60
atgattttcg tttccaatca gctcgatttt atccaggatg tccttaaaca ggacttcctc   120
ttcgtgctgc tcgccacgt accactgcag aaagttgaag gtagcatgat ctttgctctt   180
gatgcgctgg tccacaatat tgttgataga ctcggaaata tgctgttcgt gtcgtaagc   240
tttctgaaag atctgagtca ggccttcgaa cttatgctca ggtgcgctga ttgatgtcag   300
ctggacgggc acgttgtttt cgttcaggaa aatgatcagt ttcttagcat gctcgtactc   360
ttcggctgcg tggtcaaaca ggaacagccc ggcgccatcc agagagtgag tataaccaca   420
actagacatg gacatgtaca ggttgagct ctgcatttcc ttattcactt gctcgttcag   480
cagcttgatg atgtcgcccc cgctcttgat ttcattcgg ttcagttttg actcttcctg   540
atacttggga taatcgctatg tgccatttt gacactgttc atacactcat cgtcgcactt   600
atggtaaaat tcgaagcatc cattcccag ctccttcacg ttgtctctca gctgcatccg   660
gactttatca tacagattct tcacgttaga gtcgtgaaac agcagtgtcc actgattcag   720
cagcagcacc agcagttctg ccaggtcggt tccgagcct ccgctgccca tcttctcaat   780
gactgaattc accatgtttg tgatgccatc gaaggctttc tgagtactct ccttatcagc   840
ggcgtagcca cttccttggt cgttagaatg gtggtagccg taccaccat caatcattcc   900
ctgccacccg ccttcaataa accctgcgat agcgccgaac agtccgcggg actcgatctg   960
tgggacattc ctcagtccgg ttgccagcac cagtccgctg ccaatgtctt tagcgtgtgt  1020
gacggtcacg ttccgctcca ggatagtatc caccttctca gttgaattat tagcgtggta  1080
gccgatgcaa atctggtccc cccgcacagc agtgaacagc aggatcaggt agatgatagc  1140
cat                                                                1143

SEQ ID NO: 115          moltype = DNA  length = 1158
FEATURE                 Location/Qualifiers
misc_feature            1..1158
                        note = Synthetic
```

|             |                          |      |
|-------------|--------------------------|------|
| source      | 1..1158                  |      |
|             | mol_type = other DNA     |      |
|             | organism = synthetic construct |  |

SEQUENCE: 115

```
atggaaaaaa tcgtgctgct gctggctatc gtgtccctgg tgaagtccga ccagatctgt   60
attgggtatc atgctaacaa ctccacagaa caggtggata ctatcatgga aaagaacgtg  120
accgtcacac acgctcagga cattggatgg ggactggtcc tggcaaccgg actgagaaat  180
tcaccacaga gggaaagccg gagaaagaaa cgcggactgt tcggcgctat cgcagggttt  240
attgagggcg ggtggcaggg aatggtggat gggtggtacg gctaccacca ttccaacgaa  300
cagggatctg gctacgccgc tgataaggag tctactcaga aagctatcga cggcgtgacc  360
aacatggtca atagtatcat tgataagatg ggctctggag cagtggaac  cgacctggca  420
gagctgctgt tgctgctgct gaaccagtgg acactgctgt tccacgactc taacgtgaag  480
aatctgtatg ataaagtccg actgcagctg cgggacaacg ccaaggaact ggggaatgga  540
tgcttcgagt tctaccataa gtgcgataac gaatgtatgg agagcatccg aaacggcacg  600
tacaattatc cccagtattc cgaggaagct aggctgaaac gcgaggaaat tagctccggg  660
ggagacatca ttaagctgct gaacgaacag gtgaacaagg agatgcagtc tagtaacctg  720
tacatgagta tgtcaagctg gtgttatact cactcactgg atggcgccgg gctgttcctg  780
tttgaccacg cagccgagga atacgaacat gctaagaaac tgatcatttt cctgaatgag  840
aacaatgtgc ccgtccagct gacatccatc tctgcacctg aacataagtt cgagggcctg  900
actcagatct ttcagaaagc ctacgaacac gagcagcata ttagtgagtc aatcaacaat  960
attgtggacc acgccatcaa gagcaaagat catgctacct tcaatttctt gcagtggtac 1020
gtggccgagc agcacgagga agaggtcctg tttaaggaca tcctggataa aatcgaactg 1080
attggaaacg agaatcatgg cctgtacctg gcagaccagt atgtgaaggg cattgccaag 1140
tccaggaaaa gcgggtcc                                                1158
```

| SEQ ID NO: 116 | moltype = AA length = 386 |
|----------------|---------------------------|
| FEATURE        | Location/Qualifiers       |
| REGION         | 1..386                    |
|                | note = Synthetic          |
| source         | 1..386                    |
|                | mol_type = protein        |
|                | organism = synthetic construct |

SEQUENCE: 116

```
MEKIVLLLAI VSLVKSDQIC IGYHANNSTE QVDTIMEKNV TVTHAQDIGW GLVLATGLRN   60
SPQRESRRKK RGLFGAIAGF IEGGWQGMVD GWYGYHHSNE QGSGYAADKE STQKAIDGVT  120
NMVNSIIDKM GSGGSGTDLA ELLVLLLNQW TLLFHDSNVK NLYDKVRLQL RDNAKELGNG  180
CFEFYHKCDN ECMESIRNGT YNYPQYSEEA RLKREEISSG GDIIKLLNEQ VNKEMQSSNL  240
YMSMSSWCYT HSLDGAGLFL FDHAAEEYEH AKKLIIFLNE NNVPVQLTSI SAPEHKFEGL  300
TQIFQKAYEH EQHISESINN IVDHAIKSKD HATFNFLQWY VAEQHEEEVL FKDILDKIEL  360
IGNENHGLYL ADQYVKGIAK SRKSGS                                       386
```

| SEQ ID NO: 117 | moltype = DNA length = 1158 |
|----------------|-----------------------------|
| FEATURE        | Location/Qualifiers         |
| misc_feature   | 1..1158                     |
|                | note = Synthetic            |
| source         | 1..1158                     |
|                | mol_type = other DNA        |
|                | organism = synthetic construct |

SEQUENCE: 117

```
ggacccgctt ttcctggact tggcaatgcc cttcacatac tggtctgcca ggtacaggcc   60
atgattctcg tttccaatca gttcgatttt atccaggatg tccttaaaca ggacctcttc  120
ctcgtgctgc tcggccacgt accactgcag aaaattgaag gtagcatgat ctttgctctt  180
gatggcgtgg tccacaatat tgttgattga ctcactaata tgctgctcgt gttcgtaggc  240
tttctgaaag atctgagtca ggccctcgaa cttatgttca ggtgcagaga tggatgtcag  300
ctggacgggc acattgttct cattcaggaa aatgatcagt tcttagcat  gttcgtattc  360
ctcgtgctgcg tggtcaaaca ggaacagccc ggcgccatcc agtgagtgag tataacaca  420
gcttgacata ctcatgtaca ggttactaga ctgcatctcc ttgttcacct gttcgttcag  480
cagcttaatg atgtctcccc cggagctaat ttcctcgcgt tcagcctag cttcctcgga  540
atactgggga taattgtatg tgccgtttcg gatgctctcc atacattcgt tatcgcactt  600
atggtagaac tcgaagcatc cattcccag  ttccttggcg ttgtcccgca gctgcagtcg  660
gactttatca tacagattct tcacgttaga gtcgtggaac agcagtgtcc actgttcag  720
cagcagcacc agcagctctg ccaggtcggt tccactgcct ccagagccca tcttatcaat  780
gatactattg accatgttgg tcacgccgtc gatagcttttc tgagtagact ccttatcagc  840
ggcgtagcca gatccctgtt cgttggaatg gtggtagccg taccaccat  ccaccattcc  900
ctgccacccg ccctcaataa accctgcgat agcgccgaac agtccgcgtt tctttctccg  960
gcttccctc tgtggtgaat ttctcagtcc ggttgccagg accagtcccc atccaatgtc 1020
ctgagcgtgt gtgacggtca cgttcttctc catgatagta tccacctgtt ctgtggagtt 1080
gttagcatga tacccaatac agatctggtc ggacttcacc agggacacga tagccagcag 1140
cagcacgatt ttttccat                                                1158
```

| SEQ ID NO: 118 | moltype = DNA length = 1149 |
|----------------|-----------------------------|
| FEATURE        | Location/Qualifiers         |
| misc_feature   | 1..1149                     |
|                | note = Synthetic            |
| source         | 1..1149                     |
|                | mol_type = other DNA        |
|                | organism = synthetic construct |

```
SEQUENCE: 118
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg ggctgttcct gtttgatcac   780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                          1149

SEQ ID NO: 119            moltype = AA    length = 383
FEATURE                   Location/Qualifiers
REGION                    1..383
                          note = Synthetic
source                    1..383
                          mol_type = protein
                          organism = synthetic construct
SEQUENCE: 119
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                          383

SEQ ID NO: 120            moltype = DNA    length = 1149
FEATURE                   Location/Qualifiers
misc_feature              1..1149
                          note = Synthetic
source                    1..1149
                          mol_type = other DNA
                          organism = synthetic construct
SEQUENCE: 120
tgacccactt tttctggact tggcaatgcc cttcacatac tgatctgcca ggtacaggcc    60
atgattctcg tttccaatca gttcgatttt atccaggatg tccttaaaca ggacctcctc   120
ctcgtgctgc tcggccacgt accactgcag aaagttgaag gtagcatgat ctttgctctt   180
aatggcgtgg tccacaatat tgttgataga ttcgaaaata tgctgctcgt gttcgtaagc   240
tttctgaaag atctgggtca ggccctcgaa ctttatgttca ggggcgctga ttgaagtcga   300
ctggacgggc acattgttct cattcaggaa aatgatcagt ttctttgcat gttcgtattc   360
ctcggctgcg tgatcaaaca ggaacagccc agcgccgtcc agtgagtgtg tataacacca   420
actagacata ctcatgtaca ggttggagct ctgcatctcc ttgttcacct gttcgttcag   480
cagcttgatg atgtcgcccc cactgtcaat ttctctctga ttcagcttac tctcttcaga   540
atatttggga tagtcgtaag tgccgttctt cacagactcc atacattcat tgttgcactt   600
atggtaaaac tcgaagcatc cattcccgat ttctttggca ttgttcttca gctgggattt   660
gaccttctca tacagattct tcacgttgct atcgtggaaa tccagagtcc gctcgttcag   720
cagcagcacc agcagctcag ccaggtctgt tccggagcct ccgctgccca ttttttcgat   780
gacagaattc accatgttag taatgccatt gattgcgttc tgtgtagact tctgatcagc   840
ggcgtagccg ctgccctgct cattctgatg gtggtagccg taccaccgt ccaccattcc   900
tgtccacccg ccctcaataa accctgcgat agcgccgaac agtcctcttg tttcccgctg   960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 121            moltype = DNA    length = 1149
FEATURE                   Location/Qualifiers
misc_feature              1..1149
                          note = Synthetic
source                    1..1149
                          mol_type = other DNA
                          organism = synthetic construct
SEQUENCE: 121
atgaaggcca aactgctggt cctgctgtgt acttttaccg caacctacgc tgacactatc    60
tgcatcggct atcacgcaaa caactccacc gacacagtgg ataccattct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
```

```
gggtggacag gaatggtgga cgggtggtac ggctaccacc atcagaatga gcagggcagc    300
ggctacgccg ctgatcagaa gtctacacag aacgcaatca atggcattac taacatggtg    360
aattctgtca tcgaaaaaat gggcagcgga ggctccggaa cagacctggc tgagctgctg    420
gtgctgatgc tgaaccagtt cactctgctg ttccacgata gcaacgtgaa gaatctgtat    480
gagaaggtca aatcccagct gaagaacaat gccaaagaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgacagtgg gggcgacatc    660
atcaagctgc tgaacgaaca ggtgaacaag agatgcaga gctccaacct gtacatgagt     720
atgtctagtt ggtgttatac acactcactg gacggcgctg ggctgttcct gtttgatcac    780
gcagccgagg aatacgaaca tgcaaagaaa ctgatcattt tcctgaatga gaacaatgtg    840
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg cattgccaa gtccagaaaa    1140
agtgggtca                                                           1149

SEQ ID NO: 122           moltype = AA  length = 383
FEATURE                  Location/Qualifiers
REGION                   1..383
                         note = Synthetic
source                   1..383
                         mol_type = protein
                         organism = synthetic construct
SEQUENCE: 122
MKAKLLVLLC TFTATYADTI CIGYHANNST DTVDTILEKN VTVTHSVNLG SGLRMVTGLR     60
NIPQRETRGL FGAIAGFIEG GWTGMVDGWY GYHHQNEQGS GYAADQKSTQ NAINGITNMV    120
NSVIEKMGSG GSGTDLAELL VLMLNQFTLL FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEVLFKD ILDKIELIGN     360
ENHGLYLADQ YVKGIAKSRK SGS                                            383

SEQ ID NO: 123           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 123
tgacccactt tttctggact tggcaatgcc cttcacatac tgatctgcca ggtacaggcc     60
atgattctcg tttccaatca gttcgatttt atccaggatg tccttaaaca ggacctcctc    120
ctcgtgctgc tcggccacgt accactgcag aaagttgaag gtagcatgat ctttgctctt    180
aatggcgtgg tccacaatat tgttgataga ttcggaaata tgctgctcgt gttcgtaagc    240
tttctgaaag atctgggtca ggccctcgaa cttatgttca gggcgctga ttgaagtcag     300
ctggacgggc acattgttct cattcaggaa aatgatcagt ttctttgcat gttcgtattc    360
ctcggctgcg tgatcaaaca ggaacagccc agccgccgtcc agtgagtgtg tataacacca   420
actagacata ctcatgtaca ggttggagct ctgcatctcc ttgttcacct gttcgttcag    480
cagcttgatg atgtcgcccc cactgtcaat tttctctcga ttcagcttac tctcttcaga    540
atatttggga tagtcgtaag tgccgttctt cacagactcc atacattcat tgttgcatt    600
atggtaaaac tcgaagcatc cattcccgat tctttggca ttgttcttca gctgggattt    660
gaccttctca tacagattct tcacgttgct atcgtggaac agcagagtga actggttcag    720
catcagcacc agcagctcag ccaggtctgt tccggagcct ccgctgccca ttttttcgat    780
gacagaattc accatgttag taatgccatt gattgcgttc tgtgtagact tctgatcagc    840
ggcgtagccg ctgccctgct cattctgatg gtggtagccg taccaccgt ccaccattcc     900
tgtccacccg ccctcaataa accctgcgat agcgccgaac agtccttg tttccccgctg     960
tgggatgttg cgcagtccgg tgaccatcct cagtccgctg cccagattca ctgagtgggt   1020
gacagtcacg ttcttctcca gaatggtatc cactgtgtcg gtggagttgt tgcgtgata    1080
gccgatgcag atagtgtcag cgtaggttgc ggtaaaagta cacagcagga ccagcagttt   1140
ggccttcat                                                           1149

SEQ ID NO: 124           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 124
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga gatggtcac cggactgcgc     180
aacatcccac agcgggaaac aagaggactg ttcggcgcta tcgccggctt tattgaggc     240
gggtggacag gaatggtgga cgggtggtac ggctaccacc atcagaatga gcagggcagc    300
ggctacgccg ctgatcagaa gtctacacag aacgcaatca atggcattac taacatggtg    360
aattctgtca tcgaaaaaat gggcaatgga acaggcggag ctgacctggc tgagctgctg    420
gtgctgctgc tgaaccagtg gactctgctg ttccacgata gcaacgtgaa gaatctgtat    480
gagaaggtca aatcccagct gaagaacaat gccaaagaaa tcgggaatgg atgcttcgag    540
```

```
ttttaccata agtgcaacaa tgaatgtatg gagtctgtga agaacggcac ttacgactat    600
cccaaatatt ctgaagagag taagctgaat cgagagaaaa ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg ggctgttcct gtttgatcac    780
gcagccgagg aatacgaaca tgcaaagaaa ctgatcattt tcctgaatga gaacaatgtg    840
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta gagcaaagat catgctacct tcaactttc tgcagtggta cgtggccgag    1020
cagcacgagg aggaggtcct gtttaaggac atcctggata aaatcgaact gattggaaac    1080
gagaatcatg gcctgtacct ggcagatcag tatgtgaagg gcattgccaa gtccagaaaa    1140
agtgggtca                                                             1149

SEQ ID NO: 125            moltype = AA  length = 383
FEATURE                   Location/Qualifiers
REGION                    1..383
                          note = Synthetic
source                    1..383
                          mol_type = protein
                          organism = synthetic construct
SEQUENCE: 125
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV    120
NSVIEKMGNG TGGADLAELL VLLLNQWTLL FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                             383

SEQ ID NO: 126            moltype = DNA  length = 1149
FEATURE                   Location/Qualifiers
misc_feature              1..1149
                          note = Synthetic
source                    1..1149
                          mol_type = other DNA
                          organism = synthetic construct
SEQUENCE: 126
tgacccactt tttctggact tggcaatgcc cttcacatac tgatctgcca ggtacaggcc    60
atgattctcg tttccaatca gttcgatttt atccaggatg tccttaaaca ggacctcctc    120
ctcgtgctgc tcggccacgt accactgcag aaagttgaag gtagcatgat ctttgctctt    180
aatggcgtgg tccacaatat tgttgataga ttcggaaata tgctgctcgt gttcgtaagc    240
tttctgaaag atctgggtca ggccctcgaa cttatgttca ggggcgctga ttgaagtcag    300
ctggacgggc acattgttct cattcaggaa aatgatcagt ttctttgcat gttcgtattc    360
ctcggctgcg tgatcaaaca ggaacagccc agcgccgtcc agtagtgtg tataaccacca    420
actagacata ctcatgtaca ggttggagct ctgcatctcc ttgttcacct gttcgttcag    480
cagcttgatg atgtcgcccc cactgtcaat tttctctcga ttcagcttac tctcttcaga    540
atatttggga tagtcgtaag tgccgttctt cacagactcc atacattcat tgttgcactt    600
atggtaaaac tcgaagcatc cattcccgat ttctttggca ttgttcttca gctgggattt    660
gaccttctca tacagattct tcacgttgct atcgtgaac agcagagtcc actggttcag    720
cagcagcacc agcagctcag ccaggtcagc tccgcctgtt ccattgccca tttttttcgat    780
gacagaattc accatgttag taatgccatt gattgcgttc tgtgtagact tctgatcagc    840
ggcgtagccg ctgccctgct cattctgatg gtggtagcca taccaccgt ccaccattcc    900
tgtccacccg ccctcaataa accctgcgat agccgccgaac agtcctcttg tttcccgctg    960
tgggatgttg cgcagtccgg tgaccatcct cagtccgctg cccagattca ctgagtgggt    1020
gacagtcacg ttcttctcca ggacggtatc cactgtgtcg gtggagttgt ttgcgtgata    1080
gccgatgcag atagtgtcag cgtaggttgc ggtaaaagta cacagcagga ccagcagttt    1140
ggccttcat                                                             1149

SEQ ID NO: 127            moltype = DNA  length = 1149
FEATURE                   Location/Qualifiers
misc_feature              1..1149
                          note = Synthetic
source                    1..1149
                          mol_type = other DNA
                          organism = synthetic construct
SEQUENCE: 127
atgaaggcca aactgctggt cctgctgtgt acttttaccg caacctacgc tgacactatc    60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcgcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca tggcattac taacatggtg    360
aattctgtca tcgaaaaaat gggcggaaat ggcactggag ctgacctggc tgagctgctg    420
gtgctgctgc tgaaccagtg gactctgctg ttccacgata gcaacgtgaa gaatctgtat    480
gaaaaggtca atcccagct gaagaacaat gccaaagaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg ggctgttcct gtttgatcac    780
gcagccgagg aatacgaaca tgcaaagaaa ctgatcattt tcctgaatga gaacaatgtg    840
```

```
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtca                                                           1149

SEQ ID NO: 128           moltype = AA   length = 383
FEATURE                  Location/Qualifiers
REGION                   1..383
                         note = Synthetic
source                   1..383
                         mol_type = protein
                         organism = synthetic construct
SEQUENCE: 128
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 129           moltype = DNA   length = 1149
FEATURE                  Location/Qualifiers
misc_feature             1..1149
                         note = Synthetic
source                   1..1149
                         mol_type = other DNA
                         organism = synthetic construct
SEQUENCE: 129
tgacccactt tttctggact tggcaatgcc cttcacatac tgatctgcca ggtacaggcc    60
atgattctcg tttccaatca gttcgatttt atccaggatg tccttaaaca ggacctcctc   120
ctcgtgctgc tcgccacgt accactgcag aaagttgaag gtagcatgat ctttgctctt   180
aatgcgtgg tccacaatat tgttgataga ttcggaaata tgctgctcgt gttcgtaagc   240
tttctgaaag atctgggtca ggccctcgaa cttatgttca ggggcgctga ttgaagtcag   300
ctggacgggc acattgttct cattcaggaa aatgatcagt ttcttgcat gttcgtattc   360
ctcggctgcg tgatcaaaca ggaacagccc agcgccgtcc agtgagtgtg tataacacca   420
actagacata ctcatgtaca ggttggagct ctgcatctcc ttgttcacct gttcgttcag   480
cagcttgatg atgtcgcccc cactgtcaat ttttctcgta ttcagcttac tctcttcaga   540
atatttggga tagtcgtaag tgccgttctt cacagactcc atacattcat tgttgcactt   600
atggtaaaac tcgaagcatc cattcccgat ttctttggca ttgttcttca gctgggattt   660
gaccttctca tacagattct tcacgttgct atcgtgaac agcagagtcc actggttcag   720
cagcagcacc agcagctcag ccaggtcagc tccagtgcca tttccgccca tttttttgat   780
gacagaattc accatgttag taatgccatt gattgcgttc tgtgtagact tctgatcagc   840
ggcgtagccg ctgccctgct cattctgatg gtggtagccg taccaccgt ccaccattcc    900
tgtccacccg ccctcaataa accctgcgat agcgccgaac agtcctcctg tttcccgctg   960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 130           moltype = DNA   length = 1149
FEATURE                  Location/Qualifiers
misc_feature             1..1149
                         note = Synthetic
source                   1..1149
                         mol_type = other DNA
                         organism = synthetic construct
SEQUENCE: 130
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggcaacagaa cagacctggc tgagctgcga   420
gtgctgctgc tgaaccagtg gactctgctg ttccacgata gcaacgtgaa gaatctgtat   480
gagaaggtca atcccagctc gaagaacaat gccaaagaaa tcgggaatgg atgcttcgag   540
ttttaccata agtgcaacaa tgaatgtatg agtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaaa gctccaacct gtacatgagt   720
atgtctagtt ggtgttatac acactcactg gacggcgctg gctgttcct gtttgatcac   780
gcagccgagg aatacgaaca tgcaaagaaa ctgatcattt tcctgaatga aaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta agagcaaaga tcatgctacc ttcaactttc tgcagtggta cgtggccgag  1020
```

```
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtca                                                           1149

SEQ ID NO: 131          moltype = AA  length = 383
FEATURE                 Location/Qualifiers
REGION                  1..383
                        note = Synthetic
source                  1..383
                        mol_type = protein
                        organism = synthetic construct
SEQUENCE: 131
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GNGTDLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWVYAE QHEEEVLFKD ILDKIELIGN   360
ENHGLYLADQ YVKGIAKSRK SGS                                          383

SEQ ID NO: 132          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 132
tgacccactt tttctggact tggcaatgcc cttcacatac tgatctgcca ggtacaggcc    60
atgattctcg tttccaatca gttcgatttt atccaggatg tccttaaaca ggacctcctc   120
ctcgtgctgc tcggccacgt accactgcag aaagttgaag gtagcatgat ctttgctctt   180
aatggcgtgg tccacaatat tgttgataga ttcggaaata tgctgctcgt gttcgtaagc   240
tttctgaaag atctgggtca ggccctcgaa cttatgttca ggggcgctga ttgaagtcag   300
ctggacgggc acattgttct cattcaggaa aatgatcagt ttctttgcat gttcgtattc   360
ctcggctgcg tgatcaaaca ggaacagccc agcgccgtcc agtgagtgtg tataaccaca   420
actagacata tcatgtaca ggttggagct ctgcatctcc ttgttcacct gttcgttcag   480
cagcttgatg atgtcgcccc cactgtcaat tttctctcga ttcagcttac tctcttcaga   540
atatttggga tagtcgtaag tgccgttctt cacagactcc atacattcat tgttgcactt   600
atggtaaaac tcgaagcatc cattcccgat ttctttgaca ttgttcttca gctgggattt   660
gaccttctca tacagattct tcacgttgct atcgtggaac agcagagtcc actggttcag   720
cagcagcacc agcagctcag ccaggtctgt tccgttgcct ccgctgccca ttttttcgat   780
gacagaattc accatgttag taatgccatt gattgcgttc tgtgtagact tctgatcagc   840
ggccgtagcg ctgccctgct cattctgatg gtggtagccg taccacccgt ccaccattcc   900
tgtccacccg ccctcaataa accctgcgat agcgccgaac agtcctcttg tttcccgctg   960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                          1149

SEQ ID NO: 133          moltype = AA  length = 33
FEATURE                 Location/Qualifiers
source                  1..33
                        mol_type = protein
                        organism = Influenza A virus
SEQUENCE: 133
NTQFTAVGKE FNKLERRMEN LNKKVDDGFL DIW                                33

SEQ ID NO: 134          moltype = AA  length = 12
FEATURE                 Location/Qualifiers
source                  1..12
                        mol_type = protein
                        organism = Influenza A virus
SEQUENCE: 134
NTQFTAVGKE FN                                                       12

SEQ ID NO: 135          moltype = AA  length = 12
FEATURE                 Location/Qualifiers
source                  1..12
                        mol_type = protein
                        organism = Influenza A virus
SEQUENCE: 135
NKLERRMENL NK                                                       12

SEQ ID NO: 136          moltype = AA  length = 11
FEATURE                 Location/Qualifiers
source                  1..11
                        mol_type = protein
                        organism = Influenza A virus
```

```
SEQUENCE: 136
KKVDDGFLDI W                                                              11

SEQ ID NO: 137          moltype = AA  length = 33
FEATURE                 Location/Qualifiers
source                  1..33
                        mol_type = protein
                        organism = Influenza A virus
SEQUENCE: 137
NTQFTAVGKE FNHLEKRIEN LNKKVDDGFL DIW                                      33

SEQ ID NO: 138          moltype = AA  length = 11
FEATURE                 Location/Qualifiers
source                  1..11
                        mol_type = protein
                        organism = Influenza A virus
SEQUENCE: 138
NTQFTAVGKE F                                                              11

SEQ ID NO: 139          moltype = AA  length = 11
FEATURE                 Location/Qualifiers
source                  1..11
                        mol_type = protein
                        organism = Influenza A virus
SEQUENCE: 139
FNHLEKRIEN L                                                              11

SEQ ID NO: 140          moltype = AA  length = 13
FEATURE                 Location/Qualifiers
source                  1..13
                        mol_type = protein
                        organism = Influenza A virus
SEQUENCE: 140
LNKKVDDGFL DIW                                                            13

SEQ ID NO: 141          moltype = AA  length = 33
FEATURE                 Location/Qualifiers
source                  1..33
                        mol_type = protein
                        organism = Influenza A virus
SEQUENCE: 141
NTQFEAVGKE FSNLERRLEN LNKKMEDGFL DVW                                      33

SEQ ID NO: 142          moltype = AA  length = 11
FEATURE                 Location/Qualifiers
source                  1..11
                        mol_type = protein
                        organism = Influenza A virus
SEQUENCE: 142
NTQFEAVGKE F                                                              11

SEQ ID NO: 143          moltype = AA  length = 12
FEATURE                 Location/Qualifiers
source                  1..12
                        mol_type = protein
                        organism = Influenza A virus
SEQUENCE: 143
FSNLERRLEN LN                                                             12

SEQ ID NO: 144          moltype = AA  length = 12
FEATURE                 Location/Qualifiers
source                  1..12
                        mol_type = protein
                        organism = Influenza A virus
SEQUENCE: 144
NKKMEDGFLD VW                                                             12

SEQ ID NO: 145          moltype = AA  length = 33
FEATURE                 Location/Qualifiers
source                  1..33
                        mol_type = protein
                        organism = Influenza A virus
SEQUENCE: 145
NTQFEAVGRE FNNLERRIEN LNKKMEDGFL DVW                                      33
```

```
SEQ ID NO: 146          moltype = AA  length = 11
FEATURE                 Location/Qualifiers
source                  1..11
                        mol_type = protein
                        organism = Influenza A virus
SEQUENCE: 146
NTQFEAVGRE F                                                           11

SEQ ID NO: 147          moltype = AA  length = 12
FEATURE                 Location/Qualifiers
source                  1..12
                        mol_type = protein
                        organism = Influenza A virus
SEQUENCE: 147
FNNLERRIEN LN                                                          12

SEQ ID NO: 148          moltype = AA  length = 12
FEATURE                 Location/Qualifiers
source                  1..12
                        mol_type = protein
                        organism = Influenza A virus
SEQUENCE: 148
NKKMEDGFLD VW                                                          12

SEQ ID NO: 149          moltype = AA  length = 53
FEATURE                 Location/Qualifiers
source                  1..53
                        mol_type = protein
                        organism = Influenza A virus
SEQUENCE: 149
KVNSVIEKMN TQFTAVGKEF NKLERRMENL NKKVDDGFLD IWTYNAELLV LLE             53

SEQ ID NO: 150          moltype = AA  length = 20
FEATURE                 Location/Qualifiers
source                  1..20
                        mol_type = protein
                        organism = Influenza A virus
SEQUENCE: 150
KVNSVIEKMT YNAELLVLLE                                                  20

SEQ ID NO: 151          moltype = AA  length = 53
FEATURE                 Location/Qualifiers
source                  1..53
                        mol_type = protein
                        organism = Influenza A virus
SEQUENCE: 151
KVNSVIEKMN TQFTAVGKEF NHLEKRIENL NKKVDDGFLD IWTYNAELLV LLE             53

SEQ ID NO: 152          moltype = AA  length = 20
FEATURE                 Location/Qualifiers
source                  1..20
                        mol_type = protein
                        organism = Influenza A virus
SEQUENCE: 152
KVNSVIEKMT YNAELLVLLE                                                  20

SEQ ID NO: 153          moltype = AA  length = 53
FEATURE                 Location/Qualifiers
source                  1..53
                        mol_type = protein
                        organism = Influenza A virus
SEQUENCE: 153
KVNSVIEKMN TQFEAVGKEF SNLERRLENL NKKMEDGFLD VWTYNAELLV LME             53

SEQ ID NO: 154          moltype = AA  length = 20
FEATURE                 Location/Qualifiers
source                  1..20
                        mol_type = protein
                        organism = Influenza A virus
SEQUENCE: 154
KVNSVIEKMT YNAELLVLME                                                  20

SEQ ID NO: 155          moltype = AA  length = 53
FEATURE                 Location/Qualifiers
source                  1..53
                        mol_type = protein
                        organism = Influenza A virus
```

| | | |
|---|---|---|
| SEQUENCE: 155 | | |
| KVNSIIDKMN TQFEAVGREF NNLERRIENL NKKMEDGFLD VWTYNAELLV LME | | 53 |
| | | |
| SEQ ID NO: 156 | moltype = AA  length = 20 | |
| FEATURE | Location/Qualifiers | |
| source | 1..20 | |
| | mol_type = protein | |
| | organism = Influenza A virus | |
| SEQUENCE: 156 | | |
| KVNSIIDKMT YNAELLVLME | | 20 |
| | | |
| SEQ ID NO: 157 | moltype = DNA  length = 645 | |
| FEATURE | Location/Qualifiers | |
| misc_feature | 1..645 | |
| | note = Synthetic | |
| source | 1..645 | |
| | mol_type = other DNA | |
| | organism = synthetic construct | |
| SEQUENCE: 157 | | |
| atgaaggcca aactgctggt cctgctgtgt acttttaccg caacctacgc tgacactatc | | 60 |
| tgcatcggct atcacgcaaa caactccacc gacacagtgg ataccgtcct ggagaagaac | | 120 |
| gtgactgtca cccactcagt gaatctgggc agcggactga ggatggtcac cggactgcgc | | 180 |
| aacatcccac agcgggaaac aagaggactg ttcggcgcta tcgcaggggtt tattgagggc | | 240 |
| gggtggacag gatggtggaa cgggtggtac ggctaccacc atcagaatga gcagggcagc | | 300 |
| ggctacgccc tgatcagaa gtctacacag aacgcaatca atggcattac taacatggtg | | 360 |
| aattctgtca tcgaaaaat gggcagcgga ggctccggaa cagacctggc tgagctgctg | | 420 |
| gtgctgctga tgaacgagcg gactctggat ttccacgata gcaacgtgaa gaatctgtat | | 480 |
| gagaaggtca aatcccagct gaagaacaat gccaaagaaa tcgggaatgg atgcttcgag | | 540 |
| ttttaccata agtgcaacaa tgaatgtatg gagtctgtga gaacggcac ttacgactat | | 600 |
| cccaaatatt ctgaagagag taagctgaat cgagagaaaa ttgac | | 645 |
| | | |
| SEQ ID NO: 158 | moltype = AA  length = 215 | |
| FEATURE | Location/Qualifiers | |
| REGION | 1..215 | |
| | note = Synthetic | |
| source | 1..215 | |
| | mol_type = protein | |
| | organism = synthetic construct | |
| SEQUENCE: 158 | | |
| MKAKLLVLLC TFTATYADTI CIGYHANNST DTVDTVLEKN VTVTHSVNLG SGLRMVTGLR | | 60 |
| NIPQRETRGL FGAIAGFIEG GWTGMVDGWY GYHHQNEQGS GYAADQKSTQ NAINGITNMV | | 120 |
| NSVIEKMGSG GSGTDLAELL VLLMNERTLD FHDSNVKNLY EKVKSQLKNN AKEIGNGCFE | | 180 |
| FYHKCNNECM ESVKNGTYDY PKYSEESKLN REKID | | 215 |
| | | |
| SEQ ID NO: 159 | moltype = DNA  length = 645 | |
| FEATURE | Location/Qualifiers | |
| misc_feature | 1..645 | |
| | note = Synthetic | |
| source | 1..645 | |
| | mol_type = other DNA | |
| | organism = synthetic construct | |
| SEQUENCE: 159 | | |
| gtcaattttc tctcgattca gcttactctc ttcagaatat tgggatagt cgtaagtgcc | | 60 |
| gttcttcaca gactccatac attcattgtt gcacttatgg taaaactcga agcatccatt | | 120 |
| cccgatttct ttggcattgt tcttcagctg ggatttgacc ttctcataca gattcttcac | | 180 |
| gttgctatcg tggaaatcca gagtccgctc gttcatcagc agcaccagca gctcagccag | | 240 |
| gtctgttccg gagcctccgc tgcccatttt ttcgatgaca gaattcacca tgttagtaat | | 300 |
| gccattgatt gcgttctgtg tagacttctg atcagcggcg tagccgctgc cctgctcatt | | 360 |
| ctgatggtgg tagccgtacc acccgtccac cattcctgtc cacccgcct caataaaccc | | 420 |
| tgcgatagcg ccgaacagtc ctcttgtttc ccgctgtggg atgttgcgca gtccggtgac | | 480 |
| catcctcagt ccgctgccca gattcactga gtgggtgaca gtcacgttct tctccaggac | | 540 |
| ggtatccact gtgtcggtgg agttgtttgc gtgatagccg atgcagatag tgtcagcgta | | 600 |
| ggttgcggta aaagtacaca gcaggaccag cagtttggcc ttcat | | 645 |
| | | |
| SEQ ID NO: 160 | moltype = DNA  length = 1149 | |
| FEATURE | Location/Qualifiers | |
| misc_feature | 1..1149 | |
| | note = Synthetic | |
| source | 1..1149 | |
| | mol_type = other DNA | |
| | organism = synthetic construct | |
| SEQUENCE: 160 | | |
| atgaaggcca aactgctggt cctgctgtgt acttttaccg caacctacgc tgacactatc | | 60 |
| tgcatcggct atcacgcaaa caactccacc gacacagtgg ataccgtcct ggagaagaac | | 120 |
| gtgactgtca cccactcagt gaatctgggc agcggactga ggatggtcac cggactgcgc | | 180 |
| aacatcccac agcgggaaac aagaggactg ttcggcgcta tcgcaggggtt tattgagggc | | 240 |
| gggtggacag gatggtggaa cgggtggtac ggctaccacc atcagaatga gcagggcagc | | 300 |
| ggctacgccc tgatcagaa gtctacacag aacgcaatca atggcattac taacatggtg | | 360 |
| aattctgtca tcgaaaaat gggcagcgga ggctccggaa cagacctggc tgagctgctg | | 420 |

```
gtgctgctga tgaacgagcg gactctggat ttccacgata gcaacgtgaa gaatctgtat    480
gagaaggtca aatcccagct gaagaacaat gccaaagaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg gctgttcct gtttgatcac     780
gcagccgagg aatacgaaca tgcaaagaaa ctgatcattt tcctgaatga gaacaatgtg    840
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtca                                                          1149

SEQ ID NO: 161          moltype = AA  length = 383
FEATURE                 Location/Qualifiers
REGION                  1..383
                        note = Synthetic
source                  1..383
                        mol_type = protein
                        organism = synthetic construct
SEQUENCE: 161
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNMV   120
NSVIEKMGSG GSGTDLAELL VLLMNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 162          moltype = DNA  length = 1149
FEATURE                 Location/Qualifiers
misc_feature            1..1149
                        note = Synthetic
source                  1..1149
                        mol_type = other DNA
                        organism = synthetic construct
SEQUENCE: 162
tgacccactt tttctggact tggcaatgcc cttcacatac tgatctgcca ggtacaggcc     60
atgattctcg tttccaatca gttcgatttt atccaggatg tccttaaaca ggacctcctc   120
ctcgtgctgc tcggccacgt accactgcag aaagttgaag gtagcatgat ctttgctctt   180
aatggcgtgt ccacaatat tgttgataga ttcggaaata tgctgctcgt gttcgtaagc    240
tttctgaaag atctgggtca ggccctcgaa cttatgttcg ggcgctga ttgaagtcga     300
ctggacgggc acattgttct cattcaggaa aatgatcagt ttctttgcat gttcgtattc   360
ctcggctgcg tgatcaaaca ggaacagccc agcgccgtcc agtgagtgtg tataacacca   420
actagacata ctcatgtaca ggttgagct ctgcatctcc ttgttcacct gttcgttcag     480
cagcttgatg atgtcgcccc cactgtcaat tttctctcga ttcagcttac tctcttcaga   540
atatttggga tagtcgtaag tgccgttctt cacagactcc atacattcat tgttgcactt   600
atggtaaaac tcgaagcatc cattcccgat ttctttggca ttgttcttca gctgggattt   660
gaccttctca tacagattct tcacgttgct atcgtgaaa tccagagtcc gctcgttcat    720
cagcagcacc agcagctcag ccaggtctgt tccggagcct ccgtcgccca tttttttcgat  780
gacagaattc accatgttag taatgccatt gattgcgttc tgtgtagact tctgatcagc   840
ggcgtagccg ctgccctgct cattctgatg gtggtagccg taccaccgt ccaccattcc    900
tgtccacccg ccctcaataa accctgcgat agcgccgaac agtcctcttg tttcccgctg   960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                         1149

SEQ ID NO: 163          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 163
atgaaggcca aactgctggt cctgctgtgt acttttaccg caacctacgc tgacactatc     60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcaggggt tattgagggc   240
gggtggacag gaatggtgga cggctggtac ggctaccacc atcagaatga gcagggcagc   300
ggctacgccg ctgatcagaa gtctacacag aacgcaatca atggcattac taacatcgtg   360
aatgtcagca tcgaaaaaat gggcagcgga ggctccggaa cagacctggc tgagctggtg   420
gtgctgctga tgaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                  645
```

```
SEQ ID NO: 164            moltype = AA  length = 215
FEATURE                   Location/Qualifiers
REGION                    1..215
                          note = Synthetic
source                    1..215
                          mol_type = protein
                          organism = synthetic construct
SEQUENCE: 164
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNIV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKID                              215

SEQ ID NO: 165            moltype = DNA  length = 645
FEATURE                   Location/Qualifiers
misc_feature              1..645
                          note = Synthetic
source                    1..645
                          mol_type = other DNA
                          organism = synthetic construct
SEQUENCE: 165
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaaatcca gagtccgctc gttgatcagc agcaccagca gctcagccag   240
gtctgttccg gagcctccgc tgcccatttt tcgatgaca gaattcacga tgttagtaat   300
gccattgatt gcgttctgtg tagacttctg atcagcggcg tagccgctgc cctgctcatt   360
ctgatggtgg tagccgtacc acccgtccac cattcctgtc caccccgccct caataaaccc   420
tgcgatagcc ccgaacagtc ctcttgtttc ccgctgtggg atgttgcgca gtccggtgac   480
catcctcagt ccgctgccca gattcactga gtgggtacag gtcacgttct ctctccaggac   540
ggtatccact gtgtcggtgg agttgtttgc gtgatagccg atgcagatag tgtcagcgta   600
ggttgcggta aaagtacaca gcaggaccag cagtttggcc ttcat                   645

SEQ ID NO: 166            moltype = DNA  length = 1149
FEATURE                   Location/Qualifiers
misc_feature              1..1149
                          note = Synthetic
source                    1..1149
                          mol_type = other DNA
                          organism = synthetic construct
SEQUENCE: 166
atgaaggcca aactgctggt cctgctgtgt acttttaccg caacctacgc tgacactatc    60
tgcatcggct atcacgcaaa caactccacc gacacagtcc ttgagaagaac                                                                    120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatcgtg   360
aattctgtca tcgaaaaat gggcagcgga ggctccggaa cagacctggc tgagctgctg    420
gtgctgctga tcaacgagcg gactctggat ttccacgata gcaacgtgaa gaatctgtat   480
gagaaggtca atcccagct gaagaacaat gccaaagaaa tcgggaatgg atgcttcgag    540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg gctgttcct gtttgatcac    780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta gagcaaagda tcatgctacc ttcaacttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg cattgccaa gtccagaaaa   1140
agtgggtca                                                         1149

SEQ ID NO: 167            moltype = AA  length = 383
FEATURE                   Location/Qualifiers
REGION                    1..383
                          note = Synthetic
source                    1..383
                          mol_type = protein
                          organism = synthetic construct
SEQUENCE: 167
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNIV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 168            moltype = DNA  length = 1149
```

| FEATURE | Location/Qualifiers |
|---|---|
| misc_feature | 1..1149 |
| | note = Synthetic |
| source | 1..1149 |
| | mol_type = other DNA |
| | organism = synthetic construct |

SEQUENCE: 168

```
tgacccactt tttctggact tggcaatgcc cttcacatac tgatctgcca ggtacaggcc    60
atgattctcg tttccaatca gttcgatttt atccaggatg tccttaaaca ggacctcctc   120
ctcgtgctgc tcggccacgt accactgcag aaagttgaag gtagcatgat ctttgctctt   180
aatggcgtgg tccacaatat tgttgataga ttcggaaata tgctgctcgt gttcgtaagc   240
tttctgaaag atctgggtca ggccctcgaa cttatgttca ggggcgctga ttgaagtcag   300
ctggacgggc acattgttct cattcaggaa aatgatcagt ttctttgcat gttcgtattc   360
ctcggctgcg tgatcaaaca ggaacagccc agcgccgtcc agtgagtgtg tataaccaca   420
actagacata ctcatgtaca ggttggagct ctgcatctcc ttgttcacct gttcgttcag   480
cagcttgatg atgtcgcccc cactgtcaat tttctctcga ttcagcttac tctcttcaga   540
atatttggga tagtcgtaag tgccgttctt cacagactcc atacattcat tgttgcactt   600
atggtaaaac tcgaagcatc cattcccgat ttctttggca ttgttcttca gctgggattt   660
gaccttctca tacagattct tcacgttgct atcgtggaaa tccagagtcc gctcgttgat   720
cagcagcacc agcagctcag ccaggtctgt tccggagcct ccgctgccca ttttttcgat   780
gacagaattc acgatgttag taatgccatt gattgcgttc tgtgtagact tctgatcagc   840
ggcgtagccg ctgccctgct cattctgatg gtggtagcgc taccacccgt ccaccattcc   900
tgtccacccg ccctcaataa accctgcgat agcgccgaac agtcctcttg tttcccgctg   960
tgggatgttg cgcagtccgg tgaccatcct cagtccgctg cccagattca ctgagtgggt  1020
gacagtcacg ttcttctcca ggacggtatc cactgtgtcg gtggagttgt ttgcgtgata  1080
gccgatgcag atagtgtcag cgtaggttgc ggtaaaagta cacagcagga ccagcagttt  1140
ggccttcat                                                           1149
```

| SEQ ID NO: 169 | moltype = DNA length = 645 |
|---|---|
| FEATURE | Location/Qualifiers |
| misc_feature | 1..645 |
| | note = Synthetic |
| source | 1..645 |
| | mol_type = other DNA |
| | organism = synthetic construct |

SEQUENCE: 169

```
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcaggggt tattgagggc   240
gggtggacag gaatggtgga cggtggtac ggctaccacc atcagaatga gcagggcagc   300
ggctacgccg ctgatcagaa gtctacacag aacgcaatca tggcattac taacctggtg   360
aattctgtca tcgaaaaaaat gggcagcgga ggctccggaa cagacctggc tgagctgctg   420
gtgctgctga tcaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga gaacggcac ttacgactat   600
cccaaatatt ctgaagagag taagctgaat cgagagaaaa ttgac                   645
```

| SEQ ID NO: 170 | moltype = AA length = 215 |
|---|---|
| FEATURE | Location/Qualifiers |
| REGION | 1..215 |
| | note = Synthetic |
| source | 1..215 |
| | mol_type = protein |
| | organism = synthetic construct |

SEQUENCE: 170

```
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNLV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKID                              215
```

| SEQ ID NO: 171 | moltype = DNA length = 645 |
|---|---|
| FEATURE | Location/Qualifiers |
| misc_feature | 1..645 |
| | note = Synthetic |
| source | 1..645 |
| | mol_type = other DNA |
| | organism = synthetic construct |

SEQUENCE: 171

```
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg gatttgacc ttctcataca gattcttcac   180
gttgctatcg tggaaatcca gagtccgctc gttgatcagc agcaccagca gctcagccag   240
gtctgttccg gagcctccgc tgcccatttt tcgatgaca gaattcacca ggttagtaat   300
gccattgatt gcgttctgtg tagacttctg atcagcggcg tagccgctgc cctgctcatt   360
ctgatggtgt agccgtacc acccgtccac cattcctgtc cacccgccct caataaaccc   420
tgcgatagcc cgaacagtc ctcttgtttc ccgctgtggg atgttgcgca gtccggtgac   480
catcctcagt ccgctgccca gattcactga gtgggtgaca gtcacgttct tctccaggac   540
```

```
ggtatccact gtgtcggtgg agttgtttgc gtgatagccg atgcagatag tgtcagcgta    600
ggttgcggta aaagtacaca gcaggaccag cagtttggcc ttcat                   645

SEQ ID NO: 172          moltype = DNA   length = 1149
FEATURE                 Location/Qualifiers
misc_feature            1..1149
                        note = Synthetic
source                  1..1149
                        mol_type = other DNA
                        organism = synthetic construct
SEQUENCE: 172
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactgagt gaatctgggc agcggactga ggatggtcac ggactgcgct   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacctggtg   360
aattctgtca tcgaaaaaat gggcagcgga ggctccggaa cagacctgtc tgagctgctg   420
gtgctgctga tcaacgagcg gactctggat ttccacgata gcaacgtgaa gaatctgtat   480
gagaaggtca atcccagct gaagaacaat gccaaagaaa tcgggaatgg atgcttcgag   540
ttttaccata agtgcaacaa tgaatgtatg agtctgtga agaacggcac ttacgactat   600
cccaaatatt ctgaagagaa taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg gctgttcct gtttgatcac   780
gcagccgagg aatacgaaca tgcaaagaaa ctgatcattt tcctgaatga gaacaatgtg   840
cccgtccagc tgacttcaat cagcgccccc gaacataagt tcgagggcct gacccagatc   900
tttcagaaag cttacgaaca cgagcagcat atttccgaat ctatcaacaa tattgtggac   960
cacgccatta gagcaaagaa tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg cattgccaa gtccagaaaa  1140
agtgggtca                                                          1149

SEQ ID NO: 173          moltype = AA    length = 383
FEATURE                 Location/Qualifiers
REGION                  1..383
                        note = Synthetic
source                  1..383
                        mol_type = protein
                        organism = synthetic construct
SEQUENCE: 173
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNLV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 174          moltype = DNA   length = 1149
FEATURE                 Location/Qualifiers
misc_feature            1..1149
                        note = Synthetic
source                  1..1149
                        mol_type = other DNA
                        organism = synthetic construct
SEQUENCE: 174
tgacccactt ttctggact tggcaatgcc cttcacatac tgatctgcca ggtacaggcc     60
atgattctcg tttccaatca gttcgatttt atccaggatg tccttaaaca ggacctcctc   120
ctcgtgctgc tcggccacgt accactgcag aaagttgaag gtagcatgat ctttgctctt   180
aatggcgtgg tccacaatat tgttgataga ttccggaaata tgctgctcgt gttcgtaagc   240
tttctgaaag atctgggtca ggccctcgaa cttatgttca ggggcgctga ttgaagtcag   300
ctggacgggc acattgttct cattcaggaa aatgatcagt ttctttgcat gttcgtattc   360
ctcggctgcg tgatcaaaca ggaacagccc agcgccgtcc agtgagtgtg tataacacca   420
actagacata ctcatgtaca ggttggagct ctgcatctcc ttgttcacct gttcgttcag   480
cagcttgatg atgtcgcccc cactgtcaat tttctctcga ttcagcttac tctcttcaga   540
atatttggga tagtcgtaag tgccgttctt cacagactcc atacattcat tgttgcactt   600
atggtaaaac tcgaagcatc cattcccgat ttctttggca ttgttcttca gctgggatt   660
gaccttctca tacagattct tcacgttgct atcgtggaaa tccagagtcc gctcgttgat   720
cagcagcacc agcagctcag ccaggtctgt tccggagcct ccgctgccca ttttttcgat   780
gacagaattc accaggttag taatgccatt gattgcgttc tgtgtagact ctgatcagc    840
ggcgtagccg ctgccctgct cattctgatg gtggtagccg taccaccgt ccaccattcc    900
tgtccacccg ccctcaataa accctgcgat agcgccgaac agtcctcttg tttcccgctg   960
tgggatgttg cgcagtccgg tggacatcct cagtccgctg cccagattca ctgagtgggt  1020
gacagtcacg ttcttctcca ggacggtatc cactgtgtcg gtggagttgt ttgcgcgata  1080
gccgatgcag atagtgtcag cgtaggttgc ggtaaaagta cacagcagga ccagcagttt  1140
ggccttcat                                                           1149

SEQ ID NO: 175          moltype = DNA   length = 645
FEATURE                 Location/Qualifiers
```

```
misc_feature         1..645
                     note = Synthetic
source               1..645
                     mol_type = other DNA
                     organism = synthetic construct
SEQUENCE: 175
atgaaggcca aactgctggt cctgctgtgt acttttaccg caacctacgc tgacactatc   60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgac             645

SEQ ID NO: 176       moltype = AA   length = 215
FEATURE              Location/Qualifiers
REGION               1..215
                     note = Synthetic
source               1..215
                     mol_type = protein
                     organism = synthetic construct
SEQUENCE: 176
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNLV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKID                            215

SEQ ID NO: 177       moltype = DNA   length = 645
FEATURE              Location/Qualifiers
misc_feature         1..645
                     note = Synthetic
source               1..645
                     mol_type = other DNA
                     organism = synthetic construct
SEQUENCE: 177
gtcaattttc tctcgattca gcttactctc ttcagaatat ttgggatagt cgtaagtgcc   60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttcagcagc agcaccagca gctcagccag  240
gtctgttccg gagcctccgc tgcccatttt ttcgatgaca gaattcacca ggttagtaat  300
gccattgatt gcgttctgtg tagacttctg atcagcggcg tagccgctgc cctgctcatt  360
ctgatggtgg tagccgtacc acccgtccac cattcctgtc caccgccct caataaaccc   420
tgcgatagcg ccgaacagtc ctcttgtttc ccgctgctgg atgttgcgca gtccggtgac  480
catcctcagt ccgctgccca gattcactga gtgggtgaca gtcacgttct tctccagac  540
ggtatccact gtgtcggtgg agttgtttgc gtgatagccg atgcagatag tgtcagcgta  600
ggttgcggta aaagtacaca gcaggaccag cagtttggcc ttcat             645

SEQ ID NO: 178       moltype = DNA   length = 1149
FEATURE              Location/Qualifiers
misc_feature         1..1149
                     note = Synthetic
source               1..1149
                     mol_type = other DNA
                     organism = synthetic construct
SEQUENCE: 178
atgaaggcca aactgctggt cctgctgtgt acttttaccg caacctacgc tgacactatc   60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aacgcaatca atggcattac taacctggtg  360
aattctgtca tcgaaaaaat gggcagcgga ggctccggaa cagacctggc tgagctgctg  420
gtgctgctgc tgaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg ggcgacatc   660
atcaagctgc tgaacgaaca ggtgaacaag agatgcagag ctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt cgagggcct gacccagatc  900
tttcagaaag cttacgaaca cgagcagcat atttccgaat ctatcaacaa tattgtggac  960
cacgccatta gagacaaaga tcatgctacc ttcaactttc tgcagtggta cgtggccgag 1020
cagcacgagg aggaggtcct gtttaaggac atcctggata aaatcgaact gattgaaac  1080
gagaatcatg gcctgtacct ggcagatcag tatgtgaagg gcattgccaa gtccagaaaa 1140
agtgggtca                                                         1149
```

| SEQ ID NO: 179 | moltype = AA   length = 383 |
| --- | --- |
| FEATURE | Location/Qualifiers |
| REGION | 1..383 |
| | note = Synthetic |
| source | 1..383 |
| | mol_type = protein |
| | organism = synthetic construct |

SEQUENCE: 179

```
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNLV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383
```

| SEQ ID NO: 180 | moltype = DNA   length = 1149 |
| --- | --- |
| FEATURE | Location/Qualifiers |
| misc_feature | 1..1149 |
| | note = Synthetic |
| source | 1..1149 |
| | mol_type = other DNA |
| | organism = synthetic construct |

SEQUENCE: 180

```
tgacccactt tttctggact tggcaatgcc cttcacatac tgatctgcca ggtacaggcc     60
atgattctcg tttccaatca gttcgatttt atccaggatg tccttaaaca ggacctcctc    120
ctcgtgctgc tcggccacgt accactgcag aaagttgaag gtagcatgat ctttgctctt    180
aatggcgtgg tccacaatat tgttgataga ttcggaaata tgctgctcgt gttcgtaagc    240
tttctgaaaa atctgggtca ggccctcgaa cttatgttca ggggcgctga ttgaagtcag    300
ctggacgggc acattgttct cattcaggaa aatgatcagt ttcttttgca gttcgtattc    360
ctcggctgcg tgatcaaaca ggaacagccc agcgccgtcc agtgagtgtg tataaccaca    420
actagacata tccatgtaca ggttggagct ctgcatctcc ttgttcacct gttcgttcag    480
cagcttgatg atgtcgcccc cactgtcaat tttctctcga ttcagcttac tctcttcaga    540
atatttggga tagtcgtaag tgccgttctt cacagactcc atacattcat tgttgcactt    600
atggtaaaac tcgaagcatc cattcccgat ttctttggca ttgttcttca gctgggattt    660
gaccttctca tacagattct tcacgttgct atcgtggaaa tccagagtcc gctcgttcag    720
cagcagcacc agcagctcag ccaggtctgt tccggagcct ccgctgccca ttttttcgat    780
gacagaattc accaggttag taatgccatt gattgcgttc tgtgtagact tctgatcagc    840
ggcgtagccg ctgccctgct cattctgatg gtggtagcgc taccacccgt ccaccattcc    900
tgtccacccg ccctcaataa accctgcgat agcgccgaac agtcctcctg ttttcccgctg    960
tgggatgttg cgcagtccgg tgaccatcct cagtccgctg cccagattca ctgagtgggt   1020
gacagtcacg ttcttctcca ggacggtatc cactgtgtcg gtggagttgt ttgcgtgata   1080
gccgatgcag atagtgtcag cgtaggttgc ggtaaaagta cacagcagga ccagcagttt   1140
ggccttcat                                                           1149
```

| SEQ ID NO: 181 | moltype = DNA   length = 645 |
| --- | --- |
| FEATURE | Location/Qualifiers |
| misc_feature | 1..645 |
| | note = Synthetic |
| source | 1..645 |
| | mol_type = other DNA |
| | organism = synthetic construct |

SEQUENCE: 181

```
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactgg ggatggtcac cggactgcgc    180
aacatcccac agcgggaaac aagaggactg ttcggcgcta tcgcagggtt tattgagggc    240
gggtggacag gaatggtgga cggctggtac ggctaccacc ataacaatac ccagggcagc    300
ggctacgccg ctgatcagaa gtctacacag aacgcaatca atggcattac taacatggtg    360
aattctgtca tcgaaaaaat ggggcggaaa tggcactgga gctgacctgg tgagctgcag    420
gtgctgctgc tgaaccagtg gactctgctg ttccacgata gcaacgtgaa gaatctgtat    480
gagaaggtca atcccagctg aagaacaat gccaaagaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgac                    645
```

| SEQ ID NO: 182 | moltype = AA   length = 215 |
| --- | --- |
| FEATURE | Location/Qualifiers |
| REGION | 1..215 |
| | note = Synthetic |
| source | 1..215 |
| | mol_type = protein |
| | organism = synthetic construct |

SEQUENCE: 182

```
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKID                             215
```

| SEQ ID NO: 183 | moltype = DNA   length = 645 |
| --- | --- |

```
FEATURE                 Location/Qualifiers
misc_feature            1..645
                        note = Synthetic
source                  1..645
                        mol_type = other DNA
                        organism = synthetic construct
SEQUENCE: 183
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagccag   240
gtcagctcca gtgccatttc cgccatttt ttcgatgaca gaattcacca tgttagtaat   300
gccattgatt gcgttctgtg tagacttctg atcagcggcg tagccgctgc cctgggtatt   360
gttatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct ctcccaggac   540
ggtatccact gtgtcggtgg agttgtttgc gtgatagccg atgcagatag tgtcagcgta   600
ggttgcggta aaagtacaca gcaggaccag cagtttggcc ttcat                   645

SEQ ID NO: 184          moltype = DNA   length = 1149
FEATURE                 Location/Qualifiers
misc_feature            1..1149
                        note = Synthetic
source                  1..1149
                        mol_type = other DNA
                        organism = synthetic construct
SEQUENCE: 184
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac ggactgcgc   180
aacatcccac agcgggaaac aagaggactg ttcggcgcta tcgcaggggtt tattgagggc   240
gggtggacag gaatggtgga cgggtggtac ggctaccacc ataacaatac ccagggcagc   300
ggctacgccg ctgatcagaa gtcacacag aacgcaatca atggcattac taacatggtg   360
aattctgtca tcgaaaaaat ggggcggaaa tggcactgga ctgacctggc tgacgctgctg   420
gtgctgctgc tgaaccagtg gactctgctg ttccacgata gcaacgtgaa gaatctgtat   480
gagaaggtca atcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgaaca gcaccaacct gtacatgagt   720
atgtctagtt ggtgttatac acactcactg gacggcgctg gctgttcct gtttgatcac   780
gcagccgagg aatacgaaca tgcaaagaaa ctgatcattt tcctgaatga aaacaatgtg   840
cccgtccagc tgacttcaat cagcgcccct gaacataagt tcgagggcct gacccagatc   900
tttcagaaag cttacgaat cgagcagcat atttccagat ctatcaacaa tattgtggac   960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtca                                                           1149

SEQ ID NO: 185          moltype = AA   length = 383
FEATURE                 Location/Qualifiers
REGION                  1..383
                        note = Synthetic
source                  1..383
                        mol_type = protein
                        organism = synthetic construct
SEQUENCE: 185
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHNNTQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMNSTNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 186          moltype = DNA   length = 1149
FEATURE                 Location/Qualifiers
misc_feature            1..1149
                        note = Synthetic
source                  1..1149
                        mol_type = other DNA
                        organism = synthetic construct
SEQUENCE: 186
tgacccactt tttctggact tggcaatgcc cttcacatac tgatctgcca ggtacaggcc    60
atgattctcg tttccaatca gttcgatttt atccaggatg tccttaaaca ggacctcctc   120
ctcgtgctgc tcggcacgt accactgcag aaagttgaag gtagcatgat ctttgctctt   180
aatggcgtgg tccacaatat tgttgataga ttccggaaata tgctgctcgt gttcgtaagc   240
tttctgaaag atctgggtca ggccctcgaa cttatgttca ggggcgctga ttgaagtcag   300
ctggacgggc acattgttct cattcaggaa aatgatcagt ttctttgcat gttcgtattc   360
ctcggctgcg tgatcaaaca ggaacagccc agcgccgtcc agtgagtgtg tataacacca   420
```

```
actagacata ctcatgtaca ggttggtgct gttcatctcc ttgttcacct gttcgttcag   480
cagcttgatg atgtcgcccc cactgtcaat tttctctcga ttcagcttac tctcttcaga   540
atatttggga tagtcgtaag tgccgttctt cacagactcc atacattcat tgttgcactt   600
atggtaaaac tcgaagcatc cattcccgat tctttggca ttgttcttca gctgggattt    660
gaccttctca tacagattct tcacgttgct atcgtgacaa agcagagtcc actggttcag   720
cagcagcacc agcagctcag ccaggtcagc tccagtgcca tttccgccca ttttttcgat   780
gacagaattc accatgttag taatgccatt gattgcgttc tgtgtagact tctgatcagc   840
ggcgtagcc ctgccctggg tattgttatg gtggtagccg taccaccgt ccaccattcc     900
tgtccaccg ccctcaataa accctgcgat agcgccgaac agtcctcttg tttcccgctg    960
tgggatgttg cgcagtccgg tgaccatcct cagtccgctg cccagattca ctgagtgggt   1020
gacagtcacg ttcttctcca ggacggtatc cactgtgtcg gtggagttgt ttgcgtgata   1080
gccgatgcag atagtgtcag cgtaggttgc ggtaaaagta cacagcagga ccagcagttt   1140
ggccttcat                                                           1149
```

```
SEQ ID NO: 187           moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 187
atgaaggcca aactgctggt cctgctgtgt acttttaccg caacctacgc tgacactatc   60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc ataacaatac ccagggcagc   300
ggctacgccg ctgatcagaa gtctacacag aacgcaatca atggcattac taacatggtg   360
aattctgtca tcgaaaaaat gggcggaaat ggcactggag ctgacctggc tgagctgctg   420
gtgctgctgc tgaaccagtg gactctgctg ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645
```

```
SEQ ID NO: 188           moltype = AA   length = 215
FEATURE                  Location/Qualifiers
REGION                   1..215
                         note = Synthetic
source                   1..215
                         mol_type = protein
                         organism = synthetic construct
SEQUENCE: 188
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHNNTQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKID                              215
```

```
SEQ ID NO: 189           moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 189
gtcaattttc tctcgattca gcttactctc ttcagaatat ttgggatagt cgtaagtgcc   60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagccag   240
gtcagctcca gtgccatttc cgccccattt tcgatgaca gaattcacca tgttagtaat   300
gccattgatt gcgttctgtg tagacttctg atcagcggcg tagccgctgc cctgggtatt   360
gttatggtgg tagccgtacc accgtccac cattcctgtc caccgccct caataaaccc     420
tgcgatagcc cgaacagtc ctcttgtttc ccgctgtggg atgttgcgca gtccggtgac    480
catcctcagt ccgctgccca gattcactga gtgggtgaca gttcctctcc aggacggtatc 540
cactgtgtcg gtggagttgt ttgcgtgata gccgatgcag atagtgtcag cgtaggttgc   600
ggtaaaagta cacagcagga ccagcagttt ggccttcat                          645
```

```
SEQ ID NO: 190           moltype = DNA   length = 1149
FEATURE                  Location/Qualifiers
misc_feature             1..1149
                         note = Synthetic
source                   1..1149
                         mol_type = other DNA
                         organism = synthetic construct
SEQUENCE: 190
atgaaggcca aactgctggt cctgctgtgt acttttaccg caacctacgc tgacactatc   60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
```

```
gggtggacag gaatggtgga cgggtggtac ggctaccacc ataacaatac ccagggcagc    300
ggctacgccg ctgatcagaa gtctacacag aacgcaatca atggcattac taacatggtg    360
aattctgtca tcgaaaaaat gggcggaaat ggcactggag ctgacctggc tgagctgctg    420
gtgctgctgc tgaaccagtg gactctgctg ttccacgata gcaacgtgaa gaatctgtat    480
gagaaggtca aatcccagct gaagaacaat gccaaagaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgacagtgg gggcgacatc    660
atcaagctgc tgaacgaaca ggtgaacaag gagatgaaca gcaccaacct gtacatgagt    720
atgtctagtt ggtgttatac acactcactg gacggcgctg ggctgttcct gtttgatcac    780
gcagccgagg aatacgaaca tgcaaagaaa ctgatcattt tcctgaataa gaacaatgtg    840
cccgtcaacc tgacttcaat cagcgcccct gaacataagt tcgagggcct gacccagatc    900
tttcagaaag cttacgaaca cgagcagcat atttccgaat ctatcaacaa tattgtggac    960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg cattgccaa gtccagaaaa   1140
agtgggtca                                                           1149

SEQ ID NO: 191           moltype = AA   length = 383
FEATURE                  Location/Qualifiers
REGION                   1..383
                         note = Synthetic
source                   1..383
                         mol_type = protein
                         organism = synthetic construct
SEQUENCE: 191
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHNNTQGS GYAADQKSTQ NAINGITNMV    120
NSVIEKMGGN GTGADLAELL VLLLNQWTLL FHDSNVKNLY EKVKSQLKNN AKEIGNGCFE    180
FYHKCNNECM ESVKNGTYDY PKYSEESKLN REKIDSGGDI IKLLNEQVNK EMNSTNLYMS    240
MSSWCYTHSL DGAGLFLFDH AAEEYEHAKK LIIFLNENNV PVNLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383

SEQ ID NO: 192           moltype = DNA   length = 1149
FEATURE                  Location/Qualifiers
misc_feature             1..1149
                         note = Synthetic
source                   1..1149
                         mol_type = other DNA
                         organism = synthetic construct
SEQUENCE: 192
tgacccactt tttctggact tggcaatgcc cttcacatac tgatctgcca ggtacaggcc     60
atgattctcg tttccaatca gttcgatttt atccaggatg tccttaaaca ggacctcctc    120
ctcgtgctgc tcggccacgt accactgcag aaagttgaag gtagcatgat ctttgctctt    180
aatggcgtgg tccacaatat tgttgataga tccggaaata tgctgctcgt gttcgtaagc    240
tttctgaaag atctgggtca ggccctcgaa cttatgttca gggcgctga ttgaagtcag     300
gttgacgggc acattgttct cattcaggaa aatgatcagt ttctttgcat gttcgtattc    360
ctcggctgcg tgatcaaaca ggaacagccc agcgccgtcc agtgagtgtg tataacacca    420
actagacata ctccatgtaca ggttggtgct gttcatctcc ttgttcacct gttcgttcag    480
cagcttgatg atgtcgcccc cactgtcaat ttttctctcga ttcagcttac tctcttcaga   540
atatttggga tagtcgtaag tgccgttctt cacagactcc atacattcat tgttgcatt    600
atggtaaaac tcgaagcatc cattcccgat ttctttggca ttgttcttca gctgggattt    660
gaccttctca tacagattct tcacgttgct atcgtggaac agcagagtcc actggttcag    720
cagcagcacc agcagctcag ccaggtcagc tccagtgcca tttccgccca ttttttgat    780
gacagaattc accatgttag taatgccatt gattgcgttc tgtgtagact tctgatcagc    840
ggcgtagccg ctgccctggg tattgttatg tgtgtagccg taccaccgt ccaccattcc     900
tgtccacccg ccctcaataa accctgcgat agcgccgaac agtcctcttg tttcccgctg    960
tgggatgttg cgcagtccgg tgaccatcct cagtccgctg cccagattca ctgagtgggt   1020
gacagtcacg ttcttctcca ggacggtatc cactgtgtcg gtggagttgt ttgcgtgata   1080
gccgatgcag atagtgtcag cgtaggttgc ggtaaaagta cacagcagga ccagcagttt   1140
ggccttcat                                                           1149

SEQ ID NO: 193           moltype = DNA   length = 465
FEATURE                  Location/Qualifiers
source                   1..465
                         mol_type = unassigned DNA
                         organism = Aquifex aeolicus
SEQUENCE: 193
atgcaaattt acgaagggaa actaaccgct gaagggctga ggttcggtat agtggcttcc     60
aggttcaacc acgcactcgt ggatagacta gttgagggag ctatagactg catagtaaga    120
cacggggaa gggaagaaga cataacgctc gttagagtgc cgggctcctg ggaaattccc     180
gtggctgcgg gagagcttgc gagaaaaagag gacatagacg ctgtgatagc gatagagtt    240
ctaataaggg gggctactcc ccactttgat tacatagcct ctgaagtgtc aaagggctt     300
gcgaaccttt ccttagaact gagaaaaacc ataaccttac gtgttataac tgcggacacc    360
ttggagcagg cgatagaaag ggcgggaaca aagcacggga ataagggctg ggaagctgca    420
ctttccgcaa tagaaatggc aaacttattt aagagtctga gatga                    465

SEQ ID NO: 194           moltype = AA   length = 154
FEATURE                  Location/Qualifiers
```

| | | |
|---|---|---|
| source | 1..154 | |
| | mol_type = protein | |
| | organism = Aquifex aeolicus | |
| SEQUENCE: 194 | | |

```
MQIYEGKLTA EGLRFGIVAS RFNHALVDRL VEGAIDCIVR HGGREEDITL VRVPGSWEIP    60
VAAGELARKE DIDAVIAIGV LIRGATPHFD YIASEVSKGL ANLSLELRKP ITFGVITADT   120
LEQAIERAGT KHGNKGWEAA LSAIEMANLF KSLR                               154
```

| | | |
|---|---|---|
| SEQ ID NO: 195 | moltype = DNA  length = 465 | |
| FEATURE | Location/Qualifiers | |
| source | 1..465 | |
| | mol_type = unassigned DNA | |
| | organism = Aquifex aeolicus | |
| SEQUENCE: 195 | | |

```
tcatctcaga ctcttaaata agtttgccat ttctattgcg gaaagtgcag cttcccagcc    60
cttattcccg tgctttgttc ccgccctttc tatcgcctgc tccaaggtgt ccgcagttat   120
aacaccgaag gttatgggtt ttctcagttc taaggaaagg ttcgcaagcc cttttgacac   180
ttcagaggct atgtaatcaa agtggggagt agccccccTT attagaactc ctatcgtat   240
cacagcgtct atgtcctctt ttctcgcaag ctctcccgca gccacgggaa tttcccagga   300
gcccggcact ctaacgagcg ttatgtcttc ttcccttccc ccgtgtctta ctatgcagtc   360
tatagctccc tcaactagtc tatccacgag tgcgtggttg aacctggaag ccactatacc   420
gaacctcagc ccttcagcgg ttagtttccc ttcgtaaatt tgcat                   465
```

| | | |
|---|---|---|
| SEQ ID NO: 196 | moltype = DNA  length = 642 | |
| FEATURE | Location/Qualifiers | |
| misc_feature | 1..642 | |
| | note = Synthetic | |
| source | 1..642 | |
| | mol_type = other DNA | |
| | organism = synthetic construct | |
| SEQUENCE: 196 | | |

```
atgaaggcca agctgctggt gctcctgtgc accttcaccg ccacctacgc cgacaccatc    60
tgcatcggct accacgccaa caacagcacc gacaccgtga ataccgtgct ggaaaagaac   120
gtgaccgtga cccacagcgt gaacctgggc agcggcctgc ggatggtgac aggcctgcgg   180
aacatccccc agagagagac acggggcctg ttcggcgcca ttgccggctt tatcgagggc   240
ggctggaccg gcatggtgga cggtggtac ggctaccacc accagaacga gcagggcagc   300
ggctacgccg ccgaccagaa gtccacccag aacgccatca acggcatcac caacatggtg   360
aacagcgtga tcgagaagat gggctccggc ggcagcggca ccgatctgc tgaactgctg   420
gtcctgctgc tgaacgagcg gaccctggac ttccacgaca gcaacgtgaa gaacctgtac   480
gagaaagtga agtcccagct gaagaacaac gccaaagaga tcggcaacgg ctgcttcgag   540
ttctaccaca gtgcaacaa cgagtgcatg gaaagcgtga agaacggcac ctacgactac   600
cccaagtaca gcgaggaaag caagctgaac cgcgagggag gc                      642
```

| | | |
|---|---|---|
| SEQ ID NO: 197 | moltype = AA  length = 214 | |
| FEATURE | Location/Qualifiers | |
| REGION | 1..214 | |
| | note = Synthetic | |
| source | 1..214 | |
| | mol_type = protein | |
| | organism = synthetic construct | |
| SEQUENCE: 197 | | |

```
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGG                               214
```

| | | |
|---|---|---|
| SEQ ID NO: 198 | moltype = DNA  length = 642 | |
| FEATURE | Location/Qualifiers | |
| misc_feature | 1..642 | |
| | note = Synthetic | |
| source | 1..642 | |
| | mol_type = other DNA | |
| | organism = synthetic construct | |
| SEQUENCE: 198 | | |

```
gcctccctcg cggttcagct tgctttcctc gctgtacttg gggtagtcgt aggtgccgtt    60
cttcacgctt tccatgcact cgttgttgca cttgtggtag aactcgaagc agccgttgcc   120
gatctctttg gcgttgttct tcagctggga cttcactttc tcgtacaggt tcttcacgtt   180
gctgtcgtga aagtccaggg tccgctcgtt cagcagcagg accagcagtt cagccagatc   240
ggtgccgctg ccgccggagc ccatcttctc gatcacgctg ttcaccatgt tggtgatgcc   300
gttgatggcg ttctgggtgg acttctggtc ggcggcgtag ccgctgccct gctcgttctg   360
gtggtggtag ccgtaccacc cgtccaccat gccggtccag ccgccctcga taaagccggc   420
aatggcgccg aacaggcccc gtgtctctct ctggggatg ttccgcaggc ctgtcaccat   480
ccgcaggccg ctgcccaggt tcacgctgtg ggtcacggtc acgttctttt ccagcacggt   540
atccacggtg tcggtgctgt tgttggcgtg gtagccgatg cagatggtgt cggcgtaggt   600
ggcggtgaag gtgcacagga gcaccagcag cttggccttc at                      642
```

```
SEQ ID NO: 199            moltype = DNA  length = 1104
FEATURE                   Location/Qualifiers
misc_feature              1..1104
                          note = Synthetic
source                    1..1104
                          mol_type = other DNA
                          organism = synthetic construct
SEQUENCE: 199
atgaaggcca agctgctggt gctcctgtgc accttcaccg ccacctacgc cgacaccatc    60
tgcatcggct accacgccaa caacagcacc gacaccgtgg ataccgtgct ggaaaagaac   120
gtgaccgtga cccacagcgt gaacctgggc agcggcctgc ggatggtgac aggcctgcgg   180
aacatccccc agagagagac acggggcctg ttcggcgcca ttgccggctt tatcgagggc   240
ggctggaccg gcatggtgga cgggtggtac ggctaccacc agcaggggag gcagggcagc   300
ggctacgccg ccgaccagaa gtccacccag aacgccatca acggcatcac caacatggtg   360
aacagcgtga tcgagaagat gggctccggc ggcagcggca ccgatctggc tgaactgctg   420
gtcctgctgc tgaacgagcg gaccctggac ttccacgaca gcaacgtgaa gaacctgtac   480
gagaaagtga gtcccagct gaagaacaac gccaaagaga tcggcaacgg ctgcttcgag   540
ttctaccaca gtgcaacaa cgagtgcatg gaaagcgtga gaacggcac ctacgactac   600
cccaagtaca gcgaggaaag caagctgaac cgcgagggag gcatgcaaat ctacgagggc   660
aagctgacag ccgagggcct gagattcggc atcgtggcca gccggttcaa ccacgccctg   720
gtggacagac tggtggaagg cgccatcgac tgcatccgtc ggcacggcgg cagagaagag   780
gacatcaccc tggtccgcgt gcccggcagc tgggaaattc ctgtggctgc cggcgagctg   840
gcccggaaag aggatatcga cgccgtcatc gccatcggcg tgctgatcag aggcgccacc   900
cccacttcg actatatcgc cagcgaggtg tccaaggggc tggccaacct gagcctggaa   960
ctgcggaagc ccatcacctt cggagtgatc accgccgaca ccctgaaaca ggccatcgag  1020
agagccggca ccaagcacgg caacaaggga tgggaagccg ccctgagcgc catcgagatg  1080
gccaatctgt tcaagagcct gcgc                                          1104

SEQ ID NO: 200            moltype = AA  length = 368
FEATURE                   Location/Qualifiers
REGION                    1..368
                          note = Synthetic
source                    1..368
                          mol_type = protein
                          organism = synthetic construct
SEQUENCE: 200
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGGMQIYEG KLTAEGLRFG IVASRFNHAL   240
VDRLVEGAID CIVRHGGREE DITLVRVPGS WEIPVAAGEL ARKEDIDAVI AIGVLIRGAT   300
PHFDYIASEV SKGLANLSLE LRKPITFGVI TADTLEQAIE RAGTKHGNKG WEAALSAIEM   360
ANLFKSLR                                                            368

SEQ ID NO: 201            moltype = DNA  length = 1104
FEATURE                   Location/Qualifiers
misc_feature              1..1104
                          note = Synthetic
source                    1..1104
                          mol_type = other DNA
                          organism = synthetic construct
SEQUENCE: 201
gcgcaggctc ttgaacagat tggccatctc gatggcgctc agggcggctt cccatcccctt    60
gttgccgtga ttggtgccgg ctctctcgat ggcctgttcc agggtgtcgg cggtgatcac   120
tccggaaggtg atgggcttcc gcagttccag gctcaggttg gccaggccct tggacacctt   180
gctggcgata tagtcgaagt ggggggtggc gcctctgatc agcacgccga tggcgatgac   240
ggcgtcgata tcctctttcc gggccagctc gccggcagcc acaggaattt cccagctgcc   300
gggcacgcgg accagggtga tgtcctcttc tctgccgccg tgccgcacga tgcagtcgat   360
ggcgccttcc accagtctgt ccaccagggc gtggttgaac cggctggcca cgatgccgaa   420
tctcaggccc tcggctgtca gcttgccctc gtagatttga atgcctccct ggcggttgta   480
cttgctttcc tcgctgtact tggggtagtc gtaggtgccg ttcttcacgc tttccatgca   540
ctcgttgttg cacttgtggt agaactcgaa gcagccgttg ccgatctctt tggcgttgtt   600
cttcagctgg gacttcactt tctcgtacag gttcttcacg ttgctgtcgt ggaagtccga   660
ggtccgctcg ttcagcagca ggaccagcag ttcagccaga tcggtgccgc tgccgccgga   720
gcccatcttc tcgatcacgc tgttcaccat gttggtgatg ccgtcgatgg cgttctggt   780
ggacttctgg tcggccggcgt agccgctgcc ctgctgctgt ggtggtggt agccgtacca   840
cccgtccacc atgccggtcc agccgccctc gataaagccg gcaatggcgc cgaacaggcc   900
ccgtgtctct ctctggggga tgttccgcag gcctgtcacc atccgcaggc cgctgcccag   960
gttcacgctg tgggtcacgg tcacgttctt ttccagcacg gtatccacgg tgtcggtgct  1020
gttgttggcg tggtagccga tgcagatggt gtcggcgtag gtgtgcggtga aggtgcacag  1080
gagcaccagc agcttggcct tcat                                          1104

SEQ ID NO: 202            moltype = DNA  length = 645
FEATURE                   Location/Qualifiers
misc_feature              1..645
                          note = Synthetic
```

```
source                  1..645
                        mol_type = other DNA
                        organism = synthetic construct
SEQUENCE: 202
atgaaggcca agctgctggt gctcctgtgc accttcaccg ccacctacgc cgacaccatc   60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca cggcatcac caacatggtg   360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga gaacggcac ctacgactac   600
cccaagtaca gcgaggaaag caagctgaac cgcgagggaa gcggc               645

SEQ ID NO: 203          moltype = AA  length = 215
FEATURE                 Location/Qualifiers
REGION                  1..215
                        note = Synthetic
source                  1..215
                        mol_type = protein
                        organism = synthetic construct
SEQUENCE: 203
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGSG                             215

SEQ ID NO: 204          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 204
gccgcttccc tcgcggttca gcttgctttc ctcgctgtac ttggggtagt cgtaggtgcc   60
gttcttcacg ctttccatgc actcgttgtt gcacttgtgg tagaactcga agcagcgtt   120
gccgatctct ttggcgttgt tcttcagctg gacttcact ttctcgtaca ggttcttcac   180
gttgctgtcg tggaagtcca gggtccgctc gttcagcagc aggaccagca gttcagccag  240
atcggtgccg ctgccgccgg agcccatctt ctcgatcacg ctgttcacca tgttggtgat  300
gccgttgatg gcgttctggg tggacttctg gtcggcggcg tagccgtcgc cctgctcgtt  360
ctggtggtgg tagccgtacc acccgtccac catgccggtc cagccgccct cgataaagcc  420
ggcaatggcg ccgaacaggc cccgtgtctc tctgggggg atgttccgca ggcctgtcac   480
catccgcagg ccgctgccca ggttcacgct gtgggtcacg gtcacgttct tttccagcac  540
ggtatccacg gtgtcggtgc tgttgttggc gtggtagccg atgcagatgg tgtcggcgta  600
ggtggcggtg aaggtgcaca ggagcaccag cagcttggcc ttcat               645

SEQ ID NO: 205          moltype = DNA  length = 1107
FEATURE                 Location/Qualifiers
misc_feature            1..1107
                        note = Synthetic
source                  1..1107
                        mol_type = other DNA
                        organism = synthetic construct
SEQUENCE: 205
atgaaggcca agctgctggt gctcctgtgc accttcaccg ccacctacgc cgacaccatc   60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca cggcatcac caacatggtg   360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca agtgcaacaa cgagtgcatg gaaagcgtga gaacggcac ctacgactac   600
cccaagtaca gcgaggaaag caagctgaac cgcgagggaa gcggcatgca aatctacgag  660
gcaagctga cagccgaggg cctgagattc ggcatcgtgg ccagccggtt caaccacgcc   720
ctggtggaca gactggtgga aggcgccatc gactgcatcg tgcggcacgg cggcagagaa  780
gaggacatca ccctggtccg cgtgcccggc agctgggaaa ttcctgtggc tgccggcgag  840
ctggcccgga agaggatat cgacgccgtc atcgccatcg cgtgctgat cagaggcgcc   900
accccccact tcgactatat cgccagcgag gtgtccaagg gcctgccaa cctgagcctg  960
gaactgcgga gcccatcac cttcggagtg ctcagcaggc tatccgccg cacccctgga acaggccatc  1020
gagagagccg gcaccaagca cggcaacaag ggatgggaag ccgcccctga gcgccatcgag 1080
atggccaatc tgttcaagag cctgcgc                                    1107

SEQ ID NO: 206          moltype = AA  length = 369
FEATURE                 Location/Qualifiers
```

```
REGION                        1..369
                              note = Synthetic
source                        1..369
                              mol_type = protein
                              organism = synthetic construct
SEQUENCE: 206
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGSGMQIYE GKLTAEGLRF GIVASRFNHA   240
LVDRLVEGAI DCIVRHGGRE EDITLVRVPG SWEIPVAAGE LARKEDIDAV IAIGVLIRGA   300
TPHFDYIASE VSKGLANLSL ELRKPITFGV ITADTLEQAI ERAGTKHGNK GWEAALSAIE   360
MANLFKSLR                                                          369

SEQ ID NO: 207                moltype = DNA  length = 1107
FEATURE                       Location/Qualifiers
misc_feature                  1..1107
                              note = Synthetic
source                        1..1107
                              mol_type = other DNA
                              organism = synthetic construct
SEQUENCE: 207
gcgcaggctc ttgaacagat tggccatctc gatggcgctc agggcggctt cccatccctt    60
gttgccgtgc ttggtgccgg ctctctcgat ggcctgttcc agggtgtcgg cggtgatcac   120
tccgaaggtg atgggcttcc gcagttccag gctcaggttg ccaggccct tggacacctc   180
gctggcgata tagtcgaagt gggggtggc cctctgatc agcacgccga tggcgatgac   240
ggcgtcgata tcctctttcc gggcagctc gccggcagcc acaggaattt cccagctgcc   300
gggcacgcgg accagggtga tgtcctcttc tctgccgccg tgccgcacga tgcagtcgat   360
ggcgccttcc accagtctgt ccaccagggc gtggttgaac cggctggcca cgatgccgaa   420
tctcaggccc tcggctgtca gcttgccctc gtagatttga atgccgcttc cctcgcggtt   480
cagcttgctt cctcgctgt acttgggta gtcgtaggtg ccgttcttca cgcttttcat   540
gcactcgttg ttgcacttgt ggtagaactc gaagcagccg ttgccgatct ctttggcgtt   600
gttcttcagc tgggacttca ctttctcgta caggttcttc acgttgctgt cgtggaagtc   660
cagggtccgc tcgttcagca gcaggaccag cagttcagcc agatcggtgc cgctgccgcc   720
ggagcccatc ttctcgatca cgctgttcac catgttggtg atgccgttga tggcgttctg   780
ggtggacttc tggtcggcgg cgtagccgct gccctgctcg ttctggtggt ggtagccgta   840
ccacccgtcc accatgccgg tccagccgcc ctcgataaag ccggcaatgg cgccgaacag   900
gccccgtgtc tctctctggg ggatgttccg caggcctgtc accatccgca ggccgctgcc   960
caggttcacg ctgtgggtca cggtcacgtt cttttccagc acggtatcca cggtgtcggt  1020
gctgttgttg gcgtggtagc cgatgcagat ggtgtcggcg taggtggcgg tgaaggtgca  1080
caggagcacc agcagcttgg ccttcat                                      1107

SEQ ID NO: 208                moltype = DNA  length = 645
FEATURE                       Location/Qualifiers
misc_feature                  1..645
                              note = Synthetic
source                        1..645
                              mol_type = other DNA
                              organism = synthetic construct
SEQUENCE: 208
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccaa gcatccagag cagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaaccagtg gactctgctg ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645

SEQ ID NO: 209                moltype = AA  length = 215
FEATURE                       Location/Qualifiers
REGION                        1..215
                              note = Synthetic
source                        1..215
                              mol_type = protein
                              organism = synthetic construct
SEQUENCE: 209
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNQWTLL FHDSNVKNLY EKVKSQLKNN AKEIGNGCFE   180
FYHKCNNECM ESVKNGTYDY PKYSEESKLN REKID                              215

SEQ ID NO: 210                moltype = DNA  length = 645
FEATURE                       Location/Qualifiers
misc_feature                  1..645
                              note = Synthetic
```

```
source                  1..645
                        mol_type = other DNA
                        organism = synthetic construct
SEQUENCE: 210
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagccag   240
gtctgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctctgctctg gatgcttggg atgttgcgca gtccggtgac   480
catcctcagt ccgctgccca gattcactga gtgggtgaca gtcacgttct ctccaggac    540
ggtatccact gtgtcggtgg agttgtttgc gtgatagccg atgcagatag tgtcagcgta   600
ggttgcggta aaagtacaca gcaggaccag cagtttggac ttcat                   645

SEQ ID NO: 211          moltype = DNA   length = 1149
FEATURE                 Location/Qualifiers
misc_feature            1..1149
                        note = Synthetic
source                  1..1149
                        mol_type = other DNA
                        organism = synthetic construct
SEQUENCE: 211
atgaaggcca aactgctggt cctgctgtgt acttttaccg caacctacgc tgacactatc     60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccaa gcatccagag cagaggactg ttcggcgcta tcgcagggtt tattgagggc   240
gggtggacag gaatggtgga cggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaaccagtg gactctgctg ttccacgata gcaacgtgaa gaatctgtat   480
gagaaggtca atcccagct gaagaacaat gccaaagaaa tcgggaatgg atgcttcgag   540
ttttaccata agtgcaacaa tgaatgtatg agtctgtga agaacggcac ttacgactat   600
cccaaatatt ctgaagagag taagctgaat cgagagaaaa ttgacagtgg ggcgacatc    660
atcaagctgc tgaacgaaca ggtgaacaag gagatgcaga gctccaacct gtacatgagt   720
atgtctagtt ggtgttatac acactcactg gacggcgctg gctgttcct gtttgatcac    780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta gagcaaagat catgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg cattgccaa gtccagaaaa   1140
agtgggtca                                                          1149

SEQ ID NO: 212          moltype = AA    length = 383
FEATURE                 Location/Qualifiers
REGION                  1..383
                        note = Synthetic
source                  1..383
                        mol_type = protein
                        organism = synthetic construct
SEQUENCE: 212
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 213          moltype = DNA   length = 1149
FEATURE                 Location/Qualifiers
misc_feature            1..1149
                        note = Synthetic
source                  1..1149
                        mol_type = other DNA
                        organism = synthetic construct
SEQUENCE: 213
tgacccactt tttctggact tggcaatgcc cttcacatac tgatctgcca ggtacaggcc     60
atgattctcg tttccaatca gttcgatttt atccaggatg tccttaaaca ggacctcctc   120
ctcgtgctgc tcggccacgt accactgcag aaagttgaag gtagcatgat ctttgctctt   180
aatggcgtgt ccacaatat tgttgataga ttcggaaata tgctgctcgt gttcgtaagc   240
tttctgaaag atctgggtca ggccctcgaa ctttatgttca ggggcgctga ttgaagtcga   300
ctggacgggc acattgttct cattcaggaa aatgatcagt ttctttgcat gttcgtattc   360
ctcggctgcg tgatcaaaca ggaacagccc agcgccgtcc agtgagtgtg taacaccac    420
actagacata ctcatgtaca ggttggagct ctgcatctcc ttgttcacct gttcgttcag   480
cagcttgatg atgtcgcccc cactgtcaat tttctctcga ttcagcttac tctcttcaga   540
atatttggga tagtcgtaag tgccgttctt cacagactcc atacattcat tgttgcactt   600
```

```
atggtaaaac tcgaagcatc cattcccgat ttctttggca ttgttcttca gctgggattt    660
gaccttctca tacagattct tcacgttgct atcgtggaac agcagagtcc actggttcag    720
cagcagcacc agcagctcag ccaggtctgt tccggagcct ccgctgccca ttttttcgat    780
gacagaattc accatgttag taatgccatt gattgcgttc tgtgtagact tctgatcagc    840
ggcgtagccg ctgccctgct cattctgatg gtggtagccg taccacccgt ccaccattcc    900
tgtccacccg ccctcaataa accctgcgat agcgccgaac agtcctctgc tctggatgct    960
tgggatgttg cgcagtccgg tgaccatcct cagtccgctg cccagattca ctgagtgggt   1020
gacagtcacg ttcttctcca ggacggtatc cactgtgtcg gtggagttgt ttgcgtgata   1080
gccgatgcag atagtgtcag cgtaggttgc ggtaaaagta cacagcagga ccagcagttt   1140
ggccttcat                                                            1149

SEQ ID NO: 214          moltype = AA  length = 215
FEATURE                 Location/Qualifiers
REGION                  1..215
                        note = Synthetic
source                  1..215
                        mol_type = protein
                        organism = synthetic construct
SEQUENCE: 214
MKAKLLVLLC TFTATYADTL CIGYHANNST DTVDTVLEKN VTVTHSVNLG SGLRLATGLR     60
NIPSIQSRGL FGAIAGFIEG GWTGMVDGWY GYHHQNEQGS GYAADLKSTQ NAIDEITNMV   120
NSVIEKMGSS GSGTDLAELL VLLLNQWTLL YHDSNVKNLY EKVRSQLKNN AKEIGNGCFE   180
FYHKCDNTCM ESVKNGTYDY PKYSEEAKLN REKID                              215

SEQ ID NO: 215          moltype = AA  length = 383
FEATURE                 Location/Qualifiers
REGION                  1..383
                        note = Synthetic
source                  1..383
                        mol_type = protein
                        organism = synthetic construct
SEQUENCE: 215
MKAKLLVLLC TFTATYADTL CIGYHANNST DTVDTVLEKN VTVTHSVNLG SGLRLATGLR     60
NIPSIQSRGL FGAIAGFIEG GWTGMVDGWY GYHHQNEQGS GYAADLKSTQ NAIDEITNMV   120
NSVIEKMGSS GSGTDLAELL VLLLNQWTLL YHDSNVKNLY EKVRSQLKNN AKEIGNGCFE   180
FYHKCDNTCM ESVKNGTYDY PKYSEEAKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 216          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 216
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca atggcattac taacatggtg    360
aattctgtca tcgaaaaaat gggcagcgga ggctccggaa catacaacgc tgagctgctg    420
gtgctgctgc tgaacgagcg gactctggat ttccacgata gcaacgtgaa gaatctgtat    480
gagaaggtca aatcccagct gaagaacaat gccaaagaaa tcgggaatgg atgcttcgag    540
ttttaccata gtgcaacaa tgaatgtatg gagtctgtga agaacggcac ttacgactat    600
cccaaatatt ctgaagagag taagctgaat cgagagaaaa ttgac                    645

SEQ ID NO: 217          moltype = AA  length = 215
FEATURE                 Location/Qualifiers
REGION                  1..215
                        note = Synthetic
source                  1..215
                        mol_type = protein
                        organism = synthetic construct
SEQUENCE: 217
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNMV   120
NSVIEKMGSS GSGTYNAELL VLLLNERTLD FHDSNVKNLY EKVKSQLKNN AKEIGNGCFE   180
FYHKCNNECM ESVKNGTYDY PKYSEESKLN REKID                              215

SEQ ID NO: 218          moltype = DNA  length = 645
FEATURE                 Location/Qualifiers
misc_feature            1..645
                        note = Synthetic
```

```
source                    1..645
                          mol_type = other DNA
                          organism = synthetic construct
SEQUENCE: 218
gtcaatttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaaatcca gagtccgctc gttcagcagc agcaccagca gctcagcgtt   240
gtatgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct tctccaggac   540
ggtatccact gtgtcggtgg agttgtttgc gtgatagccg atgcagatag tgtcagcgta   600
ggttgcggta aaagtacaca gcaggaccag cagtttggcc ttcat                   645

SEQ ID NO: 219            moltype = DNA  length = 1149
FEATURE                   Location/Qualifiers
misc_feature              1..1149
                          note = Synthetic
source                    1..1149
                          mol_type = other DNA
                          organism = synthetic construct
SEQUENCE: 219
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aaggaggctg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa catacaacgc tgagctgctg   420
gtgctgctgc tgaacgagcg gactctggat ttccacgata gcaacgtgaa gaatctgtat   480
gagaaggtca atccccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg gctgttcct gtttgatcac   780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta gagcaaagat catgctaccc tcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtca                                                          1149

SEQ ID NO: 220            moltype = AA  length = 383
FEATURE                   Location/Qualifiers
REGION                    1..383
                          note = Synthetic
source                    1..383
                          mol_type = protein
                          organism = synthetic construct
SEQUENCE: 220
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTYNAELL VLLLNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 221            moltype = DNA  length = 1151
FEATURE                   Location/Qualifiers
misc_feature              1..1151
                          note = Synthetic
source                    1..1151
                          mol_type = other DNA
                          organism = synthetic construct
SEQUENCE: 221
rctgacccac tttttctgga cttggcaatg cccttcacat actgatctgc caggtacagg    60
ccatgattct cgtttccaat cagttcgatt ttatccagga tgtccttaaa caggacctcc   120
tcctcgtgct gctcggccac gtaccactgc agaaagttga aggtagcatg atctttgctc   180
ttaatggcgt ggtccacaat attgttgata gattcggaaa tatgctgctc gtgttcgtaa   240
gctttctgaa agatctgggt caggccctcg aacttatgtt cagggggcgct gattgaagtc   300
agctggacgg gcacattgtt ctcattcagg aaaatgatca gtttctttgc atgttcgtat   360
tcctcggctg cgtgatcaaa caggaacagc cagcgccgt ccagtgagtg tgtataaaac   420
caactagaca tactcatgta caggttggag ctctgcatct ccttgttcac ctgttcgttc   480
agcagcttga tgatgtcgcc cccactgtca atttctctc gattcagctt actctcttca   540
gaatatttgg atagtcgta agtgccgttc ttcagagact ccatacattc attgttcac    600
```

```
ttatggtaaa actcgaagca tccattcccg atttctttgg cattgttctt cagctgggat    660
ttgaccttct catacagatt cttcacgttg ctatcgtgga aatccagagt ccgctcgttc    720
agcagcagca ccagcagctc agcgttgtat gttccggagc ctccgctgcc cattttttcg    780
atgcacagaa tcaccatgtt agtaatgcca ttgattgcgt tctgtgtaga cttctgatca    840
gcggcgtagc cgctgccctg ctcattctga tggtggtagc cgtaccaccc gtccaccatt    900
cctgtccacc cgccctcaat aaaccctgcg atagcgccga acagtcctct tgtttcccgc    960
tgtgggatgt tgcgcagtcc ggtgaccatc ctcagtccgc tgcccagatt cactgagtgg   1020
gtgacagtca cgttcttctc caggacggta tccactgtgt cggtggagtt gtttgcgtga   1080
tagccgatgc agatagtgtc agcgtaggtt gcggtaaaag tacacagcag gaccagcagt   1140
ttggccttca t                                                        1151

SEQ ID NO: 222          moltype = AA  length = 215
FEATURE                 Location/Qualifiers
REGION                  1..215
                        note = Synthetic
source                  1..215
                        mol_type = protein
                        organism = synthetic construct
SEQUENCE: 222
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNMV    120
NSVIEKMGSG GSGTDLAELL VLLLNERTLD FHDSNVKNLY EKVKSQLKNN AKEIGNGCFE    180
FYHKCNNECM ESVKNGTYDY PKYSEESKLN REKID                               215

SEQ ID NO: 223          moltype = AA  length = 383
FEATURE                 Location/Qualifiers
REGION                  1..383
                        note = Synthetic
source                  1..383
                        mol_type = protein
                        organism = synthetic construct
SEQUENCE: 223
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNMV    120
NSVIEKMGSG GSGTDLAELL VLLLNERTLD FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383

SEQ ID NO: 224          moltype = AA  length = 215
FEATURE                 Location/Qualifiers
REGION                  1..215
                        note = Synthetic
source                  1..215
                        mol_type = protein
                        organism = synthetic construct
SEQUENCE: 224
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNIV    120
NSVIEKMGSG GSGTDLAELL VLLINERTLD FHDSNVKNLY EKVKSQLKNN AKEIGNGCFE    180
FYHKCNNECM ESVKNGTYDY PKYSEESKLN REKID                               215

SEQ ID NO: 225          moltype = AA  length = 383
FEATURE                 Location/Qualifiers
REGION                  1..383
                        note = Synthetic
source                  1..383
                        mol_type = protein
                        organism = synthetic construct
SEQUENCE: 225
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNIV    120
NSVIEKMGSG GSGTDLAELL VLLINERTLD FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383

SEQ ID NO: 226          moltype = AA  length = 215
FEATURE                 Location/Qualifiers
REGION                  1..215
                        note = Synthetic
source                  1..215
                        mol_type = protein
                        organism = synthetic construct
SEQUENCE: 226
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNLV    120
```

```
NSVIEKMGSG GSGTDLAELL VLLINERTLD FHDSNVKNLY EKVKSQLKNN AKEIGNGCFE    180
FYHKCNNECM ESVKNGTYDY PKYSEESKLN REKID                              215

SEQ ID NO: 227          moltype = AA  length = 383
FEATURE                 Location/Qualifiers
REGION                  1..383
                        note = Synthetic
source                  1..383
                        mol_type = protein
                        organism = synthetic construct
SEQUENCE: 227
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNLV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 228          moltype = AA  length = 215
FEATURE                 Location/Qualifiers
REGION                  1..215
                        note = Synthetic
source                  1..215
                        mol_type = protein
                        organism = synthetic construct
SEQUENCE: 228
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNLV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKID                              215

SEQ ID NO: 229          moltype = AA  length = 383
FEATURE                 Location/Qualifiers
REGION                  1..383
                        note = Synthetic
source                  1..383
                        mol_type = protein
                        organism = synthetic construct
SEQUENCE: 229
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNLV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 230          moltype = AA  length = 215
FEATURE                 Location/Qualifiers
REGION                  1..215
                        note = Synthetic
source                  1..215
                        mol_type = protein
                        organism = synthetic construct
SEQUENCE: 230
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLMNERTLD FHDSNVKNLY EKVKSQLKNN AKEIGNGCFE   180
FYHKCNNECM ESVKNGTYDY PKYSEESKLN REKID                              215

SEQ ID NO: 231          moltype = AA  length = 383
FEATURE                 Location/Qualifiers
REGION                  1..383
                        note = Synthetic
source                  1..383
                        mol_type = protein
                        organism = synthetic construct
SEQUENCE: 231
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLMNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 232          moltype = AA  length = 215
FEATURE                 Location/Qualifiers
```

```
REGION                      1..215
                            note = Synthetic
source                      1..215
                            mol_type = protein
                            organism = synthetic construct
SEQUENCE: 232
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNQV   120
NSVIEKMGSG GSGTDLAELL VLLQNERTLD FHDSNVKNLY EKVKSQLKNN AKEIGNGCFE   180
FYHKCNNECM ESVKNGTYDY PKYSEESKLN REKID                              215

SEQ ID NO: 233              moltype = AA  length = 383
FEATURE                     Location/Qualifiers
REGION                      1..383
                            note = Synthetic
source                      1..383
                            mol_type = protein
                            organism = synthetic construct
SEQUENCE: 233
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNQV   120
NSVIEKMGSG GSGTDLAELL VLLQNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 234              moltype = DNA  length = 645
FEATURE                     Location/Qualifiers
misc_feature                1..645
                            note = Synthetic
source                      1..645
                            mol_type = other DNA
                            organism = synthetic construct
SEQUENCE: 234
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca ccaactcaac taatctgggc agcggactga ggatggtcac cggactgcgc   180
aacatcccac agcgggaaac aagaggactg ttcggcgcta tcgcagggtt tattgaggcg   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat ttccacgata gcaacgtgaa gaatctgtat   480
gagaaggtca aatcccagct gaagaacaat gccaagaaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645

SEQ ID NO: 235              moltype = AA  length = 215
FEATURE                     Location/Qualifiers
REGION                      1..215
                            note = Synthetic
source                      1..215
                            mol_type = protein
                            organism = synthetic construct
SEQUENCE: 235
MKAKLLVLLC TFTATYADTI CIGYHANNST DTVDTVLEKN VTVTNSTNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKID                              215

SEQ ID NO: 236              moltype = DNA  length = 645
FEATURE                     Location/Qualifiers
misc_feature                1..645
                            note = Synthetic
source                      1..645
                            mol_type = other DNA
                            organism = synthetic construct
SEQUENCE: 236
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct tggcattgtt tcttcagctg gatttgacc ttctcataca gattcttcac    180
gttgctatcg tggaaatcca gagtccgctc gttcagcagc agcaccagca gctcagccag   240
gtctgttccg gagcctccgc tgcccatttt tcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattagttga gttggtgaca gtcacgttct tctccaggac   540
ggtatccact gtgtcggtgg agttgttgc gtgatagccg atgcagatag tgtcagcgta   600
ggttgcggta aaagtacaca gcaggaccag cagtttggcc ttcat                   645
```

```
SEQ ID NO: 237           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 237
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca ccaactcaac taatctgggc agcggactga ggatggtcac cggactgcgc   180
aacatcccac agcgggaaac aagaggactg ttcggcgcta tcgcagggtt tattgagggc   240
gggtggacag gaatggtgga cggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg agtctgtga agaacggcac ttacgactat   600
cccaaatatt ctgaagagag taagctgaat cgagagaaaa ttgacagtgg gggcgacatc   660
atcaagctgc tgaacgaaca ggtgaacaag agatgcaga gctccaacct gtacatgagt   720
atgtctagtt ggtgttatac acactcactg gacggcgctg ggctgttcct gtttgatcac   780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg cattgccaa gtccagaaaa  1140
agtgggtca                                                          1149

SEQ ID NO: 238           moltype = AA  length = 383
FEATURE                  Location/Qualifiers
REGION                   1..383
                         note = Synthetic
source                   1..383
                         mol_type = protein
                         organism = synthetic construct
SEQUENCE: 238
MKAKLLVLLC TFTATYADTI CIGYHANNST DTVDTVLEKN VTVTNSTNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENV PVQLTSISAP EHKFEGLTQI    300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 239           moltype = DNA  length = 1149
FEATURE                  Location/Qualifiers
misc_feature             1..1149
                         note = Synthetic
source                   1..1149
                         mol_type = other DNA
                         organism = synthetic construct
SEQUENCE: 239
tgacccactt tttctggact tggcaatgcc cttcacatac tgatctgcca ggtacaggcc    60
atgattctcg tttccaatca gttcgatttt atccaggatg tccttaaaca ggacctcctc   120
ctcgtgctgc tcggcacgt accactgcag aaagttgaag gtagcatgat ctttgctctt   180
aatggcgtgg tccacaatat tgttgataga ttcggaaata tgctgctcgt gttcgtaagc   240
tttctgaaag atctgggtca ggccctcgaa ctttatgttca ggggcgctga ttgaagtcag   300
ctggacgggc acattgttct cattcaggaa aatgatcagt ttctttgcat gttcgtattc   360
ctcggctgcg tgatcaaaca ggaacagccc agcgccgtcc agtgagtgtg tataacacca   420
actagacata ctccatgtaca ggttggagct ctgcatctcc ttgttcacct gttcgttcag   480
cagcttgatg atgtcgcccc cactgtcaat tttctctcga ttcagcttac tctcttcaga   540
atatttggga tagtcgtaag tgccgttctt cacagactcc atacattcat tgttgcactt   600
atggtaaaac tcgaagcatc cattcccgat ttctttggca ttgttcttca gctgggattt   660
gaccttctca tacagattct tcacgttgct atcgtggaaa tccagagtcc gctcgttcag   720
cagcagcacc agcagctcag ccaggtctgt tccgagcct ccgctgccca ttttttcgat   780
gacagaattc accatgttag taatgccatt gattgcgttc tgtgtagact tctgatcagc   840
ggcgtagccg ctgccctgct cattctgatg gtggtagcca taccacccgt ccaccattcc   900
tgtccacccg ccctcaataa accctgcgat agcgccgaac agtcctcttg tttcccgctg   960
tgggatgttg cgcagtccgg tgaccatcct cagtccgctg cccagattag ttgagttggt  1020
gacagtcacg ttcttctcca ggacggtatc cactgtgtcg gtggagttgt ttgcgtgata  1080
gccgatgcag atagtgtcag cgtaggttgc ggtaaagta cacagcagga ccagcagttt   1140
ggccttcat                                                          1149

SEQ ID NO: 240           moltype = AA  length = 215
FEATURE                  Location/Qualifiers
REGION                   1..215
                         note = Synthetic
```

```
source                  1..215
                        mol_type = protein
                        organism = synthetic construct
SEQUENCE: 240
MKAKLLVLLC TFTATYADTI CIGYHANNST DTVDTILEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLMLNQFTLL FHDSNVKNLY EKVKSQLKNN AKEIGNGCFE   180
FYHKCNNECM ESVKNGTYDY PKYSEESKLN REKID                              215

SEQ ID NO: 241          moltype = AA   length = 383
FEATURE                 Location/Qualifiers
REGION                  1..383
                        note = Synthetic
source                  1..383
                        mol_type = protein
                        organism = synthetic construct
SEQUENCE: 241
MKAKLLVLLC TFTATYADTI CIGYHANNST DTVDTILEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLMLNQFTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 242          moltype = AA   length = 215
FEATURE                 Location/Qualifiers
REGION                  1..215
                        note = Synthetic
source                  1..215
                        mol_type = protein
                        organism = synthetic construct
SEQUENCE: 242
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGNG TGGADLAELL VLLLNQWTLL FHDSNVKNLY EKVKSQLKNN AKEIGNGCFE   180
FYHKCNNECM ESVKNGTYDY PKYSEESKLN REKID                              215

SEQ ID NO: 243          moltype = AA   length = 383
FEATURE                 Location/Qualifiers
REGION                  1..383
                        note = Synthetic
source                  1..383
                        mol_type = protein
                        organism = synthetic construct
SEQUENCE: 243
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGNG TGGADLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 244          moltype = AA   length = 215
FEATURE                 Location/Qualifiers
REGION                  1..215
                        note = Synthetic
source                  1..215
                        mol_type = protein
                        organism = synthetic construct
SEQUENCE: 244
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKID                              215

SEQ ID NO: 245          moltype = AA   length = 383
FEATURE                 Location/Qualifiers
REGION                  1..383
                        note = Synthetic
source                  1..383
                        mol_type = protein
                        organism = synthetic construct
SEQUENCE: 245
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
```

```
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                           383

SEQ ID NO: 246          moltype = AA   length = 215
FEATURE                 Location/Qualifiers
REGION                  1..215
                        note = Synthetic
source                  1..215
                        mol_type = protein
                        organism = synthetic construct
SEQUENCE: 246
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNMV    120
NSVIEKMGSG GNGTDLAELL VLLLNQWTLL FHDSNVKNLY EKVKSQLKNN AKEIGNGCFE    180
FYHKCNNECM ESVKNGTYDY PKYSEESKLN REKID                              215

SEQ ID NO: 247          moltype = AA   length = 383
FEATURE                 Location/Qualifiers
REGION                  1..383
                        note = Synthetic
source                  1..383
                        mol_type = protein
                        organism = synthetic construct
SEQUENCE: 247
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHQNEQGS GYAADQKSTQ NAINGITNMV    120
NSVIEKMGSG GNGTDLAELL VLLLNQWTLL FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                           383

SEQ ID NO: 248          moltype = AA   length = 215
FEATURE                 Location/Qualifiers
REGION                  1..215
                        note = Synthetic
source                  1..215
                        mol_type = protein
                        organism = synthetic construct
SEQUENCE: 248
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHNNTQGS GYAADQKSTQ NAINGITNMV    120
NSVIEKMGGN GTGADLAELL VLLLNQWTLL FHDSNVKNLY EKVKSQLKNN AKEIGNGCFE    180
FYHKCNNECM ESVKNGTYDY PKYSEESKLN REKID                              215

SEQ ID NO: 249          moltype = AA   length = 383
FEATURE                 Location/Qualifiers
REGION                  1..383
                        note = Synthetic
source                  1..383
                        mol_type = protein
                        organism = synthetic construct
SEQUENCE: 249
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHNNTQGS GYAADQKSTQ NAINGITNMV    120
NSVIEKMGGN GTGADLAELL VLLLNQWTLL FHDSNVKNLY EKVKSQLKNN AKEIGNGCFE    180
FYHKCNNECM ESVKNGTYDY PKYSEESKLN REKIDSGGDI IKLLNEQVNK EMNSTNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                           383

SEQ ID NO: 250          moltype = AA   length = 215
FEATURE                 Location/Qualifiers
REGION                  1..215
                        note = Synthetic
source                  1..215
                        mol_type = protein
                        organism = synthetic construct
SEQUENCE: 250
MKAKLLVLLC TFTATYADTI CIGYHANNST DTVDTVLEKN VTVTHSVNLG SGLRMVTGLR     60
NIPSIQSRGL FGAIAGFIEG GWTGMVDGWY GYHHNNTQGS GYAADQKSTQ NAINGITNMV    120
NSVIEKMGGN GTGADLAELL VLLLNQWTLL FHDSNVKNLY EKVKSQLKNN AKEIGNGCFE    180
FYHKCNNECM ESVKNGTYDY PKYSEESKLN REKID                              215

SEQ ID NO: 251          moltype = AA   length = 383
FEATURE                 Location/Qualifiers
REGION                  1..383
                        note = Synthetic
```

```
source                  1..383
                        mol_type = protein
                        organism = synthetic construct
SEQUENCE: 251
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHNNTQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMNSTNLYMS   240
MSSWCYTHSL DGAGLFLFDH AAEEYEHAKK LIIFLNENMV PVNLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                          383

SEQ ID NO: 252          moltype = AA   length = 214
FEATURE                 Location/Qualifiers
REGION                  1..214
                        note = Synthetic
source                  1..214
                        mol_type = protein
                        organism = synthetic construct
SEQUENCE: 252
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGG                              214

SEQ ID NO: 253          moltype = AA   length = 368
FEATURE                 Location/Qualifiers
REGION                  1..368
                        note = Synthetic
source                  1..368
                        mol_type = protein
                        organism = synthetic construct
SEQUENCE: 253
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGGMQIYEG KLTAEGLRFG IVASRFNHAL   240
VDRLVEGAID CIVRHGGREE DITLVRVPGS WEIPVAAGEL ARKEDIDAVI AIGVLIRGAT   300
PHFDYIASEV SKGLANLSLE LRKPITFGVI TADTLEQAIE RAGTKHGNKG WEAALSAIEM   360
ANLFKSLR                                                           368

SEQ ID NO: 254          moltype = AA   length = 215
FEATURE                 Location/Qualifiers
REGION                  1..215
                        note = Synthetic
source                  1..215
                        mol_type = protein
                        organism = synthetic construct
SEQUENCE: 254
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGSG                             215

SEQ ID NO: 255          moltype = AA   length = 369
FEATURE                 Location/Qualifiers
REGION                  1..369
                        note = Synthetic
source                  1..369
                        mol_type = protein
                        organism = synthetic construct
SEQUENCE: 255
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REGSGMQIYE GKLTAEGLRF GIVASRFNHA   240
LVDRLVEGAI DCIVRHGGRE EDITLVRVPG SWEIPVAAGE LARKEDIDAV IAIGVLIRGA   300
TPHFDYIASE VSKGLANLSL ELRKPITFGV ITADTLEQAI ERAGTKHGNK GWEAALSAIE   360
MANLFKSLR                                                          369

SEQ ID NO: 256          moltype = AA   length = 211
FEATURE                 Location/Qualifiers
REGION                  1..211
                        note = Synthetic
source                  1..211
                        mol_type = protein
                        organism = synthetic construct
```

```
SEQUENCE: 256
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLG G                                  211

SEQ ID NO: 257          moltype = AA   length = 364
FEATURE                 Location/Qualifiers
REGION                  1..364
                        note = Synthetic
source                  1..364
                        mol_type = protein
                        organism = synthetic construct
SEQUENCE: 257
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLG GQIYEGKLTA EGLRFGIVAS RFNHALVDRL   240
VEGAIDCIVR HGGREEDITL VRVPGSWEIP VAAGELARKE DIDAVIAIGV LIRGATPHFD   300
YIASEVSKGL ANLSLELRKP ITFGVITADT LEQAIERAGT KHGNKGWEAA LSAIEMANLF   360
KSLR                                                                364

SEQ ID NO: 258          moltype = AA   length = 212
FEATURE                 Location/Qualifiers
REGION                  1..212
                        note = Synthetic
source                  1..212
                        mol_type = protein
                        organism = synthetic construct
SEQUENCE: 258
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLG SG                                 212

SEQ ID NO: 259          moltype = AA   length = 365
FEATURE                 Location/Qualifiers
REGION                  1..365
                        note = Synthetic
source                  1..365
                        mol_type = protein
                        organism = synthetic construct
SEQUENCE: 259
MKAKLLVLLC TFTATYADTI CIGYHANNST DTVDTVLEKN VTVTHSVNLG SGLRMVTGLR    60
NIPSIQSRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLG SGQIYEGKLT AEGLRFGIVA SRFNHALVDR   240
LVEGAIDCIV RHGGREEDIT LVRVPGSWEI PVAAGELARK EDIDAVIAIG VLIRGATPHF   300
DYIASEVSKG LANLSLELRK PITFGVITAD TLEQAIERAG TKHGNKGWEA ALSAIEMANL   360
FKSLR                                                               365

SEQ ID NO: 260          moltype = DNA   length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 260
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga gatggtcac cggactgcgc   180
aacatcccac agcgggaaac aagaggactg ttcggcgcta tcgcaggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaaccagtg gactctgctg ttccacgata gcaacgtgaa gaatctgtat   480
gagaaggtca aatcccagct gaagaacaat gccaaagaaa tcgggaatgg atgcttcgag   540
ttttaccata gtgcaacaa tgaatgtatg gagtctgtga agaacggcac ttacgactat   600
cccaaatatt ctgaagagag taagctgaat cgagagaaaa ttgac                   645

SEQ ID NO: 261          moltype = AA   length = 215
FEATURE                 Location/Qualifiers
REGION                  1..215
                        note = Synthetic Construct
source                  1..215
                        mol_type = protein
                        organism = synthetic construct
```

```
SEQUENCE: 261
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNQWTLL FHDSNVKNLY EKVKSQLKNN AKEIGNGCFE   180
FYHKCNNECM ESVKNGTYDY PKYSEESKLN REKID                              215

SEQ ID NO: 262             moltype = DNA  length = 645
FEATURE                    Location/Qualifiers
misc_feature               1..645
                           note = Synthetic
source                     1..645
                           mol_type = other DNA
                           organism = synthetic construct
SEQUENCE: 262
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagcagg   240
gtctgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc caccogcccct caataaaccc   420
tgcgatagcg ccgaacagtc ctcttgtttc ccgctgcgtg atgttgcgca gtccggtgac   480
catcctcagt ccgctgccca gattcactga gtgggtgaca gtcacgttct tctccaggac   540
ggtatccact gtgtcggtgg agttgtttgc gtgatagccg atgcagatag tgtcagcgta   600
ggttgcggta aagtacaca gcaggaccag cagtttggcc ttcat                    645

SEQ ID NO: 263             moltype = DNA  length = 1155
FEATURE                    Location/Qualifiers
misc_feature               1..1155
                           note = Synthetic
source                     1..1155
                           mol_type = other DNA
                           organism = synthetic construct
CDS                        1..1155
SEQUENCE: 263
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaaccagtg gactctgctg ttccacgata gcaacgtgaa gaatctgtat   480
gagaaggtca atccccagct gaagaacaat gccaagaaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg gctgttcct gttgatcac    780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccagcg agtccaacaa tattgtggac   960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 264             moltype = AA  length = 383
FEATURE                    Location/Qualifiers
REGION                     1..383
                           note = Synthetic Construct
source                     1..383
                           mol_type = protein
                           organism = synthetic construct
SEQUENCE: 264
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNQWTLL FHDSNVKNLY EKVKSQLKNN AKEIGNGCFE   180
FYHKCNNECM ESVKNGTYDY PKYSEESKLN REKIDSGGID IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 265             moltype = DNA  length = 1155
FEATURE                    Location/Qualifiers
misc_feature               1..1155
                           note = Synthetic
source                     1..1155
                           mol_type = other DNA
                           organism = synthetic construct
```

```
SEQUENCE: 265
tcatcatgac ccactttttc tggacttggc aatgcccttc acatactgat ctgccaggta    60
caggccatga ttctcgtttc caatcagttc gattttatcc aggatgtcct taaacaggac   120
ctcctcctcg tgctgctcgg ccacgtacca ctgcagaaag ttgaaggtag catgatcttc   180
gctcttaatg gcgtggtcca caatattgtt gatagattcg gaaatatgct gctcgtgttc   240
gtaagctttc tgaaagatct gggtcaggcc ctcgaactta tgttcagggg cgctgattga   300
agtcagctgg acgggcacat tgttctcatt caggaaaatg atcagtttct ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgcccccact gtcaattttc tctcgattca gcttactctc   540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaacagca gagtccactg   720
gttcagcagc agcaccagca gctcagccag gtctgttccg gagcctccgc tgcccattgt   780
ttcgatgaca gaattcacca tgttagtaat gccattgatt gcgttctgtg tagacttctg   840
atcagcggcg tagccgctgc cctgctcatt ctgatggtgg tagccgtacc acccgtccac   900
cattcctgtc caccegccct caataaaccc tgcgatagcg ccgaacagtc ctcttgtttc   960
ccgctgtggg atgttgcga gtccgtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 266          moltype = DNA   length = 5579
FEATURE                 Location/Qualifiers
misc_feature            1..5579
                        note = Synthetic
source                  1..5579
                        mol_type = other DNA
                        organism = synthetic construct
SEQUENCE: 266
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaataggga cttttccattg acgtcaatgg gtggagtatt tacggtaaac   540
tgcccacttg gcagtacatc aagtgtatca tatgccaagt acgcccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatgggc gtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctccgta tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgccgg cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cggtggacag ggatggtgg acggtggta cggctaccac catcagaatg  1680
agcagggcag cggctacgcc gctgatcaga agtctacaca gaacgcaatc aatggcatta  1740
ctaacatggt gaattcgtc atcgaaaaaa tgggcagcgg aggctccgga acagacctgg  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga ggaagtcgaa tcgagagaaa attgacaggg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gccccgtccag ctgacttcaa tcagcgcccc tgaactaag ttcgagggcc  2280
tgacccagat cttttcagaaa gattacgcac acgagcaca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag gcattgcca  2520
agtccagaaa aagtgggtca tgatgaacac gtgggatcca gatctgctgt gccttctagt  2580
tgccagccat ctgttgtttg ccctcccccc gtgccttcct ggaccctgga aggtgccact  2640
cccactgtcc tttcctaata aaatgaggaa attgcatcgc attgtctgag taggtgtcat  2700
tctattctgg ggggtgggt ggggcaggac agcaaggggg aggattggga agacaatagc  2760
aggcatgctg gggatgcggt gggctctatg gtacccaggg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
```

```
tcaatcccac cgctaaagt acttggagcg gtctctccct ccctcatcag cccaccaaac 3000
caaacctagc ctccaagagt gggaagaaat taaagcaaga taggctatta agtgcagagg 3060
gagagaaaat gcctccaaca tgtgaggaag taatgagaga aatcatagaa ttttaaggcc 3120
atgatttaag gccatcatgg ccttaatctt ccgcttcctc gctcactgac tcgctgcgct 3180
cggtcgttcg gctgcggcga gcggtatcag ctcactcaaa ggcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgcccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccgga 3480
acctgtccgc ctttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt tttttgtttg caagcagcag attacgcgca 3900
gaaaaaaagg atctcaagaa gatcctttga tcttttctac ggggtctgac gctcagtgga 3960
acgaaaactc acgttaaggg attttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc ccccgggggg ggcgctgagg tctgcctcgt gaagaaggtg 4200
ttgctgactc ataccaggcc tgaatcgccc catcatccag ccagaaagtg agggagccac 4260
ggttgatgag agctttgttg taggtggacc agttggtgat tttgaacttt tgctttgcca 4320
cggaacggtc tgcgttgtcg ggaagatgcg tgatctgatc cttcaactca gcaaaagttc 4380
gatttattca acaaagccgc cgtcccgtca agtcagcgta atgctctgcc agtgttacaa 4440
ccaattaacc aattctgatt agaaaaactc atcgagcatc aaatgaaact gcaatttatt 4500
catatcagga ttatcaatac catattttg aaaaagccgt ttctgtaatg aaggagaaaa 4560
ctcaccgagg cagttccata ggatggcaag atcctggtat cggtctgcga ttccgactcg 4620
tccaacatca atacaaccta ttaatttccc ctcgtcaaaa ataaggttat caagtgagaa 4680
atcaccatga gtgacgactg aatccggtga gaatggcaaa agcttatgca tttctttcca 4740
gacttgttca acaggccagc cattacgctc gtcatcaaaa tcactcgcat caaccaaacc 4800
gttattcatt cgtgattgcg cctgagcgag acgaaatacg cgatcgctgt taaaaggaca 4860
attacaaaca ggaatcgaat gcaaccggcg caggaacact gccagcgcat caacaatatt 4920
ttcacctgaa tcaggatatt cttctaatac ctggaatgct gttttcccgg ggatcgcagt 4980
ggtgagtaac catgcatcat caggagtacg gataaaatgc ttgatggtcg gaagaggcat 5040
aaattccgtc agccagttta gtctgaccat ctcatctgta acatcattgg caacgctacc 5100
tttgccatgt ttcagaaaca actctggcgc atcgggcttc ccatacaatc gatagattgt 5160
cgcacctgat tgcccgacat tatcgcgagc ccatttatac ccatataaat cagcatccat 5220
gttggaattt aatcgcggcc tcgagcaaga cgtttcccgt tgaatatggc tcataacacc 5280
ccttgtatta ctgtttatgt aagcagacag ttttattgtt catgatgata tatttttatc 5340
ttgtgcaatg taacatcaga gattttgaga cacaacgtgg ctttcccccc ccccccatta 5400
ttgaagcatt tatcagggtt attgtctcat gagcggatac atatttgaat gtatttagaa 5460
aaataaacaa atagggggttc cgcgcacatt tccccgaaaa gtgccacctg acgtctaaga 5520
aaccattatt atcatgacat taacctataa aaataggcgt atcacgaggc cctttcgtc 5579

SEQ ID NO: 267          moltype = DNA   length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 267
atgaaggcaa tcctggtcgt cctgctgtat actttcgcta ccgctaacgc tgacaccctg   60
tgcatcggct atcacgctaa caactcaacc gacacagtgg atactgtcct ggagaagaac  120
gtgactgtca cccactctgt gaatctgggc agtggactga gctggcaac tggactgcga  180
aacatcccac agcgggaaac cagaggactg ttcggcgcta tcgcagggtt tattgagggc  240
gggtggacag gaatggtgga cgggtggtac ggctaccacc atcagaacga gcagggatca  300
ggctacgccg ctgacctgaa gagcacacag aatgcaatcg atgaaattac taacatggtg  360
aattccgtca tcgagaaaat gggcagcgga ggctccggaa ccgacctggc agaactgctg  420
gtgctgctgc tgaaccagtg gacactgctg taccacgata gtaacgtgaa gaatctgtat  480
gagaaagtcc gatcacagct gaagaacaat gctaaagaaa tcgggaatgg atgcttcgag  540
ttttaccata agtgcgacaa cacctgtatg gagagcgtga aaaatggcac atacgattat  600
cccaagtatt ccgaggaagc caaactgaac agagaggaaa ttgac                  645

SEQ ID NO: 268          moltype = AA   length = 215
FEATURE                 Location/Qualifiers
REGION                  1..215
                        note = Synthetic Construct
source                  1..215
                        mol_type = protein
                        organism = synthetic construct
SEQUENCE: 268
MKAILVVLLY TFATANADTL CIGYHANNST DTVDTVLEKN VTVTHSVNLG SGLRLATGLR   60
NIPQRETRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REEID                             215
```

| SEQ ID NO: 269 | moltype = DNA length = 645 |
| --- | --- |
| FEATURE | Location/Qualifiers |
| misc_feature | 1..645 |
| | note = Synthetic |
| source | 1..645 |
| | mol_type = other DNA |
| | organism = synthetic construct |

SEQUENCE: 269
```
gtcaatttcc tctctgttca gtttggcttc ctcggaatac ttgggataat cgtatgtgcc   60
attttcacg ctctccatac aggtgttgtc gcacttatgg taaaactcga agcatccatt  120
cccgatttct ttagcattgt tcttcagctg tgatcggact ttctcataca gattcttcac  180
gttactatcg tggtacagca gtgtccactg gttcagcagc agcaccagca gttctgccag  240
gtcggttccg gagcctccgc tgcccatttt ctcgatgacg gaattcacca tgttagtaat  300
ttcatcgatt gcattctgtg tgctcttcag gtcagcggcg tagcctgatc cctgctcgtt  360
ctgatggtgg tagccgtacc acccgtccac cattcctgtc cacccgccct caataaaccc  420
tgcgatagcg ccgaacagtc ctctggtttc ccgctgtggg atgtttcgca gtccagttgc  480
cagcctcagt ccactgccca gattcacaga gtgggtgaca gtcacgttct ctccaggac   540
agtatccact gtgtcggttg agttgttagc gtgatagccg atgcacaggg tgtcagcgtt  600
agcggtagcg aaagtataca gcaggacgac caggattgcc ttcat               645
```

| SEQ ID NO: 270 | moltype = DNA length = 1155 |
| --- | --- |
| FEATURE | Location/Qualifiers |
| misc_feature | 1..1155 |
| | note = Synthetic |
| source | 1..1155 |
| | mol_type = other DNA |
| | organism = synthetic construct |
| CDS | 1..1155 |

SEQUENCE: 270
```
atgaaggcaa tcctggtcgt cctgctgtat actttcgcta ccgctaacgc tgacaccctg   60
tgcatcggct atcacgctaa caactcaacc gacacagtgg atactgtcct ggagaagaac  120
gtgactgtca cccactctgt gaatctgggc agtggactga ggctggcaac tggactgcga  180
aacatcccac agcgggaaac cagaggactg ttcggcgcta tcgcagggtt tattgagggc  240
gggtggacag gaatggtgga cgggtggtac ggctaccacc atcagaacga gcagggatca  300
ggctacgccg ctgacctgaa gagcacacag aatgcaatcg atgaaattac taacatggtg  360
aattccgtca tcgagaaaat gggcagcgga ggctccggaa ccgacctggc agaactgctg  420
gtgctgctgc tgaaccagtg gacactgctg taccacgata gtaacgtgaa gaatctgtat  480
gagaaagtcc gatcacagct gaagaacaat gctaagaaa tcgggaatgg atgcttcgag  540
ttttaccata agtgcgacaa cacctgtatg gagagcgtga aaaatggcac atacgattat  600
cccaagtatt ccgaggaagc caaactgaac agagaggaaa ttgactctgg gggcgacatc  660
atcaagctgc tgaacgaaca ggtcaacaag gagatgcaga gctccaatct gtacatgtcc  720
atgtctagtt ggtgttatac ccactctctg gacgcgctg gctgttcct gtttgatcac  780
gcagccgagg aatacgaaca tgcaaagaaa ctgatcattt tcctcaacga gaacaatgtg  840
cccgtccagc tgacatcaat cagcgcccct gaacataagt tcgagggcct gactcagatc  900
tttcagaaag cttacgaaca cgagcagcat atttccgaat ctatcaacaa tattgtggac  960
cacgccatta gagtaaaga tcatgctacc ttcaattttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg gcattgccaa gagccggaaa 1140
agtgggtcat gatga                                                  1155
```

| SEQ ID NO: 271 | moltype = AA length = 383 |
| --- | --- |
| FEATURE | Location/Qualifiers |
| REGION | 1..383 |
| | note = Synthetic Construct |
| source | 1..383 |
| | mol_type = protein |
| | organism = synthetic construct |

SEQUENCE: 271
```
MKAILVVLLY TFATANADTL CIGYHANNST DTVDTVLEKN VTVTHSVNLG SGLRLATGLR   60
NIPQRETRGL FGAIAGFIEG GWTGMVDGWY GYHHQNEQGS GYAADLKSTQ NAIDEITNMV  120
NSVIEKMGSG GSGTDLAELL VLLLNQWTLL YHDSNVKNLY EKVRSQLKNN AKEIGNGCFE  180
FYHKCDNTCM ESVKNGTYDY PKYSEEAKLN REEIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383
```

| SEQ ID NO: 272 | moltype = DNA length = 1155 |
| --- | --- |
| FEATURE | Location/Qualifiers |
| misc_feature | 1..1155 |
| | note = Synthetic |
| source | 1..1155 |
| | mol_type = other DNA |
| | organism = synthetic construct |

SEQUENCE: 272
```
tcatcatgac ccacttttcc ggctcttggc aatgccttc acatactgat ctgccaggta   60
caggccatga ttctcgtttc caatcagttc gatttatcc aggatgtcct taaacaggac  120
ctcctcctcg tgctgctcgg ccacgtacca ctgcagaaaa ttgaaggtag catgatcttt  180
actcttaatg gcgtggtcca caatattgtt gatagattcg gaaatatgct gctcgtgttc  240
gtaagctttc tgaaagatct gagtcaggcc ctcgaactta tgttcagggg cgctgattga  300
```

```
tgtcagctgg acgggcacat tgttctcgtt caggaaaatg atcagtttct ttgcatgttc   360
gtattcctcg gctgcgtgat caaacaggaa cagcccagcg ccgtccgagg agtgggtata   420
acaccaacta gacatggaca tgtacagatt ggagctctgc atctccttgt tgacctgttc   480
gttcagcagc ttgatgatgt cgcccccaga gtcaatttcc tctctgttca gtttggcttc   540
ctcggaatac ttgggataat cgtatgtgcc attttcacg ctctccatac aggtgttgtc   600
gcacttatgg taaaactcga agcatccatt cccgatttct ttagcattgt tcttcagctg   660
tgatcggact ttctcataca gattcttcac gttactatcg tggtacagca gtgtccactg   720
gttcagcagc agcaccagca gttctgccag gtcggttccg gagcctccgc tgcccatttt   780
ctcgatgacg gaattcacca tgttagtaat ttcatcgatt gcattctgtg tgctcttcag   840
gtcagcggcg tagcctgatc cctgctcgtt ctgatggtgg tagccgtacc acccgtccac   900
cattcctgtc caccgccct caataaaccc tgcgatagcg ccgaacagtc ctctggtttc   960
ccgctgtggg atgtttcgca gtccagttgc cagcctcagt ccactgccca gattcacaga  1020
gtgggtgaca gtcacgttct tctccaggac agtatccact gtgtcggttg agttgttagc  1080
gtgatagccg atgcacaggg tgtcagcgtt agcggtagcg aaagtataca gcaggacgac  1140
caggattgcc ttcat                                                    1155

SEQ ID NO: 273          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 273
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagga cttccattg acgtcaatgg gtggagtatt tacggtaaac   540
tgcccacttg gcagtacatc aagtgtatca tatgccaagt acgcccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggt  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgccgg cgctctagag  1380
atatcgccac catgaaggca atcctggtcg tcctgctgta ctttcgct accgctaacg  1440
ctgacaccct gtgcatcggc tatcacgcta acaactcaac cgacacagtg gatactgtcc  1500
tggagaagaa cgtgactgtc acccactctg tgaatctggg cagtggactg aggctggcaa  1560
ctggactgcg aaacatccca cagcgggaaa ccagaggact gttcggcgct atcgcaggt  1620
ttattgaggg cgggtggaca ggaatggtgg acggggtgga cggctaccac catcagaacg  1680
agcagggatc aggctacgcc gctgacctga agagcacaca gaatgcaatc gatgaaatta  1740
ctaacatggt gaattccgtc atcgagaaaa tgggcagcgg aggctccgga accgacctgg  1800
cagaactgct ggtgctgctg ctgaaccagt gacactgct gtaccacgat agtaacgtga  1860
agaatctgta tgagaaagtc cgatcacagc tgaagaacaa tgctaaagaa atcgggaatg  1920
gatgcttcga gttttaccat aagtgcgaca cacctgtat ggagagctgt gaaaaatggca  1980
catacgatta tcccaagtat tccgaggaag ccaaactgaa cagagaggaa attgactctg  2040
ggggcgaca tcatcaagctg ctgaacgaac aggtcaacaa ggaagtgcaa agctccaatc  2100
tgtacatgtc catgtctagt ggtgttata cccactctct ggacggcgct gggctgttcc  2160
tgtttgatca cgcagccgag gaatacgaac atgcaaagaa actgatcatt ttcctgaacg  2220
agaacaatgt gcccgtccag ctgacatcaa tcagcgcccc tgaacataag ttcgagggcc  2280
tgactcagat ctttcagaaa gcttacgaac acgagcagca tatttccgaa tctatcaaca  2340
atattgtgga ccacgccatt aagagtaaag atcatgctac cttcaatttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag gcattgccga  2520
agagccggaa aagtgggtca tgatgaacac gtgggatcca gatctgctgt gccttctagt  2580
tgccagccat ctgttgtttg ccctctcccc gtgccttcct tgaccctgga aggtgccact  2640
cccactgtcc tttcctaata aatgaggaa attgcatcgt attgctctgga taggtgtcat  2700
tctattctgg ggggtggggt gggggcaggac agcaagggg aggattggga agacaatagc  2760
aggcatgctg gggatgcgt gggctctatg gtacccaggt gctgaagaa ttgacccggt  2820
tcctcctggg ccagaaagaa gcaggcacat ccccttctct gtgacacacc ctgtccacgc  2880
ccctggttcc tagttccagc ccactcata ggacactcat agctcaggag ggctccgcct  2940
tcaatcccac cgctaaagt acttggagcg gtctctcccc tcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatgaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
```

```
accgtaaaaa ggccgcgttg ctggcgtttt tccataggct ccgcccccct gacgagcatc   3360
acaaaaatcg acgctcaagt cagaggtggc gaaaccccgac aggactataa agataccagg   3420
cgtttccccc tggaagctcc ctcgtgcgct ctcctgttcc gaccctgccg cttaccggat   3480
acctgtccgc ctttctccct tcgggaagcg tggcgctttc tcatagctca cgctgtaggt   3540
atctcagttc ggtgtaggtc gttcgctcca agctgggctg tgtgcacgaa ccccccgttc   3600
agcccgaccg ctgcgcctta tccggtaact atcgtcttga gtccaacccg gtaagcacg    3660
acttatcgcc actggcagca gccactggta acaggattag cagagcgagg tatgtaggcg   3720
gtgctacaga gttcttgaag tggtggccta actacggcta cactagaaga acagtatttg   3780
gtatctgcgc tctgctgaag ccagttacct tcggaaaaag agttggtagc tcttgatcgg   3840
gcaaacaaac caccgctggt agcggtggtt ttttttgtttg caagcagcag attacgcgca   3900
gaaaaaaagg atctcaagaa gatcctttga tctttctac ggggtctgac gctcagtgga    3960
acgaaaactc acgttaaggg attttggtca tgagattatc aaaaggatc ttcacctaga    4020
tccttttaaa ttaaaaatga agttttaaat caatctaaag tatatatgag taaacttggt   4080
ctgacagtta ccaatgctta atcagtgagg cacctatctc agcgatctgt ctatttcgtt   4140
catccatagt tgcctgactc gggggggggg ggcgctgagg tctgcctcgt gaagaaggtg   4200
ttgctgactc ataccaggcc tgaatcgccc catcatccag ccagaaagtg agggagccac   4260
ggttgatgag agctttgttg taggtggacc agttggtgat tttgaacttt tgctttgcca   4320
cggaacggtc tgcgttgtcg ggaagatgca tgatctgatc cttcaactca gcaaaagttc   4380
gatttattca acaaagccgc cgtcccgtca agtcagcgta atgctctgcc agtgttacaa   4440
ccaattaacc aattctgatt agaaaaactc atcgagcatc aaatgaaact gcaatttatt   4500
catatcagga ttatcaatac catatttttg aaaaagccgt ttctgtaatg aaggagaaaa   4560
ctcaccgagg cagttccata ggatgcaag atcctggtat cggtctgcga ttccgactcg   4620
tccaacatca atacaaccta ttaatttccc ctcgtcaaaa ataaggttat caagtgagaa   4680
atcaccatga gtgacgactg aatccggtga gaatggcaaa agcttatgca tttctttcca   4740
gacttgttca acaggccagc cattacgctc gtcatcaaaa tcactcgcat caaccaaacc   4800
gttattcatt cgtgattgcg cctgagcgag acgaaatacg cgatcgctgt taaaaggaca   4860
attacaaaca ggaatcgaat gcaaccggcg caggaacact gccagcgcat caacaatatt   4920
ttcacctgaa tcaggatatt cttctaatac ctggaatgct gttttcccgg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc gatagattgt   5160
cgcacctgat tgcccgacat tatcgcgagc ccatttatac ccatataaat cagcatccat   5220
gttggaattt aatcgcggcc tcgagcaaga cgtttcccgt tgaatatggc tcataacacc   5280
ccttgtatta ctgtttatgt aagcagacag ttttattgtt catgatgata tatttttatc   5340
ttgtgcaatg taacatcaga gattttgaga cacaacgtgg ctttcccccc ccccccatta   5400
ttgaagcatt tatcagggtt attgtctcat gagcggatac atatttgaat gtatttagaa   5460
aaataaacaa ataggggttc cgcgcacatt tccccgaaaa gtgccacctg acgtctaaga   5520
aaccattatt atcatgacat taacctataa aaataggcgt atcacgaggc cctttcgtc    5579

SEQ ID NO: 274           moltype = DNA   length = 639
FEATURE                  Location/Qualifiers
misc_feature             1..639
                         note = Synthetic
source                   1..639
                         mol_type = other DNA
                         organism = synthetic construct
CDS                      1..639
SEQUENCE: 274
atggctatca tctacctgat cctgctgttc actgctgtgc gggggggacca gatttgcatc   60
ggctaccacg ctaataattc aactgagaag gtggatacta tcctggagcg gaacgtgacc   120
gtcacacacg ctaaagacat tggcagcgga ctggtgctgg caaccggact gaggaatgtc   180
ccacagatcg agtcccgcgg actgttcggc gctatcgcag ggtttattga aggcgggtgg   240
cagggaatga ttgatgggtg gtacggctac caccattcta cgaccaagg aagtggctac    300
gccgctgata aggagagtac tcagaaagcc ttcgatggca tcaccaacat ggtgaattca   360
gtcattgaga agatgggcag cggaggctcc ggaaccgacc tggcagaact gctggtgctg   420
ctgctgaatc agtggacact gctgtttcac gactctaacg tgaagaatct gtatgataaa   480
gtccggatgc agctgagaga caacgtgaag gagctgggga tggatgcttt cgaattttac   540
cataagtgcg acgatgagtg tatgaacagt gtcaaaatg gcacatacga ttatcccaag   600
tatgaggaag agtcaaaact gaaccgaaat gaaatcaag                           639

SEQ ID NO: 275           moltype = AA    length = 213
FEATURE                  Location/Qualifiers
REGION                   1..213
                         note = Synthetic Construct
source                   1..213
                         mol_type = protein
                         organism = synthetic construct
SEQUENCE: 275
MAIIYLILLF TAVRGDQICI GYHANNSTEK VDTILERNVT VTHAKDIGSG LVLATGLRNV    60
PQIESRGLFG AIAGFIEGGW QGMIDGWYGY HHSNDQGSGY AADKESTQKA FDGITNMVNS   120
VIEKMGSGGS GTDLAELLVL LLNQWTLLFH DSNVKNLYDK VRMQLRDNVK ELGNGCFEFY   180
HKCDDECMNS VKNGTYDYPK YEEESKLNRN EIK                                 213

SEQ ID NO: 276           moltype = DNA   length = 639
FEATURE                  Location/Qualifiers
misc_feature             1..639
                         note = Synthetic
```

```
source                    1..639
                          mol_type = other DNA
                          organism = synthetic construct
SEQUENCE: 276
cttgatttca tttcggttca gttttgactc ttcctcatac ttgggataat cgtatgtgcc    60
attttttgaca ctgttcatac actcatcgtc gcacttatgg taaaattcga agcatccatt  120
ccccagctcc ttcacgttgt ctctcagctg catccggact ttatcataca gattcttcac   180
gttagagtcg tgaaacagca gtgtccactg attcagcagc agcaccagca gttctgccag   240
gtcggttccg gagcctccgc tgcccatctt ctcaatgact gaattcacca tgttggtgat   300
gccatcgaag gctttctgag tactctcctt atcagcggcg tagccacttc cttggtcgtt   360
agaatggtgg tagccgtacc acccatcaat cattccctgc cacccgcctt caataaaccc   420
tgcgatagcg ccgaacagtc cgcgggactg atctgtggg acattcctca gtccggttgc    480
cagcaccagt ccgctgccaa tgtctttagc gtgtgtgacg gtcacgttcc gctccaggat   540
agtatccacc ttctcagttg aattattagc gtggtagccg atgcaaatct ggtcccccg    600
cacagcagtg aacagcagga tcaggtagat gatagccat                          639

SEQ ID NO: 277            moltype = DNA  length = 1149
FEATURE                   Location/Qualifiers
misc_feature              1..1149
                          note = Synthetic
source                    1..1149
                          mol_type = other DNA
                          organism = synthetic construct
CDS                       1..1149
SEQUENCE: 277
atggctatca tctacctgat cctgctgttc actgctgtgc gggggaccaa gatttgcatc    60
ggctaccacg ctaataattc aactgagaag gtggatacta tcctggagcg gaacgtgacc   120
gtcacacacg ctaaagacat tggcagcgga ctggtgctgg caaccggact gaggaatgtc   180
ccacagatcg agtcccgcgg actgttcggc gctatcgcag gtttattga aggcgggtgg    240
cagggaatga ttgggggtg gtacggctac caccattcta acgaccaagg aagtggctac   300
gccgctgata aggagagtac tcagaaagcc ttcgatggga tcaccaacat ggtgaattca   360
gtcattgaga gatgggcag cggaggctcc ggaaccgacc tggcagaact gctggtgctg   420
ctgctgaatc agtggacact gctgtttcac gactctaacg tgaagaatct gtatgataaa   480
gtccggatgc agctgagaga caacgtgaag gagctgggga atggatgctt cgaattttac   540
cataagtgcg acgatgagtg tatgaacagt gtcaaaaatg gcacatacga ttatcccaag   600
tatgaggaag agtcaaaact gaaccgaaat gaaatcaaga gcgggggcga catcatcaag   660
ctgctgaacg agcaagtgaa taggaaatgc agagctcca acctgtacat gtccatgtct   720
agttggtgtt atactcactc tctggatggc gccgggctgt tcctgtttga ccacgcagcc   780
gaagagtacg agcatgctaa gaaactgatc attttcctga acgaaaacaa cgtgcccgtc   840
cagctgacat caatcagcgc acctgagcat aagttcgaag gcctgactca gatctttcag   900
aaagcttacg agcacgaaca gcatatttcc gagtctatca caatattgt ggaccacgcc    960
atcaagagca agatcatgc taccttcaac tttctgcagt ggtacgtggc cgagcagcac   1020
gaagaggaag tcctgtttaa ggacatcctg gataaaatcg agctgattgg aaacgaaaat   1080
catgcctgt acctggcaga ccagtatgtg aagggcattg ccaagtccag aaaaagtggg   1140
tcatgatga                                                          1149

SEQ ID NO: 278            moltype = AA  length = 381
FEATURE                   Location/Qualifiers
REGION                    1..381
                          note = Synthetic Construct
source                    1..381
                          mol_type = protein
                          organism = synthetic construct
SEQUENCE: 278
MAIIYLILLF TAVRGDQICI GYHANNSTEK VDTILERNVT VTHAKDIGSG LVLATGLRNV    60
PQIESRGLFG AIAGFIEGGW QGMIDGWYGY HHSNDQGSGY AADKESTQKA FDGITNMVNS   120
VIEKMGSGGS GTDLAELLVL LLNQWTLLPH DSNVKNLYDK VRMQLRDNVK ELGNGCFEFY   180
HKCDDECMNS VKNGTYDYPK YEEESKLNRN EIKSGGDIIK LLNEQVNKEM QSSNLYMSMS   240
SWCYTHSLDG AGLFLFDHAA EEYEHAKKLI IFLNENNVPV QLTSISAPEH KFEGLTQIFQ   300
KAYEHEQHIS ESINNIVDHA IKSKDHATFN FLQWYVAEQH EEEVLFKDIL DKIELIGNEN   360
HGLYLADQYV KGIAKSRKSG S                                             381

SEQ ID NO: 279            moltype = DNA  length = 1149
FEATURE                   Location/Qualifiers
misc_feature              1..1149
                          note = Synthetic
source                    1..1149
                          mol_type = other DNA
                          organism = synthetic construct
SEQUENCE: 279
tcatcatgac ccactttttc tggacttggc aatgccttc acatactggt ctgccaggta     60
caggccatga ttttcgtttc caatcagctc gattttatcc aggatgtcct taaacaggac   120
ttcctcttcg tgctgctcgg ccacgtacca ctgcagaaag ttgaaggtag catgatcttt   180
gctctttgatg gcgtggtcca caatattgtt gatagactgg gaaatatgct gttcgtgctc   240
gtaagctttc tgaaagatct gagtcaggcc ttcgaactta tgctcaggtg cgctgattga   300
tgtcagctgg acgggcacgt tgttttcgtt caggaaaatg atcagtttct tagcatgctc   360
gtactcttcg gctgcgtggt caaacaggaa cagcccggcg ccatccagag agtgagtata   420
acaccaacta gacatggaca tgtacaggtt ggagctctgc atttccttat tcacttgctc   480
gttcagcagc ttgatgatgt cgccccgct cttgatttca tttcggttca gttttgactc    540
```

```
ttcctcatac ttgggataat cgtatgtgcc attttttgaca ctgttcatac actcatcgtc    600
gcacttatgg taaaattcga agcatccatt ccccagctcc ttcacgttgt ctctcagctg    660
catccggact ttatcataca gattcttcac gttagagtcg tgaaacagca gtgtccactg    720
attcagcagc agcaccagca gttctgccag gtcggttccg gagcctccgc tgcccatctt    780
ctcaatgact gaattcacca tgttggtgat gccatcgaag gctttctgag tactctcctt    840
atcagcggcg tagccacttc cttggtcgtt agaatggtgg tagccgtacc acccatcaat    900
cattccctgc caccgccttt caataaaccc tgcgatagcg ccgaacagtc cgcgggactc    960
gatctgtggg acattcctca gtccggttgc cagcaccagt ccgctgccaa tgtctttagc   1020
gtgtgtgacg gtcacgttcc gctccaggat agtatccacc ttctcagttg aattattagc   1080
gtggtagccg atgcaaatct ggtcccccg cacagcagtg aacagcagga tcaggtagat   1140
gatagccat                                                            1149

SEQ ID NO: 280          moltype = DNA  length = 5573
FEATURE                 Location/Qualifiers
misc_feature            1..5573
                        note = Synthetic
source                  1..5573
                        mol_type = other DNA
                        organism = synthetic construct
SEQUENCE: 280
tcgcgcgttt cggtgatgac ggtgaaaacc tctgacacat gcagctcccg gagacggtca     60
cagcttgtct gtaagcggat gccggggagca gacaagccgg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggga cttttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag cgtgtacggt gggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggg cgctctagag   1380
atatcgccac catggctatc atctacctga tcctgctgtt cactgctgtg cgggggggacc   1440
agatttgcat cggctaccac gctaataatt caactgagaa ggtggatact atcctggagc   1500
ggaacgtgac cgtcacacac gctaaagaca ttggcagcgg actggtgctg gcaaccggac   1560
tgaggaatgt cccacagatc gagtcccgcg gactgttcgg cgctatcgca gggtttattg   1620
aaggcgggtg gcagggaatg attgatgggt ggtacggcta ccaccattct aacgaccaag   1680
gaagtggcta cgccgctgat aaggagagta ctcagaaagc cttcgatggc atcaccaaca   1740
tggtgaattc agtcattgag aagatgggca gcggaggctc cggaaccgac ctggcagaac   1800
tgctggtgct gctgctgaat cagtggacac tgctgtttca cgactctaac gtgaagaatc   1860
tgtatgataa agtccggatg cagctgagag acaacgtgaa ggagctgggg aatggatgct   1920
tcgaatttta ccataagtgc gacgatgagt gtatgaacag tgtcaaaaat ggcacatacg   1980
attatcccaa gtatgaggaa gagtcaaaac tgaaccgaaa tgaaatcaag agcggggggcg   2040
acatcatcaa gctgctgaac gagcaagtga ataaggaaat gcagagctcc aacctgtaca   2100
tgtccatgtc tagttggtgt tatactcact ctctgatgg cgccgggctg ttcctgtttg   2160
accacgcagc cgaagagtac gagcatgcta agaaactgat catttcctg aacgaaaaca   2220
acgtgcccgt ccagctgaca tcaatcagcg cacctgagca taagttcgaa ggcctgactc   2280
agatctttca gaaagcttac gagcacgaac agcatatttc cgagtctata aacaatattg   2340
tggaccacgc catcaagagc aaagatcatg ctaccttcaa cttttctgcag tggtacgtgg   2400
ccgagcagca cgaagaggaa gtcctgttta aggacatcct ggataaaatc gagctgattg   2460
gaaacgaaaa tcatggcctg tacctggcag accagtatgt gaagggcatt gccaagtcca   2520
gaaaaagtgg gtcatgatga acacgtggga tccagatctg ctgtgccttc tagttgccag   2580
ccatctgttg tttgcccctc cccgtgcctt ccttgaccct ggaaggtgcc cactcccact   2640
gtcctttcct aataaaatga ggaaattgca tcgcattgtc tgagtaggtg tcattctatt   2700
ctggggggtg gggtggggca ggacagcaag ggggaggatt gggaagacaa tagcaggcat   2760
gctgggggatg cggtgggctc tatgggtacc caggtgctga agaattgacc cggttcctcc   2820
tgggccagaa agaagcaggc acatcccctt ctctgtgaca caccctgtcc acgcccctgg   2880
ttcttagttc cagccccact cataggacac tcatagctcc gaggggctcc gccttcaatc   2940
ccacccgcta aagtacttgg agcggtctct cctccctca tcagcccacc aaaccaaacc   3000
tagcctccaa gagtgggaag aaattaaagc aagataggct attaagtgca gagggagaga   3060
aaatgcctcc aacatgtgag gaagtaatga gagaaatcat agaatttaa ggccatgatt   3120
taaggccatc atggccttaa tcttccgctt cctcgctcac tgactcgctg cgctcggtcg   3180
ttcggctgcg gcgagcggta tcagctcact caaaaggcgg aatacggtta ccacagaat   3240
caggggataa cgcaggaaag aacatgtgag caaaaggcca gcaaaaggcc aggaaccgta   3300
aaaaggccgc gttgctggcg ttttttccata ggctccgccc cctgacgag catcacaaaa   3360
atcgacgctc aagtcagagg tggcgaaacc cgacaggact ataaagatac caggcgtttc   3420
cccctggaag ctccctcgtg cgctctcctg ttccgaccct gccgcttacc ggatacctgt   3480
ccgcctttct ccctttcggga agcgtggcgc tttctcatag ctcacgctgt aggtatctca   3540
```

```
gttcggtgta ggtcgttcgc tccaagctgg gctgtgtgca cgaacccccc gttcagcccg   3600
accgctgcgc cttatccggt aactatcgtc ttgagtccaa cccggtaaga cacgacttat   3660
cgccactggc agcagccact ggtaacagga ttagcagagc gaggtatgta ggcggtgcta   3720
cagagttctt gaagtggtgg cctaactacg gctacactag aagaacagta tttggtatct   3780
gcgctctgct gaagccagtt accttcggaa aaagagttgg tagctcttga tccggcaaac   3840
aaaccaccgc tggtagcggt ggttttttt tttgcaagca gcagattacg cgcagaaaaa   3900
aaggatctca agaagatcct ttgatctttt ctacggggtc tgacgctcag tggaacgaaa   3960
actcacgtta agggattttg gtcatgagat tatcaaaaag gatcttcacc tagatccttt   4020
taaattaaaa atgaagtttt aaatcaatct aaagtatata tgagtaaact tggtctgaca   4080
gttaccaatg cttaatcagt gaggcaccta tctcagcgat ctgtctattt cgttcatcca   4140
tagttgcctg actcgggggg ggggggcgct gaggtctgcc tcgtgaagaa ggtgttgctg   4200
actcatacca ggcctgaatc gccccatcat ccagccagaa agtgagggag ccacggttga   4260
tgagagcttt gttgtaggtg gaccagttgg tgattttgaa cttttgcttt gccacggaac   4320
ggtctgcgtt gtcgggaaga tgcgtgatct gatccttcaa ctcagcaaaa gttcgattta   4380
ttcaacaaag ccgccgtccc gtcaagtcag cgtaatgctc tgccagtgtt acaaccaatt   4440
aaccaattct gattagaaaa actcatcgag catcaaatga aactgcaatt tattcatatc   4500
aggattatca ataccatatt tttgaaaaag ccgtttctgt aatgaaggag aaaactcacc   4560
gaggcagttc cataggatgg caagatcctg gtatcgttcg cgcgattccga ctcgtccaac   4620
atcaatacaa cctattaatt tcccctcgtc aaaaataagg ttatcaagtg agaaatcacc   4680
atgagtgacg actgaatccg gtgagaatgg caaaagctta tgcatttctt ccagacttg   4740
ttcaacaggc cagccattac gctcgtcatc aaaatcactc gcatcaacca aaccgttatt   4800
cattcgtgat tgcgcctgag cgagacgaaa tacgcgatcg ctgttaaaag gacaattaca   4860
aacaggaatc gaatgcaacc ggcgcaggaa cactgccagc gcatcaacaa tattttcacc   4920
tgaatcagga tattcttcta atacctgaa tgctgttttc ccggggatcg cagtggtgag   4980
taaccatgca tcatcaggag tacgataaa atgcttgatg gtcggaagag gcataaattc   5040
cgtcagccag tttagtctga ccatctcatc tgtaacatca ttggcaacgc taccttgcc   5100
atgtttcaga aacaactctg gcgcatcggg cttcccatac aatcgataga ttgtcgcacc   5160
tgattgcccg acattatcgc gagcccattt atcccatat aaatcagcat ccatgttgga   5220
atttaatcgc ggcctcgagc aagacgtttc cgttcaata tggctcataa cacccccttgt   5280
attactgttt atgtaagcag acagttttat tgttcatgat gatatattc tatcttgtgc   5340
aatgtaacat cagagatttt gagacacaac gtggctttcc cccccccccc attattgaag   5400
catttatcag ggttattgtc tcatgagcgg atacatattt gaatgtattt agaaaaataa   5460
acaaataggg gttccgcgca catttccccg aaaagtgcca cctgacgtct aagaaaccat   5520
tattatcatg acattaacct ataaaaatag gcgtatcacg aggcccttc gtc          5573

SEQ ID NO: 281          moltype = DNA   length = 654
FEATURE                 Location/Qualifiers
misc_feature            1..654
                        note = Synthetic
source                  1..654
                        mol_type = other DNA
                        organism = synthetic construct
CDS                     1..654
SEQUENCE: 281
atggaaaaaa tcgtgctgct gctggctatc gtgtccctgg tgaagtccga ccagatctgt    60
attgggtatc atgctaacaa ctccacagaa caggtggata ctatcatgga agaaaacgtg   120
accgtcacac acgctcagga cattggatgg ggactggttc tggcaaccgg actgagaaat   180
tcaccacaga gggaaagccg gagaaagaaa cgcggactgt tcggcgctat cgcagggttt   240
attgagggcg ggtggcaggg aatggtggat gggtggtacg gctaccacca ttccaacgaa   300
cagggatctg gctacgccgc tgataaggag tctactcaga aagctatcga cggcgtgacc   360
aacatggtca atagtatcat tgataagatg ggctctggag gcagtggaac cgacctggca   420
gagctgctgg tgctgctgct gaaccagtgg acactgctgt tccacgactc taacgtgaag   480
aatctgtatg ataaagtccg actgcagctg cgggacaacg ccaaggaact ggggaatgga   540
tgcttcgagt tctaccataa gtgcgataac gaatgtatgg agagcatccg aaacggcaca   600
tacaattatc cccagtattc cgaggaagct aggctgaaac gcgaggaaat tagc         654

SEQ ID NO: 282          moltype = AA   length = 218
FEATURE                 Location/Qualifiers
REGION                  1..218
                        note = Synthetic Construct
source                  1..218
                        mol_type = protein
                        organism = synthetic construct
SEQUENCE: 282
MEKIVLLLAI VSLVKSDQIC IGYHANNSTE QVDTIMEKNV TVTHAQDIGW GLVLATGLRN    60
SPQRESRRKK RGLFGAIAGF IEGGWQGMVD GWYGYHHSNE QGSGYAADKE STQKAIDGVT   120
NMVNSIIDKM GSGGSGTDLA ELLVLLLNQW TLLFHDSNVK NLYDKVRLQL RDNAKELGNG   180
CFEFYHKCDN ECMESIRNGT YNYPQYSEEA RLKREEIS                           218

SEQ ID NO: 283          moltype = DNA   length = 654
FEATURE                 Location/Qualifiers
misc_feature            1..654
                        note = Synthetic
source                  1..654
                        mol_type = other DNA
                        organism = synthetic construct
SEQUENCE: 283
gctaatttcc tcgcgtttca gcctagcttc ctcggaatac tggggataat tgtatgtgcc    60
gtttcggatg ctctccatac attcgttatc gcacttatgg tagaactcga agcatccatt   120
```

-continued

```
ccccagttcc ttggcgttgt cccgcagctg cagtcggact ttatcataca gattcttcac    180
gttagagtcg tggaacagca gtgtccactg gttcagcagc agcaccagca gctctgccag    240
gtcggttcca ctgcctccag agcccatctt atcaatgata ctattgacca tgttggtcac    300
gccgtcgata gctttctgag tagactcctt atcagcggcg tagccagatc cctgttcgtt    360
ggaatggtgg tagccgtacc acccatccac cattccctgc cacccgccct caataaaccc    420
tgcgatagcg ccgaacagtc cgcgtttctt tctccggctt tccctctgtg gtgaatttct    480
cagtccggtt gccaggacca gtccccatcc aatgtcctga gcgtgtgtga cggtcacgtt    540
cttctccatg atagtatcca cctgttctgt ggagttgtta gcatgatacc caatacagat    600
ctggtcggac ttcaccaggg acacgatagc cagcagcagc acgattttt ccat           654
```

| | | |
|---|---|---|
| SEQ ID NO: 284 | moltype = DNA length = 1164 | |
| FEATURE | Location/Qualifiers | |
| misc_feature | 1..1164 | |
| | note = Synthetic | |
| source | 1..1164 | |
| | mol_type = other DNA | |
| | organism = synthetic construct | |
| CDS | 1..1164 | |

SEQUENCE: 284
```
atggaaaaaa tcgtgctgct gctggctatc gtgtccctgg tgaagtccga ccagatctgt     60
attgggtatc atgctaacaa ctccacagaa caggtggata ctatcatgga agaacgtgt    120
accgtcacac acgctcagga cattggatgg ggactggttc tggcaacggg actgagaaat    180
tcaccacaga gggaaagccg agaaagaaa cgcggactgt tcggcgctat cgcagggttt    240
attgagggcg gtggcaggg aatggtggat gggtggtacg gctaccacca ttccaacgaa    300
cagggatctg gctacgccgc tgataaggag tctactcaga aagctatcga cggcgtgacc    360
aacatggtca atagtatcat tgataagatg gctctggaac gcagtggaac cggcctggca    420
gagctgctgg tgctgctgct gaaccagtgg acactgctgt tccacgactc taacgtgaag    480
aatctgtatg ataaagtccg actgcagctg cgggacaacg ccaaggaact ggggaatgga    540
tgcttcgagt tctaccataa gtgcgataac gaatgtatgg agagcatccg aaacggcaca    600
tacaattatc cccagtattc cgaggaagct aggctgaagg aacgggaaat tagctccggg    660
ggagacatca ttaagctgct gaacgaacag gtgaacaagg agatgcagtc tagtaacctg    720
tacatgagta tgtcaagctg gtgttatact cactcactgg atggcgccgg gctgttcctg    780
tttgaccacg cagccgagga atacgaacat gctaagaaac tgatcatttt cctgaatgag    840
aacaatgtgc ccgtccagct gacatcatcc tctgcacctg aacataagtt cgagggcctg    900
actcagatct ttcagaaagc ctacgaacac gagcagcata ttagtgagtc aatcaacaat    960
attgtggacc acgccatcaa gagcaaagat catgctacct tcaatttct gcagtggtac   1020
gtggccgagc agcacgagga gaggtcctg tttaaggaca tcctggataa aatcgaactg   1080
attggaaacg agaatcatgg cctgtacctg gcagaccagt atgtgaaggg cattgccaag   1140
tccaggaaaa gcgggtcctg atga                                         1164
```

| | | |
|---|---|---|
| SEQ ID NO: 285 | moltype = AA length = 386 | |
| FEATURE | Location/Qualifiers | |
| REGION | 1..386 | |
| | note = Synthetic Construct | |
| source | 1..386 | |
| | mol_type = protein | |
| | organism = synthetic construct | |

SEQUENCE: 285
```
MEKIVLLLAI VSLVKSDQIC IGYHANNSTE QVDTIMEKNV TVTHAQDIGW GLVLATGLRN     60
SPQRESRRKK RGLFGAIAGF IEGGWQGMVD GWYGYHHSNE QGSGYAADKE STQKAIDGVT    120
NMVNSIIDKM GSGGSGTDLA ELLVLLLNQW TLLFHDSNVK NLYDKVRLQL RDNAKELGNG    180
CFEFYHKCDN ECMESIRNGT YNYPQYSEEA RLKREEISSG GDIIKLLNEQ VNKEMQSSNL    240
YMSMSSWCYT HSLDGAGLFL FDHAAEEYEH AKKLIIFLNE NNVPVQLTSI SAPEHKFEGL    300
TQIFQKAYEH EQHISESINN IVDHAIKSKD HATFNFLQWY VAEQHEEEVL FKDILDKIEL    360
IGNENHGLYL ADQYVKGIAK SRKSGS                                        386
```

| | | |
|---|---|---|
| SEQ ID NO: 286 | moltype = DNA length = 1164 | |
| FEATURE | Location/Qualifiers | |
| misc_feature | 1..1164 | |
| | note = Synthetic | |
| source | 1..1164 | |
| | mol_type = other DNA | |
| | organism = synthetic construct | |

SEQUENCE: 286
```
tcatcaggac ccgcttttcc tggacttggc aatgccttc acatactggt ctgccaggta     60
caggccatga ttctcgtttc caatcagttc gatttatcc aggatgtcct taaacaggac    120
ctcttcctcg tgctgctcgg ccacgtacca ctgcagaaaa ttgaaggtag catgatcttt    180
gctcttgatt gacgtggtcca caatattgtt gattgactca ctaatatgct gctcgtgttc    240
gtaggctttc tgaaagatct gagtcaggcc ctcgaactta tgttcaggtg cagagatgga    300
tgtcagctgg acgggcacat tgttctcatt caggaaaatg atcagttct agcatgttc     360
gtattcctcg gctgcgtggt caaacaggaa cagcccggcg ccatccagtg agtgagtata    420
acaccagctt gacatactca tgtacaggtt actagactgc atctccttgt tcacctgttc    480
gttcagcagc ttaatgatgt ctcccccgga gctaatttcc tcgcgtttca gcctagcttc    540
ctcggaatac tggggataat tgtatgtgcc attcggatg ctctccatac attcgttatc    600
gcacttatgg tagaactcga agcatccatt cccagttcc ttggcgttgt cccgcagctg    660
cagtcggact ttatcataca gattcttcac gttagagtcg tggaacagca gtgtccactg    720
gttcagcagc agcaccagca gctctgccag gtcggttcca ctgcctccag agcccatctt    780
atcaatgata ctattgacca tgttggtcac gccgtcgata gctttctgag tagactcctt    840
atcagcggcg tagccagatc cctgttcgtt ggaatggtgg tagccgtacc acccatccac    900
```

```
cattccctgc cacccgccct caataaaccc tgcgatagcg ccgaacagtc cgcgtttctt   960
tctccggctt tccctctgtg gtgaatttct cagtccggtt gccaggacca gtccccatcc  1020
aatgtcctga gcgtgtgtga cggtcacgtt cttctccatg atagtatcca cctgttctgt  1080
ggagttgtta gcatgatacc caatacagat ctggtcggac ttcaccaggg acacgatagc  1140
cagcagcagc acgattttt ccat                                          1164
```

SEQ ID NO: 287         moltype = DNA   length = 5588
FEATURE                Location/Qualifiers
misc_feature           1..5588
                       note = Synthetic
source                 1..5588
                       mol_type = other DNA
                       organism = synthetic construct
SEQUENCE: 287

```
tcgcgcgttt cggtgatgac ggtgaaaacc tctgacacat gcagctccg gagacggtca    60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaatagga cttccattg acgtcaatgg gtggagtatt tacggtaaac  540
tgcccacttg gcagtacatc aagtgtatca tatgccaagt acgccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccac ccacgctgtt ttgacctcca  960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgctctagag 1380
atatcgccac catggaaaaa atcgtgctgc tgctggctat cgtgtccctg gtgaagtccg 1440
accagatctg tattgggtat catgctaaca actccacaga acaggtggat actatcatgg 1500
agaagaacgt gaccgtcaca cacgctcagg acattggatg gggactggtc ctggcaaccg 1560
gactgagaaa ttcaccacag agggaaagcc ggagaaagaa acgcggactg ttcggcgcta 1620
tcgcagggtt tattgagggc gggtggcagg aatggtgga tgggtggtac ggctaccacc 1680
attccaacga acagggatct ggctacgccg ctgataagga gtctactcag aaagctatcg 1740
acggcgtgac caacatggtc aatagtatca ttgataagat gggctctgga ggcagtggaa 1800
ccgacctggc agagctgctg gtgctgctgc tgaaccagtg gacactgctg ttccacgact 1860
ctaacgtgaa gaatctgtat gataaagtcc gactgcagct gcgggacaac gccaaggaac 1920
tggggaatgg atgcttcgag ttctaccata agtgcgataa cgaatgtatg gagagcatcc 1980
gaaacggcac atacaattat ccccagtatt ccgaggaagc taggctgaaa cgcgaggaaa 2040
ttagctccgg gggagacatc attaagctgc tgaacaacaa ggtgaacaag agatgcagt 2100
ctagtaacct gtacatgagt atgtcaagct ggtgttatac tcactcactg gatggcgccg 2160
ggctgttcct gtttgaccac gcagccgagg aatacgaaac tgctaagaaa ctgatcattt 2220
tcctgaatga gaacaatgtg cccgtccagc tgcatccat ctctgcacct gaacataagt 2280
tcgagggcct gactcagatc tttcagaaag cctacaacca gagcagcat attagtgagt 2340
caatcaacaa tattgtggac cacgccatca agagcaaaga tcatgctacc ttcaattttc 2400
tgcagtggta cgtggccgag cagcacgagg aagaggtcct gtttaaggac atcctggata 2460
aaatcgaact gattggaaac gagaatcatg gcctgtacct ggcagcccag tatgtgaagg 2520
gcattgccaa gtccaggaaa agcgggtcct gatgaacacg tgggatccag atctgctgtg 2580
ccttctagtt gccagccatc tgttgtttgc cctccccg tgccttcctt gaccctggaa 2640
ggtgccactc ccactgtcct ttcctaataa aatgaggaaa ttgcatcgca ttgtctgagt 2700
aggtgtcatt ctattctggg gggtggggtg gggcaggaca gcaaggggga ggattgggaa 2760
gacaatagca ggcatgctgg ggatgcggtg ggctctatgg gtaccaggt gctgaagaat 2820
tgacccggtt cctcctgggc cagaaagaag caggcacatc cccttctctg tgacacaccc 2880
tgtccacgcc cctggttctt agttccagcc ccactcatag gacactcata gctcaggagg 2940
gctccgcctt caatcccacc cgctaaagta cttggagcgg tctctccctc cctcatcagc 3000
ccaccaaacc aaacctagcc tccaagagtg gaagaaatt aaagcaagat aggctcattaa 3060
gtgcagaggg agagaaaatg cctccaacat gtgaggaagt aatgagagaa atcatagaat 3120
tttaaggcca tgatttaagg ccatcatggc cttaatcttc cgcttcctcg ctcactgact 3180
cgctgcgctc ggtcgttcgg ctgcggcgag cggtatcagc tcactcaaag gcggtaatac 3240
ggttatccac agaatcaggg gataacgcag gaaagaacat gtgagcaaaa ggccagcaaa 3300
aggccaggaa ccgtaaaaag gccgcgttgc tggcgttttt ccataggctc cgcccccctg 3360
acgagcatca caaaaatcga cgctcaagtc agaggtggcg aaacccgaca ggactataaa 3420
gataccaggc gtttccccct ggaagctccc tcgtgcgctc tcctgttccg accctgccgc 3480
ttaccggata cctgtccgcc tttctccctt cgggaagcgt ggcgctttct catagctcac 3540
gctgtaggta tctcagttcg gtgtaggtcg ttcgctccaa gctgggctgt gtgcacgaac 3600
cccccgttca gcccgaccgc tgcgccttat ccggtaacta tcgtcttgag tccaacccgg 3660
taagacacga cttatcgcca ctggcagcag ccactggtaa caggattagc agagcgaggt 3720
atgtaggcgg tgctacagag ttcttgaagt ggtggcctaa ctacggctac actagaagaa 3780
cagtatttgg tatctgcgct ctgctgaagc cagttaccct cggaaaaaga gttggtagct 3840
cttgatccgg caaacaaacc accgctggta gcggtggttt tttgtttgc aagcagcaga 3900
```

-continued

```
ttacgcgcag aaaaaaagga tctcaagaag atcctttgat cttttctacg gggtctgacg    3960
ctcagtggaa cgaaaactca cgttaaggga ttttggtcat gagattatca aaaaggatct    4020
tcacctagat cctttaaat taaaaatgaa gttttaaatc aatctaaagt atatatgagt    4080
aaacttggtc tgacagttac caatgcttaa tcagtgaggc acctatctca gcgatctgtc    4140
tatttcgttc atccatagtt gcctgactcg ggggggaggg gcgctgaggt ctgcctcgtg    4200
aagaaggtgt tgctgactca taccaggcct gaatcgcccc atcatccagc cagaaagtga    4260
gggagccacg gttgatgaga gctttgttgt aggtggacca gttggtgatt ttgaacttt    4320
gctttgccac ggaacggtct gcgttgtcgg gaagatgcgt gatctgatcc ttcaactcag    4380
caaaagttcg atttattcaa caaagccgcc gtcccgtcaa gtcagcgtaa tgctctgcca    4440
gtgttacaac caattaacca attctgatta gaaaaactca tcgagcatca aatgaaactg    4500
caatttattc atatcaggat tatcaatacc atatttttga aaaagccgtt tctgtaatga    4560
aggagaaaac tcaccgaggc agttccatag gatggcaaga tcctggtatc ggtctgcgat    4620
tccgactcgt ccaacatcaa tacaacctat taatttcccc tcgtcaaaaa taaggttatc    4680
aagtgagaaa tcaccatgag tgacgactga atccgtgag aatggcaaaa gcttatgcat    4740
ttctttccag acttgttcaa caggccagcc attacgctcg tcatcaaaat cactcgcatc    4800
aaccaaaccg ttattcattc gtgattgcgc ctgagcgaga cgaaatacgc gatcgctgtt    4860
aaaaggacaa ttacaaacag gaatcgaatg caaccggcgc aggaacactg ccagcgcatc    4920
aacaatattt tcacctgaat caggatattc ttctaatacc tggaatgctg ttttcccggg    4980
gatcgcagtg gtgagtaacc atgcatcatc aggagtacgg ataaaatgct tgatggtcgg    5040
aagaggcata aattccgtca gccagtttag tctgaccatc tcatctgtaa catcattggc    5100
aacgctacct ttgccatgtt tcagaaacaa ctctggcgca tcgggcttcc catacaatcg    5160
atagattgtc gcacctgatt gcccgacatt atcgcgagcc catttatacc catataaatc    5220
agcatccatg ttggaattta atcgcggcct cgagcaagac gtttcccgtt gaatatggct    5280
cataacaccc cttgtattac tgtttatgta agcagacagt tttattgttc atgatgatat    5340
atttttatct tgtgcaatgt aacatcagag attttgagac acaacgtggc tttcccccc    5400
cccccattat tgaagcattt atcagggtta ttgtctcatg agcggataca tatttgaatg    5460
tatttagaaa aataaacaaa taggggttcc gcgcacattt ccccgaaaag tgccacctga    5520
cgtctaagaa accattatta tcatgacatt aacctataaa aataggcgta tcacgaggcc    5580
ctttcgtc                                                              5588

SEQ ID NO: 288           moltype = DNA   length = 645
FEATURE                  Location/Qualifiers
misc_feature             1..645
                         note = Synthetic
source                   1..645
                         mol_type = other DNA
                         organism = synthetic construct
CDS                      1..645
SEQUENCE: 288
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta ttgcagggtt tattgagggc    240
gggtggacag gaatggtgga cgggtggtac ggctaccacc atcagaatga gcagggcagc    300
ggctacgccg ctgatcagaa gtctacacag aacgcaatca tggcattac taacatggtg    360
aattctgtca tcgaaaaaat gggcagcgga ggctccggaa catacaacgc tgagctgctg    420
gtgctgctgc tgaacgagcg gactctggat ttccacgata gcaacgtgaa gaatctgtat    480
gagaaggtca aatcccagct gaagaacaat gccaagaaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgac                    645

SEQ ID NO: 289           moltype = AA   length = 215
FEATURE                  Location/Qualifiers
REGION                   1..215
                         note = Synthetic Construct
source                   1..215
                         mol_type = protein
                         organism = synthetic construct
SEQUENCE: 289
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNMV    120
NSVIEKMGSG GSGTYNAELL VLLLNERTLD FHDSNVKNLY EKVKSQLKNN AKEIGNGCFE    180
FYHKCNNECM ESVKNGTYDY PKYSEESKLN REKID                                215

SEQ ID NO: 290           moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 290
gtcaattttc tctcgattca gcttactctc ttcagaatat ttgggatagt cgtaagtgcc     60
gttcttcaca gactccatac attcattgtt gcacttatgg taaaactcga agcatccatt    120
cccgatttct ttggcattgt tcttcagctg ggatttgacc ttctcataca gattcttcac    180
gttgctatcg tggaaatcca gagtccgctc gttcagcagc agcaccagca gctcagcgtt    240
gtatgttccg gagcctccgc tgcccatttt ttcgatgaca gaattcacca tgttagtaat    300
gccattgatt gcgttctgtg tagacttctg atcagcggcg tagccgctgc cctgctcatt    360
ctgatggtgg tagccgtacc acccgtccac cattcctgtc cacccgccct caataaaccc    420
```

```
tgcgatagcg ccgaacagtc ctcttgtttc ccgctgtggg atgttgcgca gtccggtgac    480
catcctcagt ccgctgccca gattcactga gtgggtgaca gtcacgttct tctccaggac    540
ggtatccact gtgtcggtgg agttgtttgc gtgatagccg atgcagatag tgtcagcgta    600
ggttgcggta aaagtacaca gcaggaccag cagtttggcc ttcat                    645
```

```
SEQ ID NO: 291          moltype = DNA   length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 291
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactgg gatggtcac cggactgcgc     180
aacatcccac agcgggaaac aagaggactg ttcggcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca atggcattac taacatggtg    360
aattctgtca tcgaaaaaat gggcagcgga ggctccggaa catacaacgc tgagctgctg    420
gtgctgctgc tgaacgagcg gactctggat ttccacgata gcaacgtgaa gaatctgtat    480
gagaaggtca aatcccagct gaagaacaat gccaagaaa tcgggaatgg atgcttcgag    540
ttttaccata agtgcaacaa tgaatgtatg gagtctgtga gaacggcac ttacgactat    600
cccaaatatt ctgaagagag taagctgaat cgagagaaaa ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg ggctgttcct gtttgatcac    780
gcagccgagg aatacgaaca tgcaaagaaa ctgatcattt tcctgaatga gaacaatgtg    840
cccgtccagc tgacttcaat cagcgcccct gaacataagt tcgagggcct gacccagatc    900
tttcagaaag cttacgaaca cgagcacat atttccagca ctatcaacaa tattgtggac    960
cacgccatta agagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtcat gatga                                                    1155
```

```
SEQ ID NO: 292          moltype = AA   length = 383
FEATURE                 Location/Qualifiers
REGION                  1..383
                        note = Synthetic Construct
source                  1..383
                        mol_type = protein
                        organism = synthetic construct
SEQUENCE: 292
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNMV    120
NSVIEKMGSG GSGTYNAELL VLLLNERTLD FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383
```

```
SEQ ID NO: 293          moltype = DNA   length = 1155
FEATURE                 Location/Qualifiers
misc_feature            1..1155
                        note = Synthetic
source                  1..1155
                        mol_type = other DNA
                        organism = synthetic construct
SEQUENCE: 293
tcatcatgac ccactttttc tggacttggc aatgcccttc acatactgat ctgccaggta     60
caggccatga ttctcgtttc caatcagttc gattttatcc aggatgtcct taaacaggac    120
ctcctcctcg tgctgctcgg ccacgtacca ctgcagaaag ttgaaggtag catgatcttt    180
gctcttaatg gcgtggtcca caatattgtt gatagattcg aaatatgct gctcgtgttc    240
gtaagctttc tgaaagatct gggtcaggcc ctcgaactta tgttcagggg cgctgattga    300
agtcagctgg acgggcacat tgttctcatt caggaaaatg atcagtttct ttgcatgttc    360
gtattcctcg gctgcgtgat caaacaggaa cagcccagcg ccgtccagtg agtgtgtata    420
acaccaacta gacatactca tgtacaggtt ggagctctgc atctccttgt tcacctgttc    480
gttcagcagc ttgatgatgt cgcccccact gtcaatttc tctcgattca gcttactctc    540
ttcagaatat ttgggatagt cgtaagtgcc gttcttcaca gactccatac attcattgtt    600
gcacttatgg taaaactcga agcatccatt cccgatttct ttggcattgt tcttcagctg    660
ggatttgacc ttctcataca gattcttcac gttgctatcg tggaaatcca gagtccgctc    720
gttcagcagc agcaccagca gctcagcgtt gtatgttccg gagcctccgc tgcccatttt    780
ttcgatgaca gaattcacca tgttagtaat gccattgatt gcgttctgtg tagacttctg    840
atcagcggcg tagccgctgc cctgctcatt ctgatggtgg tagccgtacc acccgtccac    900
cattcctgtc cacccgccct caataaaccc tgcgatagcc cgaacagtc ctcttgtttc    960
ccgctgtggg atgttgcgca gtccggtgac catcctcagt ccgctgccca gattcactga   1020
gtgggtgaca gtcacgttct tctccaggac ggtatccact gtgtcggtgg agttgtttgc   1080
gtgatagccg atgcagatag tgtcagcgta ggttgcggta aaagtacaca gcaggaccag   1140
cagtttggcc ttcat                                                    1155
```

```
SEQ ID NO: 294         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 294
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcata  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga cttttccattg acgtcaatgg gtggagtatt tacggtaaac  540
tgcccacttg gcagtacatc aagtgtatca tatgccaagt acgccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagctccca tcggctccca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
cttttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt ccttcccatg 1320
ggtctttct gcagtcaccg tcgtcgacac gtgtgatcag atatcgcggc cgctctagag 1380
atatcgccac catgaaggcc aaactgctgg tcctgctgtg tacttttacc gcaacctacg 1440
ctgacactat ctgcatcggc tatcacgcaa acaactccac cgacacagtg gataccgtcc 1500
tggagaagaa cgtgactgtc acccactcag tgaatctggg cagcggactg aggatggtca 1560
ccggactgcg caacatccca cagcgggaaa caagaggact gttcggcgct atcgcagggt 1620
ttattgaggg cgggtggaca ggaatggtgg acggtgtgta cggctaccac catcagaatg 1680
agcagggcag cggctacgcc gctgatcaga agtctacaca gaacgcaatc aatggcatta 1740
ctaacatggt gaattctgtc atcgaaaaaa tgggcagcgg aggctccgga acatacaacg 1800
ctgagctgct ggtgctgctg ctgaacgagc ggactctgga tttccacgat agcaacgtga 1860
agaatctgta tgagaaggtc aaatcccagc tgaagaacaa tgccaaagaa atcgggaatg 1920
gatgcttcga gttttaccat aagtgcaaca atgaatgtat ggagtctgtg aagaacggca 1980
cttacgacta tcccaaatat tctgaagaga gtaagctgaa tcgagagaaa attgacagtg 2040
ggggcgacat catcaagctg ctgaacgaac aggtgaacaa ggagatgcag agctccaacc 2100
tgtacatgag tatgtctagt tggtgttata cacactcact ggacggcgct gggctgttcc 2160
tgtttgatca cgcagccgag gaatacgaac atgcaaagaa actgatcatt ttcctgaatg 2220
agaacaatgt gcccgtccag ctgacttcaa tcagcgcccc tgaacataag ttcgagggcc 2280
tgacccagat cttttcagaaa gcttacgaac acgagcagca tatttccgaa tctatcaaca 2340
atattgtgga ccacgccatt aagagaaagt atcatgctac cttcaacttt ctgcagtggt 2400
acgtggccga gcagcacgag gaggaggtcc tgtttaagga catcctggat aaaatcgaac 2460
tgattggaaa cgagaatcat ggcctgtacc tggcagatca gtatgtgaag gcattgcca 2520
agtccagaaa aagtgggtca tgatgaacac gtgggatcca gatctgctgt gccttctagt 2580
tgccagccat ctgttgtttg ccctcccc gtgccttcct tgaccctgga aggtgccact 2640
cccactgtcc tttcctaata aaatgaggaa attgcatcgc attgtctgag taggtgtcat 2700
tctattctgg ggggtggggt ggggcaggac agcaagggg aggattggga agacaatagc 2760
aggcatgctg gggatgcggt gggctctatg gtacccagg tgctgaagaa ttgacccggt 2820
tcctcctggg ccagaaagaa gcaggcacat cccttctct gtgacacacc ctgtccacgc 2880
ccctggttct tagttccagc cccactcata ggacactcat agctcaggag gctccgcct 2940
tcaatcccac ccgctaaagt acttggagcg gtctctcct cccctcatcag cccaccaaac 3000
caaacctagc ctccaagagt gggaagaaat taaagcaaga taggctatta agtgcagagg 3060
gagagaaaat gcctccaaca tgtgaggaag taatgagaga aatcatagaa ttttaaggcc 3120
atgatttaag gccatcatgg ccttaatctt ccgcttcctc gctcactgac tcgctgcgct 3180
cggtcgttcg gctgcggcga gcggtatcag ctcactcaaa ggcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgcccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccggat 3480
acctgtccgc ctttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt ttttgtttg caagcagcag attacgcgca 3900
gaaaaaaagg atctcaagaa gatcctttga tcttttctac ggggtctgac gctcagtgga 3960
acgaaaactc acgttaaggg attttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc cccccgggg ggcgctgagg tctgcctcgt gaagaaggtg 4200
```

```
ttgctgactc ataccaggcc tgaatcgccc catcatccag ccagaaagtg agggagccac   4260
ggttgatgag agctttgttg taggtggacc agttggtgat tttgaacttt tgctttgcca   4320
cggaacggtc tgcgttgtcg ggaagatgcg tgatctgatc cttcaactca gcaaaagttc   4380
gatttattca acaaagccgc cgtcccgtca agtcagcgta atgctctgcc agtgttacaa   4440
ccaattaacc aattctgatt agaaaaactc atcgagcatc aaatgaaact gcaatttatt   4500
catatcagga ttatcaatac catattttg aaaaagccgt ttctgtaatg aaggagaaaa   4560
ctcaccgagg cagttccata ggatggcaag atcctggtat cggtctgcga ttccgactcg   4620
tccaacatca atacaaccta ttaatttccc ctcgtcaaaa ataaggttat caagtgagaa   4680
atcaccatga gtgacgactg aatccggtga gaatggcaaa agcttatgca tttctttcca   4740
gacttgttca acaggccagc cattacgctc gtcatcaaaa tcactcgcat caaccaaacc   4800
gttattcatt cgtgattgcg cctgagcgag acgaaatacg cgatcgctgt taaaaggaca   4860
attacaaaca ggaatcgaat gcaaccggcg caggaacact gccagcgcat caacaatatt   4920
ttcacctgaa tcaggatatt cttctaatac ctggaatgct gttttcccgg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc gatagattgt   5160
cgcacctgat tgcccgacat atcgcgagc  catttatac  ccatataaat cagcatccat   5220
gttggaattt aatcgcggcc tcgagcaaga cgtttcccgt tgaatatggc tcataacacc   5280
ccttgtatta ctgtttatgt aagcagacag ttttattgtt catgatgata tatttttatc   5340
ttgtgcaatg taacatcaga gattttgaga cacaacgtgg ctttccccc ccccccatta   5400
ttgaagcatt tatcagggtt attgtctcat gagcggatac atatttgaat gtatttgaaa   5460
aaataaacaa atagggggttc cgcgcacatt tccccgaaaa gtgccacctg acgtctaaga   5520
aaccattatt atcatgacat taacctataa aataggcgt  atcacgaggc cctttcgtc    5579

SEQ ID NO: 295              moltype = DNA   length = 645
FEATURE                     Location/Qualifiers
misc_feature                1..645
                            note = Synthetic
source                      1..645
                            mol_type = other DNA
                            organism = synthetic construct
CDS                         1..645
SEQUENCE: 295
atgaaggcca aactgctggt cctgctgtgt acttttaccg caacctacgc tgacactatc    60
tgcatcggct atcacgcaaa caactccacc gacacagtgc ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat tccacgata gcaacgtgaa gaatctgtat    480
gagaaggtca atcccagct  gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac                   645

SEQ ID NO: 296              moltype = AA    length = 215
FEATURE                     Location/Qualifiers
REGION                      1..215
                            note = Synthetic Construct
source                      1..215
                            mol_type = protein
                            organism = synthetic construct
SEQUENCE: 296
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKID                              215

SEQ ID NO: 297              moltype = DNA   length = 645
FEATURE                     Location/Qualifiers
misc_feature                1..645
                            note = Synthetic
source                      1..645
                            mol_type = other DNA
                            organism = synthetic construct
SEQUENCE: 297
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg gatttgacc  ttctcataca gattcttcac   180
gttgctatcg tggaaatcca gagtccgctc gttcagcagc agcaccagca gctcagccag   240
gtctgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct ctccaggac    540
ggtatccact gtgtcggtgg agttgttgc  gtgatagccg atgcagatag tgtcagcgta   600
ggttgcggta aagtacaca  gcaggaccag cagtttggcc ttcat                   645
```

```
SEQ ID NO: 298           moltype = DNA  length = 1155
FEATURE                  Location/Qualifiers
misc_feature             1..1155
                         note = Synthetic
source                   1..1155
                         mol_type = other DNA
                         organism = synthetic construct
CDS                      1..1155
SEQUENCE: 298
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgaggcg   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg gctgttcct gtttgatcac    780
gcagccgagg aatacgaaca tgcaaagaaa ctgatcattt tcctgaatga gaacaatgtg   840
cccgtccagc tgacttcaat cagcgcccct aacataagt cgagggcct gacccagatc     900
tttcagaaag cttacgaat cgagcagcat atttccagat ctatcaacaa tattgtggac   960
cacgccatta agagcaaaga tcatgctacc ttcaactttc tgcagtggta cgtggccgaa   1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 299           moltype = AA  length = 383
FEATURE                  Location/Qualifiers
REGION                   1..383
                         note = Synthetic Construct
source                   1..383
                         mol_type = protein
                         organism = synthetic construct
SEQUENCE: 299
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                           383

SEQ ID NO: 300           moltype = DNA  length = 1155
FEATURE                  Location/Qualifiers
misc_feature             1..1155
                         note = Synthetic
source                   1..1155
                         mol_type = other DNA
                         organism = synthetic construct
SEQUENCE: 300
tcatcatgac ccactttttc tggacttggc aatgcccttc acatactgat ctgccaggta    60
caggccatga ttctcgtttc caatcagttc gattttatcc aggatgtcct taaacaggac   120
ctcctcctcg tgctgctcgg ccacgtacca ctgcagaaag ttgaaggtag catgatcttt   180
gctcttaatg gcgtggtcca caatattgtt gatagattcg gaaatatgct gctcgtgttc   240
gtaagctttc tgaaagatct gggtcaggcc ctcgaactta tgttcagggg cgctgattga   300
agtcagctga cgggcacat tgttctcatt caggaaaatg atcagtttct tgcatgttc     360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgccccact gtcaattttc tctcgattca gcttactctc    540
ttcagaatat ttgggatagt cgtaagtgcc gttcttcaca gactccatac attcattgtt   600
gcacttatgg taaaactcga agcatccatt ccgatttct tggcattgt tcttcagctg     660
ggatttgacc ttctcataca gattcttcac gttgctatcg tggaaatcca gtccgtcc     720
gttcagcgac agcaccagca gctcagccag gtctgtcccg gagcctccgc tgcccatttt   780
ttcgatgaca gaattcacca tgttagtaat gccattgatt gcgttctgtg tagacttctg   840
atcagcggcg tagccgctgc cctgctcatt ctgatggtgg tagccgtacc acccgtccac   900
cattcctgtc cacccgccct caataaaccc tgcgatagcg ccgaacagtc ctcttgtttc  960
ccgctgtggg atgttgcgca gtccggtgac catcctcagt ccgctgccca gattcactga  1020
gtgggtgaca gtcacgttct tctccaggac ggtatccact gtcggtgg agttgtttgc    1080
gtgatagccg atgcagatag tgtcagcgta ggtgcggta aagtacaca gcaggaccag    1140
cagtttggcc ttcat                                                   1155

SEQ ID NO: 301           moltype = DNA  length = 5579
FEATURE                  Location/Qualifiers
```

| misc_feature | 1..5579 |
| | note = Synthetic |
| source | 1..5579 |
| | mol_type = other DNA |
| | organism = synthetic construct |

SEQUENCE: 301

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgaccccccg cccattgacg tcaataatga cgtatgttcc   480
catagtaacg ccaataggga ctttccattg acgtcaatgg gtggagtatt tacggtaaac   540
tgcccacttg gcagtacatc aagtgtatca tatgccaagt acgccccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct ataagcag    900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgctgt  1080
ggtgcctcct gaactgcgtc cgccgtctag gtaagtttaa agctcaggtc gagaccgggc  1140
ctttgtccgg cgctccctg gagcctacct agactgcgtc ggctctccac gctttgcctg  1200
accctgcttg ctcaactcta gttaacggtg gagggcagtg tagtcgagc agtactcgtt  1260
gctgccgcgc gcgccaccag acataatagc tgacagacta acagactgtt cctttccatg  1320
ggtctttcct gcagtcaccg tcgtcgacac gtgtgatcag atatcgcggc cgctctagag  1380
atatcgccac catgaaggcc aaactgctgg tcctgctgta tactttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acggtggta cggctaccac catcagaatg  1680
agcaggcag cggctacgcc gctgatcaga agtctacaca gaacgcaatc aatgcatta  1740
ctaacatggt gaattctgtc atcgaaaaaa tgggcagcgg aggctccgga acagacctgg  1800
ctgagctgct ggtgctgctg ctgaacgagc ggactctgga tttccacgat agcaacgtga  1860
agaatctgta tgagaaggtc aaatcccagc tgaagaacaa tgccaaagaa atcgggaatg  1920
gatgcttcga gtttaccat aagtgcaaca atgaatgtat ggagtctgtg aagaacgcca  1980
cttacgacta tcccaaatat tctgaagaga gtaagctgag tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgccc tgaacataag ttcgagggcc  2280
tgaccccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgttaagga catcctggat aaaaatcgaac  2460
tgattggaaa cgagaatcat ggcctgtacc tggcagatca gtatgtgaag gcattgcca  2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg gtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagatatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga gttttaaat caatcataaa tatatatgag taaacttggt  4080
ctgacagtta ccaatgctta atcagtgagg cacctatctc agcgatctgt ctatttcgtt  4140
catccatagt tgcctgactc cccgggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaactt tgcttttgcca  4320
cggaacggtc tgcgttgtcg ggaagatgcg tgatctgatc cttcaactca gcaaaagttc  4380
```

```
gatttattca acaaagccgc cgtcccgtca agtcagcgta atgctctgcc agtgttacaa   4440
ccaattaacc aatctctgatt agaaaaactc atcgagcatc aaatgaaact gcaatttatt  4500
catatcagga ttatcaatac catattttg aaaaagccgt ttctgtaatg aaggagaaaa    4560
ctcaccgagg cagttccata ggatggcaag atcctggtat cggtctgcga ttccgactcg   4620
tccaacatca atacaaccta ttaatttccc ctcgtcaaaa ataaggttat caagtgagaa   4680
atcaccatga gtgacgactg aatccgtga gaatggcaaa agcttatgca tttctttcca    4740
gacttgttca acaggccagc cattacgctc gtcatcaaaa tcactcgcat caaccaaacc   4800
gttattcatt cgtgattgcg cctgagcgag acgaaatacg cgatcgctgt taaaaggaca   4860
attacaaaca ggaatcgaat gcaaccggcg caggaacact gccagcgcat caacaatatt   4920
ttcacctgaa tcaggatatt cttctaatac ctggaatgct gttttccggg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc gatagattgt   5160
cgcacctgat tgcccgacat tatcgcgagc ccatttatac ccatataaat cagcatccat   5220
gttggaattt aatcgcggcc tcgagcaaga cgtttcccgt tgaatatggc tcataacacc   5280
ccttgtatta ctgtttatgt aagcagacag ttttattgtt catgatgata tatttttatc   5340
ttgtgcaatg taacatcaga gattttgaga cacaacgtgg ctttcccccc ccccccatta   5400
ttgaagcatt tatcagggtt attgtctcat gagcggatac atatttgaat gtatttagaa   5460
aaataaacaa ataggggttc cgcgcacatt tccccgaaaa gtgccacctg acgtctaaga   5520
aaccattatt atcatgacat taacctataa aaataggcgt atcacgaggc cctttcgtc    5579
```

SEQ ID NO: 302          moltype = DNA   length = 645
FEATURE               Location/Qualifiers
misc_feature        1..645
                        note = Synthetic
source                1..645
                        mol_type = other DNA
                        organism = synthetic construct
CDS                   1..645
SEQUENCE: 302

```
atgaaggcca aactgctggt cctgctgtgt acttttaccg caacctacgc tgacactatc   60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc atcagaatga gcagggcagc  300
ggctacgccg ctgatcagaa gtctacacag aaccgcaatca atggcattac taacatcgtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg agtctctgtga agaacggcac ttacgactat  600
cccaaatatt ctgaagagag taagctgaat cgagagaaaa ttgac               645
```

SEQ ID NO: 303          moltype = AA   length = 215
FEATURE               Location/Qualifiers
REGION                1..215
                        note = Synthetic Construct
source                1..215
                        mol_type = protein
                        organism = synthetic construct
SEQUENCE: 303

```
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKID                            215
```

SEQ ID NO: 304          moltype = DNA   length = 645
FEATURE               Location/Qualifiers
misc_feature        1..645
                        note = Synthetic
source                1..645
                        mol_type = other DNA
                        organism = synthetic construct
SEQUENCE: 304

```
gtcaattttc tctcgattca gcttactctc ttcagaatat ttgggatagt cgtaagtgcc   60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaaatcca gagtccgctc gttgatcagc agcaccagca gctcagccag  240
gtctgttccg gagcctccgc tgcccatttt ttcgatgaca gaattcacga tgttagtaat  300
gccattgatt gcgttctgtg tagacttctg atcagcggcg tagccgctgc cctgctcatt  360
ctgatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct ctccaggac   540
ggtatccact gtgtcggtgg agttgtttgc gtgatagccg atgcagatag tgtcagcgta   600
ggttgcggta aaagtacaca gcaggaccag cagtttggcc ttcat                 645
```

SEQ ID NO: 305          moltype = DNA   length = 1155
FEATURE               Location/Qualifiers
misc_feature        1..1155
                        note = Synthetic

```
source                  1..1155
                        mol_type = other DNA
                        organism = synthetic construct
CDS                     1..1155
SEQUENCE: 305
atgaaggcca aactgctggt cctgctgtgt acttttaccg caacctacgc tgacactatc   60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cggtggtac ggctaccacc atcagaatga gcagggcagc  300
ggctacgccg ctgatcagaa gtctacacag aacgcaatca atggcattac taacatcgtg  360
aattctgtca tcgaaaaaat gggcagcgga ggctccggaa cagacctggc tgagctgctg  420
gtgctgctga tcaacgagcg gactctggat ttccacgata gcaacgtgaa gaatctgtat  480
gagaaggtca atcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag agatgcagaa gctccaacct gtacatgagt  720
atgtctagtt ggtgttatac acactcactg gacggcgctg ggctgttcct gtttgatcac  780
gcagccgagg aatacgaaca tgcaaagaaa ctgatcattt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta agagcaaaga tcatgctacc ttcaactttc tgcagtggta cgtggccgag 1020
cagcacgagg aggaggtcct gtttaaggac atcctggata aaatcgaact gattggaaac 1080
gagaatcatg gcctgtacct ggcagatcag tatgtgaagg gcattgccaa gtccagaaaa 1140
agtgggtcat gatga                                                  1155

SEQ ID NO: 306          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 306
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNIV  120
NSVIEKMGSG GSGTDLAELL VLLINERTLD FHDSNVKNLY EKVKSQLKNN AKEIGNGCFE  180
FYHKCNNECM ESVKNGTYDY PKYSEESKLN REKIDSGGDI IKLLNEQVNK EMQSSNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383

SEQ ID NO: 307          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 307
tcatcatgac ccacttttc tggacttggc aatgcccttc acatactgat ctgccaggta   60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgc acgggacat tgttctcatt caggaaaatg atcagtttct ttgcatgttc  360
gtattcctcg gctgcgtgat caaacaggaa cagcccagcc ccgtccagtg agtgtgtata  420
acaccaacta gacatactca tgtacaggtt ggagctctgc atctccttgt tcacctgttc  480
gttcagcagc ttgatgatgt cgccccact gtcaattttc tctcgattca gcttactctc  540
ttcagaaat ttgggatagt cgtaagtgcc gttcttcaca gactccatac attcattgtt  600
gcacttatgt aaaactcga agcatccatt ccgatttct tggcattgt tcttcagctg  660
ggatttgacc ttctcataca gattcttcac gttgctatcg tggaaatcca gagtccgctc  720
gttgatcagc agcaccagca gctcagccag gtctgttccg gagcctccgc tgcccatttt  780
ttcgatgaca gaattcacga tgttagtaat gccattgatt gcgttctgtg tagacttctg  840
atcagcggcg tagccgctgc cctgctcatt ctgatggtgg tagccgtacc accgtccac  900
cattcctgtc cacccgccct caataaaccc tgcgatagcg ccgaacagtc tcttgtttc  960
ccgctgtggg atgttgcgca gtccggtgac catcctcagt ccgctgccca gattcactga 1020
gtgggtgaca gtcacgttct tctccaggac ggtatccact gtgtcggtgg agttgtttgc 1080
gtgatagccg atgcagatag tgtcagcgta ggttgcggta aagtacaca gcaggaccag 1140
cagtttggcc ttcat                                                 1155

SEQ ID NO: 308          moltype = DNA  length = 5579
FEATURE                 Location/Qualifiers
misc_feature            1..5579
                        note = Synthetic
source                  1..5579
                        mol_type = other DNA
                        organism = synthetic construct
```

```
SEQUENCE: 308
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgaccccg  cccattgacg tcaataatga cgtatgttcc   480
catagtaacg ccaataggga ctttccattg acgtcaatgg gtggagtatt tacggtaaac   540
tgcccacttg gcagtacatc aagtgtatca tatgccaagt acgcccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct ataagcag    900
agctcgttta gtgaaccgtc agatcgcctg gagacgccat ccacgctgtt tgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
cttttgtccg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctccatag  1380
atatcgccac catgaaggcc aaactgctgg tcctgctgtg tactttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acgggtggta cggctaccac catcagaatg  1680
agcagggcag cggctacgcc gctgatcaga agtctacaca gaacgcaatc aatggcatta  1740
ctaacatcgt gaattctgtc atcgaaaaaa tgggcagcgg aggctccgga acagacctgg  1800
ctgagctgct ggtgctgctg atcaacagcg ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacgtca  1980
cttacgacta tcccaaatat tctgaagaga gtaagctgaa tcgagagaaa attgacagtg  2040
ggggcgacat catcaagctg ctgaacaac  aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat cttttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag gcattgcca   2520
agtccagaaa aagtgggtca tgatgaacac gtgggatcca gatctgctgt gccttctagt  2580
tgccagccat ctgttgtttg cccctccccc gtgccttcct tgaccctgga aggtgccact  2640
cccactgtcc tttcctaata aaatgaggaa attgcatcgc attgtctgag taggtgtcat  2700
tctattctgg ggggtgggg  ggggcaggac agcaagggg  aggattggga agacaatagc  2760
aggcatgctg gggatgcggt gggctctatg gtaccagg  tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag gctccgcct   2940
tcaatccac  ccgctaaagt acttggagcg gtctctcctt ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatgaaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt ttttgtttg  caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatctgt ctatttcgtt  4140
catccatagt tgcctgactc cggggggggg ggcgctgagg tctgcctcgt gaagaaggtg  4200
ttgctgactc ataccaggcc tgaatcgccc atcatccag  ccagaaagtg agggagccac  4260
ggttgatgag agctttgttg taggtggacc agttggtgat tttgaacttt tgctttgcca  4320
cggaacgctg tgcgttgtcg ggaagatgcg tgatctgatc cttcaactca gcaaagttcg  4380
gatttattca acaaagccgc cgtcccgtca gtcagcgta  atgctctgcc agtgttacaa  4440
ccaattaacc aattctgatt agaaaaactc atcgagcatc aaatgaaact gcaatttatt  4500
catatcagga ttatcaatac catatttttg aaaagccgt  ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
```

```
atcaccatga gtgacgactg aatccggtga gaatggcaaa agcttatgca tttctttcca   4740
gacttgttca acaggccagc cattacgctc gtcatcaaaa tcactcgcat caaccaaacc   4800
gttattcatt cgtgattgcg cctgagcgag acgaaatacg cgatcgctgt aaaaggaca    4860
attacaaaca ggaatcgaat gcaaccggcg caggaacact gccagcgcat caacaatatt   4920
ttcacctgaa tcaggatatt cttctaatac ctggaatgct gttttcccgg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc gatagattgt   5160
cgcacctgat tgcccgacat tatcgcgagc ccatttatac ccatataaat cagcatccat   5220
gttggaattt aatcgcggcc tcgagcaaga cgtttcccgt tgaatatggc tcataacacc   5280
ccttgtatta ctgtttatgt aagcagacag ttttattgtt catgatgata tattttatc    5340
ttgtgcaatg taacatcaga gattttgaga cacaacgtgg cttccccccc ccccccatta   5400
ttgaagcatt tatcagggtt attgtctcat gagcggatac atatttgaat gtatttagaa   5460
aaataaacaa atagggggttc cgcgcacatt tccccgaaaa gtgccacctg acgtctaaga   5520
aaccattatt atcatgacat taacctataa aaataggagc atcacgaggc cctttcgtc    5579

SEQ ID NO: 309           moltype = DNA  length = 645
FEATURE                  Location/Qualifiers
misc_feature             1..645
                         note = Synthetic
source                   1..645
                         mol_type = other DNA
                         organism = synthetic construct
CDS                      1..645
SEQUENCE: 309
atgaaggcca aactgctggt cctgctgtgt acttttaccg caacctacgc tgacactatc   60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagt   300
ggctacgccg ctgatcagaa gtctacacag aacgcaatca atggcattac taacctggtg   360
aattctgtca tcgaaaaaat gggcagcgga ggctccggaa cagacctggc tgagctgctg   420
gtgctgctga tcaacgagcg gactctggat ttccacgata gcaacgtgaa gaatctgtat   480
gagaaggtca aatcccagct gaagaacaat gccaaagaaa tcgggaatgg atgcttcgag   540
tttatcacat agtgcaacaa tgaatgtatg gagtctgtga agaacggcac ttacgactat   600
cccaaatatt ctgaagagag taagctgaat cgagagaata ttgac                   645

SEQ ID NO: 310           moltype = AA  length = 215
FEATURE                  Location/Qualifiers
REGION                   1..215
                         note = Synthetic Construct
source                   1..215
                         mol_type = protein
                         organism = synthetic construct
SEQUENCE: 310
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNLV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKID                              215

SEQ ID NO: 311           moltype = DNA  length = 645
FEATURE                  Location/Qualifiers
misc_feature             1..645
                         note = Synthetic
source                   1..645
                         mol_type = other DNA
                         organism = synthetic construct
SEQUENCE: 311
gtcaattttc tctcgattca gcttactctc ttcagaatat tgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaaatcca gagtccgctc gttgatcagc agcaccagca gctcagccag   240
gtctgttccg gagcctccgc tgcccatttt ttcgatgaca gaattcacca ggttagtaat   300
gccattgatt gcgttctgtg tagacttctg atcagcggcg tagccgctgc cctgctcatt   360
ctgatggtgg tagccgtacc acccgtccac cattcctgtc caccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct ctccaggac    540
ggtatccact gtgtcggtgg agttgtttgc gtgatagccg atgcagatag tgtcagcgta   600
ggttgcggta aagtacaca gcaggaccag cagtttggcc ttcat                    645

SEQ ID NO: 312           moltype = DNA  length = 1155
FEATURE                  Location/Qualifiers
misc_feature             1..1155
                         note = Synthetic
source                   1..1155
                         mol_type = other DNA
                         organism = synthetic construct
CDS                      1..1155
```

-continued

```
SEQUENCE: 312
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacctggtg   360
aattctgtca tcgaaaaaat gggcagcgga ggctccggaa cagacctggc tgagctgctg   420
gtgctgctga tcaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg ggctgttcct gtttgatcac   780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                  1155

SEQ ID NO: 313          moltype = AA   length = 383
FEATURE                 Location/Qualifiers
REGION                  1..383
                        note = Synthetic Construct
source                  1..383
                        mol_type = protein
                        organism = synthetic construct
SEQUENCE: 313
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNLV   120
NSVIEKMGSG GSGTDLAELL VLLINERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                          383

SEQ ID NO: 314          moltype = DNA   length = 1155
FEATURE                 Location/Qualifiers
misc_feature            1..1155
                        note = Synthetic
source                  1..1155
                        mol_type = other DNA
                        organism = synthetic construct
SEQUENCE: 314
tcatcatgac ccacttttc tggacttggc aatgcccttc acatactgat ctgccaggta    60
caggccatga ttctcgtttc caatcagttc gattttatcc aggatgtcct taaacaggac   120
ctcctcctcg tgctgctcgg ccacgtacca ctgcagaaag ttgaaggtag catgatcttt   180
gctcttaatg gcgtggtcca caatattgtt gatagattcg gaaatatgct gctcgtgttc   240
gtaagctttc tgaaagatct gggtcaggcc ctcgaactta tgttcaggag cttgatgatt   300
agtcagcagc acgggcacat tgttctcatt caggaaaatg atcagttctt ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgcccccact gtcaatttc tctcgattca gcttactctc   540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaaatcca gagtccgctc   720
gttgatcagc agcaccagca gctcagccag gtctgttccg gagcctccgc tgcccatttt   780
ttcgatgaca gaattcacca ggttagtaat gccattgatt gcgttctgtg tagacttctg   840
atcagcggcg tagccgctgc cctgctcatt ctgatggtgg tagccgtacc accgtccac    900
cattcctgtc cacccgccct caataaaccc tgcgatagcg ccgaacagtc tcttgtttc    960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aagtacaca gcaggaccag   1140
cagtttggcc ttcat                                                  1155

SEQ ID NO: 315          moltype = DNA   length = 5579
FEATURE                 Location/Qualifiers
misc_feature            1..5579
                        note = Synthetic
source                  1..5579
                        mol_type = other DNA
                        organism = synthetic construct
SEQUENCE: 315
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
```

```
ctattggcca ttgcatacgt tgtatccata tcataaatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaataggga cttttccattg acgtcaatgg gtggagtatt tacggtaaac   540
tgcccacttg gcagtacatc aagtgtatca tatgccaagt acgccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtccgcg ttctgccgcc tcccgcctgt  1080
ggtgcctcct gaactgcgtc cgccgtctag gtaagtttaa agctcaggtc gagaccgggt  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatcgccac catgaaggcc aaactgctgg tcctgctgtg tactttttacc gcaacctacg  1440
ctgacactat ctgcatcggc tatcacgcaa acaactccac cgacacagtg gataccgtcc  1500
tggagaagaa cgtgactgtc acccactcag tgaatctgag aggatgtgca  1560
ccggactgcg caacatccca cagcgggaaa caagaggact gttcggcgct atcgcagggt  1620
ttattgaggc cgggtggaca ggaatggtgg acgggtggta cggctaccac catcagaatg  1680
agcagggcag cggctacgcc gctgatcaga agtctacaca gaacgcaatc aatggcatta  1740
ctaacctggt gaattctgtc atcgaaaaaa tgggcagcgg aggctccgga acagacctgg  1800
ctgagctgct ggtgctgctg atcaacgagc ggactctgga tttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga gtaagctgaa tcgagagaaa attgacagtg  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcg  2280
tgacccagat ctttcagaaa gcttacgaac acgagcagca tatttccgaa tctatcaaca  2340
atattgtgga ccacgccatt aagagcaaag atcatgctac cttcaacttt ctgcagtggt  2400
acgtggccga gcagcacgag gaggaggtcc tgtttaagga catcctggat aaaatcgaac  2460
tgattggaaa cgagaatcat ggcctgtacc tggcagatca gtatgtgaag ggcattgcca  2520
agtccagaaa aagtgggtca tgatgaacac gtgggatcca gatctgctgt gcctctagt  2580
tgccagccat ctgttgtttg ccctcccccc gtgccttcct tgaccctgga aggtgccact  2640
cccactgtcc tttcctaata aaatgaggaa attgcatcgc attgtctgag taggtgtcat  2700
tctattctgg ggggtgggt ggggcaggac agcaagggg aggattggga agacaatagc  2760
aggcatgctg gggatgcggt gggctctatg gtacccagg tgctgaagaa ttgacccggt  2820
tcctcctggg ccagaaagaa gcaggcacat cccttctct gtgacacacc ctgtccacgc  2880
ccctggttct tagttccagc cccactcata ggacactcat agctcaggag gctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatgaaa ttttaaggcc  3120
atgatttaag gccatcatgg ccttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aggccagcaa  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttcccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgagt aaacttggt   4080
ctgacagtta ccaatgctta atcagtgagg cacctatctc agcgatctgt ctatttcgtt  4140
catccatagt tgcctgactc gggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaagttcg  4380
gatttattca acaaagccgc cgtcccgtca agtcagcgta atgctctgcc agtgttacaa  4440
ccaattaacc aattctgatt agaaaaactc atcgagcatc aaatgaaact gcaatttatt  4500
catatcagga ttatcaatac catattttg aaaaagccgt ttctgtaatg aaggagaaaa  4560
ctcaccgagg cagttccata ggatggcaag atcctggtat cggtctgcga ttccgactcg  4620
tccaacata atacaaccta ttaatttccc ctcgtcaaaa ataaggttat caagtgagaa  4680
atcaccatga gtgacgactg aatccggtga agtggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccgcg caggaacact gccagcgcat caacaatatt  4920
ttcacctgaa tcaggatatt cttctaatac ctggaatgct gttttcccgg ggatcgcagt  4980
```

```
ggtgagtaac catgcatcat caggagtacg gataaaatgc ttgatggtcg gaagaggcat    5040
aaattccgtc agccagttta gtctgaccat ctccatctgta acatcattgg caacgctacc   5100
tttgccatgt ttcagaaaca actctggcgc atcgggcttc ccatacaatc gatagattgt    5160
cgcacctgat tgcccgacat tatcgcgagc ccatttatac ccatataaat cagcatccat    5220
gttggaattt aatcgcggcc tcgagcaaga cgtttcccgt tgaatatggc tcataacacc    5280
ccttgtatta ctgtttatgt aagcagacag ttttattgtt catgatgata tatttttatc    5340
ttgtgcaatg taacatcaga gattttgaga cacaacgtgg ctttccccc ccccccatta     5400
ttgaagcatt tatcagggtt attgtctcat gagcggatac atatttgaat gtatttagaa    5460
aaataaacaa atagggttc cgcgcacatt tccccgaaaa gtgccacctg acgtctaaga     5520
aaccattatt atcatgacat taacctataa aaataggcgt atcacgaggc cctttcgtc    5579
```

```
SEQ ID NO: 316           moltype = DNA   length = 645
FEATURE                  Location/Qualifiers
misc_feature             1..645
                         note = Synthetic
source                   1..645
                         mol_type = other DNA
                         organism = synthetic construct
CDS                      1..645
SEQUENCE: 316
atgaaggcca aactgctggt cctgctgtgt acttttaccg caacctacgc tgacactatc    60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca atggcattac taacctggtg    360
aattctgtca tcgaaaaaat gggcagcgga ggctccggaa cagacctggc tgagctgctg    420
gtgctgctgc tgaacgagcg gactctggat ttccacgata gcaacgtgaa gaatctgtat    480
gagaaggtca atcccagct gaagaacaat gccaaagaaa tcgggaatgg atgcttcgag    540
ttttaccata agtgcaacaa tgaatgtatg gagtctgtga gaacggcac ttacgactat    600
cccaaatatt ctgaagagag taagctgaat cgagagaaaa ttgac                    645

SEQ ID NO: 317           moltype = AA   length = 215
FEATURE                  Location/Qualifiers
REGION                   1..215
                         note = Synthetic Construct
source                   1..215
                         mol_type = protein
                         organism = synthetic construct
SEQUENCE: 317
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNLV    120
NSVIEKMGSG GSGTDLAELL VLLLNERTLD FHDSNVKNLY EKVKSQLKNN AKEIGNGCFE    180
FYHKCNNECM ESVKNGTYDY PKYSEESKLN REKID                               215

SEQ ID NO: 318           moltype = DNA   length = 645
FEATURE                  Location/Qualifiers
misc_feature             1..645
                         note = Synthetic
source                   1..645
                         mol_type = other DNA
                         organism = synthetic construct
SEQUENCE: 318
gtcaattttc tctcgattca gcttactctc ttcagaatat tgggatagtc gtaagtgcc     60
gttcttcaca gactccatac attcattgtt gcacttatgg taaaactcga agcatccatt    120
cccgatttct ttggcattgt tcttcagctg ggatttgacc ttctcataca gattcttcac    180
gttgctatcg tggaaatcca gagtccgctc gttcagcagc agcaccagca gctcagccag    240
gtctgttccg gagcctccgc tgcccatttt ttcgatgaca gaattcacca ggttagtaat    300
gccattgatt gcgttctgtg tagacttctg atcagcggcg tagcgctgc cctgctcatt    360
ctgatggtgg tagccgtacc acccgtccac cattcctgc caccgccct caataaaccc    420
tgcgatagcg ccgaacagtc ctcttgtttc ccgctgtggg atgttgcgca gtccggtgac    480
catcctcagt ccgctgccca gattcactga gtgggtgaca gtcacgttct ctcccaggac   540
ggtatccact gtgtcggtgg agttgtttgc gtgatagccg atgcagatag tgtcagcgta   600
ggttgcggta aagtacaca gcaggaccag cagtttggcc ttcat                    645

SEQ ID NO: 319           moltype = DNA   length = 1155
FEATURE                  Location/Qualifiers
misc_feature             1..1155
                         note = Synthetic
source                   1..1155
                         mol_type = other DNA
                         organism = synthetic construct
CDS                      1..1155
SEQUENCE: 319
atgaaggcca aactgctggt cctgctgtgt acttttaccg caacctacgc tgacactatc    60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcagggtt tattgagggc    240
gggtggacag gaatggtgga cgggtggtac ggctaccacc atcagaatga gcagggcagc    300
```

```
ggctacgccg ctgatcagaa gtctacacag aacgcaatca atggcattac taacctggtg    360
aattctgtca tcgaaaaaat gggcagcgga ggctccggaa cagacctggc tgagctgctg    420
gtgctgctgc tgaacgagcg gactctggat tccacgata gcaacgtgaa gaatctgtat     480
gagaaggtca aatcccagct gaagaacaat gccaaagaaa tcgggaatgg atgcttcgag    540
ttttaccata agtgcaacaa tgaatgtatg gagtctgtga gaacggcac ttacgactat     600
cccaaatatt ctgaagagag taagctgaat cgagagaaaa ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg gctgttcct gtttgatcac     780
gcagccgagg aatacgaaca tgcaaagaaa ctgatcattt tcctgaatga gaacaattgc    840
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta agagcaaaga tcatgctacc ttcaactttc tgcagtggta cgtggccgag    1020
cagcacgagg aggaggtcct gtttaaggac atcctggata aaatcgaact gattggaaac    1080
gagaatcatg gcctgtacct ggcagatcag tatgtgaagg cattgccaa gtccagaaaa    1140
agtgggtcat gatga                                                     1155

SEQ ID NO: 320            moltype = AA  length = 383
FEATURE                   Location/Qualifiers
REGION                    1..383
                          note = Synthetic Construct
source                    1..383
                          mol_type = protein
                          organism = synthetic construct
SEQUENCE: 320
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNLV    120
NSVIEKMGSG GSGTDLAELL VLLLNERTLD FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383

SEQ ID NO: 321            moltype = DNA  length = 1155
FEATURE                   Location/Qualifiers
misc_feature              1..1155
                          note = Synthetic
source                    1..1155
                          mol_type = other DNA
                          organism = synthetic construct
SEQUENCE: 321
tcatcatgac ccacttttttc tggacttggc aatgccttc acatactgat ctgccaggta     60
caggccatga ttctcgtttc caatcagttc gattttatcc aggatgtcct taaacaggac    120
ctcctcctcg tgctgctcgg ccacgtacca ctgcagaaga ttgaaggtag catgatcttt    180
gctcttaatg gcgtggtcca caatattgtt gatagattcg gaaatatgct gctcgtgttc    240
gtaagctttc tgaaagatct gggtcaggcc ctcgaactta tgttcagggg cgctgattga    300
agtcagctgg acgggcacat tgttctcatt caggaaaatg atcagtttct tgcatgttc     360
gtattcctcg gctgcgtgat caaacaggaa cagcccagtg ccgtccagtg agtgtgtata    420
acaccaacta gacatactca tgtacaggtt ggagctctgc atctccttgt tcacctgttc    480
gttcagcagc ttgatgatgt cgcccccact gtcaattttc tctcgattca gcttactctc    540
ttcagaatat ttgggatagt cgtaagtgcc gttcttcaca gactccatac attcattgtt    600
gcacttatgg taaaactcga agcatccatt cccgattct ttggcattgt tcttcagctg     660
ggatttgacc ttctcataca gattcttcac gttgctatcg tggaaatcca gagtccgctc    720
gttcagcagc agcaccagca gctcagccag gtctgttccg gagcctccgc tgcccatttt    780
ttcgatgaca gaattcacca ggttagtaat gccattgatt gcgttctgtg tagacttctg    840
atcagcggcg tagccgctgc cctgctcatt ctgatggtgg tagccgtacc acccgtccac    900
cattcctgtc cacccgccct caataaaccc tgcgatagcg ccgaacagtc ctcttgtttc    960
ccgctgtggg atgttcgcca gtccggtgac catcctcagt ccgctgccca gattcactga    1020
gtgggtgaca gtcacgttct tctccaggac ggtatccact gtgtcggtgg agttgtttgc    1080
gtgatagccc atgcagatag tgtcagcgta ggttgcggta aaagtacaca gcaggaccag    1140
cagtttggcc ttcat                                                     1155

SEQ ID NO: 322            moltype = DNA  length = 5579
FEATURE                   Location/Qualifiers
misc_feature              1..5579
                          note = Synthetic
source                    1..5579
                          mol_type = other DNA
                          organism = synthetic construct
SEQUENCE: 322
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataaatata ttggctcatg tccaacatta     300
ccgccatgtt gacattgatt attgactagt tattaatagt aatcaattac ggggtcatta    360
gttcatagcc catatatgga gttccgcgtt acataactta cggtaaatgg cccgcctggc    420
tgaccgccca acgacccccg cccattgacg tcaataatga cgtatgttcc catagtaacc    480
caataggga cttttccattg acgtcaatgg gtggagtatt tacgggtaaac tgcccacttg    540
gcagtacatc aagtgtatca tatgccaagt acgcccccta ttgacgtcaa                600
```

```
tgacggtaaa tggcccgcct ggcattatgc ccagtacatg acctttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc cgccaccag acataatagc tgacagacta acagactgtt cctttccatg    1320
ggtcttttct gcagtcaccg tcgtcgacac gtgtgatcag atatcgcggc cgctctagag   1380
atatcgccac catgaaggcc aaactgctgg tcctgctgtg tacttttacc gcaacctacg   1440
ctgacactat ctgcatcggc tatcacgcaa acaactccac cgacacagtg gataccgtcc   1500
tggagaagaa cgtgactgtc acccactcag tgaatctggg cagcggactg aggatggtca   1560
ccggactgcg caacatccca cagcgggaaa caagaggact gttcggcgct atcgcagggt   1620
ttattgaggg cggtggaca ggaatggtgg acgggtggta cggctaccac catcagaatg   1680
agcagggcag cggctacgcc gctgatcaga agtctacaca gaacgcaatc aatggcatta   1740
ctaacctggt gaattctgtc atcgaaaaaa tgggcagcgg aggctccgga acagacctgg   1800
ctgagctgct ggtgctgctg ctgaacgagc ggactctgga tttccacgat agcaacgtga   1860
agaatctgta tgagaaggtc aaatcccagc tgaagaacaa tgccaaagaa atcgggaatg   1920
gatgcttcga gttttaccat aagtgcaaca atgaatgtat ggagtctgtg aagaacggca   1980
cttacgacta tcccaaatat tctgaagaga gtaagctgaa tcgagagaaa attgacagtg   2040
ggggcgacat catcaagctg ctgaacgaac aggtgaacaa ggagatgcag agctccaacc   2100
tgtacatgag tatgtctagt tggtgttata cacactcact ggacggcgct gggctgttcc   2160
tgtttgatca cgcagccgag gaatacgaac atgcaaagaa actgatcatt ttcctgaatg   2220
agaacaatgt gcccgtccag ctgacttcaa tcagcgcccc tgaacataag ttcgagggcc   2280
tgacccagat ctttcagaaa gcttacgaac acgagcagca tatttccgaa tctatcaaca   2340
atattgtgga ccacgccatt aagagcaaag atcatgctac cttcaacttt ctgcagtgat   2400
acgtggccga gcagcacgag gaggaggtcc tgtttaagga catcctggat aaaatcgaac   2460
tgattggaaa cgagaatcat ggcctgtacc tggcagatca gtatgtgaag ggcattgcca   2520
agtccagaaa agtgggtca tgatgaacac gtgggatcca gatctgctgt gccttctagt   2580
tgccagccat ctgttgtttg cccctccccc gtgccttcct ggaccctgga aggtgccact   2640
cccactgtcc tttcctaata aaatgaggaa attgcatcgc attgtctgag taggtgtcat   2700
tctattctgg ggggtggggt ggggcaggac agcaagggg aggattggga agacaatagc   2760
aggcatgctg gggatgcggt gggctctatg gtacccagg tgctgaagaa ttgacccggt    2820
tcctcctggg ccagaaagaa gcaggcacat ccccttctct gtgacacacc ctgtccacgc   2880
ccctggttct tagttccagc cccactcata ggacactcat agctcaggag ggctccgcct   2940
tcaatcccac ccgctaaagt acttggagcg gtctctccct ccctcatcag cccaccaaac   3000
caaacctagc ctccaagagt gggaagaaat taaagcaaga taggctatta agtgcagagg   3060
gagagaaaat gcctccaaca tgtgaggaag taatgagaga atcatagaa ttttaaggcc    3120
atgatttaag gccatcatgg ccttaatctt ccgcttcctc gctcactgac tcgctgcgct   3180
cggtcgttcg gctgcggcga gcggtatcag ctcactcaaa ggcggtaata cggttatcca   3240
cagaatcagg ggataacgca ggaaagaaca tgtgagcaaa aggccagcaa aaggccagga   3300
accgtaaaaa ggccgcgttg ctggcgtttt tccataggct ccgcccccct gacgagcatc   3360
acaaaaatcg acgctcaagt cagaggtggc gaaacccgac aggactataa agataccagg   3420
cgtttccccc tggaagctcc ctcgtgcgct ctcctgttcc gaccctgccg cttaccggat   3480
acctgtccgc ctttctccct tcgggaagcg tggcgctttc tcatagctca cgctgtaggt   3540
atctcagttc ggtgtaggtc gttcgctcca agctgggctg tgtgcacgaa ccccccgttc   3600
agcccgaccg ctgcgcctta tccggtaact atcgtcttga gtccaacccg gtaagacacg   3660
acttatcgcc actggcagca gccactggta acaggattag cagagcgagg tatgtaggcg   3720
gtgctacaga gttcttgaag tggtggccta actacggcta cactagaaga acagtatttg   3780
gtatctgcgc tctgctgaag ccagttacct tcggaaaaag agttggtagc tcttgatccg   3840
gcaaacaaac caccgctggt agcggtggtt ttttgtttg caagcagcag attacgcgca   3900
gaaaaaaagg atctcaagaa gatcctttga tcttttctac ggggtctgac gctcagtgga   3960
acgaaaactc acgttaaggg attttggtca tgagattatc aaaaaggatc ttcacctaga   4020
tccttttaaa ttaaaaatga agttttaaat caatctaaag tatatatgag taaacttggt   4080
ctgacagtta ccaatgctta atcagtgagg cacctatctc agcgatctgt ctatttcgtt   4140
catccatagt tgcctgactc ggggggggg ggcgctgagg tctgcctcgt gaagaaggtg    4200
ttgctgactc ataccaggcc tgaatcgccc catcatccag ccagaaagtg agggagccac   4260
ggttgatgag agctttgttg taggtggacc agttggtgat tttgaacttt tgctttgcca   4320
cggaacggtc tgcgttgtcg ggaagatgcg tgatctgatc cttcaactca gcaaaagttc   4380
gatttattca acaaagccgc cgtcccgtca gtcagcgta atgctctgcc agtgttacaa   4440
ccaattaacc aattctgatt agaaaaactc atcgagcatc aaatgaaact gcaatttatt   4500
catatcagga ttatcaatac catattttttt aaaaagccgt ttctgtaatg aaggagaaaa   4560
ctcaccgagg cagttccata ggatggcaag atcctggtat cggtctgcga ttccgactcg   4620
tccaacatca atacaaccta ttaatttccc ctcgtcaaaa ataaggttat caagtgagaa   4680
atcaccatga gtgacgactg aatccggtga agatgcaaa agcttatgca tttctttcca   4740
gacttgttca acaggccagc cattacgctc gtcatcaaaa tcactcgcat caaccaaacc   4800
gttattcatt cgtgattgcg cctgagcgag acgaaatacg cgatcgctgt taaaaggaca   4860
attacaaaca ggaatcgaat gcaaccggcg caggaacact gccagcgcat caacaatatt   4920
ttcacctgaa tcaggatatt cttctaatac ctggaatgct gttttcccgg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc gatagattgt   5160
cgcacctgat tgcccgacat atcgcgagc ccatttatac ccatataaat cagcatccat   5220
gttggaattt aatcgcggcc tcgagcaaga cgtttcccgt tgaatatggc tcataacacc   5280
ccttgtatta ctgtttatgt aagcagacag ttttattgtt catgatgata tatttttatc   5340
```

```
ttgtgcaatg taacatcaga gattttgaga cacaacgtgg cttttccccc ccccccatta   5400
ttgaagcatt tatcagggtt attgtctcat gagcggatac atatttgaat gtatttagaa   5460
aaataaacaa atagggggttc cgcgcacatt tccccgaaaa gtgccacctg acgtctaaga   5520
aaccattatt atcatgacat taacctataa aaataggcgt atcacgaggc cctttcgtc    5579

SEQ ID NO: 323           moltype = DNA    length = 645
FEATURE                  Location/Qualifiers
misc_feature             1..645
                         note = Synthetic
source                   1..645
                         mol_type = other DNA
                         organism = synthetic construct
CDS                      1..645
SEQUENCE: 323
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga gatggtcac cggactgcgc    180
aacatcccac agcgggaaac aagaggactg ttcggcgcta tcgcagggtt tattgagggc   240
gggtggacag aatggtgga cgggtggtac ggctaccacc atcagaatga gcagggcagc    300
ggctacgccg ctgatcagaa gtctacacag aacgcaatca atggcattac taacatggtg   360
aattctgtca tcgaaaaaat gggcagcgga ggctccggaa cagacctggc tgagctgctg    420
gtgctgctga tgaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg agtctgtga agaacggcac ttacgactat    600
cccaaatatt ctgaagagag taagctgaat cgagagaaaa ttgac                    645

SEQ ID NO: 324           moltype = AA     length = 215
FEATURE                  Location/Qualifiers
REGION                   1..215
                         note = Synthetic Construct
source                   1..215
                         mol_type = protein
                         organism = synthetic construct
SEQUENCE: 324
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLMNERTLD FHDSNVKNLY EKVKSQLKNN AKEIGNGCFE   180
FYHKCNNECM ESVKNGTYDY PKYSEESKLN REKID                               215

SEQ ID NO: 325           moltype = DNA    length = 645
FEATURE                  Location/Qualifiers
misc_feature             1..645
                         note = Synthetic
source                   1..645
                         mol_type = other DNA
                         organism = synthetic construct
SEQUENCE: 325
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaaatcca gagtccgctc gttcatcagc agcaccagca gctcagccag   240
gtctgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct tctccaggac   540
ggtatccact gtgtcggtgg agttgtttgc gtgatagccg atgcagatag tgtcagcgta   600
ggttgcggta aaagtacaca gcaggaccag cagtttggcc ttcat                    645

SEQ ID NO: 326           moltype = DNA    length = 1155
FEATURE                  Location/Qualifiers
misc_feature             1..1155
                         note = Synthetic
source                   1..1155
                         mol_type = other DNA
                         organism = synthetic construct
CDS                      1..1155
SEQUENCE: 326
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga gatggtcac cggactgcgc    180
aacatcccac agcgggaaac aagaggactg ttcggcgcta tcgcagggtt tattgagggc   240
gggtggacag aatggtgga cgggtggtac ggctaccacc atcagaatga gcagggcagc    300
ggctacgccg ctgatcagaa gtctacacag aacgcaatca atggcattac taacatggtg   360
aattctgtca tcgaaaaaat gggcagcgga ggctccggaa cagacctggc tgagctgctg    420
gtgctgctga tgaacgagcg gactctggat ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg agtctgtga agaacggcac ttacgactat    600
cccaaatatt ctgaagagag taagctgaat cgagagaaaa ttgacagtgg gggcgacatc   660
```

```
atcaagctgc tgaacgaaca ggtgaacaag gagatgcaga gctccaacct gtacatgagt    720
atgtctagtt ggtgttatac acactcactg gacggcgctg ggctgttcct gtttgatcac    780
gcagccgagg aatacgaaca tgcaaagaaa ctgatcattt tcctgaatga aacaatgtg     840
cccgtccagc tgacttcaat cagcgcccct gaacataagt tcgagggcct gacccagatc    900
tttcagaaag cttacgaaca cgagcagcat atttccaaga ctatcaacaa tattgtggac    960
cacgccatta agagcaaaga tcatgctacc ttcaactttc tgcagtggta cgtggccgag    1020
cagcacgagg aggaggtcct gtttaaggac atcctggata aaatcgaact gattggaaac    1080
gagaatcatg gcctgtacct ggcagatcag tatgtgaagg gcattgccaa gtccagaaaa    1140
agtgggtcat gatga                                                     1155

SEQ ID NO: 327           moltype = AA  length = 383
FEATURE                  Location/Qualifiers
REGION                   1..383
                         note = Synthetic Construct
source                   1..383
                         mol_type = protein
                         organism = synthetic construct
SEQUENCE: 327
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNMV    120
NSVIEKMGSG GSGTDLAELL VLLMNERTLD FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383

SEQ ID NO: 328           moltype = DNA  length = 1155
FEATURE                  Location/Qualifiers
misc_feature             1..1155
                         note = Synthetic
source                   1..1155
                         mol_type = other DNA
                         organism = synthetic construct
SEQUENCE: 328
tcatcatgac ccactttttc tggacttggc aatgccctta cacatactgat ctgccaggta   60
caggccatga ttctcgtttc caatcagttc gattttatcc aggatgtcct taaacaggac   120
ctcctcctcg tgctgctcgg ccacgtacca ctgcagaaag ttgaaggtag catgatcttt   180
gctcttaatg gcgtggtcca caatattgtt gatagattcg gaaatatgct gctcgtgttc   240
gtaagcttc tgaaagatct gggtcaggcc ctcgaactta tgttcagggg cgctgattga    300
agtcagctgg acgggcacat tgttctcatt caggaaaatg atcagttcct ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgccccccact gtcaatttct tctcgattca gcttactctc   540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaaatcca gagtccgctc   720
gttcatcagc agcaccagca gctcatccag tctgttccg gagcctccgc tgcccatttt    780
ttcgatgaca gaattcacca tgttagtaat gccattgatt gcgttctgtg tagacttctg   840
atcagcggcg tagccgctgc cctgctcatt ctgatggtgg tagccgtacc acccgtccac   900
cattcctgtc caccgccct caataaaccc tgcgatagcg ccgaacagtc tcttgtttc     960
ccgctgtggg atgttcgca gtccggtgac catcctcagt ccgctgccca gattcactga   1020
gtgggtgaca gtcacgttct tctccaggac ggtatccact tgtgtcggtgg agttgtttgc  1080
gtgatagccg atgcagatag tgtcagcgta ggttgcggta aaagtacaca gcaggaccag   1140
cagtttggcc ttcat                                                    1155

SEQ ID NO: 329           moltype = DNA  length = 5579
FEATURE                  Location/Qualifiers
misc_feature             1..5579
                         note = Synthetic
source                   1..5579
                         mol_type = other DNA
                         organism = synthetic construct
SEQUENCE: 329
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
```

```
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgctctagag 1380
atatcgccac catgaaggcc aaactgctgg tcctgctgtg tacttttacc gcaacctacg 1440
ctgacactat ctgcatcggc tatcacgcaa acaactccac cgacacagtg gataccgtct 1500
tggagaagaa cgtgactgtc acccactcag tgaatctggg cagcggactg aggatggtca 1560
ccggactgcg caacatccca cagcgggaaa caagaggact gttcggcgct atcgcagggt 1620
ttattgaggg cgggtggaca ggaatggtgg acgggtggta cggctaccac catcagaatg 1680
agcagggcag cggctacgcc gctgatcaga agtctacaca gaacgcaatc aatggcatta 1740
ctaacatggt gaattctgtc atcgaaaaaa tgggcagcgg aggctccgga acagacctgg 1800
ctgagctgct ggtgctgctg atgaacgagc ggactctgga tttccacgat agcaacgtga 1860
agaatctgta tgagaaggtc aaatcccagc tgaagaacaa tgccaaagaa atcgggaatg 1920
gatgcttcga gttttaccat aagtgcaaca atgaatgtat ggagtctgtg aagaacggca 1980
cttacgacta tccccaaatat tctgaagaga gtaagctgaa tcgagagaaa attgacagtg 2040
ggggcgacat catcaagctg ctgaacgaac aggtgaacaa ggagatgcag agctccaacc 2100
tgtacatgag tatgtctagt tggtgttata cacactcact ggacggcgct gggctgttcc 2160
tgtttgatca cgcagccgag gaatacgaac atgcaaagaa actgatcatt ttcctgaatg 2220
agaacaatgt gcccgtccag ctgacttcaa tcagcgcccc tgaacataag ttcgagggcc 2280
tgacccagat ctttcagaaa gcttacgaac acgagcagca tatttccgaa tctatcaaca 2340
atattgtgga ccacgccatt aagagcaaag atcatgctac cttcaacttt ctgcagtggt 2400
acgtggccga gcagcacgag gaggaggtcc tgtttaagga catcctggat aaaatcgaac 2460
tgattggaaa cgagaatcat ggcctgtacc tggcagatca gtatgtgaga ggcattgcca 2520
agtccagaaa aagtgggtca tgatgaacac gtgggatcca gatctgctgt gccttctagt 2580
tgccagccat ctgttgtttg cccctccccc gtgccttcct tgaccctgga aggtgccact 2640
cccactgtcc tttcctaata aaatgaggaa attgcatcgc attgtctgag taggtgtcat 2700
tctattctgg ggggtggggt ggggcaggag agcaaggggg aggattggga agacaatagc 2760
aggcatgctg gggatgcggt gggctctatg ggtacccagg tgctgaagaa ttgacccggt 2820
tcctcctggg ccagaaagaa gcaggcacat ccccttctct gtgacacacc ctgtccacgc 2880
ccctggttct tagttccagc cccactcata ggacactcat agctcaggag ggctccgcct 2940
tcaatccac ccgctaaagt acttggagcg gtctctccct ccctcatcag cccaccaaac 3000
caaacctagc ctccaagagt gggaagaaat taaagcaaga taggctatta agtgcagagg 3060
gagagaaaat gcctccaaca tgtgaggaag taatgagaga aatcatagaa ttttaaggcc 3120
atgatttaag gccatcatgg ccttaatctt ccgcttcctc gctcactgac tcgctgcgct 3180
cggtcgttcg gctgcggcga gcggtatcag ctcactcaaa ggcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccggat 3480
acctgtccgc ctttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt tttttgtttg caagcagcag attacgcgca 3900
gaaaaaaagg atctcaagaa gatcctttga tcttttctac ggggtctgac gctcagtgga 3960
acgaaaactc acgttaaggg attttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc ggggggggg ggcgctgagg tctgcctcgt gaagaaggtg 4200
ttgctgactc ataccaggcc tgaatcgccc catcatccag ccagaaagtg agggagccac 4260
ggttgatgag agctttgttg taggtgacc agttggtgat tttgaacttt tgctttgcca 4320
cggaacggtc tgcgttgtcg ggaagatgcg tgatctgatc cttcaactca gcaaaagttc 4380
gatttattca acaaagccgc cgtcccgtca agtcagcgta atgctctgcc agtgttacaa 4440
ccaattaacc aattctgatt agaaaaactc atcgagcatc aaatgaaact gcaatttatt 4500
catatcagga ttatcaatac catatttttg aaaaagccgt ttctgtaatg aaggagaaaa 4560
ctcaccgagg cagttccata ggatggcaag atcctggtat cggtctgcga ttccgactcg 4620
tccaacatca atacaaccta ttaatttccc ctcgtcaaaa ataaggttat caagtgagaa 4680
atcaccatga gtgacgactg aatccggtga gaatggcaaa agcttatgca tttctttcca 4740
gacttgttca acaggccagc cattacgctc gtcatcaaaa tcactcgcat caaccaaacc 4800
gttattcatt cgtgattgcg cctgagcgag acgaaatacg cgatcgctgt taaaaggaca 4860
attacaaaca ggaatcgaat gcaaccggcg caggaacact gccagcgcat caacaatatt 4920
ttcacctgaa tcaggatatt cttctaatac ctggaatgct gttttcccgg ggatcgcagt 4980
ggtgagtaac catgcatcat caggagtacg gataaaatgc ttgatggtcg gaagaggcat 5040
aaattccgtc agccagttta gtctgaccat ctcatctgta acatcattgg caacgctacc 5100
tttgccatgt ttcagaaaca actctggcgc atcgggcttc ccatacaatc gatagattgt 5160
cgcacctgat tgcccgacat tatcgcgagc ccatttatac ccatataaat cagcatccat 5220
gttggaattt aatcgcggcc tcgagcaaga cgtttcccgt tgaatatggc tcataacacc 5280
ccttgtatta ctgtttatgt aagcagacag ttttattgtt catgatgata tatttttatc 5340
ttgtcaatg taacatcaga gattttgaga cacaacgtgg ctttcccccc cccccatta 5400
ttgaagcatt tatcagggtt attgtctcat gagcggatac atatttgaat gtatttagaa 5460
aaataaacaa ataggggttc cgcgcacatt tccccgaaaa gtgccacctg acgtctaaga 5520
aaccattatt atcatgacat taacctataa aaataggcgt atcacgaggc cctttcgtc  5579

SEQ ID NO: 330    moltype = DNA   length = 645
```

```
FEATURE                 Location/Qualifiers
misc_feature            1..645
                        note = Synthetic
source                  1..645
                        mol_type = other DNA
                        organism = synthetic construct
CDS                     1..645
SEQUENCE: 330
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taaccaggtg   360
aattctgtca tcgaaaaaat gggcagcgga ggctccggaa cagacctggc tgagctgctg   420
gtgctgctgc agaacgagcg gactctggat tccacgata gcaacgtgaa gaatctgtat    480
gagaaggtca atcccagct gaagaacaat gccaaagaaa tcgggaatgg atgcttcgag    540
ttttaccata agtgcaacaa tgaatgtatg gagtctgtga agaacggcac ttacgactat   600
cccaaatatt ctgaagagag taagctgaat cgagagaaa ttgac                    645

SEQ ID NO: 331          moltype = AA   length = 215
FEATURE                 Location/Qualifiers
REGION                  1..215
                        note = Synthetic Construct
source                  1..215
                        mol_type = protein
                        organism = synthetic construct
SEQUENCE: 331
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNQV   120
NSVIEKMGSG GSGTDLAELL VLLQNERTLD FHDSNVKNLY EKVKSQLKNN AKEIGNGCFE   180
FYHKCNNECM ESVKNGTYDY PKYSEESKLN REKID                              215

SEQ ID NO: 332          moltype = DNA   length = 645
FEATURE                 Location/Qualifiers
misc_feature            1..645
                        note = Synthetic
source                  1..645
                        mol_type = other DNA
                        organism = synthetic construct
SEQUENCE: 332
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaaatcca gagtccgctc gttctgcagc agcaccagca gctcagccag   240
gtctgttccg gagcctccgc tgcccatttt ttcgatgaca gaattcacct ggttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc cgctgtgggg atgttgcgca gtccggtgac   480
catcctcagt ccgctgccca gattcactga gtgggtgaca gtcacgttct ctccaggac    540
ggtatccact gtgtcggtgg agttgtttgc gtgatagccg atgcagatag tgtcagcgta   600
ggttgcggta aaagtacaca gcaggaccag cagtttggcc ttcat                   645

SEQ ID NO: 333          moltype = DNA   length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 333
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taaccaggtg   360
aattctgtca tcgaaaaaat gggcagcgga ggctccggaa cagacctggc tgagctgctg   420
gtgctgctgc agaacgagcg gactctggat tccacgata gcaacgtgaa gaatctgtat    480
gagaaggtca atcccagct gaagaacaat gccaaagaaa tcgggaatgg atgcttcgag    540
ttttaccata agtgcaacaa tgaatgtatg gagtctgtga agaacggcac ttacgactat   600
cccaaatatt ctgaagagag taagctgaat cgagagaaaa ttgacagtgg ggcgacatc    660
atcaagctgc tgaacgaaca ggtgaacaag gagatgcaag ctccaacct gtacatgagt   720
atgtctagtt ggtgttatac acactcactg gacggcgctg gctgttcct gtttgatcac    780
gcagccgagg aatacgaaca tgcaaagaaa ctgatcattt tcctgaatga gaacaatgtg   840
cccgtccagc tgacttcaat cagcgcccct gaacataagt cgagggcct gacccagatc   900
tttcagaaag cttacgaaca cgagcagcat atttccgaat ctatcaacaa tattgtggac   960
cacgccatta agagcaaaga tcatgctacc ttcaactttt gcagtggta cgtggccgag  1020
```

```
cagcacgagg aggaggtcct gtttaaggac atcctggata aaatcgaact gattggaaac    1080
gagaatcatg gcctgtacct ggcagatcag tatgtgaagg gcattgccaa gtccagaaaa    1140
agtgggtcat gatga                                                     1155

SEQ ID NO: 334          moltype = AA   length = 383
FEATURE                 Location/Qualifiers
REGION                  1..383
                        note = Synthetic Construct
source                  1..383
                        mol_type = protein
                        organism = synthetic construct
SEQUENCE: 334
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHQNEQGS GYAADQKSTQ NAINGITNQV    120
NSVIEKMGSG GSGTDLAELL VLLQNERTLD FHDSNVKNLY EKVKSQLKNN AKEIGNGCFE    180
FYHKCNNECM ESVKNGTYDY PKYSEESKLN REKIDSGGDI IKLLNEQVNK EMQSSNLYMS    240
MSSWCYTHSL DGAGLFLFDH AAEEYEHAKK LIIFLNENNV PVQLTSISAP EHKFEGLTQI    300
FQKAYEHEQH ISESINNIVD HAIKSKDHAT FNFLQWYVAE QHEEEVLFKD ILDKIELIGN    360
ENHGLYLADQ YVKGIAKSRK SGS                                            383

SEQ ID NO: 335          moltype = DNA   length = 1155
FEATURE                 Location/Qualifiers
misc_feature            1..1155
                        note = Synthetic
source                  1..1155
                        mol_type = other DNA
                        organism = synthetic construct
SEQUENCE: 335
tcatcatgac ccactttttc tggacttggc aatgcccttc acatactgat ctgccaggta     60
caggccatga ttctcgtttc caatcagttc gattttatcc aggatgtcct taaacaggac    120
ctcctcctcg tgctgctcgg ccacgtacca ctgcagaaag ttgaaggtag catgatcttt    180
gctcttaatg gcgtggtcca caatattgtt gatagattcg gaaatatgct gctcgtgttc    240
gtaagctttc tgaaagatct gggtcaggcc ctcgaactta tgttcagggg cgctgattga    300
agtcagctgg acgggcacat tgttctcatt caggaaaatg atcagtttct ttgcatgttt    360
gtattcctcg gctgcgtgat caaacaggaa cagcccagcg ccgtccagtg agtgtgtata    420
acaccaacta gacatactca tgtacaggtt ggagctctgc atctccttgt tcacctgttc    480
gttcagcagc ttgatgatgt cgccccccact gtcaattttc tctcgattca gcttactctc    540
ttcagaatat ttgggatagt cgtaagtgcc gttcttcaca gactccatac attcattgtt    600
gcacttatgg taaaactcga agcatccatt cccgatttct ttggcattgt tcttcagctg    660
ggatttgacc ttctcataca gattcttcac gttgctatcg tggaaatcca gagtccgctc    720
gttctgcagc agcaccagca gctcagccag gtctgttccg gagcctccgc tgcccatttt    780
ttcgatgaca gaattcacct ggttagtaat gccattgatt gcgttctgtg tagacttctg    840
atcagcggca tagccgctgc cctgctcatt ctgatgcgtg tagccgtacc acccgtccac    900
cattcctgtc caccgcccct caataaaccc tgcgatagcc cgaacagtc ctcttgtttc     960
ccgctgtggg atgttgcgca gtccggtgac catcctcagt ccgctgccca gattcactga   1020
gtgggtgaca gtcacgttct tctccaggac ggtatccact gtgtcggtgg agttgtttgc   1080
gtgatagccg atgcagatag tgtcagcgta ggttgcggta aaagtacaca gcaggaccag   1140
cagtttggcc ttcat                                                    1155

SEQ ID NO: 336          moltype = DNA   length = 5579
FEATURE                 Location/Qualifiers
misc_feature            1..5579
                        note = Synthetic
source                  1..5579
                        mol_type = other DNA
                        organism = synthetic construct
SEQUENCE: 336
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggaa ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacat accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca     960
tagaagacac cgggaccgat ccagcctcca cggctctcct tctccttcc acgcgccccgc    1020
cgcctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
cttttgtccgg cgctcccttg gagcctacct agactcagcc ggctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
```

```
ggtcttttct gcagtcaccg tcgtcgacac gtgtgatcag atatcgcggc cgctctagag 1380
atatcgccac catgaaggcc aaactgctgg tcctgctgtg tactttttacc gcaacctacg 1440
ctgacactat ctgcatcggc tatcacgcaa acaactccac cgacacagtg gataccgtcc 1500
tggagaagaa cgtgactgtc acccactcag tgaatctggg cagcggactg aggatggtca 1560
ccggactgcg caacatccca cagcgggaaa caagaggact gttcgcgcgt atcgcagggt 1620
ttattgaggg cgggtggaca ggaatggtgg acgggtggta cggctaccac catcagaatg 1680
agcagggcag cggctacgcc gctgatcaga agtctacaca gaacgcaatc aatggcatta 1740
ctaaccaggt gaattctgtc atcgaaaaaa tgggcagcgg aggctccgga acagacctgg 1800
ctgagctgct ggtgctgctg cagaacgagc ggactctgga tttccacgat agcaacgtga 1860
agaatctgta tgagaaggtc aaatcccagc tgaagaacaa tgccaaagaa atcgggaatg 1920
gatgcttcga gttttaccat aagtgcaaca atgaatgtat ggagtctgtg aagaacggca 1980
cttacgacta tcccaaatat tctgaagaga gtaagctgaa tcgagagaaa attgacagtg 2040
ggggcgacat catcaagctg ctgaacgaac aggtgaacaa ggagatgcag agctccaacc 2100
tgtacatgag tatgtctagt tggtgttata cacactcact ggacggcgct gggctgttcc 2160
tgtttgatca cgcagccgag gaatacgaac atgcaaagaa actgatcatt ttcctgaatg 2220
agaacaatgt gcccgtccag ctgacttcaa tcagcgcccc tgaacataag ttcgagggcc 2280
tgacccagat ctttcagaaa gcttacgaac acgagcagca tatttccgaa tctatcaaca 2340
atattgtgga ccacgccatt aagagcaaag atcatgctac cttcaacttt ctgcagtggt 2400
acgtggccga gcagcacgag gaggaggtcc tgtttaagga catcctggat aaaatcgaac 2460
tgattggaaa cgagaatcat ggcctgtacc tggcagatca gtatgtgaag ggcattgcca 2520
agtccagaaa aagtgggtca tgatgaacac gtgggatcca gatctgctgt gccttctagt 2580
tgccagccat ctgttgtttg ccccctcccc gtgccttcct tgaccctgga aggtgccact 2640
cccactgtcc tttcctaata aaatgaggaa attgcatcgc attgtctgag taggtgtcat 2700
tctattctgg ggggtggggt ggggcaggac agcaagggg aggattggga agacaatagc 2760
aggcatgctg gggatgcggt gggctctatg gtacccagg tgctgaagaa ttgacccggt 2820
tcctcctggg ccagaaagaa gcaggcacat ccccttctct gtgacacacc ctgtccacgc 2880
ccctggttct tagttccagc cccactcata ggacactcat agctcaggag ggctccgcct 2940
tcaatcccac ccgctaaagt acttggagcg gtctctccct ccctcatcag cccaccaaac 3000
caaacctagc ctccaagagt gggaagaaat taaagcaaga taggctatta agtgcagagg 3060
gagagaaaat gcctccaaca tgtgagaag taatgagaga aatcatagaa tttttaaggcc 3120
atgatttaag gccatcatgg ccttaatctt ccgcttcctc gctcactgac tcgctgcgct 3180
cggtcgttcg gctgcggcga gcggtatcag ctcactcaaa ggcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgcccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccggat 3480
acctgtccgc ctttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt tttttgtttg caagcagcag attacgcgca 3900
gaaaaaaagg atctcaagaa gatcctttga tcttttctac ggggtctgac gctcagtgga 3960
acgaaaactc acgttaaggg attttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc ggggggggg ggcgctgagg tctgcctcgt gaagaaggtg 4200
ttgctgactc ataccaggcc tgaatcgccc catcatccag ccagaaagtg agggagccac 4260
ggttgatgag agctttgttg taggtggacc agttggtgat tttgaacttt tgctttgcca 4320
cggaacggtc tgcgttgtcg ggaagatgcg tgatctgatc cttcaactca gcaaagttcg 4380
gatttattca acaaagccgc cgtcccgtca agtcagcgta atgctctgcc agtgttacaa 4440
ccaattaacc aattctgatt agaaaaactc atcgagcatc aaatgaaact gcaatttatt 4500
catatcagga ttatcaatac catattttg aaaagccgt ttctgtaatg aaggagaaaa 4560
ctcaccgagg cagttccata ggatgcaag atcctggtat cggtctgcga ttccgactcg 4620
tccaacatca atacaaccta ttaatttccc ctcgtcaaaa ataaggttat caagtgagaa 4680
atcaccatga gtgacgactg aatccggtga gaatggcaaa agcttatgca tttctttcca 4740
gacttgttca acaggccagc cattacgctc gtcatcaaaa tcactcgcat caaccaaacc 4800
gttattcatt cgtgattgcg cctgagcgag acgaaatacg cgatcgctgt taaaaggaca 4860
attacaaaca ggaatcgaat gcaaccggcg caggaacact gccagcgcat caacaatatt 4920
ttcacctgaa tcaggatatt cttctaatac ctggaatgct gttttcccgg ggatcgcagt 4980
ggtgagtaac catgcatcat caggagtacg gataaaatgc ttgatggtcg gaagaggcat 5040
aaattccgtc agccagttta gtctgaccat ctcatctgta acatcattgg caacgctacc 5100
tttgccatgt ttcagaaaca actctggcgc atcgggcttc ccatacaatc gatagattgt 5160
cgcacctgat tgcccgacat tatcgcgagc ccatttatac ccatataaat cagcatccat 5220
gttggaattt aatcgcggcc tcgagcaaga cgtttcccgt tgaatatggc tcataacacc 5280
ccttgtatta ctgtttatgt aagcagacag ttttattgtt catgatgata tatttttatc 5340
ttgtgcaatg taacatcaga gattttgaga cacaacgtgg ctttcccccc cccccattta 5400
ttgaagcatt tatcagggtt attgtctcat gagcggatac atatttgaat gtatttagaa 5460
aaataaacaa ataggggttc gcgcacatt tccccgaaaa gtgccacctg acgtctaaga 5520
aaccattatt atcatgacat taacctataa aaataggcgt atcacgaggc cctttcgtc  5579
```

```
SEQ ID NO: 337        moltype = DNA   length = 645
FEATURE               Location/Qualifiers
misc_feature          1..645
                      note = Synthetic
source                1..645
                      mol_type = other DNA
                      organism = synthetic construct
```

| CDS | 1..645 |
|---|---|

SEQUENCE: 337

```
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca ccaactcaac taatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat ttccacgata gcaacgtgaa gaatctgtat   480
gagaaggtca aatcccagct gaagaacaat gccaaagaaa tcgggaatgg atgcttcgag   540
tttaccata agtgcaacaa tgaatgtatg gagtctgtga agaacggcac ttacgactat   600
cccaaatatt ctgaagagag taagctgaat cgagagaaaa ttgac                   645
```

| SEQ ID NO: 338 | moltype = AA length = 215 |
|---|---|
| FEATURE | Location/Qualifiers |
| REGION | 1..215 |
| | note = Synthetic Construct |
| source | 1..215 |
| | mol_type = protein |
| | organism = synthetic construct |

SEQUENCE: 338

```
MKAKLLVLLC TFTATYADTI CIGYHANNST DTVDTVLEKN VTVTNSTNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKID                              215
```

| SEQ ID NO: 339 | moltype = DNA length = 645 |
|---|---|
| FEATURE | Location/Qualifiers |
| misc_feature | 1..645 |
| | note = Synthetic |
| source | 1..645 |
| | mol_type = other DNA |
| | organism = synthetic construct |

SEQUENCE: 339

```
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaaatcca gagtccgctc gttcagcagc agcaccagca gctcagccag   240
gtctgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc caccgcccct caataaaccc   420
tgcgatagcg ccgaacagtc ctcttgtttc ccgctgcgga tgttgcga gtccggtgac   480
catcctcagt ccgctgccca gattagttga gttggtgaca gtcacgttct tctccaggac   540
ggtatccact gtgtcgtgg agttgtttgc gtgatagccg atgcagatag tgtcagcgta   600
ggttgcggta aagtacaca gcaggaccag cagtttggcc ttcat                    645
```

| SEQ ID NO: 340 | moltype = DNA length = 1155 |
|---|---|
| FEATURE | Location/Qualifiers |
| misc_feature | 1..1155 |
| | note = Synthetic |
| source | 1..1155 |
| | mol_type = other DNA |
| | organism = synthetic construct |
| CDS | 1..1155 |

SEQUENCE: 340

```
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca ccaactcaac taatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgctgc tgaacgagcg gactctggat ttccacgata gcaacgtgaa gaatctgtat   480
gagaaggtca aatcccagct gaagaacaat gccaaagaaa tcgggaatgg atgcttcgag   540
tttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg acggcgctg gctgttcct gtttgatcac   780
gcagccgagg aatacgaaca tgcaaagaaa ctgatcattt tcctgaatga aacaatgtg   840
cccgtccagc tgacttcaat cagcgcccct gaacataagt cgagggcct gacccagatc   900
tttcagaaag cttacgaaca cgagcagcat atttccgaat ctatcaacaa tattgtgac   960
cacgccatta agagcaaaga tcatgctacc ttcaactttc tgcagtggta cgtggccgag  1020
cagcacgagg aggaggtcct gtttaaggac atccttggata aaatcgaact gattggaaac  1080
gagaatcatg gcctgtacct ggcagatcag tatgtgaagg gcattgccaa gtccagaaaa  1140
agtgggtcat gatga                                                  1155
```

| SEQ ID NO: 341 | moltype = AA length = 383 |
|---|---|
| FEATURE | Location/Qualifiers |

```
REGION                  1..383
                        note = Synthetic Construct
source                  1..383
                        mol_type = protein
                        organism = synthetic construct
SEQUENCE: 341
MKAKLLVLLC TFTATYADTI CIGYHANNST DTVDTVLEKN VTVTNSTNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLLLNERTLD FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                          383

SEQ ID NO: 342          moltype = DNA  length = 1155
FEATURE                 Location/Qualifiers
misc_feature            1..1155
                        note = Synthetic
source                  1..1155
                        mol_type = other DNA
                        organism = synthetic construct
SEQUENCE: 342
tcatcatgac ccactttttc tggacttggc aatgcccttc acatactgat ctgccaggta     60
caggccatga ttctcgtttc caatcagttc gattttatcc aggatgtcct taaacaggac    120
ctcctcctcg tgctgctcgg ccacgtacca ctgcagaaag ttgaaggtag catgatcttc    180
gctcttaatg gcgtggtcca caatattgtt gatagatcg gaaatatgct gctcgtgttc    240
gtaagctttc tgaaagatct gggtcaggcc ctcgaactta tgttcagggg cgctgattga    300
agtcagctgg acgggcacat tgttctcatt caggaaaatg atcagtttct ttgcatgttc    360
gtattcctcg gctgcgtgat caaacaggaa cagcccagcg ccgtcagtg agtgtgtata    420
acaccaacta gacatactca tgtacaggtt ggagctctgc atctccttgt tcacctgttc    480
gttcagcagc ttgatgatgt cgcccccact gtcaatttc tctcgattca gcttactctc    540
ttcagaatat ttgggatagt cgtaagtgcc gttcttcaca gactccatac attcattgtt    600
gcacttatgt taaaactcga agcatccatt cccgatttct tggcattgt tcttcagctg    660
ggatttgacc ttctcataca gattcttcac gttgctatcg tggaaatcca gagtccgatc    720
gttcagcagc agcaccagca gctcagccag gtctgttccg gagcctccgc tgcccatttt    780
ttcgatgaca gaattcacca tgttagtaat gccattgatt gcgttctgtg tagacttctg    840
atcagcggcg tagccgctgc cctgctcatt ctgatggtgg tagccgtacc acccgtccac    900
cattcctgtc caccgccct caataaaccc tgcgatagcg ccgaacagtc ctcttgttc    960
ccgctgtggg atgttgcga gtccgctgac catcctcagt ccgctgccca gattagttga  1020
gttggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                  1155

SEQ ID NO: 343          moltype = DNA  length = 5579
FEATURE                 Location/Qualifiers
misc_feature            1..5579
                        note = Synthetic
source                  1..5579
                        mol_type = other DNA
                        organism = synthetic construct
SEQUENCE: 343
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagga ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag cgtgtacgg tggaggtct atataagcag    900
agctcgttta gtgaaccgtc agatcgcctg gagacgccat ccacgctgtt tgacctcca    960
tagaagacac cgggaccgat ccagcctcca tcggctcgca tctctccttc acgcgcccgc   1020
cgccctacct gaggccgcca tccacgccg ttgagtcgta ttctgccgcc tcccgcctg   1080
ggtgcctcct gaactgcgtc cgccgtctag gtaagtttaa agctcaggtc gagaccgggc   1140
ctttgtcgg cgctccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtctttttc tgcagtcacc gtcgtgacac gttgatcag atatcgcgg tactctagag   1380
atatcgccac catgaaggcc aaactgctgg tcctgctgtg tactttttacc gcaacctacg   1440
ctgacactat ctgcatcggc tatcacgcaa acaactccac cgacacagtg gataccgtcc   1500
tggagaagaa cgtgactgtc accaactcaa ctaatctggg cagcggactg aggatggtca   1560
ccggactgcg caacatccca cagcgggaaa caagaggact gttcggcgct atcgcagggt   1620
ttattgaggg cgggtggaca ggaatggtgg acggtgtgta cggctaccac catcagaatg   1680
```

```
agcagggcag cggctacgcc gctgatcaga agtctacaca gaacgcaatc aatggcatta 1740
ctaacatggt gaattctgtc atcgaaaaaa tgggcagcgg aggctccgga acagacctgg 1800
ctgagctgct ggtgctgctg ctgaacgagc ggactctgga tttccacgat agcaacgtga 1860
agaatctgta tgagaaggtc aaatcccagc tgaagaacaa tgccaaagaa atcgggaatg 1920
gatgcttcga gttttaccat aagtgcaaca atgaatgtat ggagtctgtg aagaacggca 1980
cttacgacta tcccaaatat tctgaagaga gtaagctgaa tcgagagaaa attgacagtg 2040
ggggcgacat catcaagctg ctgaacgaac aggtgaacaa ggagatgcag agctccaacc 2100
tgtacatgag tatgtctagt tggtgttata cacactcact ggacggcgct gggctgttcc 2160
tgtttgatca cgcagccgag gaatacgaac atgcaaagaa actgatcatt ttcctgaatg 2220
agaacaatgt gcccgtccag ctgacttcaa tcagcgcccc tgaacataag ttcgagggcc 2280
tgacccagat ctttcagaaa gcttacgaac acgagcagca tatttccgaa tctatcaaca 2340
atattgtgga ccacgccatt aagagcaaag atcatgctac cttcaacttt ctgcagtggt 2400
acgtggccga gcagcacgag gaggaggtcc tgtttaagga catcctggat aaaatcgaac 2460
tgattggaaa cgagaatcat ggcctgtacc tggcagatca gtatgtgaag gcattgcca 2520
agtccagaaa aagtgggtca tgatgaacac gtgggatcca gatctgctgt gccttctagt 2580
tgccagccat ctgttgtttg ccctcccc gtgccttcct tgaccctgga aggtgccact 2640
cccactgtcc tttcctaata aaatgaggaa attgcatcgc attgtctgag taggtgtcat 2700
tctattctgg ggggtggggt ggggcaggac agcaaggggg aggattggga agacaatagc 2760
aggcatgctg gggatgcggt gggctctatg ggtacccagg tgctgaagaa ttgacccggt 2820
tcctcctggg ccagaaagaa gcaggacat cccttctct gtgacacacc ctgtccacgc 2880
ccctggttct tagttccagc cccactcata ggacactcat agctcaggag ggctccgcct 2940
tcaatcccac ccgctaaagt acttggagcg gtctctccct ccctcatcag cccaccaaac 3000
caaacctagc ctccaagagt gggaagaaat taaagcaaga taggctatta agtgcagagg 3060
gagagaaaat gcctccaaca tgtgaggaag taatgagaga aatcatgaa ttttaaggcc 3120
atgatttaag gccatcatgg ccttaatctt ccgcttcctc gctcactgac tcgctgcgct 3180
cggtcgttcg gctgcggcga gcggtatcag ctcactcaaa gcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgcccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccggat 3480
acctgtccgc cttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt tttttgttg caagcagcag attacgcgca 3900
gaaaaaaagg atctcaagaa gatccttga tcttttctac ggggtctgac gctcagtgga 3960
acgaaaactc acgttaaggg atttttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc ggggggggg ggcgctgagg tctgcctcgt gaagaaggtg 4200
ttgctgactc ataccaggcc tgaatcgccc catcatccga ccagaaagtg agggagccac 4260
ggttgatgag agctttgttg taggtggacc agttggtgat tttgaacttt tgctttgcca 4320
cggaacggtc tgcgttgtcg ggaagatgcg tgatctgatc cttcaactca gcaaagttc 4380
gatttattca acaaagccgc cgtcccgtca agtcagcgta atgctctgcc agtgttacaa 4440
ccaattaacc aattctgatt agaaaaactc atcgagcatc aaatgaaact gcaatttatt 4500
catatcagga ttatcaatac catattttg aaaaagccgt ttctgtaatg aaggagaaaa 4560
ctcaccgagg cagttccata ggatggcaag atcctggtat cggtctgcga ttccgactcg 4620
tccaacatca atacaaccta ttaatttccc ctcgtcaaaa ataaggttat caagtgagaa 4680
atcaccatga gtgacgactg aatccggtga gaatggcaaa agcttatgca tttctttcca 4740
gacttgttca acaggccagc cattacgctc gtcatcaaaa tcactcgcat caaccaaacc 4800
gttattcatt cgtgattgcg cctgagcgag acgaaatacg cgatcgctgt taaaggaca 4860
attacaaaca ggaatcgaat gcaaccggcg caggaacact gccagcgcat caacaatatt 4920
ttcacctgaa tcaggatatt cttctaatac ctggaatgct gttttcccgg ggatcgcagt 4980
ggtgagtaac catgcatcat caggagtacg gataaaatgc ttgatggtcg gaagaggcat 5040
aaattccgtc agccagttta gtctgaccat ctcatctgta acatcattgg caacgctacc 5100
tttgccatgt ttcagaaaca actctggcgc atcgggcttc ccatacaatc gatagattgt 5160
cgcacctgat tgcccgacat tcatcgcagc ccatttatac ccatataaat cagcatccat 5220
gttggaattt aatcgcggcc tcgagcaaga cgtttcccgt tgaatatggc tcataacacc 5280
ccttgtatta ctgtttatgt aagcagacag ttttattgtt catgatgata tattttatc 5340
ttgtgcaatg taacatcaga gattttgaga cacaacgtgg cttttcccccc cccccatta 5400
ttgaagcatt tatcagggtt attgtctcat gagcggatac atatttgaat gtatttagaa 5460
aaataaacaa atagggttc gcgcacatt tccccgaaaa gtgccacctg acgtctaaga 5520
aaccattatt atcatgacat taacctataa aaataggcgt atcacgaggc cctttcgtc 5579

SEQ ID NO: 344     moltype = DNA   length = 645
FEATURE            Location/Qualifiers
misc_feature       1..645
                   note = Synthetic
source             1..645
                   mol_type = other DNA
                   organism = synthetic construct
CDS                1..645
SEQUENCE: 344
atgaaggcca aactgctggt cctgctgtgt acttttaccg caacctacgc tgacactatc 60
tgcatcggct atcacgcaaa caactccacc gacacagtgg ataccattct ggagaagaac 120
gtgactgtca cccactcagt gaatctgggc agcggactga ggatggtcac cggactgcgc 180
aacatcccac agcgggaaac aagaggactg ttcggcgcta tcgcagggtt tattgagggc 240
```

```
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgatgc tgaaccagtt cactctgctg ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgac              645

SEQ ID NO: 345          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 345
MKAKLLVLLC TFTATYADTI CIGYHANNST DTVDTILEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLMLNQFTLL FHDSNVKNLY EKVKSQLKNN AKEIGNGCFE   180
FYHKCNNECM ESVKNGTYDY PKYSEESKLN REKID                             215

SEQ ID NO: 346          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 346
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtgaactg gttcagcatc agcaccagca gctcagccaa   240
gtctgttccg gagcctccgc tgcccatttt tcgatgacaa gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct tctccagaat   540
ggtatccact gtgtcggtgg agttgtttgc gtgatagccg atgcagatag tgtcagcgta   600
ggttgcggta aaagtacaca gcaggaccag cagtttggcc ttcat                  645

SEQ ID NO: 347          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 347
atgaaggcca aactgctggt cctgctgtgt acttttaccg caacctacgc tgacactatc    60
tgcatcggct atcacgcaaa caactccacc gacacagtgg ataccattct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggctccggaa cagacctggc tgagctgctg   420
gtgctgatgc tgaaccagtt cactctgctg ttccacgata gcaacgtgaa gaatctgtat   480
gagaaggtca aatcccagct gaagaacaat gccaaagaaa tcgggaatgg atgcttcgag   540
ttttaccata agtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg ggctgttcct gtttgatcac   780
gcagccgagg aatacgaaca tgcaaagaaa ctgatcattt tcctgaatga aacaatgtg    840
cccgtccagc tgacttcaat cagcgcccct gaacataagt tcgagggcct gacccagatc   900
tttcagaaag cttacgaaca cgagcagcat atttccgaat ctatcaacaa tattgtggac   960
cacgccatta gagcaaaaga tcatgctacc ttcaactttc tgcagtggta cgtggccgag  1020
cagcacgagg aggaggtcct gttttaaggac atcctgtgga aaatcgaact gattggaaac  1080
gagaatcatg gcctgtacct ggcagatcag tatgtgaagg gcattgccaa gtccagaaaa  1140
agtgggtcat gatga                                                    1155

SEQ ID NO: 348          moltype = AA  length = 383
FEATURE                 Location/Qualifiers
REGION                  1..383
                        note = Synthetic Construct
source                  1..383
                        mol_type = protein
                        organism = synthetic construct
```

```
SEQUENCE: 348
MKAKLLVLLC TFTATYADTI CIGYHANNST DTVDTILEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GSGTDLAELL VLMLNQFTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                          383

SEQ ID NO: 349         moltype = DNA  length = 1155
FEATURE                Location/Qualifiers
misc_feature           1..1155
                       note = Synthetic
source                 1..1155
                       mol_type = other DNA
                       organism = synthetic construct
SEQUENCE: 349
tcatcatgac ccactttttc tggacttggc aatgccctttc acatactgat ctgccaggta    60
caggccatga ttctcgtttc caatcagttc gatttttatcc aggatgtcct taaacaggac   120
ctcctcctcg tgctgctcgg ccacgtacca ctgcagaaag ttgaaggtag catgatctttt   180
gctcttaatg gcgtggtcca caatattgtt gatagattcg gaaatatgct gctcgtgttc   240
gtaagctttc tgaaagatct gggtcaggcc ctcgaactta tgttcaggcg cgctgattga   300
agtcagctgg acgggcacat tgttctcatt caggaaaatg atcagtttct ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgcccccact gtcaatttc tctcgattca gcttactctc    540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaacagca gagtgaactg   720
gttcagcatc agcaccagca gctcagccag gtctgttccg gagcctccgc tgcccatttt   780
ttcgatgaca gaattcacca tgttagtaat gccattgatt gcgttctgtg tagacttctg   840
atcagcggcg tagccgctgc cctgctcatt ctgatggtgg tagccgtacc acccgtccac   900
cattcctgtc caccgcccct caataaaccc tgcgatagcg ccgaacagtc ctcttgtttc   960
ccgctgtggg atgttgcgca gtccggtgac catcctcagt ccgctgccca gattcactga  1020
gtgggtgaca gtcacgttct tctccagaat ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 350         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 350
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca cgacccccgc ccattgacg tcaataatga cgtatgttcc   480
catagtaacg ccaatagga cttttccattg acgtcaatgg gtggagtatt tacggtaaac   540
tgcccacttg gcagtacatc aagtgtatca tatgccaagt acgccccta ttgacgtcaa    600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgta ttcgcgcc tcccgcctgt    1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagctgtt ccttttccatt  1320
ggtcttttct gcagtcaccg tcgtcgacac gtgtgatcag atatcgtcgg cgctctagag  1380
atatcgccac catgaaggcc aaactgctgg tcctgctgtg tactttttacc gcaacctacg  1440
ctgacactat ctgcatcggc tatcacgcaa acaactccac cgacacagtg gataccattc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cggttggaca ggaatggtgg acggttggta cggctaccac catcagaatg  1680
agcagggcag cggctacgcc gctgatcaga gtctcacaca gaacgcaatc aatggcatta  1740
ctaacatggt gaattctgtc atcgaaaaaa tgggcagcgg aggctccgga acagacctgg  1800
ctgagctgct ggtgctgatg ctgaaccagt tcactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacgggca  1980
```

-continued

```
cttacgacta tcccaaatat tctgaagaga gtaagctgaa tcgagagaaa attgacagtg    2040
ggggcgacat catcaagctg ctgaacgaac aggtgaacaa ggagatgcag agctccaacc    2100
tgtacatgag tatgtctagt tggtgttata cacactcact ggacggcgct gggctgttcc    2160
tgtttgatca cgcagccgag gaatacgaac atgcaaagaa actgatcatt ttcctgaatg    2220
agaacaatgt gcccgtccag ctgacttcaa tcagcgcccc tgaacataag ttcgagggcc    2280
tgacccagat cttttcagaaa gcttacgaac acgagcagca tatttccgaa tctatcaaca    2340
atattgtgga ccacgccatt aagagcaaag atcatgctac cttcaacttt ctgcagtggt    2400
acgtggccga gcagcacgag gaggaggtcc tgtttaagga catcctggat aaaatcgaac    2460
tgattggaaa cgagaatcat ggcctgtacc tggcagatca gtatgtgaag ggcattgcca    2520
agtcagaaa aagtgggtca tgatgaacac gtgggatcca gatctgctgt gccttctagt    2580
tgccagccat ctgttgtttg cccctccccc gtgccttcct tgaccctgga aggtgccact    2640
cccactgtcc tttcctaata aaatgaggaa attgcatcgc attgtctgag taggtgtcat    2700
tctattctgg ggggtgggt gggggcaggac agcaaggggg aggattggga agacaatagc    2760
aggcatgctg gggatgcggt gggctctatg ggtacccagg tgctgaagaa ttgacccggt    2820
tcctcctggg ccagaaagaa gcaggacat ccccttctct gtgacacacc ctgtccacgg    2880
ccctggttct tagttccagc cccactcata ggacactcat agctcaggag ggctccgcct    2940
tcaatcccac ccgctaaagt acttggagcg gtctctccct ccctcatcag cccaccaaac    3000
caaacctagc ctccaagagt gggaagaaat taaagcaaga taggctatta agtgcagagg    3060
gagagaaaat gcctccaaca tgtgaggaag taatgagaga aatcatagaa ttttaaggcc    3120
atgatttaag gccatcatgg ccttaatctt ccgcttcctc gctcactgac tcgctgcgct    3180
cggtcgttcg gctgcggcga gcggtatcag ctcactcaaa ggcggtaata cggttatcca    3240
cagaatcagg ggataacgca ggaaagaaca tgtgagcaaa aggccagcaa aaggccagga    3300
accgtaaaaa ggccgcgttg ctggcgtttt tccataggct ccgcccccct gacgagcatc    3360
acaaaaatcg acgctcaagt cagaggtggc gaaacccgac aggactataa agataccagg    3420
cgtttccccc tggaagctcc ctcgtgcgct ctcctgttcc gaccctgccg cttaccggat    3480
acctgtccgc ctttctccct tcgggaagcg tggcgctttc tcatagctca cgctgtaggt    3540
atctcagttc ggtgtaggtc gttcgctcca agctgggctg tgtgcacgaa ccccccgttc    3600
agcccgaccg ctgcgcctta tccggtaact atcgtcttga gtccaacccg gtaagacacg    3660
acttatcgcc actggcagca gccactggta acaggattag cagagcgagg tatgtaggcg    3720
gtgctacaga gttcttgaag tggtggccta actacggcta cactagaaga acagtatttg    3780
gtatctgcgc tctgctgaag ccagttacct tcggaaaaag agttggtagc tcttgatccg    3840
gcaaacaaac caccgctggt agcggtggtt ttttttgtttg caagcagcag attacgcgca    3900
gaaaaaaagg atctcaagaa gatcctttga tcttttctac ggggtctgac gctcagtgga    3960
acgaaaactc acgttaaggg attttggtca tgagattatc aaaaaggatc ttcacctaga    4020
tcctttaaaa ttaaaaatga agttttaaat caatctaaag tatatatgag taaacttggt    4080
ctgacagtta ccaatgctta atcagtgagg cacctatctc agcgatctgt ctatttcgtt    4140
catccatagt tgcctgactc gggggggggg ggcgctgagg tctgcctcgt gaagaaggtg    4200
ttgctgactc ataccaggcc tgaatcgccc catcatccag ccagaaagtg agggagccac    4260
ggttgtgag agcttttgtt taggtggacc agttggtgat tttgaactttt tgctttgcca    4320
cggaacggtc tgcgttgtcg ggaagatgcg tgatctgatc cttcaactca gcaaaagttc    4380
gatttattca acaaagccgc cgtcccgtca agtcagcgta atgctctgcc agtgttacaa    4440
ccaattaacc aattctgatt agaaaaactc atcgagcatc aaatgaaact gcaatttatt    4500
catatcagga ttatcaatac catattttg aaaaagccgt ttctgtaatg aaggagaaaa    4560
ctcaccgagg cagttccata ggatggcaag atcctggtat cggtctgcga ttccgactcg    4620
tccaacatca atacaaccta ttaatttccc ctcgtcaaaa ataaggttat caagtgagaa    4680
atcaccatga gtgacgactg aatccggtga gaatggcaaa agcttatgca tttctttcca    4740
gacttgttca acaggccagc cattacgctc gtcatcaaaa tcactcgcat caaccaaacc    4800
gttattcatt cgtgattgcg cctgagcgag acgaaatacg cgatcgctgt taaaaggaca    4860
attacaaaca ggaatcgaat gcaaccggcg caggaacact gccagcgcat caacaatatt    4920
ttcacctgaa tcaggatatt cttctaatac ctggaatgct gttttcccgg ggatcgcagt    4980
ggtgagtaac catgcatcat caggagtacg gataaaatgc ttgatggtcg gaagaggcat    5040
aaattccgtc agccagttta gtctgaccat ctcatctgta acatcattgg caacgctacc    5100
tttgccatgt ttcagaaaca actctggcgc atcgggcttc ccatacaatc gatagattgt    5160
cgcacctgat tgcccgacat tatcgcgagc ccatttatac ccatataaat cagcatccat    5220
gttgaattt aatcgcggcc tcgagcaaga cgtttcccgt tgaatatggc tcataacacc    5280
ccttgtatta ctgtttatgt aagcagacag ttttattgtt catgatgata tatttttatc    5340
ttgtgcaatg taacatcaga gattttgaga cacaacgtgg ctttcccccc cccccattca    5400
ttgaagcatt tatcagggtt attgtctcat gagcggatac atatttgaat gtatttagaa    5460
aaataaacaa atagggttc cgcgcacatt tccccgaaaa gtgccacctg acgtctaaga    5520
aaccattatt atcatgacat taacctataa aaataggcgt atcacgaggc cctttcgtc    5579
```

```
SEQ ID NO: 351          moltype = DNA   length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 351
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcaggttt tattgagggc    240
gggtggacag gaatggtgga cgggtggtac ggctaccacc atcagaatga gcaggcagc     300
ggctacgccg ctgatcagaa gtctacacag aacgcaatca tggcattac taacatggtg    360
aattctgtca tcgaaaaaat gggcaatgga acaggcggag ctgacctggc tgagctgctg    420
gtgctgctgc tgaaccagtg gactctgctg ttccacgata gcaacgtgaa gaatctgtat    480
gagaaggtca atcccagct gaagaacaat gccaagaaa tcgggaatgg atgcttcgag    540
```

```
ttttaccata agtgcaacaa tgaatgtatg gagtctgtga agaacggcac ttacgactat    600
cccaaatatt ctgaagagag taagctgaat cgagagaaaa ttgac                   645

SEQ ID NO: 352          moltype = AA  length = 215
FEATURE                 Location/Qualifiers
REGION                  1..215
                        note = Synthetic Construct
source                  1..215
                        mol_type = protein
                        organism = synthetic construct
SEQUENCE: 352
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGNG TGGADLAELL VLLLNQWTLL FHDSNVKNLY EKVKSQLKNN AKEIGNGCFE   180
FYHKCNNECM ESVKNGTYDY PKYSEESKLN REKID                              215

SEQ ID NO: 353          moltype = DNA  length = 645
FEATURE                 Location/Qualifiers
misc_feature            1..645
                        note = Synthetic
source                  1..645
                        mol_type = other DNA
                        organism = synthetic construct
SEQUENCE: 353
gtcaattttc tctcgattca gcttactctc ttcagaatat tgggatagt cgtaagtgcc     60
gttcttcaca gactccatac attcattgtt gcacttgtca taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagccag   240
gtcagctccg cctgttccat tgcccatttt ttcgatgaca gaattcacca tgttagtaat   300
gccattgatt gcgttctgtg tagacttctg atcagcgctg gacccgctgc cctgctcatt   360
ctgatggtgg tagccgtacc acccgtccac cattcctgtc cacccgccct caataaaccc   420
tgcgatagcg ccgaacagtc ctcttgtttc ccgctgtggg atgttgcgca gtccggtgac   480
catcctcagt ccgctgccca gattcactga gtgggtgaca gtcacgttct tctccaggac   540
ggtatccact gtgtcggtgg agttgtttgc gtgatagccg atgcagatag tgtcagcgta   600
ggttgcggta aagtacaca gcaggaccag cagtttggcc ttcat                    645

SEQ ID NO: 354          moltype = DNA  length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 354
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca atggcattac aacatgtgg    360
aattctgtca tcgaaaaaat gggcaatgga acaggcggag ctgacctggc tgagctgctg    420
gtgctgctgc tgaaccagtg gactctgctg ttccacgata gcaacgtgaa gaatctgtat    480
gagaaggtca atcccagct gaagaacaat gccaaagaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgacagtgg ggcgacatc    660
atcaagctgc tgaacgaaca ggtgaacaag gagatgcaga gctccaacct gtacatgagt    720
atgtctagtt ggtgttatac acactcactg gacggcgctg gctgttcct gtttgatcac    780
gcagccgagg aatacgaaca tgcaaagaaa ctgatcattt tcctgaatga gaacaatgtg    840
cccgtccagc tgacttcaat cagcgcccct gaacataagt tcgagggcct gacccagatc    900
tttcagaaag cttacgaaca cgagcagcat atttccgaat ctatcaacaa tattgtggac    960
cacgccatta gagcaaaga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg cattgccaa gtccagaaaa   1140
agtgggtcat gatga                                                   1155

SEQ ID NO: 355          moltype = AA  length = 383
FEATURE                 Location/Qualifiers
REGION                  1..383
                        note = Synthetic Construct
source                  1..383
                        mol_type = protein
                        organism = synthetic construct
SEQUENCE: 355
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGNG TGGADLAELL VLLLNQWTLL FHDSNVKNLY EKVKSQLKNN AKEIGNGCFE   180
FYHKCNNECM ESVKNGTYDY PKYSEESKLN REKIDSGGDI IKLLNEQVNK EMQSSNLYMS   240
MSSWCYTHSL DGAGLFLFDH AAEEYEHAKK LIIFLNENNV PVQLTSISAP EHKFEGLTQI   300
```

FQKAYEHEQH ISESINNIVD HAIKSKDHAT FNFLQWYVAE QHEEEVLFKD ILDKIELIGN    360
ENHGLYLADQ YVKGIAKSRK SGS                                           383

| SEQ ID NO: 356 | moltype = DNA length = 1155 |
|---|---|
| FEATURE | Location/Qualifiers |
| misc_feature | 1..1155 |
| | note = Synthetic |
| source | 1..1155 |
| | mol_type = other DNA |
| | organism = synthetic construct |

SEQUENCE: 356
tcatcatgac ccactttttc tggacttggc aatgcccttc acatactgat ctgccaggta    60
caggccatga ttctcgtttc caatcagttc gattttatcc aggatgtcct taaacaggac   120
ctcctcctcg tgctgctcgg ccacgtacca ctgcagaaag ttgaaggtag catgatcttt   180
gctcttaatg gcgtggtcca caatattgtt gatagattcg gaaatatgct gctcgtgttc   240
gtaagctttc tgaaagatct gggtcaggcc ctcgaactta tgttcagggg cgctgattga   300
agtcagctgg acgggcacat tgttctcatt caggaaaatg atcagtttct ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgccccccact gtcaattttc tctcgattca gcttactctc   540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaacagca gagtccactg   720
gttcagcagc agcaccagca gctcagccag gtcagctccg cctgttccat tgcccatttt   780
ttcgatgaca gaattcacca tgttagtaat gccattgatt gcgttctgtg tagacttctg   840
atcagcggcg tagccgctgc cctgctcatt ctgatggtag tagccgtacc acccgtccac   900
cattcctgtc cacccgccct caataaaccc tgcgatagcg ccgaacagtc ctcttgtttc   960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagttttggcc ttcat                                                  1155

| SEQ ID NO: 357 | moltype = DNA length = 5579 |
|---|---|
| FEATURE | Location/Qualifiers |
| misc_feature | 1..5579 |
| | note = Synthetic |
| source | 1..5579 |
| | mol_type = other DNA |
| | organism = synthetic construct |

SEQUENCE: 357
tcgcgcgttt cggtgatgac ggtgaaaacc tctgacacat gcagctcccg gagacggtca    60
cagcttgtct gtaagcggat gccgggagca gacaagcccg tcaggcgcg tcagcggggtg   120
ttggcgggtg tcggggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggaa ctttccattg acgtcaatgg gtggagtatt tacggtaaac   540
tgcccacttg gcagtacatc aagtgtatca tatgccaagt acgccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagag  1380
atatgccac catgaaggcc aaactgctgg tcctgctgta ctttttacc gcaacctaag  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acggtggta cggctaccac catcagaatg  1680
agcagggcag cggctacgcc gctgatcaga agtctacaca gaacgcaatc aatggcatta  1740
ctaacatggt gaattctgtc atcgaaaaaa tgggcaatgg aacaggcgga gctgacctaa  1800
ctgagctgct ggtgctgctg ctgaaccagt ggactctgct gttccacgat agcaacgtga  1860
agaatctgta tgagaaggtc aaatcccagc tgaagaacaa tgccaaagaa atcgggaatg  1920
gatgcttcga gttttaccat aagtgcaaca atgaatgtat ggagtctgtg aagaacggca  1980
cttacgacta tcccaaatat tctgaagaga taagcaagct tcgagagaaa attgacagtc  2040
ggggcgacat catcaagctg ctgaacgaac aggtgaacaa ggagatgcag agctccaacc  2100
tgtacatgag tatgtctagt tggtgttata cacactcact ggacgcgcct gggctgttcc  2160
tgtttgatca cgcagccgag gaatacgaac atgcaaagaa actgatcatt ttcctgaatg  2220
agaacaatgt gcccgtccag ctgacttcaa tcagcgcccc tgaacataag ttcgagggcc  2280
tgacccagat ctttcagaaa gcttacgaac acgagcagca tatttccgaa tctatcaaca  2340

```
atattgtgga ccacgccatt aagagcaaag atcatgctac cttcaacttt ctgcagtggt    2400
acgtggccga gcagcacgag gaggaggtcc tgtttaagga catcctggat aaaatcgaac    2460
tgattggaaa cgagaatcat ggcctgtacc tggcagatca gtatgtgaag ggcattgcca    2520
agtccagaaa aagtgggtca tgatgaacac gtgggatcca gatctgctgt gccttctagt    2580
tgccagccat ctgttgtttg cccctccccc gtgccttcct tgaccctgga aggtgccact    2640
cccactgtcc tttcctaata aaatgaggaa attgcatcgc attgtctgag taggtgtcat    2700
tctattctgg ggggtggggt ggggcaggac agcaaggggg aggattggga agacaatagc    2760
aggcatgctg gggatgcggt gggctctatg ggtacccagg tgctgaagaa ttgacccggt    2820
tcctcctggg ccagaaagaa gcaggcacat ccccttctct gtgacacaca ctgtccacgc    2880
ccctggttct tagttccagc cccactcata ggacactcat agctcaggag ggctccgcct    2940
tcaatcccac ccgctaaagt acttggagcg gtctctccct ccctcatcag cccaccaaac    3000
caaacctagc ctccaagagt gggaagaaat taaagcaaga taggctatta agtgcagagg    3060
gagagaaaat gcctccaaca tgtgaggaag taatgagaga aatcatagaa ttttaaggcc    3120
atgatttaag gccatcatgg ccttaatctt ccgcttcctc gctcactgac tcgctgcgct    3180
cggtcgttcg gctgcggcga gcggtatcag ctcactcaaa ggcggtaata cggttatcca    3240
cagaatcagg gataacgca ggaaagaaca tgtgagcaaa aggccagcaa aaggccagga    3300
accgtaaaaa ggccgcgttg ctggcgtttt tccataggct ccgcccccct gacgagcatc    3360
acaaaaatcg acgctcaagt cagaggtggc gaaacccgac aggactataa agataccagg    3420
cgtttccccc tggaagctcc ctcgtgcgct ctcctgttcc gaccctgccg cttaccggat    3480
acctgtccgc ctttctccct tcgggaagcg tggcgctttc tcatagctca cgctgtaggt    3540
atctcagttc ggtgtaggtc gttcgctcca agctgggctg tgtgcacgaa ccccccgttc    3600
agcccgaccg ctgcgcctta tccggtaact atcgtcttga gtccaacccg gtaagacacg    3660
acttatcgcc actggcagca gccactggta acaggattag cagagcgagg tatgtaggcg    3720
gtgctacaga gttcttgaag tggtggccta actacggcta cactagaaga acagtatttg    3780
gtatctgcgc tctgctgaag ccagttacct tcggaaaaag agttggtagc tcttgatccg    3840
gcaaacaaac caccgctggt agcggtggtt tttttgtttg caagcagcag attacgcgca    3900
gaaaaaaagg atctcaagaa gatcctttga tcttttctac ggggtctgac gctcagtgga    3960
acgaaaactc acgttaaggg attttggtca tgagattatc aaaaaggatc ttcacctaga    4020
tccttttaaa ttaaaaatga agttttaaat caatctaaag tatatatgag taaacttggt    4080
ctgacagtta ccaatgctta atcagtgagg cacctatctc agcgatctgt ctatttcgtt    4140
catccatagt tgcctgactc ccccgggggg ggcgctgagg tctgcctcgt gaagaaggtg    4200
ttgctgactc ataccaggcc tgaatcgccc catcatccag ccagaaagtg agggagccac    4260
ggttgatgag agctttgttg taggtggacc agttggtgat tttgaacttt tgctttgcca    4320
cggaacggtc tgcgttgtcg ggaagatgcg tgatctgatc cttcaactca gcaaaagttc    4380
gatttattca acaaagccgc cgtcccgtca gtcagcgta atgctctgcc agtgttacaa    4440
ccaattaacc aattctgatt agaaaaactc atcgagcatc aaatgaaact gcaatttatt    4500
catatcagga ttatcaatac catatttttg aaaaagccgt ttctgtaatg aaggagaaaa    4560
ctcaccgagg cagttccata ggatggcaag atcctggtat cggtctgcga ttccgactcg    4620
tccaacatca atacaaccta ttaatttccc ctcgtcaaaa ataaggttat caagtgagaa    4680
atcaccatga gtgacgactg aatccggtga gaatggcaaa agcttatgca tttctttcca    4740
gacttgttca acaggccagc cattacgctc gtcatcaaaa tcactcgcat caaccaaacc    4800
gttattcatt cgtgattgcg cctgagcgag acgaaatacg cgatcgctgt taaaaggaca    4860
attacaaaca ggaatcgaat gcaaccggcg caggaacact gccagcgcat caacaatatt    4920
ttcacctgaa tcaggatatt cttctaatac ctggaatgct gttttcccgg ggatcgcagt    4980
ggtgagtaac catgcatcat caggagtacg ataaaatgc ttgatggtcg gaagaggcat    5040
aaaattccgt cagccagttta gtctgaccat ctcatctgta acatcattgg caacgctacc    5100
tttgccatgt ttcagaaaca actctggcgc atcgggcttc ccatacaatc gatagattgt    5160
cgcacctgat tgcccgacat tatcgcgagc ccatttatac ccatataaat cagcatccat    5220
gttgaattt aatcgcggcc tcgagcaaga cgtttcccgt tgaatatggc tcataacacc    5280
ccttgtatta ctgtttatgt aagcagacag ttttattgtt catgatgata tatttttatc    5340
ttgtgcaatg taacatcaga gattttgaga cacaacgtgg ctttccccc ccccccatta    5400
ttgaagcatt tatcagggtt attgtctcat gagcggatac atatttgaat gtatttagaa    5460
aaataaacaa ataggggttc cgcgcacatt tccccgaaaa gtgccacctg acgtctaaga    5520
aaccattatt atcatgacat taacctataa aaataggcgt atcacgaggc cctttcgtc     5579

SEQ ID NO: 358         moltype = DNA  length = 645
FEATURE                Location/Qualifiers
misc_feature           1..645
                       note = Synthetic
source                 1..645
                       mol_type = other DNA
                       organism = synthetic construct
CDS                    1..645
SEQUENCE: 358
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactgg gatggtcac cggactgcgc    180
aacatcccac agcgggaaac aagaggactg ttcggcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca tggcattac taacatggtg    360
aattctgtca tcgaaaaaat gggcggaaat ggcactgagg ctgacctggc tgagctgctg    420
gtgctgctgc tgaaccagtg gactctgctg ttccacgata gcaacgtgaa gaatctgtat    480
gagaagtgga atccccagct gaagaacaat gccaaagaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgac                    645

SEQ ID NO: 359         moltype = AA  length = 215
FEATURE                Location/Qualifiers
```

```
REGION                    1..215
                          note = Synthetic Construct
source                    1..215
                          mol_type = protein
                          organism = synthetic construct
SEQUENCE: 359
MKAKLLVLLC TFTATYADTI CIGYHANNST DTVDTVLEKN VTVTHSVNLG SGLRMVTGLR      60
NIPQRETRGL FGAIAGFIEG GWTGMVDGWY GYHHQNEQGS GYAADQKSTQ NAINGITNMV     120
NSVIEKMGGN GTGADLAELL VLLLNQWTLL FHDSNVKNLY EKVKSQLKNN AKEIGNGCFE     180
FYHKCNNECM ESVKNGTYDY PKYSEESKLN REKID                                215

SEQ ID NO: 360            moltype = DNA   length = 645
FEATURE                   Location/Qualifiers
misc_feature              1..645
                          note = Synthetic
source                    1..645
                          mol_type = other DNA
                          organism = synthetic construct
SEQUENCE: 360
gtcaattttc tctcgattca gcttactctc ttcagaatat ttgggatagt cgtaagtgcc      60
gttcttcaca gactccatac attcattgtt gcacttatgg taaaactcga agcatccatt    120
cccgatttct ttggcattgt tcttcagctg ggatttgacc ttctcataca gattcttcac    180
gttgctatcg tggaacagca gagtccactg gttcagcagc agcaccagca gctcagccag    240
gtcagctcca gtgccatttc cgcccatttt ttcgatgaca gaattcacca tgttagtaat    300
gccattgatt gcgttctgtg tagacttctg atcagcggcg tagccgctgc cctgctcatt    360
ctgatggtgg tagccgtacc acccgtccac cattcctgcc cacccgccct caataaaccc    420
tgcgatagcg ccgaacagtc ctcttgtttc ccgctgtggg atgttgcgca gtccggtgac    480
catcctcagt ccgctgccca gattcactga gtgggtgaca gtcacgttct tctccaggac    540
ggtatccact gtgtcggtgg agttgtttgc gtgatagccg atgcagatag tgtcagcgta    600
ggttgcggta aaagtacaca gcaggaccag cagtttggcc ttcat                    645

SEQ ID NO: 361            moltype = DNA   length = 1155
FEATURE                   Location/Qualifiers
misc_feature              1..1155
                          note = Synthetic
source                    1..1155
                          mol_type = other DNA
                          organism = synthetic construct
CDS                       1..1155
SEQUENCE: 361
atgaaggcca aactgctggt cctgctgtgt acttttaccg caacctacgc tgacactatc      60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcagggtt tattgagggc    240
gggtggacag gaatggtgga cgggtggtac ggctaccacc atcagaatga gcagggcagc    300
ggctacgccg ctgatcagaa gtctacacag aacgcaatca atggcattac taacatggtg    360
aattctgtca tcgaaaaaat gggcggaaat ggcactggaa ctgacctggc tgagctgctg    420
gtgctgctgc tgaaccagtg gactctgctg ttccacgata gcaacgtgaa gaatctgtat    480
gagaaggtca atccccagct gaagaacaat gccaaagaaa tcgggaatgg atgcttcgag    540
ttttaccata gtgcaacaa tgaatgtatg agtctgtga agaacggcac ttacgactat      600
cccaaatatt ctgaagagag taagctgaat cgagagaaga ttgacagtgg gggcgacatc    660
atcaagctgc tgaacgaaca ggtgaacaag gagatgcaga gctccaacct gtacatgagt    720
atgtctagtt ggtgttatac acactcactg gacggcgctg gctgttcct gtttgatcac     780
gcagccgagg aatacgaaca tgcaaagaaa ctgatcattt tcctgaatga aaacaatgtg    840
cccgtccagc tgacttcaat cagcgcccct gaacataagt tccaggagcc gacccagatc    900
tttcagaaag cttacgaaca cgagcagcat atttccgaat ctatcaacaa tattgtggac    960
cacgccatta gagcaaagga tcatgctacc ttcaactttc tgcagtggta cgtggccgag   1020
cagcacgagg aggaggtcct gtttaaggac atcctggata aaatcgaact gattggaaac   1080
gagaatcatg gcctgtacct ggcagatcag tatgtgaagg gcattgccaa gtccagaaaa   1140
agtgggtcat gatga                                                    1155

SEQ ID NO: 362            moltype = AA    length = 383
FEATURE                   Location/Qualifiers
REGION                    1..383
                          note = Synthetic Construct
source                    1..383
                          mol_type = protein
                          organism = synthetic construct
SEQUENCE: 362
MKAKLLVLLC TFTATYADTI CIGYHANNST DTVDTVLEKN VTVTHSVNLG SGLRMVTGLR      60
NIPQRETRGL FGAIAGFIEG GWTGMVDGWY GYHHQNEQGS GYAADQKSTQ NAINGITNMV     120
NSVIEKMGGN GTGADLAELL VLLLNQWTLL FHDSNVKNLY EKVKSQLKNN AKEIGNGCFE     180
FYHKCNNECM ESVKNGTYDY PKYSEESKLN REKIDSGGDI IKLLNEQVNK EMQSSNLYMS     240
MSSWCYTHSL DGAGLFLFDH AAEEYEHAKK LIIFLNENNV PVQLTSISAP EHKFEGLTQI     300
FQKAYEHEQH ISESINNIVD HAIKSKDHAT FNFLQWYVAE QHEEVLFKD  ILDKIELGIN     360
ENHGLYLADQ YVKGIAKSRK SGS                                             383

SEQ ID NO: 363            moltype = DNA   length = 1155
FEATURE                   Location/Qualifiers
```

| misc_feature | 1..1155 |
| | note = Synthetic |
| source | 1..1155 |
| | mol_type = other DNA |
| | organism = synthetic construct |

SEQUENCE: 363

```
tcatcatgac ccacttttc tggacttggc aatgccttc acatactgat ctgccaggta   60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
agtcagctgg acgggacat tgttctcatt caggaaaatg atcagtttct ttgcatgttc  360
gtattcctcg gctgcgtgat caaacaggaa cagcccagcg ccgtccagtg agtgtgtata  420
acaccaacta gacatactca tgtacaggtt ggagctctgc atctccttgt tcacctgttc  480
gttcagcagc ttgatgatgt cgcccccact gtcaattttc tctcgattca gcttactctc  540
ttcagaatat ttgggatagt cgtaagtgcc gttcttcaca gactccatac attcattgtt  600
gcacttatgg taaaactcga agcatccatt cccgatttct ttggcattgt tcttcagctg  660
ggatttgacc ttctcataca gattcttcac gttgctatcg tggaacagca gagtccactg  720
gttcagcagc agcaccagca gctcagccag gtcagctcca gtgccatttc cgcccatttt  780
ttcgatgaca gaattcacca tgttagtaat gccattgatt gcgttctgtg tagacttctg  840
atcagcggcg tagccgctgc cctgctcatt ctgatggtgg tagccgtacc acccgtccac  900
cattcctgtc cacccgccct caataaaccc tgcgatagcg ccgaacagtc ctcttgtttc  960
ccgctgtggg atgttgcgca gtccggtgac catcctcagt ccgctgccca gattcactga 1020
gtgggtgaca gtcacgttct tctccaggac ggtatccact gtgtcggtgg agttgtttgc 1080
gtgatagccg atgcagatag tgtcagcgta ggttgcggta aaagtacaca gcaggaccag 1140
cagtttggcc ttcat                                                  1155
```

| SEQ ID NO: 364 | moltype = DNA  length = 5579 |
| FEATURE | Location/Qualifiers |
| misc_feature | 1..5579 |
| | note = Synthetic |
| source | 1..5579 |
| | mol_type = other DNA |
| | organism = synthetic construct |

SEQUENCE: 364

```
tcgcgcgttt cggtgatgac ggtgaaaacc tctgacacat gcagctcccg gagacggtca   60
cagcttgtct gtaagcggat gccgggagca gacaagcccg tcaggcgcg tcagcggtg  120
ttggcggtg tcgggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga cttttccattg acgtcaatgg gtggagtatt tacggtaaac  540
tgcccacttg gcagtacatc aagtgtatca tatgccaagt acgccccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcgagc ggctctccac gctttgcctg 1200
accctgcttg ctcaactcta gttaacggtg agggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcag atatcgcggc cgctctagag 1380
atatcgccac catgaaggcc aaactgctgg tcctgctgtg tactttttacc gcaacctacg 1440
ctgacactat ctgcatcggc tatcacgcaa acaactccac cgacacagtg gataccgtcc 1500
tggagaagaa cgtgactgtc acccactcag tgaatctggg cagcggactg aggatggtca 1560
ccggactgcg caacatccca cagcgggaaa caagaggact gttcggcgct atcgcagggt 1620
ttattgaggg cgggtggaca ggaatggtgg acggggtgta cggctaccac catcagaatg 1680
agcaggcag cggctacgcc gctgatcaga agtctacaca gaacgcaatc aatgccatta 1740
ctaacatggt gaattctgtc atcgaaaaaa tgggcgggaa atggcactgga gctgacctga 1800
ctgagctgct ggtgctgctg ctgaaccagt ggactctgct gttccacgat agcaacgtga 1860
agaatctgta tgagaaggtc aaatccccagc tgaagaacaa tgccaaagaa atcgggaatg 1920
gatgcttcga gttttaccat aagtgaacaa atgaatgtat ggagtctgtg aagaacggca 1980
cttacgacta tccccaaatat tctgaagaga gaaggaaat tgcagagaaa attgacagtg 2040
ggggcgacat catcaagctg ctgaacgaac aggtgaacaa ggagatgcag agctccaacc 2100
tgtacatgag tatgtctagt ggtgtttata cacactcact ggacgcgct gggctgttcc 2160
tgtttgatca cgcagccgag gaatacgaac atgcaaagaa actgatcatt ttcctgaatg 2220
agaacaatgt gcccgtccag ctgacttcaa tcagcgcccc tgaacataag ttcgagggcc 2280
tgacccagaa cttttcagaaa gcttacgaac acgagaga tatttccgaa tctatcaaca 2340
atattgtgga ccacgccatt aagagcaaaa atcatgctac cttcaacttt ctgcagtggt 2400
acgtggccga gcagcacgag gaggaggtcc tgtttaagga catcctggat aaaatcgaac 2460
tgattggaaa cgagaatcat ggcctgtacc tggcagatca gtatgtgaag gcattgcca 2520
agtccagaaa aagtgggtca tgatgaacac gtgggatcca gatctgctgt gccttctagt 2580
tgccagccat ctgttgtttg cccctccccc gtgccttcct tgaccctgga aggtgccact 2640
```

```
cccactgtcc tttcctaata aaatgaggaa attgcatcgc attgtctgag taggtgtcat  2700
tctattctgg ggggtggggt ggggcaggac agcaaggggg aggattggga agacaatagc  2760
aggcatgctg gggatgcggt gggctctatg ggtacccagg tgctgaagaa ttgacccggt  2820
tcctcctggg ccagaaagaa gcaggcacat ccccttctct gtgacacacc ctgtccacgc  2880
ccctggttct tagttccagc cccactcata ggacactcat agctcaggag ggctccgcct  2940
tcaatcccac ccgctaaagt acttggagcg gtctctccct ccctcatcag cccaccaaac  3000
caaacctagc ctccaagagt gggaagaaat taaagcaaga taggctatta agtgcagagg  3060
gagagaaaat gcctccaaca tgtgaggaag taatgagaga aatcatagaa ttttaaggcc  3120
atgatttaag gccatcatgg cctttaatctt ccgcttcctc gctcactgac tcgctgcgct  3180
cggtcgttcg gctgcggcga gcggtatcag ctcactcaaa ggcggtaata cggttatcca  3240
cagaatcagg ggataacgca ggaaagaaca tgtgagcaaa aggccagcaa aaggccagga  3300
accgtaaaaa ggccgcgttg ctggcgtttt tccataggct ccgcccccct gacgagcatc  3360
acaaaaatcg acgctcaagt cagaggtggc gaaacccgac aggactataa agataccagg  3420
cgtttccccc tggaagctcc ctcgtgcgct ctcctgttcc gaccctgccg cttaccggat  3480
acctgtccgc ctttctccct tcgggaagcg tggcgctttc tcatagctca cgctgtaggt  3540
atctcagttc ggtgtaggtc gttcgctcca agctgggctg tgtgcacgaa ccccccgttc  3600
agcccgaccg ctgcgcctta tccggtaact atcgtcttga gtccaacccg gtaagacacg  3660
acttatcgcc actggcagca gccactggta acaggattag cagagcgagg tatgtaggcg  3720
gtgctacaga gttcttgaag tggtggccta actacggcta cactagaaga acagtatttg  3780
gtatctgcgc tctgctgaag ccagttacct tcggaaaaag agttggtagc tcttgatccg  3840
gcaaacaaac caccgctggt agcggtggtt tttttgtttg caagcagcag attacgcgca  3900
gaaaaaaagg atctcaagaa gatcctttga tcttttctac ggggtctgac gctcagtgga  3960
acgaaaactc acgttaaggg attttggtca tgagattatc aaaaaggatc ttcacctaga  4020
tccttttaaa ttaaaaatga agttttaaat caatctaaag tatatatgag taaacttggt  4080
ctgacagtta ccaatgctta atcagtgagg cacctatctc agcgatcgt ctatttcgtt   4140
catccatagt tgcctgactc ggggggggggg ggcgctgagg tctgcctcgt gaagaaggtg  4200
ttgctgactc ataccaggcc tgaatcgccc catcatccag ccagaaagtg agggagccac  4260
ggttgatgag agctttgttg taggtggacc agttggtgat tttgaacttt tgctttgcca  4320
cggaacggtc tgcgttgtcg ggaagatgcg tgatctgatc cttcaactca gcaaagttc   4380
gatttattca acaaagcgc cgtcccgtca agtcagcgta atgctctgcc agtgttacaa   4440
ccaattaacc aattctgatt agaaaaactc atcgagcatc aaatgaaact gcaatttatt  4500
catatcagga ttatcaatac catatttttg aaaaagccgt ttctgtaatg aaggagaaaa  4560
ctcaccgagg cagttccata ggatggcaag atcctggtat cggtctgcga ttccgactcg  4620
tccaacatca atacaaccta ttaatttccc ctcgtcaaaa ataaggttat caagtgagaa  4680
atcaccatga gtgacgactg aatccggtga gaatggcaaa agcttatgca tttctttcca  4740
gacttgttca acaggccagc cattacgctc gtcatcaaaa tcactcgcat caaccaaacc  4800
gttattcatt cgtgattgcg cctgagcgag acgaaatacg cgatcgctgt taaaaggaca  4860
attacaaaca ggaatcgaat gcaaccggcg caggaacact gccagcgcat caacaatatt  4920
ttcacctgaa tcaggatatt cttctaatac ctggaatgct gttttcccgg ggatcgcagt  4980
ggtgagtaac catgcatcat caggagtacg gataaaatgc ttgatggtcg gaagaggcat  5040
aaattccgtc agccagttta gtctgaccat ctcatctgta acatcattgg caacgctacc  5100
tttgccatgt ttcagaaaca actctggcgc atcgggcttc ccatacaatc gatagattgt  5160
cgcacctgat tgcccgacat tatcgcgagc ccatttatac ccatataaat cagcatccat  5220
gttggaattt aatcgcggcc tcgagcaaga cgtttcccgt tgaatatggc tcataacacc  5280
ccttgtatta ctgtttatgt aagcagacag ttttattgtt catgatgata tatttttatc  5340
ttgtgcaatg taacatcaga gattttgaga cacaacgtgg ctttcccccc ccccccatta  5400
ttgaagcatt tatcaggggtt atttgtctcat gagcggatac atatttgaat gtatttagaa  5460
aaataaacaa ataggggttc gcgcacatt ccccgaaaa gtgccacctg acgtctaaga   5520
aaccattatt atcatgacat taaccactaaa aaataggcgt atcacgaggc cctttcgtc   5579

SEQ ID NO: 365          moltype = DNA  length = 645
FEATURE                 Location/Qualifiers
misc_feature            1..645
                        note = Synthetic
source                  1..645
                        mol_type = other DNA
                        organism = synthetic construct
CDS                     1..645
SEQUENCE: 365
atgaaggcca aactgctggt cctgctgtgt acttttaccg caacctacgc tgacactatc   60
tgcatcggct atcacgcaaa caactccacc gacacagtgg ataccgtcct ggagaagaac  120
gtgactgtca cccactcagt gaatctgggc agcggactga ggatggtcac cggactgcgn  180
aacatcccac agcgggaaac aagaggactg ttcggcgcta tcgcaggggtt tattgggc   240
gggtggacag gaatggtgga cgggtggtac ggctaccacc atcagaatga gcagggcagc  300
ggctacgccc tgatcagaa gtctacacag aacgcaatca atggcattac taacatggtg  360
aattctgtca tcgaaaaaat gggcagcgga gcaacggaa cagacctggc tgagctgctg  420
gtgctgctgc tgaaccagtg gactctgctg ttccacgata gcaacgtgaa gaatctgtat  480
gagaaggtca aatcccagct gaagaacaat gccaaagaaa tcgggaatgg atgcttcgag  540
ttttaccata agtgcaacaa tgaatgtatg gagtctgtga gaacggcac ttacgactat  600
cccaaatatt ctgaagagag taagctgaat cgagagaaaa ttgac                 645

SEQ ID NO: 366          moltype = AA  length = 215
FEATURE                 Location/Qualifiers
REGION                  1..215
                        note = Synthetic Construct
source                  1..215
                        mol_type = protein
                        organism = synthetic construct
```

```
SEQUENCE: 366
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GNGTDLAELL VLLLNQWTLL FHDSNVKNLY EKVKSQLKNN AKEIGNGCFE   180
FYHKCNNECM ESVKNGTYDY PKYSEESKLN REKID                             215

SEQ ID NO: 367          moltype = DNA   length = 645
FEATURE                 Location/Qualifiers
misc_feature            1..645
                        note = Synthetic
source                  1..645
                        mol_type = other DNA
                        organism = synthetic construct
SEQUENCE: 367
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagcgag   240
gtctgttccg ttgcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cacccgccct caataaaccc   420
tgcgatagcg ccgaacagtc ctcttgtttc ccgctgcctg atgttgcgca gtccggtgac   480
catcctcagt ccgctgccca gattcactga gtgggtgaca gtcacgttct tctccaggac   540
ggtatccact gtgtcgtggg agttgtttgc gtgatagccg atgcagatag tgtcagcgta   600
ggttgcggta aagtacaca gcaggaccag cagtttggcc ttcat                    645

SEQ ID NO: 368          moltype = DNA   length = 1155
FEATURE                 Location/Qualifiers
misc_feature            1..1155
                        note = Synthetic
source                  1..1155
                        mol_type = other DNA
                        organism = synthetic construct
CDS                     1..1155
SEQUENCE: 368
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttccggcgcta tcgcagggtt tattgagggc   240
gggtggacag gaatggtgga cgggtggtac ggctaccacc atcagaatga gcagggcagc   300
ggctacgccg ctgatcagaa gtctacacag aacgcaatca atggcattac taacatggtg   360
aattctgtca tcgaaaaaat gggcagcgga ggcaacggaa cagacctggc tgagctgctg   420
gtgctgctgc tgaaccagtg gactctgctg ttccacgata gcaacgtgaa gaatctgtat   480
gagaaggtca atccccagct gaagaacaat gccaagaaaa tcgggaatgg atgcttcgag   540
ttttaccata gtgcaacaa tgaatgtatg gagtctgtga agaacggcac ttacgactat   600
cccaaatatt ctgaagagag taagctgaat cgagagaaaa ttgacagtgg gggcgacatc   660
atcaagctgc tgaacgaaca ggtgaacaag gagatgcaga gctccaacct gtacatgagt   720
atgtctagtt ggtgttatac acactcactg gacggcgctg gctgttcct gtttgatcac   780
gcagccgagg aatacgaaca tgcaaagaaa ctgatcattt tcctgaatga gaacaatgtg   840
cccgtccagc tgacttcaat cagcgcccct gaacataagt tcgagggcct gacccagatc   900
tttcagaaag cttacgaaca cgagcacat atttccagat ctatcaacaa tattgtggac   960
cacgccatta agagcaaaga tcatgctacc ttcaactttc tgcagtggta cgtggccgag  1020
cagcacgagg aggaggtcct gtttaaggac atcctggata aaatcgaact gattggaaac  1080
gagaatcatg gcctgtacct ggcagatcag tatgtgaagg gcattgccaa gtccagaaaa  1140
agtgggtcat gatga                                                   1155

SEQ ID NO: 369          moltype = AA   length = 383
FEATURE                 Location/Qualifiers
REGION                  1..383
                        note = Synthetic Construct
source                  1..383
                        mol_type = protein
                        organism = synthetic construct
SEQUENCE: 369
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV   120
NSVIEKMGSG GNGTDLAELL VLLLNQWTLL FHDSNVKNLY EKVKSQLKNN AKEIGNGCFE   180
FYHKCNNECM ESVKNGTYDY PKYSEESKLN REKIDSGGID IKLLNEQVNK EMQSSNLYMS   240
MSSWCYTHSL DGAGLFLFDH AAEEYEHAKK LIIFLNENNV PVQLTSISAP EHKFEGLTQI   300
FQKAYEHEQH ISESINNIVD HAIKSKDHAT FNFLQWYVAE QHEEEVLFKD ILDKIELIGN   360
ENHGLYLADQ YVKGIAKSRK SGS                                          383

SEQ ID NO: 370          moltype = DNA   length = 1155
FEATURE                 Location/Qualifiers
misc_feature            1..1155
                        note = Synthetic
source                  1..1155
                        mol_type = other DNA
                        organism = synthetic construct
```

```
SEQUENCE: 370
tcatcatgac ccacttttc tggacttggc aatgcccttc acatactgat ctgccaggta    60
caggccatga ttctcgtttc caatcagttc gattttatcc aggatgtcct taaacaggac   120
ctcctcctcg tgctgctcgg ccacgtacca ctgcagaaag ttgaaggtag catgatcttc   180
gctcttaatg gcgtggtcca caatattgtt gatagattcg gaaatatgct gctcgtgttc   240
gtaagctttc tgaaagatct gggtcaggcc ctcgaactta tgttcagggg cgctgtgatta  300
agtcagctgg acgggcacat tgttctcatt caggaaaatg atcagtttct ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgcccccact gtcaatttc tctcgattca gcttactctc    540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaacagca gagtccactg   720
gttcagcagc agcaccagca gctcagccag gtctgttccg ttcctccgc tgcccattt     780
ttcgatgaca gaattcacca tgttagtaat gccattgatt gcgttctgtg tagacttctg   840
atcagcggcg tagccgctgc cctgctcatt ctgatggtgg tagccgtacc acccgtccac   900
cattcctgtc caccgcccct caataaaccc tgcgatagcg ccgaacagtc ctcttgtttc   960
ccgctgtggg atgttgcgca gtccggtgac catcctcagt ccgctgccca gattcactga  1020
gtgggtgaca gtcacgttct tctccaggac ggtatccact gtgtcggtgg agttgtttgc  1080
gtgatagccg atgcagatag tgtcagcgta ggttgcggta aaagtacaca gcaggaccag  1140
cagtttggcc ttcat                                                   1155

SEQ ID NO: 371         moltype = DNA   length = 5579
FEATURE                Location/Qualifiers
misc_feature           1..5579
                       note = Synthetic
source                 1..5579
                       mol_type = other DNA
                       organism = synthetic construct
SEQUENCE: 371
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataattta cacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgaccccgg cccattgacg tcaataatga cgtatgttcc    480
catagtaacg ccaataggga cttttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatgcg gtggatagc ggtttgactc acgggactt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt tgacctcca    960
tagaagacac cgggaccgat ccagcctcca tcggctccga tctctccttc acgcgcccgc  1020
cgccctacct gaggccgcca tccacgccgg ttgagtcgcg ttctgccgcc tcccgccgt   1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgaga agtactcgtt  1260
gctgccgcgc gcgccaccag acataatagc tgacagacta acagactgtt cctttccatg  1320
ggtcttttct gcagtcaccg tcgtcgacac gtgtgatcag atatcgccgg cgctctagag  1380
atatcgccac catgaaggcc aaactgctgg tcctgctgtg tacttttacc gcaacctacg  1440
ctgacactat ctgcatcggc tatcacgcaa acaactccac cgacacagtg gataccgtcc  1500
tggagaagaa cgtgactgtc acccactcag tgaatctggg cagcggactg aggatggtca  1560
ccggactgcg caacatccca cagcgggaaa caagaggact gttcggcgct atcgcagggt  1620
ttattgaggg cgggtggaca ggaatggtgg acggtggta cggctaccac catcagaatg  1680
agcagggcag cggctacgcc gctgatcaga agtctacaca gaacgcaatc aatggcatta  1740
ctaacatggt gaattcgtc atcgaaaaa tgggcagcgg aggcaacgga acagacctgg   1800
ctgagctgct ggtgctgctg ctgaaccagt ggactctgct gttccacgat agcaacgtga  1860
agaatcgta tgagaaggtc aaatcccagc tgaagaacaa tgccaaagaa atcgggaatg  1920
gatgcttcga gtttttaccat aagtgcaaca atgaatgtat ggagtctgtg aagaacggca  1980
cttacgacta tcccaaatat tctgaagaga ctaagctgaa tcgagagaaa attgacggca  2040
ggggcgacat catcaagctg ctgaacgaac aggtgaacaa ggagatgcag agctccaacc  2100
tgtacatgag tatgtctagt tggtgttata cacactcact ggacggcgct gggctgttcc  2160
tgtttgatca cgcagccgag gaatacgaac atgcaaagaa actgatcatt ttcctgaatg  2220
agaacaatgt gccgtccag ctgacttcaa tcagcgcccc tgaacataag ttcgagggcc   2280
tgacccagat cttttcagaaa gctacgaac acgagcgaca tatttccgaa tctatcaaca  2340
atattgtgga ccacgccatt aagagcaaag atcatgctac cttcaacttt ctgcagtggt  2400
acgtggccga gcagcacgag gaggaggtcc tgttttaagga catcctggat aaaatcgaac  2460
tgattggaaa cgagaatcat ggcctgtacc tggcagatca gtatgtgaag gcattgcca   2520
agtccagaaa aagtgggtca tgatgaacac gtgggatcca gatctgctgt gccttctagt  2580
tgccagccat ctgttgtttg cccctcccc gtgccttcct gaccctggaa aggtgccact  2640
cccactgtcc tttcctaata aaatgaggaa attgcatcgc attgtctgag taggtgtcat  2700
tctattctgg ggggtggggt ggggcaggac agcaagggg aggattggga agacaatagc   2760
aggcatgctg gggatgcggt gggctctatg gtacccagg tgctgaagaa ttgacccggt   2820
tcctcctggg ccagaaagaa gcaggcacat cccttctct gtgacacacc ctgtccacg    2880
ccctggttct tagttccagc cccactcata ggacactcat agctcaggag ggctccgcct  2940
```

```
tcaatcccac cgctaaagt acttggagcg gtctctccct ccctcatcag cccaccaaac 3000
caaacctagc ctccaagagt gggaagaaat taaagcaaga taggctatta agtgcagagg 3060
gagagaaaat gcctccaaca tgtgaggaag taatgagaga aatcatagaa ttttaaggcc 3120
atgatttaag gccatcatgg ccttaatctt ccgcttcctc gctcactgac tcgctgcgct 3180
cggtcgttcg gctgcggcga gcggtatcag ctcactcaaa ggcggtaata cggttatcca 3240
cagaatcagg ggataacgca ggaaagaaca tgtgagcaaa aggccagcaa aaggccagga 3300
accgtaaaaa ggccgcgttg ctggcgtttt tccataggct ccgcccccct gacgagcatc 3360
acaaaaatcg acgctcaagt cagaggtggc gaaacccgac aggactataa agataccagg 3420
cgtttccccc tggaagctcc ctcgtgcgct ctcctgttcc gaccctgccg cttaccgtag 3480 
acctgtccgc ctttctccct tcgggaagcg tggcgctttc tcatagctca cgctgtaggt 3540
atctcagttc ggtgtaggtc gttcgctcca agctgggctg tgtgcacgaa ccccccgttc 3600
agcccgaccg ctgcgcctta tccggtaact atcgtcttga gtccaacccg gtaagacacg 3660
acttatcgcc actggcagca gccactggta acaggattag cagagcgagg tatgtaggcg 3720
gtgctacaga gttcttgaag tggtggccta actacggcta cactagaaga acagtatttg 3780
gtatctgcgc tctgctgaag ccagttacct tcggaaaaag agttggtagc tcttgatccg 3840
gcaaacaaac caccgctggt agcggtggtt tttttgtttg caagcagcag attacgcgca 3900
gaaaaaaagg atctcaagaa gatcctttga tcttttctac ggggtctgac gctcagtgga 3960
acgaaaactc acgttaaggg attttggtca tgagattatc aaaaaggatc ttcacctaga 4020
tccttttaaa ttaaaaatga agttttaaat caatctaaag tatatatgag taaacttggt 4080
ctgacagtta ccaatgctta atcagtgagg cacctatctc agcgatctgt ctatttcgtt 4140
catccatagt tgcctgactc ccccgggggg ggcgctgagg tctgcctcgt gaagaaggtg 4200
ttgctgactc ataccaggcc tgaatcgccc catcatccag ccagaaagtg agggagccac 4260
ggttgatgag agctttgttg taggtggacc agttggtgat tttgaacttt tgctttgcca 4320
cggaacggtc tgcgttgtcg ggaagatgcg tgatctgatc cttcaactca gcaaaagttc 4380
gatttattca acaaagccgc cgtcccgtca agtcagcgta atgctctgcc agtgttacaa 4440
ccaattaacc aattctgatt agaaaaactc atcgagcatc aaatgaaact gcaatttatt 4500
catatcagga ttatcaatac catatttttg aaaaagccgt ttctgtaatg aaggagaaaa 4560
ctcaccgagg cagttccata ggatggcaag atcctggtat cggtctgcga ttccgactcg 4620
tccaacatca atacaaccta ttaatttccc ctcgtcaaaa ataaggttat caagtgagaa 4680
atcaccatga gtgacgactg aatccggtga agcttatgca tttctttcca 4740
gacttgttca acaggccagc cattacgctc gtcatcaaaa tcactcgcat caaccaaacc 4800
gttattcatt cgtgattgcg cctgagcgag acgaaatacg cgatcgctgt taaaaggaca 4860
attacaaaca ggaatcgaat gcaaccggcg caggaacact gccagcgcat caacaatatt 4920
ttcacctgaa tcaggatatt cttctaatac ctggaatgct gttttcccgg ggatcgcagt 4980
ggtgagtaac catgcatcat caggagtacg gataaaatgc ttgatggtcg gaagaggcat 5040
aaattccgtc agccagttta gtctgaccat ctcatctgta acatcattgg caacgctacc 5100
tttgccatgt ttcagaaaca actctggcgc atcgggcttc ccatacaatc gatagattgt 5160
cgcacctgat tgcccgacat tatcgcgagc ccatttatac ccatatatat cagcatccat 5220
gttggaattt aatcgcggcc tcgagcaaga cgtttcccgt tgaatatgat tcataacacc 5280
ccttgtatta ctgtttatgt aagcagacag ttttattgtt catgatgata tatttttatc 5340
ttgtgcaatg taacatcaga gattttgaga cacaacgtgg ctttcccccc cccccattag 5400
ttgaagcatt tatcagggtt attgtctcat gagcggatac atatttgaat gtatttagaa 5460
aaataaacaa atagggggttc gcgcacatt tccccgaaaa gtgccacctg acgtctaaga 5520
aaccattatt atcatgacat taacctataa aataggcgt atcacgaggc cctttcgtc 5579

SEQ ID NO: 372            moltype = DNA  length = 645
FEATURE                   Location/Qualifiers
misc_feature              1..645
                          note = Synthetic
source                    1..645
                          mol_type = other DNA
                          organism = synthetic construct
CDS                       1..645
SEQUENCE: 372
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacatcccac agcgggaaac aagaggactg ttcggcgcta tcgcagggtt tattgagggc   240
gggtggacag gaatggtgga cgggtggtac ggctaccacc ataacaatac ccagggcagc   300
ggctacgccg ctgatcagaa gtctacacag aacgcaatca atggcattac taacatgttg   360
aattctgtca tcgaaaaaat gggcggaaat ggcactggag ctgacctggc tgagctgctg   420
gtgctgctgc tgaaccagtg gactctgctg ttccacgata gcaacgtgaa gaatctgtat   480
gagaaggtca atcccagct gaagaacaat gccaaagaaa tcgggaatgg atgcttcgag   540
ttttaccata agtgcaacaa tgaatgtatg gagtctgtga gaacggcac ttacgactat   600
cccaaatatt ctgaagagag taagctgaat cgagagaaaa ttgac               645

SEQ ID NO: 373            moltype = AA   length = 215
FEATURE                   Location/Qualifiers
REGION                    1..215
                          note = Synthetic Construct
source                    1..215
                          mol_type = protein
                          organism = synthetic construct
SEQUENCE: 373
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHNNTQGS GYAADQKSTQ NAINGITNMV   120
NSVIEKMGGN GTGADLAELL VLLLNQWTLL FHDSNVKNLY EKVKSQLKNN AKEIGNGCFE   180
FYHKCNNECM ESVKNGTYDY PKYSEESKLN REKID                              215
```

| SEQ ID NO: 374 | moltype = DNA length = 645 |
| --- | --- |
| FEATURE | Location/Qualifiers |
| misc_feature | 1..645 |
| | note = Synthetic |
| source | 1..645 |
| | mol_type = other DNA |
| | organism = synthetic construct |

SEQUENCE: 374

```
gtcaattttc tctcgattca gcttactctc ttcagaatat ttgggatagt cgtaagtgcc   60
gttcttcaca gactccatac attcattgtt gcacttatgg taaaactcga agcatccatt  120
cccgatttct ttggcattgt tcttcagctg ggatttgacc ttctcataca gattcttcac  180
gttgctatcg tggaacagca gagtccactg gttcagcagc agcaccagca gctcagccag  240
gtcagctcca gtgccatttc cgcccatttt ttcgatgaca gaattcacca tgttagtaat  300
gccattgatt gcgttctgtg tagacttctg atcagcggcg tagccgctgc cctgggtatt  360
gttatggtgg tagccgtacc acccgtccac cattcctgtc cacccgccct caataaaccc  420
tgcgatagcg ccgaacagtc ctcttgtttc ccgctgtggg atgttgcgca gtccggtgac  480
catcctcagt ccgctgccca gattcactga gtgggtgaca gtcacgttct tctccaggac  540
ggtatccact gtgtcgtgg agttgtttgc gtgatagccg atgcagatag tgtcagcgta  600
ggttgcggta aaagtacaca gcaggaccag cagtttggcc ttcat               645
```

| SEQ ID NO: 375 | moltype = DNA length = 1155 |
| --- | --- |
| FEATURE | Location/Qualifiers |
| misc_feature | 1..1155 |
| | note = Synthetic |
| source | 1..1155 |
| | mol_type = other DNA |
| | organism = synthetic construct |
| CDS | 1..1155 |

SEQUENCE: 375

```
atgaaggcca aactgctggt cctgctgtgt acttttaccg caacctacgc tgacactatc   60
tgcatcggct atcacgcaaa caactccacc gacacagtgg ataccgtcct ggagaagaac  120
gtgactgtca cccactcagt gaatctgggc agcggactga ggatggtcac cggactgcgc  180
aacatcccac agcgggaaac aagaggactg ttcggcgcta tcgcagggtt tattgagggc  240
gggtggacag gaatggtgga cgggtggtac ggctaccacc ataacaatac ccagggcagc  300
ggctacgccg ctgatcagaa gtctacacag aacgcaatca tggcattac taacatggtg  360
aattctgtca tcgaaaaaat gggcggaaat ggcactggag ctgacctggc tgagctgctg  420
gtgctgctgc tgaaccagtg gactctgctg ttccacgata gcaacgtgaa gaatctgtat  480
gagaaggtca atcccagct gaagaacaat gccaaagaaa tcgggaatgg atgcttcgag  540
ttttaccata agtgcaacaa tgaatgtatg gagtctgtga agaacggcac ttacgactat  600
cccaaatatt ctgaagagag taagctgaat cgagagaaaa ttgacagtgg gggcgacatc  660
atcaagctgc tgaacgaaca ggtgaacaag gagatgaaca gcaccaacct gtacatgagt  720
atgtctagtt ggtgttatac acactcactg gacggcgctg gctgttcct gtttgatcac  780
gcagccgagg aatacgaaca ctgcaaagaa aactgatcatt tcctgaatga gaacaatgtg  840
cccgtccagc tgacttcaat cagcgcccct gaacataagt tcgagggcct gacccagatc  900
tttcagaaag cttacgaaca cgagcagcat atttccgaat ctatcaacaa tattgtggac  960
cacgccatta gagcaaaga tcatgctacc ttcaactttc tgcagtggta cgtggccgag 1020
cagcacgagg aggaggtcct gtttaaggac atcctggata aatcgaact gattggaaac 1080
gagaatcatg gcctgtacct ggcagatcag tatgtgaagg gcattgccaa gtccagaaaa 1140
agtgggtcat gatga                                                1155
```

| SEQ ID NO: 376 | moltype = AA length = 383 |
| --- | --- |
| FEATURE | Location/Qualifiers |
| REGION | 1..383 |
| | note = Synthetic Construct |
| source | 1..383 |
| | mol_type = protein |
| | organism = synthetic construct |

SEQUENCE: 376

```
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHNNTQGS GYAADQKSTQ NAINGITNMV  120
NSVIEKMGGN GTGADLAELL VLLLNQWTLL FHDSNVKNLY EKVKSQLKNN AKEIGNGCFE  180
FYHKCNNECM ESVKNGTYDY PKYSEESKLN REKIDSGGDI IKLLNEQVNK EMNSTNLYMS  240
MSSWCYTHSL DGAGLFLFDH AAEEYEHAKK LIIFLNENNV PVQLTSISAP EHKFEGLTQI  300
FQKAYEHEQH ISESINNIVD HAIKSKDHAT FNFLQWYVAE QHEEEVLFKD ILDKIELIGN  360
ENHGLYLADQ YVKGIAKSRK SGS                                         383
```

| SEQ ID NO: 377 | moltype = DNA length = 1155 |
| --- | --- |
| FEATURE | Location/Qualifiers |
| misc_feature | 1..1155 |
| | note = Synthetic |
| source | 1..1155 |
| | mol_type = other DNA |
| | organism = synthetic construct |

SEQUENCE: 377

```
tcatcatgac ccacttttc tggacttggc aatgccttc acatactgat ctgccaggta   60
caggccatga ttctcgtttc caatcagttc gattttatcc aggatgtcct taaacaggac  120
ctcctcctcg tgctgctcgg ccacgtacca ctgcagaaag ttgaaggtag catgatcttt  180
gctcttaatg gcgtggtcca caatattgtt gatagattcg gaaatatgct gctcgtgttc  240
gtaagctttc tgaaagatct gggtcaggcc ctcgaactta tgttcagggg cgctgattga  300
```

```
agtcagctgg acgggcacat tgttctcatt caggaaaatg atcagtttct ttgcatgttc    360
gtattcctcg gctgcgtgat caaacaggaa cagcccagcg ccgtccagtg agtgtgtata    420
acaccaacta gacatactca tgtacaggtt ggtgctgttc atctccttgt tcacctgttc    480
gttcagcagc ttgatgatgt cgcccccact gtcaattttc tctcgattca gcttactctc    540
ttcagaatat ttgggatagt cgtaagtgcc gttcttcaca gactccatac attcattgtt    600
gcacttatgg taaaactcga agcatccatt cccgatttct ttggcattgt tcttcagctg    660
ggatttgacc ttctcataca gattcttcac gttgctatcg tggaacagca gagtccactg    720
gttcagcagc agcaccagca gctcagccag gtcagctcca gtgccatttc cgcccatttt    780
ttcgatgaca gaattcacca tgttagtaat gccattgatt gcgttctgtg tagacttctg    840
atcagcggcg tagccgctgc cctgggtatt gttatggtgg tagccgtacc accccgtccac   900
cattcctgtc cacccgccct caataaaccc tgcgatagcg ccgaacagtc ctcttgtttc    960
ccgctgtggg atgttgcgca gtccggtgac catcctcagt ccgctgccca gattcactga   1020
gtgggtgaca gtcacgttct tctccaggac ggtatccact gtgtcggtgg agttgtttgc   1080
gtgatagccg atgcagatag tgtcagcgta ggttgcggta aaagtacaca gcaggaccag   1140
cagtttggcc ttcat                                                    1155

SEQ ID NO: 378         moltype = DNA  length = 5579
FEATURE                Location/Qualifiers
misc_feature           1..5579
                       note = Synthetic
source                 1..5579
                       mol_type = other DNA
                       organism = synthetic construct
SEQUENCE: 378
tcgcgcgttt cggtgatgac ggtgaaaacc tctgacacat gcagctcccg gagacggtca    60
cagcttgtct gtaagcggat gccgggagca gacaagcccg tcagcgggtg                120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga cttttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg acttcctca    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tggagggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
cttttgtccgg cgctccccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgccgg cgctctagag   1380
atatcgccac catgaaggcc aaactgctgg tcctgctgtg tactttttacc gcaacctacg   1440
ctgacactat ctgcatcggc tatcacgcaa acaactccac cgacacagtg gataccgtcc   1500
tggagaagaa cgtgactgtc acccactcag tgaatctggg cagcggactg aggatggtca   1560
ccggactgcg caacatccca cagcgggaaa caagaggact gttcggcgct atcgcaggt   1620
ttattgaggg cgggtggaca ggaatggtgg acggttggta cggctaccac cataacaata   1680
cccagggcag cggctacgcc gctgatcaga agtctacaca gaacgcaatc aatggcatta   1740
ctaacatggt gaattctgtc atcgaaaaaa tgggcgaaa tggcactgga gctgacctgg   1800
ctgagctgct ggtgctgctg ctgaaccagt ggactgtgtc gttccacgat agcaacgtga   1860
agaatctgta tgagaaggtc aaatcccagc tgaagaacaa tgccaaagaa atcgggaatg   1920
gatgcttcga gttttaccat aagtgcaaca atgaatgtat ggagtctgtg aagaacggca   1980
cttacgacta tcccaaatat tctgaagaga gtaagctgaa tcgagagaaa attgacagtg   2040
ggggcgacat catcaagctg ctgaacgaac aggtgaacaa ggagatgaac agcaccaacc   2100
tgtacatgag tatgtctagt ggtgttata cacactcact ggacggcgct gggctgttcc   2160
tgtttgatca cgcagccgag gaatacgaac atgcaaagaa actgatcatt ttcctgaatg   2220
agaacaatgt gccccgtccag ctgacttcaa tcagcgcccc tgaacataag ttcgagggcc   2280
tgacccagat ctttcagaaa gcttacgaac acgagcagca tatttccgaa tctatcaaca   2340
atattgtgga ccacgccatt aagagcaaag atcatgctac cttcaacttt ctgcagttgt   2400
acgtggccga gcagcacgag gaggaggtcc tgtttaagga catcctggat aaaatcgaac   2460
tgattggaaa cgagaatcat ggcctgtacc tggcagatca gtatgtgaag gcattgcca   2520
agtccagaaa aagtgggtca tgatgaacac gtgggatcca gatctgctgt gccttctagt   2580
tgccagccat ctgttgtttg ccctccccc gtgccttcct tgaccctgga aggtgccact   2640
cccactgtcc tttcctaata aatgaggaaa attgcatcgc attgtctgag taggtgtcat   2700
tctattctgg ggggtggggt ggggcaggac agcaagggg aggattggga agacaatagc   2760
aggcatgctg gggatgcgtg gggctctatg gtacccagg tgctgaagaa ttgaccccggt   2820
tcctcctggg ccagaaagaa gcaggcacat cccttctct gtgacacacc ctgtccacgc   2880
ccctggttct tagttccagc cccactcata ggacactcat agctcaggag ggctccgcct   2940
tcaatcccac cgctcaaagt acttggagcg gtctctccct ccctcatcag cccaccaaac   3000
caaacctagc ctccaagagt gggaagaaat taaagcaaga taggctatta agtgcagagg   3060
gagagaaaat gcctccaaca tgtgaggaag taatgagaga aatcatagaa tttttaaggcc   3120
atgatttaag gccatcatgg ccttaatctt ccgcttcctc gctcactgac tcgctgcgct   3180
cggtcgttcg gctgcggcga gcggtatcag ctcactcaaa ggcggtaata cggttatcca   3240
cagaatcagg ggataacgca ggaaagaaca tgtgagcaaa aggccagcaa aaggccagga   3300
```

-continued

```
accgtaaaaa ggccgcgttg ctggcgtttt tccataggct ccgcccccct gacgagcatc    3360
acaaaaatcg acgctcaagt cagaggtggc gaaacccgac aggactataa agataccagg    3420
cgtttccccc tggaagctcc ctcgtgcgct ctcctgttcc gaccctgccg cttaccggat    3480
acctgtccgc ctttctccct tcgggaagcg tggcgctttc tcatagctca cgctgtaggt    3540
atctcagttc ggtgtaggtc gttcgctcca agctgggctg tgtgcacgaa ccccccgttc    3600
agcccgaccg ctgcgcctta tccggtaact atcgtcttga gtccaacccg gtaagacacg    3660
acttatcgcc actggcagca gccactggta acaggattag cagagcgagg tatgtaggcg    3720
gtgctacaga gttcttgaag tggtggccta actacggcta cactagaaga acagtatttg    3780
gtatctgcgc tctgctgaag ccagttacct tcggaaaaag agttggtagc tcttgatcgt    3840
gcaaacaaac caccgctggt agcggtggtt ttttttgtttg caagcagcag attacgcgca    3900
gaaaaaaagg atctcaagaa gatcctttga tcttttctac ggggtctgac gctcagtgga    3960
acgaaaactc acgttaaggg attttggtca tgagattatc aaaaggatc ttcacctaga    4020
tccttttaaa ttaaaaatga agtttaaat caatctaaag tatatatgag taaacttggt    4080
ctgacagtta ccaatgctta atcagtgagg cacctatctc agcgatctgt ctatttcgtt    4140
catccatagt tgcctgactc gggggggggg ggcgctgagg tctgcctcgt gaagaaggtg    4200
ttgctgactc ataccaggcc tgaatcgccc catcatccag ccagaaagtg agggagccac    4260
ggttgatgag agctttgttg taggtggacc agttggtgat tttgaacttt tgctttgcca    4320
cggaacggtc tgcgttgtcg ggaagatgcg tgatctgatc cttcaactca gcaaaagttc    4380
gatttattca acaaagccgc cgtcccgtca agtcagcgta atgctctgcc agtgttacaa    4440
ccaattaacc aattctgatt agaaaaactc atcgagcatc aaatgaaact gcaatttatt    4500
catatcagga ttatcaatac catattttg aaaaagccgt ttctgtaatg aaggagaaaa    4560
ctcaccgagg cagttccata ggatgccaag atcctggtat cggtctgcga ttccgactcg    4620
tccaacatca atacaaccta ttaatttccc ctcgtcaaaa ataaggttat caagtgagaa    4680
atcaccatga gtgacgactg aatccggtga gaatggcaaa agcttatgca tttctttcca    4740
gacttgttca acaggccagc cattacgctc gtcatcaaaa tcactcgcat caaccaaacc    4800
gttattcatt cgtgattgcg cctgagcgag acgaaatacg cgatcgctgt taaaaggaca    4860
attacaaaca ggaatcgaat gcaaccggcg caggaacact gccagcgcat caacaatatt    4920
ttcacctgaa tcaggatatt cttctaatac ctggaatgct gttttcccgg ggatcgcagt    4980
ggtgagtaac catgcatcat caggagtacg gataaaatgc ttgatggtcg gaagaggcat    5040
aaattccgtc agccagttta gtctgaccat ctcatctgta acatcattgg caacgctacc    5100
tttgccatgt ttcagaaaca actctggcgc atcgggcttc ccatacaatc gatagattgt    5160
cgcacctgat tgcccgacat atcgcgagc catttatac ccatataaat cagcatccat    5220
gttggaattt aatcgcggcc tcgagcaaga cgtttcccgt tgaatatggc tcataacacc    5280
ccttgtatta ctgtttatgt aagcagacag ttttattgtt catgatgata tatttttatc    5340
ttgtcaatg taacatcaga gattttgaga cacaacgtgg ctttcccccc cccccatta    5400
ttgaagcatt tatcagggtt attgtctcat gagcggatac atatttgaat gtatttagaa    5460
aaataaacaa ataggggttc cgcgcacatt tccccgaaaa gtgccacctg acgtctaaga    5520
aaccattatt atcatgacat taacctataa aaataggcgt atcacgaggc cctttcgtc    5579
```

```
SEQ ID NO: 379         moltype = DNA  length = 645
FEATURE                Location/Qualifiers
misc_feature           1..645
                       note = Synthetic
source                 1..645
                       mol_type = other DNA
                       organism = synthetic construct
CDS                    1..645
SEQUENCE: 379
atgaaggcca aactgctggt cctgctgtgt acttttaccg caacctacgc tgacactatc     60
tgcatcggct atcacgcaaa caactccacc gacacagtgg ataccgtcct ggagaagaac    120
gtgactgtca cccactcagt gaatctgggc agcggactga ggatggtcac cggactgcgc    180
aacatcccac agcgggaaac aagaggactg ttcggcgcta tcgcagggtt tattgagggc    240
gggtggacag gaatggtgga cgggtggtac ggctaccacc ataacaatac ccagggcagc    300
ggctacgccg ctgatcagaa gtctacacag aacgcaatca atggcattac taacatggtg    360
aattctgtca tcgaaaaaat gggcggaaat ggcactggag ctgacctggc tgagctgctg    420
gtgctgctgc tgaaccagtg gactctgctg ttccacgata gcaacgtgaa gaatctgtat    480
gagaaggtca atcccagct gaagaacaat gccaaagaaa tcgggaatgg atgcttcgag    540
ttttaccata agtgcaacaa tgaatgtatg gagtctgtga agaacggcac ttacgactat    600
cccaaatatt ctgaagagag taagctgaat cgagagaaaa ttgac                   645
```

```
SEQ ID NO: 380         moltype = AA   length = 215
FEATURE                Location/Qualifiers
REGION                 1..215
                       note = Synthetic Construct
source                 1..215
                       mol_type = protein
                       organism = synthetic construct
SEQUENCE: 380
MKAKLLVLLC TFTATYADTI CIGYHANNST DTVDTVLEKN VTVTHSVNLG SGLRMVTGLR     60
NIPQRETRGL FGAIAGFIEG GWTGMVDGWY GYHHNNTQGS GYAADQKSTQ NAINGITNMV    120
NSVIEKMGGN GTGADLAELL VLLLNQWTLL FHDSNVKNLY EKVKSQLKNN AKEIGNGCFE    180
FYHKCNNECM ESVKNGTYDY PKYSEESKLN REKID                              215
```

```
SEQ ID NO: 381         moltype = DNA  length = 645
FEATURE                Location/Qualifiers
misc_feature           1..645
                       note = Synthetic
```

```
source                   1..645
                         mol_type = other DNA
                         organism = synthetic construct
SEQUENCE: 381
gtcaatttc  tctcgattca  gcttactctc  ttcagaatat  tgggatagt   cgtaagtgcc    60
gttcttcaca  gactccatac  attcattgtt  gcacttatgg  taaaactcga  agcatccatt   120
cccgatttct  ttggcattgt  tcttcagctg  ggatttgacc  ttctcataca  gattcttcac   180
gttgctatcg  tggaacagca  gagtccactg  gttcagcagc  agcaccagca  gctcagccag   240
gtcagctcca  gtgccatttc  cgcccatttt  ttcgatgaca  gaattcacca  tgttagtaat   300
gccattgatt  gcgttctgtg  tagacttctg  atcagcggcg  tagccgctgc  cctgggtatt   360
gttatggtgg  tagccgtacc  acccgtccac  cattcctgtc  cacccgccct  caataaaccc   420
tgcgatagcg  ccgaacagtc  ctcttgtttc  ccgctgtggg  atgttgcgca  gtccggtgac   480
catcctcagt  ccgctgccca  gattcactga  gtgggtgaca  gtcacgttct  tctccaggac   540
ggtatccact  gtgtcggtgg  agttgtttgc  gtgatagccg  atgcagatag  tgtcagcgta   600
ggttgcggta  aaagtacaca  gcaggaccag  cagtttggcc  ttcat                    645

SEQ ID NO: 382           moltype = DNA  length = 1155
FEATURE                  Location/Qualifiers
misc_feature             1..1155
                         note = Synthetic
source                   1..1155
                         mol_type = other DNA
                         organism = synthetic construct
CDS                      1..1155
SEQUENCE: 382
atgaaggcca  aactgctggt  cctgctgtgt  acttttaccg  caacctacgc  tgacactatc    60
tgcatcggct  atcacgcaaa  caactccacc  gacacagtgg  ataccgtcct  ggagaagaac   120
gtgactgtca  cccactcagt  gaatctgggc  agcggactga  ggatggtcac  cggactgcgc   180
aacatcccac  agcgggaaac  aagaggactg  ttcggcgcta  tcgcagggtt  tattgagggc   240
gggtggacag  gaatggtgga  cgggtggtac  ggctaccacc  ataacaatac  ccagggcagc   300
ggctacgccg  ctgatcagaa  gtctacacag  aacgcaatca  atggcattac  taacatggtg   360
aattctgtca  tcgaaaaaat  gggcggaaat  ggcactggag  ctgacctggc  tgagctgctg   420
gtgctgctgc  tgaaccagtg  gactctgctg  ttccacgata  gcaacgtgaa  gaatctgtat   480
gagaaggtca  aatcccagct  gaagaacaat  gccaaagaaa  tcgggaatgg  atgcttcgag   540
ttttaccata  agtgcaacaa  tgaatgtatg  gagtctgtga  agaacggcac  ttacgactat   600
cccaaatatt  ctgaagagag  taagctgaat  cgagagaaaa  ttgacagtgg  gggcgacatc   660
atcaagctgc  tgaacgaaca  ggtgaacaag  gagatgaaca  gcaccaacct  gtacatgagt   720
atgtctagtt  ggtgttatac  acactcactg  gacggcgctg  ggctgttcct  gtttgatcac   780
gcagccgagg  aatactacga  tgcaaagaaa  ctgatcattt  tcctgaataa  gaacaatgtg   840
cccgtcaacc  tgacttcaat  cagcgcccct  gaacataagt  tcgagggcct  gacccagatc   900
tttcagaaag  cttacgaaca  cgagcagcat  atttccgaat  ctatcaacaa  tattgtggac   960
cacgccatta  agagcaaaga  tcatgctacc  ttcaactttc  tgcagtggta  cgtggccgag  1020
cagcacgagg  aggaggtcct  gttttaaggac  atcctggata  aaatcgaact  gattggaaac  1080
gagaatcatg  gcctgtacct  ggcagatcag  tatgtgaagg  gcattgccaa  gtccagaaaa  1140
agtgggtcat  gatga                                                       1155

SEQ ID NO: 383           moltype = AA  length = 383
FEATURE                  Location/Qualifiers
REGION                   1..383
                         note = Synthetic Construct
source                   1..383
                         mol_type = protein
                         organism = synthetic construct
SEQUENCE: 383
MKAKLLVLLC  TFTATYADTI  CIGYHANNST  DTVDTVLEKN  VTVTHSVNLG  SGLRMVTGLR    60
NIPQRETRGL  FGAIAGFIEG  GWTGMVDGWY  GYHHNNTQGS  GYAADQKSTQ  NAINGITNMV   120
NSVIEKMGGN  GTGADLAELL  VLLLNQWTLL  FHDSNVKNLY  EKVKSQLKNN  AKEIGNGCFE   180
FYHKCNNECM  ESVKNGTYDY  PKYSEESKLN  REKIDSGGDI  IKLLNEQVNK  EMNSTNLYMS   240
MSSWCYTHSL  DGAGLFLFDH  AAEEYEHAKK  LIIFLNENNV  PVNLTSISAP  EHKFEGLTQI   300
FQKAYEHEQH  ISESINNIVD  HAIKSKDHAT  FNFLQWYVAE  QHEEEVLFKD  ILDKIELIGN   360
ENHGLYLADQ  YVKGIAKSRK  SGS                                              383

SEQ ID NO: 384           moltype = DNA  length = 1155
FEATURE                  Location/Qualifiers
misc_feature             1..1155
                         note = Synthetic
source                   1..1155
                         mol_type = other DNA
                         organism = synthetic construct
SEQUENCE: 384
tcatcatgac  ccacttttc   tggacttggc  aatgccttc   acatactgat  ctgccaggta    60
caggccatga  ttctcgtttc  caatcagttc  gattttatcc  aggatgtcct  taaacaggac   120
ctcctcctgt  gctgctcgg   ccacgtacca  ctgcagaaaa  ttgaaggtag  catgatcttt   180
gctcttaatg  gcgtggtcca  caatattgtt  gatagattcg  gaaatatgct  gctcgtgttc   240
gtaagctttc  tgaaagatct  gggtcaggcc  ctcgaactta  tgttcagggg  cgctgattga   300
agtcaggttg  acgggcacat  tgttctcatt  caggaaaatg  atcagtttct  tgcatgttc   360
gtattcctcg  gctgcgtgat  caaacaggaa  cagcccagcg  ccgtcagtg   agtgtgtata   420
acaccaacta  gacatactca  tgtacaggtt  ggtgctgttc  atctccttgt  tcacctgttc   480
gttcagcagc  ttgatgatgt  cgcccccact  gtcaattttc  tctcgattca  gcttactctc   540
```

```
ttcagaatat ttgggatagt cgtaagtgcc gttcttcaca gactccatac attcattgtt    600
gcacttatgg taaaactcga agcatccatt cccgatttct ttggcattgt tcttcagctg    660
ggatttgacc ttctcataca gattcttcac gttgctatcg tggaacagca gagtccactg    720
gttcagcagc agcaccagca gctcagccag gtcagctcca gtgccatttc cgcccatttt    780
ttcgatgaca gaattcacca tgttagtaat gccattgatt gcgttctgtg tagacttctg    840
atcagcggcg tagccgctgc cctgggtatt gttatggtgg tagccgtacc acccgtccac    900
cattcctgtc cacccgccct caataaaccc tgccgatagcg ccgaacagtc tcttgtttc    960
ccgctgtggg atgttgcgca gtccggtgac catcctcagt ccgctgccca gattcactga   1020
gtgggtgaca gtcacgttct tctccaggac ggtatccact gtgtcggtgg agttgtttgc   1080
gtgatagccg atgcagatag tgtcagcgta ggttgcggta aaagtacaca gcaggaccag   1140
cagtttggcc ttcat                                                    1155

SEQ ID NO: 385         moltype = DNA   length = 5579
FEATURE                Location/Qualifiers
misc_feature           1..5579
                       note = Synthetic
source                 1..5579
                       mol_type = other DNA
                       organism = synthetic construct
SEQUENCE: 385
tcgcgcgttt cggtgatgac ggtgaaaacc tctgacacat gcagctcccg gagacggtca     60
cagcttgtct gtaagcggat gccgggagca gacaagcccg tcagggcgcg tcagcggtg    120
ttggcgggtg tcgggctggc cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggg cttttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag cgtgtaccgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctaggtcc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgccgg cgctctagag   1380
atatcgccac catgaaggcc aaactgctgg tcctgctgtg tacttttacc gcaacctacg   1440
ctgacactat ctgcatcggc tatcacgcaa acaactccac cgacacagtg gataccgtcc   1500
tggagaagaa cgtgactgtc acccactcag tgaatctggg cagcggactg aggatggtca   1560
ccgactgcg caacatccca cagcgggaaa caagaggact gttcggcgct atcgcaggtt   1620
ttattgaggg cgggtggaca ggaatgatgg acgggtggta cggctaccac cataacaata   1680
cccagggcag cggctacgcc gctgatcaga gtctacaca gaacgcaatc aatggcatta   1740
ctaacatggt gaattctgtc atcgaaaaaa tgggcggaaa tggcactgga gctgacctgg   1800
ctgagctgct ggtgctgctg ctgaaccagt ggactctgct gttccacgat agcaacgtga   1860
agaatctgta tgagaaggtc aaatcccagc tgaagaacaa tgccaaagaa atcgggaatg   1920
gatgcttcga gttttaccat aagtgcaaca atgaatgtat ggagtctgtg aagaacggca   1980
cttacgacta tcccaaatat tctgaagaga gtaagctgaa tcgagagaaa attgacagtg   2040
gggcgacat catcaagctg ctgaacgaac aggtgaacaa gagatgaac agcaccaacc   2100
tgtacatgag tatgtctagt tggtgttata cacactcact ggacggcgct gggctgttcc   2160
tgtttgatca cgcagccgag gaatacgaac atgcaaagaa actgatcatt ttcctgaatg   2220
agaacaatgt gcccgtcaac ctgacttcaa tcagcgcccc tgaacataag ttcgagggcc   2280
tgacccagat cttccagaaa gcttacgaac acgagcgaca tatttccgaa tctatcaaca   2340
atattgtgga ccacgccatt aagagcaaag atcatgctac cttcaacttt ctgcagtggt   2400
acgtggccga gcagcacgag gaggaggtcc tgtttaagga catcctggat aaaatcgaac   2460
tgattggaaa cgaaatcat ggcctgtacc tggcagatca gtatgtgaag gcattgcca   2520
agtccagaaa aagtgggtca tgatgaacac gtgggatcca gatctgctgt gccttctagt   2580
tgccagccat ctgttgtttg cccctccccc gtgccttcct tgaccctgga aggtgccact   2640
cccactgtcc tttcctaata aaatgaggaa attgcatcgc attgtctgag taggtgtcat   2700
tctattctgg ggggtgggt gggcaggac agcaagggg aggattggga agacaatagc   2760
aggcatgctg gggatgcggt gggctctatg gtacccaggg tgctgaagaa ttgacccggt   2820
tcctcctggg ccagaaagaa gcaggcacat ccccttctct gtgacacacc ctgtccacgc   2880
ccctggttct tagttccagc cccactcata ggacactcat agctcaggag ggctccgcc   2940
tcaatcccac ccgctaaagt acttggagcg gtctctccct ccctcatcag cccaccaaac   3000
caaacctagc ctccaagagt gggaagaaat taaagcaaga taggctatta agtgcagagg   3060
gagagaaaat gcctccaaca tgtgaggaag taatgagaga aatcatagaa ttttaaggcc   3120
atgatttaag gccatcatgg ccttaatctt ccgcttcctc gctcactgac tcgctgcgct   3180
cggtcgttcg gctgcggcga gcggtatcag ctcactcaaa gcggtaata cggttatcca   3240
cagaatcagg ggataacgca ggaaagaaca tgtgagcaaa aggccagcaa aaggccagga   3300
accgtaaaaa ggccgcgttg ctggcgtttt tccataggct ccgccccct gacgagcatc   3360
acaaaaatcg acgctcaagt cagaggtggc gaaacccgac aggactataa agataccagg   3420
cgtttccccc tggaagctcc ctcgtgcgct ctcctgttcc gaccctgccg cttaccggat   3480
acctgtccgc ctttctccct tcgggaagcg tggcgctttc tcatagctca cgctgtaggt   3540
```

```
atctcagttc ggtgtaggtc gttcgctcca agctgggctg tgtgcacgaa ccccccgttc    3600
agcccgaccg ctgcgcctta tccggtaact atcgtcttga gtccaacccg gtaagcacg     3660
acttatcgcc actggcagca gccactggta acaggattag cagagcgagg tatgtaggcg    3720
gtgctacaga gttcttgaag tggtggccta actacggcta cactagaaga acagtatttg    3780
gtatctgcgc tctgctgaag ccagttacct tcggaaaaag agttggtagc tcttgatccg    3840
gcaaacaaac caccgctggt agcggtggtt ttttgtttg caagcagcag attacgcgca     3900
gaaaaaaagg atctcaagaa gatcctttga tcttttctac ggggtctgac gctcagtgga    3960
acgaaaactc acgttaaggg attttggtca tgagattatc aaaaggatc ttcacctaga     4020
tccttttaaa ttaaaaatga agttttaaat caatctaaag tatatatgag taaacttggt    4080
ctgacagtta ccaatgctta atcagtgagg cacctatctc agcgatctgt ctatttcgtt    4140
catccatagt tgcctgactc ggggggggg ggcgctgagg tctgcctcgt gaagaaggtg     4200
ttgctgactc ataccaggcc tgaatcgccc catcatccag ccagaaagtg agggagccac    4260
ggttgatgag agctttgttg taggtggacc agttggtgat tttgaacttt tgctttgcca    4320
cggaacggtc tgcgttgtcg ggaagatgcg tgatctgatc cttcaactca gcaaagttc     4380
gatttattca acaaagccgc cgtcccgtca agtcagcgta atgctctgcc agtgttacaa    4440
ccaattaacc aattctgatt agaaaaactc atcgagcatc aaatgaaact gcaatttatt    4500
catatcagga ttatcaatac catattttg aaaaagccgt ttctgtaatg aaggagaaaa     4560
ctcaccgagg cagttccata ggatggcaag atcctggtat cggtctgcga ttccgactcg    4620
tccaacatca atacaaccta ttaatttccc ctcgtcaaaa ataaggttat caagtgagaa    4680
atcaccatga gtgacgactg aatccggtga gaatggcaaa agcttatgca tttctttcca    4740
gacttgttca acaggccagc cattacgctc gtcatcaaaa tcactcgcat caaccaaacc    4800
gttattcatt cgtgattgcg cctgagcgag acgaaatacg cgatcgctgt taaaaggaca    4860
attacaaaca ggaatcgaat gcaaccggcg caggaacacg gccagcgcat caacaatatt    4920
ttcacctgaa tcaggatatt cttctaatac ctggaatgct gttttcccgg ggatcgcagt    4980
ggtgagtaac catgcatcat caggagtacg gataaaatgc ttgatggtcg aagaggcat     5040
aaattccgtc agccagttta gtctgaccat ctcatcgtta acatcattgg caacgctacc    5100
tttgccatgt ttcagaaaca actctgcgcg atcgggcttc ccatacaatc gatagattg     5160
cgcacctgat tgcccgacat tatcgcgagc ccatttatac ccatataaat cagcatccat    5220
gttggaattt aatcgcggcc tcgagcaaga cgtttcccgt tgaatatggc tcataacacc    5280
ccttgtatta ctgtttatgt aagcagacag ttttattgt catgatgata tatttttatc    5340
ttgtgcaatg taacatcaga gattttgaga cacaacgtgg cttcccccc ccccccatta    5400
ttgaagcatt tatcagggtt attgtctcat gagcggatac atatttgaat gtatttagaa    5460
aaataaacaa atagggggttc cgcgcacatt tccccgaaaa gtgccacctg acgtctaaga    5520
aaccattatt atcatgacat taacctataa aaataggcgt atcacgaggc cctttcgtc    5579

SEQ ID NO: 386           moltype = DNA   length = 384
FEATURE                  Location/Qualifiers
misc_feature             1..384
                         note = Synthetic
source                   1..384
                         mol_type = other DNA
                         organism = synthetic construct
CDS                      1..384
SEQUENCE: 386
atgaaggcca agctgctggt gctcctgtgc accttcaccg ccacctacgc cgacaccatc    60
tgcatcggct accacgccaa caacagcacc gacaccgtgg ataccgtgct ggaaaagaac    120
gtgaccgtga cccacagcgt gaacctgggc agcggcctgc ggatggtgac aggcctgcgg    180
aacatccccc agagagagac acggggcctg ttcggcgcca ttgccggctt tatcgagggc    240
ggctggaccg gcatggtgga cgggtggtac ggctaccacc accagaacga gcagggcagc    300
ggctacgccg ccgaccagaa gtccacccag aacgccatca acggcatcac caacatggtg    360
aacagcgtga tcgagaagat gggc                                           384

SEQ ID NO: 387           moltype = AA    length = 128
FEATURE                  Location/Qualifiers
REGION                   1..128
                         note = Synthetic Construct
source                   1..128
                         mol_type = protein
                         organism = synthetic construct
SEQUENCE: 387
MKAKLLVLLC TFTATYADTI CIGYHANNST DTVDTVLEKN VTVTHSVNLG SGLRMVTGLR    60
NIPQRETRGL FGAIAGFIEG GWTGMVDGWY GYHHQNEQGS GYAADQKSTQ NAINGITNMV    120
NSVIEKMG                                                             128

SEQ ID NO: 388           moltype = DNA   length = 384
FEATURE                  Location/Qualifiers
misc_feature             1..384
                         note = Synthetic
source                   1..384
                         mol_type = other DNA
                         organism = synthetic construct
SEQUENCE: 388
gcccatcttc tcgatcacgc tgttcaccat gttggtgatg ccgttgatgg cgttctgggt    60
ggacttctgg tcggcggcgt agccgctgcc ctgctcgttc tggtggtggt agccgtacca    120
cccgtccacc atgccggtcc agccgccctc gataaagccg gcaatggcgc cgaacaggcc    180
ccgtgtctct ctctggggga tgttccgcag gcctgtcacc atccgcaggc cgctgcccag    240
gttcacgctg tgggtcacgg tcacgttctt ttccagcacg gtatccacgg tgtcggtgct    300
gttgttggcg tggtagccga tgcagatggt gtcggcgtag gtggcggtga aggtgcacag    360
gagcaccagc agcttggcct tcat                                           384
```

```
SEQ ID NO: 389            moltype = DNA  length = 1110
FEATURE                   Location/Qualifiers
misc_feature              1..1110
                          note = Synthetic
source                    1..1110
                          mol_type = other DNA
                          organism = synthetic construct
CDS                       1..1110
SEQUENCE: 389
atgaaggcca agctgctggt gctcctgtgc accttcaccg ccacctacgc cgacaccatc   60
tgcatcggct accacgccaa caacagcacc gacaccgtgg ataccgtgct ggaaaagaac  120
gtgaccgtga cccacagcgt gaacctgggc agcggcctgc ggatggtgac aggcctgcgg  180
aacatccccc agagagagac acggggcctg ttcggcgcca ttgccggctt tatcgagggc  240
ggctggaccg gcatggtgga cgggtggtac ggctaccacc accagaacga gcagggcagc  300
ggctacgccg ccgaccagaa gtccacccag aacgccatca cggcatcac caacatggtg   360
aacagcgtga tcgagaagat gggctccggc ggcagcggca ccgatctggc tgaactgctg  420
gtcctgctgc tgaacgagcg gaccctggac ttccacgaca gcaacgtgaa gaacctgtac  480
gagaaagtga agtcccagct gaagaacaac gccaaagaga tcggcaacgg ctgcttcgag  540
ttctaccaca gtgcaacaa cgagtgcatg gaaagcgtga agaacggcac ctacgactac  600
cccaagtaca gcgaggaaag caagctgaac cgcgagggag catgcaaat ctacgagggc   660
aagctgacag ccgagggcct gagattcggc atcgtgtgca gccggttcaa ccacgccctg  720
gtggacagac tggtggaagg cgccatcgac tgcatcgtgc ggcacggcgg cagagaagag  780
gacatcaccc tggtccgcgt gcccggcagc tgggaaattc ctgtggctgc cggcgagctg  840
gcccggaaaa aggatatcga cgccgtcatc gccatcggcg tgctgatcag aggcgccacc  900
ccccacttcg actatatcgc cagcgaggtg tccaaggagc tgaagaacct gagcctggaa  960
ctgcggaagc ccatcacctt cggagtgatc accgccgaca ccctggaaca ggccatcgag 1020
agagccggca ccaagcacgg caacaaggga tgggaagccg ccctgagcgc catcgagatg 1080
gccaatctgt tcaagagcct gcgctgatga                                  1110

SEQ ID NO: 390            moltype = AA  length = 368
FEATURE                   Location/Qualifiers
REGION                    1..368
                          note = Synthetic Construct
source                    1..368
                          mol_type = protein
                          organism = synthetic construct
SEQUENCE: 390
MKAKLLVLLC TFTATYADTI CIGYHANNST DTVDTVLEKN VTVTHSVNLG SGLRMVTGLR   60
NIPQRETRGL FGAIAGFIEG GWTGMVDGWY GYHHQNEQGS GYAADQKSTQ NAINGITNMV  120
NSVIEKMGSG GSGTDLAELL VLLLNERTLD FHDSNVKNLY EKVKSQLKNN AKEIGNGCFE  180
FYHKCNNECM ESVKNGTYDY PKYSEESKLN REGGMQIYEG KLTAEGLRFG IVASRFNHAL  240
VDRLVEGAID CIVRHGGREE DITLVRVPGS WEIPVAAGEL ARKEDIDAVI AIGVLIRGAT  300
PHFDYIASEV SKGLANLSLE LRKPITFGVI TADTLEQAIE RAGTKHGNKG WEAALSAIEM  360
ANLFKSLR                                                          368

SEQ ID NO: 391            moltype = DNA  length = 1110
FEATURE                   Location/Qualifiers
misc_feature              1..1110
                          note = Synthetic
source                    1..1110
                          mol_type = other DNA
                          organism = synthetic construct
SEQUENCE: 391
tcatcagcgc aggctcttga acagattggc catctcgatg gcgctcaggg cggcttccca   60
tcccttgttg ccgtgcttgg tgccggctct ctcgatggcc tgttccaggg tgtcggcggt  120
gatcactccg aaggtgatgg gcttccgcag ttccaggctc aggttggcca ggcccttgga  180
cacctcgctg gcgatatagt cgaagtgggg ggtggcgcct ctgatcagca cgccgatggc  240
gatgacggcg tcgatatcct ctttccgggc cagctcgccg gcagccacag gaatttccca  300
gctgccgggc acgcggacca gggtgatgtc ctcttctctg ccgccgtgcc gcacgatgca  360
gtcgatggcg ccttccacca gtctgtccac cagggcgtgg ttgaaccggc tgccacgat   420
gccgaatctc aggccctcgg ctgtcagctt gccctcgtag atttgcatgc ctccctgcg   480
gttcagcttg cttcctcgc tgtacttggg gtagtcgtag gtgccgttct tcacgctttc  540
catgcactcg ttgttgcact gtggtagaa ctcgaagcag ccgttgccga tctctttggc   600
gttgttcttc agctgggact tcactttctc gtacaggttc ttcacgttgc tgtcgtggaa  660
gtccagggtc cgctcgttca gcagcaggac cagcagttca gccagatcgg tgccgctgcc  720
gccggagccc atcttctcga tcacgctgtt caccatggtg tgatgccgt tgatggcgtt   780
ctgggtggac ttctggtcgg cggcgtagcc gctgccctgc tcgttctggt ggtggtagcc  840
gtaccacccg tccaccatgc cggtccagcc gccccgata aagccggcaa tggcgccgaa   900
caggccccgt gtctctctct gggggatgtt ccgcaggcct gtaccatcc gcaggccgct   960
gcccaggttc acgctgtggg tcacggtcac gttcttttcc agcacggtat ccacggtgtc 1020
ggtgctgttg ttggcgtggt agccgatgca gatggtgtcg gcgtaggtgg cggtgaaggt 1080
gcacaggagc cagcagcagct tggccttcat                                 1110

SEQ ID NO: 392            moltype = DNA  length = 5528
FEATURE                   Location/Qualifiers
misc_feature              1..5528
                          note = Synthetic
```

| source | 1..5528 |
| | mol_type = other DNA |
| | organism = synthetic construct |

SEQUENCE: 392

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcgggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaataggga ctttccattg acgtcaatgg gtggagtatt tacggtaaac  540
tgcccacttg gcagtacatc aagtgtatca tatgccaagt acgccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatt 1320
ggtcttttct gcagtcaccg tcgtcgacac gtgtgatcag atatcgcggc cgctctagaa 1380
ccaccatgaa ggccaagctg ctggtgctcc tgtgcacctt caccgccacc tacgccgaca 1440
ccatctgcat cggctaccac gccaacaaca gcaccgacac cgtggatacc gtgctggaaa 1500
agaacgtgac cgtgacccac agcgtgaacc tgggcagcgg cctgcggatg gtgacaggcc 1560
tgcggaacat cccccagaga gagacacggg gcctgttcgg cgccattgcc ggctttatcg 1620
agggcggctg gaccggcatg gtggacgggt ggtacggcta ccaccaccag aacgagcagg 1680
gcagcggcta cgccgccgac cagaagtcca cccagaacgc catcaacggc atcaccaaca 1740
tggtgaacag cgtgatcgag aagatgggct ccggcggcag cggcaccgac ctggctgaac 1800
tgctggtcct gctgctgaac gagcggaccc tggacttcca cgacagcaac gtgaagaacc 1860
tgtacgagaa agtgaagtcc cagctgaaga acaacgccaa agagatcggc aacggctgct 1920
tcgagttcta ccacaagtgc aacaacgagt gcatggaaag cgtgaagaac ggcacctacg 1980
actaccccaa gtacagcgag gaaagcaagc tgaaccgcga gggaggcatg caaatctacg 2040
agggcaagct gacagccgag ggcctgagat tcggcatcgt ggccagcggc ttcaaccacg 2100
ccctggtgga cagactggtg gaaggcgcca tcgactgcat cgtgcggcac ggcggcagag 2160
aagaggacat caccctggtc cgcgtgcccg gcagctggga aattcctgtg gctgccggcg 2220
agctggcccg gaaagaggat atcgacgccg tcatcgccat cggcgtgctg atcagaggcg 2280
ccacccccca cttcgactat atccgcagcc aggtgtccaa aacctgagcc 2340
tggaactgcg gaagcccatc accttcggag tgatcaccgc cgacaccctg aacaggcca 2400
tcgagagagc cggcaccaag cacggcaaca agggatggga agccgccctg agcgccatcg 2460
agatggccaa tctgttcaag agcctgcgct gatgaacacg tgggatccag atctgctgtg 2520
ccttctagtt gccagccatc tgttgtttgc ccctccccg tccttcctt gacccctggaa 2580
ggtgccactc ccactgtcct ttcctaataa aatgaggaaa ttgcatcgca ttgtctgagt 2640
aggtgtcatt ctattctggg gggtggggtg gggcaggaca gcaaggggga ggattgggaa 2700
gacaatagca ggcatgctgg ggatgcggtg gctctatgg gtacccaggt gctgaagaat 2760
tgacccggtt cctcctgggc cagaaagaag caggcacatc cccttctctg tgacacacat 2820
tgtccacgcc cctggttctt agttccagcc ccactcatag gacactcata gctcaggagg 2880
gctccgcctt caatcccacc cgctaaagta cttggagcgg tctctccctc cctcatcagc 2940
ccaccaaacc aaacctagcc tccaagagtg ggaagaaatt aaagcaagat aggctattaa 3000
gtgcagaggg agagaaaatg cctccaacat gtgaggaagt aatgagagaa atcatagaat 3060
tttaaggcca tgatttaagg ccatcatggc cttaatcttc cgcttcctcg ctcactgact 3120
cgctgcgctc ggtcgttcgg ctgcggcgag cggtatcagc tcactcaaag gcggtaatac 3180
ggttatccac agaatcaggg gataacgcag gaaagaacat gtgagcaaaa ggccagcaaa 3240
aggccaggaa ccgtaaaaag gccgcgttgc tggcgttttt ccataggctc cgcccccctg 3300
acgagcatca caaaaatcga cgctcaagtc agaggtggcg aaacccgaca ggactataaa 3360
gataccaggc gtttccccct ggaagctccc tcgtgcgctc tcctgttccg accctgccgc 3420
ttaccggata cctgtccgcc tttctccctt cgggaagcgt ggcgctttct catagctcac 3480
gctgtaggta tctcagttcg gtgtaggtcg ttcgctccaa gctgggctgt gtgcacgaac 3540
ccccgttca gcccgaccgc tgcgccttat ccggtaacta tcgtcttgag tccaacccgg 3600
taagacacga cttatcgcca ctggcagcag ccactggtaa caggattagc agagcgaggt 3660
atgtaggcgg tgctacagag ttcttgaagt ggtggcctaa ctacggctac actagaagaa 3720
cagtatttgg tatctgcgct ctgctgaagc cagttacctt cggaaaaaga gttggtagct 3780
cttgatccgg caaacaaacc accgctggta gcggtggttt ttttgtttgc aagcagcaga 3840
ttacgcgcag aaaaaaagga tctcaagaag atcctttgat cttttctacg ggtctgacg 3900
ctcagtggaa cgaaaactca cgttaaggga ttttggtcat gagattatca aaaaggatct 3960
tcacctagat ccttttaaat taaaaatgaa gttttaaatc aatctaaagt atatatgagt 4020
aaacttggtc tgacagttac caatgcttaa tcagtgaggc acctatctca gcgatctgtc 4080
tatttcgttc atccatagtt gcctgactcg ggggggggg gcgctgaggt ctgcctcgtg 4140
aagaaggtgt tgctgactca taccaggcct gaatcgccca tcatccaca cagaaagtga 4200
gggagccacg gttgatgaga gctttgttgt aggtggacca gttggtgatt ttgaactttt 4260
gctttgccac ggaacggtct gcgttgtcgg aagatgcgt gatctgatcc ttcaactcag 4320
caaaagttcg atttattcaa caaagccgcc gtcccgtcaa gtcagcgtaa tgctctgcca 4380
gtgttacaac caattaacca attctgatta gaaaaactca tcgagcatca aatgaaactg 4440
caatttattc atatcaggat tatcaatacc atattttga aaaagccgtt tctgtaatga 4500
```

```
aggagaaaac tcaccgaggc agttccatag gatggcaaga tcctggtatc ggtctgcgat  4560
tccgactcgt ccaacatcaa tacaacctat taatttcccc tcgtcaaaaa taaggttatc  4620
aagtgagaaa tcaccatgag tgacgactga atccggtgag aatggcaaaa gcttatgcat  4680
ttctttccag acttgttcaa caggccagcc attacgctcg tcatcaaaat cactcgcatc  4740
aaccaaaccg ttattcattc gtgattgcgc ctgagcgaga cgaaatacgc gatcgctgtt  4800
aaaaggacaa ttacaaacag gaatcgaatg caaccggcgc aggaacactg ccagcgcatc  4860
aacaatattt tcacctgaat caggatattc ttcaataccc tggaatgctg ttttcccggg  4920
gatcgcagtg gtgagtaacc atgcatcatc aggagtacgg ataaaatgct tgatggtcgg  4980
aagaggcata aattccgtca gccagtttag tctgaccatc tcatctgtaa catcattggc  5040
aacgctacct ttgccatgtt tcagaaacaa ctctggcgca tcgggcttcc catacaatcg  5100
atagattgtc gcacctgatt gcccgacatt atcgcgagcc catttatacc catataaatc  5160
agcatccatg ttgaattta atcgcggcct cgagcaagac gtttcccgtt gaatatggct  5220
cataacaccc cttgtattac tgtttatgta agcagacagt tttattgttc atgatgatat  5280
atttttatct tgtgcaatgt aacatcagag attttagcac acaacgtgcc tttcccccc   5340
ccccattat tgaagcattt atcagggtta ttgtctcatg agcggataca tatttgaatg   5400
tatttagaaa aataaacaaa tagggggttcc gcgcacattt ccccgaaaag tgccacctga  5460
cgtctaagaa accattatta tcatgacatt aacctataaa aataggcgta tcacgaggcc  5520
ctttcgtc                                                           5528

SEQ ID NO: 393          moltype = DNA   length = 594
FEATURE                 Location/Qualifiers
misc_feature            1..594
                        note = Synthetic
source                  1..594
                        mol_type = other DNA
                        organism = synthetic construct
CDS                     1..594
SEQUENCE: 393
atgaaggcca aactgctggt cctgctgtgt acttttaccg caacctacgc tgacactatc   60
tgcatcggct atcacgcaaa caactccacc gacacagtcc tggagaagaac              120
gtgactgtca cccactcagt gaatctgggc agcggactga ggatggtcac cggactgcgc  180
aacgggtcag gctggacagg aatggtggac gggtggtacg gctaccacca tcagaatgag  240
cagggcagcg gctacgccgc tgatcagaag tctacacaga acgcaatcaa tggcattact  300
aacatggtga ttctgtcat cgaaaaaatg ggcagcggag gctccggaac agacctggac  360
gagctgctgg tgctgctgct gaaccagtgg actctgctgt tccacgatag caacgtgaag  420
aatctgtatg agaaggtcaa atcccagctg aagaacaatg ccaaagaaat cgggaatgga  480
tgcttcgagt tttaccataa gtgcaacaat gaatgtatgg agtctgtgaa gaacggcact  540
tacgactatc ccaaatattc tgaagagagt aagctgaatc gagagaaaat tgac        594

SEQ ID NO: 394          moltype = AA   length = 198
FEATURE                 Location/Qualifiers
REGION                  1..198
                        note = Synthetic Construct
source                  1..198
                        mol_type = protein
                        organism = synthetic construct
SEQUENCE: 394
MKAKLLVLLC TFTATYADTI CIGYHANNST DTVDTVLEKN VTVTHSVNLG SGLRMVTGLR    60
NGSGWTGMVD GWYGYHHQNE QGSGYAADQK STQNAINGIT NMVNSVIEKM GSGGSGTDLA  120
ELLVLLLNQW TLLFHDSNVK NLYEKVKSQL KNNAKEIGNG CFEFYHKCNN ECMESVKNGT  180
YDYPKYSEES KLNREKID                                                198

SEQ ID NO: 395          moltype = DNA   length = 594
FEATURE                 Location/Qualifiers
misc_feature            1..594
                        note = Synthetic
source                  1..594
                        mol_type = other DNA
                        organism = synthetic construct
SEQUENCE: 395
gtcaattttc tctcgattca gcttactctc ttcagaatat ttgggatagt cgtaagtgcc    60
gttcttcaca gactccatac attcattgtt gcacttatgg taaaactcga agcatccatt   120
cccgatttct ttggcattgt tcttcagctg ggatttgacc ttctcataca gattcttcac   180
gttgctatcg tggaacagca gagtccactg gttcagcagc agcaccagca gctcagccga   240
gtctgttccg gagcctccgc tgcccatttt ttcgatgaca gaattcacca tgttagtaat   300
gccattgatt gcgttctgtg tagacttctg atcagcggcg tagccgctgc cctgctcatt   360
ctgatggtgg tagccgtacc acccgtccac cattcctgtc cagcctgacc cgttgcgcag  420
tccggtgacc atcctcagtc gctgcccag attcactgag tgggtgacag tcacgttctt   480
ctccaggacg gtatccactg tgtcggtgga gttgtttgcg tgatagccga tgcagatagt  540
gtcagcgtag gttgcggtaa aagtacacag caggaccagc agtttggcct tcat        594

SEQ ID NO: 396          moltype = DNA   length = 1104
FEATURE                 Location/Qualifiers
misc_feature            1..1104
                        note = Synthetic
source                  1..1104
                        mol_type = other DNA
                        organism = synthetic construct
CDS                     1..1104
```

```
SEQUENCE: 396
atgaaggcca aactgctggt cctgctgtgt acttttaccg caacctacgc tgacactatc    60
tgcatcggct atcacgcaaa caactccacc gacacagtgg ataccgtcct ggagaagaac   120
gtgactgtca cccactcagt gaatctgggc agcggactga ggatggtcac cggactgcgc   180
aacggctcag gctggacagg aatggtggac gggtggtacg gctaccacca tcagaatgag   240
cagggcagcg gctacgccgc tgatcagaag tctacacaga acgcaatcaa tggcattact   300
aacatggtga attctgtcat cgaaaaaatg ggcagcggag gctccggaac agacctggct   360
gagctgctgg tgctgctgct gaaccagtgg actctgctgt tccacgatag caacgtgaag   420
aatctgtatg agaaggtcaa atcccagctg aagaacagga ccaaagaaat cgggaatgga   480
tgcttcgagt tttaccataa gtgcaacaat gaatgtatgt agtctgtgaa gaacggcact   540
tacgactatc ccaaatattc tgaagagagt aagctgaatc gagagaaaat tgacagtggg   600
ggcgacatca tcaagctgct gaacgaacag gtgaacaagg agatgcagag ctccaacctg   660
tacatgagta tgtctagttg gtgttataca cactcactgg acggcgctgg gctgttcctg   720
tttgatcacg cagccgagga atacgaacat gcaaagaaac tgatcatttt cctgaatgag   780
aacaatgtgc ccgtccagct gacttcaatc agcgcccctg aacataagtt cgagggcctg   840
acccagatct ttcagaaagc ttacgaacac gagcagcata tttccgaatc tatcaacaat   900
attgtggacc acgccattaa gagcaaagat catgctacct tcaactttct gcagtggtac   960
gtggccgaca gcacgaggag ggaggtcctg tttaaggaca tcctggataa aatcgaactg  1020
attggaaacg agaatcatgg cctgtacctg gcagatcagt atgtgaaggg cattgccaag  1080
tccagaaaaa gtgggtcatg atga                                          1104

SEQ ID NO: 397          moltype = AA  length = 366
FEATURE                 Location/Qualifiers
REGION                  1..366
                        note = Synthetic Construct
source                  1..366
                        mol_type = protein
                        organism = synthetic construct
SEQUENCE: 397
MKAKLLVLLC TFTATYADTI CIGYHANNST DTVDTVLEKN VTVTHSVNLG SGLRMVTGLR    60
NGSGWTGMVD GWYGYHHQNE QGSGYAADQK STQNAINGIT NMVNSVIEKM GSGGSGTDLA   120
ELLVLLLNQW TLLFHDSNVK NLYEKVKSQL KNNAKEIGNG CFEFYHKCNN ECMESVKNGT   180
YDYPKYSEES KLNREKIDSG GDIIKLLNEQ VNKEMQSSNL YMSMSSWCYT HSLDGAGLFL   240
FDHAAEEYEH AKKLIIFLNE NNVPVQLTSI SAPEHKFEGL TQIFQKAYEH EQHISESINN   300
IVDHAIKSKD HATFNFLQWY VAEQHEEEVL FKDILDKIEL IGNENHGLYL ADQYVKGIAK   360
SRKSGS                                                               366

SEQ ID NO: 398          moltype = DNA  length = 1104
FEATURE                 Location/Qualifiers
misc_feature            1..1104
                        note = Synthetic
source                  1..1104
                        mol_type = other DNA
                        organism = synthetic construct
SEQUENCE: 398
tcatcatgac ccactttttc tggacttggc aatgcccttc acatactgat ctgccaggta    60
caggccatga ttctcgtttc caatcagttc gattttatcc aggatgtcct taaacaggac   120
ctcctcctcg tgctgctcgg ccacgtacca ctgcagaaag ttgaaggtag catgatcttt   180
gctcttaatg gcgtggtcca caatattgtt gatagattcg gaaatatgct gctcgtgttc   240
gtaagctttc tgaaagatct gggtcaggcc ctcgaactta tgttcagggg cgctgattga   300
agtcagctgg acgggcacat tgttctcatt caggaaaatg atcagtttct ttgcatgttc   360
gtattcctcg gctgcgtgat caaacaggaa cagcccagcg ccgtccagtg agtgtgtata   420
acaccaacta gacatactca tgtacaggtt ggagctctgc atctccttgt tcacctgttc   480
gttcagcagc ttgatgatgt cgcccccact gtcaattttc tctcgattca gcttactctc   540
ttcagaatat ttgggatagt cgtaagtgcc gttcttcaca gactccatac attcattgtt   600
gcacttatgg taaaactcga agcatccatt cccgatttct ttggcattgt tcttcagctg   660
ggatttgacc ttctcataca gattcttcac gttgctatcg tggaacagca gagtccactg   720
gttcagcagc agcaccagca gctcagccag gtctgttccg gagcctccgc tgcccatttt   780
ttcgatgaca gaattcacca tgttagtaat gccattgatt gcgttctgtg tagacttctg   840
atcagcggcg tagccgctgc cctgctcatt ctgatggtgg tagccgtacc accgtccac   900
cattcctgtc cagcctgacc cgttgcgcag tccggtgacc atcctcagtc cgctgcccag   960
attcactgag tgggtgacag tcacgttctt ctccaggacg gtatccactg tgtcggtgga  1020
gttgtttgcg tgatagccga tgcagatagt gtcagctagg ttgcggtaa aagtacacag  1080
caggaccagc agtttggcct tcat                                          1104

SEQ ID NO: 399          moltype = DNA  length = 5528
FEATURE                 Location/Qualifiers
misc_feature            1..5528
                        note = Synthetic
source                  1..5528
                        mol_type = other DNA
                        organism = synthetic construct
SEQUENCE: 399
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
```

-continued

```
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga cttttccattg acgtcaatgg gtggagtatt tacggtaaac   540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc gctctccac gctttgcctg    1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagag   1380
atatcgccac catgaaggcc aaactgctgg tcctgctgtg tacttttacc gcaacctacg   1440
ctgacactat ctgcatcggc tatcacgcaa acaactccac cgacacagtg gataccgtcc   1500
tggagaagaa cgtgactgtc acccactcag tgaatctggg cagcggactg aggatggtca   1560
ccggactgcg caacgggtca ggctggacag gaatggtgga cggtggtac ggctaccacc    1620
atcagaatga gcagggcagc ggctacgccg ctgatcagaa gtctacacag aacgcaatca   1680
atggcattac taacatggtg aattctgtca tcgaaaaaat gggcagcgga ggctccggaa   1740
cagacctggc tgagctgctg gtgctgctgc tgaaccagtg gactctgctg ttccacgata   1800
gcaacgtgaa gaatctgtat gagaaggtca aatcccagct gaagaacaat gccaagaaaa   1860
tcgggaatgg atgcttcgag ttttaccata agtgcaacaa tgaatgtatg gagtcgtgga   1920
agaacggcac ttacgactat cccaaatatt ctgaagagag taagctgaat cgagagaaaa   1980
ttgacagtgg gggcgacatc atcaagctgc tgaacgaaca ggtgaacaag agatgcagaa   2040
gctccaacct gtacatgagt atgtctagtt ggtgttatac acactcactg gacggcgctg   2100
ggctgttcct gtttgatcac gcagccgagg aatacgaaca tgcaaagaaa ctgatcattt   2160
tcctgaatga gaacaatgtg cccgtccagc tgacttcaat cagcgcccct gaacataagt   2220
tcgagggcct gacccagatc tttcagaaag cttacgaaca cgagcagcat atttccgaat   2280
ctatcaacaa tattgtggac cacgccatta agagcaaaga tcatgctacc ttcaactttc   2340
tgcagtggta cgtggccgag cagcacgagg aggaggtcct gtttaaggac atcctggata   2400
aaatcgaact gattggaaac gagaatcatg gcctgtacct ggcagatcag tatgtgaagg   2460
gcattgccaa gtccagaaaa agtgggtcat gatgaacacg tgggatccag atctgctgtg   2520
ccttctagtt gccagccatc tgttgtttgc ccctcccccg tgccttcctt gaccctggaa    2580
ggtgccactc ccactgtcct ttcctaataa aatgaggaaa ttgcatcgca ttgtctgagt   2640
aggtgtcatt ctattctggg gggtggggtg ggcaggaca caagggga ggattgggaa     2700
gacaatagca ggcatgctgg ggatgcggtg ggctctatgg gtacccaggt gctgaagaat   2760
tgacccggtt cctcctgggc cagaaagaag caggcacatc cccttctctg tgacacaccc   2820
tgtccacgcc cctggttctt agttccagcc ccactcatag gacactcata gctcaggagg   2880
gctccgcctt caatcccacc cgctaaagta cttggagcgg tctctccctc cctcatcagc   2940
ccaccaaacc aaacctagcc tccaagagtg ggaagaaatt aaagcaagat aggctattaa   3000
gtgcagaggg agagaaaatg cctccaacat gtgaggaagt aatgagagaa atcatagaat   3060
tttaaggcca tgatttaagg ccatcatggc cttaatcttc cgcttcctcg ctcactgact   3120
cgctgcgctc ggtcgttcgg ctgcggcgag cggtatcagc tcactcaaag gcggtaaatc   3180
ggttatccac agaatcaggg gataacgcag gaaagaacat gtgagcaaaa ggccagcaaa   3240
aggccaggaa ccgtaaaaag gccgcgttgc tggcgttttt ccataggctc cgccccctg    3300
acgagcatca caaaaatcga cgctcaagtc agaggtggcg aaacccgaca ggactataaa   3360
gataccaggc gtttccccct ggaagctccc tcgtgcgctc tcctgttccg accctgccgc   3420
ttaccggata cctgtccgcc tttctccctt cgggaagcgt ggcgctttct catagctcac   3480
gctgtaggta tctcagttcg gtgtaggtcg ttcgctccaa gctgggctgt gtgcacgaac   3540
ccccgttca gcccgaccgc tgcgccttat ccggtaacta tcgtcttgag tccaacccgg    3600
taagacacga cttatcgcca ctggcagcag ccactggtaa caggattagc agagcgaggt   3660
atgtaggcgg tgctacagag ttcttgaagt ggtggcctaa ctacggctac actagaagaa   3720
cagtatttgg tatctgcgct ctgctgaagc cagttacctt cggaaaaaga gttggtagct   3780
cttgatccgg caaacaaacc accgctggta gcggtggttt ttttgtttgc aagcagcaga   3840
ttacgcgcag aaaaaaagga tctcaagaag atcctttgat cttttctacg gggtctgacg   3900
ctcagtggaa cgaaaactca cgttaaggga ttttggtcat gagattatca aaaaggatct   3960
tcacctagat cctttaaat taaaatgaa gttttaaatc aatctaaagt atatatgagt     4020
aaacttggtc tgacagttac caatgcttaa tcagtgaggc acctatctca gcgatctgtc   4080
tatttcgttc atccatagtt gcctgactcg ggggggggg gcgctgaggt ctgcctcgtg   4140
aagaaggtgt tgctgactca taccaggcct gaatcgccca atcatccagc cagaaagtga   4200
gggagccacg gttgatgaga gctttgttgt aggtggacca gttggtgatt ttgaacttt     4260
gctttgccac ggaacggtct gcgttgtcgg aagatgcgt gatctgatcc ttcaactcag    4320
caaaagttcg atttattcaa caaagccgcc gtcccgtcaa gtcagcgtaa tgctctgcca   4380
gtgttacaac caattaacca attctgatta gaaaaactca tcgagcatca aatgaaactg   4440
caatttattc atatcaggat tatcaatacc atatttttga aaaagccgtt tctgtaatga   4500
aggagaaaac tcaccgaggc agttccatag gatggcaaga tcctggtatc ggtctgcgat   4560
tccgactcgt ccaacatcaa tacaacctat taatttcccc tcgtcaaaaa taaggttatc   4620
aagtgagaaa tcaccatgag tgacgactga atccggtgag aatggcaaaa gcttatgcat   4680
ttctttccag acttgttcaa caggccagcc attacgctcg tcatcaaaat cactcgcatc   4740
aaccaaaccg ttattcattc gtgattgcgc ctgagcgaga cgaaatacgc gatcgctgtt   4800
aaaaggacaa ttacaaacag gaatcgaatg caaccggcgc aggaacactg ccagcgcatc   4860
aacaatattt tcacctgaat caggatattc ttctaatacc tggaatgctg ttttcccggg   4920
gatcgcagtg gtgagtaacc atgcatcatc aggagtacgg ataaaatgct tgatggtcgg   4980
aagaggcata aattccgtca gccagtttag tctgaccatc tcatctgtaa catcattggc   5040
aacgctacct ttgccatgtt tcagaaacaa ctctggcgca tcgggcttcc catacaatcg   5100
```

```
atagattgtc gcacctgatt gcccgacatt atcgcgagcc catttatacc catataaatc    5160
agcatccatg ttggaattta atcgcggcct cgagcaagac gtttcccgtt gaatatggct    5220
cataacaccc cttgtattac tgtttatgta agcagacagt tttattgttc atgatgatat    5280
atttttatct tgtgcaatgt aacatcagag attttgagac acaacgtggc tttcccccc     5340
cccccattat tgaagcattt atcagggtta ttgtctcatg agcggataca tatttgaatg    5400
tatttagaaa aataaacaaa taggggttcc gcgcacattt ccccgaaaag tgccacctga    5460
cgtctaagaa accattatta tcatgacatt aacctataaa aataggcgta tcacgaggcc    5520
ctttcgtc                                                             5528

SEQ ID NO: 400          moltype = AA  length = 198
FEATURE                 Location/Qualifiers
REGION                  1..198
                        note = Synthetic
source                  1..198
                        mol_type = protein
                        organism = synthetic construct
SEQUENCE: 400
MKAKLLVLLC TFTATYADTI CIGYHANNST DTVDTVLEKN VTVTHSVNLG SGLRMVTGLR     60
NGSGWTGMVD GWYGYHHQNE QGSGYAADQK STQNAINGIT NMVNSVIEKM GSGGSGTDLA    120
ELLVLLLNQW TLLFHDSNVK NLYEKVKSQL KNNAKEIGNG CFEFYHKCNN ECMESVKNGT    180
YDYPKYSEES KLNREKID                                                 198

SEQ ID NO: 401          moltype = AA  length = 366
FEATURE                 Location/Qualifiers
REGION                  1..366
                        note = Synthetic
source                  1..366
                        mol_type = protein
                        organism = synthetic construct
SEQUENCE: 401
MKAKLLVLLC TFTATYADTI CIGYHANNST DTVDTVLEKN VTVTHSVNLG SGLRMVTGLR     60
NGSGWTGMVD GWYGYHHQNE QGSGYAADQK STQNAINGIT NMVNSVIEKM GSGGSGTDLA    120
ELLVLLLNQW TLLFHDSNVK NLYEKVKSQL KNNAKEIGNG CFEFYHKCNN ECMESVKNGT    180
YDYPKYSEES KLNREKIDSG GDIIKLLNEQ VNKEMQSSNL YMSMSSWCYT HSLDGAGLFL    240
FDHAAEEYEH AKKLIIFLNE NNVPVQLTSI SAPEHKFEGL TQIFQKAYEH EQHISESINN    300
IVDHAIKSKD HATFNFLQWY VAEQHEEEVL FKDILDKIEL IGNENHGLYL ADQYVKGIAK    360
SRKSGS                                                              366
```

It is claimed:

1. A method to vaccinate an individual against influenza virus, comprising administering to the individual a nucleic acid molecule encoding a protein construct, the protein construct comprising:
   an HA protein domain and a linker sequence, wherein the HA protein domain comprises the sequence of an influenza hemagglutinin (HA) protein that lacks at least 95% of the head region amino acid sequence, and in place of the missing sequence comprises a first linker sequence, wherein the first linker sequence is less than 10 amino acids in length; and wherein the HA protein domain comprises at least one alteration selected from the group consisting of:
   a. deletion of the amino acid region corresponding to amino acids N403-W435 of the internal loop region of the influenza HA protein set forth as SEQ ID NO: 8, wherein the resulting ends of the HA protein are joined directly together;
   b. replacement of the amino acid sequence corresponding to the internal loop region with a second linker sequence; and,
   c. substitution of at least one amino acid residue in a pair of amino acid residues in the HA protein domain, wherein the pair of amino acid residues form a noncovalent bond in the folded HA protein; and, wherein the strength of the noncovalent bond between the amino acid pair in the folded protein construct is greater than the strength of the noncovalent bond between the amino acid pair in a folded wild-type HA protein.

2. The method of claim 1, wherein substitutions are made to both amino acid residues in the amino acid pair.

3. The method of claim 1, wherein one amino acid of the amino acid pair corresponds to K1 of SEQ ID NO:149, and the other amino acid of the amino acid pair corresponds to E53 of SEQ ID NO:149.

4. The method of claim 3, wherein a substitution is made at the position corresponding to K1, and a second substitution is made at the position corresponding to position E53.

5. The method of claim 1, wherein the first linker sequence comprises less than 5 contiguous amino acids from the head region of an influenza HA protein.

6. The method of claim 1, wherein the HA protein domain is joined to a monomeric subunit protein that allows the protein construct to form a nanoparticle.

7. The method of claim 1, wherein the HA protein domain comprises a first amino acid sequence from the stem region of an HA protein and a second amino acid sequence from the stem region of an HA protein, the first and second amino acid sequences being covalently linked by the first linker sequence,
   wherein the first amino acid sequence comprises at least 20 contiguous amino acid residues from the amino acid sequence upstream of the amino-terminal end of the head region sequence, and
   wherein the second amino acid sequence comprises at least 20 contiguous amino acid residues from the amino acid sequence downstream of the carboxyl-terminal end of the head region sequence.

8. The method of claim 7, wherein the first amino acid sequence and the second amino acid sequence are from the stem region of an HA protein from a virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), B/Brisbane/60/2008 (2008 Bris, B).

9. The method of claim 7, wherein the first amino acid sequence comprises a sequence at least 80% identical to at least 40 contiguous amino acid residues from a sequence selected from the group consisting of SEQ ID NO: 20, SEQ ID NO:35, SEQ ID NO:50 and SEQ ID NO:65.

10. The method of claim 7, wherein the second amino acid sequence comprises a sequence at least 80% identical to at least 40 contiguous amino acid residues from a sequence selected from the group consisting of SEQ ID NO:26, SEQ ID NO:32, SEQ ID NO:41, SEQ ID NO:44, SEQ ID NO:47, SEQ ID NO:56, SEQ ID NO:62, SEQ ID NO:71 and SEQ ID NO:77.

11. The method of claim 7, wherein the second amino acid sequence comprises at least 60 contiguous amino acids from the amino acid sequence downstream of the carboxyl-terminal end of the head region sequence;
wherein the 60 contiguous amino acids comprise a polypeptide sequence corresponding to the sequence of SEQ ID NO:149 or SEQ ID NO:150 from influenza virus H1N1 NC.

12. The method of claim 7, wherein the first amino acid sequence comprises a sequence selected from the group consisting of SEQ ID NO: 20, SEQ ID NO:35, SEQ ID NO:50 and SEQ ID NO:65; and, wherein the second amino acid sequence comprises a sequence selected from the group consisting of SEQ ID NO:29, SEQ ID NO:32, SEQ ID NO:47, SEQ ID NO:59, SEQ ID NO:62, SEQ ID NO:74 and SEQ ID NO:77.

13. The method of claim 1, wherein the HA protein domain comprises at least one other mutation at an amino acid position corresponding to an amino acid position in SEQ ID NO:8 selected from the group consisting of amino acid position 36, amino acid position 45, amino acid position 47, amino acid position 49, amino acid position 339, amino acid position 340, amino acid position 341, amino acid position 342, amino acid position 361, amino acid position 372, amino acid position 394, amino acid position 402, amino acid position 437, amino acid position 438, amino acid position 445, amino acid position 446, amino acid position 448, amino acid 449, amino acid position 450 and amino acid position 452.

14. The method of claim 1, wherein the protein construct comprises an amino acid sequence at least 85% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

15. The method of claim 1, wherein the HA protein domain comprises an amino acid sequence corresponding to SEQ ID NO:150.

16. The method of claim 1, wherein the second linker sequence is between 2 and 20 amino acid residues in length.

17. The method of claim 1, wherein the influenza HA protein is from a virus selected from the group consisting of A/New Caledonia/20/1999 (1999 NC, H1), A/California/04/2009 (2009 CA, H1), A/Singapore/1/1957 (1957 Sing, H2), A/Hong Kong/1/1968 (1968 HK, H3), A/Brisbane/10/2007 (2007 Bris, H3), A/Indonesia/05/2005 (2005 Indo, H5), B/Florida/4/2006 (2006 Flo, B), A/Perth/16/2009 (2009 Per, H3), A/Brisbane/59/2007 (2007 Bris, H1), and B/Brisbane/60/2008 (2008 Bris, B).

18. The method of claim 1, wherein the protein construct comprises an amino acid sequence at least 95% identical to a sequence selected from the group consisting of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

19. The method of claim 1, wherein the protein construct comprises an amino acid sequence set forth as any one of SEQ ID NO:80, SEQ ID NO:83, SEQ ID NO:86, SEQ ID NO:89, SEQ ID NO:92, SEQ ID NO:95, SEQ ID NO:98, SEQ ID NO:101, SEQ ID NO:104, SEQ ID NO:158, SEQ ID NO:164, SEQ ID NO:170, SEQ ID NO:176, SEQ ID NO:182, SEQ ID NO:188, SEQ ID NO:197, SEQ ID NO:203, SEQ ID NO:209, SEQ ID NO:214, SEQ ID NO:217, SEQ ID NO:222, SEQ ID NO:224, SEQ ID NO:226, SEQ ID NO:228, SEQ ID NO:230, SEQ ID NO:232, SEQ ID NO:235, SEQ ID NO:240, SEQ ID NO:242, SEQ ID NO:244, SEQ ID NO:246, SEQ ID NO:248, SEQ ID NO:250, SEQ ID NO:252, SEQ ID NO:254, SEQ ID NO:256, SEQ ID NO:258, SEQ ID NO:261, SEQ ID NO:268, SEQ ID NO:275, SEQ ID NO:282, SEQ ID NO:289, SEQ ID NO:296, SEQ ID NO:303, SEQ ID NO:310, SEQ ID NO:317, SEQ ID NO:324, SEQ ID NO:331, SEQ ID NO:338, SEQ ID NO:345, SEQ ID NO:352, SEQ ID NO:359, SEQ ID NO:366, SEQ ID NO:373, SEQ ID NO:380, SEQ ID NO:387, SEQ ID NO:394 and SEQ ID NO:400.

20. The method of claim 1, wherein the protein construct comprises an amino acid sequence at least 90% identical to SEQ ID NO: 92.

21. The method of claim 1, wherein the protein construct comprises the amino acid sequence set forth as SEQ ID NO: 92.

* * * * *